(12) United States Patent
Angibaud et al.

(10) Patent No.: US 11,267,804 B2
(45) Date of Patent: *Mar. 8, 2022

(54) (R)-8-(1-((3-FLUOROPHENYL)AMINO)ETHYL)-N-(2-HYDROXYETHYL)-2-MORPHOLINOQUINOXALINE-6-CARBOXAMIDE FOR INHIBITING PHOSPHOINOSITIDE-3-KINASE ACTIVITY

(71) Applicant: Janssen Pharmaceutica NV, Beerse (BE)

(72) Inventors: Patrick Rene Angibaud, Saint Pierre d'Autils (FR); Olivier Alexis Georges Querolle, Saint Vigor (FR); Didier Jean-Claude Berthelot, La Neuville Chant d'Oisel (FR); Christophe Meyer, Les Authieux sur le Port St Ouen (FR); Matthieu Philippe Victor Willot, Dusseldorf (DE); Lieven Meerpoel, Beerse (BE); Thierry Francois Alain Jean Jousseaume, Schaffhausen (CH)

(73) Assignee: Janssen Pharmaceutica NV, Beerse (BE)

(*) Notice: Subject to any disclaimer, the term of this patent is extended or adjusted under 35 U.S.C. 154(b) by 0 days.

This patent is subject to a terminal disclaimer.

(21) Appl. No.: 16/680,605

(22) Filed: Nov. 12, 2019

(65) Prior Publication Data

US 2020/0079763 A1   Mar. 12, 2020

Related U.S. Application Data

(63) Continuation of application No. 15/766,887, filed as application No. PCT/EP2016/073962 on Oct. 7, 2016, now Pat. No. 10,526,316.

(30) Foreign Application Priority Data

Oct. 9, 2015 (EP) .................................... 15189163
Jun. 16, 2016 (EP) .................................... 16174710

(51) Int. Cl.
| | | |
|---|---|---|
| C07D 241/44 | (2006.01) | |
| C07D 403/10 | (2006.01) | |
| C07D 403/12 | (2006.01) | |
| C07D 403/14 | (2006.01) | |
| C07D 498/10 | (2006.01) | |
| C07D 487/02 | (2006.01) | |
| C07D 241/14 | (2006.01) | |
| C07D 403/06 | (2006.01) | |
| C07D 417/04 | (2006.01) | |
| C07D 403/04 | (2006.01) | |
| C07D 413/04 | (2006.01) | |
| C07D 401/06 | (2006.01) | |
| C07D 513/10 | (2006.01) | |
| C07D 491/10 | (2006.01) | |
| C07D 413/06 | (2006.01) | |
| C07D 401/04 | (2006.01) | |
| C07D 413/14 | (2006.01) | |
| C07D 495/04 | (2006.01) | |
| C07D 241/42 | (2006.01) | |
| C07D 413/10 | (2006.01) | |
| C07D 471/04 | (2006.01) | |
| C07D 487/04 | (2006.01) | |
| C07D 495/10 | (2006.01) | |

(52) U.S. Cl.
CPC ......... *C07D 403/10* (2013.01); *C07D 241/14* (2013.01); *C07D 241/42* (2013.01); *C07D 401/04* (2013.01); *C07D 401/06* (2013.01); *C07D 403/04* (2013.01); *C07D 403/06* (2013.01); *C07D 403/12* (2013.01); *C07D 403/14* (2013.01); *C07D 413/04* (2013.01); *C07D 413/06* (2013.01); *C07D 413/10* (2013.01); *C07D 413/14* (2013.01); *C07D 417/04* (2013.01); *C07D 471/04* (2013.01); *C07D 487/02* (2013.01); *C07D 487/04* (2013.01); *C07D 491/10* (2013.01); *C07D 495/04* (2013.01); *C07D 495/10* (2013.01); *C07D 498/10* (2013.01); *C07D 513/10* (2013.01)

(58) Field of Classification Search
CPC .................................................... C07D 241/44
USPC ............................................................ 544/355
See application file for complete search history.

(56) References Cited

FOREIGN PATENT DOCUMENTS

WO    WO 17/060406    *   4/2017

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Hackam, et al. JAMA, 296(14), 2006, 1731-1732.*

* cited by examiner

Primary Examiner — Douglas M Willis

(57) ABSTRACT

The present invention relates to substituted quinoxaline and pyridopyrazine derivatives of Formula (I)

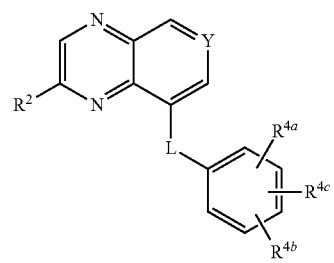

wherein the variables have the meaning defined in the claims. The compounds according to the present invention are useful as pI3Kβ inhibitors. The invention further relates to pharmaceutical compositions comprising said compounds as an active ingredient as well as the use of said compounds as a medicament.

4 Claims, No Drawings

(R)-8-(1-((3-FLUOROPHENYL)AMINO) ETHYL)-N-(2-HYDROXYETHYL)-2-MORPHOLINOQUINOXALINE-6-CARBOXAMIDE FOR INHIBITING PHOSPHOINOSITIDE-3-KINASE ACTIVITY

CROSS REFERENCE TO RELATED APPLICATIONS

This application is a continuation application claiming priority of national stage application of International Patent Application No. PCT/EP2016/073962, filed 7 Oct. 2016, which claims priority from EP Application 15189163.7 filed 9 Oct. 2015 and EP Application 16174710.0 filed on 16 Jun. 2016. The complete disclosures of the aforementioned related patent applications are hereby incorporated herein by reference for all purposes.

FIELD OF THE INVENTION

The present invention relates to substituted quinoxaline and pyridopyrazine derivatives useful as PI3Kβ inhibitors. The invention further relates to pharmaceutical compositions comprising said compounds as an active ingredient as well as the use of said compounds as a medicament.

BACKGROUND OF THE INVENTION

There are three classes of phosphoinositide-3-kinases (PI3Ks): class I, class II and class III. Class I PI3Ks are the most associated with human cancer [K. D Courtney, R. B. Corcoran and J. A. Engelman (2010), *Journal of Clinical Oncology.*, 28; 1075]. The class I phosphoinositide-3-kinases (PI3Ks) are divided into 2 subclasses: class $I_A$, composed of a p110 catalytic subunit (p110a, p110b or p110d) and a p85 regulatory subunit (p85a, p55a and p50a, p85b or p55g) and class $I_B$ PI3K represented by the p110g catalytic subunit and the p101 and p84 regulatory subunits [B. Vanhaesebroeck and M. D. Waterfield (1999) *Experimental Cell Research.*, 253, 239-254]. The class $I_A$ PI3Ks are activated in a variety of solid and non-solid tumors via mutation or deletion of the tumor suppressor PTEN (phosphatase and tensin homolog) or in the case of p110a by activating mutations [K. D Courtney, R. B. Corcoran and J. A. Engelman (2010), *Journal of Clinical Oncology.*, 28; 1075]. PI3Ks can also be activated by receptor tyrosine kinases (RTKs); p110b can be activated by G-protein coupled receptors [K. D Courtney, R. B. Corcoran and J. A. Engelman (2010), *Journal of Clinical Oncology.*, 28; 10751. Once activated the phosphoinositide-3-kinases catalyze the phosphorylation of phosphatidyl 4,5-diphosphate leading to the generation of phosphatidyl, 3, 4, 5-triphosphate (PIP3) [Zhao L., Vogt P. K. (2008) Oncogene 27, 5486-54961. PTEN antagonizes the activity of the PI3Ks through the dephosphorylation PIP3 [Myers M. P., Pass I., Batty I. H., Van der Kaay J., Stolarov J. P., Hemmings B. A., Wigler M. H., Downes C. P., Tonks N. K. (1998) *Proc. Natl. Acad. Sci. U.S.A.* 95, 13513-135181. The PIP3 generated by activation of PI3K or sustained by the inactivation of PTEN binds to a subset of lipid-binding domains in downstream targets such as the pleckstrin homology domain of the oncogene Akt thereby recruiting it to the plasma membrane [Stokoe D., Stephens L. R., Copeland T., Gaffney P. R., Reese C. B., Painter G. F., Holmes A. B., McCormick F., Hawkins P. T. (1997) *Science* 277, 567-5701. Once at the plasma membrane Akt phosphorylates several effector molecules that are involved in numerous biologically relevant processes such as metabolism, differentiation, proliferation, longevity and apoptosis [D. R. Calnan and A. Brunet (2008) *Oncogene* 27; 2276)].

Several studies suggest a key role for p110b in PTEN-deficient tumors. For example the genetic knockout of p110b, but not p110a, is able to block tumor formation and Akt activation driven by Pten loss in the anterior prostate in a mouse model [Jia S, Liu Z, Zhang S, Liu P, Zhang L, Lee S H, Zhang J, Signoretti S, Loda M, Roberts T M, Zhao J J. *Nature* 2008; 454:776-91. Furthermore other studies have shown that a subset of PTEN-deficient human tumor cell lines is sensitive to inactivation of p110b rather than p110a [Wee S, Wiederschain D, Maira S M, Loo A, Miller C, deBeaumont R, Stegmeier F, Yao Y M, Lengauer C (2008) *Proc. Nal. Acad. Sci* (USA); 105 130571. PTEN deficiency either by genetic inactivation or reduced expression frequently occurs in human cancers such as GBM, endometrial, lung, breast cancers and prostate cancer among others [K. D Courtney, R. B. Corcoran and J. A. Engelman (2010), *Journal of Clinical Oncology.*, 28; 10751.

These studies suggest that treatment of PTEN-deficient cancer with agents that inhibition p110b may be therapeutically beneficial. In addition to its role in cancer, p110b may be a target for antithrombotic therapy. It has been reported in mouse models that PI3Kb inhibition can prevent stable integrin $a_{IIb}b_3$ adhesion contacts that eliminates occulusive thrombus formation without prolongation of bleed time [S. P. Jackson et al. (2005) *Nature Medicine.*, 11, 507-5141.

Furthermore, the phosphatidylinositol-4,5-bisphosphate 3-kinase (PI3K)/AKT pathway is frequently activated during prostate cancer (PCa) progression through loss or mutation of the phosphatase and tensin homolog (PTEN) gene. Following the androgen receptor (AR) pathway, it is the second major driver of PCa growth. Combination with hormonal therapy improved efficacy of PI3K/AKT-targeted agents in PTEN-negative PCa models. Upregulation of AR-target genes upon PI3K/AKT inhibition suggests a compensatory crosstalk between the PI3K-AR pathways which, for optimal efficacy treatment, could require cotargeting of the AR axis [Marques R B, et al., High Efficacy of Combination Therapy Using PI3K/AKT Inhibitors with Androgen Deprivation in Prostate Cancer Preclinical Models. *Eur Urol* (2014), http://dx.doi.org/10.1016/j.eururo.2014.08.053]. Therefore PI3Kβ inhibitors can be advantageously combined with anti-androgen therapies including androgen receptor antagonists and inhibitors of androgen biosynthesis in PTEN-negative prostate cancers.

WO 2012/116237 discloses heterocyclic entitites that modulate PI3 kinase activity.

WO 2011/123751 describes heterocyclic compounds as selective inhibitors of PI3K activity.

WO 2011/022439 discloses heterocyclic entities that modulate PI3 kinase activity.

WO 2008/014219 describes thiozolidinedione derivatives as PI3 kinase inhibitors.

WO 2013/028263 relates to pyrazolopyrimidine derivatives as PI3 kinase inhibitors.

WO 2012/047538 relates to benzimidazole derivatives as PI3 kinase inhibitors.

WO 2013/095761 relates to imidazopyridine derivatives as PI3 kinase inhibitors.

US 2013/0157977 relates to benzimidazole boronic acid derivatives as PI3 kinase inhibitors.

WO 2009/021083 describes quinoxaline derivatives as PI3 kinase inhibitors.

WO 2007/103756 describes the preparation of thiazolones for use as PI3 kinase inhibitors.

WO 2011/041399 describes benzimidazolyl (morpholinyl) purines and related compounds as PI3Kδ inhibitors and their preparation and use for the treatment of PI3K-mediated diseases.

WO 2009/088990 describes the preparation of pyrazolo pyrimidines and other heterocyclic compounds as therapeutic PI3 kinase modulators.

WO2016/097347 relates to substituted imidazopyridazine derivatives useful as PI3Kβ inhibitors.

WO2016/097359 relates to relates to heterocyclyl linked imidazopyridazine derivatives useful as PI3Kβ inhibitors.

There is thus a strong need for novel PI3Kβ kinase inhibitors thereby opening new avenues for the treatment or prevention of cancer, in particular PTEN-deficient cancers, more in particular prostate cancer. It is accordingly an object of the present invention to provide such compounds.

SUMMARY OF THE INVENTION

It has been found that the compounds of the present invention are useful as PI3Kβ inhibitors. The compounds according to the invention and compositions thereof, may be useful for the treatment or prevention, in particular for the treatment, of diseases such as cancer, autoimmune disorders, cardiovascular diseases, inflammatory diseases, neurodegenerative diseases, allergy, pancreatitis, asthma, multiorgan failure, kidney diseases, platelet aggregation, sperm motility, transplantation rejection, graft rejection, lung injuries and the like.

This invention concerns compounds of Formula (I)

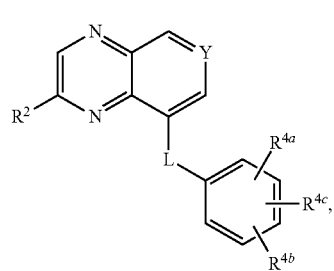

(I)

tautomers and stereoisomeric forms thereof, wherein

Y represents $CR^3$ or N;

L represents —CH($C_{1-4}$alkyl)-$CH_2$—, —$CH_2$—CH($C_{1-4}$alkyl)-, —CH($C_{1-4}$alkyl)-CH($C_{1-4}$alkyl)-, —$CHR^{1a}$—X—, or —X—$CHR^{1c}$—;

X represents O, S, or $NR^{1b}$.

$R^{1a}$ represents hydrogen, $C_{1-4}$alkyl, or $C_{1-4}$alkyl substituted with one —OH;

$R^{1c}$ represents hydrogen or $C_{1-4}$alkyl;

$R^{1b}$ represents hydrogen, $C_{1-4}$alkyl, —$CH_2$—C(=O)—$NR^{6a}R^{6b}$, or $C_{1-4}$alkyl substituted with one substituent selected from the group consisting of hydroxyl, —O—$C_{1-4}$alkyl, and —$NR^{6c}R^{6d}$;

or $R^{1b}$ is taken together with $R^{1a}$ or $R^{1c}$ to form —$(CH_2)_3$—;

or $R^{1b}$ is taken together with $R^{1c}$ to form —$(CH_2)_2$— or —$(CH_2)_4$—;

$R^2$ represents

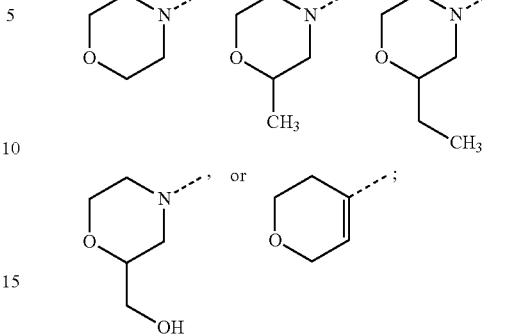

$R^{6a}$ and $R^{6b}$ each independently are selected from the group consisting of hydrogen and $C_{1-4}$alkyl;

$R^{6c}$ and $R^{6d}$ each independently are selected from the group consisting of hydrogen, $C_{1-4}$alkyl, and $C_{1-4}$alkyl substituted with one substituent selected from the group consisting of hydroxyl, —$NH_2$, —NH($C_{1-4}$alkyl), and —N($C_{1-4}$alkyl)$_2$;

$R^3$ represents $R^7$, —(C=O)H, —(C=O)—$C_{1-4}$alkyl, —(C=O)—$NR^{5a}R^{5b}$, —(C=O)—$OR^{5c}$, —C(=O)-$Het^1$, —C(=O)—NH—$Het^2$, —C(=O)—NH—$C_{1-4}$alkyl-$Het^1$, —C(=O)—N($C_{1-4}$alkyl)-$C_{1-4}$alkyl-$Het^1$, —C(=O)—N($C_{1-4}$alkyl)-$Het^2$, $C_{1-4}$alkyl, —CH=N—OH, —CH(OH)—$CH_2$—$NR^{5d}R^{5e}$, —CH(OH)—$CH_2$-$Het^1$, —CH(OH)—$C_{1-4}$alkyl, —C(OH)($C_{1-4}$alkyl)$_2$, halo, or $R^3$ represents $C_{1-4}$alkyl substituted with one substituent selected from the group consisting of hydroxyl, fluoro, —$NR^{5f}R^{5g}$, $Het^1$, —O—(C=O)—CH($NH_2$)—$C_{1-4}$alkyl, —O—(C=O)—CH($NH_2$)—$C_{1-4}$alkyl-Ar,

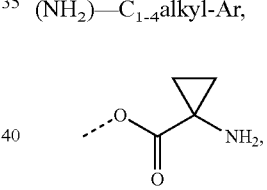

—O—$C_{1-4}$alkyl-OH, and —O—$C_{1-4}$alkyl-$NH_2$;

$R^{5a}$ and $R^{5b}$ each independently are selected from the group consisting of hydrogen, $C_{1-4}$alkyl, —O—$C_{1-4}$alkyl, —S(=O)$_2$—$NH_2$, —S(=O)$_2$—$C_{1-4}$alkyl, —S(=O)$_2$—$C_{3-6}$ cycloalkyl, $C_{1-4}$alkyl substituted with one or more halo atoms, and $C_{1-4}$alkyl substituted with one substituent selected from the group consisting of hydroxyl, —O—$C_{1-4}$alkyl, —S(=O)$_2$—$C_{1-4}$alkyl, —O—$C_{1-4}$alkyl-$NH_2$, —O—$C_{1-4}$alkyl-NH($C_{1-4}$alkyl), —O—$C_{1-4}$alkyl-N($C_{1-4}$alkyl)$_2$, —(C=O)—O—$C_{1-4}$alkyl, —(C=O)—OH, —(C=O))—$C_{1-4}$alkyl, —$NH_2$, —NH($C_{1-4}$alkyl) and —N($C_{1-4}$alkyl)$_2$;

$R^{5c}$ represents hydrogen or $C_{1-4}$alkyl;

$R^{5d}$ and $R^{5e}$ each independently are selected from the group consisting of hydrogen and $C_{1-4}$alkyl;

$R^{5f}$ and $R^{5g}$ each independently are selected from the group consisting of hydrogen, $C_{1-4}$alkyl, $C_{1-4}$alkyl substituted with one or more halo atoms, and $C_{1-4}$alkyl substituted with one substituent selected from the group consisting of hydroxyl, —O—$C_{1-4}$alkyl, —S(=O)$_2$—$C_{1-4}$alkyl, —$NH_2$, —NH($C_{1-4}$alkyl), and —N($C_{1-4}$alkyl)$_2$;

$R^{4a}$, $R^{4b}$ and $R^{4c}$ each independently are selected from the group consisting of hydrogen, cyano, $C_{1-4}$alkyl, halo, —C(=O)H, —$NR^{6e}R^{6f}$, —O—$C_{1-4}$alkyl, and $C_{1-4}$alkyl substituted with one or more substituents each independently selected from the group consisting of hydroxyl, halo, and —NR$^{6g}$R$^{6h}$;

R$^{6e}$ and R$^{6f}$ each independently are selected from the group consisting of hydrogen, C$_{1-4}$alkyl, and C$_{1-4}$alkyl substituted with one substituent selected from the group consisting of —NH$_2$, —NH(C$_{1-4}$alkyl), and hydroxyl;

R$^{6g}$ and R$^{6h}$ each independently are selected from the group consisting of hydrogen, C$_{1-4}$alkyl, and C$_{1-4}$alkyl substituted with one substituent selected from the group consisting of —NH$_2$, —NH(C$_{1-4}$alkyl), and hydroxyl;

Het$^1$ represents a monocyclic 4-, 5-, 6- or 7-membered saturated or partially saturated heterocyclyl containing at least one heteroatom each independently selected from O, S, S(=O)$_p$ and N; or Het$^1$ represents a bicyclic 8-, 9- or 10-membered saturated or partially saturated heterocyclyl containing at least one heteroatom each independently selected from O, S, S(=O)$_p$ and N;

each optionally substituted with one or two substituents each independently selected from the group consisting of halo, —NR$^{9a}$R$^{9b}$, C$_{1-4}$alkyl, —(C=O)—OR$^{5h}$, —S(=O)$_2$—C$_{1-6}$alkyl, —C$_{1-4}$alkyl-S(=O)$_2$—C$_{1-6}$alkyl, hydroxyl, —O—C$_{1-4}$alkyl, cyano, C$_{1-4}$alkyl substituted with one or more halo atoms, and C$_{1-4}$alkyl substituted with one substituent selected from the group consisting of hydroxyl, —NH$_2$, —NH(C$_{1-4}$alkyl) and —N(C$_{1-4}$alkyl)$_2$; or two substituents on the same carbon atom of said heterocyclyl are taken together to form together with the common carbon atom to which they are attached Ring A;

R$^{9a}$ and R$^{9b}$ each independently are selected from the group consisting of hydrogen, C$_{1-4}$alkyl, and C$_{1-4}$alkyl substituted with one or more halo atoms; Het$^2$ represents

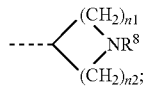

n1 represents 1 or 2;
n2 represents 1 or 2;
R$^8$ represents hydrogen, C$_{1-4}$alkyl, or C$_{1-4}$alkyl substituted with one or more halo atoms;
R$^{5h}$ represents hydrogen or C$_{1-4}$alkyl;
Ring A represents cyclobutyl, cyclopentyl, cyclohexyl, or a 4-, 5- or 6-membered saturated heterocyclyl containing at least one heteroatom each independently selected from O, S, S(=O)$_p$ and N; said cyclobutyl, cyclopentyl, cyclohexyl, or 4-, 5- or 6-membered saturated heterocyclyl is optionally substituted with one or two C$_{1-4}$alkyl substituents, with one C$_{1-4}$alkyl and one hydroxy substituent, or with one hydroxy substituent;
p represents 1 or 2;
Ar represents phenyl optionally substituted with one hydroxyl;
R$^7$ represents

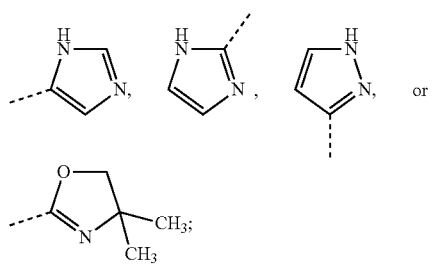

and the N-oxides, the pharmaceutically acceptable addition salts, and the solvates thereof.

The present invention also concerns methods for the preparation of compounds of the present invention and pharmaceutical compositions comprising them.

The compounds of the present invention were found to inhibit PI3Kβ per se or can undergo metabolism to a (more) active form in vivo (prodrugs), and therefore may be useful in the treatment or prevention, in particular in the treatment, of diseases such as cancer, autoimmune disorders, cardiovascular diseases, inflammatory diseases, neurodegenerative diseases, allergy, pancreatitis, asthma, multiorgan failure, kidney diseases, platelet aggregation, sperm motility, transplantation rejection, graft rejection, lung injuries and the like.

In view of the aforementioned pharmacology of the compounds of Formula (I) and N-oxides, pharmaceutically acceptable addition salts, and solvates thereof, it follows that they may be suitable for use as a medicament.

In particular the compounds of Formula (I) and N-oxides, pharmaceutically acceptable addition salts, and solvates thereof, may be suitable in the treatment or prevention, in particular in the treatment, of cancer.

The present invention also concerns the use of compounds of Formula (I) and N-oxides, pharmaceutically acceptable addition salts, and solvates thereof, for the manufacture of a medicament for the inhibition of PI3Kβ, for the treatment or prevention of cancer. The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

DETAILED DESCRIPTION OF THE INVENTION

When describing the compounds of the invention, the terms used are to be construed in accordance with the following definitions, unless a context dictates otherwise.

When any variable occurs more than one time in any constituent or in any formula (e.g. Formula (I)), its definition in each occurrence is independent of its definition at every other occurrence.

Whenever the term "substituted" is used in the present invention, it is meant, unless otherwise is indicated or is clear from the context, to indicate that one or more hydrogens, in particular from 1 to 3 hydrogens, preferably 1 or 2 hydrogens, more preferably 1 hydrogen, on the atom or radical indicated in the expression using "substituted" are replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

When two or more substituents are present on a moiety they may, unless otherwise is indicated or is clear from the context, replace hydrogens on the same atom or they may replace hydrogen atoms on different atoms in the moiety.

It will be clear for the skilled person that, unless otherwise is indicated or is clear from the context, a substituent on a heterocyclyl group may replace any hydrogen atom on a ring carbon atom or on a ring heteroatom.

The prefix "$C_{x-y}$" (where x and y are integers) as used herein refers to the number of carbon atoms in a given group. Thus, a $C_{1-6}$alkyl group contains from 1 to 6 carbon atoms, a $C_{1-4}$alkyl group contains from 1 to 4 carbon atoms, a $C_{1-3}$alkyl group contains from 1 to 3 carbon atoms, a $C_{3-6}$cycloalkyl group contains from 3 to 6 carbon atoms, and so on.

The term "halo" as a group or part of a group is generic for fluoro, chloro, bromo, iodo unless otherwise is indicated or is clear from the context.

The term "$C_{1-6}$alkyl" as a group or part of a group refers to a hydrocarbyl radical of Formula $C_nH_{2n+1}$ wherein n is a number ranging from 1 to 6. $C_{1-6}$alkyl groups comprise from 1 to 6 carbon atoms, preferably from 1 to 4 carbon atoms, more preferably from 1 to 3 carbon atoms, still more preferably 1 to 2 carbon atoms. Alkyl groups may be linear or branched and may be substituted as indicated herein. When a subscript is used herein following a carbon atom, the subscript refers to the number of carbon atoms that the named group may contain. Thus, for example, $C_{1-6}$alkyl includes all linear, or branched alkyl groups with between 1 and 6 carbon atoms, and thus includes such as for example methyl, ethyl, n-propyl, i-propyl, 2-methyl-ethyl, butyl and its isomers (e.g. n-butyl, isobutyl and tert-butyl), pentyl and its isomers, hexyl and its isomers, and the like.

The term "$C_{1-4}$alkyl" as a group or part of a group refers to a hydrocarbyl radical of Formula $C_nH_{2n+1}$ wherein n is a number ranging from 1 to 4. $C_{1-4}$alkyl groups comprise from 1 to 4 carbon atoms, preferably from 1 to 3 carbon atoms, more preferably 1 to 2 carbon atoms. $C_{1-4}$alkyl groups may be linear or branched and may be substituted as indicated herein. When a subscript is used herein following a carbon atom, the subscript refers to the number of carbon atoms that the named group may contain. $C_{1-4}$alkyl includes all linear, or branched alkyl groups with between 1 and 4 carbon atoms, and thus includes methyl, ethyl, n-propyl, i-propyl, 2-methyl-ethyl, butyl and its isomers (e.g. n-butyl, isobutyl and tert-butyl), and the like.

The term "$C_{3-6}$cycloalkyl" alone or in combination, refers to a cyclic saturated hydrocarbon radical having from 3 to 6 carbon atoms. Non-limiting examples of suitable $C_{3-6}$cycloalkyl include cyclopropyl, cyclobutyl, cyclopentyl and cyclohexyl.

Examples of compounds wherein $R^{1b}$ and $R^{1a}$ are taken together to form —$(CH_2)_3$— are compounds 1-4, 10, 14-19, 23-52, 54-55, 57-58, 62-67, 69-72, 75-77, 93-96, 101-103, 106-107, 112, 249-255.

Examples of compounds wherein $R^{1b}$ and $R^{1c}$ are taken together to form —$(CH_2)_3$— are compounds 244-245.

In case L represents —$CH(C_{1-4}alkyl)$-$CH_2$—, it is intended that the C-atom with the two hydrogens (—$CH_2$—) is attached to the phenyl ring in the structure of formula (I).

In case L represents —$CH_2$—$CH(C_{1-4}alkyl)$-, it is intended that the C-atom with the $C_{1-4}$alkyl substituent (—$CH(C_{1-4}alkyl)$-) is attached to the phenyl ring in the structure of formula (I).

In case L represents —$CHR^{1a}$—X—, it is intended that 'X' is attached to the phenyl ring in the structure of formula (I).

In case L represents —X—$CHR^{1c}$—, it is intended that the C-atom with the Ric substituent (—$CHR^{1c}$—) is attached to the phenyl ring in the structure of formula (I).

In an embodiment the expression 'at least one heteroatom' is restricted to '1, 2 or 3 heteroatoms', in a particular embodiment to '1 or 2 heteroatoms', in a more particular embodiment to '1 heteroatom'.

Examples of a 4-, 5- or 6-membered saturated heterocyclyl containing at least one heteroatom each independently selected from O, S, S(=O)$_p$ and N (e.g. in Ring A), include, but are not limited to azetidinyl, morpholinyl, piperidinyl, pyrrolidinyl, 1,1-dioxido-thietanyl, 1,1-dioxido-thiomorpholinyl, piperazinyl, dioxolanyl, oxazolidinyl, oxetanyl, tetrahydrofuranyl, and the like.

Examples of a 4-, 5-, 6- or 7-membered saturated or partially saturated heterocyclyl containing at least one heteroatom each independently selected from O, S, S(=O)$_p$ and N (e.g. in Het$^1$), include, but are not limited to azetidinyl, morpholinyl, piperidinyl, pyrrolidinyl, 1,1-dioxido-thietanyl, 1,1-dioxido-thiomorpholinyl, piperazinyl, dioxolanyl, oxazolidinyl, oxetanyl, tetrahydrofuranyl, 4,5-dihydro-1,3-oxazolyl, hexahydro-1H-1,4-diazepinyl, and the like.

Examples of a bicyclic 8-, 9- or 10-membered saturated or partially saturated heterocyclyl containing at least one heteroatom each independently selected from O, S, S(=O)$_p$ and N (e.g. in Het$^1$), include, but are not limited to 4,5,6,7-tetrahydropyrazolo[1,5-a]pyrazinyl, octahydro-pyrrolo[1,2-a]pyrazinyl, and the like.

Het$^1$ representing a bicyclic heterocyclyl, in particular is a fused bicyclic heterocyclyl.

Het$^1$ may be attached to the remainder of the molecule of Formula (I) through any available ring carbon atom or ring heteroatom as appropriate, if not otherwise specified. In a particular embodiment Het$^1$ is attached to the remainder of the molecule of Formula (I) via a nitrogen atom.

It will be clear that when two substituents on the same carbon atom in the Het$^1$ definition are taken together to form together with the common carbon atom to which they are attached Ring A, a spiro moiety is formed. For example, when Het$^1$ represents 1-piperidinyl wherein two substituents on the carbon atom in position β are taken together to form together with the common carbon atom to which they are attached ring A, the following spiro moiety is formed:

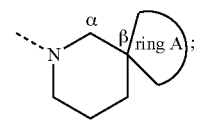

in particular if in the above example ring A represents 3-azetidinyl, the following spiro moiety is formed:

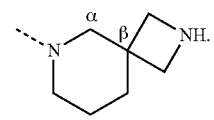

Examples of such spiro moieties, include, but are not limited to

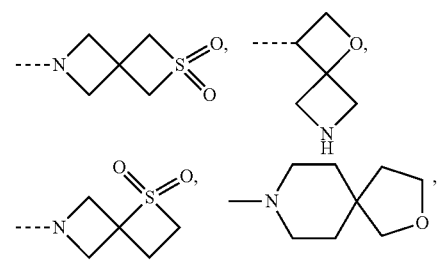

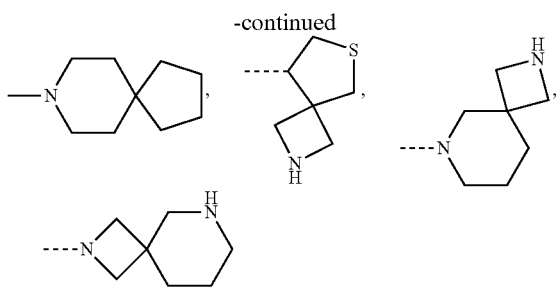

and the like.

Whenever substituents are represented by chemical structure, "---" represents the bond of attachment to the remainder of the molecule of Formula (I).

Whenever one of the ring systems, is substituted with one or more substituents, those substituents may replace, unless otherwise is indicated or is clear from the context, any hydrogen atom bound to a carbon or nitrogen atom of the ring system.

The term "subject" as used herein, refers to an animal, preferably a mammal (e.g. cat, dog, primate or human), more preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medicinal doctor or other clinician, which includes alleviation or reversal of the symptoms of the disease or disorder being treated.

The term "composition" is intended to encompass a product comprising the specified ingredients in the specified amounts, as well as any product which results, directly or indirectly, from combinations of the specified ingredients in the specified amounts.

The term "treatment", as used herein, is intended to refer to all processes wherein there may be a slowing, interrupting, arresting or stopping of the progression of a disease, but does not necessarily indicate a total elimination of all symptoms.

The term "compounds of the invention" as used herein, is meant to include the compounds of Formula (I) and N-oxides, pharmaceutically acceptable addition salts, and solvates thereof.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

Hereinbefore and hereinafter, the term "compound of Formula (I)" is meant to include the stereoisomers thereof and the tautomeric forms thereof.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers.

Enantiomers are stereoisomers that are non-superimposable mirror images of each other. A 1:1 mixture of a pair of enantiomers is a racemate or racemic mixture.

Atropisomers (or atropoisomers) are stereoisomers which have a particular spatial configuration, resulting from a restricted rotation about a single bond, due to large steric hindrance. All atropisomeric forms of the compounds of Formula (I) are intended to be included within the scope of the present invention.

Diastereomers (or diastereoisomers) are stereoisomers that are not enantiomers, i.e. they are not related as mirror images. If a compound contains a double bond, the substituents may be in the E or the Z configuration. Substituents on bivalent cyclic (partially) saturated radicals may have either the cis- or trans-configuration; for example if a compound contains a disubstituted cycloalkyl group, the substituents may be in the cis or trans configuration. Therefore, the invention includes enantiomers, atropisomers, diastereomers, racemates, E isomers, Z isomers, cis isomers, trans isomers and mixtures thereof, whenever chemically possible.

The meaning of all those terms, i.e. enantiomers, atropisomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of Formula (I) is for instance specified as (R), this means that the compound is substantially free of the (S) isomer; when a compound of Formula (I) is for instance specified as E, this means that the compound is substantially free of the Z isomer; when a compound of Formula (I) is for instance specified as cis, this means that the compound is substantially free of the trans isomer.

Some of the compounds of Formula (I) may also exist in their tautomeric form. Such forms in so far as they may exist, are intended to be included within the scope of the present invention. It follows that a single compound may exist in both stereoisomeric and tautomeric form. For example, it will be clear for the skilled person that when $R^7$ represent

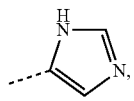

also

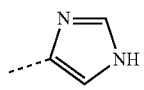

is included.

For therapeutic use, salts of the compounds of Formula (I), N-oxides and solvates thereof, are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable addition salts as mentioned hereinabove or hereinafter are meant to comprise the therapeutically active non-toxic acid and base addition salt forms which the compounds of Formula (I), N-oxides and solvates thereof, are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I), N-oxides and solvates thereof containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term solvate comprises the hydrates and solvent addition forms which the compounds of Formula (I) are able to form, as well as N-oxides and pharmaceutically acceptable addition salts thereof. Examples of such forms are e.g. hydrates, alcoholates and the like.

The compounds of the invention as prepared in the processes described below may be synthesized in the form of mixtures of enantiomers, in particular racemic mixtures of enantiomers, that can be separated from one another following art-known resolution procedures. A manner of separating the enantiomeric forms of the compounds of Formula (I), and N-oxides, pharmaceutically acceptable addition salts, and solvates thereof, involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

In the framework of this application, an element, in particular when mentioned in relation to a compound of Formula (I), comprises all isotopes and isotopic mixtures of this element, either naturally occurring or synthetically produced, either with natural abundance or in an isotopically enriched form. Radiolabelled compounds of Formula (I) may comprise a radioactive isotope selected from the group of $^{2}$H, $^{3}$H, $^{11}$C, $^{18}$F, $^{122}$I, $^{123}$I, $^{125}$I, $^{131}$I, $^{75}$Br, $^{76}$Br, $^{77}$Br and $^{82}$Br. Preferably, the radioactive isotope is selected from the group of $^{2}$H, $^{3}$H, $^{11}$C and $^{18}$F. More preferably, the radioactive isotope is $^{2}$H. In particular, deuterated compounds are intended to be included within the scope of the present invention.

In an embodiment, the present invention concerns novel compounds of Formula (I), tautomers and stereoisomeric forms thereof, wherein Y represents CR$^{3}$ or N;

L represents —CH(C$_{1-4}$alkyl)-CH$_{2}$—, —CH$_{2}$—CH(C$_{1-4}$alkyl)-, —CH(C$_{1-4}$alkyl)-CH(C$_{1-4}$alkyl)-, —CHR$^{1a}$—X—, or —X—CHR$^{1c}$—;

X represents O, S, or NR$^{1b}$;

R$^{1a}$ represents hydrogen, C$_{1-4}$alkyl, or C$_{1-4}$alkyl substituted with one —OH;

R$^{1c}$ represents hydrogen or C$_{1-4}$alkyl;

R$^{1b}$ represents hydrogen, C$_{1-4}$alkyl, —CH$_{2}$—C(=O)—NR$^{6a}$R$^{6b}$, or C$_{1-4}$alkyl substituted with one substituent selected from the group consisting of hydroxyl, —O—C$_{1-4}$alkyl, and —NR$^{6c}$R$^{6d}$;

or R$^{1b}$ is taken together with Ria or Ric to form —(CH$_{2}$)$_{3}$—;

or R$^{1b}$ is taken together with Ric to form —(CH$_{2}$)$_{2}$— or —(CH$_{2}$)$_{4}$—;

R$^{2}$ represents

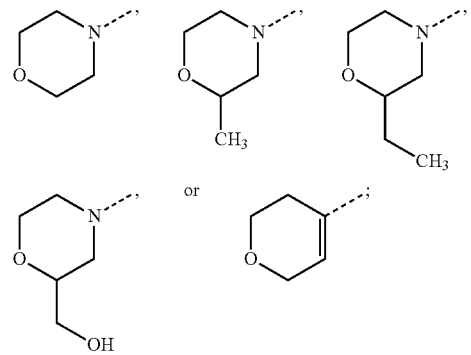

R$^{6a}$ and R$^{6b}$ each independently are selected from the group consisting of hydrogen and C$_{1-4}$alkyl;

R$^{6c}$ and R$^{6d}$ each independently are selected from the group consisting of hydrogen, C$_{1-4}$alkyl, and C$_{1-4}$alkyl substituted with one substituent selected from the group consisting of hydroxyl, —NH$_{2}$, —NH(C$_{1-4}$alkyl), and —N(C$_{1-4}$alkyl)$_{2}$;

R$^{3}$ represents R$^{7}$, —(C=O)H, —(C=O)—C$_{1-4}$alkyl, —(C=O)NR$^{5a}$R$^{5b}$, —(C=O)—OR$^{5c}$, —C(=O)-Het$^{1}$, —C(=O)—NH—Het$^{2}$, C$_{1-4}$alkyl, —CH=N—OH, —CH(OH)—CH$_{2}$—NR$^{5d}$R$^{5e}$, —CH(OH)—CH$_{2}$-Het$^{1}$, —CH(OH)—C$_{1-4}$alkyl, —C(OH)(C$_{1-4}$alkyl)$_{2}$, halo, or R$^{3}$ represents C$_{1-4}$alkyl substituted with one substituent selected from the group consisting of hydroxyl, fluoro, —NR$^{5f}$R$^{5g}$, Het$^{1}$, —O—(C=O)—CH(NH$_{2}$)—C$_{1-4}$alkyl, —O—(C=O)—CH(NH$_{2}$)—C$_{1-4}$alkyl-Ar,

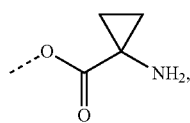

—O—C$_{1-4}$alkyl-OH, and —O—C$_{1-4}$alkyl-NH$_2$;

R$^{5a}$ and R$^{5b}$ each independently are selected from the group consisting of hydrogen, C$_{1-4}$alkyl, —O—C$_{1-4}$alkyl, —S(=O)$_2$—NH$_2$, —S(=O)$_2$—C$_{1-4}$alkyl, —S(=O)$_2$—C$_{3-6}$cycloalkyl, C$_{1-4}$alkyl substituted with one or more halo atoms, and C$_{1-4}$alkyl substituted with one substituent selected from the group consisting of hydroxyl, —O—C$_{1-4}$alkyl, —S(=O)$_2$—C$_{1-4}$alkyl, —O—C$_{1-4}$alkyl-NH$_2$, —O—C$_{1-4}$alkyl-NH(C$_{1-4}$alkyl), —O—C$_{1-4}$alkyl-N(C$_{1-4}$alkyl)$_2$, —(C=O)—O—C$_{1-4}$alkyl, —(C=O)—OH, —(C=O)—C$_{1-4}$alkyl, —NH$_2$, —NH(C$_{1-4}$alkyl) and —N(C$_{1-4}$alkyl)$_2$;

R$^{5c}$ represents hydrogen or C$_{1-4}$alkyl;

R$^{5d}$ and R$^{5e}$ each independently are selected from the group consisting of hydrogen and C$_{1-4}$alkyl;

R$^{5f}$ and R$^{5g}$ each independently are selected from the group consisting of hydrogen, C$_{1-4}$alkyl, C$_{1-4}$alkyl substituted with one or more halo atoms, and C$_{1-4}$alkyl substituted with one substituent selected from the group consisting of hydroxyl, —O—C$_{1-4}$alkyl, —S(=O)$_2$—C$_{1-4}$alkyl, —NH$_2$, —NH(C$_{1-4}$alkyl), and —N(C$_{1-4}$alkyl)$_2$;

R$^{4a}$, R$^{4b}$ and R$^{4c}$ each independently are selected from the group consisting of hydrogen, cyano, C$_{1-4}$alkyl, halo, —C(=O)H, —NR$^{6e}$R$^{6f}$, —O—C$_{1-4}$alkyl, and C$_{1-4}$alkyl substituted with one or more substituents each independently selected from the group consisting of hydroxyl, halo, and —NR$^{6g}$R$^{6h}$.

R$^{6e}$ and R$^{6f}$ each independently are selected from the group consisting of hydrogen, C$_{1-4}$alkyl, and C$_{1-4}$alkyl substituted with one substituent selected from the group consisting of —NH$_2$, —NH(C$_{1-4}$alkyl), and hydroxyl;

R$^{6g}$ and R$^{6h}$ each independently are selected from the group consisting of hydrogen, C$_{1-4}$alkyl, and C$_{1-4}$alkyl substituted with one substituent selected from the group consisting of —NH$_2$, —NH(C$_{1-4}$alkyl), and hydroxyl;

Het$^1$ represents a monocyclic 4-, 5-, 6- or 7-membered saturated or partially saturated heterocyclyl containing at least one heteroatom each independently selected from O, S, S(=O)$_p$ and N; or Het$^1$ represents a bicyclic 8-, 9- or 10-membered saturated or partially saturated heterocyclyl containing at least one heteroatom each independently selected from O, S, S(=O)$_p$ and N;

each optionally substituted with one or two substituents each independently selected from the group consisting of halo, —NR$^{9a}$R$^{9b}$, C$_{1-4}$alkyl, —(C=O)—OR$^{5h}$, —S(=O)$_2$—C$_{1-6}$alkyl, —C$_{1-4}$alkyl-S(=O)$_2$—C$_{1-6}$alkyl, hydroxyl, —O—C$_{1-4}$alkyl, cyano, C$_{1-4}$alkyl substituted with one or more halo atoms, and C$_{1-4}$alkyl substituted with one substituent selected from the group consisting of hydroxyl, —NH$_2$, —NH(C$_{1-4}$alkyl) and —N(C$_{1-4}$alkyl)$_2$; or two substituents on the same carbon atom of said heterocyclyl are taken together to form together with the common carbon atom to which they are attached Ring A;

R$^{9a}$ and R$^{9b}$ each independently are selected from the group consisting of hydrogen, C$_{1-4}$alkyl, and C$_{1-4}$alkyl substituted with one or more halo atoms;

Het$^2$ represents

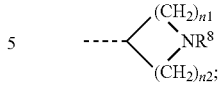

n1 represents 1 or 2;
n2 represents 1 or 2;
R$^8$ represents hydrogen, C$_{1-4}$alkyl, or C$_{1-4}$alkyl substituted with one or more halo atoms;
R$^{5h}$ represents hydrogen or C$_{1-4}$alkyl;
Ring A represents cyclobutyl, cyclopentyl, cyclohexyl, or a 4-, 5- or 6-membered saturated heterocyclyl containing at least one heteroatom each independently selected from O, S, S(=O)$_p$ and N; said cyclobutyl, cyclopentyl, cyclohexyl, or 4-, 5- or 6-membered saturated heterocyclyl is optionally substituted with one or two C$_{1-4}$alkyl substituents, with one C$_{1-4}$alkyl and one hydroxy substituent, or with one hydroxy substituent;
p represents 1 or 2;
Ar represents phenyl optionally substituted with one hydroxyl;
R$^7$ represents

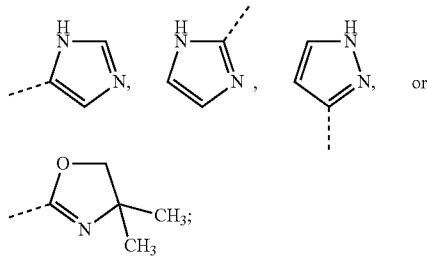

and the N-oxides, the pharmaceutically acceptable addition salts, and the solvates thereof.

In an embodiment, the present invention concerns novel compounds of Formula (I), tautomers and stereoisomeric forms thereof, wherein
Y represents CR$^3$ or N;
L represents —CH(C$_{1-4}$alkyl)-CH$_2$—, —CH$_2$—CH(C$_{1-4}$alkyl)-, —CH(C$_{1-4}$alkyl)-CH(C$_{1-4}$alkyl)-, —CHR$^{1a}$—X—, or —X—CHR$^{1c}$—;
X represents O, S, or NR$^{1b}$;
R$^{1a}$ represents C$_{1-4}$alkyl;
R$^{1c}$ represents hydrogen or C$_{1-4}$alkyl;
R$^{1b}$ represents hydrogen, C$_{1-4}$alkyl, —CH$_2$—C(=O)—NR$^{6a}$R$^{6b}$, or C$_{1-4}$alkyl substituted with one substituent selected from the group consisting of hydroxyl, —O—C$_{1-4}$alkyl, and —NR$^{6c}$R$^{6d}$;
or R$^{1b}$ is taken together with R$^{1a}$ or R$^{1c}$ to form —(CH$_2$)$_3$—;
or R$^{1b}$ is taken together with R$^{1c}$ to form —(CH$_2$)$_2$- or —(CH$_2$)$_4$—;
R$^2$ represents

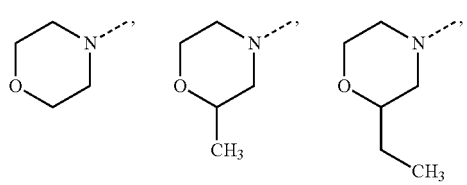

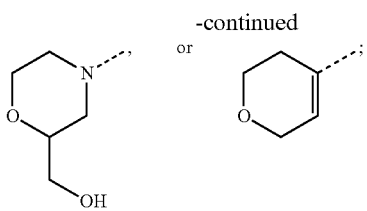

$R^{6a}$ and $R^{6b}$ each independently are selected from the group consisting of hydrogen and $C_{1-4}$ alkyl;

$R^{6c}$ and $R^{6d}$ each independently are selected from the group consisting of hydrogen, $C_{1-4}$alkyl, and $C_{1-4}$alkyl substituted with one substituent selected from the group consisting of hydroxyl, —$NH_2$, —$NH(C_{1-4}$alkyl), and —$N(C_{1-4}$alkyl)$_2$;

$R^3$ represents $R^7$, —(C=O)H, —(C=O)—$C_{1-4}$alkyl, —(C=O)—$NR^{5a}R^{5b}$, —(C=O)—$OR^{5c}$, —C(=O)-$Het^1$, —C(=O)—NH—$Het^2$, $C_{1-4}$alkyl, —CH=N—OH, —CH(OH)—$CH_2$—$NR^{5d}R^{5e}$, —CH(OH)—$CH_2$-$Het^1$, —CH(OH)—$C_{1-4}$alkyl, —C(OH)($C_{1-4}$alkyl)$_2$, halo, or $R^3$ represents $C_{1-4}$alkyl substituted with one substituent selected from the group consisting of hydroxyl, fluoro, —$NR^{5f}R^{5g}$, $Het^1$, —O—(C=O)—CH($NH_2$)—$C_{1-4}$alkyl, —O—(C=O)—CH($NH_2$)—$C_{1-4}$alkyl-Ar,

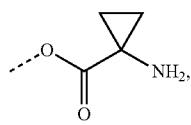

—O—$C_{1-4}$alkyl-OH, and —O—$C_{1-4}$alkyl-$NH_2$;

$R^{5a}$ and $R^{5b}$ each independently are selected from the group consisting of hydrogen, $C_{1-4}$alkyl, —O—$C_{1-4}$alkyl, —S(=O)$_2$—$NH_2$, —S(=O)$_2$—$C_{1-4}$alkyl, —S(=O)$_2$—$C_{3-6}$ cycloalkyl, $C_{1-4}$alkyl substituted with one or more halo atoms, and $C_{1-4}$alkyl substituted with one substituent selected from the group consisting of hydroxyl, —O—$C_{1-4}$alkyl, —S(=O)$_2$—$C_{1-4}$alkyl, —O—$C_{1-4}$alkyl-$NH_2$, —O—$C_{1-4}$alkyl-NH($C_{1-4}$alkyl), —O—$C_{1-4}$alkyl-N($C_{1-4}$alkyl)$_2$, —$NH_2$, —NH($C_{1-4}$alkyl) and —N($C_{1-4}$alkyl)$_2$;

$R^{5c}$ represents hydrogen or $C_{1-4}$alkyl;

$R^{5d}$ and $R^{5e}$ each independently are selected from the group consisting of hydrogen and $C_{1-4}$ alkyl;

$R^{5f}$ and $R^{5g}$ each independently are selected from the group consisting of hydrogen, $C_{1-4}$alkyl, $C_{1-4}$alkyl substituted with one or more halo atoms, and $C_{1-4}$alkyl substituted with one substituent selected from the group consisting of hydroxyl, —O—$C_{1-4}$alkyl, —S(=O)$_2$—$C_{1-4}$alkyl, —$NH_2$, —NH($C_{1-4}$alkyl), and —N($C_{1-4}$alkyl)$_2$;

$R^{4a}$, $R^{4b}$ and $R^{4c}$ each independently are selected from the group consisting of hydrogen, cyano, $C_{1-4}$alkyl, halo, —C(=O)H, —$NR^{6e}R^{6f}$, —O—$C_{1-4}$alkyl, and $C_{1-4}$alkyl substituted with one or more substituents each independently selected from the group consisting of hydroxyl, halo, and —$NR^{6g}R^{6h}$;

$R^{6e}$ and $R^{6f}$ each independently are selected from the group consisting of hydrogen, $C_{1-4}$alkyl, and $C_{1-4}$alkyl substituted with one substituent selected from the group consisting of —$NH_2$, —NH($C_{1-4}$alkyl), and hydroxyl;

$R^{6g}$ and $R^{6h}$ each independently are selected from the group consisting of hydrogen, $C_{1-4}$alkyl, and $C_{1-4}$alkyl substituted with one substituent selected from the group consisting of —$NH_2$, —NH($C_{1-4}$alkyl), and hydroxyl;

$Het^1$ represents a monocyclic 4-, 5-, 6- or 7-membered saturated or partially saturated heterocyclyl containing at least one heteroatom each independently selected from O, S, S(=O)$_p$ and N; or $Het^1$ represents a bicyclic 8-, 9- or 10-membered saturated or partially saturated heterocyclyl containing at least one heteroatom each independently selected from O, S, S(=O)$_p$ and N;

each optionally substituted with one or two substituents each independently selected from the group consisting of halo, —$NR^{9a}R^{9b}$ $C_{1-4}$alkyl, —(C=O)—$OR^{5h}$, —S(=O)$_2$—$C_{1-6}$alkyl, —$C_{1-4}$alkyl-S(=O)$_2$—$C_{1-6}$alkyl, hydroxyl, —O—$C_{1-4}$alkyl, cyano, $C_{1-4}$alkyl substituted with one or more halo atoms, and $C_{1-4}$alkyl substituted with one substituent selected from the group consisting of hydroxyl, —$NH_2$, —NH($C_{1-4}$alkyl) and —N($C_{1-4}$alkyl)$_2$; or two substituents on the same carbon atom of said heterocyclyl are taken together to form together with the common carbon atom to which they are attached Ring A;

$R^{9a}$ and $R^{9b}$ each independently are selected from the group consisting of hydrogen, $C_{1-4}$alkyl, and $C_{1-4}$alkyl substituted with one or more halo atoms;

$Het^2$ represents

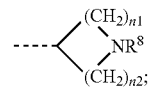

n1 represents 1 or 2;
n2 represents 1 or 2;
$R^8$ represents hydrogen, $C_{1-4}$alkyl, or $C_{1-4}$alkyl substituted with one or more halo atoms;
$R^{5h}$ represents hydrogen or $C_{1-4}$alkyl;
Ring A represents cyclobutyl, cyclopentyl, cyclohexyl, or a 4-, 5- or 6-membered saturated heterocyclyl containing at least one heteroatom each independently selected from O, S, S(=O)$_p$ and N; said cyclobutyl, cyclopentyl, cyclohexyl, or 4-, 5- or 6-membered saturated heterocyclyl is optionally substituted with one or two $C_{1-4}$alkyl substituents, with one $C_{1-4}$alkyl and one hydroxy substituent, or with one hydroxy substituent;
p represents 1 or 2;
Ar represents phenyl optionally substituted with one hydroxyl;
$R^7$ represents

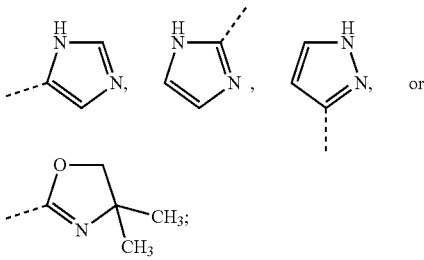

and the N-oxides, the pharmaceutically acceptable addition salts, and the solvates thereof.

In an embodiment, the present invention concerns novel compounds of Formula (I), tautomers and stereoisomeric forms thereof, wherein Y represents CR³ or N;

L represents —CH($C_{1-4}$alkyl)-$CH_2$—, —$CH_2$—CH($C_{1-4}$alkyl)-, —CH($C_{1-4}$alkyl)-CH($C_{1-4}$alkyl)-, —$CHR^{1a}$—X—, or —X—$CHR^{1c}$—;

X represents O, S, or $NR^{1b}$;

$R^{1a}$ represents $C_{1-4}$alkyl;

$R^{1c}$ represents hydrogen or $C_{1-4}$alkyl;

$R^{1b}$ represents hydrogen, $C_{1-4}$alkyl, or $C_{1-4}$alkyl substituted with one substituent selected from the group consisting of hydroxyl, —O—$C_{1-4}$alkyl, and —$NR^{6c}R^{6d}$;

or $R^{1b}$ is taken together with $R^{1a}$ or $R^{1c}$ to form —$(CH_2)_3$—;

or $R^{1b}$ is taken together with $R^{1c}$ to form —$(CH_2)_2$— or —$(CH_2)_4$—;

R² represents

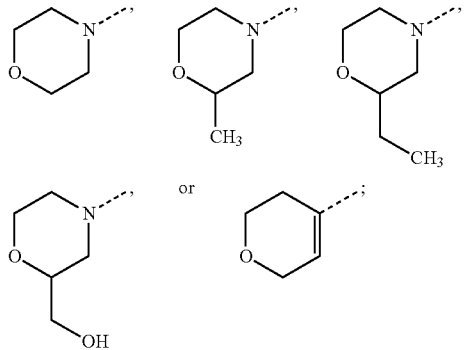

$R^{6c}$ and $R^{6d}$ each independently are selected from the group consisting of hydrogen, $C_{1-4}$alkyl, and $C_{1-4}$alkyl substituted with one substituent selected from the group consisting of hydroxyl, —$NH_2$, —NH($C_{1-4}$alkyl), and —N($C_{1-4}$alkyl)$_2$;

R³ represents R⁷, —(C=O)H, —(C=O)—$C_{1-4}$alkyl, —(C=O)—$NR^{5a}R^{5b}$, —(C=O)—$OR^{5c}$, —C(=O)-Het¹, —C(=O)—NH—Het², $C_{1-4}$alkyl, —CH=N—OH, —CH(OH)—$CH_2$—$NR^{5d}R^{5e}$, —CH(OH)—$CH_2$-Het¹, —CH(OH)—$C_{1-4}$alkyl, —C(OH)($C_{1-4}$alkyl)$_2$, halo, or R³ represents $C_{1-4}$alkyl substituted with one substituent selected from the group consisting of hydroxyl, fluoro, —$NR^{5f}R^{5g}$, Het¹, —O—(C=O)—CH($NH_2$)—$C_{1-4}$alkyl,

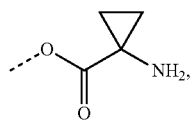

—O—$C_{1-4}$alkyl-OH, and —O—$C_{1-4}$alkyl-$NH_2$;

$R^{5a}$ and $R^{5b}$ each independently are selected from the group consisting of hydrogen, $C_{1-4}$alkyl, —O—$C_{1-4}$alkyl, —S(=O)$_2$—$NH_2$, —S(=O)$_2$—$C_{1-4}$alkyl, —S(=O)$_2$—$C_{3-6}$ cycloalkyl, $C_{1-4}$alkyl substituted with one or more halo atoms, and $C_{1-4}$alkyl substituted with one substituent selected from the group consisting of hydroxyl, —O—$C_{1-4}$alkyl, —S(=O)$_2$—$C_{1-4}$alkyl, —O—$C_{1-4}$alkyl-$NH_2$, —O—$C_{1-4}$alkyl-NH($C_{1-4}$alkyl), —O—$C_{1-4}$alkyl-N($C_{1-4}$alkyl)$_2$, —$NH_2$, —NH($C_{1-4}$alkyl) and —N($C_{1-4}$alkyl)$_2$;

$R^{5c}$ represents hydrogen or $C_{1-4}$alkyl;

$R^{5d}$ and $R^{5e}$ each independently are selected from the group consisting of hydrogen and $C_{1-4}$ alkyl;

$R^{5f}$ and $R^{5g}$ each independently are selected from the group consisting of hydrogen, $C_{1-4}$alkyl, $C_{1-4}$alkyl substituted with one or more halo atoms, and $C_{1-4}$alkyl substituted with one substituent selected from the group consisting of hydroxyl, —O—$C_{1-4}$alkyl, —S(=O)$_2$—$C_{1-4}$alkyl, —$NH_2$, —NH($C_{1-4}$alkyl), and —N($C_{1-4}$alkyl)$_2$;

$R^{4a}$, $R^{4b}$ and $R^{4c}$ each independently are selected from the group consisting of hydrogen, cyano, $C_{1-4}$alkyl, halo, —C(=O)H, —$NR^{6e}R^{6f}$, —O—$C_{1-4}$alkyl, and $C_{1-4}$alkyl substituted with one or more substituents each independently selected from the group consisting of hydroxyl, halo, and —$NR^{6g}R^{6h}$;

$R^{6e}$ and $R^{6f}$ each independently are selected from the group consisting of hydrogen, $C_{1-4}$alkyl, and $C_{1-4}$alkyl substituted with one substituent selected from the group consisting of —$NH_2$, —NH($C_{1-4}$alkyl), and hydroxyl;

$R^{6g}$ and $R^{6h}$ each independently are selected from the group consisting of hydrogen, $C_{1-4}$alkyl, and $C_{1-4}$alkyl substituted with one substituent selected from the group consisting of —$NH_2$, —NH($C_{1-4}$alkyl), and hydroxyl;

Het¹ represents a monocyclic 4-, 5-, 6- or 7-membered saturated or partially saturated heterocyclyl containing at least one heteroatom each independently selected from O, S, S(=O)$_p$ and N; or Het¹ represents a bicyclic 8-, 9- or 10-membered saturated or partially saturated heterocyclyl containing at least one heteroatom each independently selected from O, S, S(=O)$_p$ and N;

each optionally substituted with one or two substituents each independently selected from the group consisting of halo, —$NR^{9a}R^{9b}$ $C_{1-4}$alkyl, —(C=O)—$OR^{5h}$, —S(=O)$_2$—$C_{1-6}$ alkyl, —$C_{1-4}$alkyl-S(=O)$_2$—$C_{1-6}$alkyl, hydroxyl, —O—$C_{1-4}$alkyl, cyano, $C_{1-4}$alkyl substituted with one or more halo atoms, and $C_{1-4}$alkyl substituted with one substituent selected from the group consisting of hydroxyl, —$NH_2$, —NH($C_{1-4}$alkyl) and —N($C_{1-4}$alkyl)$_2$; or two substituents on the same carbon atom of said heterocyclyl are taken together to form together with the common carbon atom to which they are attached Ring A;

$R^{9a}$ and $R^{9b}$ each independently are selected from the group consisting of hydrogen, $C_{1-4}$alkyl, and $C_{1-4}$alkyl substituted with one or more halo atoms;

Het² represents

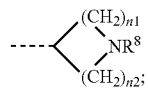

n1 represents 1 or 2;

n2 represents 1 or 2;

R⁸ represents hydrogen, $C_{1-4}$alkyl, or $C_{1-4}$alkyl substituted with one or more halo atoms;

$R^{5h}$ represents hydrogen or $C_{1-4}$alkyl;

Ring A represents cyclobutyl, cyclopentyl, cyclohexyl, or a 4-, 5- or 6-membered saturated heterocyclyl containing at least one heteroatom each independently selected from O, S, S(=O)$_p$ and N; said cyclobutyl, cyclopentyl, cyclohexyl, or 4-, 5- or 6-membered saturated heterocyclyl is optionally substituted with one or two $C_{1-4}$alkyl substituents, with one $C_{1-4}$alkyl and one hydroxy substituent, or with one hydroxy substituent;

p represents 1 or 2;

$R^7$ represents

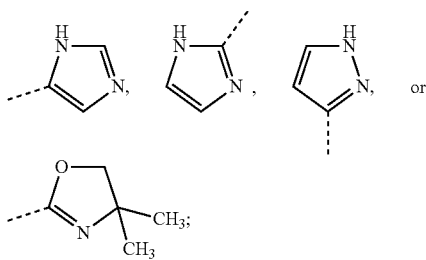

and the N-oxides, the pharmaceutically acceptable addition salts, and the solvates thereof.

In an embodiment, the present invention concerns novel compounds of Formula (I), tautomers and stereoisomeric forms thereof, wherein Y represents $CR^3$ or N;

L represents —CH($C_{1-4}$alkyl)-$CH_2$—, —$CH_2$—CH($C_{1-4}$alkyl)-, —CH($C_{1-4}$alkyl)-CH($C_{1-4}$alkyl)-, —$CHR^{1a}$—X—, or —X—$CHR^{1c}$—;

X represents O, S, or $NR^{1b}$;

$R^{1a}$ represents hydrogen, $C_{1-4}$alkyl, or $C_{1-4}$alkyl substituted with one —OH;

$R^{1c}$ represents hydrogen or $C_{1-4}$alkyl;

$R^{1b}$ represents hydrogen, $C_{1-4}$alkyl, or $C_{1-4}$alkyl substituted with one substituent selected from the group consisting of hydroxyl, —O—$C_{1-4}$alkyl, and —$NR^{6c}R^{6d}$;

or $R^{1b}$ is taken together with $R^{1a}$ or $R^{1c}$ to form —$(CH_2)_3$—;

or $R^{1b}$ is taken together with $R^{1c}$ to form —$(CH_2)_2$— or —$(CH_2)_4$—;

$R^2$ represents

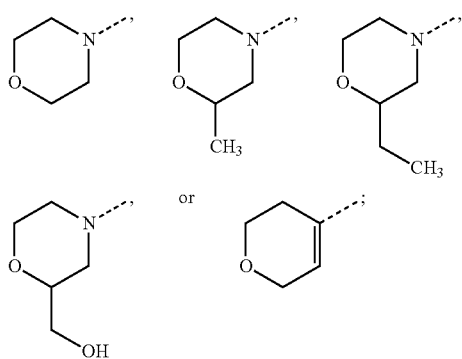

$R^{6c}$ and $R^{6d}$ each independently are selected from the group consisting of hydrogen, $C_{1-4}$alkyl, and $C_{1-4}$alkyl substituted with one substituent selected from the group consisting of hydroxyl, —$NH_2$, —NH($C_{1-4}$alkyl), and —N($C_{1-4}$alkyl)$_2$;

$R^3$ represents $R^7$, —(C=O)H, —(C=O)—$C_{1-4}$alkyl, —(C=O)—$NR^{5a}R^{5b}$, —(C=O)—$OR^{5c}$, —C(=O)-$Het^1$, —C(=O)—NH—$Het^2$, —C(=O)—NH—$C_{1-4}$alkyl-$Het^1$, —C(=O)—N($C_{1-4}$alkyl)-$C_{1-4}$alkyl-$Het^1$, —C(=O)—N($C_{1-4}$alkyl)-$Het^2$, $C_{1-4}$alkyl, —CH=N—OH, —CH(OH)—$CH_2$—$NR^{5d}R^{5e}$, —CH(OH)—$CH_2$—$Het^1$, —CH(OH)—$C_{1-4}$alkyl, —C(OH)($C_{1-4}$alkyl)$_2$, halo, or $R^3$ represents $C_{1-4}$alkyl substituted with one substituent selected from the group consisting of hydroxyl, fluoro, —$NR^{5f}R^{5g}$, $Het^1$, —O—(C=O)—CH($NH_2$)—$C_{1-4}$alkyl,

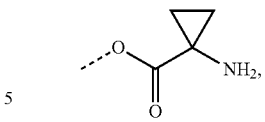

—O—$C_{1-4}$alkyl-OH, and —O—$C_{1-4}$alkyl-$NH_2$;

$R^{5a}$ and $R^{5b}$ each independently are selected from the group consisting of hydrogen, $C_{1-4}$alkyl, —O—$C_{1-4}$alkyl, —S(=O)$_2$—$NH_2$, —S(=O)$_2$—$C_{1-4}$alkyl, —S(=O)$_2$—$C_{3-6}$ cycloalkyl, $C_{1-4}$alkyl substituted with one or more halo atoms, and $C_{1-4}$alkyl substituted with one substituent selected from the group consisting of hydroxyl, —O—$C_{1-4}$alkyl, —S(=O)$_2$—$C_{1-4}$alkyl, —O—$C_{1-4}$alkyl-$NH_2$, —O—$C_{1-4}$alkyl-NH($C_{1-4}$alkyl), —O—$C_{1-4}$alkyl-N($C_{1-4}$alkyl)$_2$, —(C=O)—O—$C_{1-4}$alkyl, —(C=O)—OH, —$NH_2$, —NH($C_{1-4}$alkyl) and —N($C_{1-4}$alkyl)$_2$;

$R^{5c}$ represents hydrogen or $C_{1-4}$alkyl;

$R^{5d}$ and $R^{5e}$ each independently are selected from the group consisting of hydrogen and $C_{1-4}$ alkyl;

$R^{5f}$ and $R^{5g}$ each independently are selected from the group consisting of hydrogen, $C_{1-4}$alkyl, $C_{1-4}$alkyl substituted with one or more halo atoms, and $C_{1-4}$alkyl substituted with one substituent selected from the group consisting of hydroxyl, —O—$C_{1-4}$alkyl, —S(=O)$_2$—$C_{1-4}$alkyl, —$NH_2$, —NH($C_{1-4}$alkyl), and —N($C_{1-4}$alkyl)$_2$; $R^{4a}$, $R^{4b}$ and $R^{4c}$ each independently are selected from the group consisting of hydrogen, cyano, $C_{1-4}$alkyl, halo, —C(=O)H, —$NR^{6e}R^{6f}$, —O—$C_{1-4}$alkyl, and $C_{1-4}$alkyl substituted with one or more substituents each independently selected from the group consisting of hydroxyl, halo, and —$NR^{6g}R^{6h}$;

$R^{6e}$ and $R^{6f}$ each independently are selected from the group consisting of hydrogen, $C_{1-4}$alkyl, and $C_{1-4}$alkyl substituted with one substituent selected from the group consisting of —$NH_2$, —NH($C_{1-4}$alkyl), and hydroxyl;

$R^{6g}$ and $R^{6h}$ each independently are selected from the group consisting of hydrogen, $C_{1-4}$alkyl, and $C_{1-4}$alkyl substituted with one substituent selected from the group consisting of —$NH_2$, —NH($C_{1-4}$alkyl), and hydroxyl;

$Het^1$ represents a monocyclic 4-, 5-, 6- or 7-membered saturated or partially saturated heterocyclyl containing at least one heteroatom each independently selected from O, S, S(=O)$_p$ and N; or $Het^1$ represents a bicyclic 8-, 9- or 10-membered saturated or partially saturated heterocyclyl containing at least one heteroatom each independently selected from O, S, S(=O)$_p$ and N;

each optionally substituted with one or two substituents each independently selected from the group consisting of halo, —$NR^{9a}R^{9b}$ $C_{1-4}$alkyl, —(C=O)—$OR^{5h}$, —S(=O)$_2$—$C_{1-6}$alkyl. —$C_{1-4}$alkyl-S(=O)$_2$—$C_{1-6}$alkyl, hydroxyl, —O—$C_{1-4}$alkyl, cyano, $C_{1-4}$alkyl substituted with one or more halo atoms, and $C_{1-4}$alkyl substituted with one substituent selected from the group consisting of hydroxyl, —$NH_2$, —NH($C_{1-4}$alkyl) and —N($C_{1-4}$alkyl)$_2$; or two substituents on the same carbon atom of said heterocyclyl are taken together to form together with the common carbon atom to which they are attached Ring A;

$R^{9a}$ and $R^{9b}$ each independently are selected from the group consisting of hydrogen, $C_{1-4}$alkyl, and $C_{1-4}$alkyl substituted with one or more halo atoms;

Het² represents

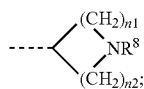

n1 represents 1 or 2;
n2 represents 1 or 2;
R⁸ represents hydrogen, $C_{1-4}$alkyl, or $C_{1-4}$alkyl substituted with one or more halo atoms;
$R^{5h}$ represents hydrogen or $C_{1-4}$alkyl;
Ring A represents cyclobutyl, cyclopentyl, cyclohexyl, or a 4-, 5- or 6-membered saturated heterocyclyl containing at least one heteroatom each independently selected from O, S, S(=O)$_p$ and N; said cyclobutyl, cyclopentyl, cyclohexyl, or 4-, 5- or 6-membered saturated heterocyclyl is optionally substituted with one or two $C_{1-4}$alkyl substituents, with one $C_{1-4}$alkyl and one hydroxy substituent, or with one hydroxy substituent;
p represents 1 or 2;
R⁷ represents

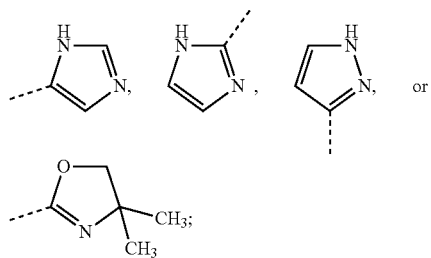

and the N-oxides, the pharmaceutically acceptable addition salts, and the solvates thereof.

In an embodiment, the present invention concerns novel compounds of Formula (I), tautomers and stereoisomeric forms thereof, wherein
Y represents CR³ or N;
L represents —CH($C_{1-4}$alkyl)-CH$_2$—, —CHR$^{1a}$—X—, or —X—CHR$^{1c}$—;
X represents O, S, or NR$^{1b}$;
R$^{1a}$ represents hydrogen, $C_{1-4}$alkyl, or $C_{1-4}$alkyl substituted with one —OH;
R$^{1c}$ represents hydrogen or $C_{1-4}$alkyl;
R$^{1b}$ represents hydrogen or $C_{1-4}$alkyl;
or R$^{1b}$ is taken together with R$^{1a}$ or R$^{1c}$ to form —(CH$_2$)$_3$—;
or R$^{1b}$ is taken together with R$^{1c}$ to form —(CH$_2$)$_2$—;
R² represents

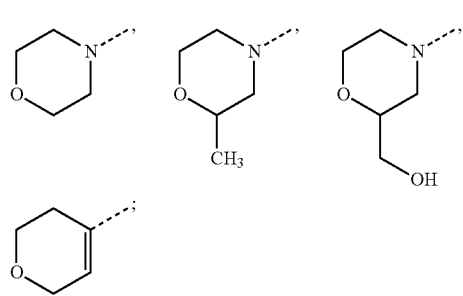

R³ represents R⁷, —(C=O)H, —(C=O)—NR$^{5a}$R$^{5b}$, —(C=O)—OR$^{5c}$, —C(=O)-Het¹, —C(=O)—NH—Het², —C(=O)—NH—$C_{1-4}$alkyl-Het¹, —C(=O)—N($C_{1-4}$alkyl)-Het², $C_{1-4}$alkyl, —CH=N—OH, —CH(OH)—CH$_2$—NR$^{5d}$R$^{5e}$, —CH(OH)—CH$_2$—Het¹, —CH(OH)—$C_{1-4}$alkyl, halo, or R³ represents $C_{1-4}$alkyl substituted with one substituent selected from the group consisting of hydroxyl, fluoro, —NR$^{5f}$R$^{5g}$, Het¹, and —O—$C_{1-4}$alkyl-OH;
R$^{5a}$ and R$^{5b}$ each independently are selected from the group consisting of hydrogen, $C_{1-4}$alkyl, —O—$C_{1-4}$alkyl, —S(=O)$_2$—NH$_2$, —S(=O)$_2$—$C_{3-6}$cycloalkyl, $C_{1-4}$alkyl substituted with one or more halo atoms, and $C_{1-4}$alkyl substituted with one substituent selected from the group consisting of hydroxyl, —O—$C_{1-4}$alkyl, —O—$C_{1-4}$alkyl-NH$_2$, —O—$C_{1-4}$alkyl-NH($C_{1-4}$alkyl), —(C=O)—O—$C_{1-4}$alkyl, —(C=O)—OH, —NH($C_{1-4}$alkyl) and —N($C_{1-4}$alkyl)$_2$;
R$^{5c}$ represents hydrogen or $C_{1-4}$alkyl;
R$^{5d}$ and R$^{5e}$ each independently are selected from the group consisting of hydrogen and $C_{1-4}$ alkyl;
R$^{5f}$ and R$^{5g}$ each independently are selected from the group consisting of hydrogen, $C_{1-4}$alkyl, $C_{1-4}$alkyl substituted with one or more halo atoms, and $C_{1-4}$alkyl substituted with one substituent selected from the group consisting of hydroxyl, —O—$C_{1-4}$alkyl, and —S(=O)$_2$—$C_{1-4}$alkyl;
R$^{4a}$, R$^{4b}$ and R$^{4c}$ each independently are selected from the group consisting of hydrogen, cyano, $C_{1-4}$alkyl, halo, —C(=O)H, —NR$^{6e}$R$^{6f}$, —O—$C_{1-4}$alkyl, and $C_{1-4}$alkyl substituted with one or more substituents each independently selected from the group consisting of hydroxyl, halo, and —NR$^{6g}$R$^{6h}$;
R$^{6e}$ and R$^{6f}$ each independently are selected from the group consisting of hydrogen, $C_{1-4}$alkyl, and $C_{1-4}$alkyl substituted with one hydroxyl substituent;
Het¹ represents a monocyclic 4-, 5-, 6- or 7-membered saturated heterocyclyl containing at least one heteroatom each independently selected from O, S(=O)$_p$ and N;
or Het¹ represents a bicyclic 9-membered saturated or partially saturated heterocyclyl containing at least one N-atom;
each optionally substituted with one or two substituents each independently selected from the group consisting of —NR$^{9a}$R$^{9b}$ 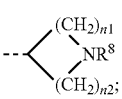 $C_{1-4}$alkyl, —(C=O)—OR$^{5h}$, hydroxyl, —O—$C_{1-4}$alkyl, $C_{1-4}$alkyl substituted with one or more halo atoms, and $C_{1-4}$alkyl substituted with one substituent selected from the group consisting of hydroxyl and —NH($C_{1-4}$alkyl); or two substituents on the same carbon atom of said heterocyclyl are taken together to form together with the common carbon atom to which they are attached Ring A;
R$^{9a}$ and R$^{9b}$ each independently are selected from the group consisting of hydrogen, $C_{1-4}$alkyl, and $C_{1-4}$alkyl substituted with one or more halo atoms;
Het² represents

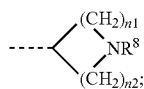

n1 represents 1;
n2 represents 1 or 2;
R⁸ represents hydrogen, or $C_{1-4}$alkyl substituted with one or more halo atoms;
R$^{5h}$ represents hydrogen or $C_{1-4}$alkyl;
Ring A represents a 4-membered saturated heterocyclyl containing at least one heteroatom each independently selected from O, and S(=O)$_p$;
p represents 2;

R[7] represents

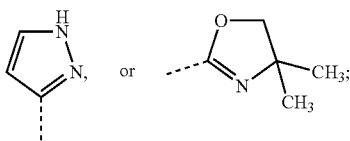

and the N-oxides, the pharmaceutically acceptable addition salts, and the solvates thereof.

In an embodiment, the present invention concerns novel compounds of Formula (I), tautomers and stereoisomeric forms thereof, wherein
Y represents $CR^3$ or N;
L represents —$CHR^{1a}$—X—, or —X—$CHR^{1c}$—;
X represents O, S, or $NR^{1b}$;
$R^{1a}$ represents $C_{1-4}$alkyl;
$R^{1c}$ represents hydrogen or $C_{1-4}$alkyl;
$R^{1b}$ represents hydrogen or $C_{1-4}$alkyl;
or $R^{1b}$ is taken together with $R^{1a}$ or $R^{1c}$ to form —$(CH_2)_3$—;
$R^2$ represents

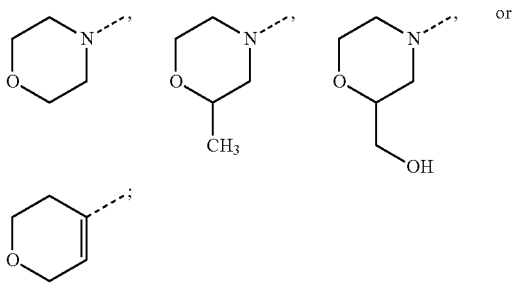

$R^3$ represents $R^7$, —(C=O)H, —(C=O)—$NR^{5a}R^{5b}$, —(C=O)—$OR^{5c}$, —C(=O)—$Het^1$, —C(=O)—NH—$Het^2$, $C_{1-4}$alkyl, —CH=N—OH, —CH(OH)—$CH_2$—$NR^{5d}R^{5e}$, —CH(OH)—$CH_2$—$Het^1$, —CH(OH)—$C_{1-4}$alkyl, halo, or $R^3$ represents $C_{1-4}$alkyl substituted with one substituent selected from the group consisting of hydroxyl, —$NR^{5f}R^{5g}$, $Het^1$, and —O—$C_{1-4}$alkyl-OH;
$R^{5a}$ and $R^{5b}$ each independently are selected from the group consisting of hydrogen, $C_{1-4}$alkyl, —O—$C_{1-4}$alkyl, —$S(=O)_2$—$NH_2$, —$S(=O)_2$—$C_{3-6}$cycloalkyl,
$C_{1-4}$alkyl substituted with one or more halo atoms, and
$C_{1-4}$alkyl substituted with one substituent selected from the group consisting of hydroxyl, —O—$C_{1-4}$alkyl, —O—$C_{1-4}$alkyl-$NH_2$, —O—$C_{1-4}$alkyl-$NH(C_{1-4}$alkyl), —$NH(C_{1-4}$alkyl) and —$N(C_{1-4}$alkyl)$_2$;
$R^{5c}$ represents hydrogen or $C_{1-4}$alkyl;
$R^{5d}$ and $R^{5e}$ each independently are selected from the group consisting of hydrogen and $C_{1-4}$alkyl;
$R^{5f}$ and $R^{5g}$ each independently are selected from the group consisting of hydrogen, $C_{1-4}$alkyl, $C_{1-4}$alkyl substituted with one or more halo atoms, and
$C_{1-4}$alkyl substituted with one substituent selected from the group consisting of hydroxyl, —O—$C_{1-4}$alkyl, and —$S(=O)_2$—$C_{1-4}$alkyl;
$R^{4a}$, $R^{4b}$ and $R^{4c}$ each independently are selected from the group consisting of hydrogen, cyano, $C_{1-4}$alkyl, halo, —C(=O)H, —$NR^{6e}R^{6f}$, —O—$C_{1-4}$alkyl, and $C_{1-4}$alkyl substituted with one or more substituents each independently selected from the group consisting of hydroxyl, halo, and —$NR^{6g}R^{6h}$;

$R^{6e}$ and $R^{6f}$ each independently are selected from the group consisting of hydrogen, and $C_{1-4}$alkyl substituted with one —$NH_2$ substituent;
$R^{6g}$ and $R^{6h}$ each independently are selected from the group consisting of hydrogen, $C_{1-4}$alkyl, and $C_{1-4}$alkyl substituted with one hydroxyl substituent;
$Het^1$ represents a monocyclic 4-, 5-, or 6-membered saturated heterocyclyl containing at least one heteroatom each independently selected from O, $S(=O)_p$ and N; or $Het^1$ represents a bicyclic 9-membered partially saturated heterocyclyl containing at least one N-atom;
each optionally substituted with one or two substituents each independently selected from the group consisting of —$NR^{9a}R^{9b}$, $C_{1-4}$alkyl, —(C=O)—$OR^{5h}$, hydroxyl, —O—$C_{1-4}$alkyl, $C_{1-4}$alkyl substituted with one or more halo atoms, and $C_{1-4}$alkyl substituted with one substituent selected from the group consisting of hydroxyl, and —NH($C_{1-4}$alkyl); or two substituents on the same carbon atom of said heterocyclyl are taken together to form together with the common carbon atom to which they are attached Ring A;
$R^{9a}$ and $R^{9b}$ each independently are selected from the group consisting of hydrogen, and $C_{1-4}$alkyl substituted with one or more halo atoms;
$Het^2$ represents

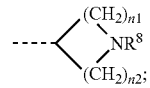

n1 represents 1;
n2 represents 1;
$R^8$ represents $C_{1-4}$alkyl substituted with one or more halo atoms;
$R^{5h}$ represents hydrogen or $C_{1-4}$alkyl;
Ring A represents a 4-membered saturated heterocyclyl containing at least one heteroatom each independently selected from O and $S(=O)_p$;
p represents 2;
$R^7$ represents

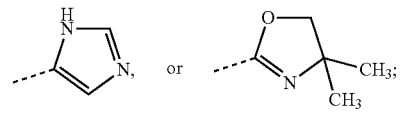

and the N-oxides, the pharmaceutically acceptable addition salts, and the solvates thereof.

Another embodiment of the present invention relates to those compounds of Formula (I) and the N-oxides, the pharmaceutically acceptable addition salts, and the solvates thereof, or any subgroup thereof as mentioned in any of the other embodiments wherein one or more of the following restrictions apply:
(i) L represents —$CHR^{1a}$—X—, or —X—$CHR^{1c}$—;
(ii) $R^{1a}$ represents $C_{1-4}$alkyl;
$R^{1c}$ represents hydrogen or $C_{1-4}$alkyl;
$R^{1b}$ represents hydrogen or $C_{1-4}$alkyl;
or $R^{1b}$ is taken together with $R^{1a}$ or $R^{1c}$ to form —$(CH_2)_3$—;

(iii) R² represents

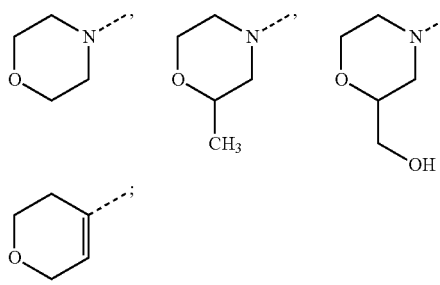

(iv) R³ represents R⁷, —(C=O)H, —(C=O)—NR⁵ᵃR⁵ᵇ, —(C=O)—OR⁵ᶜ, —C(=O)-Het¹, —C(=O)—NH-Het², $C_{1-4}$alkyl, —CH=N—OH, —CH(OH)—CH₂—NR⁵ᵈR⁵ᵉ, —CH(OH)—CH₂—Het¹, —CH(OH)—$C_{1-4}$alkyl, halo, or R³ represents $C_{1-4}$alkyl substituted with one substituent selected from the group consisting of hydroxyl, —NR⁵ᶠR⁵ᵍ, Het¹, and —O—$C_{1-4}$alkyl-OH;

(v) R⁵ᵃ and R⁵ᵇ each independently are selected from the group consisting of hydrogen, $C_{1-4}$alkyl, —O—$C_{1-4}$alkyl, —S(=O)₂—NH₂, —S(=O)₂—$C_{3-6}$cycloalkyl, $C_{1-4}$alkyl substituted with one or more halo atoms, and $C_{1-4}$alkyl substituted with one substituent selected from the group consisting of hydroxyl, —O—$C_{1-4}$alkyl, —O—$C_{1-4}$alkyl-NH₂, —O—$C_{1-4}$alkyl-NH($C_{1-4}$alkyl), —NH($C_{1-4}$alkyl) and —N($C_{1-4}$alkyl)₂;

(vi) R⁵ᶠ and R⁵ᵍ each independently are selected from the group consisting of hydrogen, $C_{1-4}$alkyl, $C_{1-4}$alkyl substituted with one or more halo atoms, and $C_{1-4}$alkyl substituted with one substituent selected from the group consisting of hydroxyl, —O—$C_{1-4}$alkyl, and —S(=O)₂—$C_{1-4}$alkyl;

(vii) R⁶ᵉ and R⁶ᶠ each independently are selected from the group consisting of hydrogen, and $C_{1-4}$alkyl substituted with one —NH₂ substituent;

(viii) R⁶ᵍ and R⁶ʰ each independently are selected from the group consisting of hydrogen, $C_{1-4}$alkyl, and $C_{1-4}$alkyl substituted with one hydroxyl substituent;

(ix) Het¹ represents a monocyclic 4-, 5-, or 6-membered saturated heterocyclyl containing at least one heteroatom each independently selected from O, S(=O)ₚ and N; or Het¹ represents a bicyclic 9-membered partially saturated heterocyclyl containing at least one N-atom; each optionally substituted with one or two substituents each independently selected from the group consisting of —NR⁹ᵃR⁹ᵇ, $C_{1-4}$alkyl, —(C=O)—OR⁵ʰ, hydroxyl, —O—$C_{1-4}$alkyl, $C_{1-4}$alkyd substituted with one or more halo atoms, and $C_{1-4}$alkyl substituted with one substituent selected from the group consisting of hydroxyl, and —NH($C_{1-4}$ alkyl); or two substituents on the same carbon atom of said heterocyclyl are taken together to form together with the common carbon atom to which they are attached Ring A;

(x) R⁹ᵃ and R⁹ᵇ each independently are selected from the group consisting of hydrogen, and $C_{1-4}$alkyl substituted with one or more halo atoms;

(xi) n1 represents 1;
n2 represents 1;

(xii) R⁸ represents $C_{1-4}$ alkyl substituted with one or more halo atoms;

(xiii) Ring A represents a 4-membered saturated heterocyclyl containing at least one heteroatom each independently selected from O and S(=O)ₚ;

(xiv) p represents 2;

(xv) R⁷ represents

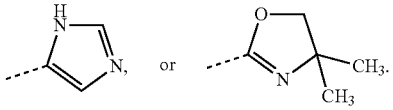

In an embodiment, the present invention concerns novel compounds of Formula (I), tautomers and stereoisomeric forms thereof, wherein
Y represents CR³ or N;
L represents —CH($C_{1-4}$alkyl)-CH₂—, —CH₂—CH($C_{1-4}$alkyl)-, —CH($C_{1-4}$alkyl)-CH($C_{1-4}$alkyl)-, —CHR¹ᵃ—X—, or —X—CHR¹ᶜ—;
X represents O, S, or NR¹ᵇ;
R¹ᵃ represents $C_{1-4}$alkyl;
R¹ᶜ represents hydrogen or $C_{1-4}$alkyl;
R¹ᵇ represents hydrogen, $C_{1-4}$alkyl, —CH₂—C(=O)—NR⁶ᵃR⁶ᵇ, or $C_{1-4}$alkyl substituted with one substituent selected from the group consisting of hydroxyl, —O—$C_{1-4}$alkyl, and —NR⁶ᶜR⁶ᵈ;
or R¹ᵇ is taken together with R¹ᵃ or R¹ᶜ to form —(CH₂)₃—;
R² represents

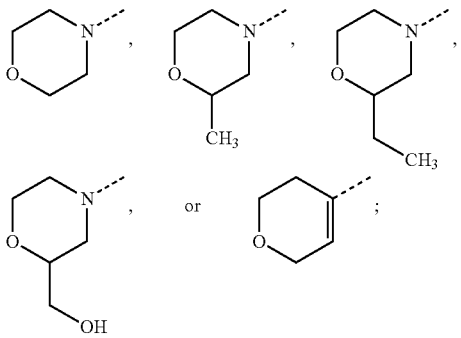

R⁶ᵃ and R⁶ᵇ each independently are selected from the group consisting of hydrogen and $C_{1-4}$ alkyl;
R⁶ᶜ and R⁶ᵈ each independently are selected from the group consisting of hydrogen, $C_{1-4}$alkyl, and $C_{1-4}$alkyl substituted with one substituent selected from the group consisting of hydroxyl, —NH₂, —NH($C_{1-4}$alkyl), and —N($C_{1-4}$alkyl)₂;
R³ represents R⁷, —(C=O)H, —(C=O)—$C_{1-4}$alkyl, —(C=O)—NR⁵ᵃR⁵ᵇ, —(C=O)—OR⁵ᶜ, —C(=O)-Het¹, —C(=O)—NH—Het², $C_{1-4}$alkyl, —CH=N—OH, —CH(OH)—CH₂—NR⁵ᵈR⁵ᵉ, —CH(OH)—CH₂—Het¹, —CH(OH)—$C_{1-4}$alkyl, —C(OH)($C_{1-4}$alkyl)₂, halo, or R³ represents $C_{1-4}$alkyl substituted with one substituent selected from the group consisting of hydroxyl, fluoro, —NR⁵ᶠR⁵ᵍ, Het¹, —O—(C=O)—CH(NH₂)—$C_{1-4}$alkyl, —O—(C=O)—CH(NH₂)—$C_{1-4}$alkyl-Ar,

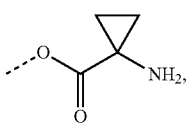

—O—$C_{1-4}$alkyl-OH, and —O—$C_{1-4}$alkyl-NH₂;
R⁵ᵃ and R⁵ᵇ each independently are selected from the group consisting of hydrogen, $C_{1-4}$alkyl, —O—$C_{1-4}$alkyl, —S(=O)₂—NH₂, —S(=O)₂—$C_{1-4}$alkyl, —S(=O)₂—$C_{3-6}$ cycloalkyl, C$_{1-4}$alkyl substituted with one or more halo atoms, and C$_{1-4}$alkyl substituted with one substituent selected from the group consisting of hydroxyl, —O—C$_{1-4}$alkyl, —S(=O)$_2$—C$_{1-4}$alkyl, —O—C$_{1-4}$alkyl-NH$_2$, —O—C$_{1-4}$alkyl-NH(C$_{1-4}$alkyl), —O—C$_{1-4}$alkyl-N(C$_{1-4}$alkyl)$_2$, —NH$_2$, —NH(C$_{1-4}$alkyl) and —N(C$_{1-4}$alkyl)$_2$; R$^{5c}$ represents hydrogen or C$_{1-4}$alkyl;

R$^{5d}$ and R$^{5e}$ each independently are selected from the group consisting of hydrogen and C$_{1-4}$ alkyl;

R$^{5f}$ and R$^{5g}$ each independently are selected from the group consisting of hydrogen, C$_{1-4}$alkyl, C$_{1-4}$alkyl substituted with one or more halo atoms, and C$_{1-4}$alkyl substituted with one substituent selected from the group consisting of hydroxyl, —O—C$_{1-4}$alkyl, —S(=O)$_2$—C$_{1-4}$alkyl, —NH$_2$, —NH(C$_{1-4}$alkyl), and —N(C$_{1-4}$alkyl)$_2$;

R$^{4a}$, R$^{4b}$ and R$^{4c}$ each independently are selected from the group consisting of hydrogen, cyano, C$_{1-4}$alkyl, halo, —C(=O)H, —NR$^{6e}$R$^{6f}$, —O—C$_{1-4}$alkyl, and C$_{1-4}$alkyl substituted with one or more substituents each independently selected from the group consisting of hydroxyl, halo, and —NR$^{6g}$R$^{6h}$;

R$^{6e}$ and R$^{6f}$ each independently are selected from the group consisting of hydrogen, C$_{1-4}$alkyl, and C$_{1-4}$alkyl substituted with one substituent selected from the group consisting of —NH$_2$, —NH(C$_{1-4}$alkyl), and hydroxyl;

R$^{6g}$ and R$^{6h}$ each independently are selected from the group consisting of hydrogen, C$_{1-4}$alkyl, and C$_{1-4}$alkyl substituted with one substituent selected from the group consisting of —NH$_2$, —NH(C$_{1-4}$alkyl), and hydroxyl;

Het$^1$ represents a monocyclic 4-, 5-, 6- or 7-membered saturated or partially saturated heterocyclyl containing at least one heteroatom each independently selected from O, S, S(=O)$_p$ and N;

each optionally substituted with one or two substituents each independently selected from the group consisting of halo, —NR$^{9a}$R$^{9b}$, C$_{1-4}$alkyl, —(C=O)—OR$^{5h}$, —S(=O)$_2$—C$_{1-6}$alkyl, —C$_{1-4}$alkyl-S(=O)$_2$—C$_{1-6}$alkyl, hydroxyl, —O—C$_{1-4}$alkyl, cyano, C$_{1-4}$alkyl substituted with one or more halo atoms, and C$_{1-4}$alkyl substituted with one substituent selected from the group consisting of hydroxyl, —NH$_2$, —NH(C$_{1-4}$alkyl) and —N(C$_{1-4}$alkyl)$_2$; or two substituents on the same carbon atom of said heterocyclyl are taken together to form together with the common carbon atom to which they are attached Ring A;

R$^{9a}$ and R$^{9b}$ each independently are selected from the group consisting of hydrogen, C$_{1-4}$alkyl, and C$_{1-4}$alkyl substituted with one or more halo atoms;

Het$^2$ represents

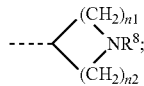

n1 represents 1 or 2;
n2 represents 1 or 2;
R$^8$ represents hydrogen, C$_{1-4}$alkyl, or C$_{1-4}$alkyl substituted with one or more halo atoms; Ring A represents cyclobutyl, cyclopentyl, cyclohexyl, or a 4-, 5- or 6-membered saturated heterocyclyl containing at least one heteroatom each independently selected from O, S, S(=O)$_p$ and N; said cyclobutyl, cyclopentyl, cyclohexyl, or 4-, 5- or 6-membered saturated heterocyclyl is optionally substituted with one or two C$_{1-4}$alkyl substituents, with one C$_{1-4}$alkyl and one hydroxy substituent, or with one hydroxy substituent;

p represents 1 or 2;
Ar represents phenyl optionally substituted with one hydroxyl;
R$^7$ represents

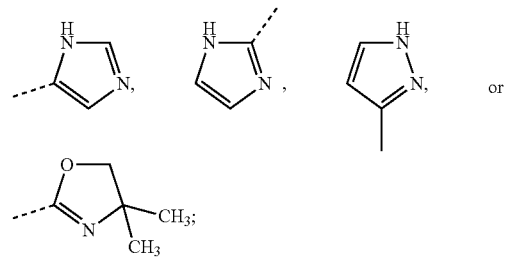

and the N-oxides, the pharmaceutically acceptable addition salts, and the solvates thereof.

In an embodiment, the present invention concerns novel compounds of Formula (I), tautomers and stereoisomeric forms thereof, wherein Y represents CR$^3$;
L represents —CHR$^{1a}$—X— or —X—CHR$^{1c}$—;
X represents O, S, or NR$^{1b}$;
R$^{1a}$ represents hydrogen or C$_{1-4}$alkyl; in particular C$_{1-4}$alkyl;
R$^{1c}$ represents hydrogen or C$_{1-4}$alkyl;
R$^{1b}$ represents hydrogen or C$_{1-4}$alkyl;
or R$^{1b}$ is taken together with R$^{1c}$ to form —(CH$_2$)$_3$—;
R$^2$ represents

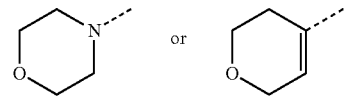

R$^3$ represents —(C=O)H, —(C=O)—C$_{1-4}$alkyl, —(C=O)—NR$^{5a}$R$^{5b}$, —(C=O)—OR$^{5c}$, —C(=O)-Het$^1$, —C(=O)—NH—Het$^2$ or R$^3$ represents C$_{1-4}$alkyl substituted with one —NR$^{5f}$R$^{5g}$ substituent;

R$^{5a}$ and R$^{5b}$ each independently are selected from the group consisting of hydrogen, C$_{1-4}$alkyl, —O—C$_{1-4}$alkyl, —S(=O)$_2$—NH$_2$, —S(=O)$_2$—C$_{1-4}$alkyl, —S(=O)$_2$—C$_{3-6}$ cycloalkyl, C$_{1-4}$alkyl substituted with one or more halo atoms, and C$_{1-4}$alkyl substituted with one substituent selected from the group consisting of hydroxyl, —O—C$_{1-4}$alkyl, —S(=O)$_2$—C$_{1-4}$alkyl, —O—C$_{1-4}$alkyl-NH$_2$, —O—C$_{1-4}$alkyl-NH(C$_{1-4}$alkyl), —O—C$_{1-4}$alkyl-N(C$_{1-4}$alkyl)$_2$, —NH$_2$, —NH(C$_{1-4}$alkyl) and —N(C$_{1-4}$alkyl)$_2$;

R$^{5c}$ represents hydrogen or C$_{1-4}$alkyl;
R$^{5f}$ and R$^{5g}$ each independently are selected from the group consisting of hydrogen, C$_{1-4}$alkyl, and C$_{1-4}$alkyl substituted with one hydroxyl substituent;

R$^{4a}$, R$^{4b}$ and R$^{4c}$ each independently are selected from the group consisting of hydrogen, cyano, C$_{1-4}$alkyl, halo, —C(=O)H, —NR$^{6e}$R$^{6f}$, —O—C$_{1-4}$alkyl, and C$_{1-4}$alkyl substituted with one or more substituents each independently selected from the group consisting of hydroxyl, halo, and —NR$^{6g}$R$^{6h}$;

R$^{6e}$ and R$^{6f}$ each independently are selected from the group consisting of hydrogen, C$_{1-4}$alkyl, and C$_{1-4}$alkyl substituted with one substituent selected from the group consisting of —NH$_2$, —NH(C$_{1-4}$alkyl), and hydroxyl;

$R^{6g}$ and $R^{6h}$ each independently are selected from the group consisting of hydrogen, $C_{1-4}$alkyl, and $C_{1-4}$alkyl substituted with one substituent selected from the group consisting of —$NH_2$, —$NH(C_{1-4}$alkyl), and hydroxyl;

$Het^1$ represents a monocyclic 4-, 5-, 6- or 7-membered saturated or partially saturated heterocyclyl containing at least one heteroatom each independently selected from O, S, $S(=O)_p$ and N;

each optionally substituted with one or two substituents each independently selected from the group consisting of halo, —$NR^{9a}R^{9b}$ $C_{1-4}$alkyl, —(C=O)—$OR^{5h}$, —S(=O)$_2$—$C_{1-6}$ alkyl, —$C_{1-4}$alkyl-S(=O)$_2$—$C_{1-6}$alkyl, hydroxyl, —O—$C_{1-4}$alkyl, cyano, $C_{1-4}$alkyl substituted with one or more halo atoms, and $C_{1-4}$alkyl substituted with one substituent selected from the group consisting of hydroxyl, —$NH_2$, —$NH(C_{1-4}$alkyl) and —$N(C_{1-4}$alkyl)$_2$; or two substituents on the same carbon atom of said heterocyclyl are taken together to form together with the common carbon atom to which they are attached Ring A;

$R^{9a}$ and $R^{9b}$ each independently are selected from the group consisting of hydrogen, $C_{1-4}$alkyl, and $C_{1-4}$alkyl substituted with one or more halo atoms;

$Het^2$ represents

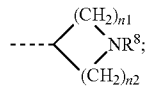

n1 represents 1 or 2;
n2 represents 1 or 2;
$R^8$ represents hydrogen, $C_{1-4}$alkyl, or $C_{1-4}$alkyl substituted with one or more halo atoms;
$R^{5h}$ represents hydrogen or $C_{1-4}$alkyl;

Ring A represents cyclobutyl, cyclopentyl, cyclohexyl, or a 4-, 5- or 6-membered saturated heterocyclyl containing at least one heteroatom each independently selected from O, S, $S(=O)_p$ and N; said cyclobutyl, cyclopentyl, cyclohexyl, or 4-, 5- or 6-membered saturated heterocyclyl is optionally substituted with one or two $C_{1-4}$alkyl substituents, with one $C_{1-4}$alkyl and one hydroxy substituent, or with one hydroxy substituent;

p represents 1 or 2;
and the N-oxides, the pharmaceutically acceptable addition salts, and the solvates thereof.

In an embodiment, the present invention concerns novel compounds of Formula (I), tautomers and stereoisomeric forms thereof, wherein
Y represents $CR^3$;
L represents —$CHR^{1a}$—X— or —X—$CHR^{1c}$—;
X represents $NR^{1b}$;
$R^{1a}$ represents hydrogen or $C_{1-4}$alkyl; in particular $C_{1-4}$alkyl;
$R^{1c}$ represents hydrogen or $C_{1-4}$alkyl;
$R^{1b}$ represents hydrogen;
or $R^{1b}$ is taken together with $R^{1c}$ to form —(CH$_2$)$_3$—;
$R^2$ represents

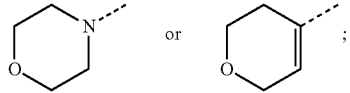

$R^3$ represents —(C=O)—$NR^{5a}R^{5b}$, —C(=O)—$Het^1$, or $R^3$ represents $C_{1-4}$alkyl substituted with one —$NR^{5f}R^{5g}$ substituent;

$R^{5a}$ and $R^{5b}$ each independently are selected from the group consisting of hydrogen, $C_{1-4}$alkyl, and $C_{1-4}$alkyl substituted with one substituent selected from the group consisting of hydroxyl, —$NH_2$, —$NH(C_{1-4}$alkyl) and —$N(C_{1-4}$alkyl)$_2$;

$R^{5f}$ and $R^{5g}$ each independently are selected from the group consisting of hydrogen, $C_{1-4}$alkyl, and $C_{1-4}$alkyl substituted with one hydroxyl substituent;

$R^{4a}$, $R^{4b}$ and $R^{4c}$ each independently are selected from the group consisting of hydrogen, cyano, $C_{1-4}$alkyl, and halo;

$Het^1$ represents a monocyclic 4-, 5-, 6- or 7-membered saturated or partially saturated heterocyclyl containing at least one heteroatom each independently selected from O, S, $S(=O)_p$ and N;

each optionally substituted with one or two substituents each independently selected from the group consisting of $C_{1-4}$alkyl;

and the N-oxides, the pharmaceutically acceptable addition salts, and the solvates thereof.

In an embodiment, the present invention concerns novel compounds of Formula (I), tautomers and stereoisomeric forms thereof, wherein
Y represents $CR^3$;
L represents —$CHR^{1a}$—X—;
X represents O, S, or $NR^{1b}$;
$R^{1a}$ represents $C_{1-4}$alkyl;
$R^{1b}$ represents hydrogen or $C_{1-4}$alkyl;
$R^2$ represents

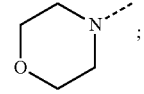

$R^3$ represents —(C=O)H, —(C=O)—$C_{1-4}$alkyl, —(C=O)—$NR^{5a}R^{5b}$, —(C=O)—$OR^{5c}$, —C(=O)-$Het^1$, —C(=O)—NH—$Het^2$;

$R^{5a}$ and $R^{5b}$ each independently are selected from the group consisting of hydrogen, $C_{1-4}$alkyl, —O—$C_{1-4}$alkyl, —S(=O)$_2$—$NH_2$, —S(=O)$_2$—$C_{1-4}$alkyl, —S(=O)$_2$—$C_{3-6}$ cycloalkyl,
$C_{1-4}$alkyl substituted with one or more halo atoms, and
$C_{1-4}$alkyl substituted with one substituent selected from the group consisting of hydroxyl, —O—$C_{1-4}$alkyl, —S(=O)$_2$—$C_{1-4}$alkyl, —O—$C_{1-4}$alkyl-$NH_2$, —O—$C_{1-4}$alkyl-$NH(C_{1-4}$alkyl), —O—$C_{1-4}$alkyl-$N(C_{1-4}$alkyl)$_2$, —$NH_2$, —$NH(C_{1-4}$alkyl) and —$N(C_{1-4}$alkyl)$_2$;

$R^{5c}$ represents hydrogen or $C_{1-4}$alkyl;
$R^{4a}$, $R^{4b}$ and $R^{4c}$ each independently are selected from the group consisting of hydrogen, cyano, $C_{1-4}$alkyl, halo, —C(=O)H, —$NR^{6e}R^{6i}$, —O—$C_{1-4}$alkyl, and $C_{1-4}$alkyl substituted with one or more substituents each independently selected from the group consisting of hydroxyl, halo, and —$NR^{6g}R^{6h}$;

$R^{6e}$ and $R^{6f}$ each independently are selected from the group consisting of hydrogen, $C_{1-4}$alkyl, and $C_{1-4}$alkyl substituted with one substituent selected from the group consisting of —$NH_2$, —$NH(C_{1-4}$alkyl), and hydroxyl;

$R^{6g}$ and $R^{6h}$ each independently are selected from the group consisting of hydrogen, $C_{1-4}$alkyl, and $C_{1-4}$alkyl substituted with one substituent selected from the group consisting of —$NH_2$, —$NH(C_{1-4}$alkyl), and hydroxyl;

Het¹ represents a monocyclic 4-, 5-, 6- or 7-membered saturated or partially saturated heterocyclyl containing at least one heteroatom each independently selected from O, S, S(=O)$_p$ and N;

each optionally substituted with one or two substituents each independently selected from the group consisting of halo, —NR$^{9a}$R$^{9b}$ C$_{1-4}$alkyl, —(C=O)—OR$^{5h}$, —S(=O)$_2$—C$_{1-6}$alkyl, —C$_{1-4}$alkyl-S(=O)$_2$—C$_{1-6}$alkyl, hydroxyl, —O—C$_{1-4}$alkyl, cyano, C$_{1-4}$alkyl substituted with one or more halo atoms, and C$_{1-4}$alkyl substituted with one substituent selected from the group consisting of hydroxyl, —NH$_2$, —NH(C$_{1-4}$alkyl) and —N(C$_{1-4}$alkyl)$_2$; or two substituents on the same carbon atom of said heterocyclyl are taken together to form together with the common carbon atom to which they are attached Ring A;

R$^{9a}$ and R$^{9b}$ each independently are selected from the group consisting of hydrogen, C$_{1-4}$alkyl, and C$_{1-4}$alkyl substituted with one or more halo atoms;

Het² represents

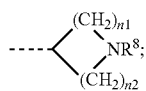

n1 represents 1 or 2;
n2 represents 1 or 2;
R$^8$ represents hydrogen, C$_{1-4}$alkyl, or C$_{1-4}$alkyl substituted with one or more halo atoms;
R$^{5h}$ represents hydrogen or C$_{1-4}$alkyl;
Ring A represents cyclobutyl, cyclopentyl, cyclohexyl, or a 4-, 5- or 6-membered saturated heterocyclyl containing at least one heteroatom each independently selected from O, S, S(=O)$_p$ and N; said cyclobutyl, cyclopentyl, cyclohexyl, or 4-, 5- or 6-membered saturated heterocyclyl is optionally substituted with one or two C$_{1-4}$alkyl substituents, with one C$_{1-4}$alkyl and one hydroxy substituent, or with one hydroxy substituent;
p represents 1 or 2;
and the N-oxides, the pharmaceutically acceptable addition salts, and the solvates thereof.

In an embodiment, the present invention concerns novel compounds of Formula (I), tautomers and stereoisomeric forms thereof, wherein
Y represents CR³;
L represents —CHR$^{1a}$—X—;
X represents O, S, or NR$^{1b}$;
R$^{1a}$ represents C$_{1-4}$alkyl;
R$^{1b}$ represents hydrogen or C$_{1-4}$alkyl;
R² represents

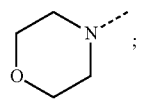

R³ represents —(C=O)H, —(C=O)—C$_{1-4}$alkyl, —(C=O)—NR$^{5a}$R$^{5b}$;
R$^{5a}$ and R$^{5b}$ each independently are selected from the group consisting of hydrogen, C$_{1-4}$alkyl, —O—C$_{1-4}$alkyl, —S(=O)$_2$—NH$_2$, —S(=O)$_2$—C$_{1-4}$alkyl, —S(=O)$_2$—C$_{3-6}$cycloalkyl,
C$_{1-4}$alkyl substituted with one or more halo atoms, and
C$_{1-4}$alkyl substituted with one substituent selected from the group consisting of hydroxyl, —O—C$_{1-4}$alkyl, —S(=O)$_2$—C$_{1-4}$alkyl, —O—C$_{1-4}$alkyl-NH$_2$, —O—C$_{1-4}$alkyl-NH(C$_{1-4}$alkyl), —O—C$_{1-4}$alkyl-N(C$_{1-4}$alkyl)$_2$, —NH$_2$, —NH(C$_{1-4}$alkyl) and —N(C$_{1-4}$alkyl)$_2$;
R$^{4a}$, R$^{4b}$ and R$^{4c}$ each independently are selected from the group consisting of hydrogen, cyano, C$_{1-4}$alkyl, halo, and —O—C$_{1-4}$alkyl;
and the N-oxides, the pharmaceutically acceptable addition salts, and the solvates thereof.

In an embodiment, the present invention concerns novel compounds of Formula (I), tautomers and stereoisomeric forms thereof, wherein
Y represents CR³;
L represents —CHR$^{1a}$—X—;
X represents NR$^{1b}$;
R$^{1a}$ represents C$_{1-4}$alkyl;
R$^{1b}$ represents hydrogen or C$_{1-4}$alkyl; in particular hydrogen;
R² represents

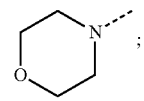

R³ represents —(C=O)—NR$^{5a}$R$^{5b}$;
R$^{5a}$ and R$^{5b}$ each independently are selected from the group consisting of hydrogen, C$_{1-4}$alkyl, C$_{1-4}$alkyl substituted with one or more halo atoms, and
C$_{1-4}$alkyl substituted with one substituent selected from the group consisting of hydroxyl and —O—C$_{1-4}$alkyl;
R$^{4a}$, R$^{4b}$ and R$^{4c}$ each independently are selected from the group consisting of hydrogen and halo;
and the N-oxides, the pharmaceutically acceptable addition salts, and the solvates thereof.

In an embodiment, the present invention relates to those compounds of Formula (I) and the N-oxides, the pharmaceutically acceptable addition salts, and the solvates thereof, or any subgroup thereof as mentioned in any of the other embodiments, wherein
R$^{1b}$ represents hydrogen, C$_{1-4}$alkyl, —CH$_2$—C(=O)—NR$^{6a}$R$^{6b}$, or C$_{1-4}$alkyl substituted with one substituent selected from the group consisting of hydroxyl, —O—C$_{1-4}$alkyl, and —NR$^{6c}$R$^{6d}$;
or R$^{1b}$ is taken together with R$^{1a}$ or R$^{1c}$ to form —(CH$_2$)$_3$—;
Het¹ represents a monocyclic 4-, 5-, 6- or 7-membered saturated or partially saturated heterocyclyl containing at least one heteroatom each independently selected from O, S, S(=O)$_p$ and N;
each optionally substituted with one or two substituents each independently selected from the group consisting of halo, —NR$^{9a}$R$^{9b}$ C$_{1-4}$alkyl, —(C=O)—OR$^{5h}$, —S(=O)$_2$—C$_{1-6}$alkyl, —C$_{1-4}$alkyl-S(=O)$_2$—C$_{1-6}$alkyl, hydroxyl, —O—C$_{1-4}$alkyl, cyano, C$_{1-4}$alkyl substituted with one or more halo atoms, and C$_{1-4}$alkyl substituted with one substituent selected from the group consisting of hydroxyl, —NH$_2$, —NH(C$_{1-4}$alkyl) and —N(C$_{1-4}$alkyl)$_2$; or two substituents on the same carbon atom of said heterocyclyl are taken together to form together with the common carbon atom to which they are attached Ring A.

In an embodiment, the present invention relates to those compounds of Formula (I) and the N-oxides, the pharmaceutically acceptable addition salts, and the solvates thereof, or any subgroup thereof as mentioned in any of the other embodiments, wherein R$^{1a}$ represents C$_{1-4}$alkyl, or C$_{1-4}$alkyl substituted with one —OH.

In an embodiment, the present invention relates to those compounds of Formula (I) and the N-oxides, the pharmaceutically acceptable addition salts, and the solvates thereof, or any subgroup thereof as mentioned in any of the other embodiments, wherein $R^{1a}$ represents $C_{1-4}$alkyl.

In an embodiment, the present invention relates to those compounds of Formula (I) and the N-oxides, the pharmaceutically acceptable addition salts, and the solvates thereof, or any subgroup thereof as mentioned in any of the other embodiments, wherein
  $R^{1a}$ represents $C_{1-4}$alkyl;
  $R^{1c}$ represents hydrogen or $C_{1-4}$alkyl;
  $R^{1b}$ represents hydrogen, $C_{1-4}$alkyl, or $C_{1-4}$alkyl substituted with one substituent selected from the group consisting of hydroxyl, —O—$C_{1-4}$ alkyl, and —$NR^{6c}R^{6d}$.

In an embodiment, the present invention relates to those compounds of Formula (I) and the N-oxides, the pharmaceutically acceptable addition salts, and the solvates thereof, or any subgroup thereof as mentioned in any of the other embodiments, wherein $R^{1b}$ is always taken together with $R^{1a}$ or $R^{1c}$ to form —$(CH_2)_3$—.

In an embodiment, the present invention relates to those compounds of Formula (I) and the N-oxides, the pharmaceutically acceptable addition salts, and the solvates thereof, or any subgroup thereof as mentioned in any of the other embodiments, wherein
  Y represents $CR^3$;
  L represents —$CHR^{1a}$—X— or —X—$CHR^{1c}$—;
  X represents $NR^{1b}$;
  $R^{1a}$ represents $C_{1-4}$alkyl;
  $R^{1c}$ represents hydrogen or $C_{1-4}$alkyl;
  $R^{1b}$ represents hydrogen;
  or $R^{1b}$ is taken together with $R^{1c}$ to form —$(CH_2)_3$—.

In an embodiment, the present invention relates to those compounds of Formula (I) and the N-oxides, the pharmaceutically acceptable addition salts, and the solvates thereof, or any subgroup thereof as mentioned in any of the other embodiments, wherein
  Y represents $CR^3$;
  L represents —$CHR^{1a}$—X— or —X—$CHR^{1c}$—;
  X represents $NR^{1b}$;
  $R^{1a}$ represents $C_{1-4}$alkyl;
  $R^{1c}$ represents hydrogen or $C_{1-4}$alkyl;
  $R^{1b}$ represents hydrogen.

In an embodiment, the present invention relates to those compounds of Formula (I) and the N-oxides, the pharmaceutically acceptable addition salts, and the solvates thereof, or any subgroup thereof as mentioned in any of the other embodiments, wherein Y represents $CR^3$.

In an embodiment, the present invention relates to those compounds of Formula (I) and the N-oxides, the pharmaceutically acceptable addition salts, and the solvates thereof, or any subgroup thereof as mentioned in any of the other embodiments, wherein
  Y represents $CR^3$;
  $R^3$ represents —(C=O)—$NR^{5a}R^{5b}$.

In an embodiment, the present invention relates to those compounds of Formula (I) and the N-oxides, the pharmaceutically acceptable addition salts, and the solvates thereof, or any subgroup thereof as mentioned in any of the other embodiments, wherein Y represents N.

In an embodiment, the present invention relates to those compounds of Formula (I) and the N-oxides, the pharmaceutically acceptable addition salts, and the solvates thereof, or any subgroup thereof as mentioned in any of the other embodiments, wherein L represents —$CHR^{1a}$—X— or —X—$CHR^{1c}$—.

In an embodiment, the present invention relates to those compounds of Formula (I) and the N-oxides, the pharmaceutically acceptable addition salts, and the solvates thereof, or any subgroup thereof as mentioned in any of the other embodiments, wherein X represents $NR^{1b}$.

In an embodiment, the present invention relates to those compounds of Formula (I) and the N-oxides, the pharmaceutically acceptable addition salts, and the solvates thereof, or any subgroup thereof as mentioned in any of the other embodiments, wherein $R^{5c}$ represents hydrogen.

In an embodiment, the present invention relates to those compounds of Formula (I) and the N-oxides, the pharmaceutically acceptable addition salts, and the solvates thereof, or any subgroup thereof as mentioned in any of the other embodiments, wherein $R^{1b}$ is not taken together with $R^{1a}$ or $R^{1c}$.

In an embodiment, the present invention relates to those compounds of Formula (I) and the N-oxides, the pharmaceutically acceptable addition salts, and the solvates thereof, or any subgroup thereof as mentioned in any of the other embodiments, wherein $Het^1$ represents a monocyclic 4-, 5-, 6- or 7-membered saturated or partially saturated heterocyclyl containing at least one heteroatom each independently selected from O, S, $S(=O)_p$ and N; each optionally substituted with one or two substituents each independently selected from the group consisting of halo, —$NR^{9a}R^{9b}$ $C_{1-4}$alkyl, —(C=O)—$OR^{5h}$, —$S(=O)_2$—$C_{1-6}$alkyl, —$C_{1-4}$alkyl-$S(=O)_2$—$C_{1-6}$alkyl, hydroxyl, —O—$C_{1-4}$alkyl, cyano, $C_{1-4}$alkyl substituted with one or more halo atoms, and $C_{1-4}$alkyl substituted with one substituent selected from the group consisting of hydroxyl, —$NH_2$, —$NH(C_{1-4}$ alkyl) and —$N(C_{1-4}$alkyl$)_2$; or two substituents on the same carbon atom of said heterocyclyl are taken together to form together with the common carbon atom to which they are attached Ring A.

In an embodiment, the present invention relates to those compounds of Formula (I) and the N-oxides, the pharmaceutically acceptable addition salts, and the solvates thereof, or any subgroup thereof as mentioned in any of the other embodiments, wherein $Het^1$ represents a bicyclic 8-, 9- or 10-membered saturated or partially saturated heterocyclyl containing at least one heteroatom each independently selected from O, S, $S(=O)_p$ and N; each optionally substituted with one or two substituents each independently selected from the group consisting of halo, —$NR^{9a}R^{9b}$ $C_{1-4}$alkyl, —(C=O)—$OR^{5h}$, —$S(=O)_2$—$C_{1-6}$alkyl, —$C_{1-4}$alkyl-$S(=O)_2$—$C_{1-6}$alkyl, hydroxyl, —O—$C_{1-4}$alkyl, cyano, $C_{1-4}$alkyl substituted with one or more halo atoms, and $C_{1-4}$alkyl substituted with one substituent selected from the group consisting of hydroxyl, —$NH_2$, —$NH(C_{1-4}$alkyl) and —$N(C_{1-4}$alkyl$)_2$; or two substituents on the same carbon atom of said heterocyclyl are taken together to form together with the common carbon atom to which they are attached Ring A. In an embodiment, the present invention relates to those compounds of Formula (I) and the N-oxides, the pharmaceutically acceptable addition salts, and the solvates thereof, or any subgroup thereof as mentioned in any of the other embodiments, wherein $Het^1$ represents a monocyclic 4-, 5-, 6- or 7-membered saturated or partially saturated heterocyclyl containing at least one heteroatom each independently selected from O, S, $S(=O)_p$ and N; wherein two substituents on the same carbon atom of said heterocyclyl are taken together to form together with the common carbon atom to which they are attached Ring A.

In an embodiment, the present invention relates to those compounds of Formula (I) and the N-oxides, the pharmaceutically acceptable addition salts, and the solvates thereof, or any subgroup thereof as mentioned in any of the other embodiments, wherein L represents —CH(CH$_3$)—NH—.

In an embodiment, the present invention relates to those compounds of Formula (I) and the N-oxides, the pharmaceutically acceptable addition salts, and the solvates thereof, or any subgroup thereof as mentioned in any of the other embodiments, wherein L represents

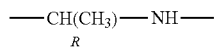

(R stereochemistry).

In an embodiment, the present invention relates to those compounds of Formula (I) and the N-oxides, the pharmaceutically acceptable addition salts, and the solvates thereof, or any subgroup thereof as mentioned in any of the other embodiments, wherein Het$^1$ as defined in any of the other embodiments is attached to the remainder of the molecule via a N-atom.

In an embodiment, the present invention relates to those compounds of Formula (I) and the N-oxides, the pharmaceutically acceptable addition salts, and the solvates thereof, or any subgroup thereof as mentioned in any of the other embodiments, wherein Het$^1$ is piperazin-1-yl optionally substituted as defined in any of the other embodiments.

In an embodiment, the present invention relates to those compounds of Formula (I) and the N-oxides, the pharmaceutically acceptable addition salts, and the solvates thereof, or any subgroup thereof as mentioned in any of the other embodiments, wherein Het$^1$ is piperazin-1-yl substituted with two C$_{1-4}$alkyl substituents.

In an embodiment, the present invention relates to those compounds of Formula (I) and the N-oxides, the pharmaceutically acceptable addition salts, and the solvates thereof, or any subgroup thereof as mentioned in any of the other embodiments, wherein Het$^1$ is piperazin-1-yl substituted with one C$_{1-4}$alkyl substituent in position 3 and one C$_{1-4}$alkyl substituent in position 5.

In an embodiment, the present invention relates to those compounds of Formula (I) and the N-oxides, the pharmaceutically acceptable addition salts, and the solvates thereof, or any subgroup thereof as mentioned in any of the other embodiments, wherein R$^2$ represents

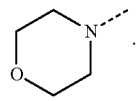

In an embodiment, the present invention relates to those compounds of Formula (I) and the N-oxides, the pharmaceutically acceptable addition salts, and the solvates thereof, or any subgroup thereof as mentioned in any of the other embodiments, wherein R$^2$ represents

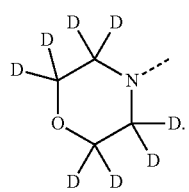

In an embodiment, the present invention relates to those compounds of Formula (I) and the N-oxides, the pharmaceutically acceptable addition salts, and the solvates thereof, or any subgroup thereof as mentioned in any of the other embodiments, wherein R$^2$ represents

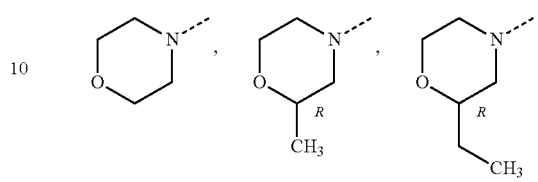

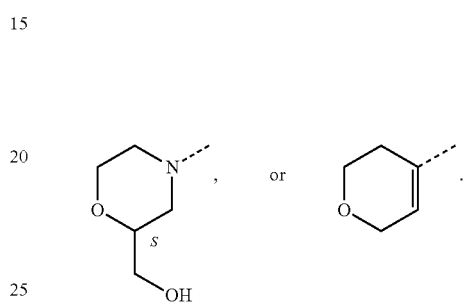

In an embodiment, the present invention relates to those compounds of Formula (I) and the N-oxides, the pharmaceutically acceptable addition salts, and the solvates thereof, or any subgroup thereof as mentioned in any of the other embodiments, wherein R$^2$ representing

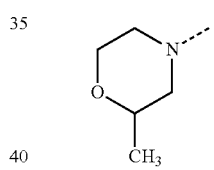

is limited to

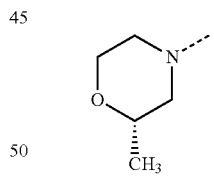

In an embodiment, the present invention relates to those compounds of Formula (I) and the N-oxides, the pharmaceutically acceptable addition salts, and the solvates thereof, or any subgroup thereof as mentioned in any of the other embodiments, wherein R$^2$ representing

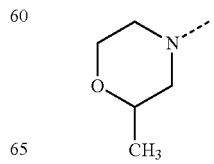

is limited to

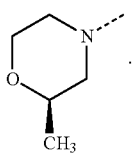

In an embodiment, the present invention relates to those compounds of Formula (I) and the N-oxides, the pharmaceutically acceptable addition salts, and the solvates thereof, or any subgroup thereof as mentioned in any of the other embodiments, wherein $R^2$ represents

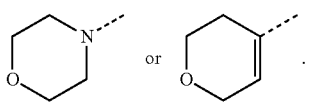

In an embodiment, the present invention relates to those compounds of Formula (I) and the N-oxides, the pharmaceutically acceptable addition salts, and the solvates thereof, or any subgroup thereof as mentioned in any of the other embodiments, wherein $R^3$ represents —(C=O)H, —(C=O)—$C_{1-4}$alkyl, —(C=O)—$NR^{5a}R^{5b}$, —(C=O)—$OR^{5c}$, —C(=O)—$Het^1$, —C(=O)—NH—$Het^2$, $C_{1-4}$alkyl, —CH=N—OH, —CH(OH)—$CH_2$—$NR^{5d}R^{5e}$, —CH(OH)—$CH_2$—$Het^1$, —CH(OH)—$C_{1-4}$alkyl, —C(OH)($C_{1-4}$alkyl)$_2$, halo, or $R^3$ represents $C_{1-4}$alkyl substituted with one substituent selected from the group consisting of hydroxyl, fluoro, —$NR^{5f}R^{5g}$, $Het^1$, —O—(C=O)—CH($NH_2$)—$C_{1-4}$alkyl, —O—(C=O)—CH($NH_2$)—$C_{1-4}$alkyl-Ar,

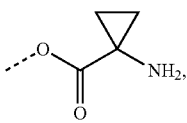

—O—$C_{1-4}$alkyl-OH, and —O—$C_{1-4}$alkyl-$NH_2$.

In an embodiment, the present invention relates to those compounds of Formula (I) and the N-oxides, the pharmaceutically acceptable addition salts, and the solvates thereof, or any subgroup thereof as mentioned in any of the other embodiments, wherein $R^3$ is other than $R^7$.

In an embodiment the compound of Formula (I) is selected from the group consisting of compounds 12, 14, 39, 117, 158, 184 and 276, tautomers and stereoisomeric forms thereof, and the N-oxides, the pharmaceutically acceptable addition salts, and the solvates thereof.

In an embodiment the compound of Formula (I) is selected from the group consisting of compounds 12, 14, 39, 117, 158, 184, 328, 211 and 276, tautomers and stereoisomeric forms thereof, and the N-oxides, the pharmaceutically acceptable addition salts, and the solvates thereof.

In an embodiment the compound of Formula (I) is selected from the group consisting of compound 117, tautomers and stereoisomeric forms thereof, and the N-oxides, the pharmaceutically acceptable addition salts, and the solvates thereof.

In an embodiment the compound of Formula (I) is compound 117.

In an embodiment the compound of Formula (I) is selected from the group consisting of compound 184, tautomers and stereoisomeric forms thereof, and the N-oxides, the pharmaceutically acceptable addition salts, and the solvates thereof.

In an embodiment the compound of Formula (I) is compound 184.

In an embodiment the compound of Formula (I) is selected from the group consisting of compound 276, tautomers and stereoisomeric forms thereof, and the N-oxides, the pharmaceutically acceptable addition salts, and the solvates thereof.

In an embodiment the compound of Formula (I) is compound 276.

In an embodiment the compound of Formula (I) is selected from the group consisting of compound 158, tautomers and stereoisomeric forms thereof, and the N-oxides, the pharmaceutically acceptable addition salts, and the solvates thereof.

In an embodiment the compound of Formula (I) is compound 158.

In an embodiment the compound of Formula (I) is selected from the group consisting of compound 14, tautomers and stereoisomeric forms thereof, and the N-oxides, the pharmaceutically acceptable addition salts, and the solvates thereof.

In an embodiment the compound of Formula (I) is compound 14.

In an embodiment the compound of Formula (I) is selected from the group consisting of compound 12, tautomers and stereoisomeric forms thereof, and the N-oxides, the pharmaceutically acceptable addition salts, and the solvates thereof.

In an embodiment the compound of Formula (I) is compound 12.

In an embodiment the compound of Formula (I) is selected from the group consisting of compound 39, tautomers and stereoisomeric forms thereof, and the N-oxides, the pharmaceutically acceptable addition salts, and the solvates thereof.

In an embodiment the compound of Formula (I) is compound 39.

In an embodiment the compound of Formula (I) is selected from the group consisting of compound 328, tautomers and stereoisomeric forms thereof, and the N-oxides, the pharmaceutically acceptable addition salts, and the solvates thereof.

In an embodiment the compound of Formula (I) is compound 328.

In an embodiment the compound of Formula (I) is selected from the group consisting of compound 211, tautomers and stereoisomeric forms thereof, and the N-oxides, the pharmaceutically acceptable addition salts, and the solvates thereof.

In an embodiment the compound of Formula (I) is compound 211.

All possible combinations of the above-indicated embodiments are considered to be embraced within the scope of this invention.

Methods for the Preparation of Compounds of Formula (I)

In this section, as in all other sections unless the context indicates otherwise, references to Formula (I) also include all other sub-groups and examples thereof as defined herein.

The general preparation of some typical examples of the compounds of Formula (I) is described hereunder and in the specific examples, and are generally prepared from starting materials which are either commercially available or prepared by standard synthetic processes commonly used by those skilled in the art. The following schemes are only meant to represent examples of the invention and are in no way meant to be a limit of the invention. For example, the skilled person will realize that some of the general schemes wherein Y is $Y^1$ may, dependent on the reaction conditions, also apply for cases wherein Y represents —(C═O)—O—H or $C_{1-4}$alkyl substituted with OH.

Alternatively, compounds of the present invention may also be prepared by analogous reaction protocols as described in the general schemes below, combined with standard synthetic processes commonly used by those skilled in the art of organic chemistry.

The skilled person will realize that in the reactions described in the Schemes, although this is not always explicitly shown, it may be necessary to protect reactive functional groups (for example hydroxy, amino, or carboxy groups) where these are desired in the final product, to avoid their unwanted participation in the reactions. Conventional protecting groups can be used in accordance with standard practice. The protecting groups may be removed at a convenient subsequent stage using methods known from the art. This is illustrated in the specific examples. For example, a skilled person will realize that e.g. preparation of compound 17 according to Scheme 1 requires cleavage of the tert-butoxycarbonyl (Boc) in acidic media such as for example hydrochloric acid 4N in acetonitrile at 0° C. or room temperature. For example compound 244 is obtained after cleavage of the tert-butyldimethylsilyl in the presence of tetrabutylammonium Fluoride (1M in tetrahydrofuran) in tetrahydrofuran at room temperature. For example compound 79 is prepared according to Scheme 3 from compound 78 by a palladium catalyzed amination reaction using A-boc-1,2-diaminoethane followed by cleavage of the tert-butoxy carbonyl (Boc) with trifluoroactic acid as the acid source.

The skilled person will realize that in the reactions described in the Schemes, it may be advisable or necessary to perform the reaction under an inert atmosphere, such as for example under $N_2$-gas atmosphere.

It will be apparent for the skilled person that it may be necessary to cool the reaction mixture before reaction work-up (refers to the series of manipulations required to isolate and purify the product(s) of a chemical reaction such as for example quenching, column chromatography, extraction).

The skilled person will realize that heating the reaction mixture under stirring may enhance the reaction outcome. In some reactions microwave heating may be used instead of conventional heating to shorten the overall reaction time. The skilled person will realize that another sequence of the chemical reactions shown in the Schemes below, may also result in the desired compound of formula (I). The skilled person will realize that intermediates and final compounds shown in the schemes below may be further functionalized according to methods well-known by the person skilled in the art.

In general, compounds of formula (I) wherein L is defined as shown in scheme 1 and Y is $Y^1$ being N or $CR^3$ wherein $R^3$ is defined as —$C_{1-4}$alkyl, —(C═O)—O—$C_{1-4}$alkyl, —(C═O)—$NR^{5a}R^{5b}$, —C(═O)—$Het^1$ or halo, said compounds being represented by formula (Ia) can be prepared according to the following reaction Scheme 1 wherein $PG^1$ is a protecting group such as for example a tert-Butyloxycarbonyl (Boc) and $halo^2$ is defined as Cl, Br or I. All other variables in Scheme 1 are defined according to the scope of the present invention.

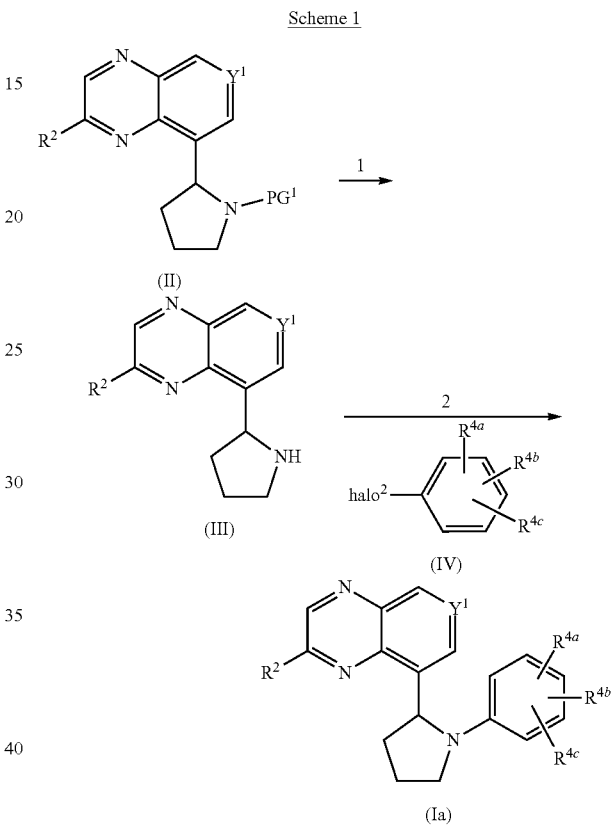

Scheme 1

In Scheme 1, the following reaction conditions apply:

1: in the presence of a suitable acid such as for example hydrochloric acid (HCl) or trifluoroacetic acid (TFA), a suitable solvent such as for example dichloromethane (DCM), at a suitable temperature such as room temperature;

2: in the presence of a suitable catalyst such as for example palladium acetate (Pd(OAc)$_2$) or tris(dibenzylideneacetone)dipalladium(0) (Pd$_2$dba$_3$), a suitable ligand such as for example Xanthphos or 2-(di-tert-butylphosphino) biphenyl a suitable base such as for example cesium carbonate or sodium tert-butoxide, a suitable solvent such as for example 1,4-dioxane, at a suitable temperature such as 100° C., in a sealed vessel;

In general, compounds of formula (I) wherein L is defined as shown in scheme 2 and Y is $Y^1$ being N or $CR^3$ wherein $R^3$ is defined as —$C_{1-4}$alkyl, —(C═O)—O—$C_{1-4}$alkyl, —(C═O)—$NR^{5a}R^{5b}$, —C(═O)—$Het^1$ or halo, and $R^{1a}$ is defined as $C_{1-4}$alkyl, said compounds being represented by formula (Ib) and (Ic) can be prepared according to the following reaction Scheme 2 wherein $halo^1$ is defined as Cl, Br and I, and $halo^3$ is defined as Cl or Br. 'n-Bu' means n-butyl. All other variables in Scheme 2 are defined according to the scope of the present invention.

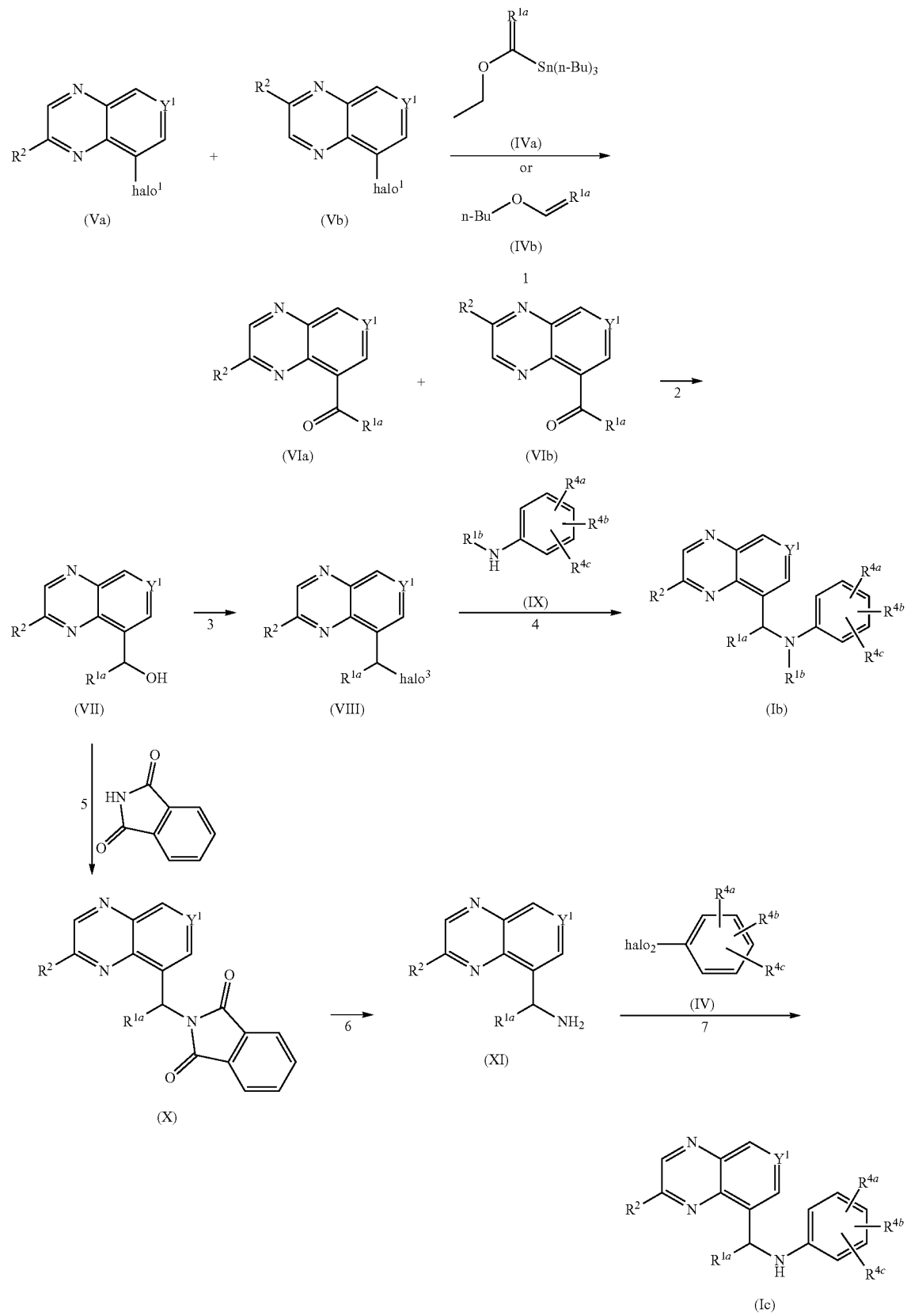

In Scheme 2, the following reaction conditions apply:

1: In case of reagent (IVa), in the presence of a suitable catalyst such as for example dichlorobis(triphenylphosphine) palladium (II) or tetrakis(triphenylphosphine)palladium(0) (Pd(Ph$_3$)$_4$), a suitable solvent such as for example 1,4-dioxane, at a suitable temperature such as 100° C. in a sealed or an open vessel; Then, in the presence of a suitable acid such as for example aqueous HCl, at a suitable temperature such as room temperature;

In case of reagent (IVb), in the presence of a suitable catalyst such as for example Pd(OAc)$_2$, a suitable ligand such as for example 1,3-Bis(diphenylphosphino)propane (DPPP), a suitable base such as for example triethylamine, a suitable solvent such as for example dimethylsulfoxide, at a suitable temperature such as 100° C.; Then, in the presence of a suitable acid such as for example HCl, at a suitable temperature such as 0° C.;

2: in the presence of a suitable reducing reagent such as for example sodium borohydride, a suitable solvent such as for example a mixture of methanol and dichloromethane, at a suitable temperature such as room temperature, in the presence or not of a suitable additive such as for example cerium (III) chloride;

6: in the presence of a suitable reagent such as for example hydrazine monohydrate, a suitable solvent such as for example ethanol, at a suitable temperature such as for example 80° C.;

7: in the presence of a suitable catalyst such as for example chloro[2-(dicyclohexylphosphino)-3,6-dimethoxy-2',4',6'-triisopropyl-1,1'-biphenyl] [2-(2-aminoethyl)phenyl] palladium(II) (Brettphos precatalyst first gen), a suitable base such as for example cesium carbonate, a suitable solvent such as for example 2-methyl-2-butanol, at a suitable temperature such as 100° C., in a sealed vessel.

In general, compounds of formula (I) wherein
L is defined as shown in scheme 3;
Y is Y$^1$ being N or CR$^3$ wherein R$^3$ is defined as —C$_{1-4}$alkyl, —(C=O)—O— C$_{1-4}$alkyl, —(C=O)— NR$^{5a}$R$^{5b}$, —C(=O)—Het$^1$ or halo;
R$^{1a}$ is defined as C$_{1-4}$alkyl or hydrogen for step 1 and 2, and is defined according to the scope of the present invention for step 3);

said compounds being represented by formula (Id) can be prepared according to the following reaction Scheme 3 wherein halo$^1$ is defined as Cl, Br or I and halo$^3$ is defined as Cl or Br. All other variables in Scheme 3 are defined according to the scope of the present invention.

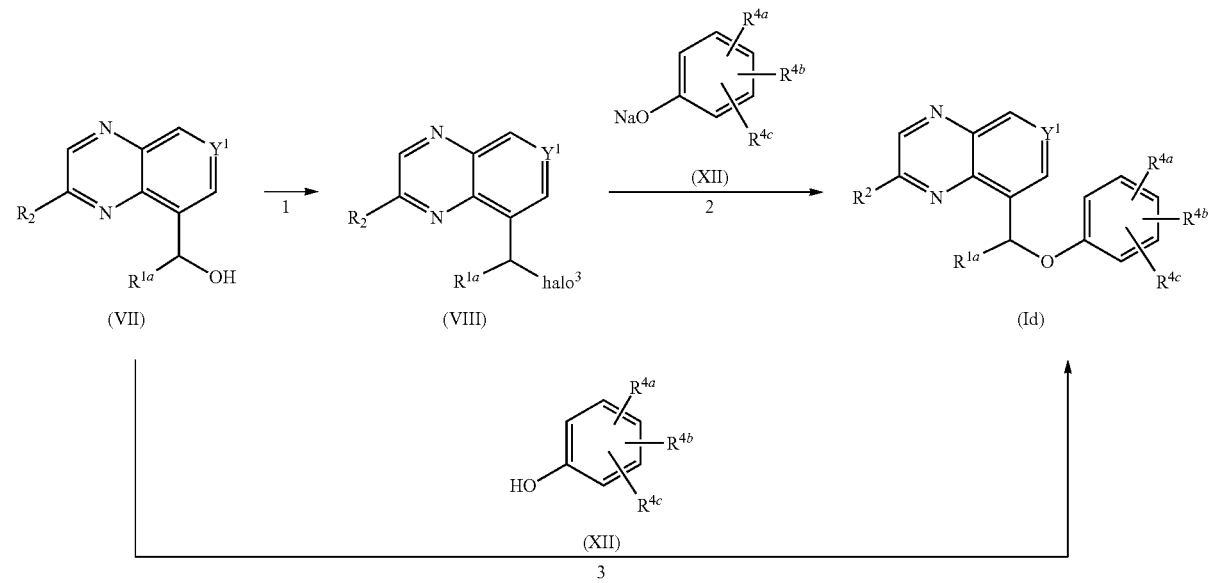

Scheme 3

In Scheme 3, the following reaction conditions apply:

3: in the presence of a suitable halogenating reagent such as for example phosphorous tribromide or thionyl chloride, a suitable solvent such as for example dichloromethane, at a suitable temperature such as for example 10° C. or room temperature;

4: in the presence of a suitable solvent such as for example N,N-dimethylformamide, at a suitable temperature such as for example 50 or 60° C., in a sealed vessel;

5: in the presence of a suitable reagent such as for example di-tert-butyl azodicarboxylate, a suitable phosphine such as for example triphenylphosphine, a suitable solvent such as for example tetrahydrofuran, at a suitable temperature such as for example room temperature;

1: in the presence of a suitable halogenating reagent such as for example phosphorous tribromide or thionyl chloride, a suitable solvent such as for example dichloromethane, at a suitable temperature such as for example 10° C. or room temperature;

2: in the presence of a suitable solvent such as for example N,N-dimethylformamide, at a suitable temperature such as for example 50 or 60° C., in a sealed vessel;

3: in the presence of a suitable reagent such as for example di-tert-butylazodicarboxylate, a suitable phosphine such as for example triphenylphosphine, a solvent such as for example tetrahydrofuran, at a suitable temperature such as for example room temperature;

Alternatively, in the presence of a suitable reagent such as for example cyanoethylenetributylphosphorane, a solvent such as for example toluene, at a suitable temperature such as for example 60° C., in a sealed vessel.

In general, compounds of formula (I) wherein
L is defined as shown in scheme 4;
Y is $Y^1$ being N or $CR^3$ wherein $R^3$ is defined as $—C_{1-4}$alkyl, $—(C=O)—O—C_{1-4}$alkyl, $—(C=O)—NR^{5a}R^{5b}$, $—C(=O)—Het^1$ or halo;
$R^{1a}$ is defined as $C_{1-4}$alkyl or hydrogen;
said compounds being represented by formula (Ie), can be prepared according to the following reaction Scheme 4 wherein $halo^3$ is defined as Cl or Br. All other variables in Scheme 4 are defined according to the scope of the present invention.

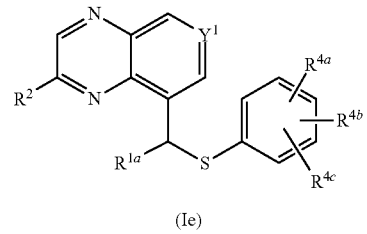

(Ie)

Scheme 4

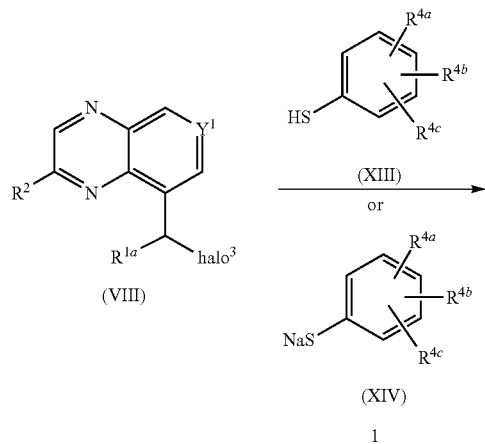

In Scheme 4, the following reaction conditions apply:
1: in the presence of a suitable solvent such as for example N,Y-dimethyl formamide, at a suitable temperature such as for example 50 or 60° C., in a sealed vessel.

In general, compounds of formula (I) wherein L is defined as shown in scheme 5 and Y is $Y^1$ being N or $CR^3$ wherein $R^3$ is defined as $—C_{1-4}$alkyl, $—(C=O)—O—C_{1-4}$alkyl, $—(C=O)—NR^{5a}R^{5b}$, $—C(=O)—Het^1$ or halo, said compounds being represented by formula (If) can be prepared according to the following reaction Scheme 5 wherein $halo^1$ is defined as Cl, Br or I, $W^1$ is a leaving group such as for example Cl, Br or I, and n is 0, 1 or 2. Moreover $R^{5a}$ and $R^{5b}$ are other than hydrogen for the purpose of Scheme 5. All other variables in Scheme 5 are defined according to the scope of the present invention.

Scheme 5

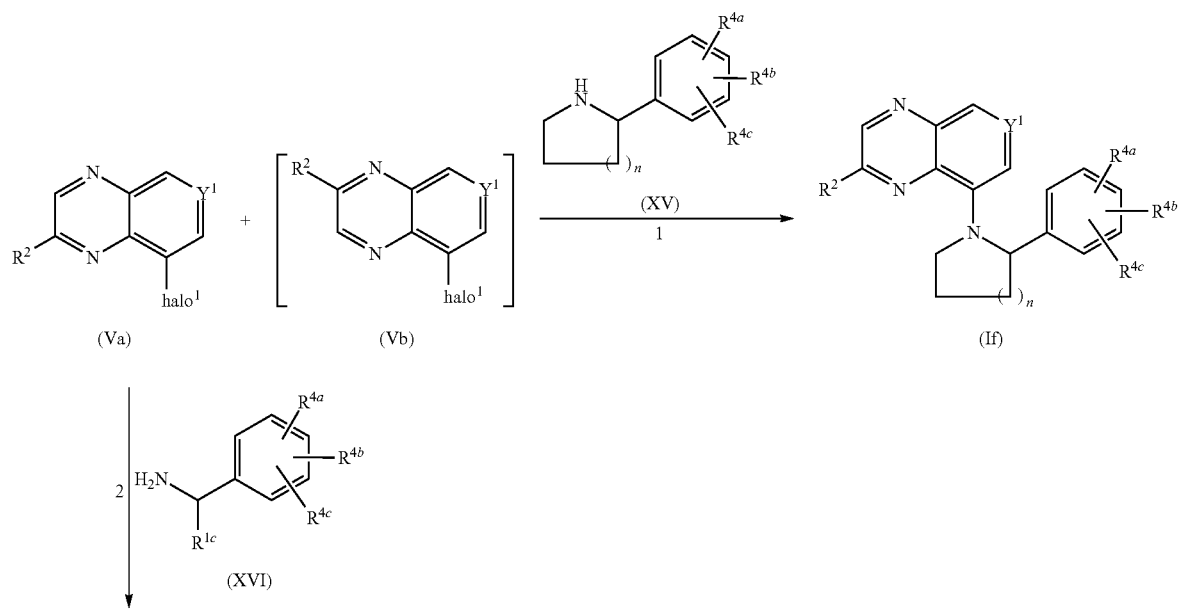

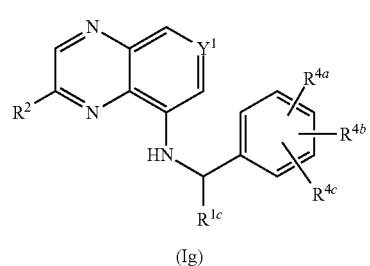
(Ig)

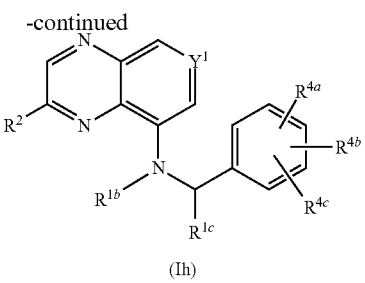
(Ih)

In Scheme 5, the following reaction conditions apply:

1: in the presence of a suitable catalyst such as for example chloro[2-(dicyclohexylphosphino)-3,6-dimethoxy-2',4',6'-triisopropyl-1,1'-biphenyl] [2-(2-aminoethyl)phenyl] palladium(II) (Brettphos precatalyst first gen), with or without a suitable ligand such as for example 2-dicyclohexylphosphino-2',6'-diisopropoxy-1,1'-biphenyl, a suitable base such as for example cesium carbonate, a suitable solvent such as for example tert-amyl alcohol (2-methyl-2-butanol) or toluene, at a suitable temperature such as 100° C., in a sealed vessel;

2: in the presence of a suitable catalyst such as for example chloro[2-(dicyclohexylphosphino)-3,6-dimethoxy-2',4',6'-triisopropyl-1,1'-biphenyl] [2-(2-aminoethyl)phenyl] palladium(II) (Brettphos precatalyst first gen) or palladium acetate, with or without a suitable ligand such as for example 2-dicyclohexylphosphino-2',6'-diisopropoxy-1,1'-biphenyl or 4,5-Bis(diphenylphosphino)-9,9-dimethylxanthene, a suitable base such as for example cesium carbonate, a suitable solvent such as for example tert-amyl alcohol, toluene or dioxane, at a suitable temperature ranged from 80 to 100° C., in a sealed vessel;

3: in the presence of a suitable deprotonating agent such as for example sodium hydride, a suitable solvent such as for example dimethylformamide, at a suitable temperature such as for example room temperature.

A subgroup of the Intermediates of formula (II) used in the above Scheme 1, hereby named Intermediates of formula (II-1) wherein L is limited according to scheme 6 and Y is $Y^{1a}$ being N, —C—$C_{1-4}$alkyl, —C—(C=O)—O—$C_{1-4}$alkyl and $C_{1-4}$alkyl can be prepared according to the following reaction Scheme 6 wherein $PG^1$ is a protecting group such as for example a Boc, and $halo^2$ is defined as Cl, Br or I. All other variables in Scheme 6 are defined according to the scope of the present invention.

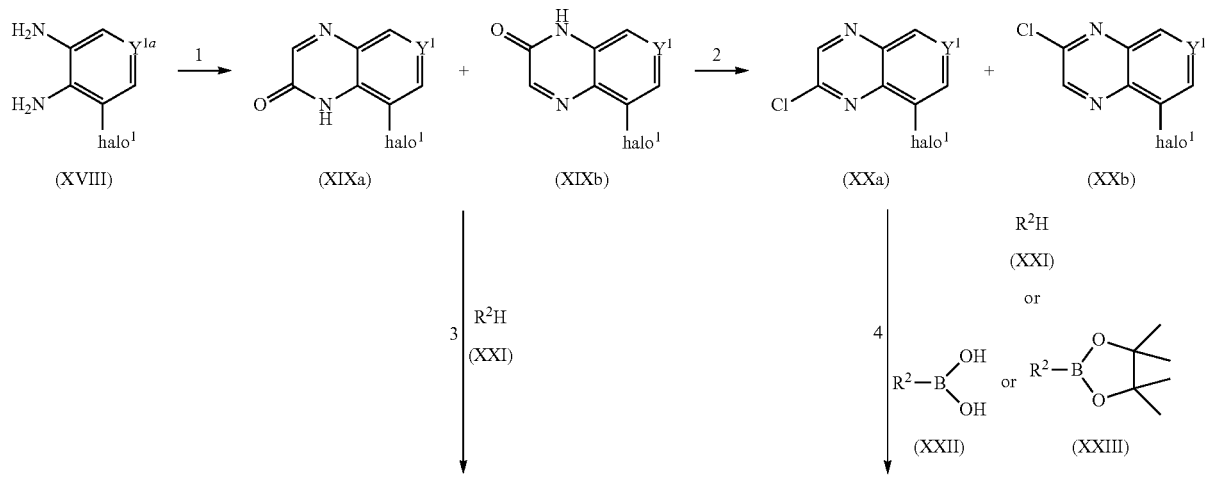
Scheme 6

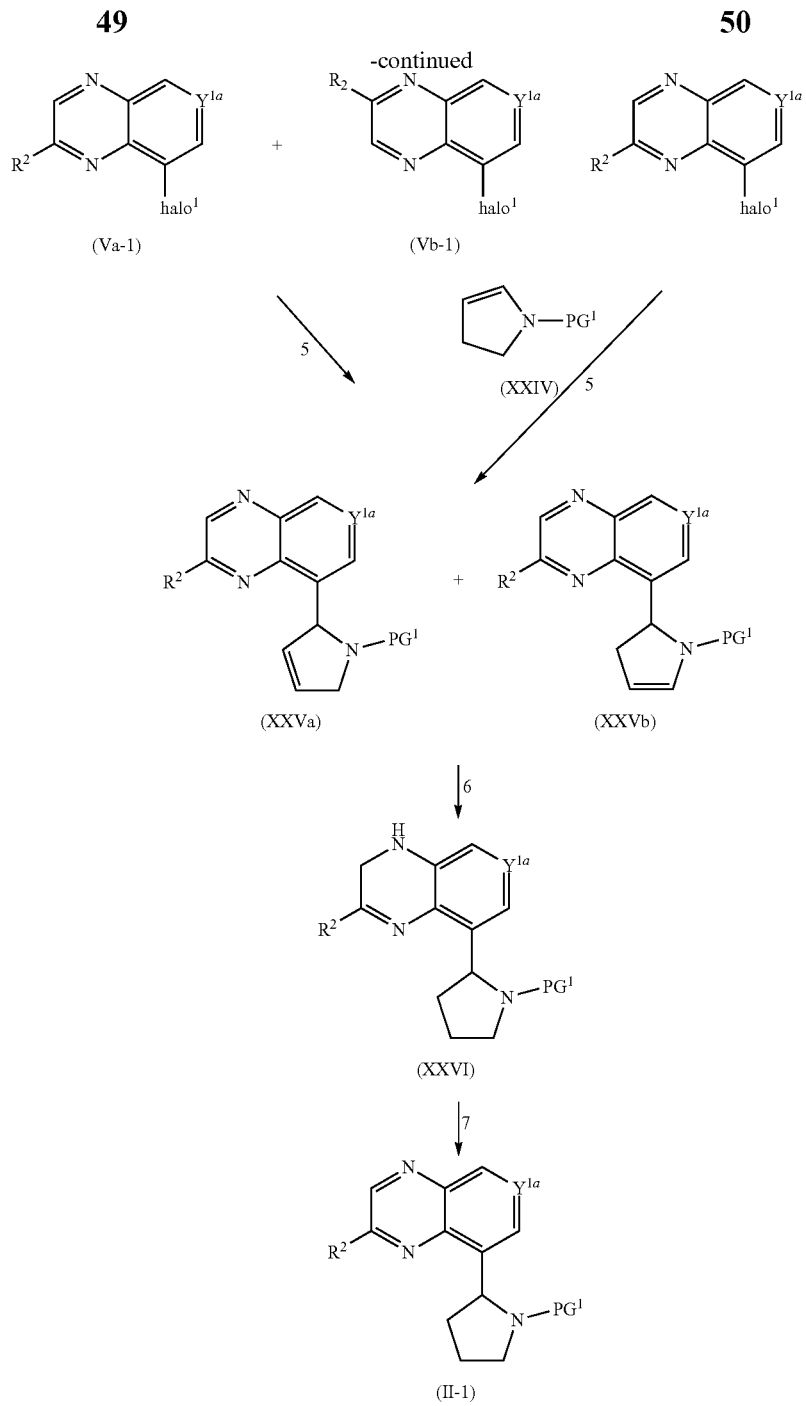

In Scheme 6, the following reaction conditions apply:

1: in the presence of a suitable reagent such as for example 2,2-dihydroxy acetic acid, a suitable solvent such as for example a mixture of water and methanol, at a suitable temperature such as room temperature;

Alternatively, in the presence of a suitable reagent such as for example an ethyl glyoxalate solution in toluene, a suitable solvent such as for example ethanol, at a suitable temperature such as solvent reflux;

2: in the presence of a suitable chlorinating reagent such as for example phosphoryl trichloride (POCh), at a suitable temperature such as 80° C.;

3: in the presence of a suitable coupling reagent such as for example phosphoryl bromo-tris-pyrrolidino-phosphonium hexafluorophosphate, a suitable base such as for example triethylamine, a suitable solvent such as for example tetrahydrofuran, at a suitable temperature such as room temperature;

4: in case of an intermediate of formula (XXI): in the presence of a suitable solvent such as for example tetrahydrofuran, at a suitable temperature such as solvent reflux; in case of an intermediate of formula (XXII) or in case of an intermediate of formula
(XXIII): in the presence of a suitable catalyst such as for example [1,1'-Bis(diphenylphosphino)ferrocene]

dichloropalladium(II), complex with dichloromethane, suitable base such as for example potassium phosphate, a suitable solvent such as for example 1,4-dioxane, at a suitable temperature such as for example 80° C., in a sealed vessel;

5: in the presence of a suitable catalyst such as for example Pd(OAc)$_2$, a suitable phosphine such as for example triphenylphosphine, a suitable base such as for example potassium carbonate, a suitable solvent such as for example N, N-dimethylformamide or 1,4-dioxane, at a suitable temperature such as for example 100° C., in a sealed vessel;

6: in the presence of hydrogen, a suitable catalyst such as for example platinum (IV) oxide, a suitable solvent such as for example methanol, at a suitable temperature such as for example room temperature;

7: in the presence of a suitable oxidative reagent such as for example manganese oxide, a suitable solvent such as for example dichloromethane, at a suitable temperature such as for example room temperature.

In general, compounds of formula (I) wherein L is $L^1$ being —CHR$^{1a}$—X— or —X—CHR$^{1c}$—; and Y is $Y^a$ being CR$^3$ wherein R$^3$ is defined as —COOH, —CH$_2$OH, —(C=O)H, —CH(OH)—CH$_2$—NR$^{5d}$R$^{5e}$, —CH(OH)—CH$_2$—Het$^1$, —(C=O)—NR$^{5a}$R$^{5b}$, —C(=O)—Het$^1$, —CH$_2$—NR$^{5f}$R$^{5g}$ or —CH$_2$—Het$^1$, said compounds being represented respectively by compounds of formula (Ii), (Ij), (Ik), (Il), (Im), (Iad), I(ae), I(an) and I(ao), can be prepared according to the following reaction Scheme 7.

All other variables in Scheme 7 are defined according to the scope of the present invention.

Scheme 7

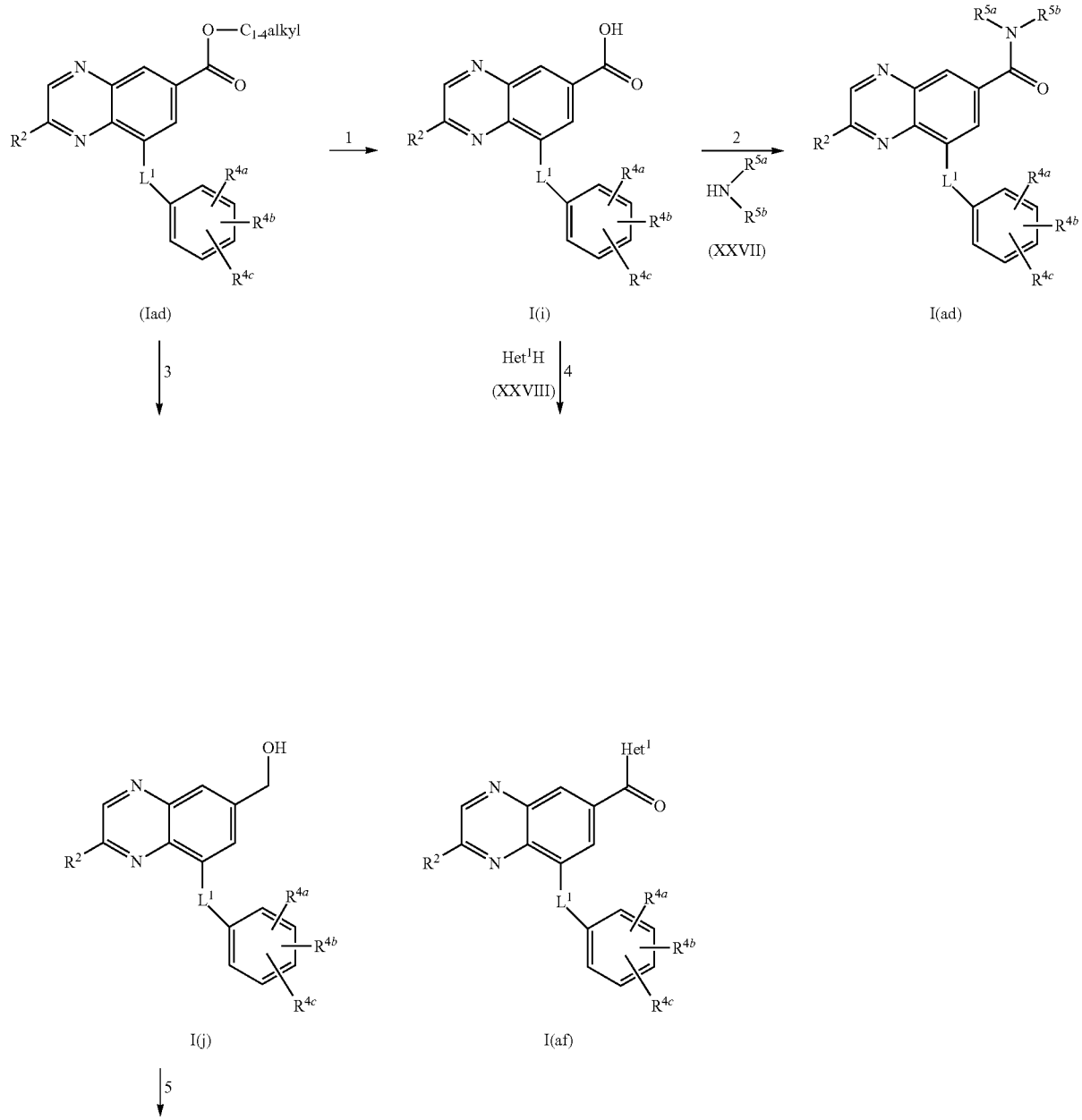

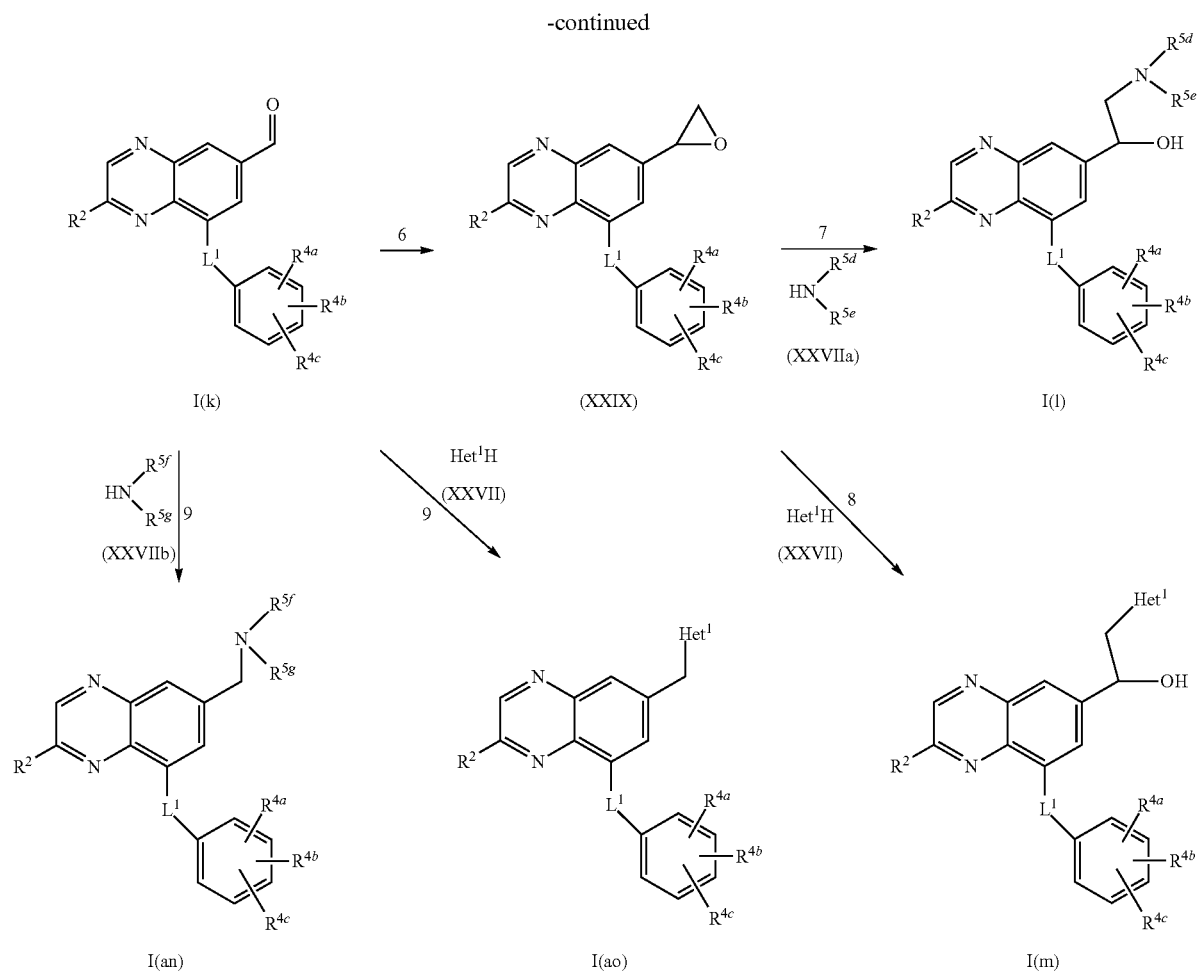

In Scheme 7, the following reaction conditions apply:

1: in the presence of a suitable base such as for example lithium hydroxide monohydrate or sodium carbonate, a suitable solvent such as for example a mixture of water and tetrahydrofuran or a mixture of water, methanol and tetrahydrofuran, at a suitable temperature such as for example 50° C. or room temperature;

2: in the presence of a suitable coupling reagent such as for example N,N,N',N'-Tetramethyl-<9-(1H-benzotriazol-1-yl)uronium hexafluorophosphate, O-(Benzotriazol-1-yl)-N,N,N',N'-tetramethyluronium hexafluorophosphate (HBTU), (1-Cyano-2-ethoxy-2-oxoethylidenaminooxy)dimethyl-amino-morpholino-carbenium hexafluorophosphate (COMU), 1-[Bis(dimethylamino)methylene]-1H-1,2,3-triazolo[4,5-b]pyridinium 3-oxid hexafluorophosphate (HATU) or 1,1'-carbonyldiimidazole, a suitable base such as for example diisopropylethylamine, triethylamine or 1,8-diazabicyclo[5.4.0]undec-7-ene, a suitable solvent such as for example A, A-di methyl formamide or methyltetrahydrofuran, at a suitable temperature such as for example room temperature;

3: in the presence of a suitable reducing reagent such as for example diisobutylaluminium hydride, a suitable solvent such as for example tetrahydrofuran, at a suitable temperature such as for example −70° C.;

4: in the presence of a suitable coupling reagent such as for example HBTU, COMU, HATU or 1,1'-carbonyldiimidazole, a suitable base such as for example diisopropylethylamine, triethylamine or 1,8-diazabicyclo[5.4.0]undec-7-ene, a suitable solvent such as for example N. A-di methyl formamide or methyltetrahydrofuran, at a suitable temperature such as for example room temperature;

5: in the presence of a suitable oxidative reagent such as for example manganese dioxide, a suitable solvent such as for example dichloromethane, at a suitable temperature such as for example room temperature;

6: in the presence of a suitable reagent such as for example trimethylsulfonium iodide, a suitable deprotonating reagent such as for example sodium hydride, a suitable solvent such as for example tetrahydrofuran, at a suitable temperature such as for example 70° C.;

7: in the presence of a suitable solvent such as for example tetrahydrofuran, at a suitable temperature such as for example 100° C., in a sealed vessel;

8: in the presence of a suitable solvent such as for example tetrahydrofuran, at a suitable temperature such as for example 100° C., in a sealed vessel;

9: in the presence of a suitable reducing agent such as for example sodium borohydride, eventually a suitable base such as for example sodium acetate, in a suitable solvent such as for example methanol at a suitable temperature such as room temperature.

In general, compounds of formula (I) wherein L is $L^3$ defined as —CH($C_{1-4}$alkyl)-CH$_2$—, —CH$_2$—CH($C_{1-4}$alkyl)-, or —CH($C_{1-4}$alkyl)-CH($C_{1-4}$alkyl)- and Y is defined as $CR^3$ and $R^3$ is defined as —(C═O)-NR$^{5a}$R$^{5b}$, said compounds being represented by formula (In), can be prepared according to the following reaction Scheme 8 wherein halo¹ is defined as Cl, Br or I. All other variables in Scheme 8 are defined as above or according to the scope of the present invention.

example 1,4-dioxane, at a suitable temperature such as for example ranged between 80° C., and 110° C.

In general, compounds of formula (I) wherein L is $L^2$ being —CH(C$_{1-4}$alkyl)-CH$_2$—, —CH$_2$—CH(C$_{1-4}$alkyl)-, —CH(C$_{1-4}$alkyl)-CH(C$_{1-4}$alkyl)-, CHR$^{1a}$—X—, or

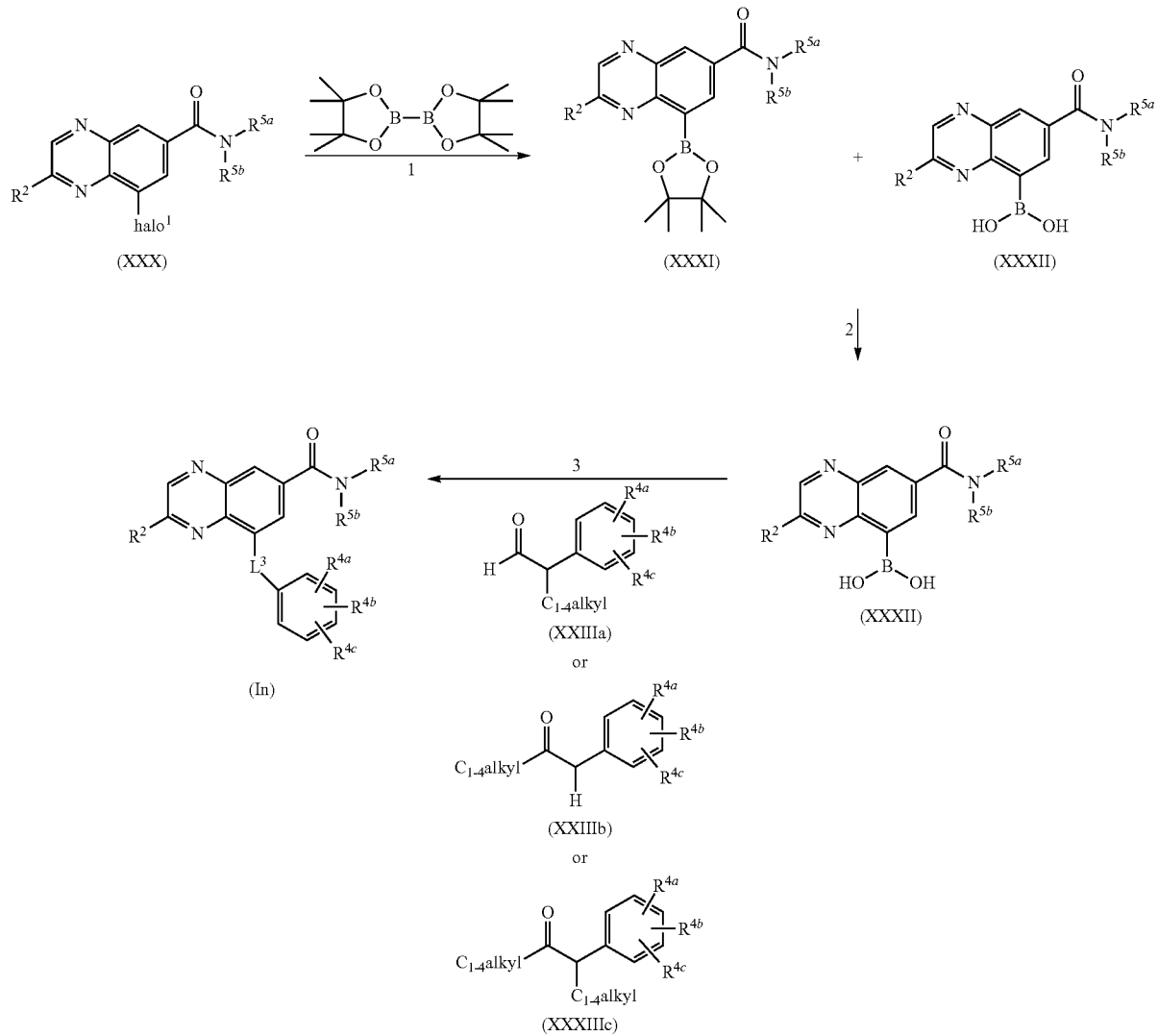

In Scheme 8, the following reaction conditions apply:

1: in the presence of a suitable reagent such as for example Bis(pinacolato)diboron, a suitable catalyst such as for example [1,1'-Bis(diphenylphosphino)ferrocene]dichloropalladium(II), a suitable base such as for example potassium acetate, a suitable solvent such as for example 1,4-dioxane, at a suitable temperature such as for example 100° C.;

2: in the presence of a suitable reagent such as for example sodium periodate, a suitable acid such as for example hydrochloric acid, a suitable solvent such as for example a mixture of water and tetrahydrofuran, at a suitable temperature such as for example room temperature;

3: in the presence of a suitable reagent such as for example N-tosylhydrazine, a suitable base such as for example potassium carbonate, a suitable solvent such as for —X—CHR$^{1c}$—; and wherein Y is $Y^2$ being CR$^3$ and R$^3$ is defined as —CH(OH)C$_{1-4}$alkyl or —C(OH)(C$_{1-4}$alkyl)$_2$, said compounds being respectively represented by formula (Io) and (Ip), can be prepared according to the following reaction Scheme 9.

For the purpose of Scheme 9, halo⁴ is defined as Cl or Br;

X represents O, S, or NR$^{1b}$;

R$^{1a}$ represents C$_{1-4}$alkyl;

R$^{1b}$ represents C$_{1-4}$alkyl or R$^{1b}$ is taken together with R$^{1a}$ or R$^{1c}$ to form —(CH$_2$)$_3$—;

or R$^{1b}$ is taken together with R$^{1c}$ to form —(CH$_2$)$_2$— or —(CH$_2$)$_4$—.

All other variables in Scheme 9 are defined according to the scope of the present invention.

Scheme 9

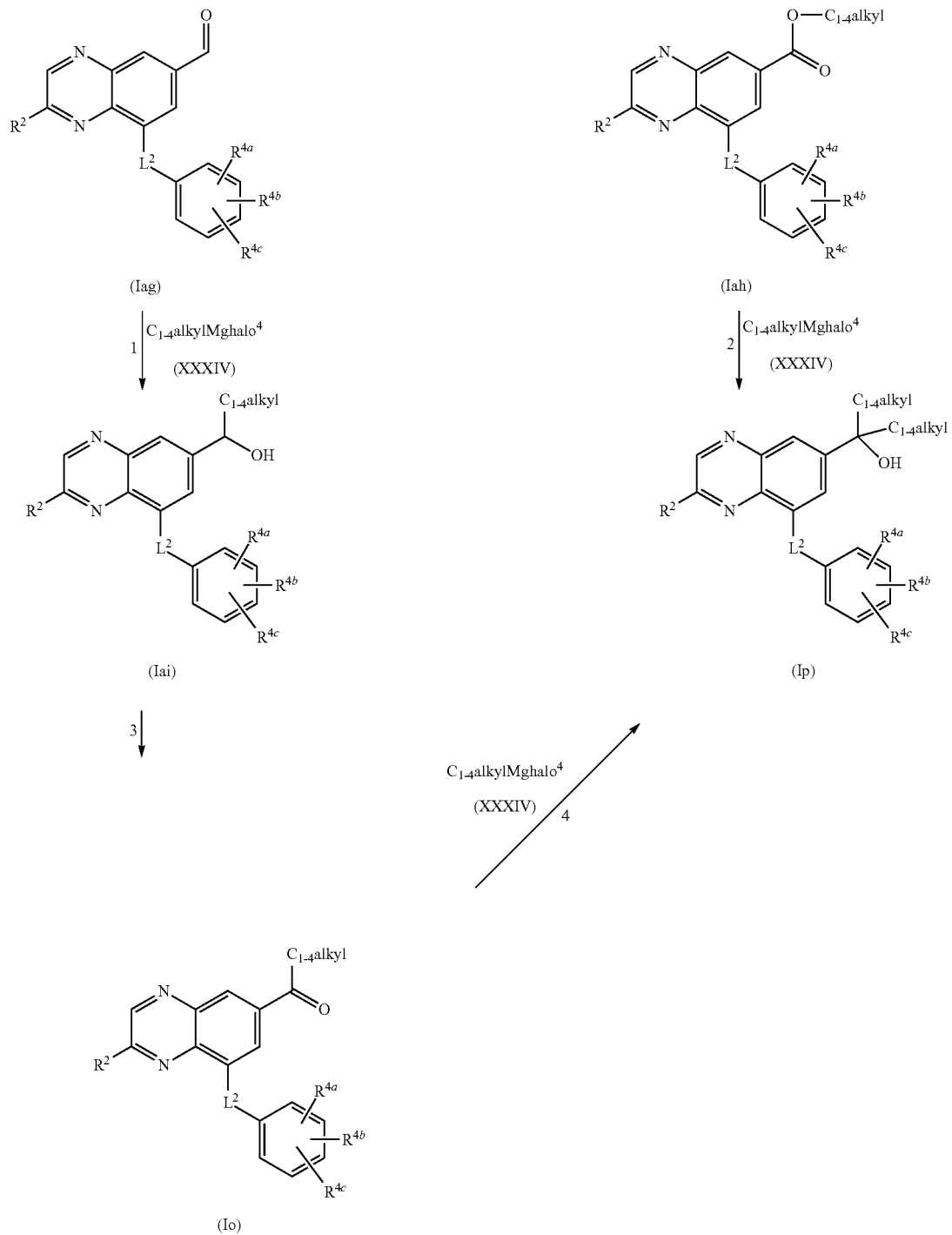

In Scheme 9, the following reaction conditions apply:

1: in the presence of a suitable solvent such as for example tetrahydrofuran, at a suitable temperature such as for example 10° C.;

2: in the presence of a suitable solvent such as for example tetrahydrofuran, at a suitable temperature such as for example 10° C.;

3: in the presence of a suitable oxidative reagent such as for example manganese dioxide, a suitable solvent such as for example dichloromethane, at a suitable temperature such as room temperature;

4: in the presence of a suitable solvent such as for example tetrahydrofuran, at a suitable temperature such as for example 10° C.

In general, compounds of formula (I) wherein Y is $Y^3$ being $CR^3$ and $R^3$ is restricted to $R^{7a}$ being defined as

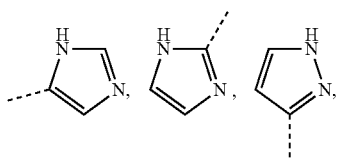

said compounds being represented by formula (Iq), can be prepared according to the following reaction Scheme wherein halo⁵ is defined as Cl, Br or I. All other variables in Scheme 10 are defined according to the scope of the present invention.

In Scheme 10, the following reaction conditions apply:

1: in the presence of a suitable catalyst such as for example 1,1'-Bis(diphenylphosphino)ferrocene]dichloropalladium(II) complex with dichloromethane, a suitable solvent such as for example tetrahydrofuran, at a suitable temperature such as for example 95° C., and eventually followed by protective groups cleavage using state of the art methods.

In general, compounds of formula (I) wherein Y is $Y^4$ being $CR^3$ and $R^3$ is defined as $CH_2$ substituted with one substituent selected from the group consisting of fluoro, $-NR^{5f}R^{5g}$, $Het^1$, $-O-C_{1-4}alkyl-OH$, and $-O-C_{1-4}alkyl-NH_2$, said compounds being respectively represented by formula (Ir), (Is), (It), (Iu), (Iv) and (Iw) can be prepared according to the following reaction Scheme 11 wherein halo⁶ is defined as Cl or Br, $W^2$ as a leaving group such as for example Cl or Br and $PG^2$ a protective group such as for example a tert-Butyldimethylsilyl (TBDMS). All other variables in Scheme 11 are defined according to the scope of the present invention.

Scheme 10

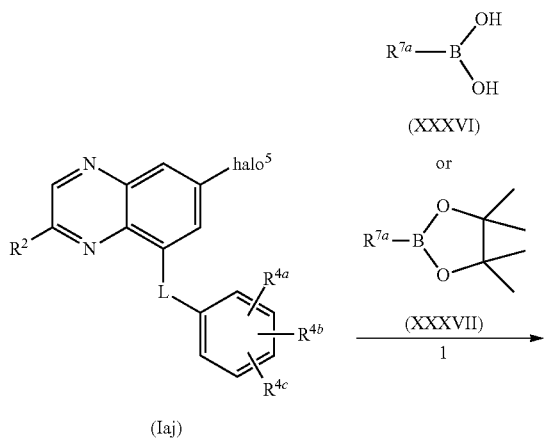

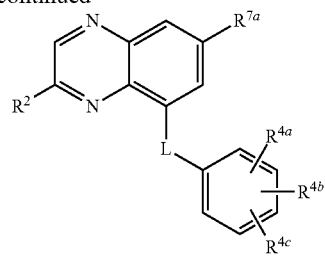

Scheme 11

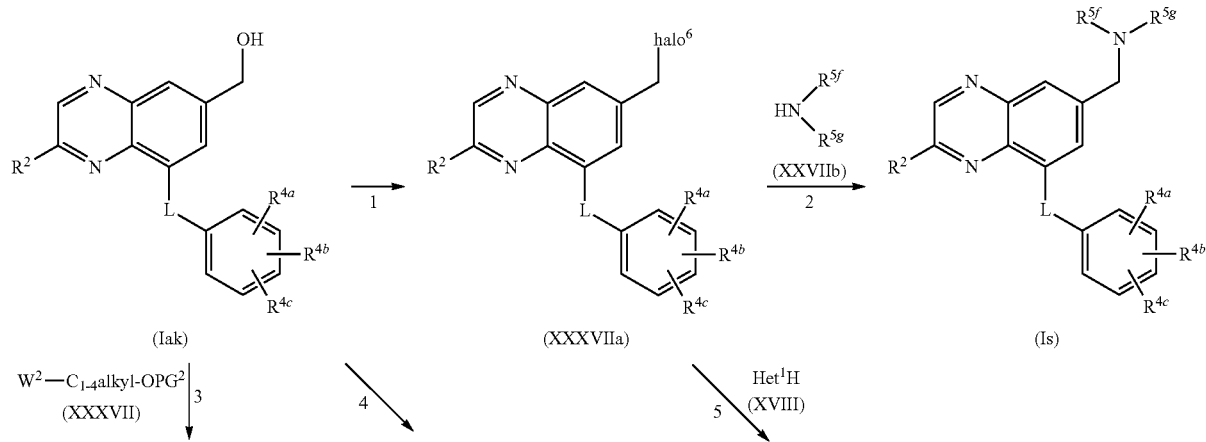

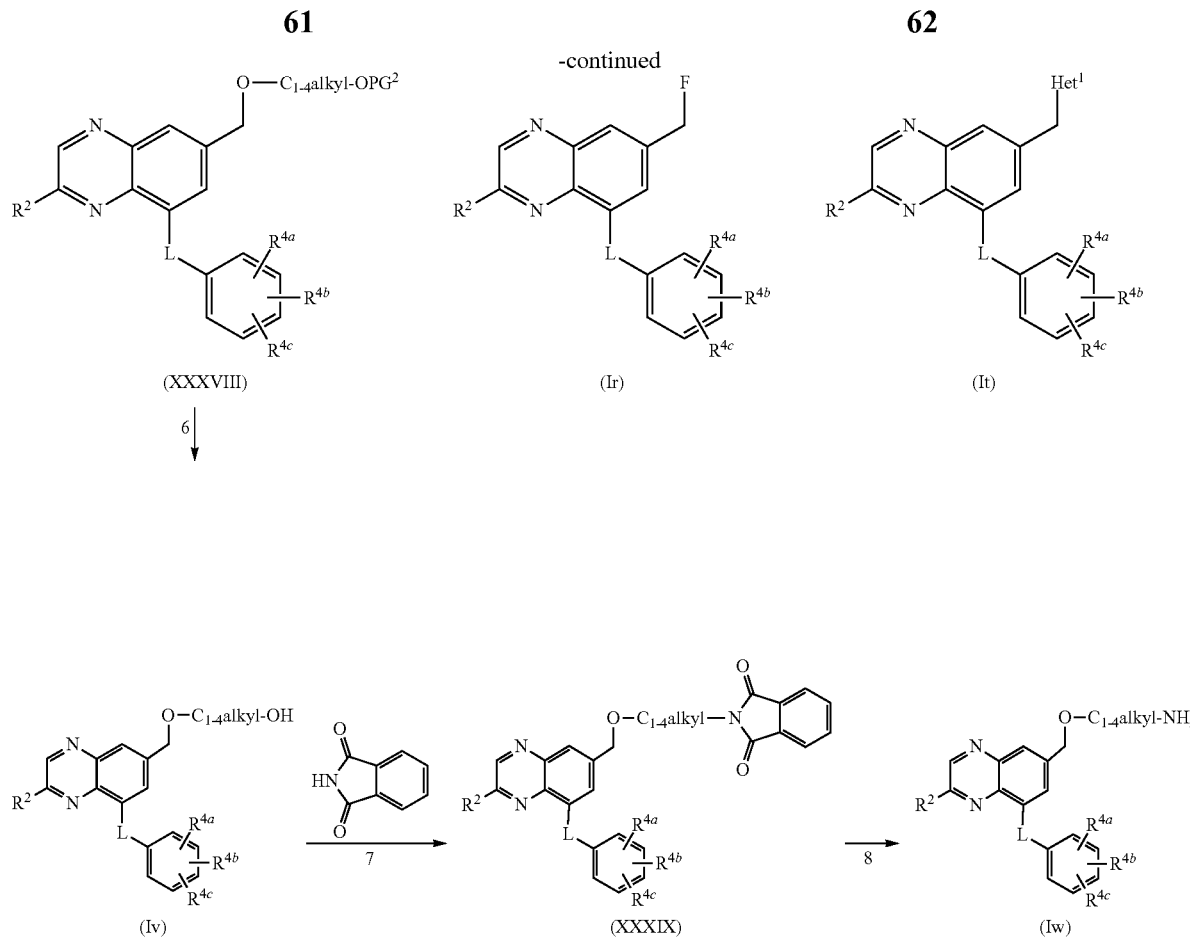

In Scheme 11, the following reaction conditions apply:

1: in the presence of a suitable halogenating reagent such as for example thionyl chloride, in the presence of a suitable solvent such as for example dichloromethane, at a suitable temperature such as for example room temperature;

2: in the presence of a suitable solvent such as for example acetonitrile, at a suitable temperature such as for example 80° C.;

3: in the presence of a suitable deprotonating reagent such as for example sodium hydride, a suitable solvent such as for example N,N-dimethylformamide, at a suitable temperature such as for example room temperature;

4: in the presence of a suitable fluorinating reagent such as for example diethylaminosulfur trifluoride, a suitable solvent such as for example dichloromethane, at a suitable temperature such as for example room temperature;

5: in the presence of a suitable solvent such as for example acetonitrile, at a suitable temperature such as for example 80° C.;

6: in the presence of a suitable acid such as for example trifluoroacetic acid, a suitable solvent such as for example methanol, at a suitable temperature such as room temperature;

7: in the presence of a suitable reagent such as for example di-tert-butyl azodicarboxylate, a suitable phosphine such as for example triphenylphosphine, a suitable solvent such as for example tetrahydrofuran, at a suitable temperature such as for example room temperature;

8: in the presence of a suitable reagent such as for example hydrazine monohydrate, a suitable solvent such as for example ethanol, at a suitable temperature such as for example 80° C.

Compounds of formula (I) wherein Y is $Y^5$ being $CR^3$ and $R^3$ is defined $C_{2-4}$alkyl substituted with one substituent selected from the group consisting of fluoro, —$NR^{5f}R^{5g}$, $Het^1$, —O—$C_{1-4}$alkyl-OH, and —O—$C_{1-4}$alkyl-$NH_2$ can be prepared from the aldehyde I(k) using coupling such as Wittig or Homer Emmons olefinaltion with the appropriate coupling partner followed by reduction of the double bond.

In general, compounds of formula (I) wherein Y is $Y^6$ being $CR^3$ and $R^3$ is defined as $C_{1-4}$alkyl substituted with one substituent selected from the group consisting of —O—(C═O)—CH($NH_2$)—$C_{1-4}$alky 1, —O—(C═O)—CH($NH_2$)—$C_{1-4}$alkyl-Ar and

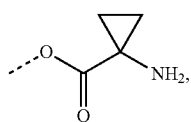

said compounds being respectively represented by formula (Ix), (Iy) and (Iz) can be prepared according to the following reaction Scheme 12 wherein $PG^3$ is defined as a protective group such for example Boc. All other variables in Scheme 12 are defined as above or according to the scope of the present invention.

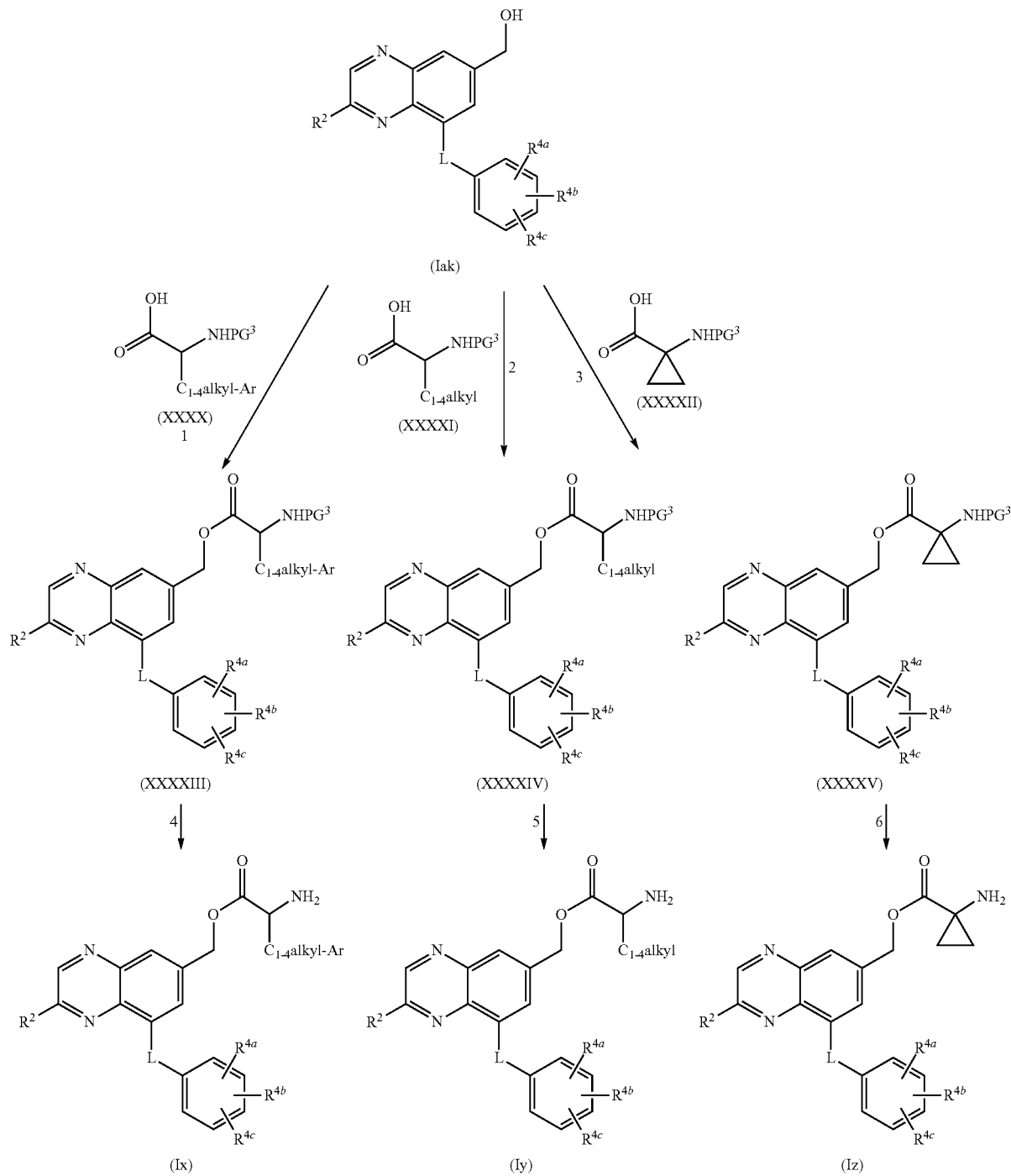

Scheme 12

In Scheme 12, the following reaction conditions apply:
1: in the presence of a suitable coupling reagent such as for example 1-[bis(dimethylamino)methylene]-1H-1,2,3-Triazolo[4,5-b]pyridinium, 3-oxide, a suitable additive such as for example dimethylaminopyridine, a suitable base such as for example diisopropylethylamine, and in a suitable solvent such as for example of DMF;
2: in the presence of an acide such as for example trifluoroacetic acid or hydrogen chloride in a suitable solvent such as for example dichloromethane or methanol. Alternatively, in the presence of palladium on charcoal, in a suitable solvent such as methanol under an atmosphere of hydrogen.

Intermediates of formula (XIXaa) when Y is $Y^7$ being $CR^3$ wherein $R^3$ is defined as —(C=O)—O—$C_{1-4}$alkyl used in the above Scheme 6 can alternatively be prepared according to the following reaction scheme 13 wherein $halo^1$ is defined as above. All other variables in Scheme 13 are defined according to the scope of the present invention.

Scheme 13

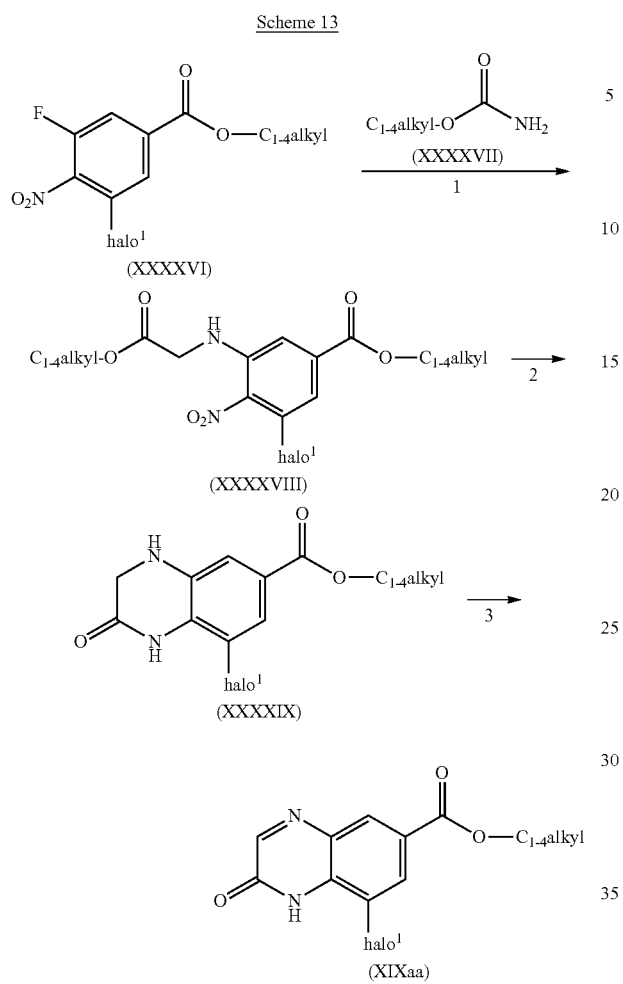

Scheme 14

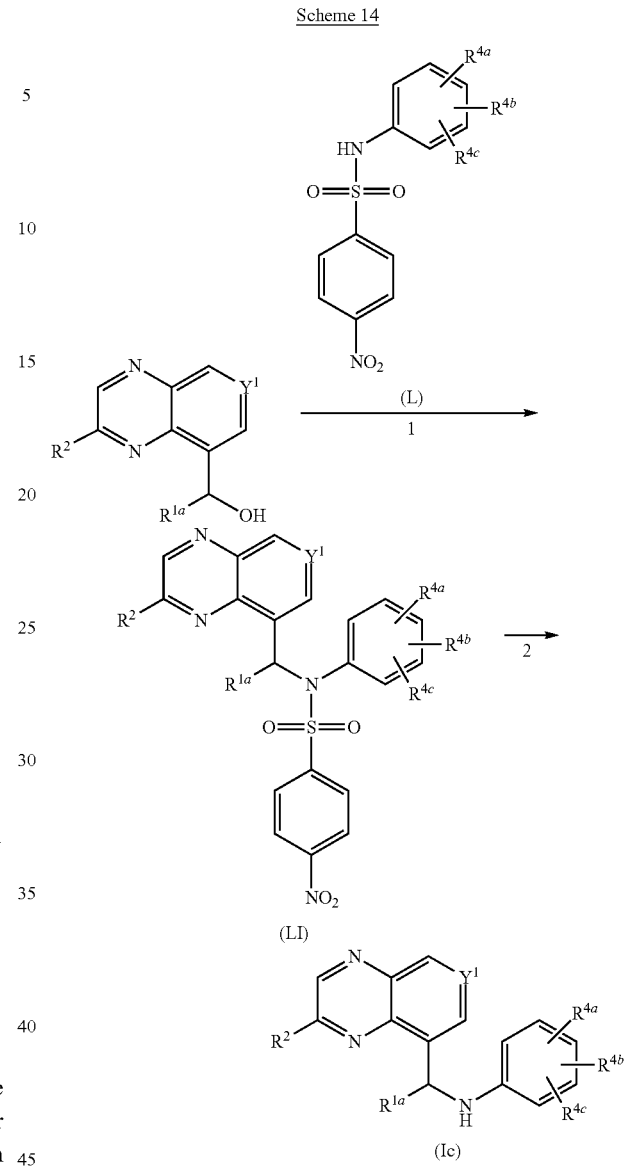

In Scheme 13, the following reaction conditions apply:

1: in the presence of a suitable base such as for example diisopropylethylamine, a suitable solvent such as for example dimethylacetamide, at a suitable temperature such as room temperature;

2: in the presence of a suitable reducing reagent such as for example Tin(II) chloride dihydrate, a suitable solvent such as for example ethanol, at a suitable temperature such as 80° C.;

3: in the presence of a suitable oxidative reagent such as for example manganese dioxide, a suitable solvent such as for example dichloromethane at a suitable temperature such as room temperature.

In general, compounds of formula (I), wherein Y is $Y_1$ being N or $CR^3$ wherein $R^3$ is defined as —$C_{1-4}$alkyl, —(C=O)—O—$C_{1-4}$alkyl, —(C=O)—O—$NR^{5a}R^{5b}$, —C(=O)—$Het^1$ or halo, said compounds being represented by formula (Ic), already described in scheme 2, can alternatively be prepared according to the following reaction Scheme 14. All variables in Scheme 14 are defined according to the scope of the present invention.

In Scheme 14, the following reaction conditions apply:

1: in the presence of a suitable reagent such as for example cyanomethylenetributylphosphorane, a suitable solvent such as for example toluene, at a suitable temperature such as for example 60° C., optionally in a sealed vessel;

Alternatively, in the presence of a suitable reagent such as for example diisopropylazodicarboxylate, a suitable phosphine such as for example tributylphosphine, in a suitable solvent such as for example tetrahydrofuran, keeping temperature at 0° C. during reagents addition and then, increase to 30° C.;

2: in the presence of a suitable acid such as for example thioglycolic acid, a suitable base such as for example 1,8-diazabicyclo(5.4.0)undec-7-ene, a suitable solvent such as for example acetonitrile, at a suitable temperature such as room temperature.

Intermediates of formula (LIII) and (LIV), wherein Y is $Y^8$ being $CR^3$ wherein $R^3$ is defined as —(C=O)—O—$NR^{5a}R^{5b}$, —C(=O)—$Het^1$, which may be used as starting material in the above Schemes 2 and 5 can be prepared according to the following reaction Scheme 15. All variables in Scheme 15 are defined as before or according to the scope of the present invention.

Scheme 15

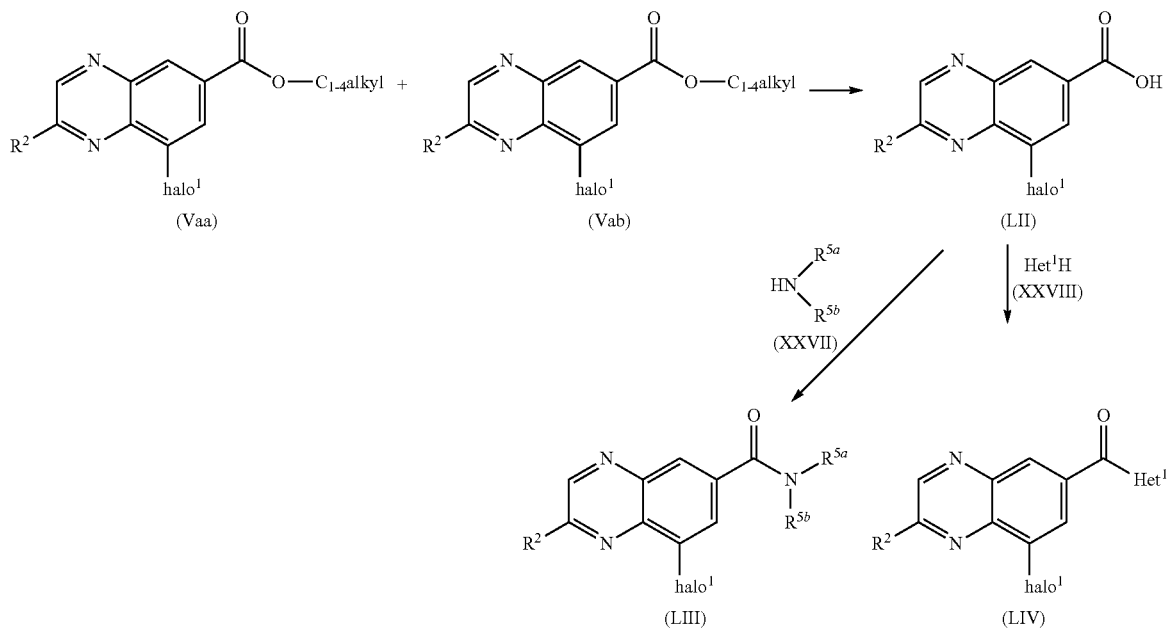

In Scheme 15, the following reaction conditions apply:

1: in the presence of a suitable base such as for example lithium hydroxide monohydrate or sodium hydroxide, a suitable solvent such as for example a mixture of water and tetrahydrofuran or a mixture of water, ethanol and tetrahydrofuran, at a suitable temperature such as room temperature;

2: in the presence of a suitable coupling reagent such as for example HBTU or 1,1'-carbonyldiimidazole, a suitable base such as for example ²diisopropylethylamine or 1,8-diazabicyclo[5.4.0]undec-7-ene, a suitable solvent such as for example N,N-dimethylformamide or methyltetrahydrofuran, at a suitable temperature such as for example room temperature.

In general, compounds of formula (I) wherein Y is $Y^9$ being $CR^3$ and $R^3$ is defined as —$CH_2$—$NH_2$, said compounds being represented by formula (Iaa) can be prepared according to the following reaction Scheme 16. All variables in Scheme 16 are defined as above or according to the scope of the present invention.

Scheme 16

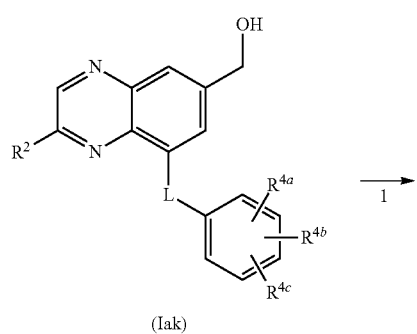

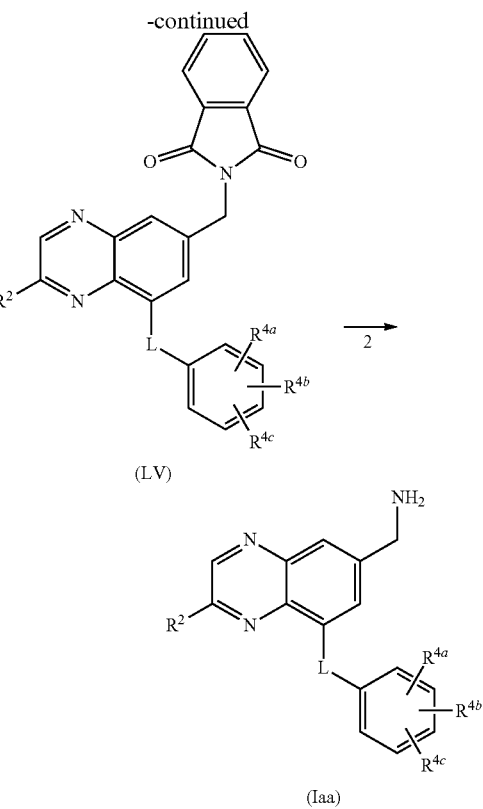

In Scheme 16, the following reaction conditions apply:

1: in the presence of a suitable reagent such as for example di-tert-butyl azodicarboxylate, a suitable phosphine such as for example triphenylphosphine, a suitable solvent such as for example tetrahydrofuran, at a suitable temperature such as for example 40° C.;

2: in the presence of a suitable reagent such as for example hydrazine monohydrate, a suitable solvent such as for example methanol, at a suitable temperature such as for example 70° C.

Intermediates of formula (LIX) (subgroup of intermediates of formula (XI) used in the above Scheme 2) wherein Y is $Y^{10}$ being $CR^3$ wherein $R^3$ is defined as —(C=O)—O—$C_{1-4}$alkyl, can be prepared in enantiomerically pure form according to the following reaction Scheme 17. All variables in Scheme 17 are defined according to the scope of the present invention.

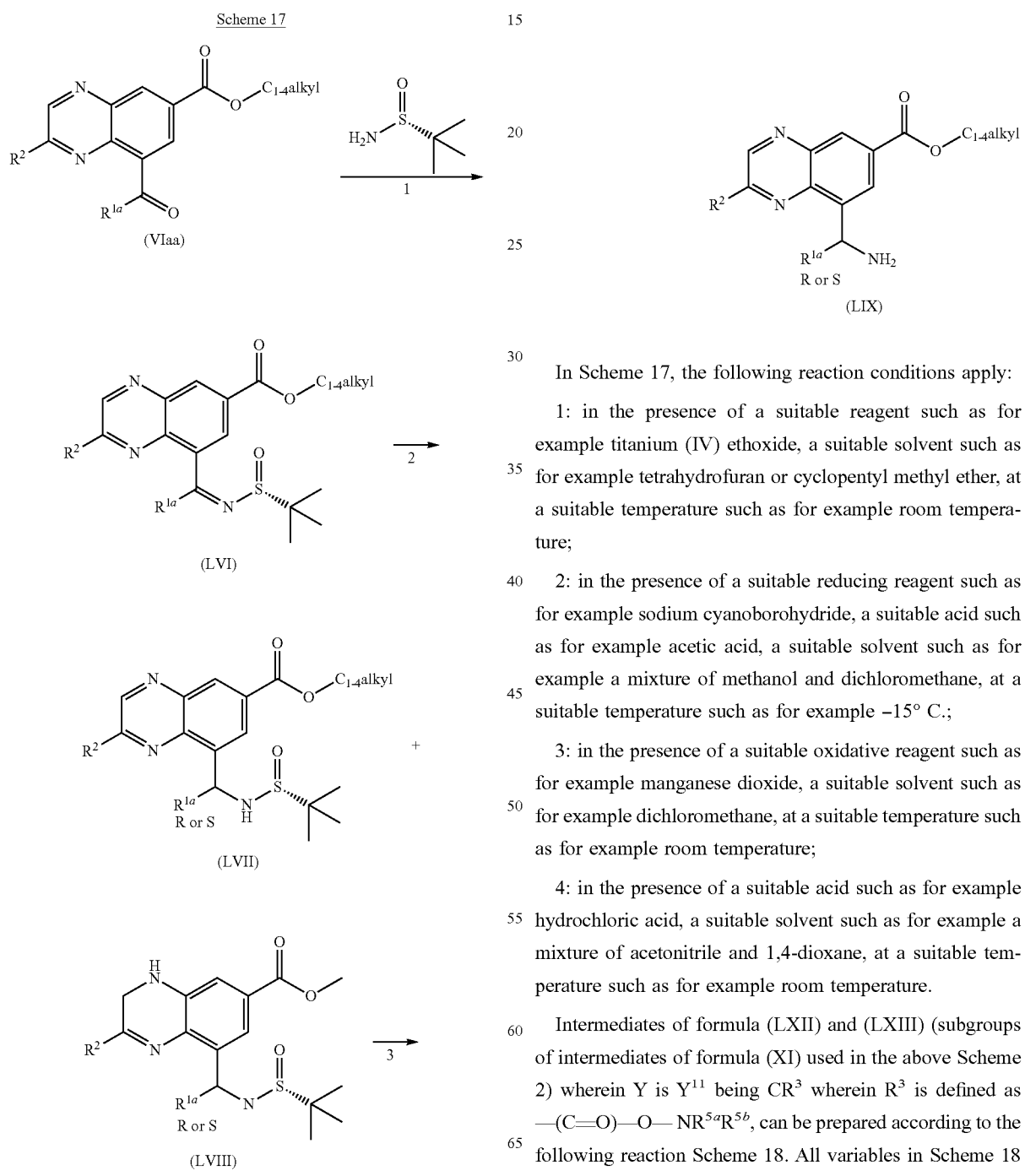

In Scheme 17, the following reaction conditions apply:

1: in the presence of a suitable reagent such as for example titanium (IV) ethoxide, a suitable solvent such as for example tetrahydrofuran or cyclopentyl methyl ether, at a suitable temperature such as for example room temperature;

2: in the presence of a suitable reducing reagent such as for example sodium cyanoborohydride, a suitable acid such as for example acetic acid, a suitable solvent such as for example a mixture of methanol and dichloromethane, at a suitable temperature such as for example −15° C.;

3: in the presence of a suitable oxidative reagent such as for example manganese dioxide, a suitable solvent such as for example dichloromethane, at a suitable temperature such as for example room temperature;

4: in the presence of a suitable acid such as for example hydrochloric acid, a suitable solvent such as for example a mixture of acetonitrile and 1,4-dioxane, at a suitable temperature such as for example room temperature.

Intermediates of formula (LXII) and (LXIII) (subgroups of intermediates of formula (XI) used in the above Scheme 2) wherein Y is $Y^{11}$ being $CR^3$ wherein $R^3$ is defined as —(C=O)—O—$NR^{5a}R^{5b}$, can be prepared according to the following reaction Scheme 18. All variables in Scheme 18 are defined according to the scope of the present invention.

Scheme 18

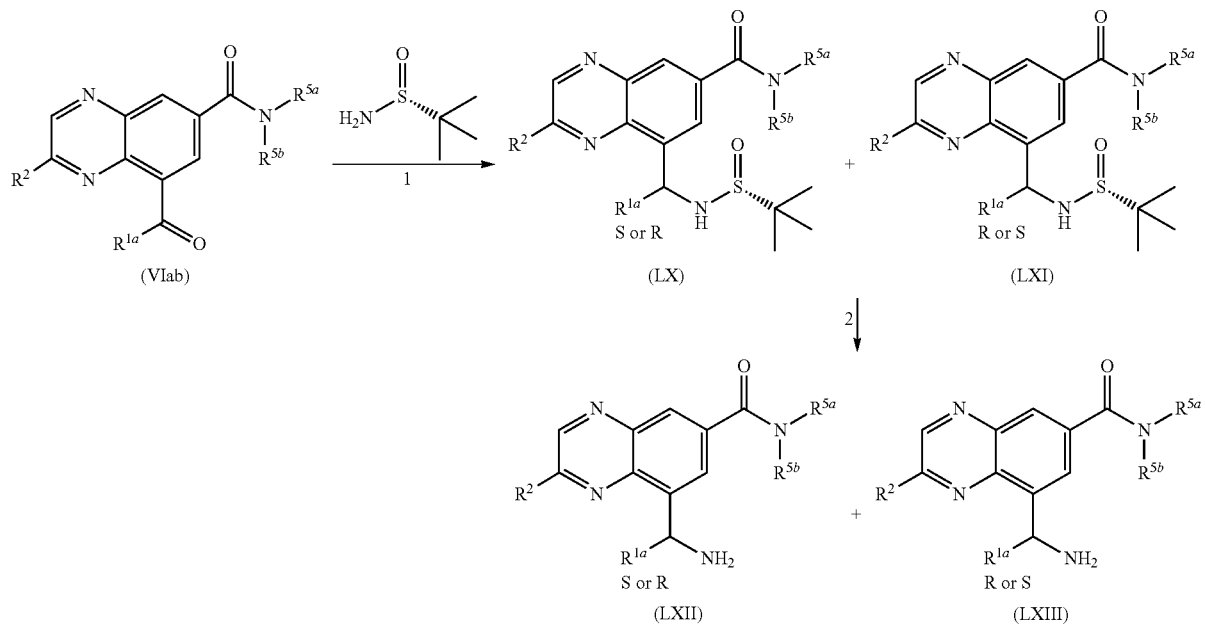

In Scheme 18, the following reaction conditions apply:

1: in the presence of a suitable reagent such as for example titanium (IV) ethoxide, a suitable solvent such as for example tetrahydrofuran or cyclopentyl methyl ether, at a suitable temperature such as for example ranged from room temperature to solvent reflux; then, in the presence of a suitable reducing reagent such as for example sodium borohydride, at a suitable temperature such as for example ranged between −50° C. and room temperature;

2: in the presence of a suitable acid such as for example hydrochloric acid, a suitable solvent such as for example 1,4-dioxane, at a suitable temperature such as for example room temperature.

In general, compounds of formula (I) wherein L is $L^1$ being —$CHR^{1a}$—X— or —X—$CHR^{1c}$—; and Y is $Y^{12}$ being $CR^3$ wherein $R^3$ is defined as said compounds being represented respectively by formula (Iab) and (Iac), can be prepared according to the following reaction Scheme 19.

For the purpose of Scheme 19, X represents O, S, or $NR^{1b}$;

$R^{1a}$ represents $C_{1-4}$alkyl;

$R^{1c}$ represents hydrogen or $C_{1-4}$alkyl;

$R^{1b}$ represents hydrogen, $C_{1-4}$alkyl, —$CH_2$—C(=O)—$NR^{6a}R^{6b}$, or $C_{1-4}$alkyl substituted with one substituent selected from the group consisting of hydroxyl, —O—$C_{1-4}$alkyl, and —$NR^{6c}R^{6d}$;

or $R^{1b}$ is taken together with $R^{1a}$ or $R^{1c}$ to form —$(CH_2)_3$—;

or $R^{1b}$ is taken together with $R^{1c}$ to form —$(CH_2)_2$— or —$(CH_2)_4$—.

All other variables in Scheme 19 are defined according to the scope of the present invention.

Scheme 19

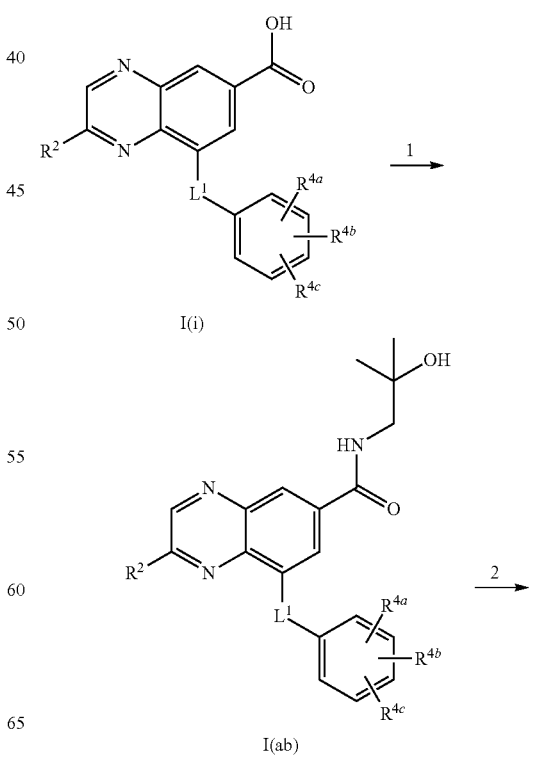

-continued

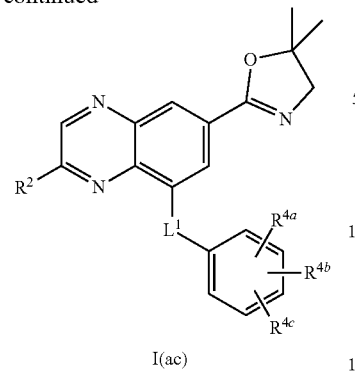

I(ac)

Scheme 20

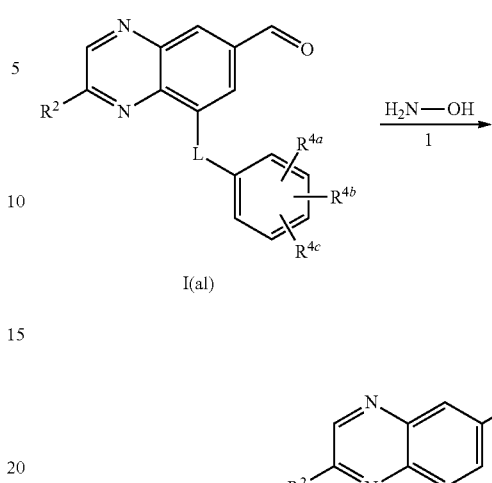

In Scheme 19, the following reaction conditions apply:

1: in the presence of a suitable coupling reagent such as for example HBTU or 1,1'-carbonyldiimidazole, a suitable base such as for example diisopropylethylamine or 1,8-diazabicyclo[5.4.0]undec-7-ene, a suitable solvent such as for example N,N-dimethylformamide or methyltetrahydrofuran, at a suitable temperature such as for example room temperature;

2: in the presence of a suitable halogenating reagent such as for example thionyl chlorine, a suitable solvent such as for example dichloromethane, at a suitable temperature such as for example room temperature.

In general, compounds of formula (I) wherein Y is $Y^{13}$ being $CR^3$ wherein $R^3$ is defined as —CH=N—OH, said compounds being respectively represented by formula (Iam), can be prepared according to the following reaction Scheme 20 wherein all other variables are defined according to the scope of the present invention.

In Scheme 20, the following reaction conditions apply:

1: in the presence of a suitable solvent such as for example ethanol, at a suitable temperature such as for example 100° C.

In general, compounds of formula (I) wherein L is defined as —$CH_2$—X—; and Y is $Y^1$ being being N or $CR^3$ wherein $R^3$ is defined as —$C_{1-4}$alkyl, —(C=O)—O—$C_{1-4}$alkyl. —(C=O)—$NR^{5a}R^{5b}$, —C(=O)—$Het^1$ or halo; said compounds being represented respectively by formula (Iba) and (Iea), can be prepared according to the following reaction Scheme 21.

All other variables in Scheme 21 are defined as above or according to the scope of the present invention.

Scheme 21

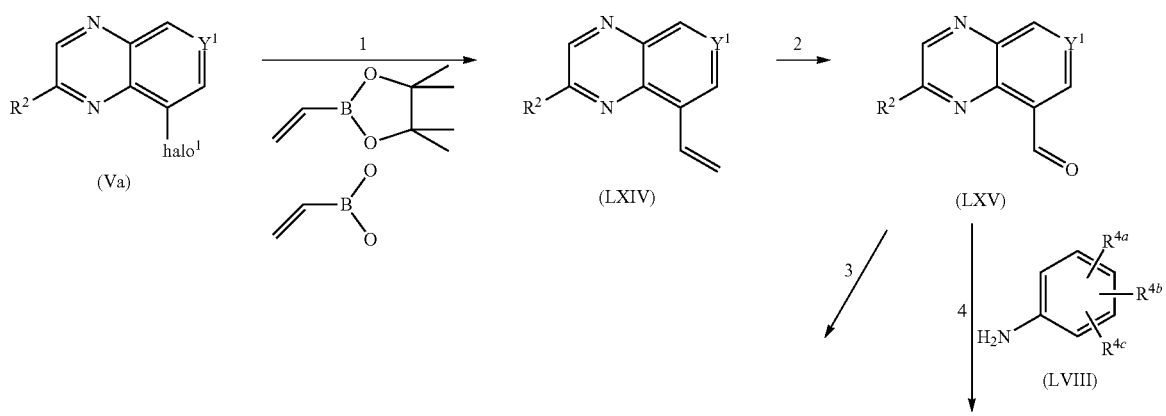

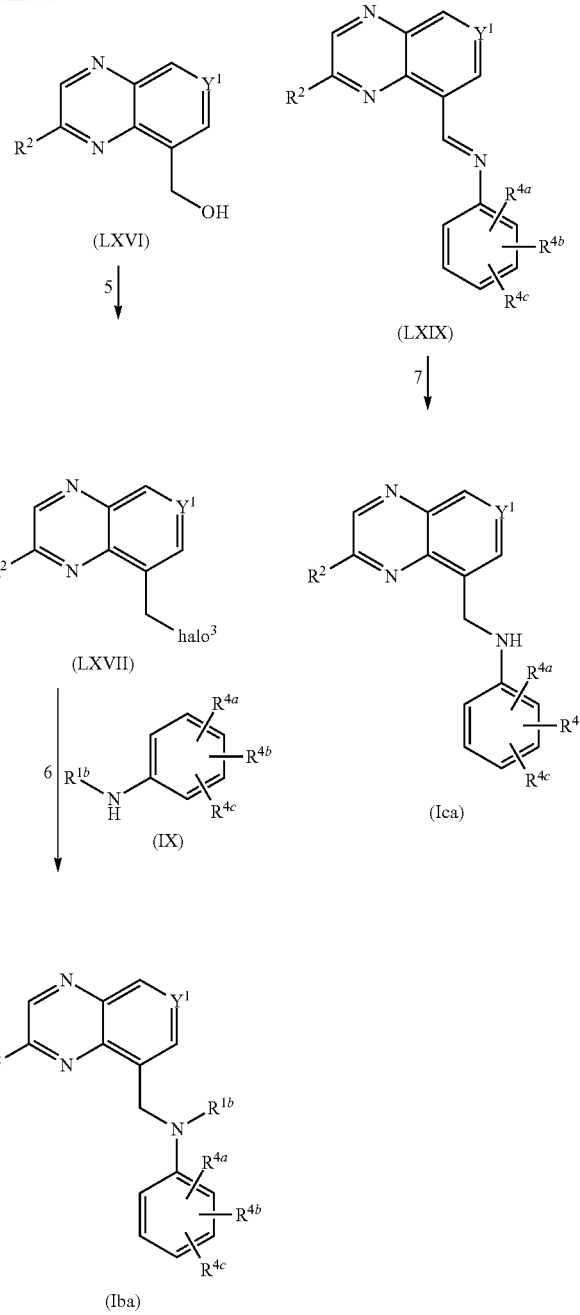

In Scheme 21, the following reaction conditions apply:

1: in the presence of a suitable catalyst such as for example [1,1′-bis(diphenylphosphino)ferrocene]dichloropalladium(II), complex with dichloromethane, a suitable base such as for example potassium phosphate, in a suitable solvent such as for example a mixture of dioxane and water, at a suitable temperature such as 90° C., optionally in a sealed reactor;

2: in the presence of a suitable oxidative agent such as for example osmium tetroxide and sodium periodate, in a suitable solvent such as for example tetrahydrofuran;

3: in the presence of a suitable reducing reagent such as for example sodium borohydride, a suitable solvent such as for example a mixture of methanol and dichloromethane, at a suitable temperature such as room temperature, in the presence or not of a suitable additive such as for example cerium (III) chloride;

4: in the presence of molecular sieve 4 Å, in a suitable solvent such as for example dichloromethane, optionally in a sealed reactor;

5: in the presence of a suitable halogenating reagent such as for example phosphorous tribromide or thionyl chloride, a suitable solvent such as for example dichloromethane, at a suitable temperature such as for example 10° C. or room temperature;

6: in the presence of a suitable solvent such as for example N,N-dimethylformamide, at a suitable temperature such as for example 50 or 60° C., in a sealed vessel;

7: in the presence of a suitable reducing agent such as for example sodium triacetoxyborohydride, in a suitable solvent such as for example dichloromethane;

In general, compounds of formula (I) wherein L is defined as —CH($C_{1-4}$alkyl-OH)—X—, and Y is defined as $CR^3$ wherein $R^3$ is defined as —(C=O)—$NR^{3a}R^{5b}$; said compounds being represented by formula I(ao), can be prepared according to the following reaction Scheme 22. All other variables in Scheme 22 are defined as above or according to the scope of the present invention.

Scheme 22

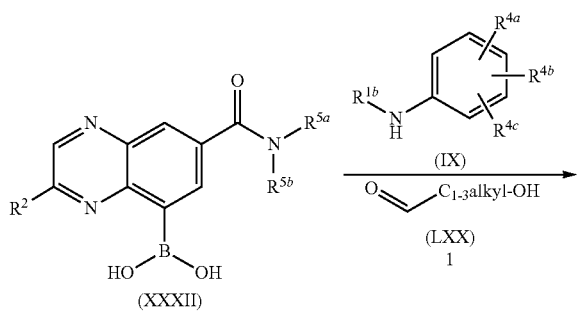

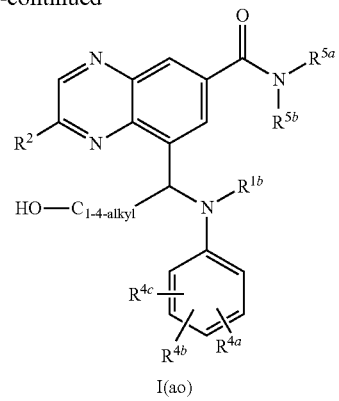

I(ao)

In Scheme 22, the following reaction conditions apply:

1: in a suitable solvent such as for example hexafluoroisopropanol.

In general, compounds of formula (I) wherein L is $L^1$ being —$CHR^{1a}$—X— or —X—$CHR^{1c}$—; and Y is $Y^a$ being $CR^3$ wherein $R^3$ is defined as —(C=O)—NH—$C_{1-4}$alkyl-$Het^1$, —(C=O)—N($C_{1-4}$alkyl)—$C_{1-4}$alkyl-$Het^1$, —$CH_2$—$NHHet^2$ or as —(C=O)—NH—$C_{1-4}$alkyl-$Het^2$, said compounds being represented respectively by compounds of formula I(ap), I(aq), I(ar), and I(as), can be prepared according to the following reaction Scheme 23.

All other variables in Scheme 23 are defined according to the scope of the present invention.

Scheme 23

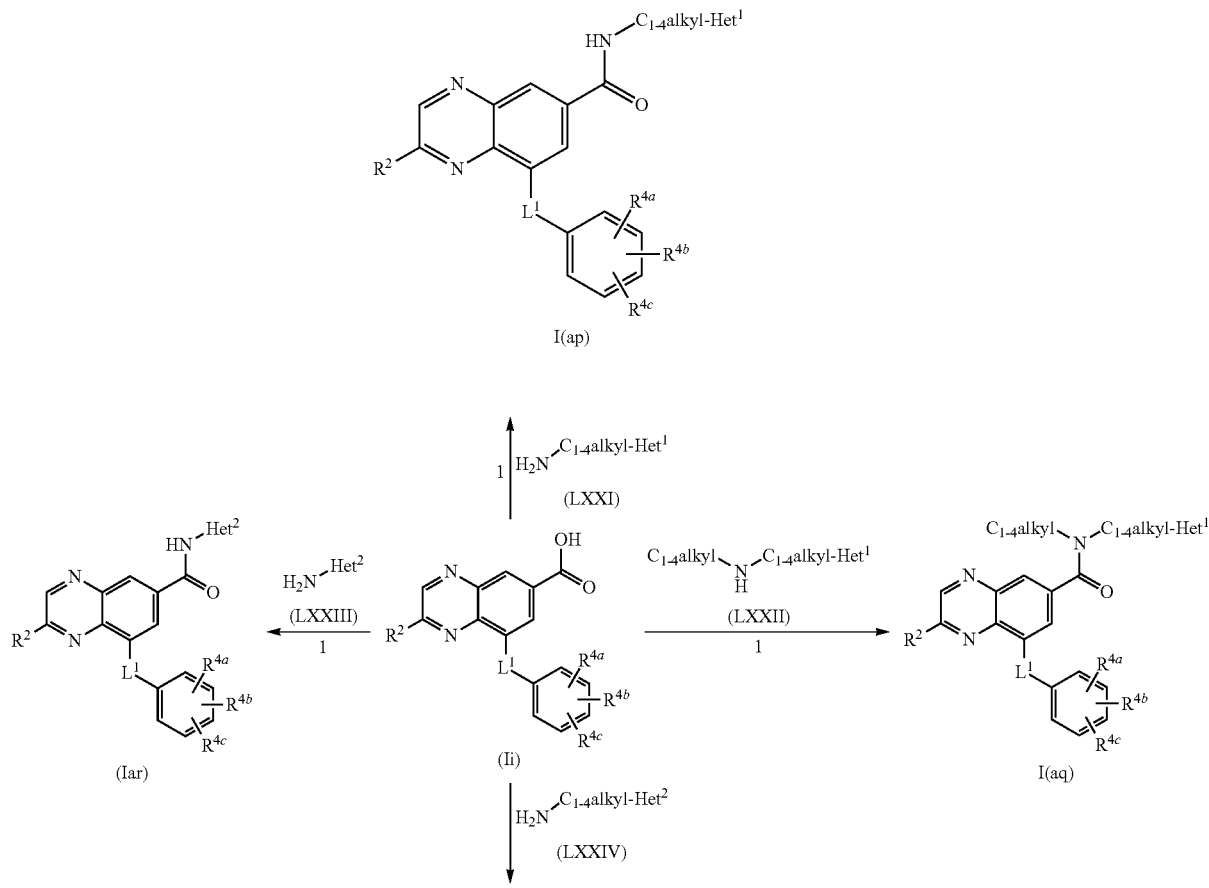

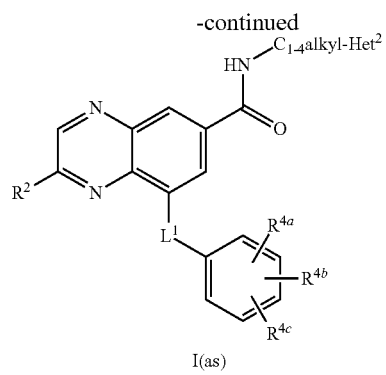

I(as)

In Scheme 23, the following reaction conditions apply:

1: in the presence of a suitable coupling reagent such as for example N,N,N',N'-Tetramethyl-O-(1H-benzotriazol-1-yl)uronium hexafluorophosphate, O-(Benzotriazol-1-yl)-N,N,N',N'-tetramethyluronium hexafluorophosphate (HBTU), (1-Cyano-2-ethoxy-2-oxoethylidenaminooxy)dimethyl-amino-morpholino-carbenium hexafluorophosphate (COMU), 1-[Bis(dimethylamino)methylene]-1H-1,2,3-triazolo[4,5-b]pyridinium 3-oxid hexafluorophosphate (HATU) or 1,1'-carbonyldiimidazole, a suitable base such as for example diisopropylethylamine, triethylamine or 1,8-diazabicyclo[5.4.0]undec-7-ene, a suitable solvent such as for example A, A-di methyl formamide or methyltetrahydofuran, at a suitable temperature such as for example room temperature.

A subgroup of the Intermediates of formula (VII) used in the above Scheme 2, hereby named Intermediates of formula (VIIaa) wherein $R^2$ is restricted to

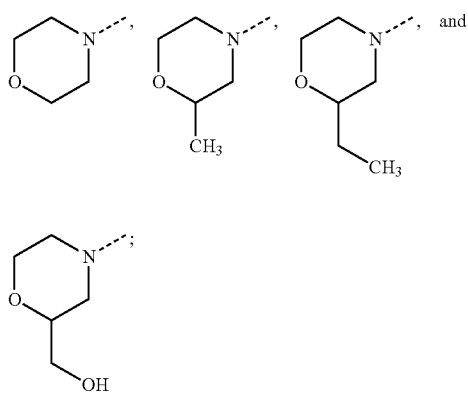

and Y is restricted to —C—(C=O)—O—$C_{1-4}$alkyl can be prepared according to the following reaction Scheme 24. All other variables in Scheme 24 are defined according to the scope of the present invention.

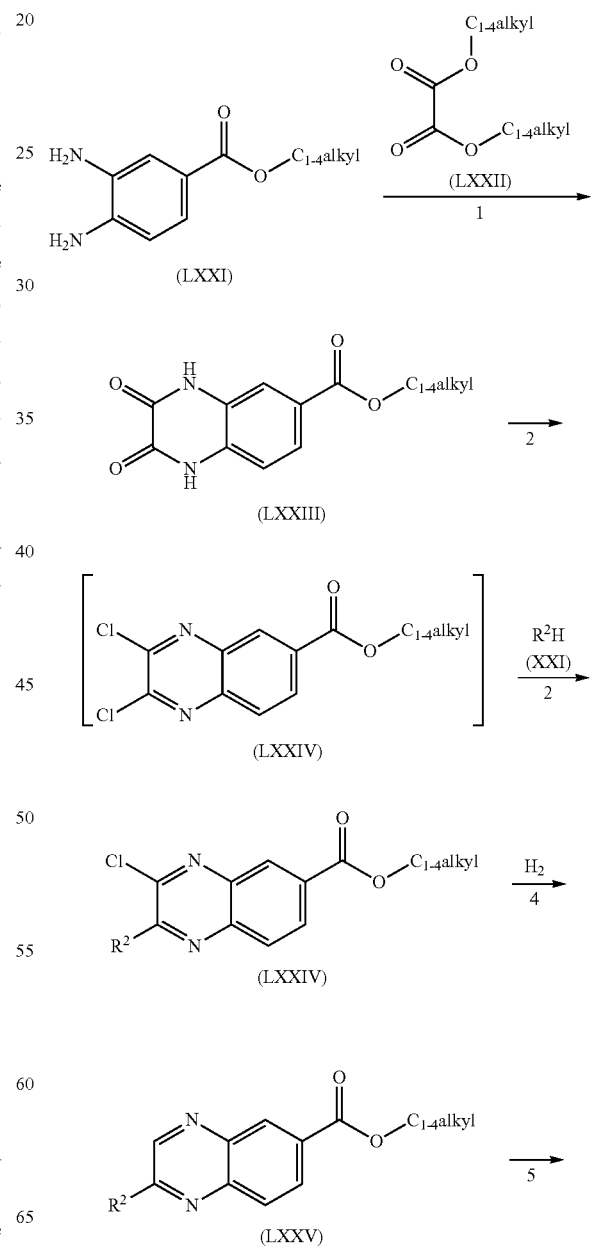

Scheme 24

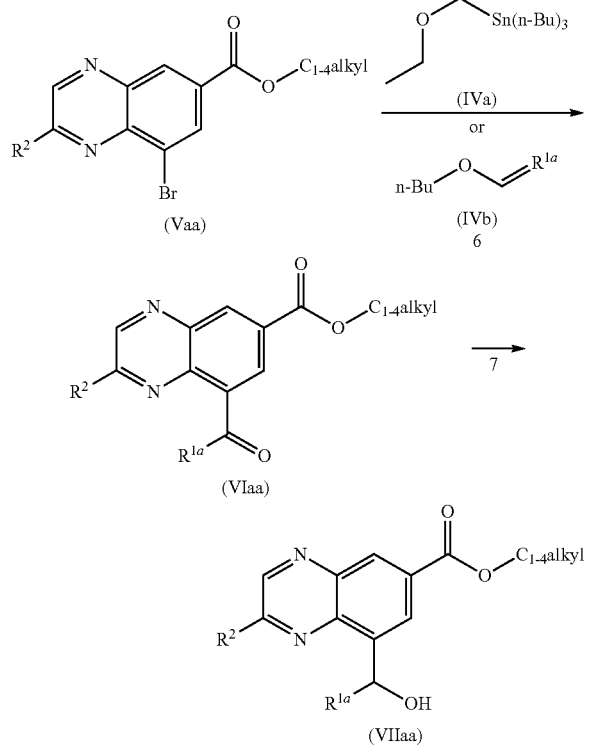

In Scheme 24, the following reaction conditions apply:

1: in a suitable solvent such as for example toluene at a suitable temperature such as reflux;

2: in the presence of a suitable chlorinating reagent such as for example thionyl chloride, a suitable additive such as for example dimethylformide, in a suitable solvent such as for example 1,2-dichloroethane at a suitable temperature such as 80° C.;

3: in the presence of a suitable base such as for example trimethylamine, in a suitable solvent such as for example 2-methyltetrahydrofuran;

4: in the presence of a suitable base such as for example 1,8-Diazabicyclo[5.4.0]undec-7-ene, a suitable catalyst such as for example palladium on carbon (Pd/C), in a suitable solvent such as for example dichloromethane;

Then, after filtration of the catalyst, filtrate is treated with a suitable oxy dating agent such as manganese dioxide, at a suitable temperature such as for example 30 to 40° C.;

5: in the presence of a suitable halogenating agent such as for example dimethyldibromohydantoin, in a suitable solvent such as for example dichloromethane at a suitable temperature such as for example 30 to 40° C.;

6: In case of reagent (IVa), in the presence of a suitable catalyst such as for example dichlorobis(triphenylphosphine) palladium (II) or tetrakis(triphenylphosphine)palladium(0) (Pd(Ph$_3$)$_4$), a suitable solvent such as for example 1,4-dioxane, at a suitable temperature such as for example 100° C. in a sealed or an open vessel; Then, in the presence of a suitable acid such as for example aqueous HCl, at a suitable temperature such as room temperature;

In case of reagent (IVb), in the presence of a suitable catalyst such as for example Pd(OAc)$_2$, a suitable ligand such as for example 1,3-Bis(diphenylphosphino)propane (DPPP), a suitable base such as for example triethylamine, a suitable solvent such as for example dimethylsulfoxide, at a suitable temperature such as 100° C.; Then, in the presence of a suitable acid such as for example HCl, at a suitable temperature such as 0° C.;

7: in the presence of an enantioselective reducing agent such as for example (−)-B-chlorodiisopinocampheylborane, in a suitable solvent such as for example dichloromethane, at a suitable temperature such as −35° C.

In all these preparations, the reaction products may be isolated from the reaction medium and, if necessary, further purified according to methodologies generally known in the art such as, for example, extraction, crystallization, trituration and chromatography.

The chirally pure forms of the compounds of Formula (I) form a preferred group of compounds. It is therefore that the chirally pure forms of the intermediates and their salt forms are particularly useful in the preparation of chirally pure compounds of Formula (I). Also enantiomeric mixtures of the intermediates are useful in the preparation of compounds of Formula (I) with the corresponding configuration.

Pharmacology

It has been found that the compounds of the present invention inhibit PI3Kβ kinase activity, and optionally also have PI3Kδ inhibitory activity.

It is therefore anticipated that the compounds according to the present invention or pharmaceutical compositions thereof may be useful for treating or preventing, in particular treating, of diseases such as cancer, autoimmune disorders, cardiovascular diseases, inflammatory diseases, neurodegenerative diseases, allergy, pancreatitis, asthma, multiorgan failure, kidney diseases, platelet aggregation, sperm motility, transplantation rejection, graft rejection, lung injuries and the like; in particular cancer.

Because the pharmaceutically active compounds of the present invention are active as PI3Kβ inhibitors, they exhibit therapeutic utility in treatment or prevention, in particular treatment, of susceptible neoplasms, particularly those neoplasms that exhibit a PTEN deficiency.

As used herein, the phrase "PTEN deficient" or "PTEN deficiency" shall describe tumors with deficiencies of the tumor suppressor function of PTEN (Phosphatase and Tensin Homolog). Such deficiency includes mutation in the PTEN gene, reduction or absence of PTEN proteins when compared to PTEN wild-type, or mutation or absence of other genes that cause suppression of PTEN function.

"Susceptible neoplasm" as used herein refers to neoplasms which are susceptible to treatment by a kinase inhibitor and particularly neoplasms that are susceptible to treatment by a PI3Kβ inhibitor. Neoplasms which have been associated with inappropriate activity of the PTEN phosphatase and particularly neoplasms which exhibit mutation of PTEN, or mutation of an upstream activator of PI3Kβ kinase or overexpression of an upstream activator of PI3Kβ kinase, and are therefore susceptible to treatment with an PI3Kβ inhibitor, are known in the art, and include both primary and metastatic tumors and cancers. According to an embodiment, description of the treatment of a susceptible neoplasm may be used interchangeably with description of the treatment of a cancer.

According to one embodiment, "susceptible neoplasms" include but are not limited to PTEN-deficient neoplasms listed as follows: brain (gliomas), glioblastomas, leukemias, Bannayan-Zonana syndrome, Cowden disease, Lhermitte-Duclos disease, breast cancer, inflammatory breast cancer, colorectal cancer Wilm's tumor, Ewing's sarcoma, Rhabdomyosarcoma, ependymoma, medulloblastoma, colon cancer, head and neck cancer, liver cancer, kidney cancer, lung cancer, melanoma, squamous cell carcinoma, ovarian cancer, pancreatic cancer, prostate cancer, sarcoma cancer, osteosarcoma, giant cell tumor of bone, thyroid cancer, lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, Plasmacytoma, Immunoblastic large cell leukemia, Mantle cell leukemia, Multiple myeloma, Megakaryoblastic leukemia. Acute megakaryocytic leukemia, promyelocytic leukemia, Erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, cervical cancer, vulval cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor), and testicular cancer.

According to an alternative embodiment, the term "susceptible neoplasm" includes and is limited to hormone refractory prostate cancer, non-small-cell lung cancer, endometrial cancer, gastric cancer, melanoma, head and neck cancer, breast cancer, including tripnegative breast cancer, and glioma.

In an embodiment, the term "susceptible neoplasm" includes and is limited to prostate cancer, in particular hormone refractory prostate cancer.

The compounds of the present invention may also have therapeutic applications in sensitising tumour cells for radiotherapy and chemotherapy.

Hence the compounds of the present invention may be used as "radiosensitizer" and/or "chemosensitizer" or can be given in combination with another "radiosensitizer" and/or "chemosensitizer".

The term "radiosensitizer", as used herein, is defined as a molecule, preferably a low molecular weight molecule, administered to animals in therapeutically effective amounts to increase the sensitivity of the cells to ionizing radiation and/or to promote the treatment of diseases which are treatable with ionizing radiation.

The term "chemosensitizer", as used herein, is defined as a molecule, preferably a low molecular weight molecule, administered to animals in therapeutically effective amounts to increase the sensitivity of cells to chemotherapy and/or promote the treatment of diseases which are treatable with chemotherapeutics.

Several mechanisms for the mode of action of radiosensitizers have been suggested in the literature including: hypoxic cell radiosensitizers (e.g., 2-nitroimidazole compounds, and benzotriazine dioxide compounds) mimicking oxygen or alternatively behave like bioreductive agents under hypoxia; non-hypoxic cell radiosensitizers (e.g., halogenated pyrimidines) can be analogoues of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other diseases.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumour or other therapeutically effective compounds for treating cancer or other disease. Calcium antagonists, for example verapamil, are found useful in combination with antineoplastic agents to establish chemosensitivity in tumor cells resistant to accepted chemotherapeutic agents and to potentiate the efficacy of such compounds in drug-sensitive malignancies.

The invention relates to compounds of Formula (I) and N-oxides, pharmaceutically acceptable addition salts, and solvates thereof, for use as a medicament.

The invention also relates to compounds of Formula (I) and N-oxides, pharmaceutically acceptable addition salts, and solvates thereof, for use in the inhibition of PI3Kβ kinase activity and optionally also for use in the inhibition of PI3Kδ.

The compounds of the present invention can be "anticancer agents", which term also encompasses "anti-tumor cell growth agents" and "anti-neoplastic agents".

The invention also relates to compounds of Formula (I) and N-oxides, pharmaceutically acceptable addition salts, and solvates thereof, for use in the treatment of diseases mentioned above.

The invention also relates to compounds of Formula (I) and N-oxides, pharmaceutically acceptable addition salts, and solvates thereof, for the treatment or prevention, in particular for the treatment, of said diseases.

The invention also relates to compounds of Formula (I) and N-oxides, pharmaceutically acceptable addition salts, and solvates thereof, for the treatment or prevention, in particular in the treatment, of PI3Kβ mediated diseases or conditions.

The invention also relates to compounds of Formula (I) and N-oxides, pharmaceutically acceptable addition salts, and solvates thereof, for the treatment or prevention, in particular in the treatment, of PI3Kβ and optionally PI3Kδ mediated diseases or conditions.

The invention also relates to the use of compounds of Formula (I) and N-oxides, pharmaceutically acceptable addition salts, and solvates thereof, for the manufacture of a medicament.

The invention also relates to the use of compounds of Formula (I) and N-oxides, pharmaceutically acceptable addition salts, and solvates thereof, for the manufacture of a medicament for the inhibition of PI3Kβ.

The invention also relates to the use of compounds of Formula (I) and N-oxides, pharmaceutically acceptable addition salts, and solvates thereof, for the manufacture of a medicament for the inhibition of PI3Kβ and optionally also for the inhibition of PI3Kδ.

The invention also relates to the use of compounds of Formula (I) and N-oxides, pharmaceutically acceptable addition salts, and solvates thereof, for the manufacture of a medicament for the treatment or prevention, in particular for the treatment, of any one of the disease conditions mentioned hereinbefore.

The invention also relates to the use of compounds of Formula (I) and N-oxides, pharmaceutically acceptable addition salts, and solvates thereof, for the manufacture of a medicament for the treatment of any one of the disease conditions mentioned hereinbefore.

The compounds of Formula (I) and N-oxides, pharmaceutically acceptable addition salts, and solvates thereof, can be administered to mammals, preferably humans for the treatment or prevention of any one of the diseases mentioned hereinbefore.

In view of the utility of the compounds of Formula (I) and N-oxides, pharmaceutically acceptable addition salts, and solvates thereof, there is provided a method of treating warm-blooded animals, including humans, suffering from or a method of preventing warm-blooded animals, including humans, to suffer from any one of the diseases mentioned hereinbefore.

Said methods comprise the administration, i.e. the systemic or topical administration, preferably oral administration, of an effective amount of a compound of Formula (I) or a N-oxide, a pharmaceutically acceptable addition salt, or a solvate thereof, to warm-blooded animals, including humans.

Those of skill in the treatment of such diseases could determine the effective therapeutic daily amount from the test results presented hereinafter. An effective therapeutic daily amount would be from about 0.005 mg/kg to 50 mg/kg, in particular 0.01 mg/kg to 50 mg/kg body weight, more in particular from 0.01 mg/kg to 25 mg/kg body weight, preferably from about 0.01 mg/kg to 15 mg/kg, more preferably from about 0.01 mg/kg to about 10 mg/kg, even more preferably from about 0.01 mg/kg to about 1 mg/kg, most preferably from about 0.05 mg/kg to about 1 mg/kg body weight. The amount of a compound according to the present invention, also referred to here as the active ingredient, which is required to achieve a therapeutically effect will of course, vary on case-by-case basis, for example with the particular compound, the route of administration, the age and condition of the recipient, and the particular disorder or disease being treated.

A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

The compounds of the present invention, that can be suitable to treat or prevent cancer or cancer-related conditions, may be administered alone or in combination with one or more additional therapeutic agents. Combination therapy includes administration of a single pharmaceutical dosage formulation which contains a compound of Formula (If a N-oxide, a pharmaceutically acceptable addition salt, or a solvate thereof, and one or more additional therapeutic agents, as well as administration of the compound of Formula (I), a N-oxide, a pharmaceutically acceptable addition salt, or a solvate thereof, and each additional therapeutic agents in its own separate pharmaceutical dosage formulation. For example, a compound of Formula (I), a N-oxide, a pharmaceutically acceptable addition salt, or a solvate thereof, and a therapeutic agent may be administered to the patient together in a single oral dosage composition such as a tablet or capsule, or each agent may be administered in separate oral dosage formulations.

While it is possible for the active ingredient to be administered alone, it is preferable to present it as a pharmaceutical composition.

Accordingly, the present invention further provides a pharmaceutical composition comprising a pharmaceutically acceptable carrier and, as active ingredient, a therapeutically effective amount of a compound of Formula (I), a N-oxide, a pharmaceutically acceptable addition salt, or a solvate thereof.

The carrier or diluent must be "acceptable" in the sense of being compatible with the other ingredients of the composition and not deleterious to the recipients thereof.

For ease of administration, the subject compounds may be formulated into various pharmaceutical forms for administration purposes. The compounds according to the invention, in particular the compounds of Formula (I) and N-oxides, pharmaceutically acceptable addition salts, and solvates thereof, or any subgroup or combination thereof may be formulated into various pharmaceutical forms for administration purposes. As appropriate compositions there may be cited all compositions usually employed for systemically administering drugs.

To prepare the pharmaceutical compositions of this invention, an effective amount of the particular compound as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions containing a compound of Formula (I), a N-oxide, a pharmaceutically acceptable addition salt, or a solvate thereof, may be formulated in an oil for prolonged action. Appropriate oils for this purpose are, for example, peanut oil, sesame oil, cottonseed oil, corn oil, soybean oil, synthetic glycerol esters of long chain fatty acids and mixtures of these and other oils. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. Acid or base addition salts of compounds of Formula (I) due to their increased water solubility over the corresponding base or acid form, are more suitable in the preparation of aqueous compositions.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

In order to enhance the solubility and/or the stability of the compounds of Formula (I) and N-oxides, pharmaceutically acceptable addition salts, and solvates thereof, in pharmaceutical compositions, it can be advantageous to employ α-, β- or γ-cyclodextrins or their derivatives, in particular hydroxy alkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the invention in pharmaceutical compositions.

Depending on the mode of administration, the pharmaceutical composition will preferably comprise from 0.05 to 99% by weight, more preferably from 0.1 to 70% by weight, even more preferably from 0.1 to 50% by weight of the compound of Formula (I), a N-oxide, a pharmaceutically acceptable addition salt, or a solvate thereof, and from 1 to 99.95% by weight, more preferably from 30 to 99.9% by weight, even more preferably from 50 to 99.9% by weight of a pharmaceutically acceptable carrier, all percentages being based on the total weight of the composition.

As another aspect of the present invention, a combination of a compound of the present invention with another anti-cancer agent is envisaged, especially for use as a medicine, more specifically for use in the treatment of cancer or related diseases.

For the treatment of the above conditions, the compounds of the invention may be advantageously employed in combination with one or more other medicinal agents, more particularly, with other anti-cancer agents or adjuvants in cancer therapy. Examples of anti-cancer agents or adjuvants (supporting agents in the therapy) include but are not limited to:
- platinum coordination compounds for example cisplatin optionally combined with amifostine, carboplatin or oxaliplatin;
- taxane compounds for example paclitaxel, paclitaxel protein bound particles (Abraxane™) or docetaxel;
- topoisomerase I inhibitors such as camptothecin compounds for example irinotecan, SN-38, topotecan, topotecan hcl;
- topoisomerase II inhibitors such as anti-tumour epipodophyllotoxins or podophyllotoxin derivatives for example etoposide, etoposide phosphate or teniposide;
- anti-tumour vinca alkaloids for example vinblastine, vincristine or vinorelbine;
- anti-tumour nucleoside derivatives for example 5-fluorouracil, leucovorin, gemcitabine, gemcitabine hcl, capecitabine, cladribine, fludarabine, nelarabine;
- alkylating agents such as nitrogen mustard or nitrosourea for example cyclophosphamide, chlorambucil, carmustine, thiotepa, mephalan (melphalan), lomustine, altretamine, busulfan, dacarbazine, estramustine, ifosfamide optionally in combination with mesna, pipobroman, procarbazine, streptozocin, temozolomide, uracil;
- anti-tumour anthracycline derivatives for example daunorubicin, doxorubicin optionally in combination with dexrazoxane, doxil, idarubicin, mitoxantrone, epirubicin, epirubicin hcl, valrubicin;
- molecules that target the IGF-1 receptor for example picropodophilin;
- tetracarcin derivatives for example tetrocarcin A;
- glucocorticoïden for example prednisone;
- antibodies for example trastuzumab (HER2 antibody), rituximab (CD20 antibody), gemtuzumab, gemtuzumab ozogamicin, cetuximab, pertuzumab, bevacizumab, alemtuzumab, eculizumab, ibritumomab tiuxetan, nofetumomab, panitumumab, tositumomab, CNTO 328;
- estrogen receptor antagonists or selective estrogen receptor modulators or inhibitors of estrogen synthesis for example tamoxifen, fulvestrant, toremifene, droloxifene, faslodex, raloxifene or letrozole;
- aromatase inhibitors such as exemestane, anastrozole, letrazole, testolactone and vorozole;
- differentiating agents such as retinoids, vitamin D or retinoic acid and retinoic acid metabolism blocking agents (RAMBA) for example accutane;
- DNA methyl transferase inhibitors for example azacytidine or decitabine;
- antifolates for example premetrexed disodium;
- antibiotics for example antinomycin D, bleomycin, mitomycin C, dactinomycin, carminomycin, daunomycin, levamisole, plicamycin, mithramycin;
- antimetabolites for example clofarabine, aminopterin, cytosine arabinoside or methotrexate, azacitidine, cytarabine, floxuridine, pentostatin, thioguanine;
- apoptosis inducing agents and anti angiogenic agents such as Bcl-2 inhibitors for example YC 137, BFI 312, ABT 737, gossypol, HA 14-1, TW 37 or decanoic acid;
- tubuline-binding agents for example combrestatin, colchicines or nocodazole;
- kinase inhibitors (e.g. EGFR (epithelial growth factor receptor) inhibitors, MTKI (multi target kinase inhibitors), mTOR inhibitors) for example flavoperidol, imatinib mesylate, erlotinib, gefitinib, dasatinib, lapatinib, lapatinib ditosylate, sorafenib, sunitinib, sunitinib maleate, temsirolimus;
- farnesyltransferase inhibitors for example tipifamib;
- histone deacetylase (HDAC) inhibitors for example sodium butyrate, suberoylanilide hydroxamic acid (SAHA), depsipeptide (FR 901228), NVP-LAQ824, R306465, JNJ-26481585, trichostatin A, vorinostat;
- Inhibitors of the ubiquitin-proteasome pathway for example PS-341, MEN 0.41 or bortezomib;

Yondelis;
Telomerase inhibitors for example telomestatin;
Matrix metalloproteinase inhibitors for example batimastat, marimastat, prinostat or metastat;
Recombinant interleukins for example aldesleukin, denileukin diftitox, interferon alfa 2a, interferon alfa 2b, peginterferon alfa 2b;
MAPK inhibitors;
Retinoids for example alitretinoin, bexarotene, tretinoin;
Arsenic trioxide;
Asparaginase;
Steroids for example dromostanolone propionate, megestrol acetate, nandrolone (decanoate, phenpropionate), dexamethasone;
Gonadotropin releasing hormone agonists or antagonists for example abarelix, goserelin acetate, histrelin acetate, leuprolide acetate;
Thalidomide, lenalidomide;
Mercaptopurine, mitotane, pamidronate, pegademase, pegaspargase, rasburicase;
BH3 mimetics for example ABT-737;
MEK inhibitors for example PD98059, AZD6244, CI-1040;
colony-stimulating factor analogs for example filgrastim, pegfilgrastim, sargramostim; erythropoietin or analogues thereof (e.g, darbepoetin alfa); interleukin 11; oprelvekin; zoledronate, zoledronic acid; fentanyl; bisphosphonate; palifermin;
a steroidal cytochrome P450 17alpha-hydroxylase-17,20-lyase inhibitor (CYP17), e.g. abiraterone, abiraterone acetate;
Glycolysis inhibitors, such as 2-deoxyglucose;
mTOR inhibitors such as rapamycins and rapalogs, and mTOR kinase inhibitors; PI3K inhibitors and dual mTOR/PI3K inhibitors;
autophagy inhibitors, such as chloroquine and hydroxychloroquine;
antibodies that re-activate the immune response to tumors, for example nivolumab (anti-PD-1), lambrolizumab (anti-PD-1), ipilimumab (anti-CTLA4), and MPDL3280A (anti-PD-L1).

The compounds of the invention can also be advantageously combined with anti-androgen therapies including androgen receptor antagonists and inhibitors of androgen biosynthesis in PTEN-negative prostate cancers.

The present invention further relates to a product containing as first active ingredient a compound according to the invention and as further active ingredient one or more anticancer agents, as a combined preparation for simultaneous, separate or sequential use in the treatment of patients suffering from cancer.

The one or more other medicinal agents and the compound according to the present invention may be administered simultaneously (e.g. in separate or unitary compositions) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein. The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of Formula (I) and another anti cancer agent may range from 1/10 to 10/1, more in particular from 1/5 to 5/1, even more in particular from 1/3 to 3/1.

The platinum coordination compound is advantageously administered in a dosage of 1 to 500 mg per square meter (mg/m$^2$) of body surface area, for example 50 to 400 mg/m$^2$, particularity for cisplatin in a dosage of about 75 mg/m$^2$ and for carboplatin in about 300 mg/m$^2$ per course of treatment.

The taxane compound is advantageously administered in a dosage of 50 to 400 mg per square meter (mg/m$^2$) of body surface area, for example 75 to 250 mg/m$^2$, particularly for paclitaxel in a dosage of about 175 to 250 mg/m$^2$ and for docetaxel in about 75 to 150 mg/m$^2$ per course of treatment.

The camptothecin compound is advantageously administered in a dosage of 0.1 to 400 mg per square meter (mg/m$^2$) of body surface area, for example 1 to 300 mg/m$^2$, particularly for irinotecan in a dosage of about 100 to 350 mg/m$^2$ and for topotecan in about 1 to 2 mg/m$^2$ per course of treatment.

The anti-tumour podophyllotoxin derivative is advantageously administered in a dosage of 30 to 300 mg per square meter (mg/m$^2$) of body surface area, for example 50 to 250 mg/m$^2$, particularly for etoposide in a dosage of about 35 to 100 mg/m$^2$ and for teniposide in about 50 to 250 mg/m$^2$ per course of treatment.

The anti-tumour *vinca* alkaloid is advantageously administered in a dosage of 2 to 30 mg per square meter (mg/m$^2$) of body surface area, particularly for vinblastine in a dosage of about 3 to 12 mg/m$^2$, for vincristine in a dosage of about 1 to 2 mg/m$^2$, and for vinorelbine in dosage of about 10 to 30 mg/m$^2$ per course of treatment.

The anti-tumour nucleoside derivative is advantageously administered in a dosage of 200 to 2500 mg per square meter (mg/m$^2$) of body surface area, for example 700 to 1500 mg/m$^2$, particularly for 5-FU in a dosage of 200 to 500 mg/m$^2$, for gemcitabine in a dosage of about 800 to 1200 mg/m$^2$ and for capecitabine in about 1000 to 2500 mg/m$^2$ per course of treatment.

The alkylating agents such as nitrogen mustard or nitrosourea is advantageously administered in a dosage of 100 to 500 mg per square meter (mg/m$^2$) of body surface area, for example 120 to 200 mg/m$^2$, particularly for cyclophosphamide in a dosage of about 100 to 500 mg/m$^2$, for chlorambucil in a dosage of about 0.1 to 0.2 mg/kg, for carmustine in a dosage of about 150 to 200 mg/m$^2$, and for lomustine in a dosage of about 100 to 150 mg/m$^2$ per course of treatment.

The anti-tumour anthracycline derivative is advantageously administered in a dosage of to 75 mg per square meter (mg/m²) of body surface area, for example 15 to 60 mg/m², particularly for doxorubicin in a dosage of about 40 to 75 mg/m², for daunorubicin in a dosage of about 25 to 45 mg/m², and for idarubicin in a dosage of about 10 to 15 mg/m² per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter (mg/m²) of body surface area, or as known in the art, if different. Trastuzumab is advantageously administered in a dosage of 1 to 5 mg per square meter (mg/m²) of body surface area, particularly 2 to 4 mg/m² per course of treatment. These dosages may be administered for example once, twice or more per course of treatment, which may be repeated for example every 7, 14, 21 or 28 days.

EXAMPLES

The following examples illustrate the present invention.

Hereinafter, the term 'BOC', 'Boc' or 'boc' means tert-butoxycarbonyl, means 'DCM' means dichloromethane, 'MeOH' means methanol, 'EtOH' means ethanol, 'ACN' means acetonitrile, 'THF' means tetrahydrofuran, 'Me-THF' means methyltetrahydrofuran, 'DMF' means dimethylformamide, 'EtOAc' means ethyl acetate, 'H₂O' means water, 'DMA' means dimethylacetamide, 'DME' means ethylene glycol dimethyl ether, 'Et₂O' means diethyl ether, 'iPrOH' means isopropanol, 'K₂CO₃' means potassium carbonate, 'K₃PO₄' means potassium phosphate, 'NH₄OH' means ammonia aqueous solution, 'NaHCO₃' means sodium bicarbonate, 'NaOH' means sodium hydroxide, 'NaCl' means sodium chloride, 'NH₄Cl' means ammonium chloride, 'Celite®' means diatomaceous earth, 'NMP' means A-methylpyrrolidine, 'LiCl' means lithium chloride, 'NH₄HCO₃' means ammonium bicarbonate, 'KOAc' means potassium acetate, 'DIPEA' means diisopropylethylamine, 'iPrNH₂' means isopropylamine, 'MgSO₄' means magnesium sulfate, 'Na₂SO₄' means sodium sulfate, 'N₂' means nitrogen, 'HCl' means hydrochloric acid, 'quant.' means quantitative, 'TFA' means trifluoroacetic acid, 'NaBH₄' means sodium borohydride, 'LiAlH₄' means lithium aluminium hydride, 'MnO₂' means manganese(IV) oxide, 'CO₂' means carbon dioxide, 'CO' means carbon monoxide, 'SFC' means supercritical fluid chromatography, 'HBTU' means N,N,N',N'-tetramethyl-<9-(1H-benzotriazol-1-yl) uronium hexafluorophosphate, O-(Benzotriazol-1-yl)-N,N,N',N'-tetramethyluronium hexafluorophosphate, 'TBAF' means tetrabutylammonium fluoride, 'PPh₃' means triphenylphosphine, 'Pd(OAc)₂' means palladium(II) acetate, 'Pd₂(dba)₃' means tris(dibenzylideneacetone)dipalladium (0), 'Pd(PPh₃)₄' means tetrakis(triphenylphosphine) palladium(0), 'Pd.Cl₂(dppf).DCM' means dichloro [1,1'-bis(di-phenylphosphino) ferrocene] palladium(II) dichloromethane adduct, 'BrettPhos' means 2-(dicyclohexylphosphino)3,6-dimethoxy-2',4',6'-triisopropyl-1,1'-biphenyl, 'rt' means room temperature, 'OR' means optical rotation, 'BrettPhos Precatalyst First Gen' means chloro[2-(dicyclohexylphosphino)-3,6-dimethoxy-2',4',6'-triisopropyl-1,1'-biphenyl] [2-(2-aminoethyl)phenyl]palladium(II), 'Xantphos' means 4,5-Bis(diphenylphosphino)-9,9-dimethylxanthene, 'de' means diastereomeric excess, 'ee' or 'e.e.' means enantiomeric excess, 'M.P.' means melting point, 'DSC' means differential scanning calorimetry, 'K' means Kofler; 'COMU' means (1-Cyano-2-ethoxy-2-oxoethylidenaminooxy)dimethylamino-morpholino-carbenium hexafluorophosphate, 'HATU' means 1-[Bis(dimethylamino)methylene]-1H-1,2,3-triazolo[4,5-b]pyridinium 3-oxid hexafluorophosphate, 'MeTHF' means 2-methyltetrahydrofuran.

When a stereocenter is indicated with 'RS' this means that a racemic mixture was obtained.

A. Preparation of the Intermediate

Example A1

Preparation of Intermediate 1a and Intermediate 1b

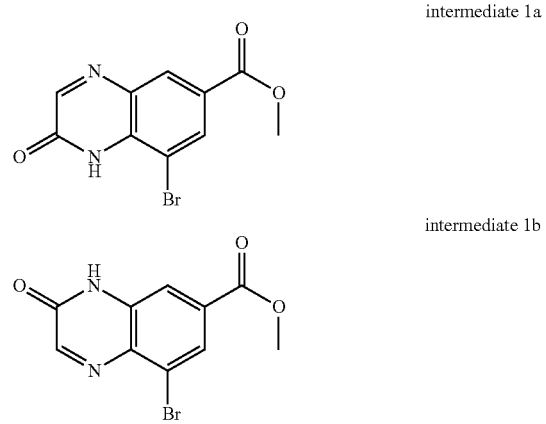

At −40° C. 2,2-dihydroxy-acetic acid (85.61 g; 930 mmol) in H₂O (35 mL) was added dropwise to a solution of methyl-3,4-diamino-5-bromobenzoate (190 g; 775.28 mmol) in MeOH (2 L). Then, the reaction mixture was allowed to warm to rt and stirred for 2 h. The solid was filtered, washed with Et₂O and dried under vacuum to give 214 g (98%) of a mixture of two intermediates 1a and 1b (ratio ~85/15 by ¹H NMR).

Alternative Pathway:

Ethyl glyoxalate solution (6.6 mL; 66.1 mmol; 50% in toluene) was added to a solution of methyl-3,4-diamino-5-bromobenzoate (8.1 g; 33.05 mmol) in EtOH (150 mL). The reaction mixture was heated at reflux for 3 h. The mixture was cooled down to rt and the precipitate was filtered, washed with diethylether and dried under vacuum to give 7.3 g (78%) of a mixture of intermediates 1a and 1b.

Alternative Preparation of Intermediate 1a
Preparation of Intermediate 1c:

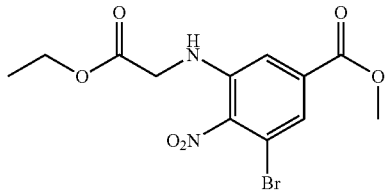 [SMILES: CCOC(=O)CNc1cc(C(=O)OC)cc(Br)c1[N+](=O)[O-]]

To a solution of methyl-3-bromo-5-fluoro-4-nitrobenzoate (2 g; 7.2 mmol) and glycine ethyl ester hydrochloride (1.1 g; 7.9 mmol) in DMA (20 mL) was added DIPEA (4.9 mL; 28.8 mmol) at rt. The mixture was stirred at rt for 2 days. H$_2$O and EtOAc were added. The organic layer was extracted, dried over MgSO$_4$, filtered and evaporated to dryness under vacuum to give 3.3 g of crude intermediate. A purification was performed by silica gel chromatography (irregular SiOH 20-45 µm, 40 g, mobile phase: gradient from 100% heptane to 70% heptane, 30% EtOAc). The fractions containing the product were mixed and evaporated to give 2.1 g (81%) of intermediate 1c.

Preparation of Intermediate 1d:

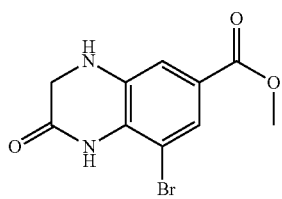 [SMILES: COC(=O)c1cc(Br)c2c(c1)NCC(=O)N2]

Intermediate 1c (200 mg; 0.55 mmol) was dissolved in EtOH (5 mL). Tin (II) chloride dihydrate (315 mg; 1.66 mmol) was added and the mixture was heated at 80° C. for 4 hours and cooled down to rt. The resulting precipitate was filtered, washed with EtOH and dried (vacuum, 60° C., overnight) to give 90 mg (57%) of intermediate Id.

Preparation of Intermediate 1a:

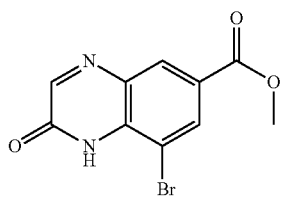 [SMILES: COC(=O)c1cc(Br)c2[nH]c(=O)cnc2c1]

To a solution of intermediate Id (90 mg; 0.32 mmol) in DCM (10 mL) was added manganese dioxide (110 mg; 1.26 mmol). The solution was stirred at rt for 2 hours. Manganese dioxide (55 mg; 0.63 mmol) was again added and the solution was stirred overnight at rt. The mixture was filtered through a pad of Celite®, washed with DCM and the solvent was evaporated to dryness to give 58 mg (65%) of intermediate 1a.

Preparation of Intermediate 2a and Intermediate 2b

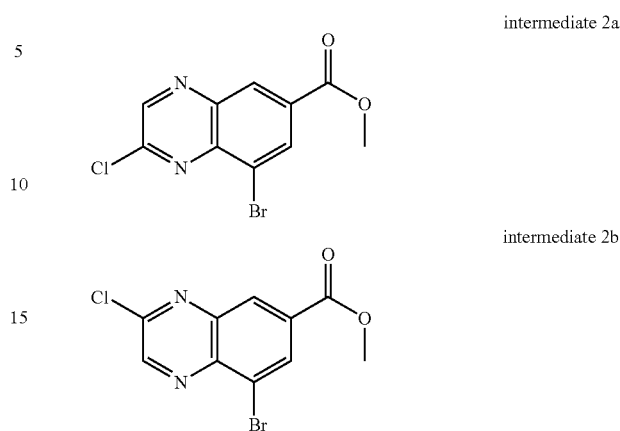

intermediate 2a intermediate 2b

A mixture of intermediate 1a and 1b (85/15) (25 g; 75.07 mmol) was added slowly to POCl$_3$ (300 mL). The reaction mixture was heated at 80° C. for 3 h. POCh was evaporated and DCM was added to the residue. The mixture was poured into ice-water and extracted with DCM. The organic layer was dried over MgSO$_4$, filtered and evaporated. The residue was purified by chromatography over silica gel (eluent: from 9/1 petroleum ether/EtOAc to 4/1 petroleum ether/EtOAc). The pure fractions were collected and the solvent was evaporated to give 17 g (75%) of intermediate 2a and 3 g (13%) of intermediate 2b.

Alternative Pathway:

A mixture of intermediate 1a (5 g; 17.7 mmol) in POCh (75 mL) was heated at 80° C. for 4 h. The mixture was evaporated under vacuum and the residue was taken-up in ice water and DCM. The mixture was slowly basified with a 10% aqueous solution of K$_2$CO$_3$ and stirred at rt for 2 h. The aqueous layer was separated and extracted with DCM (2×). The combined organic layers were dried over MgSO$_4$, filtered and evaporated under vacuum to give 4.89 g (92%, beige solid) of intermediate 2a.

Preparation of Intermediate 3a and Intermediate 3b

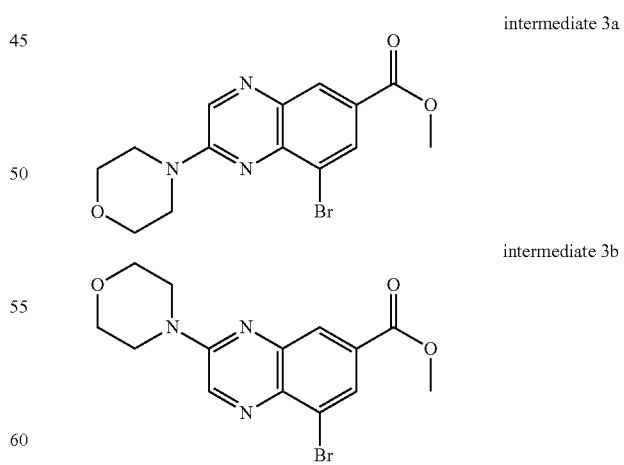

intermediate 3a intermediate 3b

Triethylamine (95.4 mL; 660 mmol) was added to a mixture of intermediates 1a and 1b (75 g; 132.47 mmol) (ratio 1a/1b undetermined) in THF (3 L) at 0° C. The reaction mixture was stirred at 0° C. for 10 min. Then, morpholine (55.8 mL; 634 mmol) and bromo-tris-pyrrolidino-phosphonium hexafluorophosphate (135.2 g; 290 mmol) were added. The reaction mixture was stirred at rt for 12 h. The solvent was evaporated and the residue was washed with H₂O. The solid (yellow) was filtered, washed with ACN, then Et₂O and dried under vacuum to give 80 g (85%) of a mixture intermediates 3a and 3b (ratio ~4/1 by 1H NMR).

Alternative Pathway:

A mixture of intermediate 2a (3.3 g; 10.94 mmol) and morpholine (2.9 mL; 32.83 mmol) in THF (50 mL) was heated at reflux for 3 h. The reaction mixture was cooled down to rt, then poured into ice-water and extracted with EtOAc. The organic layer was washed with brine (2×), then water, dried over MgSO₄, filtered and evaporated to give 3.7 g (95%) of intermediate 3a.

Alternative Preparation of Intermediate 3a:

Intermediate 186 was dissolved in dichloromethane (10 volumes) and dimethyl dibromohydantoin (0.8 equivalents) was added. After reacting at 30-40° C. for 30 hours, the reaction mixture was washed with a saturated solution of ammonium chloride and the organic phase was concentrated to give intermediate 3a in quantitative yield (78 purity).

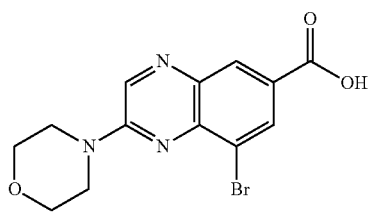 [SMILES: O=C(O)c1cc(Br)c2nc(N3CCOCC3)cnc2c1]

Preparation of Intermediate 4:

A solution of lithium hydroxide monohydrate (5.96 g; 141.97 mmol) in H₂O (60 mL) was added to a solution of a mixture of intermediates 3a and 3b (5/1) (10 g; 28.39 mmol) in THF (200 mL) at rt. The reaction mixture was stirred at rt overnight. At 0° C., the solution was slowly acidified with a 3N aqueous solution of HCl and stirred at 10° C. for 1 h. The precipitate was filtered, then washed with water and dried to give 7.4 g (70%. yellow solid. 91% of purity evaluated by LC/MS) of intermediate 4. M.P.: >260° C. (Kofler).

Alternative Pathway:

A 3M aqueous solution of NaOH (11.6 mL; 34.8 mmol) was added to a mixture of intermediates 3a and 3b (4.08 g; 11.6 mmol) in EtOH (60 mL) and THF (60 mL). The reaction mixture was stirred at rt overnight and evaporated under vacuum. The residue was acidified with a 0.5 N aqueous solution of HCl to give a precipitate. The solid was filtered off, washed with water, then diethylether and dried under vacuum to give 3.86 g (99%, yellow solid) of intermediate 4.

Preparation of Intermediate 5:

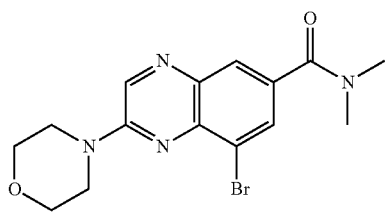 [SMILES: CN(C)C(=O)c1cc(Br)c2nc(N3CCOCC3)cnc2c1]

At 10° C., HBTU (10.7 g; 28.1 mmol) was added portion wise to a mixture of intermediate 4(9.5 g; 28.1 mmol), DIPEA (12.3 mL; 70.2 mmol) and dimethylamine (2M in THF) (21.1 mL; 42.1 mmol) in DMF (180 mL). The reaction mixture was stirred at rt for the week-end. The solution was poured into ice-water, extracted with EtOAc (2×). The organic layer was washed with brine (2×), then dried over MgSO₄, filtered and evaporated until dryness. The residue was taken-up with diethylether, filtered and dried to give 9.5 g (93%) of intermediate 5.

Preparation of Intermediate 217

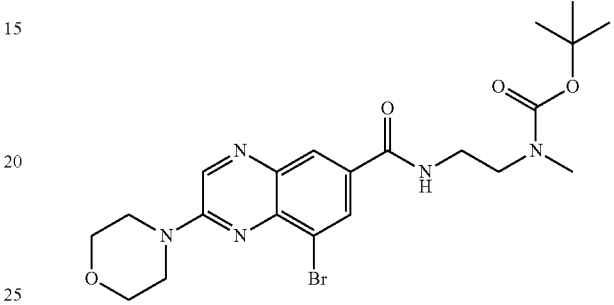

Intermediate 217 was prepared according to an analogous procedure as described for the synthesis of intermediate 5, using intermediate 4 and N-(2-aminoethyl)-N-Methyl carbamic acid tert-butyl ester as starting materials (720 mg g; 49%).

Preparation of Intermediate 237

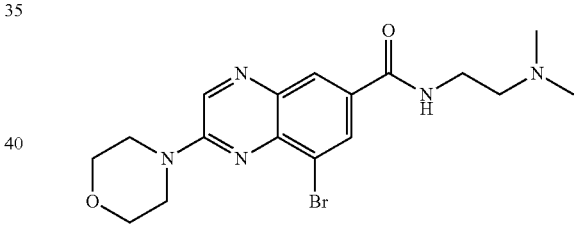

Intermediate 237 was prepared according to an analogous procedure as described for the synthesis of intermediate 5, using intermediate 4 and N,N-Dimethylethylenediamine as starting materials (420 mg g; 70%).

Preparation of Intermediate 238

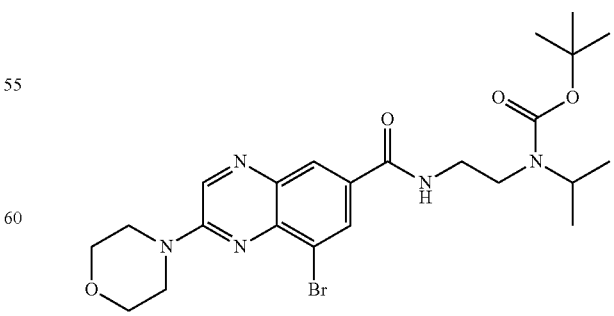

Intermediate 238 was prepared according to an analogous procedure as described for the synthesis of intermediate 5, using intermediate 4 and 2-Amino-Ethyl)isopropyl-carbamic acid tert-butylester as starting materials (5.6 g; 81%).

Example A2

Preparation of Intermediate 6a and Intermediate 6b

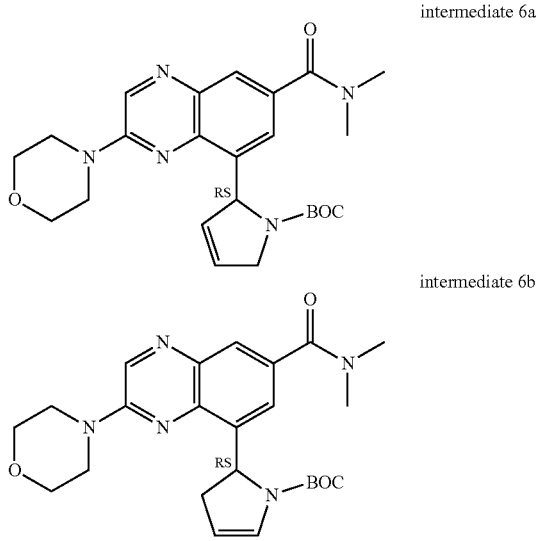

intermediate 6a intermediate 6b

In a sealed vessel, a mixture of intermediate 5 (8 g; 21.9 mmol), N-boc-2,3-dihydro-1H-pyrrole (5.3 mL; 30.67 mmol) and $K_2CO_3$ (9.08 g; 65.71 mmol) in anhydrous DMF (200 mL) was degazed under $N_2$. $PPh_3$ (1.15 g; 4.38 mmol) then $Pd(OAc)_2$ (492 mg; 2.19 mmol) were added and the reaction mixture was heated at 100° C. for 15 h. The reaction was cooled down to rt, poured into $H_2O$ and EtOAc was added. The mixture was filtered through a pad of Celite® and the filtrate was extracted with EtOAc. The organic layer was washed with brine, dried over $MgSO_4$, filtered and evaporated until dryness. The residue (12 g) was purified by chromatography over silica gel (irregular SiOH; 15-40 µm; 120 g; gradient: from 0.1% $NH_4OH$, 96% DCM, 4% MeOH to 0.1% $NH_4OH$, 92% DCM, 8% MeOH). The pure fractions were collected and the solvent was evaporated to give 6.2 g (62%, 50/50 by LCMS) of a mixture of intermediates 6a and 6b.

Preparation of Intermediate 7:

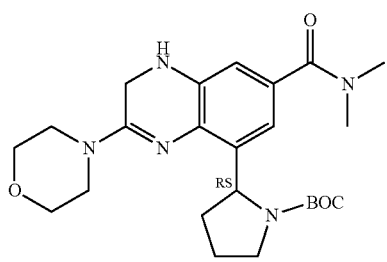 [SMILES: CN(C)C(=O)c1cc2c(c(C3CCCN3C(=O)OC(C)(C)C)c1)N=C(N1CCOCC1)CN2]

A mixture of intermediates 6a and 6b (7 g; 15.43 mmol) and platinum (IV) oxide (713 mg; 3.09 mmol) in EtOH (200 mL) was hydrogenated at rt under a pressure of 1.2 bar of $H_2$ for 4 h. The reaction was filtered through a pad of Celite®, rinsed with MeOH and the filtrate was evaporated to give 6.8 g (97%) of intermediate 7. The product was used without purification for the next step.

Preparation of Intermediate 8:

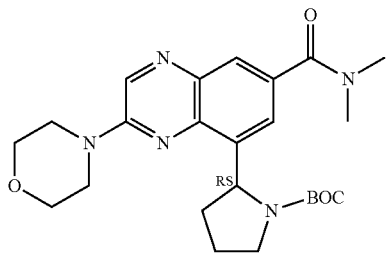 [SMILES: CN(C)C(=O)c1cc(C2CCCN2C(=O)OC(C)(C)C)c2nc(N3CCOCC3)cnc2c1]

A mixture of intermediate 7 (6.8 g; 14.86 mmol), manganese oxide (3.9 g; 44.58 mmol) in DCM (150 mL) was stirred at rt for 1 h. The reaction mixture was filtered through a pad of Celite®, rinsed with MeOH and the filtrate was evaporated to give 7 g (quant.) of intermediate 8. The product was used without purification for the next step.

Preparation of Intermediate 9:

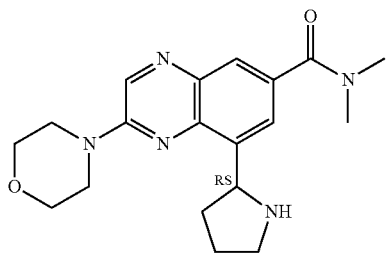 [SMILES: CN(C)C(=O)c1cc(C2CCCN2)c2nc(N3CCOCC3)cnc2c1]

The experiment was performed twice on 3.5 g of intermediate 8:

At 10° C., HCl (4M in 1,4-dioxane) (9.6 mL; 38.41 mmol) was added dropwise to a solution of intermediate 8 (3.5 g; 7.68 mmol) in DCM (115 mL). The reaction mixture was stirred at rt for 5 h. The mixture was taken-up with DCM and iced-water, basified with $NH_4OH$ and extracted with DCM. The organic layer was dried over $MgSO_4$, filtered and evaporated to dryness. The combined residues (5.46 g obtained from 2 experiments) was purified by chromatography over silica gel (irregular SiOH; 15-40 µm; 120 g; mobile phase: 0.1% $NH_4OH$, 90% DCM, 10% MeOH). The pure fractions were collected and the solvent was evaporated to give 3.94 g (72%) of intermediate 9.

Example A3

Preparation of Intermediate 10a and Intermediate 10b

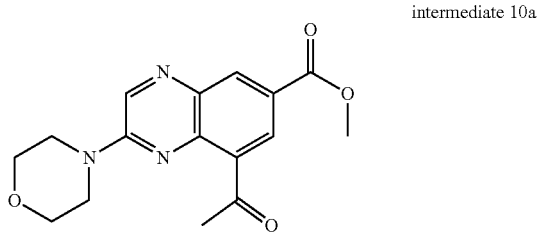

intermediate 10a

-continued intermediate 10b

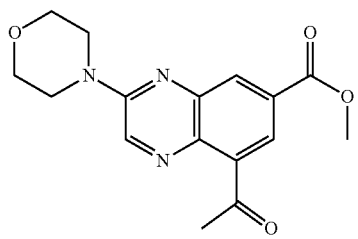

Tributyl(1-ethoxy vinyl)tin (67.68 g; 187.40 mmol) was added to a solution of a mixture of intermediates 3a and 3b (60 g; 85.18 mmol) in anhydrous 1,4-dioxane (1.2 L) under $N_2$. Dichlorobis(triphenylphosphine) palladium (II) (3.59 g; 5.11 mmol) was added and the mixture was purged again with $N_2$. The reaction mixture was heated at 100° C. overnight. After cooling down to rt, a 3M aqueous solution of HCl was added and the mixture was stirred at rt for 40 min. The mixture was slowly basified with a saturated aqueous solution of $NaHCO_3$ and EtOAc was added. The mixture was extracted with EtOAc and the organic layer was washed with brine, dried with $Na_2SO_4$ and evaporated. The residue was purified by column chromatography over silica gel (eluent: from DCM/EtOAc 10/1 to DCM/EtOAc 8/1). The pure fractions were collected and the solvent was evaporated to give a 10 g of mixture of intermediate 10a and intermediate 10b and 30.5 g (54%) of intermediate 10a. The 10 g mixture of intermediate 10a and intermediate 10b was further purified by chromatography over silica gel (eluent: from DCM/EtOAc 10/1 to DCM/EtOAc 4/1). The pure fractions were collected and the solvent was evaporated to give 1.6 g (3%) of intermediate 10b and 7 g of mixture (intermediate 10a and intermediate 10b) (ratio 1/1 by NMR).

Alternative Preparation:

To a solution of a mixture of intermediates 3a and 3b (75/25 evaluated by LC/MS) (195 g, 554 mmol) in DMSO (2000 mL) was added vinylbutylether (166 g, 1661. mmol) and TEA (400 mL, 2768 mmol, 0.7 g/mL) under $N_2$ atmosphere. $Pd(OAc)_2$ (12.4 g, 55 mmol) and DPPP (45.6 g, 111 mmol) were added. The mixture was purged again with $N_2$ and heated to 100° C. overnight. After cooling down to room temperature, HCl (3M, 1845 mL, 5536 mmol) was added portionwise under ice batch and the mixture was stirred for 1 hour. The pH of the mixture was adjusted to 8 with $NaHCO_3$. The mixture was filtered. The cake was washed with ethyl acetate (1000 mL), then dissolved in $CH_2Cl_2$ (1500 mL*2) and filtered. The filtrate was washed with brine (500 mL), evaporated to give a crude yellow solid (200 g) mainly containing intermediate 10a. This residue was purified by silica gel chromatography (eluent: ethyl acetate=100%). The desired fractions were collected and the solvent was concentrated to dryness under vacuum to give 100 g (57%) of intermediate 10a as yellow solid.

Alternatively, the previous reaction was also carried out using EtOH as solvent at a temperature of 70° C.

Preparation of Intermediate 11:

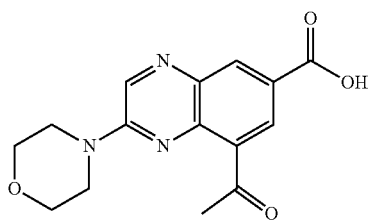 [SMILES: CC(=O)c1cc(C(=O)O)cc2ncc(N3CCOCC3)nc12]

Intermediate 11 was prepared according to an analogous procedure as described for the synthesis of intermediate 4, using intermediate 10a as starting material. The aqueous layer was extracted with DCM (2×). The organic layers were separated, washed with water, dried over $MgSO_4$, filtered and evaporated to dryness. The crude product was taken-up with diethylether, the precipitate was filtered off and dried under vacuum to give 3 g (63%, yellow solid) of intermediate 11. The product was used without purification for the next step.

Alternative Pathway:

A 1M aqueous solution of NaOH (89 mL; 89.0 mmol) was added to a solution of intermediate 10a (9.35 g; 29.7 mmol) in THF (140 mL) and MeOH (140 mL). The reaction mixture was stirred at rt for 1 h then evaporated until dryness under vacuum. The solid obtained was slowly acidified with 1N aqueous solution of HCl and filtered. The cake was dried under vacuum then taken-up in EtOH and evaporated under vacuum to give 8.90 g (quant., yellow solid) of intermediate 11. The product was used without purification for the next step.

Preparation of Intermediate 12:

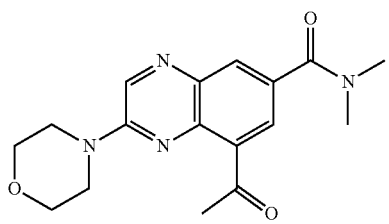 [SMILES: CC(=O)c1cc(C(=O)N(C)C)cc2ncc(N3CCOCC3)nc12]

Intermediate 12 was prepared according to an analogous procedure as described for the synthesis of intermediate 5, using intermediate 11 as starting material. The reaction mixture was stirred at rt for 1 h then evaporated under vacuum. The residue was taken-up in EtOAc and a mixture of a saturated aqueous solution of $NaHCO_3$ and water (50/50) was added. The aqueous layer was separated and extracted with EtOAc (3×). The combined organic layers were washed with a saturated aqueous solution of brine (3×), dried over $MgSO_4$, filtered off and evaporated in vacuum. The residue (14.2 g, orange foam) was purified by chromatography over silica gel (Irregular SiOH; 15-40 µm; 300 g; mobile phase: 30% heptane, 70% EtOAc/MeOH (9/1)). The pure fractions were collected and the solvent was evaporated to give 7.80 g (80%, yellow solid) of intermediate 12.

Example A4

Preparation of Intermediate 13a and Intermediate 13b

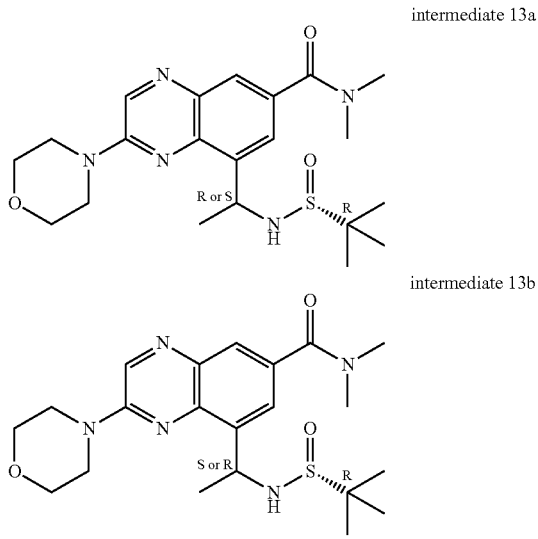

intermediate 13a intermediate 13b

Intermediate 12 (1.30 g; 3.96 mmol) was added to a solution of (R)-(+)-2-methyl-2-propanesulfinamide (1.44 g; 11.9 mmol) and titanium(IV) ethoxide (4.98 mL; 23.8 mmol) in THF (42 mL) at rt. The reaction mixture was heated at reflux (70° C.) for 18 h. Then, the reaction mixture was cooled down to −50° C. and NaBH₄ (150 mg; 3.96 mmol) was added portion wise. The mixture was allowed to slowly warm to rt and stirred for 1 h. The mixture was cooled down to 0° C. and MeOH was slowly added (bubbling in the mixture). The crude was then poured into a saturated aqueous solution of NaCl and filtered. The cake was rinsed with EtOAc and the filtrate was extracted with EtOAc. The organic layer was separated, washed with water, dried over MgSO₄, filtered off and evaporated under vacuum. The residue (2.30 g) was purified by chromatography over silica gel (Irregular SiOH; 15-40 µm; 80 g; mobile phase: 70% heptane, 30% iPrOH/NH₄OH (9/1)). The pure fractions were collected and the solvent was evaporated. The residue (800 mg) was combined with another little batch (34 mg) and the mixture was purified by chromatography over silica gel (Irregular SiOH; 15-40 µm; 30 g; gradient: from 100% DCM to 90% DCM, 10% iPrOH). The pure fractions were collected and the solvent was evaporated to give 260 mg (15%) of intermediate 13a and 175 mg (10%) of intermediate 13b (first product eluted by chromatography).

Preparation of Intermediate 14:

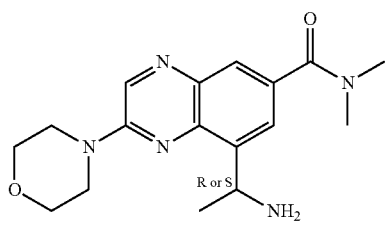 [SMILES: CC(N)c1cc(C(=O)N(C)C)cc2ncc(N3CCOCC3)nc12]

HCl (4M in 1,4-dioxane) (192 µL; 767 µmol) was added to a solution of intermediate 13a (334 mg; 767 µmol) in 1,4-dioxane (7.6 mL). The reaction mixture was stirred at rt for 1 h. The mixture was combined with another batch coming from a reaction performed on 20 mg of intermediate 13a and basified with a saturated aqueous solution of NaHCO₃. The aqueous layer was separated and extracted with EtOAc (3×). The combined organic layers were dried over MgSO₄, filtered and evaporated under vacuum. The residue (265 mg) was purified by chromatography over silica gel (Irregular SiOH; 15-40 µm; 10 g; gradient: from 100% DCM to 90% DCM, 10% (9/1) MeOH/NH₄OH). The pure fractions were collected and the solvent was evaporated to give 95 mg (37%, yellow foam) of fraction 1 and 53 mg (21%, yellow foam) of fraction 2. Fraction 2 was purified by achiral SFC (CHIRALPAK AD-H; 5 µm 250×20 mm; mobile phase: 75% CO₂, 25% MeOH (0.3% iPrNH₂)). The pure fractions were collected and the solvent was evaporated to give 37 mg (15%, yellow film) of intermediate 14.

Fraction 1 was purified by chromatography over silica gel (Irregular SiOH; 15-40 µm; 10 g; gradient: from 100% DCM to 90% DCM, 10% (9/1) MeOH/NH₄OH). The pure fractions were collected and the solvent was evaporated. The residue (yellow foam) was purified by chiral SFC (CHIRALPAK AD-H 5 µm 250×20 mm; mobile phase: 75% CO₂, 25% MeOH (0.3% iPrNH₂)). The pure fractions were collected and the solvent was evaporated to give 59 mg (23%, pale yellow film) of intermediate 14.

Example A5

Preparation of Intermediate 15:

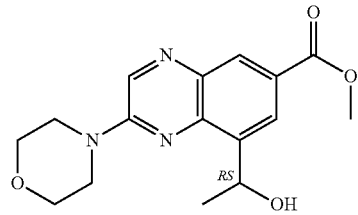 [SMILES: COC(=O)c1cc(C(C)O)c2nc(N3CCOCC3)cnc2c1]

Cerium(III) chloride (8.2 g; 33.3 mmol) was added to a solution of intermediate 10a (10 g; 31.7 mmol) in MeOH (220 mL) and DCM (100 mL). The reaction mixture was stirred at rt for 30 min. The mixture was cooled down to 0° C. and NaBH₄ (1.32 g; 34.9 mmol) was added portionwise (bubbling in the mixture). The reaction mixture was stirred at rt for 1 h 30. Then, DCM and water were added. The layers were separated, the aqueous layer was extracted with DCM (2×) and the combined organics layers were dried over MgSO₄, filtered off and evaporated in vacuum. The residue (9.65 g) was recrystallized with MeOH and diethylether. The precipitate was filtered and dried to give 7.98 g (79%) of intermediate 15.

Alternative Pathway:

NaBH₄ (1.01 g; 26.6 mmol) was added to a solution of intermediate 10a (7.94 g; 22.2 mmol) in MeOH (140 mL) and DCM (70 mL) at 0° C. The reaction mixture was slowly warmed to rt and stirred for 30 min. The mixture was slowly quenched with water. DCM was added and the layers were separated. The aqueous layer was extracted with DCM (2×). The combined organic layers were dried over MgSO₄, filtered and evaporated under vacuum. The residue (7.9 g, orange solid) was purified by chromatography over silica gel (regular SiOH; 30 µm; 300 g; gradient: from 70% DCM, 30% EtOAc to 30% DCM, 70% EtOAc). The pure fractions were collected and the solvent was evaporated. The residue (5.35 g, yellow solid) was triturated in diethylether and filtered to give 4.95 g (70%, pale yellow solid) of intermediate 15.

Preparation of Intermediate 15a and Intermediate 15b

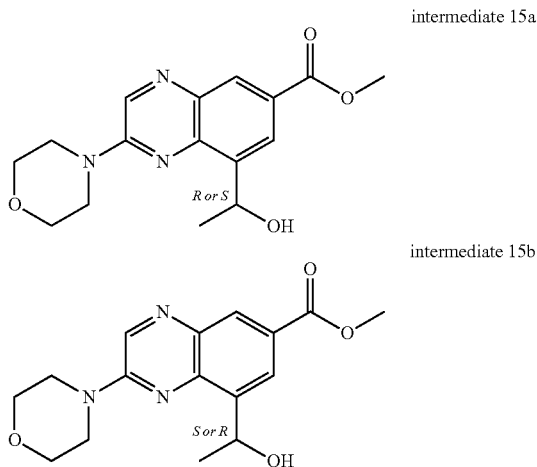

intermediate 15a intermediate 15b

Intermediate 15a and intermediate 15b were obtained after chiral SFC (Stationary phase: CHIRALPAK IC 5 μm 250×30 mm, Mobile phase: 55% $CO_2$, 45% EtOH (0.3% $iPrNH_2$)) of intermediate 15. Crystallization from ACN and diethylether afforded 444 mg (22%) of intermediate 15a (M.P.: 163° C., DSC) and 593 mg (30%) of intermediate 15b (M.P.: 146° C., DSC).

Alternative Preparation of Intermediate 15b

Intermediate 10a and (−)-B-chlorodiisopinocampheylborane (1.25 eq.) were stirred in dichloromethane (10 volumes) at −35° C. After complete conversion, diethanolamine (2.7 eq.) was added to remove the boron byproducts. The mixture was refluxed for two hours and the solid formed was filtered and discarded. The filtrate was washed twice with water, concentrated to 1-2 volumes and petrol ether was added. The solid was filtered and re-slurried in methyl tertiobutylether. The procedure was executed on 50 g, 200 g and 300 g scale of intermediate 10a in 93% average yield (e.e.: 90%).

Preparation of Intermediate 16:

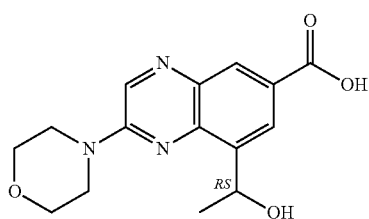 [SMILES: CC(O)c1cc(C(=O)O)cc2ncc(N3CCOCC3)nc12]

Intermediate 16 was prepared according to an analogous procedure as described for the synthesis of intermediate 4, using intermediate 15 as starting material. At 0° C., the solution was acidified with 3N aqueous solution of HCl slowly and stirred at 10° C. for 1 h. The precipitate was filtered and dried to give 1.4 g (39%) of intermediate 16. The filtrate was extracted with DCM (2×). The organic layers were combined, washed with water, dried over $MgSO_4$, filtered and evaporated to give additional 1.8 g (50%, yellow solid) of intermediate 16. The 2 batches were combined to give 3.2 g (89% global yield) of intermediate 16 directly use in the next step without any further purification.

Alternative Pathway:

Intermediate 16 was prepared according to an analogous procedure as described for the synthesis of intermediate 11 (alternative preparation), using intermediate 15 as starting material. The reaction mixture was stirred at rt overnight then evaporated until dryness under vacuum. The solid obtained was slowly acidified with a 1N aqueous solution of HCl and filtered on a glass frit to give 1.4 g (100%, off-white solid) of intermediate 16.

Preparation of Intermediate 17:

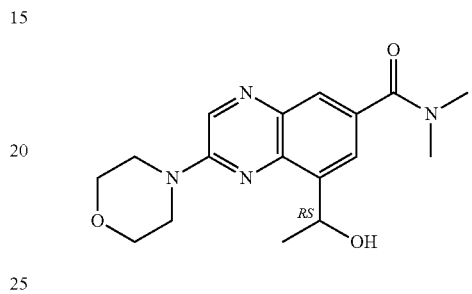

Intermediate 17 was prepared according to an analogous procedure as described for the synthesis of intermediate 5, using intermediate 16 as starting material. The residue was taken-up in EtOAc and a mixture of a saturated aqueous solution of $NaHCO_3$ was added. The aqueous layer was separated and extracted with EtOAc (2×) and DCM/MeOH (9/1) (2×). The combined organic layers were dried over $MgSO_4$, filtered off and evaporated under vacuum. The residue (2.1 g, orange oil) was purified by chromatography over silica gel (regular SiOH; 30 μm; 80 g; gradient: 100% DCM to 30% DCM, 70% EtOAc). The pure fractions were collected and the solvent was evaporated to give 220 mg (14%, orange foam, not pure by NMR) of intermediate 17 and 905 mg (59%, yellow foam) of intermediate 17.

Alternative Pathway:

Intermediate 17 was prepared according to an analogous procedure as described for the synthesis of intermediate 15 (alternative pathway), using intermediate 12 as starting material. The reaction mixture was stirred at 0° C. for 15 min. The mixture was quenched with water and slowly warmed to rt. The aqueous layer was extracted with DCM (2×), then DCM/MeOH (9/1) (2×). The combined organics layers were dried over $MgSO_4$, filtered off and evaporated in vacuum. The residue (1.68 g, pale yellow foam) was purified by chromatography over silica gel (irregular SiOH; 15-40 μm; 50 g; eluent: from 100% DCM to 96% DCM, 4% MeOH). The pure fractions were collected and the solvent was evaporated to give 1.29 g (79%, pale yellow foam) of intermediate 17.

Alternative Pathway:

Intermediate 17 was prepared according to an analogous procedure as described for the synthesis of intermediate 15, using intermediate 12 as starting material. The reaction mixture was stirred at rt for 15 h. Then, DCM and ice-water were added and the mixture was stirred at rt for 1 h. The aqueous layer was extracted with DCM (2×) and the combined organics layers were dried over $MgSO_4$, filtered off and evaporated in vacuum. The residue was taken-up with diethylether, the precipitate was filtered and dried to give 1.73 g (87%) of intermediate 17.

Example A6

Preparation of Intermediate 18:

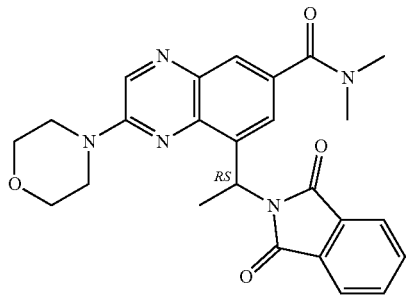 [SMILES: CC(c1cc(C(=O)N(C)C)cc2ncc(N3CCOCC3)nc12)N1C(=O)c2ccccc2C1=O]

Phtalimide (2.54 g; 17.3 mmol), PPh₃ (4.53 g; 17.3 mmol) and di-tert-butyl azodicarboxylate (3.97 g; 17.3 mmol) were added to a solution of intermediate 17 (3.80 g; 11.5 mmol) in THF (110 mL). The reaction mixture was stirred at rt for 18 h. Then, the mixture was evaporated under vacuum and the residue (16 g, orange foam) was purified by chromatography over silica gel (regular SiOH; 30 µm; 300 g; gradient: from 70% heptane, 30% EtOAc/MeOH (9/1) to 30% heptane, 70% EtOAc/MeOH (9/1)). The pure fractions were collected and the solvent was evaporated to give 4.62 g (49%, pale brown foam) of intermediate 18.

Preparation of Intermediate 19:

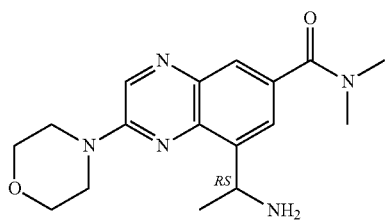 [SMILES: CC(N)c1cc(C(=O)N(C)C)cc2ncc(N3CCOCC3)nc12]

Hydrazine monohydrate (1.50 mL; 24.5 mmol) was added to a suspension of intermediate 18 (2.35 g; 2.46 mmol) in EtOH (24 mL). The reaction mixture was heated at 80° C. for 18 h. Then, the mixture was cooled down to rt and filtered. The solid was rinsed with EtOH and the filtrate was evaporated under vacuum. The residue (2.35 g, orange solid) was combined with another batch coming from a reaction performed on 2.27 g of intermediate 18, and the resulting product was diluted in DCM/MeOH (9/1). The precipitate was filtered on a glass frit and the filtrate was evaporated under vacuum and purified by chromatography over silica gel (regular SiOH; 30 µm; 200 g; gradient: from 100% DCM to 90% DCM, 10% MeOH/NH₄OH (9/1)). The pure fractions were collected and the solvent was evaporated to give 835 mg (45%, brown oil) of intermediate 19.

Example A7

Preparation of Intermediate 20a and Intermediate 20b

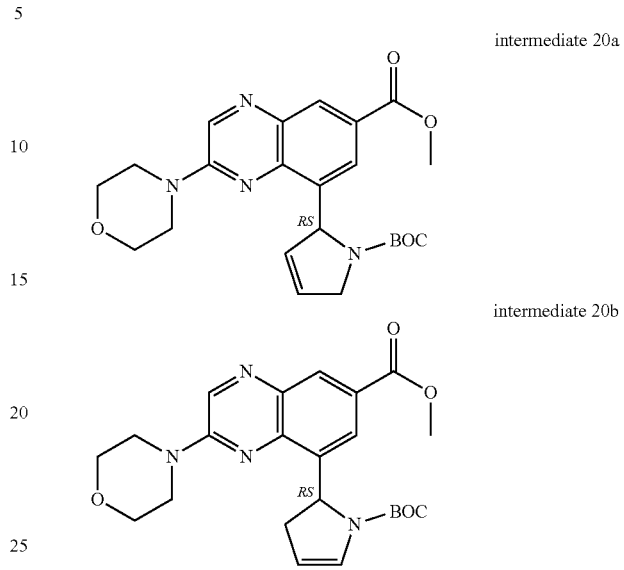

A mixture of intermediate 20a and intermediate 20b was prepared according to an analogous procedure as described for the synthesis of intermediate 6, using intermediate 3a as starting material. The residue (3.2 g) was purified by chromatography over silica gel (irregular SiOH; 15-40 µm; 80 g; eluent: 99% DCM, 1% MeOH). The pure fractions were collected and the solvent was evaporated to give 1.9 g (79%) of a mixture of intermediate 20a and intermediate 20b.

Alternative Pathway:

In a sealed glassware, a mixture of intermediate 3a and intermediate 3b (75/25) (10 g; 28.39 mmol), N-boc-2,3-dihydro-1H-pyrrole (6.86 mL; 39.75 mmol) and K₂CO₃ (11.8 g; 85.18 mmol) in 1,4-dioxane (250 mL) was bubbled with N₂. Then, PPh₃ (1.49 g; 5.68 mmol) and Pd(OAc)₂ (640 mg; 2.84 mmol) were added. The reaction mixture was heated to 100° C. for 5 h. The reaction mixture was cooled down to rt, poured onto water and extracted with EtOAc. The organic layer was decanted, washed with brine, dried over MgSO₄, filtered and evaporated to dryness. The residue (21 g) was purified by chromatography over silica gel (irregular SiOH; 20-45 µm; 450 g; mobile phase: 62% heptane, 3% MeOH (+10% NH₄OH), 35% EtOAc). The pure fractions were collected and evaporated to dryness yielding 2.3 g (17%, impure) of intermediate 20a and 8.2 g (59%) of intermediate 20a.

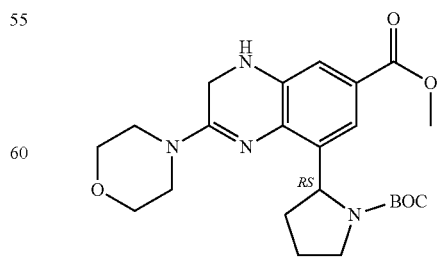

Intermediate 21 was prepared according to an analogous procedure as described for the synthesis of intermediate 7, using intermediate 20a as starting material. The reaction mixture was stirred at rt for 45 min. intermediate 21 (11 g, 100%) was directly used without any further purification in the next step.

Preparation of Intermediate 22a, Intermediate 22b and Intermediate 22c

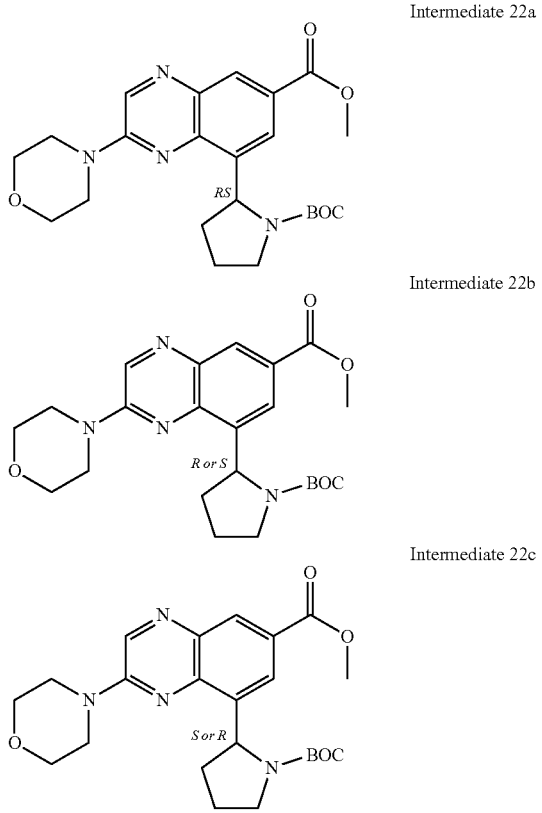

Intermediate 22a

Intermediate 22b

Intermediate 22c

Intermediate 22a were prepared according to an analogous procedure as described for the synthesis of intermediate 8, using intermediate 21 as starting material. The residue (12 g) was purified by chromatography over silica gel (irregular SiOH; 15-40 μm; 800 g; mobile phase: 99% DCM, 1% MeOH). The pure fractions were collected and the solvent was evaporated to give respectively 3.7 g (31%) of intermediate 22a and additional 7.3 g (61%) of intermediate 22a. This last fraction was purified by chiral SFC (Whelk 01 (S,S) 5 μm; 250*21.1 mm; mobile phase: 60% $CO_2$, 40% EtOH). The pure fractions were collected and the solvent was evaporated to give 3.45 g (29%) of intermediate 22b and 3.38 g (28%) of intermediate 22c.

Preparation of Intermediate 23:

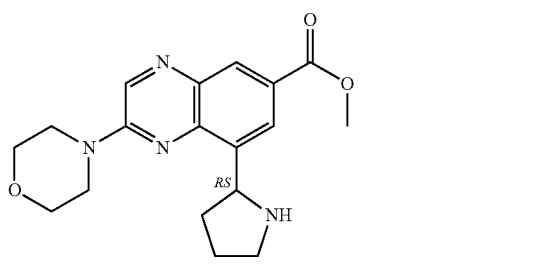 [SMILES: COC(=O)c1cc(C2CCCN2)c2nc(N3CCOCC3)cnc2c1]

Intermediate 23 was prepared according to an analogous procedure as described for the synthesis of intermediate 9, using intermediate 22a as starting material. The reaction mixture was stirred at rt for 15 h. The mixture was poured into DCM and a saturated aqueous solution of $NaHCO_3$ then, extracted with DCM (3×). The organic layer was separated, dried over $MgSO_4$, filtered and evaporated to dryness. The residue was taken-up with $Et_2O$. The precipitate was filtered and dried to give 3.5 g (90%) of intermediate 23.

Preparation of Intermediate 24:

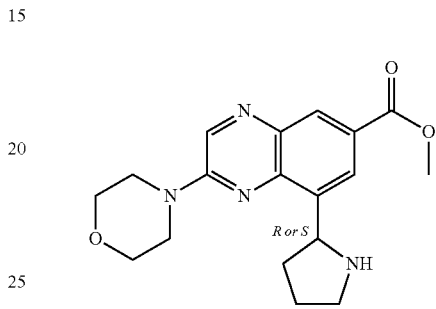

Intermediate 24 was prepared according to an analogous procedure as described for the synthesis of intermediate 23, using intermediate 22b as starting material. 8.4 g (88%) of intermediate 24 was obtained.

Preparation of Intermediate 25:

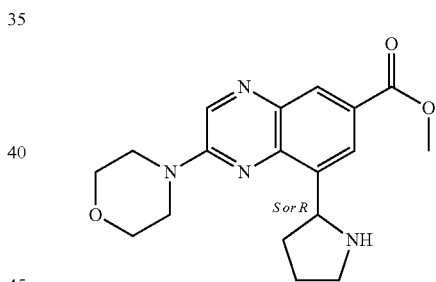

Intermediate 25 was prepared according to an analogous procedure as described for the synthesis of intermediate 23, using intermediate 22c as starting material. 2 1.68 g (75%) of intermediate 25 was obtained.

Example A8

Preparation of Intermediate 26a and Intermediate 26b intermediate 26a

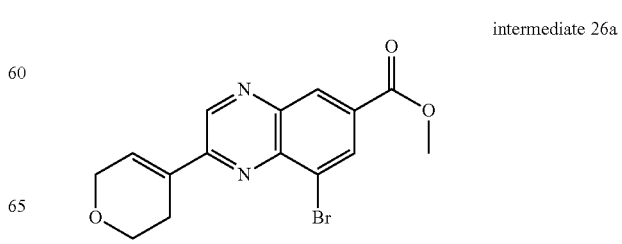

-continued

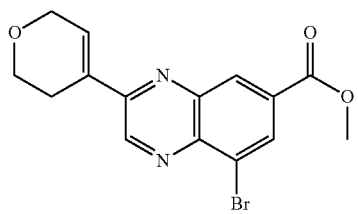
intermediate 26b

In a Schlenk tube, a mixture of intermediate 2a (4.0 g; 13.27 mmol), 3,6-dihydro-2H-pyran-4-boronic acid pinacol ester (3.34 g; 15.92 mmol), $K_3PO_4$ (8.45 g; 39.80 mmol) in 1,4-dioxane (80 mL) and $H_2O$ (8 mL) was carefully degassed under vacuum and back-filled with N2 (3×). Then, $Pd.Cl_2(dppf).DCM$ (0.54 g; 0.66 mmol) was added. The mixture was carefully degassed under vacuum and back-filled with $N_2$ (3×) and then stirred at 80° C. for 8 h. After cooling down to rt, the mixture was diluted with DCM and filtered through a pad of Celite®. The filtrate was evaporated under vacuum. The residue (brown) was purified by chromatography over silica gel (Regular SiOH; 30 μm; 200 g; eluent: from 100% DCM to 85% DCM, 15% EtOAc). The pure fractions were collected and the solvent was concentrated until precipitation. The solid was filtered and dried to give 2.7 g (58%, beige solid) of a mixture of intermediate 26a and 26b (92/8 evaluated by 1H NMR). The filtrate was evaporated under vacuum to give additional 455 mg (10%, pale brown solid) of a mixture of intermediate 26a and 26b (80/20 evaluated by $^1$H NMR)

Preparation of Intermediate 27a and Intermediate 27b

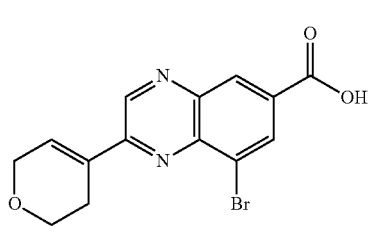
intermediate 27a

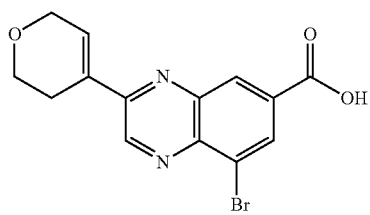
intermediate 27b

In a round bottom flask, at 0° C., to a mixture of intermediate 26a and 26b (2.7 g; 7.35 mmol; 92/8) in EtOH (50 mL) and THF (50 mL) was added 1M aqueous NaOH (14.7 mL, 14.7 mmol). The reaction mixture was stirred allowing the temperature to reach rt over 1 h. Additional THF (20 mL) and EtOH (20 mL) were added and the stirring was continue for 1 hour. Then, the solvent were evaporated. The resulting residue was diluted with water and acidified with 1M aqueous solution of HCl to pH 2. The aqueous layer was extracted with a mixture of DCM/MeOH (9/1, 7×). The combined organic layers were washed with a saturated aqueous solution of $NH_4Cl$, dried over $MgSO_4$, filtered and the solvent was evaporated to give 2.27 g (92%, beige solid) of a mixture of intermediate 27a and 27b (93/7 evaluated by $^1$H NMR).

Preparation of Intermediate 28a and Intermediate 28b

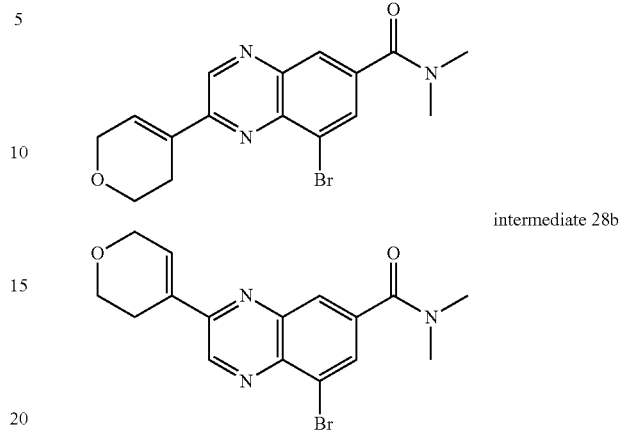
intermediate 28a intermediate 28b

A mixture of intermediate 28a and 28b was prepared according to an analogous procedure as described for the synthesis of intermediate 5, using a mixture of intermediate 27a and 27b as starting material. The reaction mixture was stirred at rt for 18 h. The residue (6.6 g) was mixed with crude coming from a reaction performed on 380 mg of a mixture of intermediate 27a and 27b (~85/15, evaluated by $^1$H NMR) and the resulting residue was purified by chromatography over silica gel (regular SiOH; 30 μm; 200 g; mobile phase: from 100% DCM to 98% DCM, 2% MeOH). The pure fractions were collected and the solvent was evaporated. The residue (4.03 g, sticky yellow solid) was dried under vacuum for 16 h to give 3.40 g (yellow sticky solid) which was triturated in $Et_2O$ (~10 mL). The supernatant was removed and the solid was triturated once more with $Et_2O$ (~10 mL). The supernatant was removed and the solid was dried to give 3.24 g (yellow solid, impure) of a mixture of intermediate 28a and 28b (92/8 evaluated by $^1$H NMR). The product was used without further purification for the next step.

Example A9

Preparation of Intermediate 29:

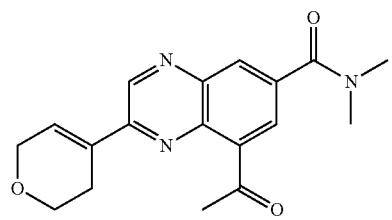 [SMILES: CC(=O)c1cc(C(=O)N(C)C)cc2ncc(C3=CCOCC3)nc12]

Intermediate 29 was prepared according to an analogous procedure as described for the synthesis of intermediate 10, using intermediate 28 as starting material. The reaction mixture was stirred at 80° C. for 8 h. The residue was purified by chromatography over silica gel (regular SiOH; 30 μm; 200 g; gradient: from 99% DCM, 1% iPrOH to 95% DCM, 5% iPrOH). The pure fractions were collected and the solvent was evaporated to give 969 mg (40%, clear orange solid) of intermediate 29.

Preparation of Intermediate 30:

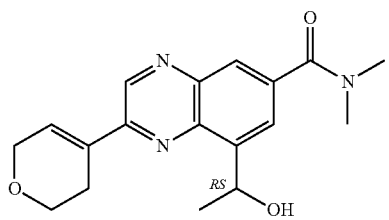 [SMILES: CC(O)c1cc(C(=O)N(C)C)cc2ncc(C3=CCOCC3)nc12]

Intermediate 30 was prepared according to an analogous procedure as described for the synthesis of intermediate 15, using intermediate 29 as starting material. The reaction mixture was stirred at rt for 15 h. The residue was purified by chromatography over silica gel (irregular 15-40 μm; 24 g; mobile phase: from 50% heptane, 5% MeOH, 35% EtOAc). The pure fractions were collected and the solvent was evaporated to give 600 mg (73%) of intermediate 30.

Example A10

Preparation of Intermediate 31:

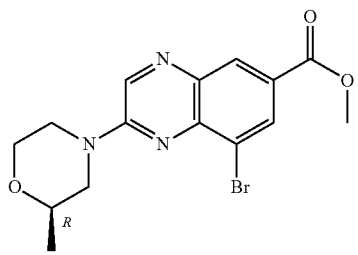

(R)-2-methylmorpholine hydrochloride (1.53 g; 11.11 mmol) and triethylamine (3.09 mL; 22.22 mmol) were added to a solution of intermediates 2a and 2b (67/23) (5 g; 11.11 mmol) in THF (100 mL). The reaction mixture was stirred at rt for 2 h. The precipitate was filtered off and the cake was washed with EtOAc. The filtrate was evaporated under vacuum and the residue (6.52 g, brown oil) was purified by chromatography over silica gel (irregular SiOH 15-40 μm; 200 g; mobile phase: from 100% DCM to 70% DCM, 30% EtOAc). The pure fractions were collected and the solvent was evaporated to give 2.61 g (59%, yellow solid) of intermediate 31.

Preparation of Intermediate 32:

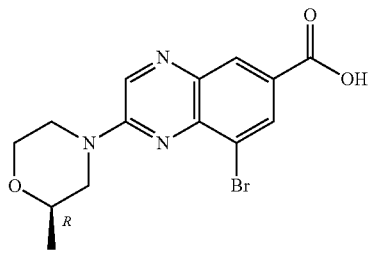

Intermediate 32 was prepared according to an analogous procedure as described for the synthesis of intermediate 4, using intermediate 31 as starting material (2.06 g, 90%, yellow solid).

Preparation of Intermediate 33:

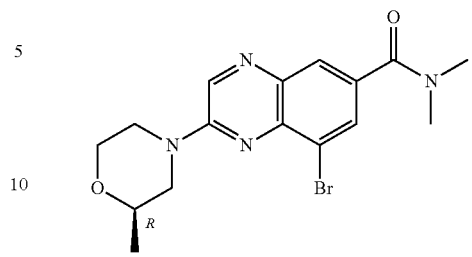

Intermediate 33 was prepared according to an analogous procedure as described for the synthesis of intermediate 5, using intermediate 32 as starting material (1.97 g, quant., orange foam).

Preparation of Intermediate 34a and Intermediate 34b

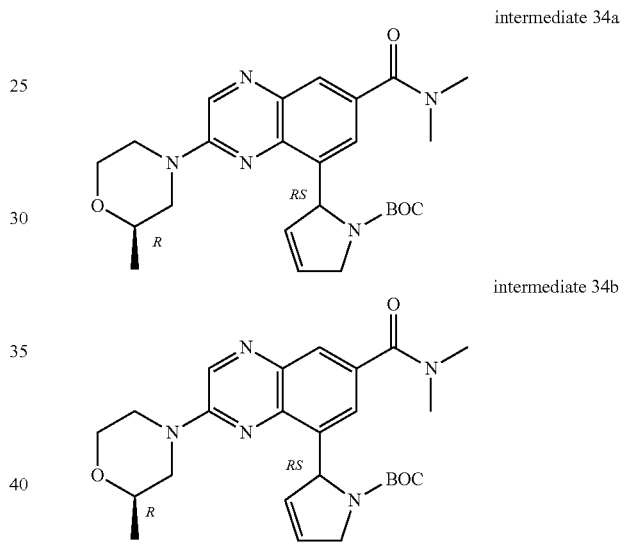

intermediate 34a intermediate 34b

A mixture of intermediates 34a and 34b was prepared according to an analogous procedure as described for the synthesis of intermediate 6, using intermediate 33 and N-boc-2,3-dihydro-1H-pyrrole as starting materials (1.88 g, 82%, yellow foam).

Preparation of Intermediate 35:

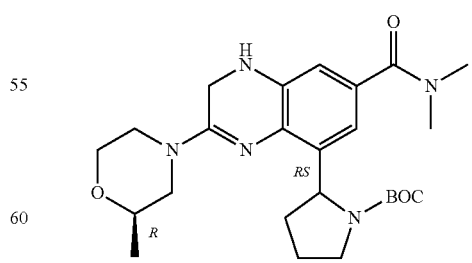

Intermediate 35 was prepared according to an analogous procedure as described for the synthesis of intermediate 7, using a mixture of intermediate 34a and 34b as starting material (1.76 g, 93%, green foam).

Preparation of Intermediate 36:

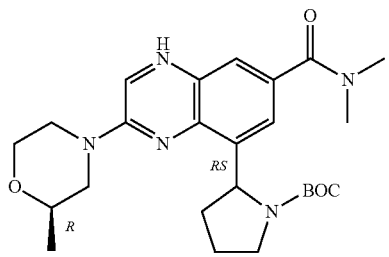

Intermediate 36 was prepared according to an analogous procedure as described for the synthesis of intermediate 8, using intermediate 35 as starting material (1.79 g, 100%, yellow foam).

Preparation of Intermediate 37:

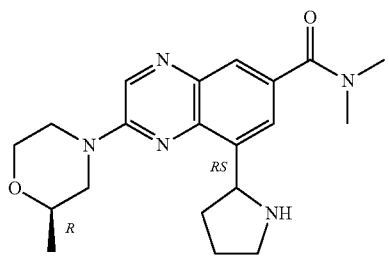

HCl (4M in 1,4-dioxane) (4.67 mL; 18.68 mmol) was added to a solution of intermediate 36 (1.79 g; 3.74 mmol) in 1,4-dioxane (37 mL). The reaction mixture was stirred at 50° C. overnight. The mixture was cooled to rt and evaporated under vacuum. The residue was taken-up in DCM and water. The aqueous layer was slowly basified with NaHCO$_3$ (solid). The layers were separated and the aqueous layer was extracted with DCM (2×) and with DCM/MeOH (9/1) (2×). The combined organic layer were dried over MgSO$_4$, filtered and evaporated under vacuum. The residue (1.32 g, orange foam) was purified by chromatography over silica gel (irregular SiOH 15-40 µm; 50 g; gradient: from 100% DCM to 90% DCM, 10% MeOH (+5% NH$_4$OH)). The pure fractions were collected and the solvent was evaporated to give 1.08 g (77%, yellow foam) of intermediate 37.

Example A11

Preparation of Intermediate 40:

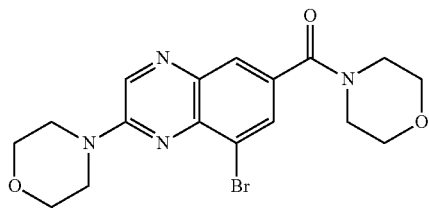 [SMILES: O=C(c1cc(Br)c2nc(N3CCOCC3)cnc2c1)N1CCOCC1]

Intermediate 40 was prepared according to an analogous procedure as described for the synthesis of intermediate 5, using intermediate 4 and morpholine as starting material (1.61 g, 84%).

Preparation of Intermediate 41:

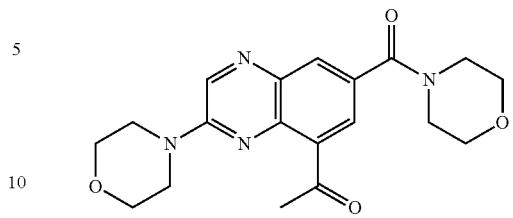

Intermediate 41 was prepared according to an analogous procedure as described for the synthesis of intermediate 10, using intermediate 40 as starting material (1.28 g, 87%).

Alternative Pathway:

Intermediate 41 was prepared according to an analogous procedure as described for the synthesis of intermediate 5, using intermediate 11 and morpholine as starting material (2.6 g, 85%).

Preparation of Intermediate 42:

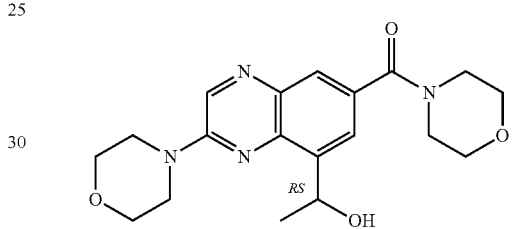

Intermediate 42 was prepared according to an analogous procedure as described for the synthesis of intermediate 15, using intermediate 41 as starting material (1 g, 83%).

Alternative Pathway:

Intermediate 42 was prepared according to an analogous procedure as described for the synthesis of intermediate 5, using intermediate 16 and morpholine as starting material (3 g, 76%).

Example A12

Preparation of Intermediate 43:

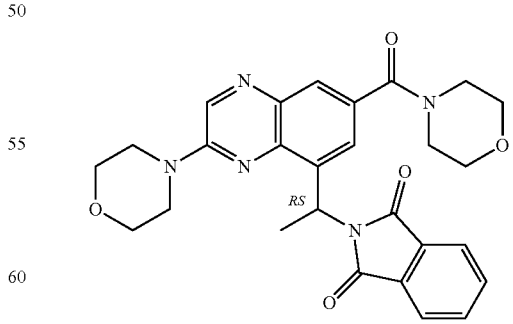

Intermediate 43 was prepared according to an analogous procedure as described for the synthesis of intermediate 18, using intermediate 42 and phtalimide as starting material (386 mg, 79%).

Preparation of Intermediate 44:

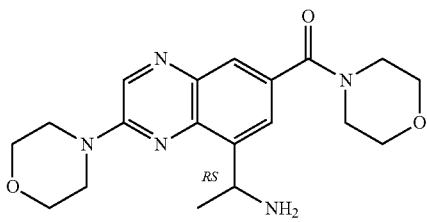 [SMILES: CC(N)c1cc(C(=O)N2CCOCC2)cc2ncc(N3CCOCC3)nc12]

Intermediate 44 was prepared according to an analogous procedure as described for the synthesis of intermediate 19, using intermediate 43 and hydrazine monohydrate as starting material (152 mg, 53%).

Example A13

Preparation of Intermediate 45:

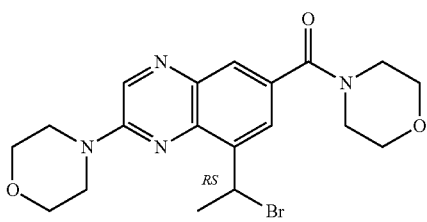 [SMILES: CC(Br)c1cc(C(=O)N2CCOCC2)cc2ncc(N3CCOCC3)nc12]

In a sealed tube, at 10° C., phosphorus tribromide (0.67 mL; 7.05 mmol) was added dropwise to a solution of intermediate 42 (1.75 g; 4.70 mmol) in DCM (20 mL). The reaction mixture was stirred at rt for 72 h. A precipitate was filtered, washed with Et₂O and dried to give 1.5 g (62%) of intermediate 45.

Preparation of Intermediate 87:

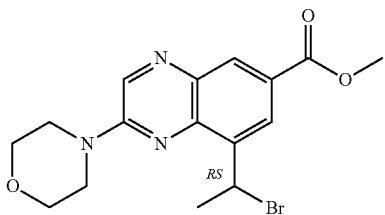 [SMILES: COC(=O)c1cc(C(C)Br)c2nc(N3CCOCC3)cnc2c1]

Intermediate 87 was prepared according to an analogous procedure as described for the synthesis of intermediate 45, using intermediate 15 as starting material (3.3 g, 57%).

Example A14

Preparation of Intermediate 49:

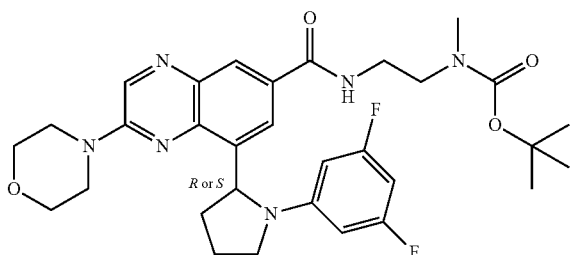

Under N₂, N-(2-aminoethyl)-N-methyl carbamic acid tert-butyl ester (108 μL; 0.59 mmol) was added to a solution of compound 251 (130 mg; 0.30 mmol), HBTU (224 mg; 0.59 mmol) and DIPEA (305 μL; 1.77 mmol) in DMF (4 mL) at rt. The solution was stirred at rt for 72 h. The solution was poured into ice-water. The product was extracted with EtOAc and washed with brine. The organic layer was dried over MgSO₄, filtered and evaporated to dryness. The residue (190 mg) was purified by chromatography over silica gel (irregular 15-40 μm; 24 g; mobile phase: 95% DCM, 5% MeOH, 0.1% NH₄OH). The pure fractions were collected and the solvent was evaporated to give 150 mg (85%) of intermediate 49.

Preparation of Intermediate 50:

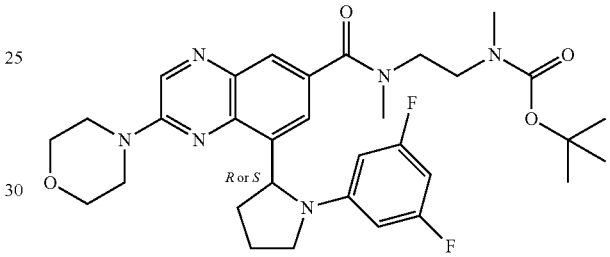

Intermediate 50 was prepared according to an analogous procedure as described for the synthesis of intermediate 49, using compound 251 and N-methyl-N-[2-(methylamino)ethyl]-1,1-dimethylethyl ester carbamic acid as starting material (450 mg, >100%).

Preparation of Intermediate 85:

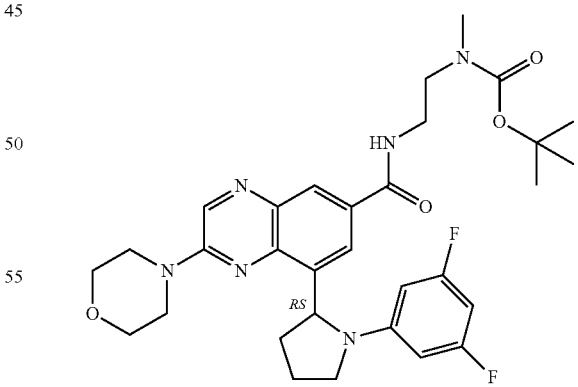

Intermediate 85 was prepared according to an analogous procedure as described for the synthesis of intermediate 49, using compound 62 and N-(2-aminoethyl)-N-methyl carbamic acid tert-butyl ester as starting materials (193 mg, 71%).

Preparation of Intermediate 187:

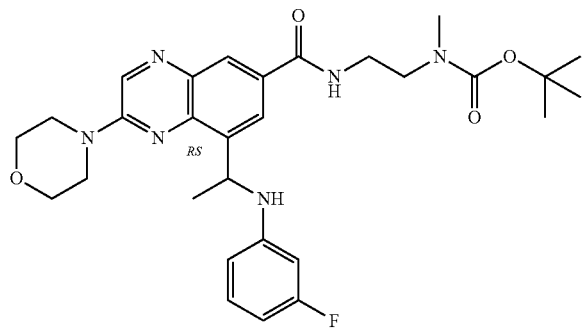 [SMILES: CC(Nc1cccc(F)c1)c1cc(C(=O)NCCN(C)C(=O)OC(C)(C)C)cc2ncc(N3CCOCC3)nc12]

Intermediate 187 was prepared according to an analogous procedure as described for the synthesis of intermediate 49 using compound 263 as starting materials (1.17 g, used without purification for the next step).

Preparation of Intermediate 188:

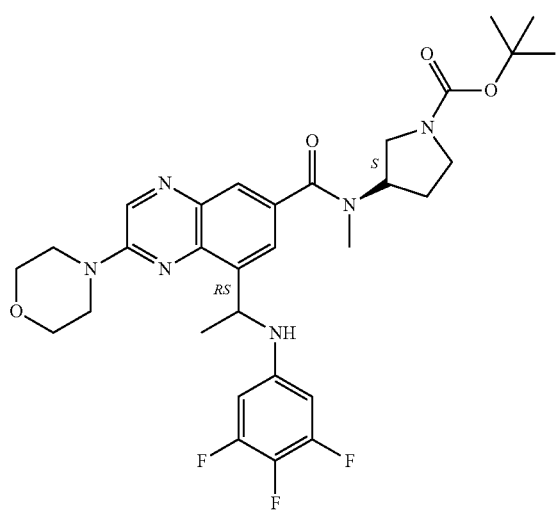

Intermediate 188 was prepared according to an analogous procedure as described for the synthesis of intermediate 49, using compound 170 and (S)-tert-Butyl 3-(methylamino) pyrrolidine-1-carboxylate as starting materials (1.02 g; 44% of purity evaluated by LC/MS).

Preparation of Intermediate 189:

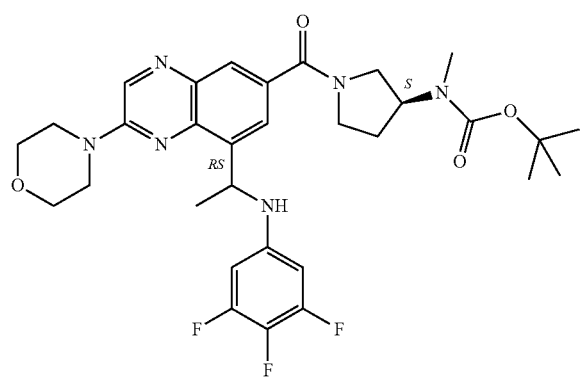

Intermediate 189 was prepared according to an analogous procedure as described for the synthesis of intermediate 49 using compound 170 and (S)-3-(N-Boc-N-methylamino) pyrrolidin as starting materials (760 mg, used without purification).

Example A15

Preparation of Intermediate 51:

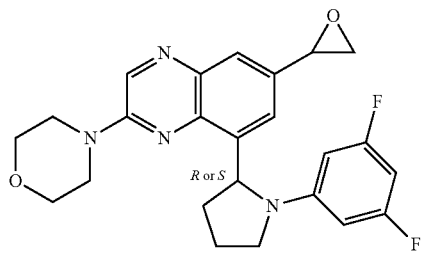 [SMILES: Fc1cc(F)cc(N2CCCC2c2cc(C3CO3)cc3ncc(N4CCOCC4)nc23)c1]

Sodium hydride (71 mg; 1.77 mmol) was added to a solution of trimethylsulfonium iodide (361 mg; 1.77 mmol) in THF (10 mL) at rt under $N_2$ flow. After 1 h at 50° C., a solution of compound 250 (500 mg; 1.18 mmol) in THF (10 mL) was added dropwise. The reaction mixture was heated at 70° C. for 1 h. The mixture was poured into water and the product was extracted with EtOAc. The organic layer was washed with brine, dried over $MgSO_4$, filtered and evaporated. The residue (650 mg) was purified by chromatography over silica gel (50 g; mobile phase: 98% DCM, 2% MeOH, 0.1% $NH_4OH$). The pure fractions were collected and the solvent was evaporated to give 450 mg (87%) of intermediate 51.

Example A16

Preparation of Intermediate 52:

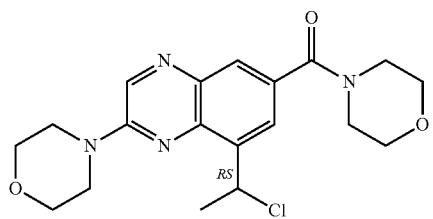 [SMILES: CC(Cl)c1cc(C(=O)N2CCOCC2)cc2ncc(N3CCOCC3)nc12]

At 10° C., thionyl chloride (0.39 mL; 5.37 mmol) was added to a solution of intermediate 42 (1 g; 2.69 mmol) in DCM (20 mL) under $N_2$. The solution was stirred at 10° C. for 4 h. The mixture was evaporated to give 1.05 g (100%) of intermediate 52. The crude intermediate was directly used without purification in the next step.

Preparation of Intermediate 105:

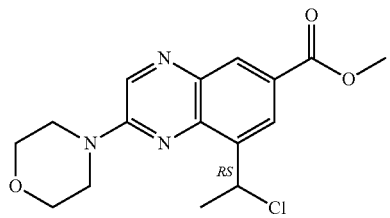 [SMILES: COC(=O)c1cc(C(C)Cl)c2nc(N3CCOCC3)cnc2c1]

Intermediate 105 was prepared according to an analogous procedure as described for the synthesis of intermediate 52, using intermediate 15 as starting material (15 g).

Preparation of Intermediate 119:

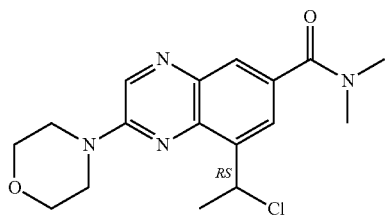 [SMILES: CC(Cl)c1cc(C(=O)N(C)C)cc2ncc(N3CCOCC3)nc12]

Intermediate 119 was prepared according to an analogous procedure as described for the synthesis of intermediate 52, using intermediate 17 as starting material (1 g, >100%). The crude product was used without purification in the next step.

Preparation of Intermediate 139:

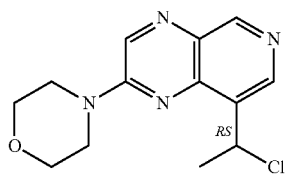 [SMILES: CC(Cl)c1cncc2ncc(N3CCOCC3)nc12]

Intermediate 139 was prepared according to an analogous procedure as described for the synthesis of intermediate 52, using intermediate 138 as starting material (370 mg, quant.). The product was used without purification in the next step.

Preparation of Intermediate 145:

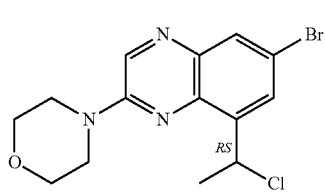 [SMILES: CC(Cl)c1cc(Br)cc2ncc(N3CCOCC3)nc12]

Intermediate 145 was prepared according to an analogous procedure as described for the synthesis of intermediate 52, using intermediate 56 as starting material (9 g, quant.). The product was used without purification for the next step.

Example A17

Preparation of Intermediate 53a: And Intermediate 53b

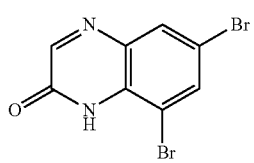
intermediate 53a

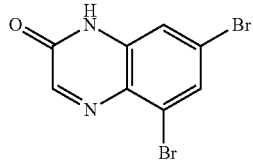
intermediate 53b

A mixture of intermediate 53a and intermediate 53b was prepared according to an analogous procedure as described for the synthesis of intermediate 1a, using 3,5-dibromo-1,2-benzenediamine and 2,2-dihydroxy-acetic acid as starting material (59 g, 90%).

Preparation of Intermediate 54a and Intermediate 54b

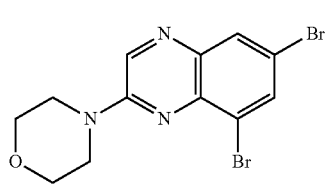
intermediate 54a

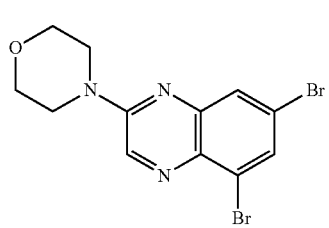
intermediate 54b

A mixture of intermediate 54a and intermediate 54b was prepared according to an analogous procedure as described for the synthesis of intermediate 3a, using a mixture of intermediates 54a and 54b and morpholine as starting material (41.5 g, 92%).

Preparation of Intermediate 55a and Intermediate 55b

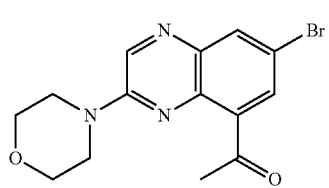
intermediate 55a

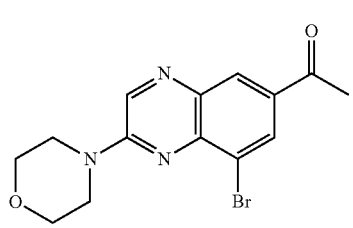
intermediate 55b

The experiment was performed twice on the same quantity (15 g; 40.2 mmol) of a mixture of intermediates 54a and 54b:

In a Schlenck reactor, a solution of mixture of intermediates 54a and 54b (15 g; 40.2 mmol) and tributyl(1-ethoxyvinyl)tin (14.9 mL; 44.2 mmol) in 1,4-dioxane (400 mL) was degassed under $N_2$. $Pd(PPh_3)_4$ (2.32 g; 2.01 mmol)

was added and the mixture was degassed under $N_2$ and was heated at 100° C. overnight. Then, more $Pd(PPh_3)_4$ (2.32 g; 2.01 mmol) was added. The reaction mixture was degassed under $N_2$ and heated at 100° C. for 24 h. The mixture was quenched with a 1M aqueous solution of HCl (120 mL) and stirred at rt for 30 min. The resulting solution was basified with $NaHCO_3$ solid. The 2 batches were combined and filtered through a pad of Celite®. The cake was washed with water and EtOAc. The aqueous layer was extracted with EtOAc. The combined organic layers were dried over $MgSO_4$, filtered and evaporated under vacuum. The crude product was triturated in $Et_2O$ and filtered. The precipitate (23 g, yellow solid) was purified by chromatography over silica gel (irregular SiOH; 15-40 μm; 330+220 g; gradient: 63% heptane, 35% EtOAc, 2% MeOH). The fractions containing the product were collected and the solvent was evaporated. The residue (15 g, pale yellow solid) was further purified by chromatography over silica gel (Irregular SiOH 20-45 μm; 450 g; mobile phase: 99.5% DCM, 0.5% MeOH) and then by achiral SFC (CHIRALPAK IC 5 μm 250×30 mm; mobile phase: 45% $CO_2$, 55% MeOH (0.3% $iPrNH_2$) (7.3% DCM)). The pure fractions were collected and the solvent was evaporated to give 2.7 g (9%, pale yellow solid) of intermediate 54a, 3.0 g (11%, yellow solid) of intermediate 55a and 1.06 g (3%, yellow solid) of intermediate 55b.

Preparation of Intermediate 56:

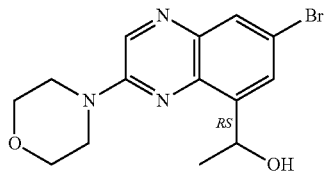 [SMILES: CC(O)c1cc(Br)cc2ncc(N3CCOCC3)nc12]

Intermediate 56 was prepared according to an analogous procedure as described for the synthesis of intermediate 15, using intermediate 55a as starting material (200 mg, 99%).

Alternative Pathway:

Intermediate 56 was prepared according to an analogous procedure as described for the synthesis of intermediate 15 (alternative pathway), using intermediate 55a as starting material (396 mg, 54%).

Preparation of Intermediate 58:

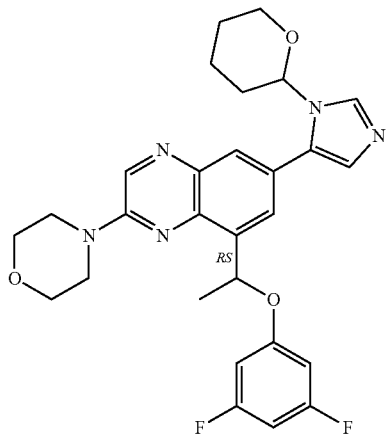 [SMILES: CC(Oc1cc(F)cc(F)c1)c1cc(-c2cncn2C2CCCCO2)cc2ncc(N3CCOCC3)nc12]

A solution of compound 277 (282 mg; 0.63 mmol), 1-(tetrahydro-2H-pyran-2-yl)-5-(4,4,5,5-tetramethyl-1,3,2- dioxaborolan-2-yl)-1H-imidazole (226 mg; 0.81 mmol) and $K_2CO_3$ (173 mg; 1.25 mmol) in 1,4-dioxane (4.27 mL) and water (0.64 mL) was degassed under $N_2$. $Pd.Cl_2(dppf).DCM$ (51 mg; 62.6 μmol) was added and the reaction mixture was heated at 95° C. overnight. The resulting suspension was quenched with water (10 mL) and extracted with EtOAc (3×20 mL). The combined organic layers were dried over $MgSO_4$, filtered and evaporated under reduced pressure. The residue was purified by chromatography over silica gel (irregular SiOH; 15-40 μm; 12 g; gradient: from 100% heptane to 90% EtOAc, 10% MeOH (+5% $NH_4OH$)). The pure fractions were collected and the solvent was evaporated to give 127 mg (39%, brown solid) of intermediate 58.

Example A18

Preparation of Intermediate 59:

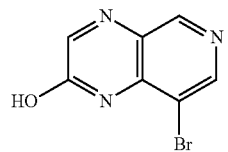 [SMILES: Oc1cnc2cncc(Br)c2n1]

Intermediate 59 was prepared according to an analogous procedure as described for the synthesis of intermediate 1a, using intermediate 5-bromo-3,4-pyridinediamine and ethyl glyoxalate solution (50% in toluene) as starting materials (53.5 g, 47%).

Preparation of Intermediate 60:

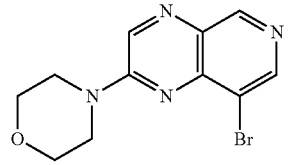 [SMILES: Brc1cncc2ncc(N3CCOCC3)nc12]

Intermediate 60 was prepared according to an analogous procedure as described for the synthesis of intermediate 3a, using intermediate 59 and morpholine as starting materials (30 g, 44%).

Preparation of Intermediate 61a and Intermediate 61b

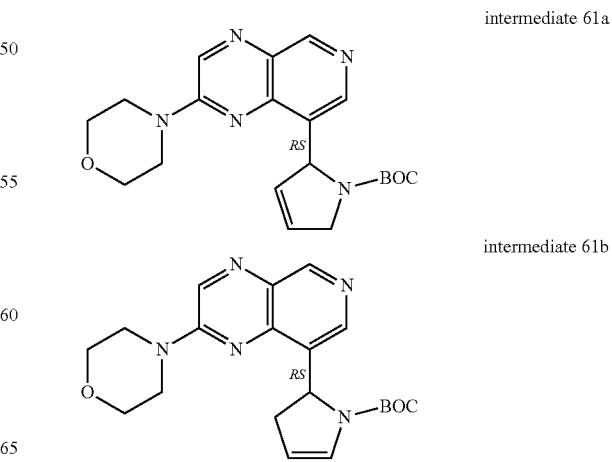

A mixture of intermediate 61a and 61b was prepared according to an analogous procedure as described for the synthesis of intermediate 6a and intermediate 6b, using intermediate 60 and N-boc-2,3-dihydro-1H-pyrrole as starting materials (800 mg, 62%).

Preparation of Intermediate 62a and Intermediate 62b

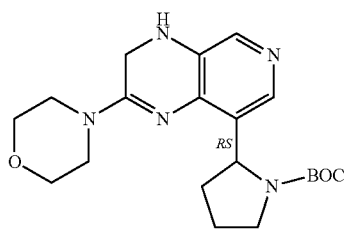
intermediate 62a

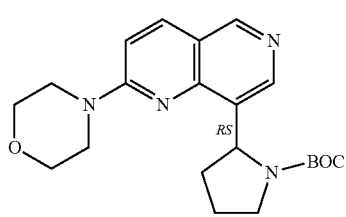
intermediate 62b

A mixture of intermediates 62a and 62b was prepared according to an analogous procedure as described for the synthesis of intermediate 7, using a mixture of intermediates 61a and 61b and platinum (IV) oxide as starting materials at atmospheric pressure for 3 h (750 mg, quant.).

Preparation of Intermediate 63:

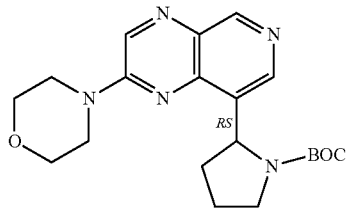 [SMILES: CC(C)(C)OC(=O)N1CCCC1c1cncc2ncc(N3CCOCC3)nc12]

Intermediate 63 was prepared according to an analogous procedure as described for the synthesis of intermediate 8, using a mixture of intermediates 62a and 62b and manganese oxide as starting materials (623 mg, 83%).

Preparation of Intermediate 64:

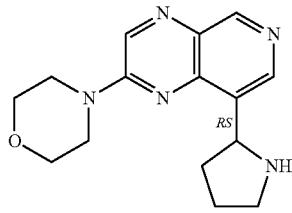

Intermediate 64 was prepared according to an analogous procedure as described for the synthesis of intermediate 9, using intermediate 63 as starting material (300 mg, 65%).

Example A19

Preparation of Intermediate 65:

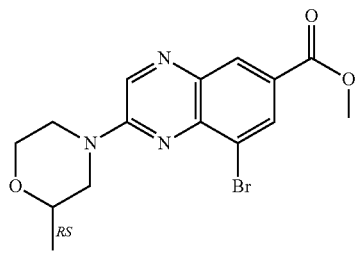 [SMILES: COC(=O)c1cc(Br)c2nc(N3CCOC(C)C3)cnc2c1]

Intermediate 65 was prepared according to an analogous procedure as described for the synthesis of intermediate 3a, using intermediate 2a and 2-methylmorpholine as starting materials (1.58 g, 81%, yellow solid).

Preparation of Intermediate 66:

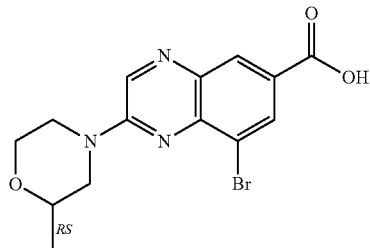 [SMILES: CC1CN(c2cnc3cc(C(=O)O)cc(Br)c3n2)CCO1]

Intermediate 36 was prepared according to an analogous procedure as described for the synthesis of intermediate 4, using intermediate 65 as starting material (1.39 g, 92%, yellow solid).

Preparation of Intermediate 67:

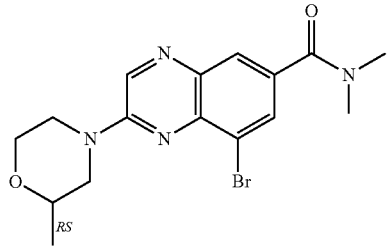 [SMILES: CC1CN(c2cnc3cc(C(=O)N(C)C)cc(Br)c3n2)CCO1]

Intermediate 67 was prepared according to an analogous procedure as described for the synthesis of intermediate 5, using intermediate 66 as starting material (1.43 g, 96%, yellow foam).

Preparation of Intermediate 68a and Intermediate 68b

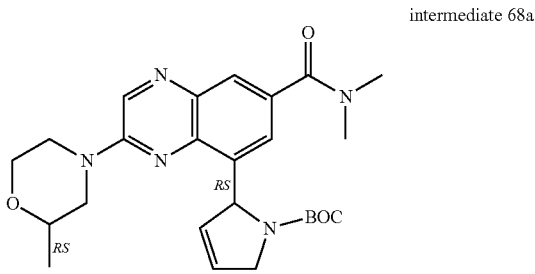

intermediate 68a

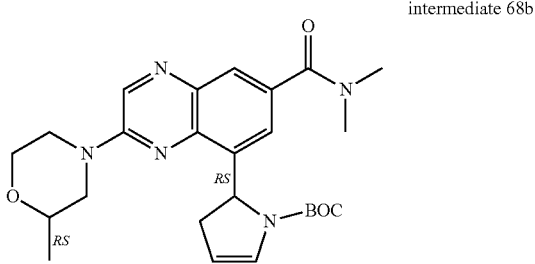

intermediate 68b

A mixture of intermediates 68a and 68b was prepared according to an analogous procedure as described for the synthesis of intermediate 6, using intermediate 67 and N-boc-2,3-dihydro-1H-pyrrole as starting materials (370 mg, 81%, yellow oil).

Preparation of Intermediate 69:

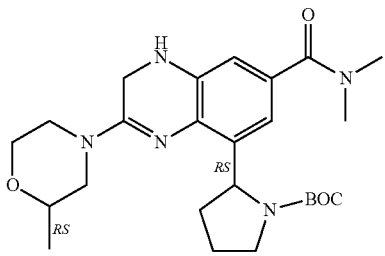 [SMILES: CC1CN(C2=Nc3c(cc(C(=O)N(C)C)cc3C3CCCN3C(=O)OC(C)(C)C)NC2)CCO1]

A mixture of intermediates 68a and 68b (370 mg; 0.79 mmol) and platinum (IV) oxide (37 mg; 0.16 mmol) in MeOH (4 mL) and THF (4 mL) was hydrogenated at rt under pressure of 1 bar of Eh for 16 h. Then, more platinum (IV) oxide (18 mg; 0.08 mmol) was added and the mixture was hydrogenated at rt under pressure of 1 bar of $H_2$ for 16 h. The reaction was filtered through a pad of Celite® and rinsed with MeOH. The filtrate was combined with another batch from 30 mg of intermediates 68a and 68b and was evaporated to give 355 mg (82%) of intermediate 69. The product was directly used in the next step without any further purification.

Preparation of Intermediate 70:

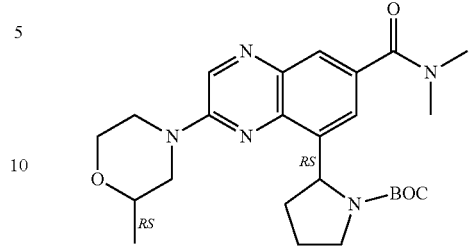

Intermediate 70 was prepared according to an analogous procedure as described for the synthesis of intermediate 8, using intermediate 69 as starting material (279 mg, 79%, yellow foam).

Alternative Pathway:

Sec-Butyllithium (1.3M in THF) (2.29 mL; 2.97 mmol) was added to a solution of N-Boc-pyrrolidine (521 µL; 2.97 mmol) and N,N,N',N'-tetramethylenediamine (446 µL; 2.97 mmol) in THF (3.72 mL) under $N_2$ at −78° C. The solution was stirred 1 h 30 at −78° C. Zinc chloride (2M in Me-THF) (1.49 mL; 2.97 mmol) was added slowly. The reaction was stirred 30 min at −78° C. then 1 h at rt. Intermediate 67 (600 mg; 1.49 mmol), Pd(OAc)$_2$ (13 mg; 0.06 mmol) and tri-tert-butylphosphonium tetrafluoroborate (35 mg; 0.12 mmol) were added. Then, the reaction mixture was heated at 60° C. for 30 min. The mixture was combined with another batch coming from a reaction performed on 500 mg of intermediate 67. The mixture was quenched with a saturated solution of $NH_4Cl$ and extracted with EtOAc. The organic layer was dried over $MgSO_4$, filtered and evaporated in vacuum. The residue (2.2 g, orange oil) was purified by chromatography over silica gel (regular SiOH 30 µm; 80 g; gradient: from 80% DCM, 20% EtOAc to 100% EtOAc). The pure fractions were collected and the solvent was evaporated to give 156 mg (12%, yellow foam) of intermediate 70.

Preparation of Intermediate 71:

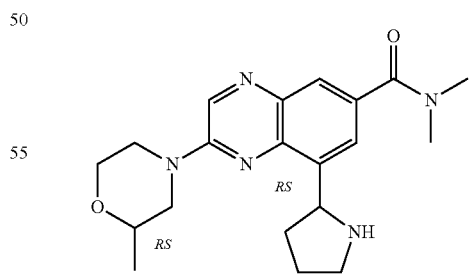

Intermediate 71 was prepared according to an analogous procedure as described for the synthesis of intermediate 37, using intermediate 70 as starting material (157 mg, 69%, orange oil).

Example A20

Preparation of Intermediate 74:

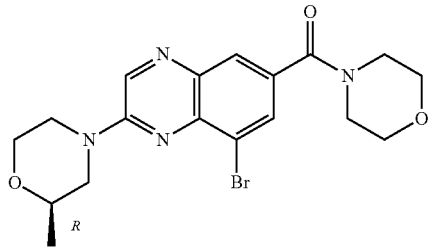

Intermediate 74 was prepared according to an analogous procedure as described for the synthesis of intermediate 5, using intermediate 32 and (R)-2-methylmorpholine as starting materials (2.76 g, quant.). The product was directly used without any purification in the next step.

Preparation of Intermediate 75:

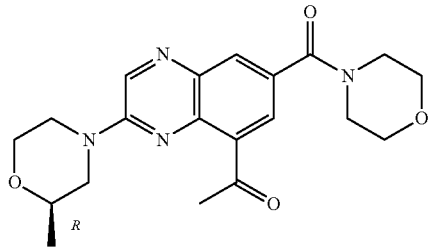

Intermediate 75 was prepared according to an analogous procedure as described for the synthesis of intermediate 10a, using intermediate 74 as starting material (316 mg, 74%).

Preparation of Intermediate 76:

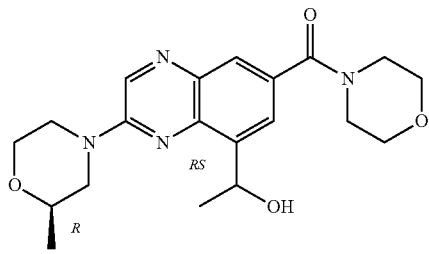

Intermediate 76 was prepared according to an analogous procedure as described for the synthesis of intermediate 15, using intermediate 75 as starting material (81 mg, 67%).

Example A21

Preparation of Intermediate 77:

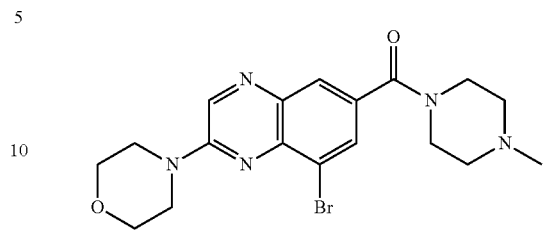

Intermediate 77 was prepared according to an analogous procedure as described for the synthesis of intermediate 5, using intermediate 4 and 1-methylpiperazine as starting materials (1.6 g, 86%).

Preparation of Intermediate 78a and Intermediate 78b intermediate 78a

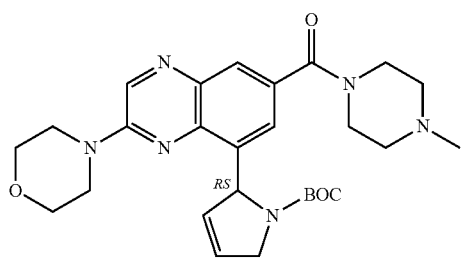 [SMILES: CN1CCN(C(=O)c2cc3c(c(C4CCCN4C(=O)OC(C)(C)C)c2)N=C(N2CCOCC2)CN3)CC1]

intermediate 78b

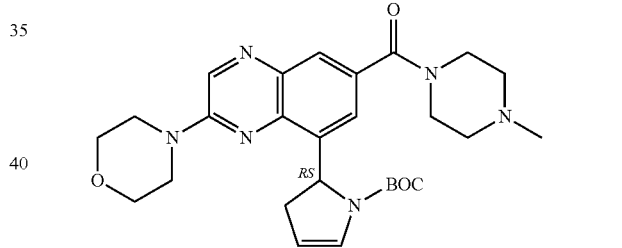

A mixture of intermediate 78a and 78b was prepared according to an analogous procedure as described for the synthesis of intermediates 6a and 6b, using intermediate 77 and N-boc-2,3-dihydro-1H-pyrrole as starting materials (1.2 g, 62%, ratio by $^1$H NMR: 65/35).

Preparation of Intermediate 79:

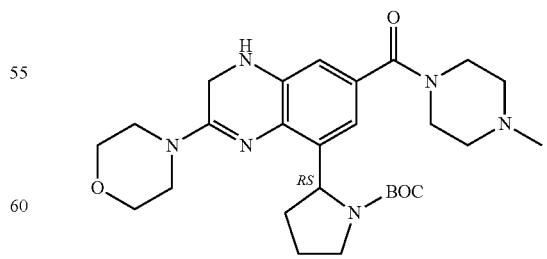

Intermediate 79 was prepared according to an analogous procedure as described for the synthesis of intermediate 7, using a mixture of intermediates 78a and 78b in MeOH as starting materials (1.2 g, quant.).

Preparation of Intermediate 80a, Intermediate 80b and Intermediate 80c

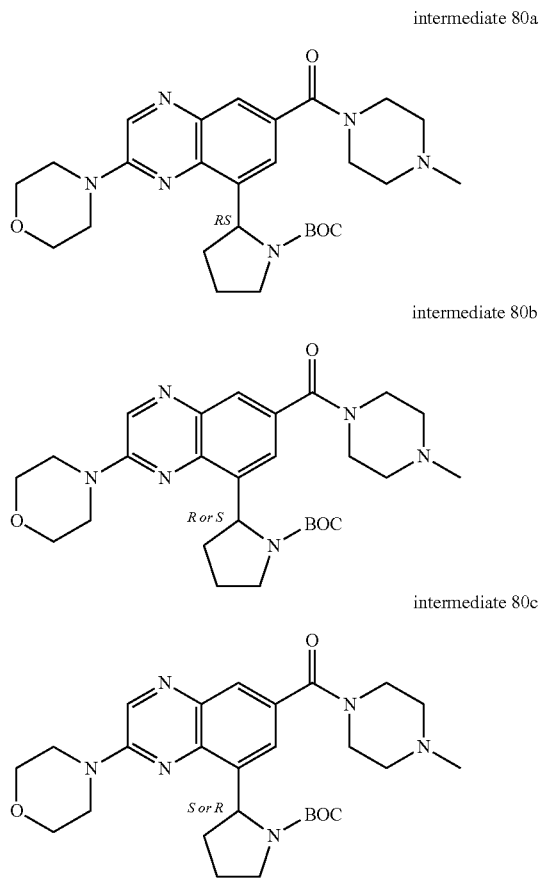

intermediate 80a intermediate 80b intermediate 80c

A mixture of intermediate 79 (1.2 g; 2.34 mmol), manganese oxide (0.61 g; 7.02 mmol) in DCM (30 mL) was stirred at rt for 1 h. The reaction mixture was filtered through a pad of Celite®, rinsed with MeOH and the filtrate was evaporated. The residue (1.1 g) was purified by chromatography over silica gel (irregular 15-40 μm; 50 g; mobile phase: 40% heptane, 10% MeOH (+10% NH$_4$OH), 50% EtOAc). The pure fractions were collected and the solvent was evaporated to give 0.58 g (48%) of intermediate 80a. The racemic product was purified by chiral SFC (Whelk 01 (S,S) 5 μm 250*21.1 mm; mobile phase: 45% CO$_2$, 55% MeOH). The pure fractions were collected and the solvent was evaporated to give 265 mg (22%) of intermediate 80b and 265 mg (22%) of intermediate 80c.

Preparation of Intermediate 81:

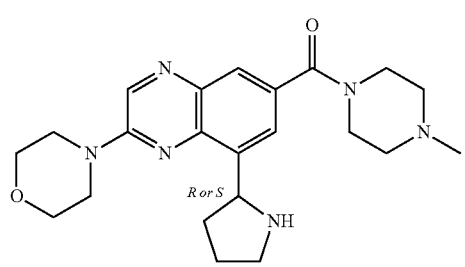 [SMILES: CN1CCN(C(=O)c2cc(C3CCCN3)c3nc(N4CCOCC4)cnc3c2)CC1]

Intermediate 81 was prepared according to an analogous procedure as described for the synthesis of intermediate 9, using intermediate 80b as starting material (100 mg, 47%).

Preparation of Intermediate 82

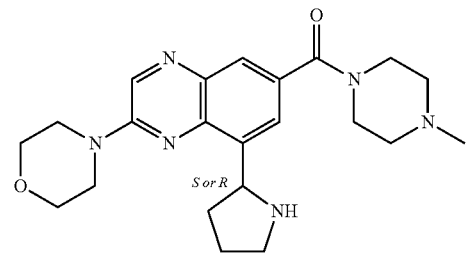 [SMILES: CN1CCN(C(=O)c2cc(C3CCCN3)c3nc(N4CCOCC4)cnc3c2)CC1]

Intermediate 82 was prepared according to an analogous procedure as described for the synthesis of intermediate 9, using intermediate 80c as starting material (120 mg, 56%).

Example A22

Preparation Intermediate 86:

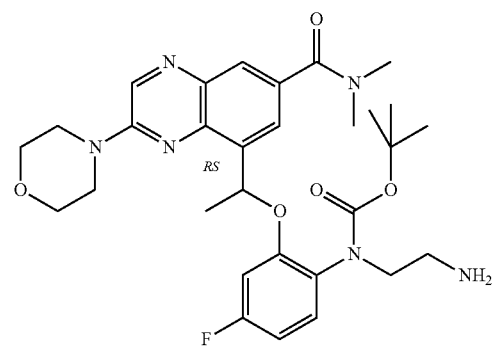 [SMILES: CC(Oc1cc(F)ccc1N(CCN)C(=O)OC(C)(C)C)c1cc(C(=O)N(C)C)cc2ncc(N3CCOCC3)nc12]

In a sealed tube, a mixture of compound 78 (290 mg; 0.57 mmol), N-boc-1,2-diaminoethane (179 μL; 1.13 mmol) and Cs$_2$CO$_3$ (554 mg; 1.70 mmol) in 2-methyl-2-butanol (2.76 mL) was carefully degassed under vacuum and back-filled with N$_2$. BrettPhos Precatalyst First Gen (23 mg; 0.03 mmol) and BrettPhos (6 mg; 0.01 mmol) were added. The reaction mixture was carefully degassed under vacuum and back-filled with N$_2$ and heated at 110° C. for 3 h. After cooling down to rt, BrettPhos Precatalyst First Gen (23 mg; 0.03 mmol) and BrettPhos (6 mg; 0.01 mmol) were added. The reaction mixture was degassed in vacuum and back-filled with N$_2$ and heated at 110° C. for 4 h. After cooling down to rt, the mixture was combined with a batch coming from a reaction performed on 40 mg of compound 78. The crude was diluted with EtOAc and filtered through a pad of Celite®. The filtrate was evaporated in vacuum to dryness. The residue (758 mg, brown oil) was purified by chromatography over silica gel (Irregular SiOH 15-40 μm; 40 g; gradient: from 85% heptane, 13.5% EtOAc, 1.5% MeOH to 50% heptane, 45% EtOAc, 5% MeOH). The pure fractions were collected and the solvent was evaporated. The residue (309 mg) was purified by chromatography over silica gel (Irregular bare silica; 40 g; mobile phase: 53% heptane, 7% MeOH (+10% NH$_4$OH), 35% EtOAc). The pure fractions were collected and the solvent was evaporated to give 180 mg (55%, pale yellow foam) of intermediate 86.

Example A23

Preparation of Intermediate 88:

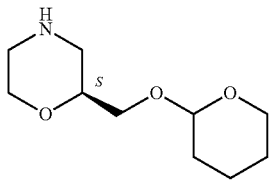

Pyridinium p-toluenesulfonate (409 mg; 1.63 mmol) and 3,4-dihydro-2H-pyran (2.98 mL; 32.6 mmol) were added to a solution of (S)-2-hydroxymethylmorpholine hydrochloride (2.5 g; 16.28 mmol) in DCM (160 mL). The reaction mixture was stirred at rt overnight. Then, a saturated aqueous solution of NaHCO$_3$ was added and the layers were separated. The organic layer was dried over MgSO$_4$, filtered and the solvent was evaporated under vacuum to give 2.29 g (70%, yellow oil) of intermediate 88.

Preparation of Intermediate 89:

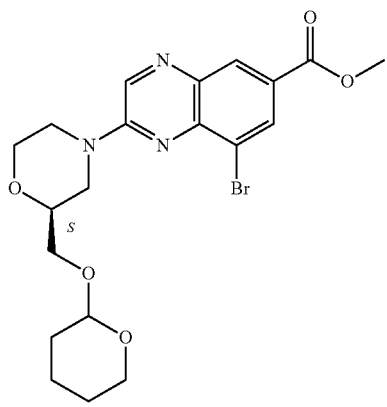

Intermediate 89 was prepared according to an analogous procedure as described for the synthesis of intermediate 31, using intermediate 2a and intermediate 88 as starting materials (1.42 g, 92%, yellow crystals).

Preparation of Intermediate 90:

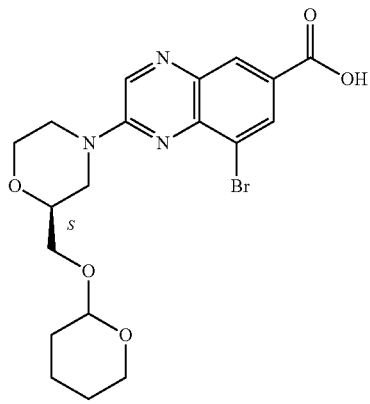

Intermediate 90 was prepared according to an analogous procedure as described for the synthesis of intermediate 11, using intermediate 89 as starting material. The reaction mixture was stirred at rt overnight. The mixture was evaporated under vacuum and the residue was slowly acidified with 10% aqueous solution of NH$_4$Cl. Then, DCM was added and the layers were separated. The organic layer was washed with saturated aqueous solution of NH$_4$Cl and the product was extracted with DCM/MeOH (9/1) (3×). The combined organic layer were dried over Na$_2$SO$_4$, filtered and evaporated under vacuum to give 1.5 g (yellow solid) of intermediate 90.

Preparation of Intermediate 91:

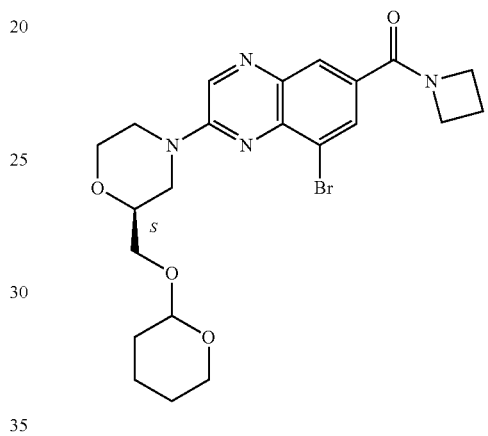

Intermediate 81 was prepared according to an analogous procedure as described for the synthesis of intermediate 5, using intermediate 90 and azetidine hydrochloride as starting materials (407 mg, 55%, yellow foam).

Preparation of Intermediate 92:

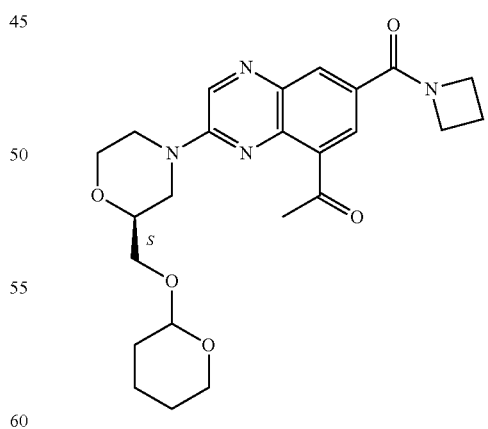

Intermediate 92 was prepared according to an analogous procedure as described for the synthesis of intermediate 10a, using intermediate 91 as starting material (110 mg, 33%, yellow oil).

Preparation of Intermediate 93:

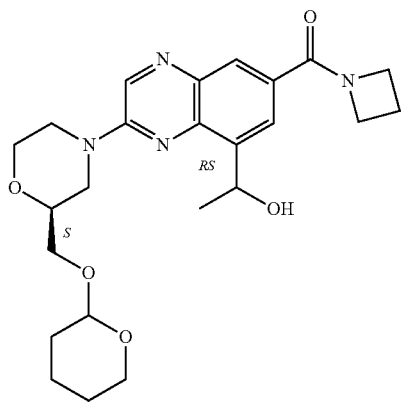

Intermediate 93 was prepared according to an analogous procedure as described for the synthesis of intermediate 15 (alternative pathway), using intermediate 92 as starting material (116 mg, pale yellow foam).

Preparation of Intermediate 94:

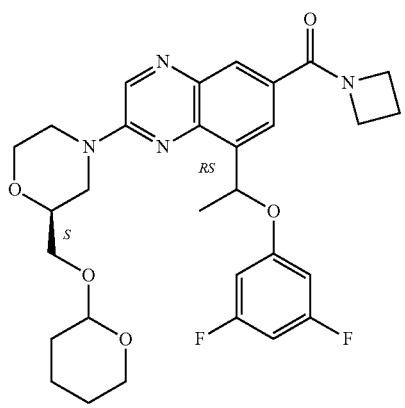

Intermediate 94 was prepared according to an analogous procedure as described for the synthesis of compound 247, using intermediate 93 and 3,5-difluorophenol as starting materials (46 mg, 34%, colorless oil).

Example A24

Preparation of Intermediate 95:

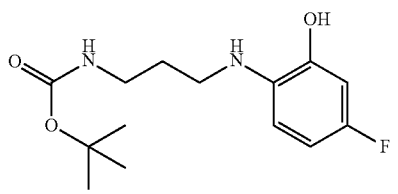 [SMILES: CC(C)(C)OC(=O)NCCCNc1ccc(F)cc1O]

Tert-butyl 3-aminopropylcarbamate (1.31 mL; 7.49 mmol) was added to a solution of 4-fluoro-2-hydroxybenzaldehyde (1 g; 7.14 mmol) in MeOH (70 mL). The reaction mixture was stirred at rt overnight. Then, sodium borohydride (540 mg; 14.27 mmol) was added portionwise and the reaction mixture was stirred at rt for 1 h 30. The mixture was slowly quenched with a saturated aqueous solution of NH$_4$Cl. The mixture was evaporated under vacuum and the residue was taken-up with EtOAc and water. The layers were separated. The organic layer was dried over MgSO$_4$, filtered and evaporated in vacuum. The residue (2.25 g, pale yellow oil) was triturated in Et$_2$O and evaporated under vacuum (2×) to give 2.10 g (99%, white solid) of intermediate 95.

Preparation of Intermediate 96:

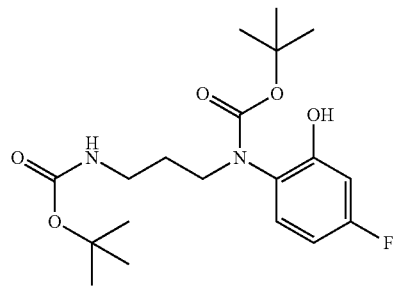 [SMILES: CC(C)(C)OC(=O)NCCCN(C(=O)OC(C)(C)C)c1ccc(F)cc1O]

Ditert-butyl dicarbonate (878 mg; 4.02 mmol) was added to a solution of intermediate 95 (1 g; 3.35 mmol) and triethylamine (1.40 mL; 10.06 mmol) in DCM (34 mL) at 0° C. The reaction mixture was stirred at rt overnight. Then, the mixture was washed with a saturated aqueous solution of NaHCO$_3$. The organic layer was dried over MgSO$_4$, filtered and evaporated under vacuum. The residue (1.7 g, colourless oil) was purified by chromatography over silica gel (irregular SiOH; 15-40 µm; 80 g; eluent: from 90% heptane, 10% DCM to 10% heptane, 90% DCM). The pure fractions were collected and the solvent was evaporated to give 614 mg (46%, white foam) of intermediate 96.

Preparation of Intermediate 97:

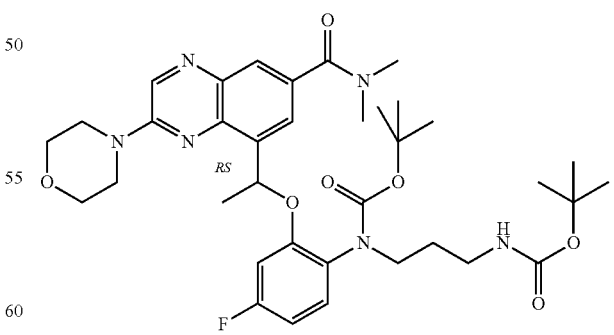

Intermediate 97 was prepared according to an analogous procedure as described for the synthesis of compound 247, using intermediate 17 and intermediate 96 as starting materials (435 mg, 61%, yellow foam).

Example A25

Preparation of Intermediate 98:

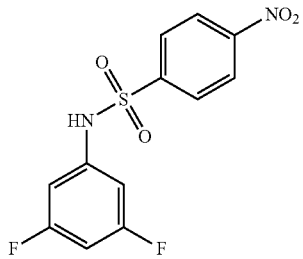 [SMILES: O=[N+]([O-])c1ccc(S(=O)(=O)Nc2cc(F)cc(F)c2)cc1]

A solution of 3,5-difluoroaniline (2 g; 15.49 mmol), 4-nitrobenzenesulfonyl chloride (3.61 g; 16.27 mmol) and 4-dimethylaminopyridine (37.9 mg; 0.31 mmol) in pyridine (60 mL) was heated at 100° C. for 18 h. After cooling down to rt, the solution was evaporated under vacuum and taken-up in DCM. The organic layer was successively washed with 1N aqueous solution of HCl (×2), water and a saturated aqueous solution of NaCl. Then, it was dried over $MgSO_4$, filtered and evaporated under vacuum to give 4.5 g (92%, beige solid) of intermediate 98.

Alternative Pathway:

In a microwave tube, 4-nitrobenzenesulfonyl chloride (2.7 g; 12.20 mmol) was added to a mixture of 3,5-difluoroaniline (1.5 g; 11.62 mmol) and 4-dimethylaminopyridine (28 mg; 232 μmol) in pyridine (15 mL). The mixture was heated at 100° C. using one single mode microwave with a power output ranging from 0 to 400 W for 30 min. The mixture was then evaporated under vacuum and taken-up in DCM. The organic layer was successively washed with 1N aqueous solution of HCl (×2), water and a saturated aqueous solution of NaCl. Then, it was dried over $MgSO_4$, filtered and evaporated under vacuum to give 2.9 g (79%, beige solid) of intermediate 98.

Preparation of Intermediate 99:

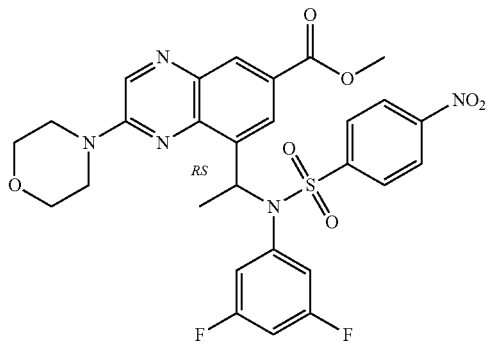 [SMILES: COC(=O)c1cc(C(C)N(c2cc(F)cc(F)c2)S(=O)(=O)c2ccc([N+](=O)[O-])cc2)c2nc(N3CCOCC3)cnc2c1]

Intermediate 99 was prepared according to an analogous procedure as described for the synthesis of compound 277, using intermediate 15 and intermediate 98 as starting materials. The reaction mixture was heated at 110° C. overnight. The mixture was cooled down to rt, poured into water and extracted with EtOAc. The organic layer was washed with brine, dried over $MgSO_4$, filtered and evaporated to dryness. The residue was purified by chromatography over silica gel (irregular 15-40 μm; 50 g; mobile phase: 98% DCM, 2% MeOH). The pure fractions were collected and the solvent was evaporated. The residue (0.85 g) was purified by chromatography over silica gel (irregular 15-40 μm; 50 g; mobile phase: 50% heptane, 45% EtOAc, 5% MeOH). The pure fractions were collected and the solvent was evaporated to give 430 mg (45%) of intermediate 99.

Preparation of Intermediate 100:

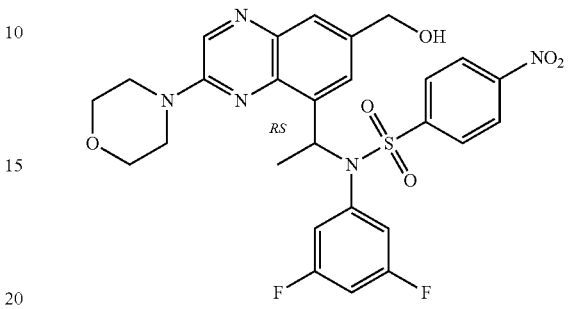

Diisobutylaluminium hydride (Solution 20% in toluene) (3 mL; 3.59 mmol) was added dropwise to a solution of intermediate 99 (440 mg; 0.72 mmol) in THF (15 mL) at −70° C. under $N_2$. The reaction mixture was stirred for 4 h at −70° C. The mixture was poured carefully into a solution of ice and $NH_4Cl$, then extracted with DCM. The organic layer was washed with water and dried over $MgSO_4$, filtered and evaporated to dryness. The residue (450 mg) was purified by chromatography over silica gel (irregular 15-40 μm; 40 g; gradient: from 0.1% $NH_4OH$, 3% MeOH, 97% DCM to 0.1% $NH_4OH$, 5% MeOH, 95% DCM). The pure fractions were collected and the solvent was evaporated to give 100 mg (24%) of intermediate 100.

Example A26

Preparation of Intermediate 103:

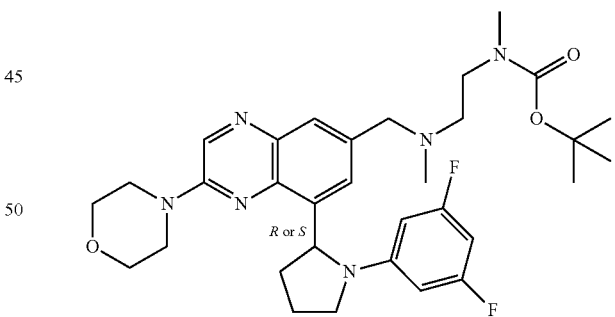

Compound 250 (100 mg; 0.24 mmol) was added to a solution of tert-butyl methyl[2-methylamino]ethyl]carbamate (221 mg; 1.18 mmol) and sodium acetate (97 mg; 1.18 mmol) in MeOH (3 mL). The reaction mixture was stirred at rt for 4 h. Then, sodium borohydride (18 mg; 0.47 mmol) was added portionwise at 0° C. and the reaction mixture was stirred at rt for 1 h 30. Then, water was added and the product extracted with EtOAc. The organic layer was washed with brine (×2), then dried over $MgSO_4$, filtered and evaporated to give 279 mg (quant.) of intermediate 103. The crude product was used without purification in the next step.

Example A27

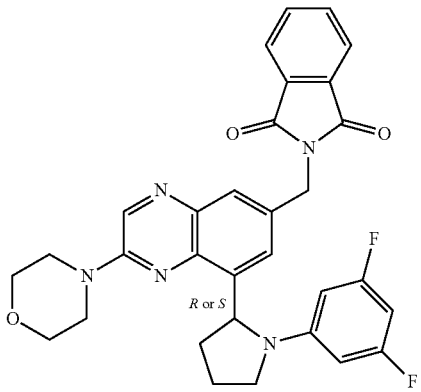 [SMILES: O=C1c2ccccc2C(=O)N1Cc1cc(C2CCCN2c2cc(F)cc(F)c2)c2nc(N3CCOCC3)cnc2c1]

Preparation of Intermediate 104:

Diisopropyl azodicarboxylate (277 µL; 1.41 mmol) and PPh$_3$ (369 mg; 1.41 mmol) in THF (5 mL) was stirred at rt for 15 min. A solution of compound 10 (200 mg; 0.47 mmol) and phtalimide (207 mg; 1.41 mmol) in THF (5 mL) was added dropwise and the reaction mixture was heated at 40° C. for 24 h. The mixture was evaporated until dryness. The residue (985 mg) was purified by chromatography over silica gel (irregular 15-40 µm; 40 g; mobile phase: 60% heptane, 5% MeOH, 35% EtOAc). The pure fractions were collected and evaporated to give 750 mg (quant.) of intermediate 104.

Example A28

Preparation of Intermediate 106:

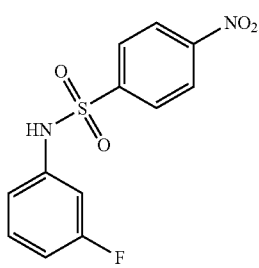 [SMILES: O=[N+]([O-])c1ccc(S(=O)(=O)Nc2cccc(F)c2)cc1]

Intermediate 106 was prepared according to an analogous procedure as described for the synthesis of intermediate 98, using 3-fluoroaniline and 4-nitrobenzenesulfonyl chloride as starting material (4.97 g, 93%, pale brown solid).

Preparation of Intermediate 107:

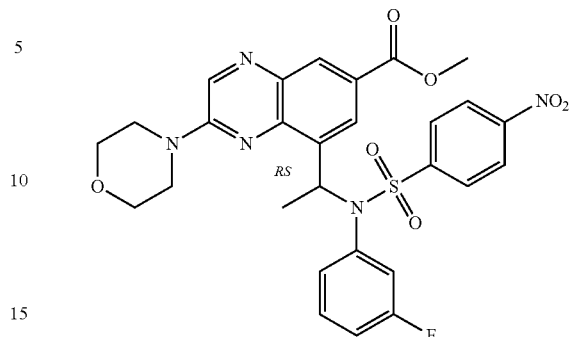

Intermediate 107 was prepared according to an analogous procedure as described for the synthesis of compound 277, using intermediate 15 and intermediate 106 as starting materials (2.63 g, 47%, brown solid). The reaction mixture was heated at 120° C. for 18 h.

Preparation of Intermediate 108:

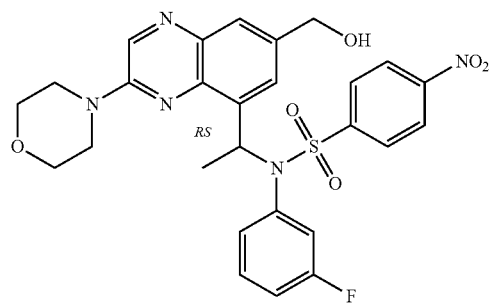 [SMILES: CC(c1cc(CO)cc2ncc(N3CCOCC3)nc12)N(c1cccc(F)c1)S(=O)(=O)c1ccc([N+](=O)[O-])cc1]

Intermediate 108 was prepared according to an analogous procedure as described for the synthesis of intermediate 100, using intermediate 107 as starting material (73 mg, 33%, yellow solid).

Example A29

Preparation of Intermediate 109a and Intermediate 109b

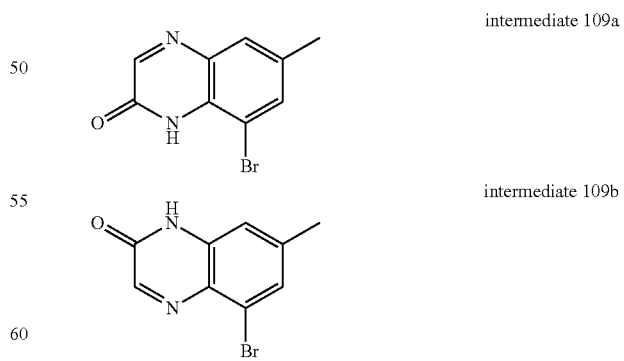

A mixture of intermediates 109a and 109b was prepared according to an analogous procedure as described for the synthesis of intermediate 1, using 3-bromo-5-methylbenzene-1,2-diamine and 2,2-dihydroxy-acetic acid as starting materials (21 g, 100%).

Preparation of Intermediate 110a and Intermediate 110b

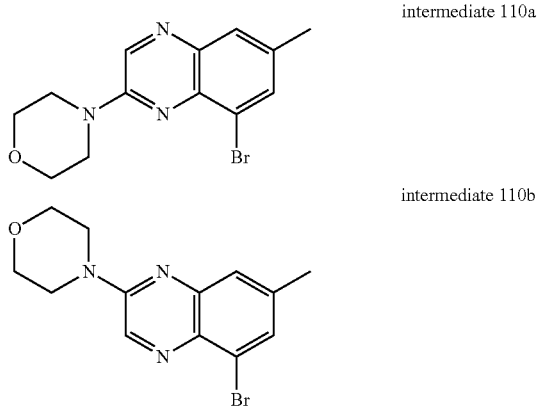

A mixture of intermediates 110a and 110b was prepared according to an analogous procedure as described for the synthesis of intermediates 3a and 3b, using a mixture of intermediates 109a and 109b and morpholine as starting materials (14.3 g, 52%, ration 1/1 by NMR).

Preparation of Intermediate 111a: And Intermediate 111b

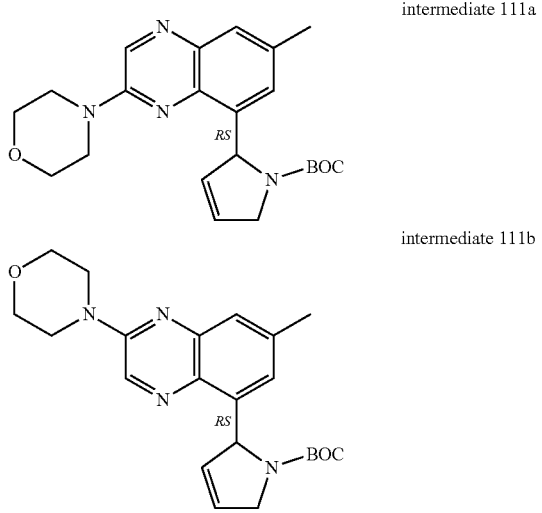 [SMILES: Cc1cc(C2C=CCN2C(=O)OC(C)(C)C)c2nc(N3CCOCC3)cnc2c1 ; Cc1cc(C2C=CCN2C(=O)OC(C)(C)C)c2ncc(N3CCOCC3)nc2c1]

Intermediates 111a and 111b were prepared according to an analogous procedure as described for the synthesis of intermediate 20a (alternative pathway), using a mixture of intermediates 110a and 110b and N-boc-2,3-dihydro-1H-pyrrole as starting materials (257 mg, 13% of intermediate 111b and 833 mg, 43% of intermediate 111a).

Preparation of Intermediate 112:

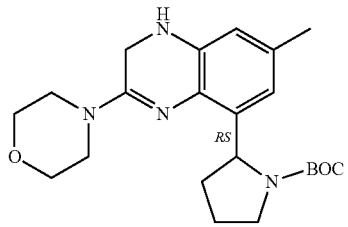 [SMILES: Cc1cc2c(c(C3CCCN3C(=O)OC(C)(C)C)c1)N=C(N1CCOCC1)CN2]

Intermediate 112 was prepared according to an analogous procedure as described for the synthesis of intermediate 7, using intermediate 111a as starting material (879 mg, quant.). The reaction mixture was stirred for 1 h 30. The crude was used without purification for the next step.

Preparation of Intermediate 113:

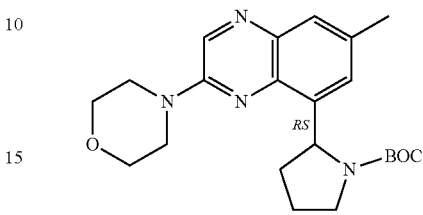

Intermediate 113 was prepared according to an analogous procedure as described for the synthesis of intermediate 8, using intermediate 112 as starting material (782 mg, 94%). The reaction mixture was stirred at rt for 18 h.

Preparation of Intermediate 114:

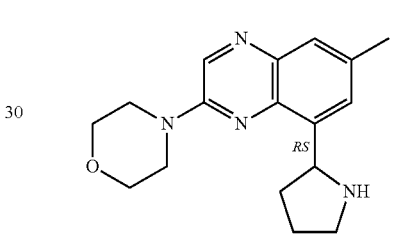

Intermediate 114 was prepared according to an analogous procedure as described for the synthesis of intermediate 9, using intermediate 113 as starting material (405 mg, 74%). The reaction mixture was stirred at rt for 15 h.

Example A30

Preparation of Intermediate 118a and Intermediate 118b

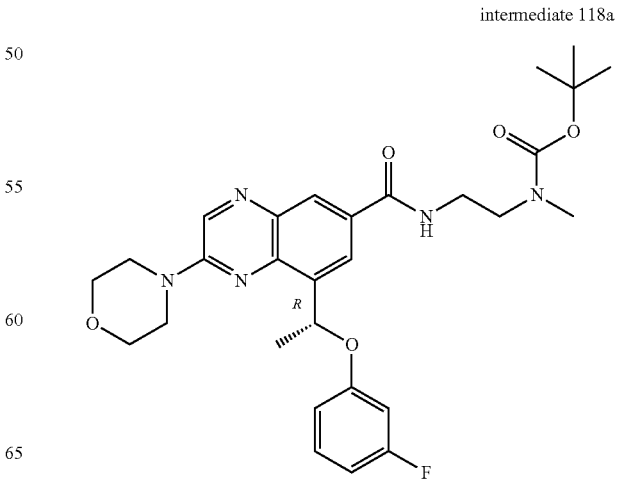

intermediate 118b

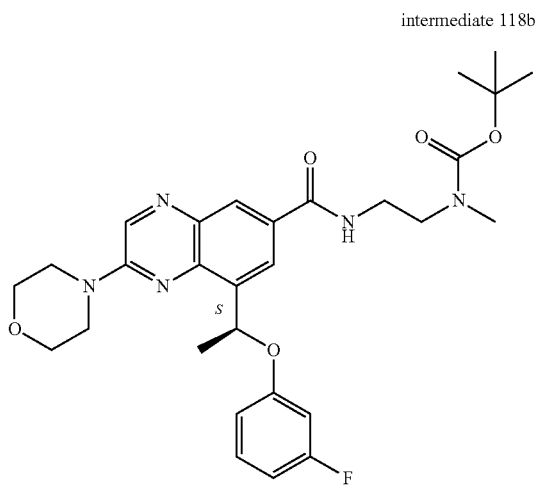

Intermediate 118a and intermediate 118b were prepared according to an analogous procedure as described for the synthesis of compound 5, using compound 257a and N-(2-aminoethyl)-N-methyl carbamic acid tert-butyl ester as starting materials (163 mg, 34%, pale yellow oil of intermediate 118a and 172 mg, 32%, pale yellow oil of intermediate 118b.

Preparation of Intermediate 122:

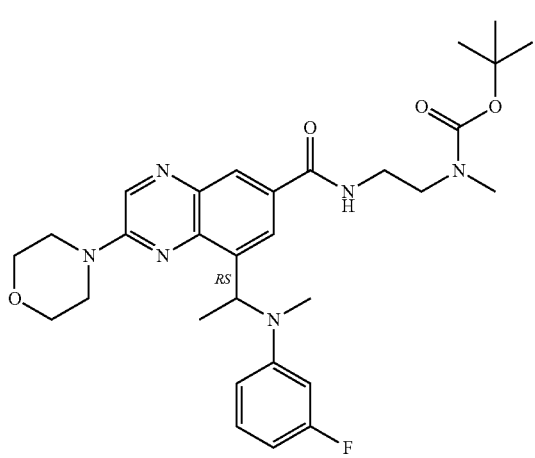

Intermediate 122 was prepared according to an analogous procedure as described for the synthesis of intermediate 5, using compound 98 as starting material (324 mg, 77%).

Preparation of Intermediate 125:

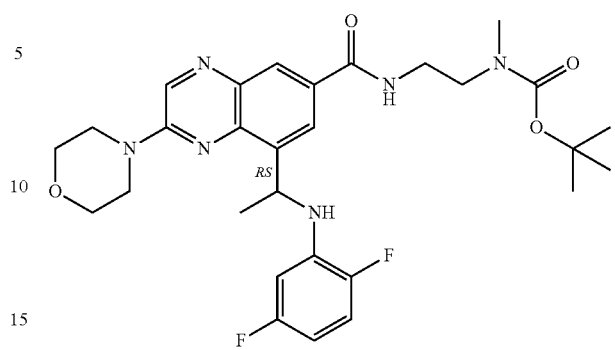

Intermediate 125 was prepared according to an analogous procedure as described for the synthesis of intermediate 5, using compound 261 and N-(2-aminoethyl)-N-methyl carbamic acid tert-butyl ester as starting materials (450 mg, quant.).

Preparation of Intermediate 129:

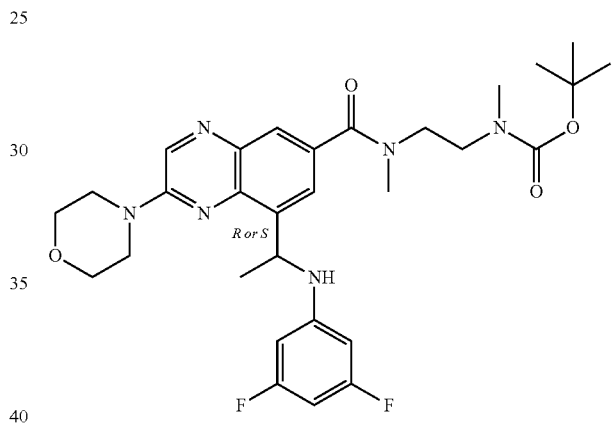

Intermediate 129 was prepared according to an analogous procedure as described for the synthesis of intermediate 5, using compound 83b and N-methyl-N-[2-(methylamino)ethyl]-1,1-dimethylethyl ester carbamic acid as starting materials (95 mg, 27%).

Example A31

Preparation of Intermediate 120:

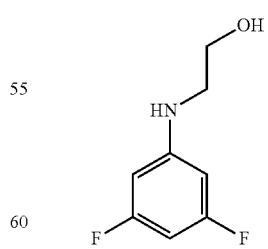

A mixture of 3,5-difluoroaniline (15 g; 116.2 mmol), 2-bromoethanol (14.5 g; 116.2 mmol) and DIPEA (140 mL) was heated at 140° C. overnight in a sealed vessel. The reaction mixture was filtered to give 18 g (90%) of intermediate 120.

143

Preparation of Intermediate 121:

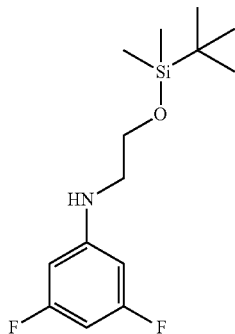 [SMILES: CC(C)(C)[Si](C)(C)OCCNc1cc(F)cc(F)c1]

A mixture of intermediate 120 (10 g; 57.8 mmol), tert-butyldimethylsilyl chloride (8.7 g; 57.8 mmol), imidazole (3.9 g; 57.8 mmol) in DMF (300 mL) was stirred at rt overnight. The reaction was poured into water and extracted with EtOAc. The organic layer was dried over Na$_2$SO$_4$, filtered and the solvent was evaporated to give 12 g (75%) of intermediate 121.

Alternative Pathway:

In a sealed tube, a mixture of 3,5-difluoroaniline (1 g; 7.75 mmol), (2-bromoethoxy)-tertbutyldimethylsilane (1.83 mL; 8.52 mmol) and DIPEA (3.3 mL) was stirred at 140° C. overnight. The reaction mixture was poured into water, extracted with DCM, washed with brine then with H$_2$O (2×). The organic layer was dried over MgSO$_4$, filtered and evaporated until dryness. The residue (3 g, brown oil) was purified by chromatography over silica gel (irregular 15-40 µm; 50 g; mobile phase: 98% heptane, 2% EtOAc). The pure fractions were collected and evaporated until dryness to give 0.5 g (22%) of intermediate 121 and 1.5 g (not pure) which was purified by chromatography over silica gel (irregular 15-40 µm; 80 g; mobile phase: 99% heptane, 1% EtOAc). The pure fractions were collected and evaporated to give additional 650 mg (29%) of intermediate 121.

Example A32

Preparation of Intermediate 126:

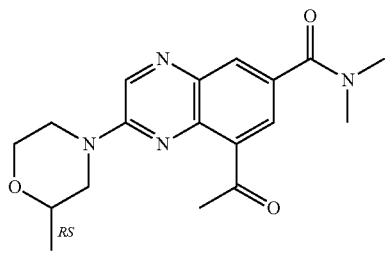 [SMILES: CC(=O)c1cc(C(=O)N(C)C)cc2ncc(N3CCOC(C)C3)nc12]

Intermediate 126 was prepared according to an analogous procedure as described for the synthesis of intermediate 10, using intermediate 67 and tributyl(1-ethoxyvinyl)tin as starting materials (385 mg, 69%, yellow solid).

144

Preparation of Intermediate 127:

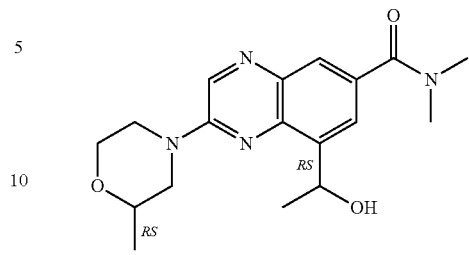

Intermediate 127 (undetermined mixture of 4 diastereoisomers) was prepared according to an analogous procedure as described for the synthesis of intermediate 15 (alternative pathway), using intermediate 126 as starting material (254 mg, 66%, yellow foam).

Example A33

Preparation of Intermediate 128:

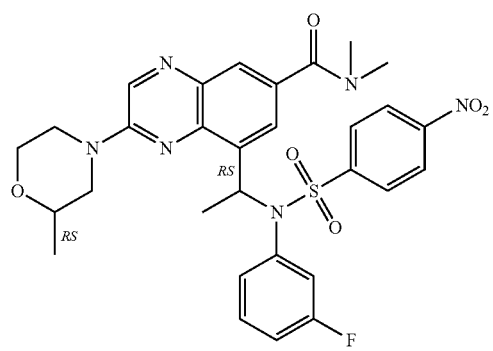 [SMILES: CC1CN(c2cnc3cc(C(=O)N(C)C)cc(C(C)N(c4cccc(F)c4)S(=O)(=O)c4ccc([N+](=O)[O-])cc4)c3n2)CCO1]

Intermediate 128 (undetermined mixture of 4 diastereoisomers) was prepared according to an analogous procedure as described for the synthesis of compound 277, using intermediate 127 and intermediate 106 as starting materials (126 mg, 18%, yellow solid). The reaction mixture was stirred at 110° C. for 18 h.

Example A34

Preparation of Intermediate 132a, Intermediate 132b and Intermediate 132c

Intermediate 132a

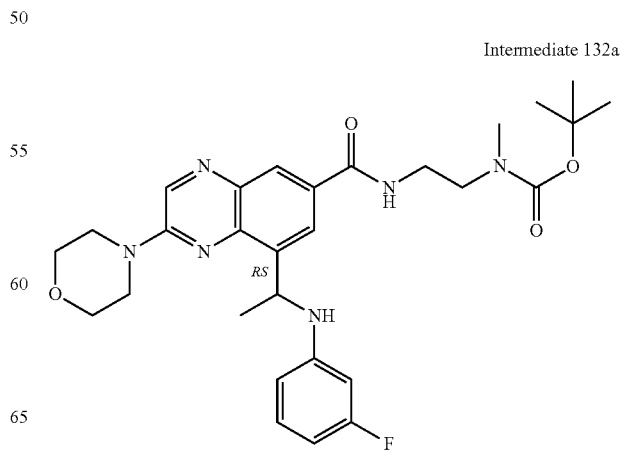

-continued

Intermediate 132b

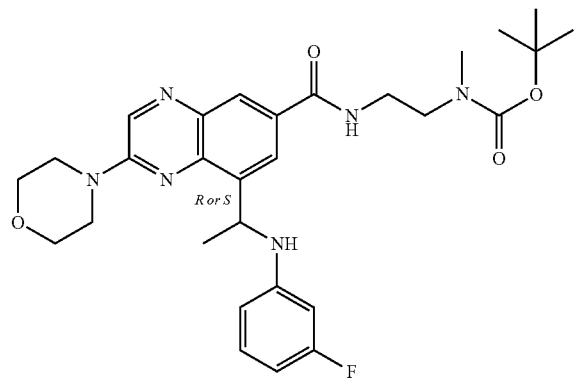 [SMILES: CC(Nc1cc(F)cc(Cl)c1)c1cc(C(=O)NCCN(C)C(=O)OC(C)(C)C)cc2ncc(N3CCOCC3)nc12]

Intermediate 132c

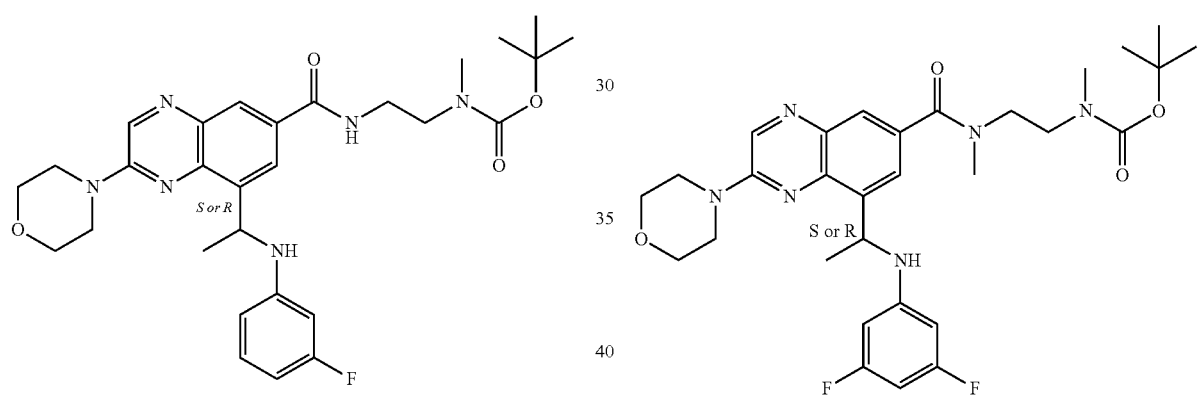

Intermediate 132a were prepared according to an analogous procedure as described for the synthesis of intermediate 5, using compound 263 and N-Boc-N-methylethylenediamine as starting materials. The residue (593 mg, orange oil) was purified by chromatography over silica gel (Irregular SiOH 15-40 µm; 24 g; gradient: from 100% DCM to 90% DCM, 10% iPrOH/NH$_4$OH (95/5)). The pure fractions were collected and the solvent was evaporated. The residue (186 mg, yellow foam, intermediate 132a) was purified by chiral SFC (CHIRALCEL OJ-H 5 µm; 250×20 mm; mobile phase: 75% CO$_2$, 25% iPrOH (0.3% iPrNH$_2$)). The pure fractions were collected and the solvent was evaporated to give two fractions which were separately dissolved in a minimum of DCM, precipitated with pentane then evaporated and dried under vacuum to give respectively 89 mg (38%, yellow solid) of intermediate 132b and 90 mg (38%, yellow solid) of intermediate 132c.

Preparation of Intermediate 135:

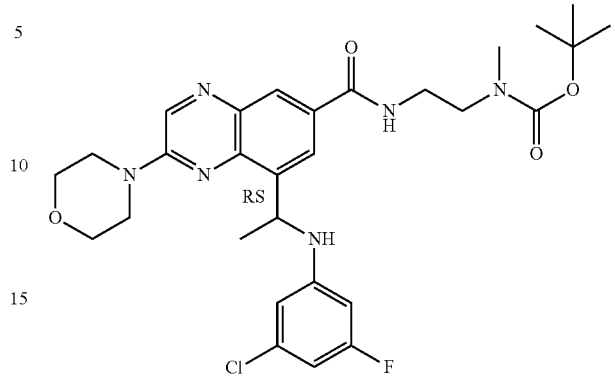

Intermediate 135 was prepared according to an analogous procedure as described for the synthesis of intermediate 5, using compound 265 and N-Boc-N-methylethylenediamine as starting materials (240 mg, quant.).

Preparation of Intermediate 136:

Intermediate 136 was prepared according to an analogous procedure as described for the synthesis of intermediate 5, using intermediate 83c and (N-Boc-N,N'-dimethyl)ethylenediamine as starting materials (200 mg, 59%).

Preparation of Intermediate 148a, Intermediate 148b and Intermediate 148c

Intermediate 148a

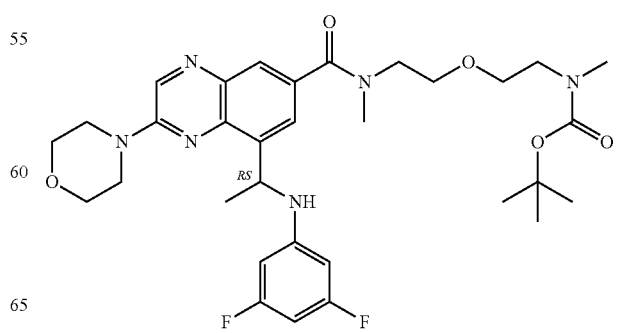

148

Preparation of Intermediate 144 and Intermediate 145

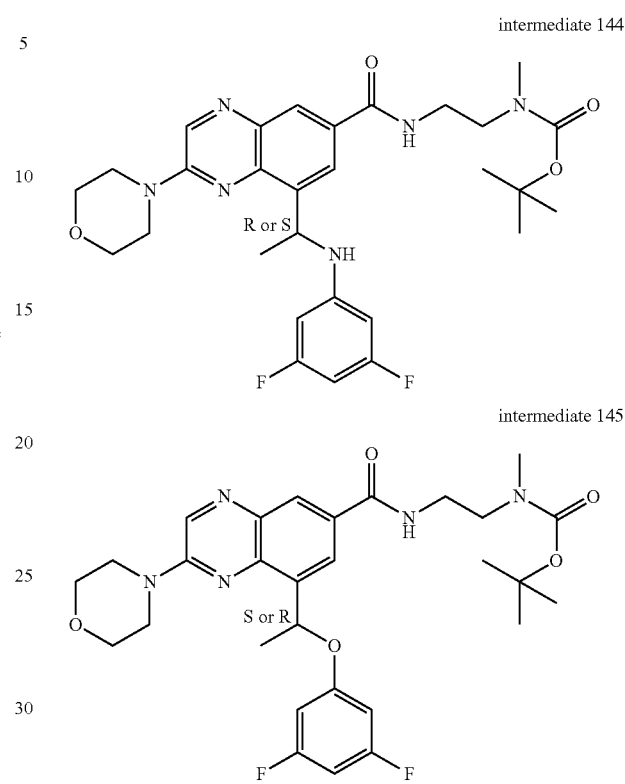

Intermediate 148b

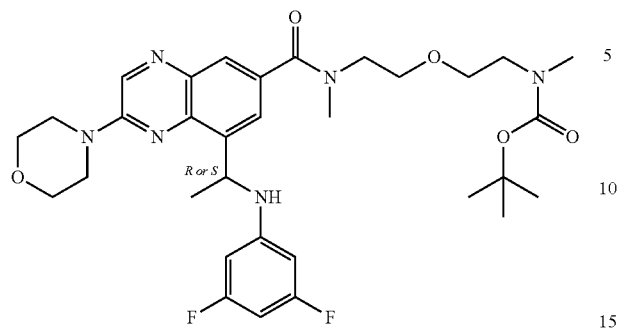

Intermediate 148c

Intermediate 148a was prepared according to an analogous procedure as described for the synthesis of intermediate 5, using compound 83a and intermediate 147 as starting material. Intermediate 148a (346 mg; 91%) was purified by chiral SFC (Chiralpak AS-H 5 μm; 250*20 mm; mobile phase: 80% $CO_2$, 20% EtOH (0.3% $iPrNH_2$)). The pure fractions were collected and the solvent was evaporated to give 103 mg (27%) of intermediate 148b and 100 mg (26%) of intermediate 148c.

Preparation of Intermediate 149:

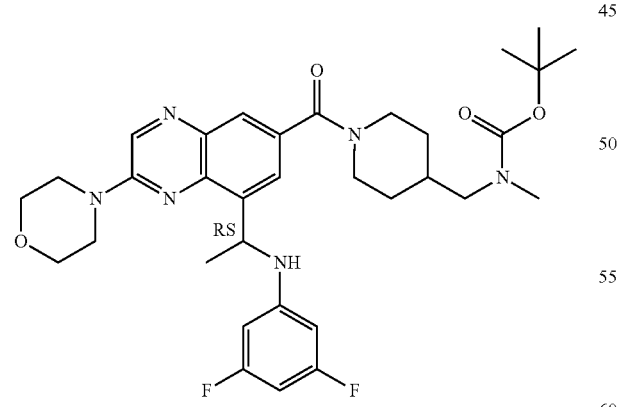

Intermediate 149 was prepared according to an analogous procedure as described for the synthesis of intermediate 5, using compound 83a and tert-butyl methyl(piperidin-4-yl-methyl)carbamate as starting materials (370 mg; quant.). The product was used without purification in the next step.

Intermediate 144 and intermediate 145 were prepared according to an analogous procedure as described for the synthesis of intermediate 5, using compound 248 as starting materials. The racemic (737 mg) was purified by chiral SFC (CHIRALCEL OJ-H 5 μm; 250×20 mm; mobile phase: 90% $CO_2$, 10% EtOH). The pure fractions were collected and the solvent was evaporated to give respectively 297 mg (27%) of intermediate 144 and 339 mg (31%) of intermediate 145.

Preparation of Intermediate 160:

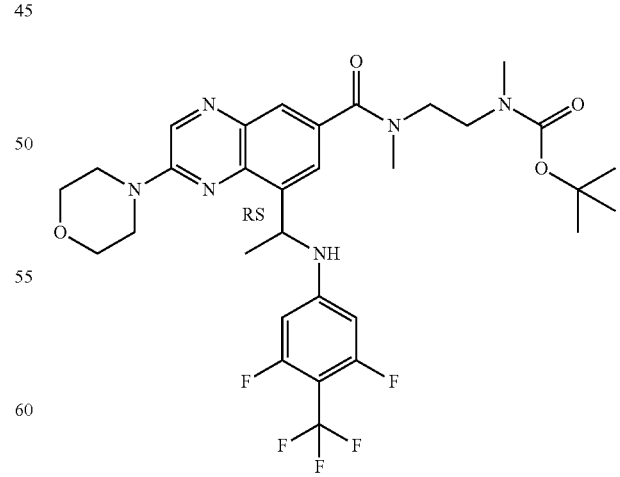

Intermediate 160 was prepared according to an analogous procedure as described for the synthesis of intermediate 5, using compound 270 as starting material (500 mg; 63%).

Preparation of Intermediate 195, Intermediate 195a and Intermediate 195b

Preparation of Intermediate 206, Intermediate 206a and Intermediate 206b

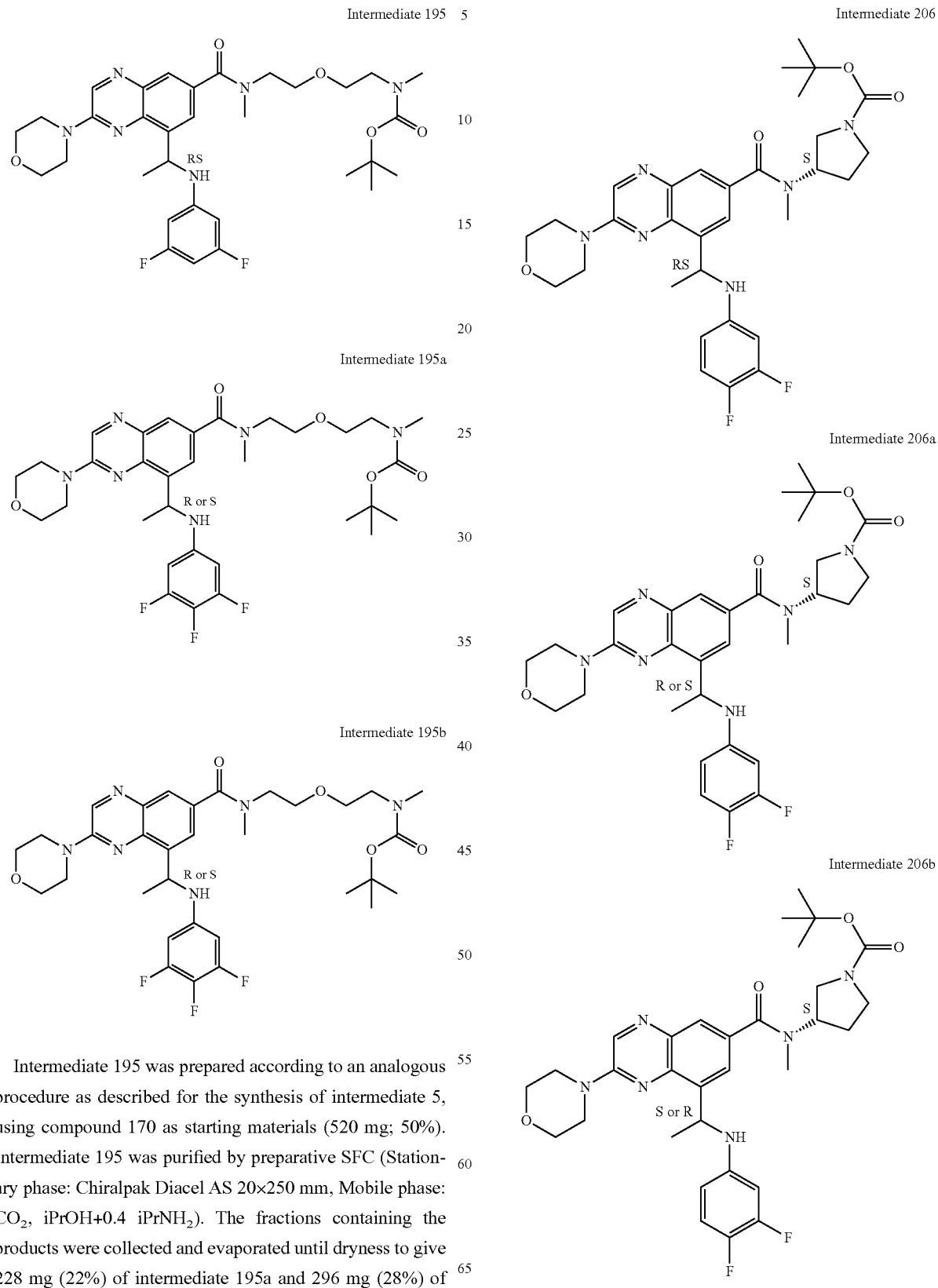

Intermediate 195 was prepared according to an analogous procedure as described for the synthesis of intermediate 5, using compound 170 as starting materials (520 mg; 50%). Intermediate 195 was purified by preparative SFC (Stationary phase: Chiralpak Diacel AS 20×250 mm, Mobile phase: $CO_2$, iPrOH+0.4 iPrNH$_2$). The fractions containing the products were collected and evaporated until dryness to give 228 mg (22%) of intermediate 195a and 296 mg (28%) of intermediate 195b.

Intermediate 206 was prepared according to an analogous procedure as described for the synthesis of intermediate 5 using compound 234 and (S)-tert-Butyl 3-(methylamino) pyrrolidine-1-carboxylate as starting materials (1.1 g; 95%). The separation of the enantiomers from 1.1 g of intermediate 206 was performed by chiral SFC (CHIRALPAK AS-H 5 μm 250×20 mm; mobile phase: 70% $CO_2$, 30% EtOH (0.3% $iPrNH_2$)). The pure fractions were collected and the solvent was evaporated to give 462 mg (40%) of intermediate 206a and 495 mg (43%) of intermediate 206b.

Preparation of Intermediate 207, Intermediate 207a and Intermediate 207b

Intermediate 207

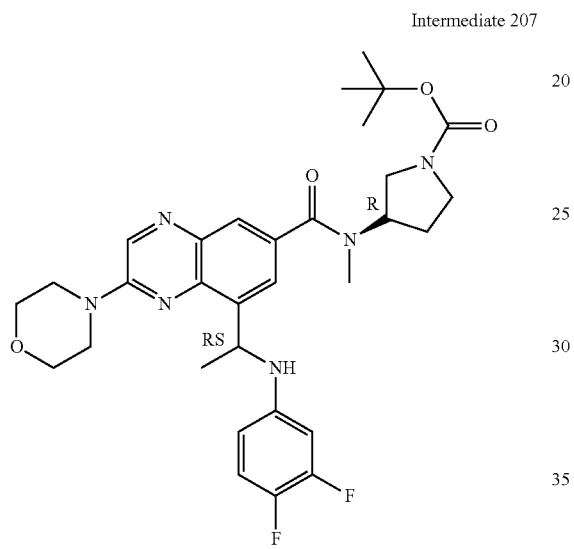

Intermediate 207a

Intermediate 207b

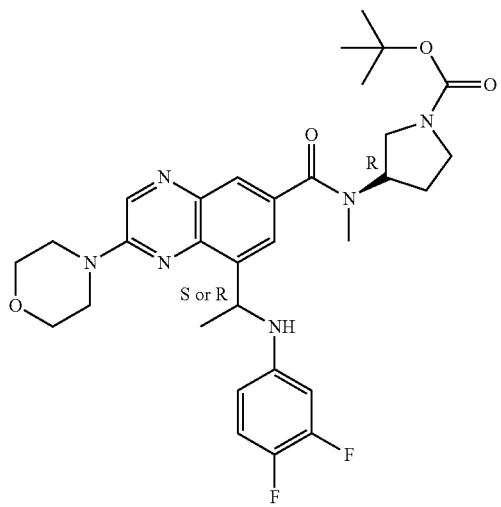

Intermediate 207 was prepared according to an analogous procedure as described for the synthesis of intermediate 5 using compound 234 and (R)-1-Boc-3-Methylaminopyrrolidine as starting materials (1.05 g; 91%). The separation of the enantiomers from 1.05 g of intermediate 207 was performed by chiral SFC (CHIRALPAK DIACEL 250×20 mm; mobile phase: $CO_2$, EtOH (0.4% $iPrNH_2$)). The pure fractions were collected and the solvent was evaporated to give 480 mg (42%) of intermediate 207a and 504 mg (44%) of intermediate 207b.

Preparation of Intermediate 208, Intermediate 208a and Intermediate 208b

Intermediate 208

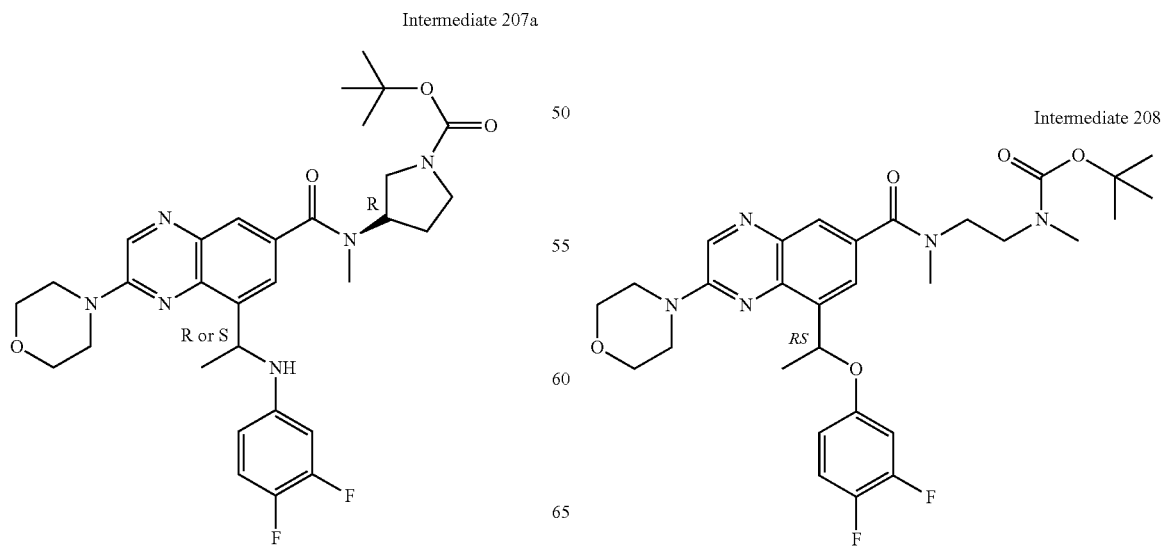

153
-continued

Intermediate 208a

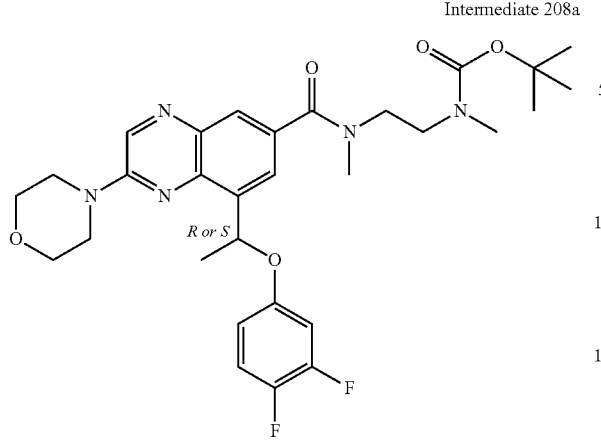

Intermediate 208b

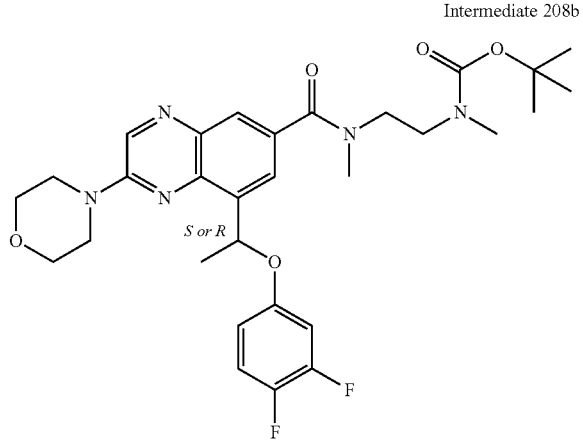

Intermediate 208 was prepared according to an analogous procedure as described for the synthesis of intermediate 5 compound 285 and N-(2-aminoethyl)-N-methyl carbamic acid tert-butyl ester as starting materials (1.12 g; 79%). The separation of the enantiomers from 1.12 g of intermediate 208 was performed by chiral SFC (CHIRALPAK DIACEL AD 250×20 mm; mobile phase: $CO_2$, EtOH (0.4% $iPrNH_2$)). The pure fractions were collected and the solvent was evaporated to give 518 mg (37%) of intermediate 208a and 533 mg (38%) of intermediate 208b.

154

Preparation of Intermediate 209, Intermediate 209a and Intermediate 209b

Intermediate 209

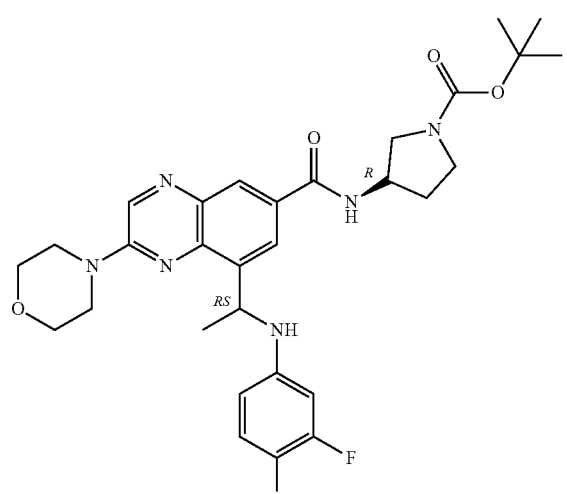

Intermediate 209a

Intermediate 209b

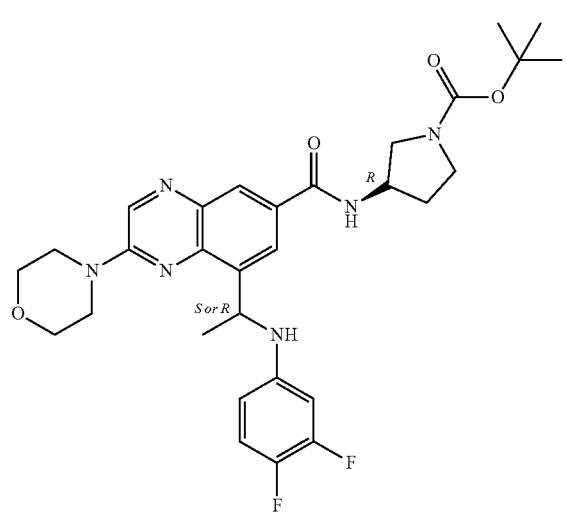

Intermediate 209 prepared according to an analogous procedure as described for the synthesis of intermediate 5 using compound 234 and (R)-1-boc-3-aminopyrrolidine as starting materials (960 mg; 93%). The separation of the enantiomers from 960 mg of intermediate 209 was performed by chiral SFC (CHIRALPAK AD-H 5 μm 250×30 mm; mobile phase: 50% CO$_2$, 50% iPrOH (0.3% iPrNH$_2$)). The pure fractions were collected and the solvent was evaporated to give 407 mg (39%) of intermediate 209a and 420 mg (41%) of intermediate 209b.

Preparation of Intermediate 213, Intermediate 213a and Intermediate 213b

Intermediate 213 was prepared according to an analogous procedure as described for the synthesis of intermediate 5 using compound 234 and (S)-2-aminomethyl-1-boc-pyrrolidine as starting materials (1 g; 86%). The separation of the enantiomers from 1 g intermediate 213 was performed by chiral SFC (CHIRALPAK AD-H 5 μm 250×30 mm; mobile phase: 60% CO$_2$, 40% MeOH (0.3% iPrNH$_2$)). The pure fractions were collected and the solvent was evaporated to give 416 mg (36%) of intermediate 213a and 445 mg (38%) of intermediate 213b.

Preparation of Intermediate 215, Intermediate 215a and Intermediate 215b

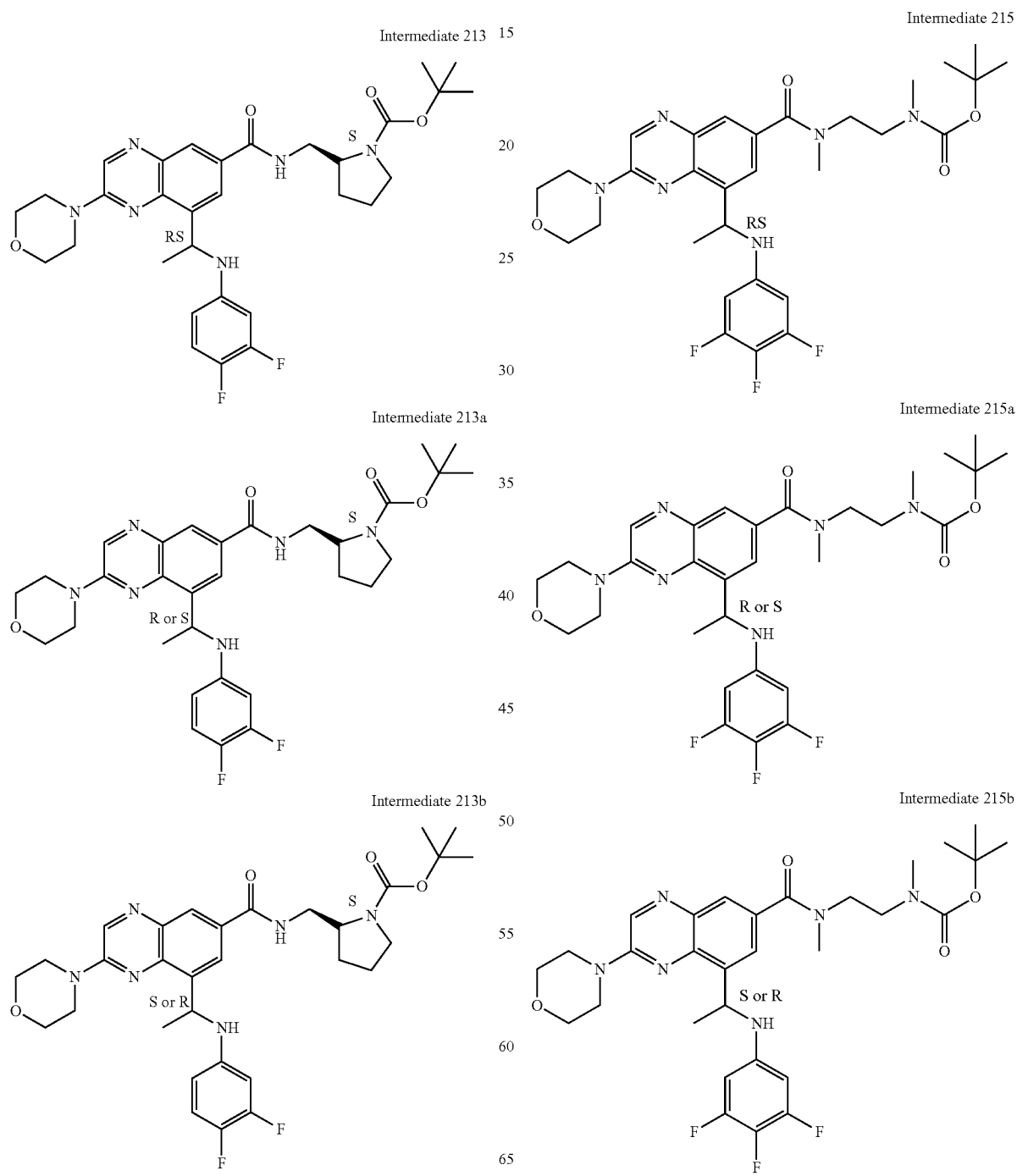

Intermediate 215 was prepared according to an analogous procedure as described for the synthesis of intermediate 5 using compound 170 and N-(2-aminoethyl)-N-methyl carbamic acid tert-butyl ester as starting materials (550 mg; 99%). The separation of the enantiomers from 550 mg intermediate 215 was performed by chiral SFC (Stationary phase: Chiralpak AD-H 5 µm 250*30 mm, Mobile phase: 85% CO$_2$, 15% EtOH (0.3% iPrNH$_2$)). The pure fractions were collected and the solvent was evaporated to give 200 mg (36%) of intermediate 215a and 237 mg (43%) of intermediate 215b.

Preparation of Intermediate 220, Intermediate 220a and Intermediate 220b

Intermediate 220

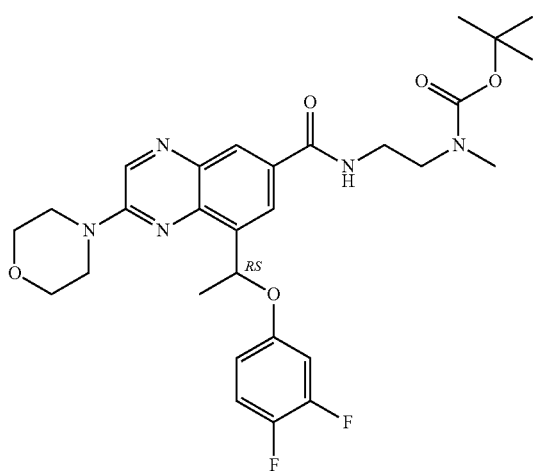

Intermediate 220b

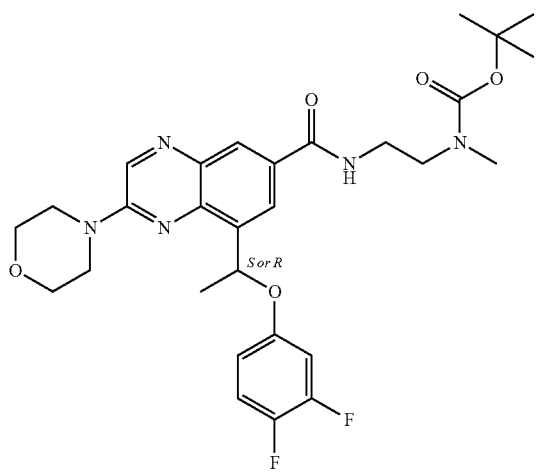

Intermediate 220 was prepared according to an analogous procedure as described for the synthesis of intermediate 5 using compound 285 and A-(2-aminoethyl)-A-Methyl carbamic acid tert-butyl ester as starting materials (1.28 g; 77%). The separation of the enantiomers from 1.28 g intermediate 220 was performed via chiral SFC (Stationary phase: CHIRALPAK AD-H 5 µm 250×20 mm, Mobile phase: 70% CO$_2$, 30% EtOH (0.3% iPrNH$_2$)). The pure fraction were collected and evaporated until dryness to give 730 mg (44%) of intermediate 220a and 716 mg (43%) of intermediate 220b.

Preparation of Intermediate 221:

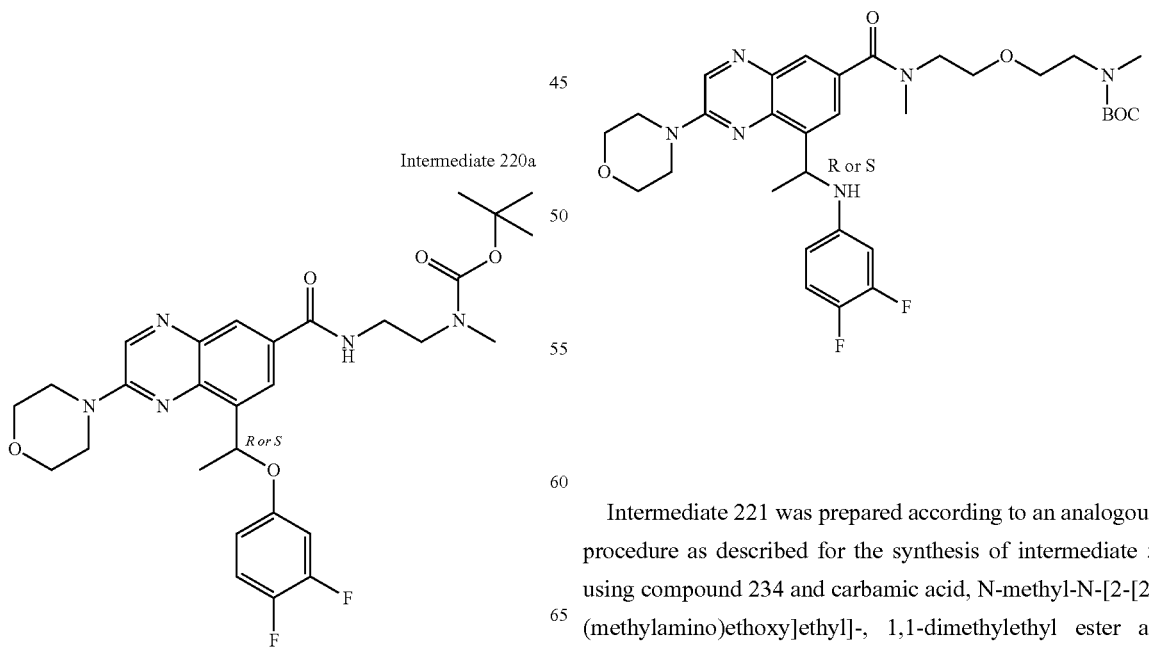

Intermediate 221 was prepared according to an analogous procedure as described for the synthesis of intermediate 5 using compound 234 and carbamic acid, N-methyl-N-[2-[2-(methylamino)ethoxy]ethyl]-, 1,1-dimethylethyl ester as starting materials (950 mg; 78%).

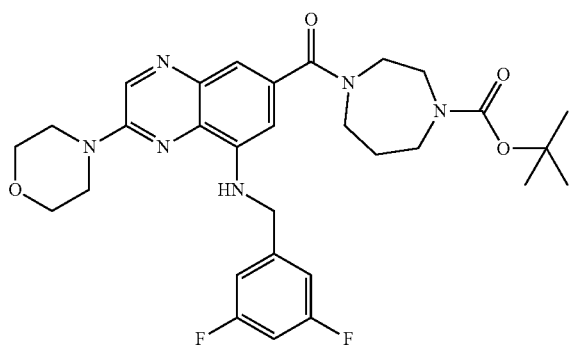 [SMILES: CC(C)(C)OC(=O)N1CCCN(C(=O)c2cc(NCc3cc(F)cc(F)c3)c3nc(N4CCOCC4)cnc3c2)CC1]

Intermediate 222 was prepared according to an analogous procedure as described for the synthesis of intermediate 5 using compound 289 and tert-butyl 1,4-diazepane-1-carboxylate as starting materials (860 mg, 100%).

Preparation of Intermediate 223:

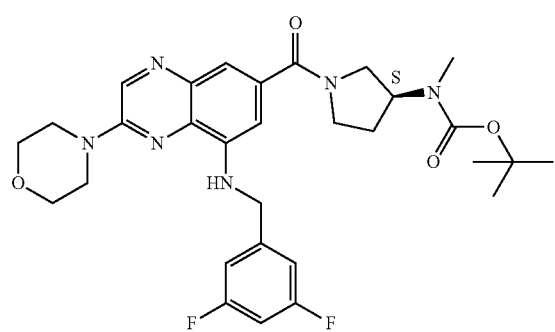

Intermediate 223 was prepared according to an analogous procedure as described for the synthesis of intermediate 5 using compound 289 and (S)-3-(N-3-Boc-Nmethylamino) pyrolidine as starting materials (390 mg g; 89%).

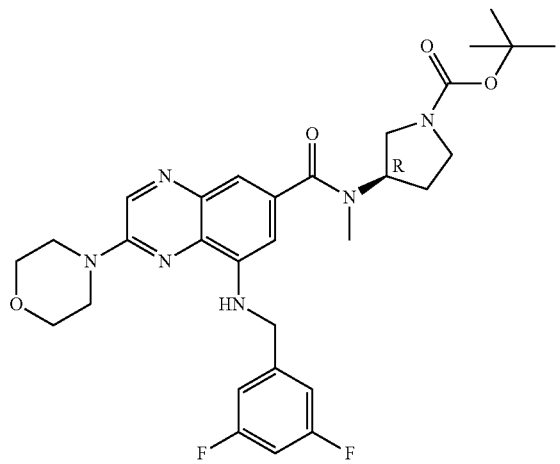

Preparation of Intermediate 224:

Intermediate 224 was prepared according to an analogous procedure as described for the synthesis of intermediate 5, using compound 289 and (R)-3-(methylamino)pyrrolidine-1-carboxylic acid tert-butyl ester as starting materials (780 mg g; 100%).

Preparation of Intermediate 225, Intermediate 225a and Intermediate 225b

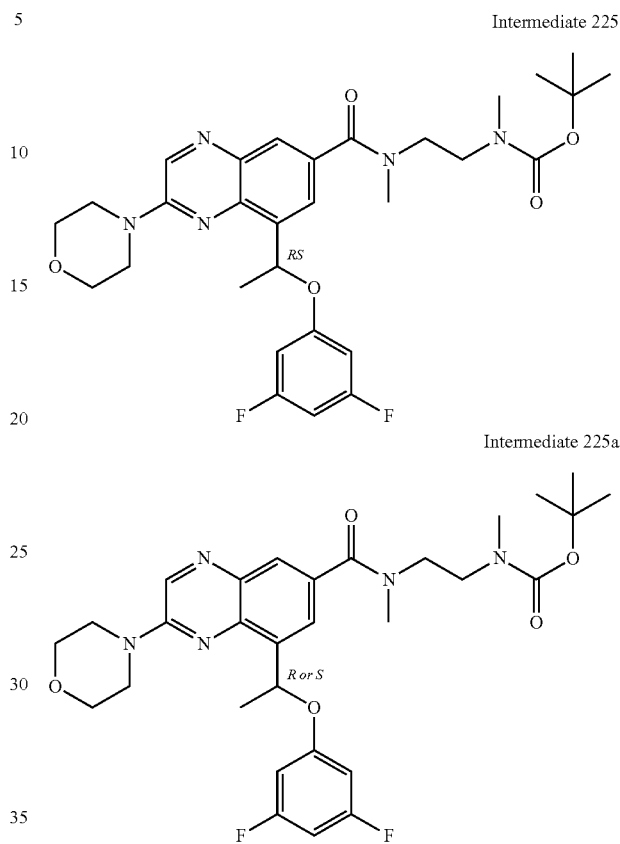

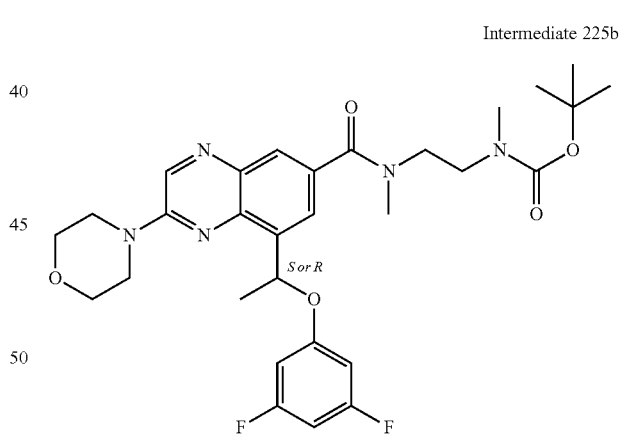

Intermediate 225 was prepared according to an analogous procedure as described for the synthesis of intermediate 5 using compound 248 and N-(2-aminoethyl)-N-methyl carbamic acid tert-butyl ester as starting materials (220 mg).

The separation of the enantiomers was performed from 220 mg of intermediate 225 via chiral SFC (Stationary phase: CHIRALPAK AD-H 5 μm 250×20 mm, Mobile phase: 80% CO2, 20% EtOH). The pure fractions were collected and evaporated until dryness to give 43 mg (6%) of intermediate 225a and 45 mg (6%) of intermediate 225b.

Preparation of Intermediate 226

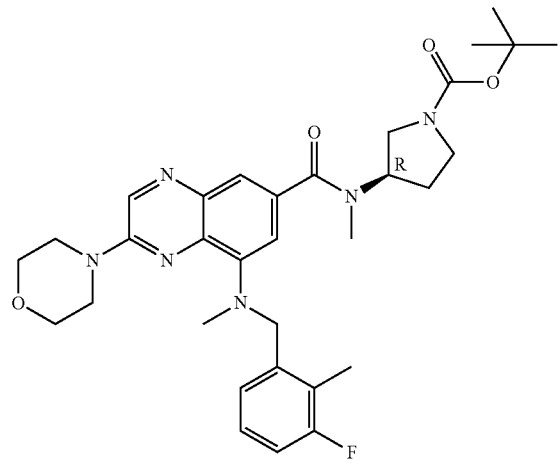

Intermediate 226 was prepared according to an analogous procedure as described for the synthesis of intermediate 5, using compound 307 and (R)-3-(methylamino)pyrrolidine-1-carboxylic acid tert-butyl ester as starting materials (298 mg, 100%).

Preparation of Intermediate 227

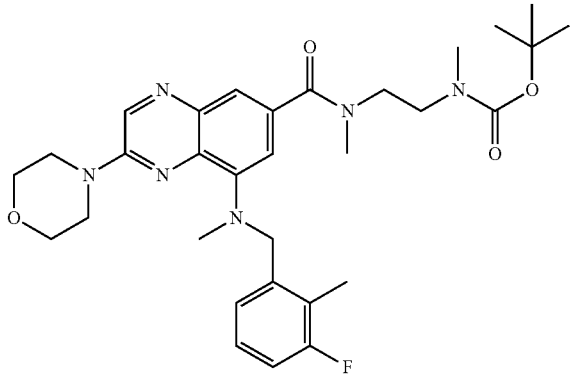 [SMILES: Cc1c(F)cccc1CN(C)c1cc(C(=O)N(C)CCN(C)C(=O)OC(C)(C)C)cc2ncc(N3CCOCC3)nc12]

Intermediate 227 was prepared according to an analogous procedure as described for the synthesis of intermediate 5, using compound 307 as starting material (346 mg, 82%).

Preparation of Intermediate 228, Intermediate 228a and Intermediate 228b

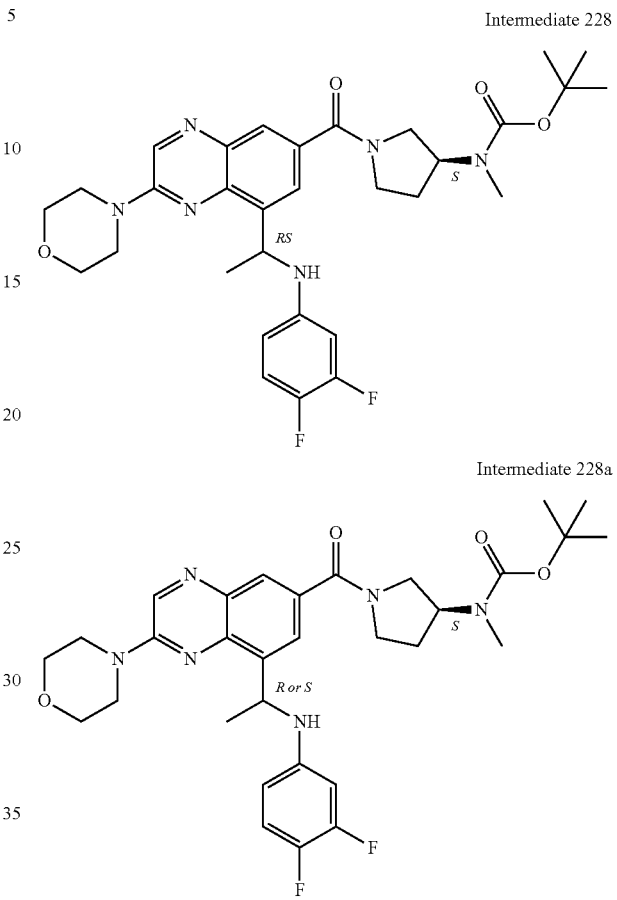

Intermediate 228 was prepared according to an analogous procedure as described for the synthesis of intermediate 5, using compound 234 and (S)-Tert-butylmethyl(pyrrolidin-3-yl)carbamate as starting materials (675 mg; 78%). The separation of the enantiomers was performed by SFC (Stationary phase: CHIRALPAK AD-H 5 µm 250×20 mm, Mobile phase: 60% $CO_2$, 40% EtOH (0.3% $iPrNH_2$)). The fractions containing the product were mixed and concentrated to afford 179 mg of intermediate 228a( and 190 mg of intermediate 228b.

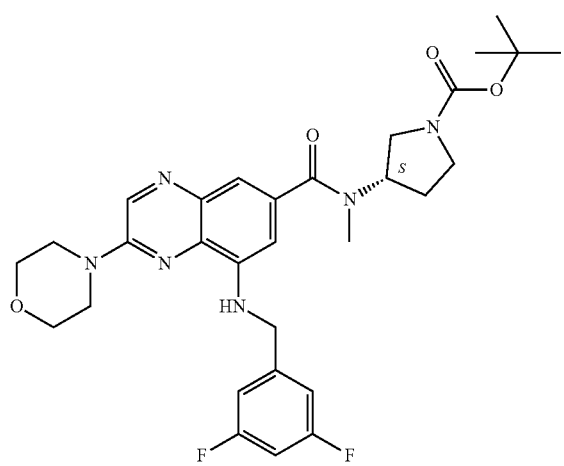

Preparation of Intermediate 229

Intermediate 229 was prepared according to an analogous procedure as described for the synthesis of intermediate 5, using compound 289 and (S)-1-Boc-3-(methylamino)pyrrolidine as starting material (1.1 g, 100%).

Preparation of Intermediate 230. Intermediate 230a and Intermediate 230b

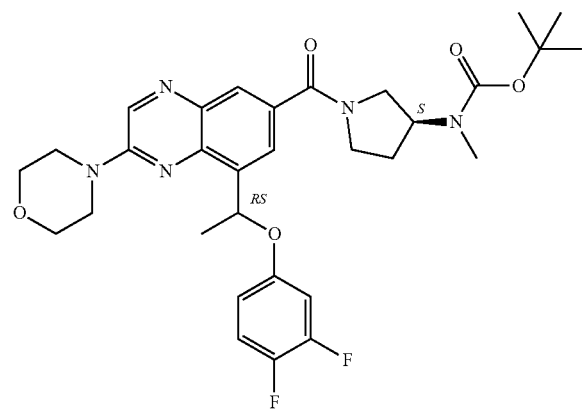

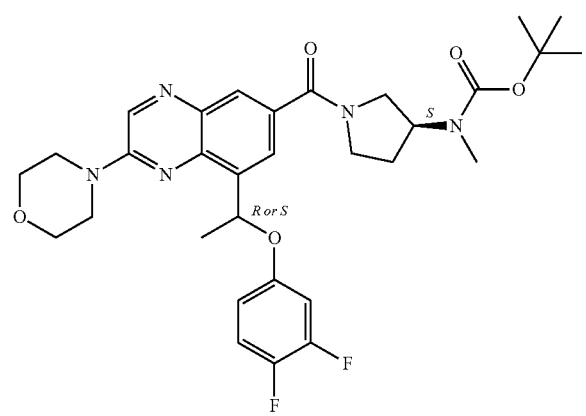

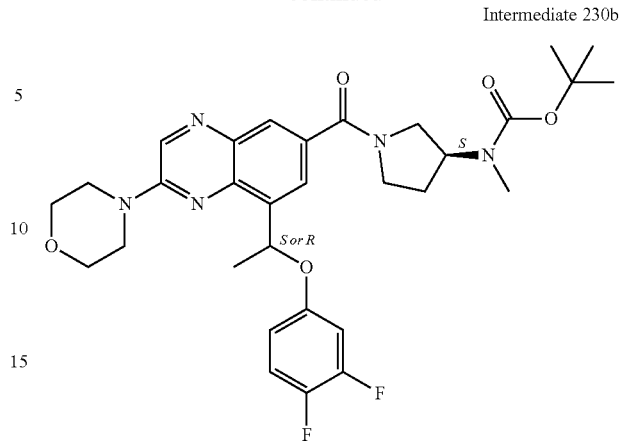

Intermediate 230 was prepared according to an analogous procedure as described for the synthesis of intermediate 5, using compound 285 and (S)-tert-butylmethyl(pyrrolidin-3-yl)carbamate as starting materials (900 mg). The separation of the enantiomers from 900 mg of intermediate 230 was performed via chiral SFC (Stationary phase: CHIRALPAK DIACEL AD 250×20 mm, Mobile phase: CO$_2$, EtOH+0.4% iPrNH$_2$). The pure fractions were collected, evaporated until dryness and crystallized from pentane to give 450 mg of intermediate 230a and 500 mg of intermediate 230b Preparation of Intermediate 231, Intermediate 231a and Intermediate 231b

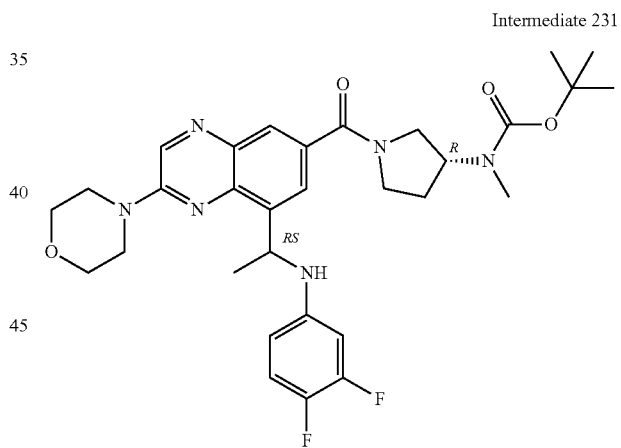

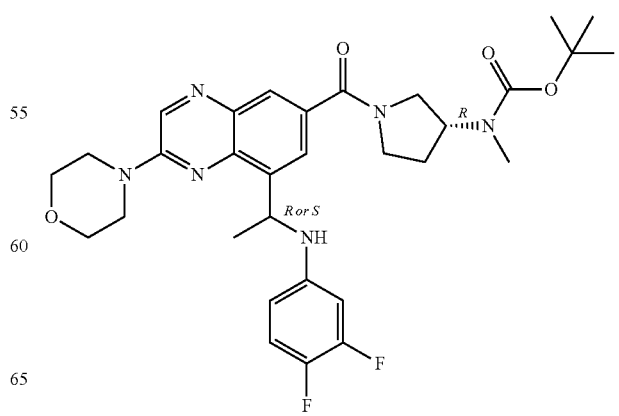

-continued

Intermediate 231b

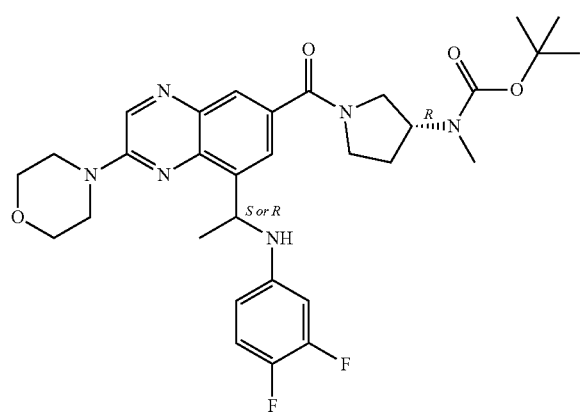

Intermediate 231 was prepared according to an analogous procedure as described for the synthesis of compound 5, using compound 234 and (R)-3-(A-Boc-A-methylamino) pyrrolidine as starting materials (1.03 g; 89%). The separation of the enantiomers from 1.03 g of intermediate 231 was performed via chiral SFC (Stationary phase: CHIRALPAK IC 250×30 mm, Mobile phase: 60% $CO_2$, 40% EtOH (0.3% $iPrNH_2$)). The pure fractions were collected, evaporated until dryness and crystallized from pentane to give 481 mg (42%) of intermediate 231a and 435 mg (38%) of intermediate 231b.

Preparation of intermediate 232:

Intermediate 232 was prepared according to an analogous procedure as described for the synthesis of intermediate 5, using compound 291 and tert-butyl-1,4-diazepane-1-carboxylate as starting materials (228 mg, 79%).

Preparation of Intermediate 233, Intermediate 233a and Intermediate 233b

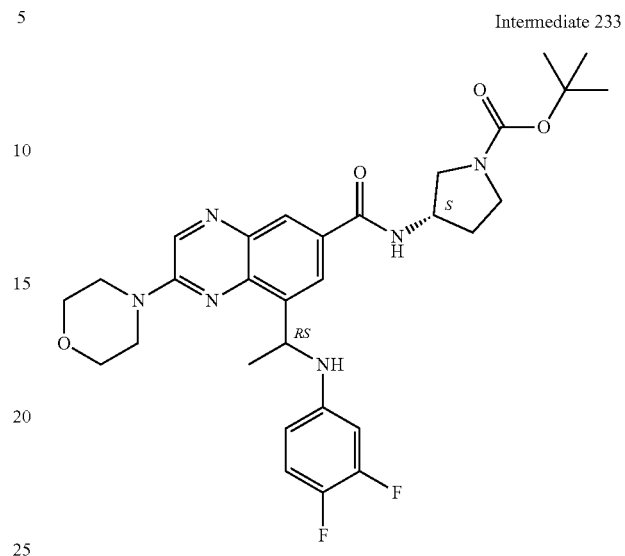

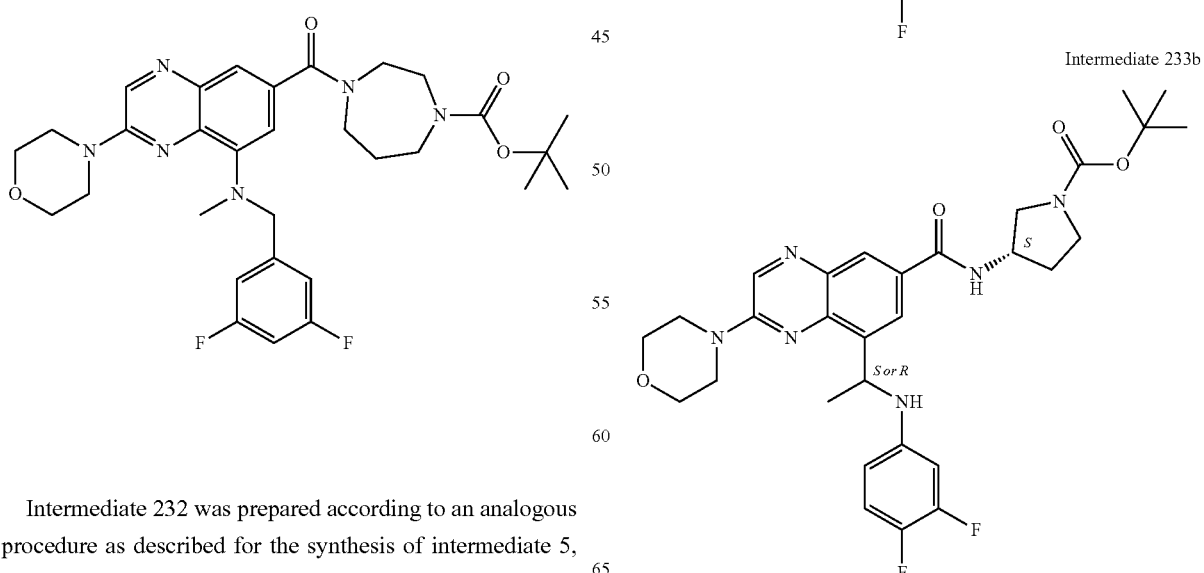

Intermediate 233 was prepared according to an analogous procedure as described for the synthesis of intermediate 5, using compound 234 and (S)-1-Boc-3-aminopyrrolidine as starting materials (845 mg; 82%). The separation of the enantiomers from 845 mg of intermediate 233 was performed via chiral SFC (Stationary phase: CHIRALPAK AD-H 5 μm 250×30 mm, Mobile phase: 60% $CO_2$, 40% EtOH (0.3% iPrNH$_2$)). The pure fractions were collected, evaporated until dryness and crystallized from pentane to give 357 mg (35%) of intermediate 233a and 305 mg (31%) of intermediate 48.

Preparation of Intermediate 234

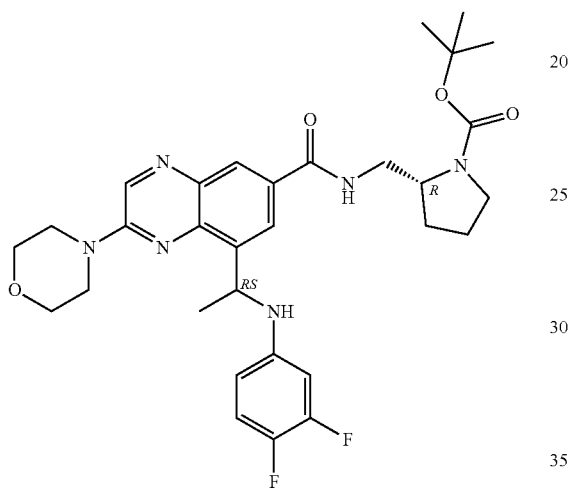

Intermediate 234 was prepared according to an analogous procedure as described for the synthesis of intermediate 5, using compound 234 and (R)-2-(Aminoethyl)-1-Boc-pyrrolidine as starting materials (0.65 g, 87%).

Preparation of Intermediate 235, Intermediate 235a and Intermediate 235b

Intermediate 235

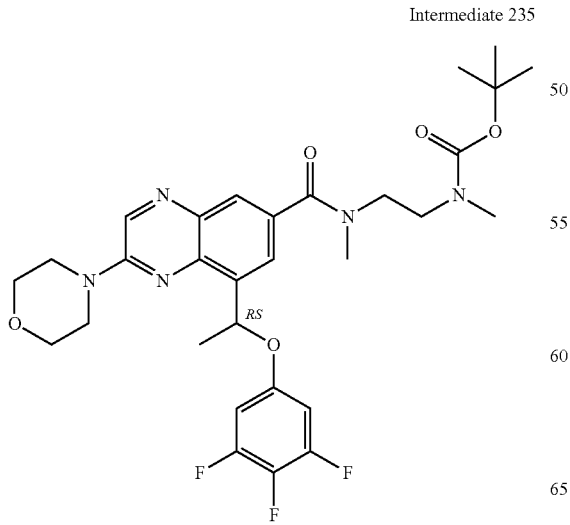

Intermediate 235a

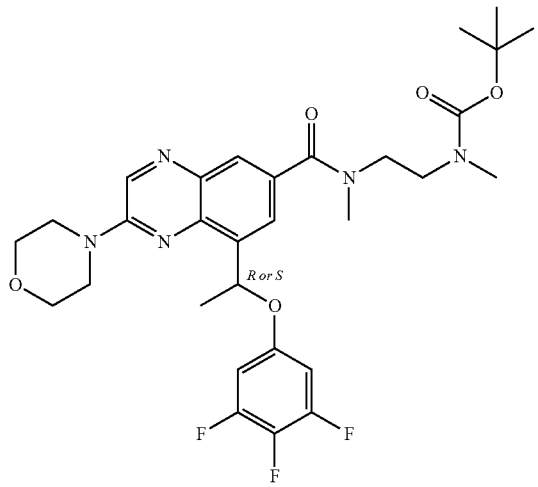

Intermediate 235b

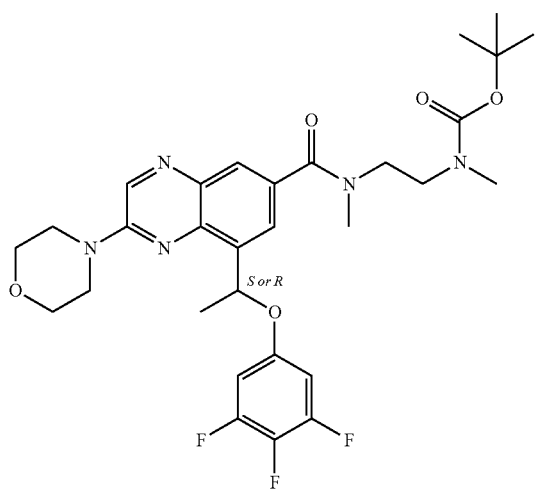

Intermediate 235 was prepared according to an analogous procedure as described for the synthesis of intermediate 5, using compound 378 as starting material (805 mg; 98%). The separation of the enantiomers from 805 mg of intermediate 235 was performed via chiral SFC (Stationary phase: CHIRALPAK DIACEL 250×20 mm, Mobile phase: 70% $CO_2$, 30% EtOH (0.4% iPrNH$_2$)). The pure fractions were collected and evaporated until dryness to give 158 mg (20%) of intermediate 235a and 150 mg (19%) of intermediate 235b.

Preparation of Intermediate 236, Intermediate 236a and Intermediate 236b

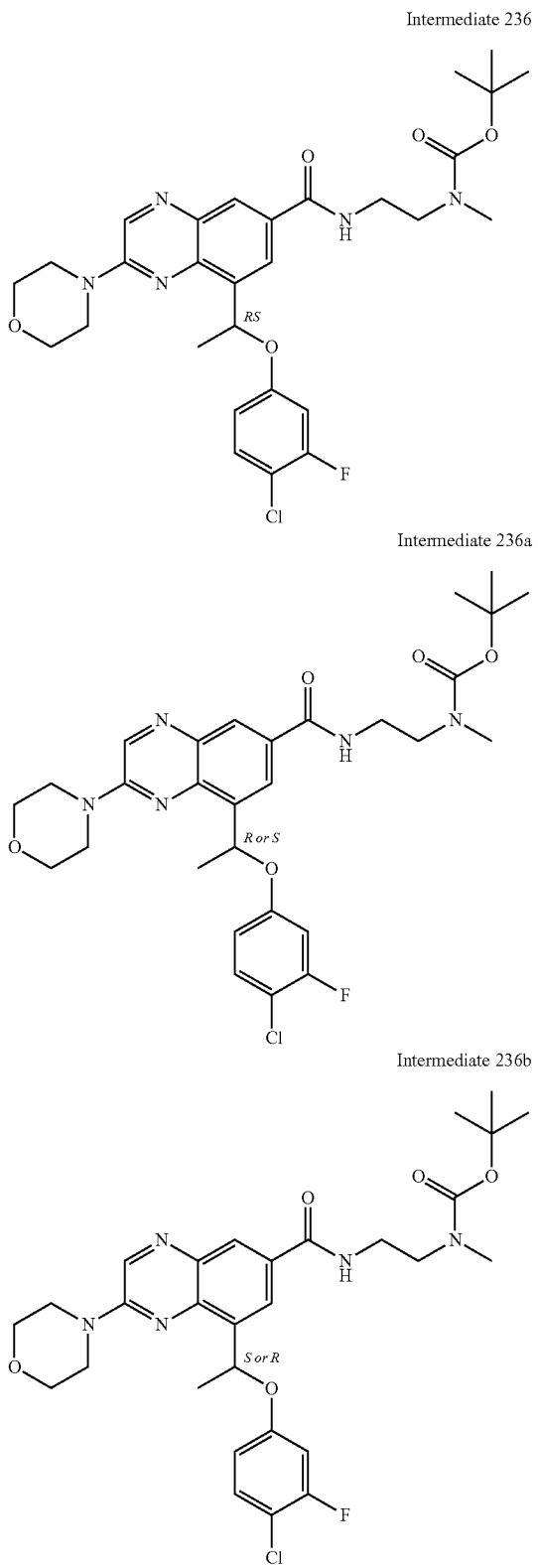

To a solution of compound 311 (150 mg; 0.347 mmol), N-(2-aminoethyl)-N-methylL carbamic acid tert-butyl ester (74 µL; 0.417 mmol; 1.2 eq.) and DIPEA (120 µL; 0.695 mmol) in DMF (3 mL) was added COMU (223 mg; 0.521 mmol). The solution was stirred at rt for 18 h. Additional N-(2-aminoethyl)-N-methylL carbamic acid tert-butyl ester (18.6 µL; 0.104 mmol; 0.3 eq) was added and the solution was stirred at rt for 1 h. The crude was combined with another reaction performed on 50 mg of compound 311. Water and EtOAc were added. The organic layer was separated and the aqueous layer was extracted with EtOAc (3×). The combined organic layers were washed with a saturated aqueous solution of NaCl (3×), dried over MgSO$_4$, filtered off and evaporated in vacuo. The crude (485 mg) was purified by silica gel chromatography (Stationary phase: irregular bare silica 40 g, Mobile phase: 0.2% NH$_4$OH, 98% DCM, 2% MeOH) to give 294 mg of intermediate 236 as a yellow oil. The separation of the enantiomers from 294 mg of intermediate 236 was performed by chiral SFC (Stationary phase: CHIRALPAK AD-H 5 µm 250×20 mm, Mobile phase: 55% CO$_2$, 45% MeOH) to give 116 mg (43%) of intermediate 236a as a yellow film and 115 mg (42%) of intermediate 236b as a yellow film.

Preparation of Intermediate 242

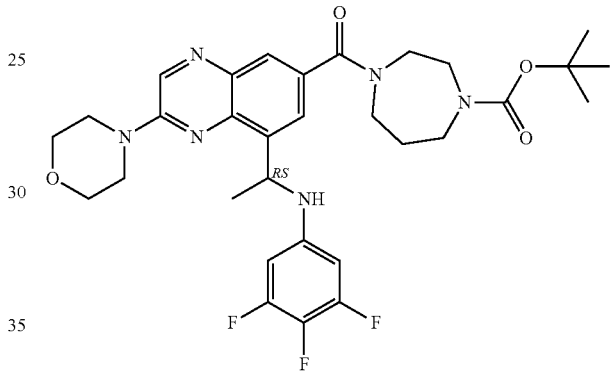

Intermediate 242 was prepared according to an analogous procedure as described for the synthesis of intermediate 5, using compound 170 and tert-butyl-1,4-diazepane-1-carboxylate as starting materials (465 mg, 82%)

Preparation of Intermediate 246, Intermediate 246a and Intermediate 246b

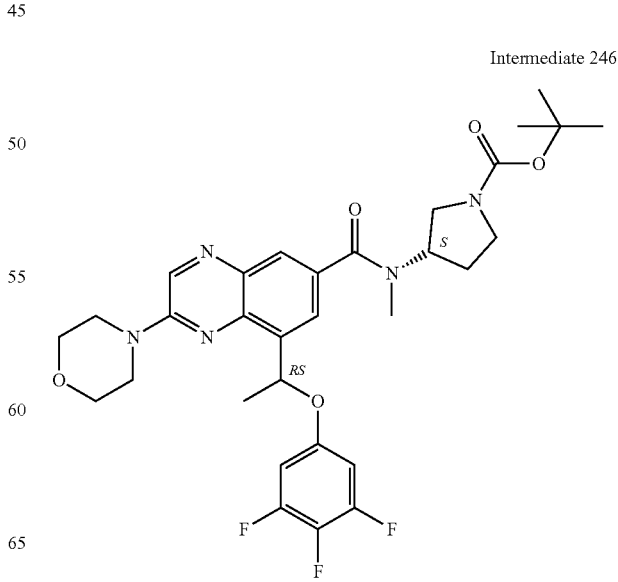

171

-continued

Intermediate 246a

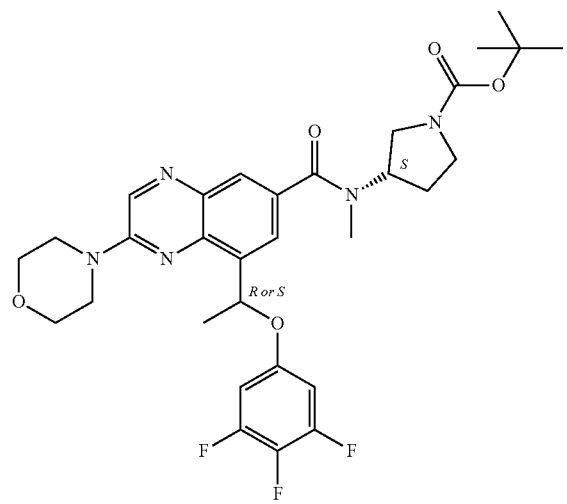

Intermediate 246b

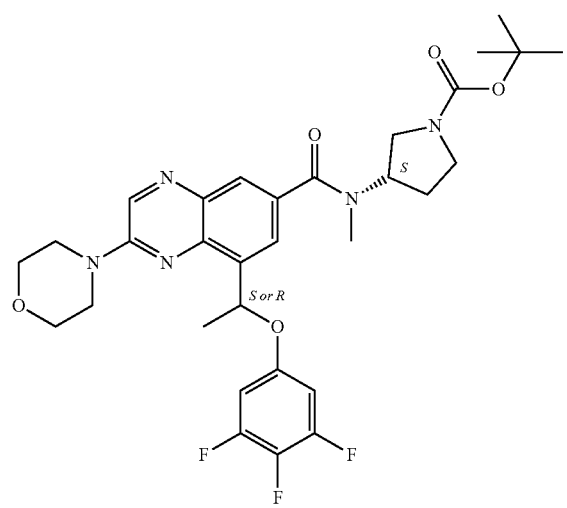

Intermediate 246 was prepared according to an analogous procedure as described for the synthesis of intermediate 236, using compound 378 and (S)-1-Boc-(methylamino)pyrrolidine as starting materials (600 mg).

The separation of the enantiomers from 600 mg of intermediate 246 was performed by chiral SFC (Stationary phase: Chiralpak AD-H 5 μm 250*30 mm, Mobile phase: 60% CO2, 40% EtOH) to give 210 mg (37%) of intermediate 246a as a yellow film and 223 mg (40%) of intermediate 246b as a yellow film.

172

Preparation of Intermediate 247, Intermediate 247a and Intermediate 247b

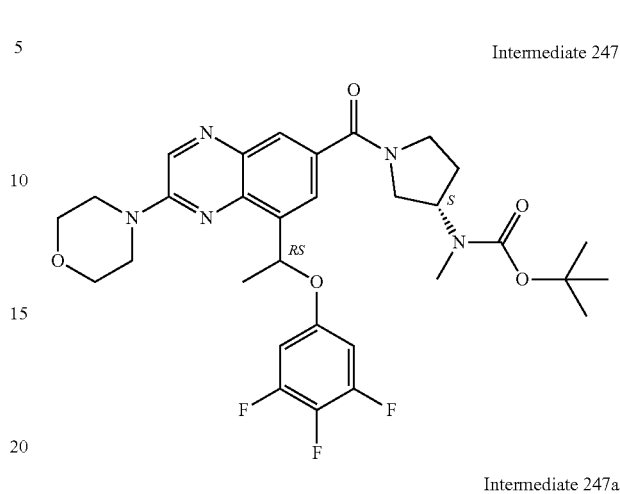

Intermediate 247 was prepared according to an analogous procedure as described for the synthesis of intermediate 236, using compound 378 and (S)-tert-butylmethyl(pyrolidine-3-yl)carbamate as starting materials.

The separation of the enantiomers was performed by chiral SFC (Stationary phase: CHIRALPAK AD-H 5 μm 250×20 mm, Mobile phase: 65% $CO_2$, 35% EtOH (0.3% $iPrNH_2$)) to give 217 mg (39%) of intermediate 247a as a yellow foam and 209 mg (37%) of intermediate 247b as a yellow foam.

Preparation of Intermediate 248, Intermediate 248a and Intermediate 248b

Intermediate 248

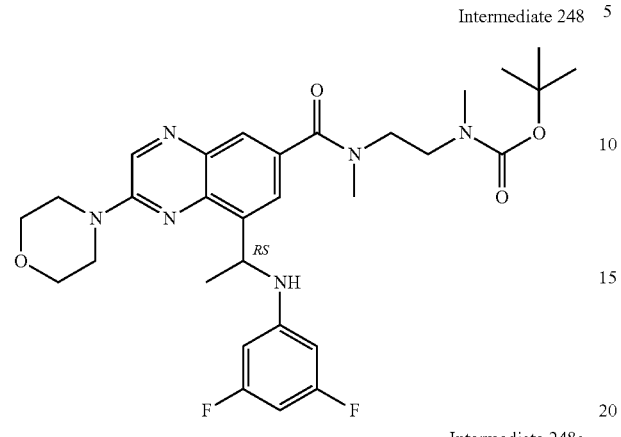

Intermediate 248a

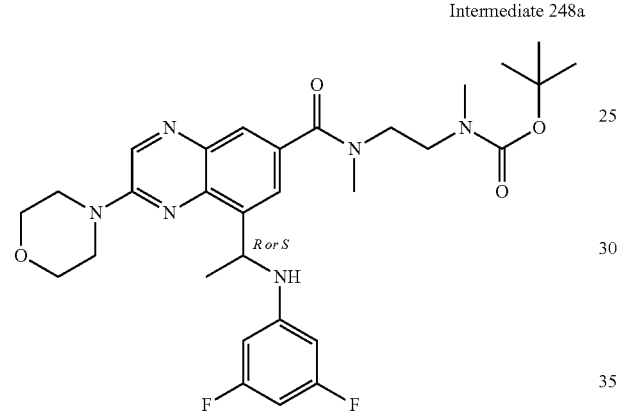

Intermediate 248b

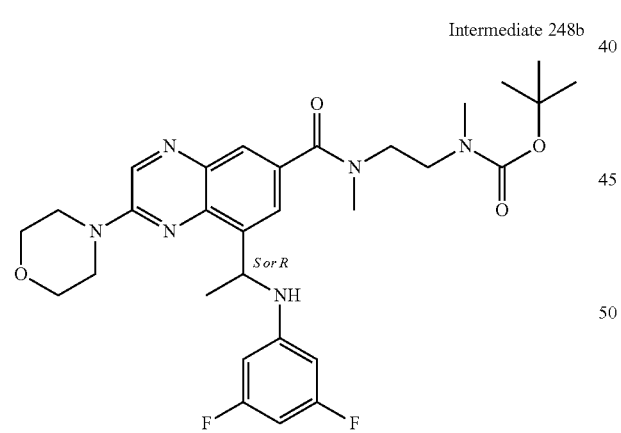

Intermediate 248 was prepared according to an analogous procedure as described for the synthesis of intermediate 5, using compound 83a as starting material (1.4 g; 78%). The separation of the enantiomers from 1.4 g of intermediate 248 was performed via chiral SFC (Stationary phase: Chiralpak AD-H 5 μm 250*30 mm, Mobile phase: 55% CO$_2$, 45% MeOH (0.3% iPrNH$_2$)). The pure fractions were collected and evaporated until dryness to give 563 mg (31%) of intermediate 248a and 551 mg (31%) of intermediate 248b.

Example A35

Preparation of Intermediate 137:

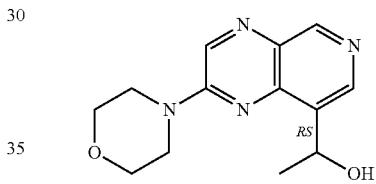

Tributyl(1-ethoxy vinyl)tin (14.23 g; 39.40 mmol) was added to a solution of intermediate 60 (9.12 g; 27.63 mmol) in anhydrous 1,4-dioxane (250 mL) under N$_2$. Dichlorobis(triphenylphosphine) palladium (II) (0.97 g; 1.38 mmol) was added and the mixture was purged again with N$_2$. The reaction mixture was heated at 100° C. for 48 h. After cooling down to rt, formic acid (30 mL) was added and the mixture was stirred at rt overnight. The mixture was slowly basified with a saturated solution of NaHCO$_3$, then filtered and the filtrate was evaporated under vacuum. The residue (9 g) was washed with water (2×30 mL), ACN (3×30 mL) and evaporated under vacuum to give 5 g (64%) of intermediate 137.

Preparation of Intermediate 138:

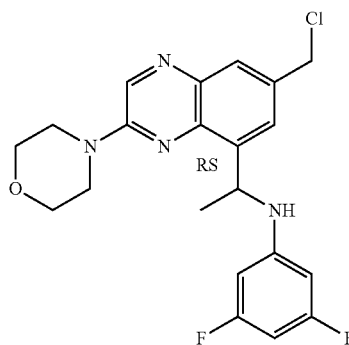

Intermediate 138 was prepared according to an analogous procedure as described for the synthesis of intermediate 15, using intermediate 137 as starting material (310 mg, 68%).

Example A36

Preparation of Intermediate 140:

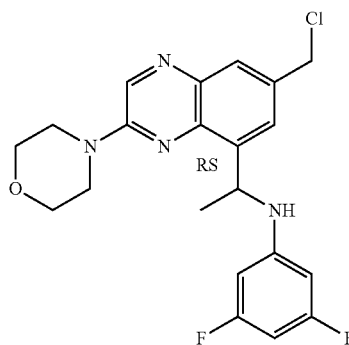

At 0° C., thionyl chloride (200 μL; 2.75 mmol) was added to a solution of compound 84 (550 mg; 1.37 mmol) in DCM (25 mL). The solution was allowed to warm to rt, stirred for 2 h and, then evaporated under vacuum to give 575 mg (100%) of intermediate 140. The crude product was used without purification in the next step.

Preparation of Intermediate 142:

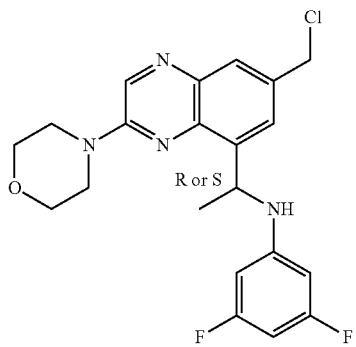 [SMILES: CC(Nc1cc(F)cc(F)c1)c1cc(CCl)cc2ncc(N3CCOCC3)nc12]

Intermediate 142 was prepared according to an analogous procedure as described for the synthesis of intermediate 140, using compound 154a as starting material (275 mg, quant.). The product was used without purification in the next step.

Preparation of Intermediate 143:

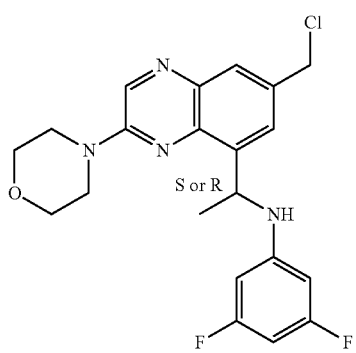 [SMILES: CC(Nc1cc(F)cc(F)c1)c1cc(CCl)cc2ncc(N3CCOCC3)nc12]

Intermediate 143 was prepared according to an analogous procedure as described for the synthesis of intermediate 140, using compound 154b as starting material (234 mg, quant.). The product was used without purification in the next step.

Example A37

Preparation of Intermediate 147:

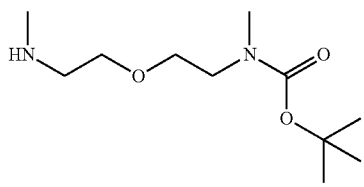 [SMILES: CNCCOCCN(C)C(=O)OC(C)(C)C]

At 0° C., a solution of di-tert-butyl dicarbonate (371 mg; 1.70 mmol) in THF (5 mL) was added dropwise to a solution of 2,2'-oxybis[A-methyl-ethanamine] (900 mg; 6.8 mmol) in THF (5 mL). The reaction mixture was stirred at rt overnight. The reaction mixture was poured into water, extracted with EtOAC. The organic layer was separated and washed with brine, then dried over $MgSO_4$, filtered and evaporated to give 330 mg of (83%) of intermediate 147. The product was used without purification in the next step.

Example A38

Preparation of Intermediate 150:

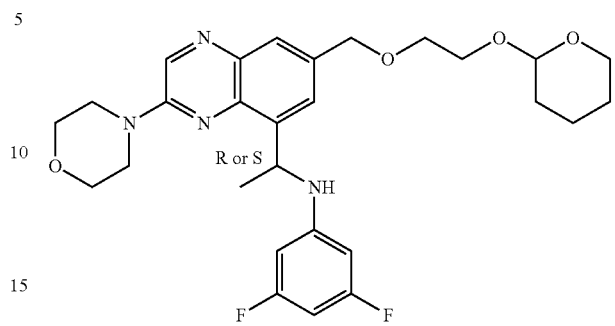

Under $N_2$ at 10° C., sodium hydride (72 mg; 1.80 mmol) was added to a solution of compound 154a (180 mg; 0.45 mmol) in DMF (2 mL). The solution was stirred at 10° C. for 30 min. Then, 2-(2-bromoethoxy)tetrahydro-2H-pyran (85 μL; 0.54 mmol) was added and the solution was allowed to slowly rise to rt for 5 h. The solution was cooled and the mixture was poured into cooled water. The product was extracted with EtOAc. The organic layer was washed with water and dried over $MgSO_4$, filtered and evaporated to dryness. The residue (300 mg) was purified by chromatography over silica gel (irregular bare silica 10 g; mobile phase: 95% DCM, 5% MeOH, 0.1% $NH_4OH$). The pure fractions were collected and the solvent was evaporated to give 181 mg (76%) of intermediate 150.

Preparation of Intermediate 151:

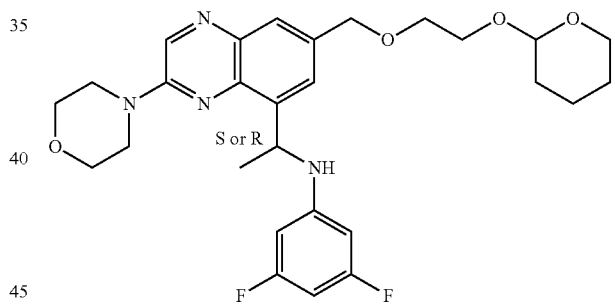

Intermediate 151 was prepared according to an analogous procedure as described for the synthesis of intermediate 150, using compound 154b and 2-(2-bromoethoxy)tetrahydro-2H-pyran as starting materials (238 mg; 72%).

Example A39

Preparation of Intermediate 162 (Identical to Intermediate 179):

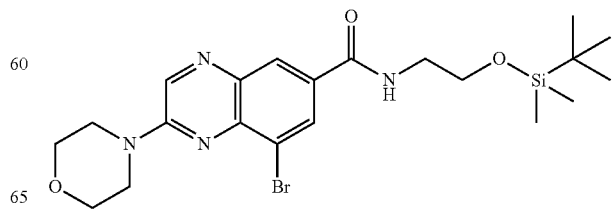

Intermediate 162 was prepared according to an analogous procedure as described for the synthesis of intermediate 5, using intermediate 4 and 2-[[(1,1-dimethylethyl)dimethylsilyl]oxy]-ethanamine as starting materials (9.6 g; 73%).

Preparation of Intermediate 163:

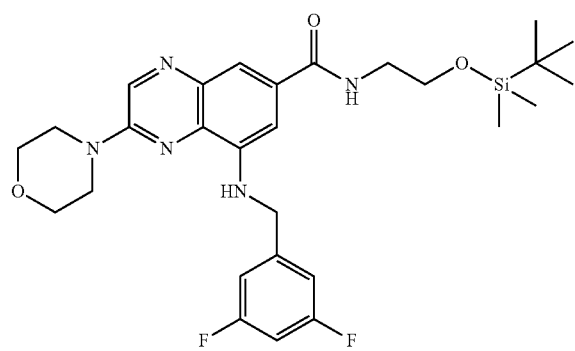 [SMILES: CC(C)(C)[Si](C)(C)OCCNC(=O)c1cc(NCc2cc(F)cc(F)c2)c2nc(N3CCOCC3)cnc2c1]

In a sealed tube, a mixture of intermediate 162 (1 g; 2.02 mmol), 3,5-difluorobenzylamine (0.286 mL; 2.42 mmol) and $Cs_2CO_3$ (1.32 g; 4.04 mmol) in tert-amyl alcohol (10 mL) was degased with $N_2$. 2-dicyclohexylphosphino-2',6'-diisopropoxy-1,1'-biphenyl (47 mg; 0.10 mmol) and Brett-Phos Precatalyst First Gen (80.6 mg, 0.101 mmol) were added. The reaction mixture was purged with $N_2$ and heated at 100° C. for 18 h. Water and EtOAc were added. Then the mixture was extracted. The organic layer was separated, dried over $MgSO_4$, filtered and evaporated. The residue (1.3 g) was purified by chromatography over silica gel (40 g of SiOH 20-45 µm; gradient: from 100% DCM to 95% DCM, 5% MeOH, 0.1% $NH_4OH$). The pure fractions were collected and the solvent was evaporated to give 780 mg (69%) of intermediate 163.

Preparation of Intermediate 164:

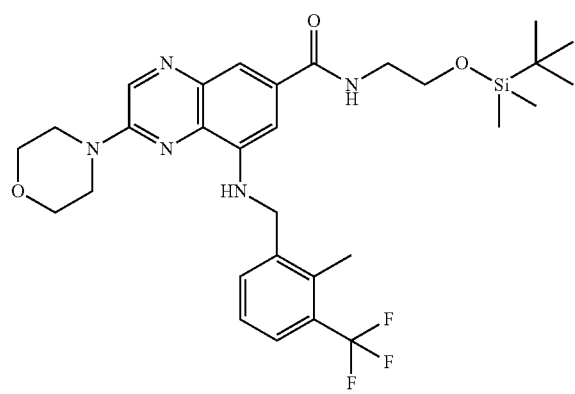 [SMILES: Cc1c(CNc2cc(C(=O)NCCO[Si](C)(C)C(C)(C)C)cc3ncc(N4CCOCC4)nc23)cccc1C(F)(F)F]

Intermediate 164 was prepared according to an analogous procedure as described for the synthesis of intermediate 163, using intermediate 162 and 2-methyl-3-(trifluoromethyl)benzylamine as starting materials (670 mg; 62%).

Preparation of Intermediate 165:

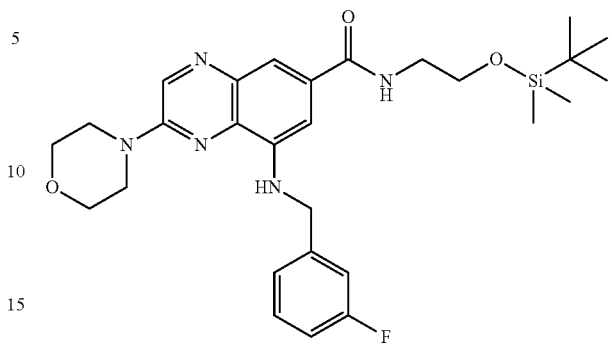

Intermediate 164 was prepared according to an analogous procedure as described for the synthesis of intermediate 163, using intermediate 162 and 3-fluorobenzylamine as starting materials (765 mg; 63%).

Preparation of Intermediate 166:

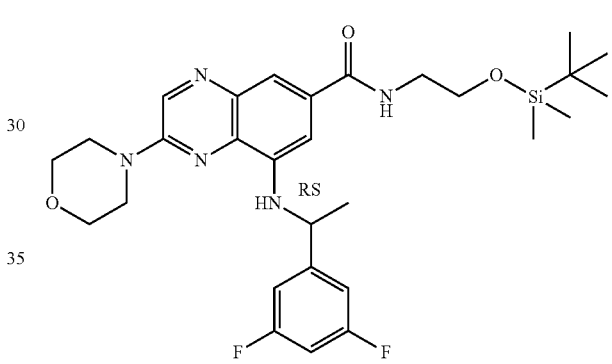

Intermediate 166 was prepared according to an analogous procedure as described for the synthesis of intermediate 163, using intermediate 162 and (RS)-1-(3,5-difluorophenyl)ethylamine as starting materials (700 mg; 61%).

Preparation of Intermediate 203:

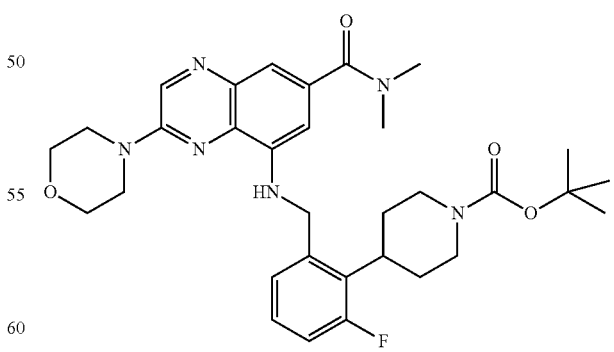

Intermediate 203 was prepared according to an analogous procedure as described for the synthesis of intermediate 163 using intermediate 202 and intermediate 5 as starting materials (300 mg, 62%).

Preparation of Intermediate 204:

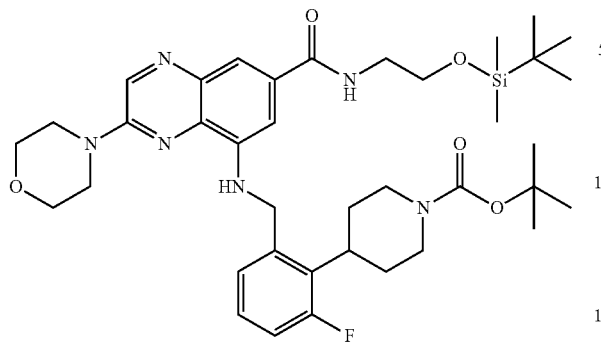

Intermediate 204 was prepared according to an analogous procedure as described for the synthesis of intermediate 163, using intermediate 162 and intermediate 202 as starting material (410 mg, 88%)

Preparation of Intermediate 216:

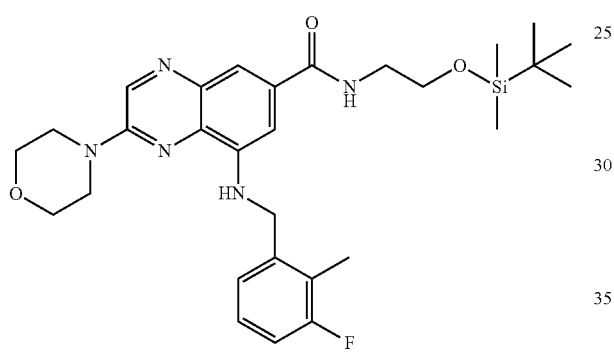

Intermediate 216 was prepared according to an analogous procedure as described for the synthesis of intermediate 163, using intermediate 162 as starting material and 2-Methyl-3-fluorobenzylamine (845 mg, 76%).

Preparation of Intermediate 218:

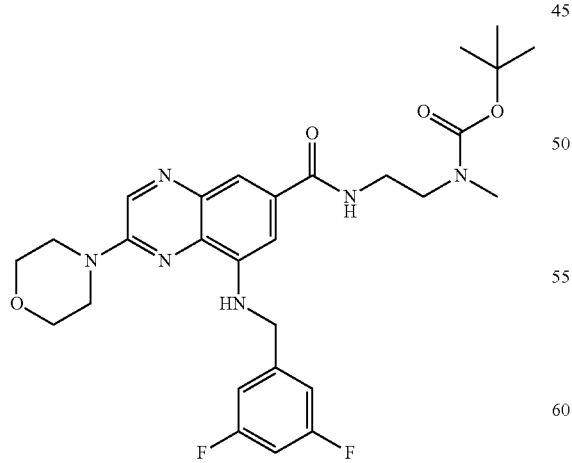

Intermediate 218 was prepared according to an analogous procedure as described for the synthesis of intermediate 163, using intermediate 217 as starting material and 3,5-difluorobenzylamine (310 mg, 66%).

Preparation of Intermediate 219:

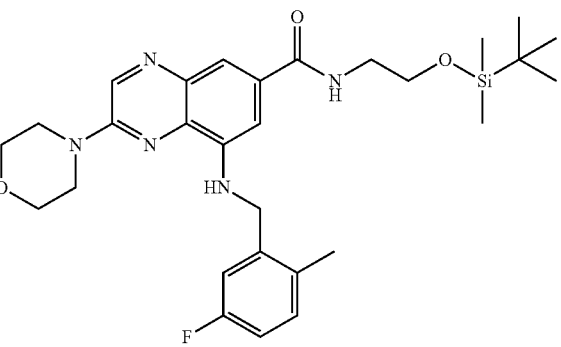

intermediate 219 was prepared according to an analogous procedure as described for the synthesis of intermediate 163, using intermediate 162 as starting material and 2-methyl-5-fluorobenzylamine (420 mg, 75%).

Preparation of Intermediate 240:

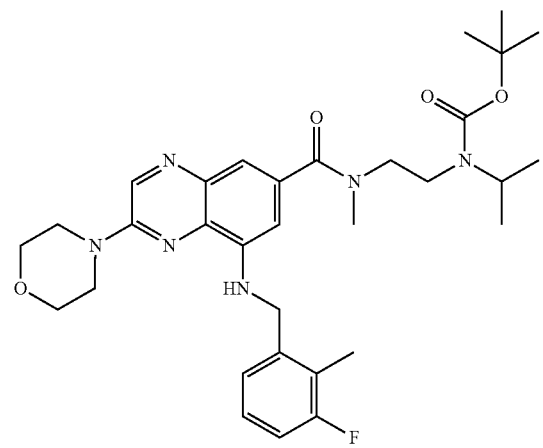 [SMILES: Cc1c(F)cccc1CNc1cc(C(=O)N(C)CCN(C(=O)OC(C)(C)C)C(C)C)cc2ncc(N3CCOCC3)nc12]

Intermediate 240 was prepared according to an analogous procedure as described for the synthesis of intermediate 163 using intermediate 239 and 3-Fluoro-2-methylbenzylamine as starting materials (450 mg, 81%).

Preparation of Intermediate 243:

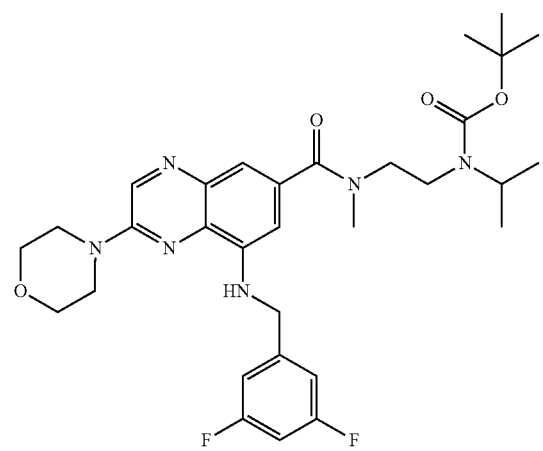 [SMILES: CC(C)N(CCN(C)C(=O)c1cc(NCc2cc(F)cc(F)c2)c2nc(N3CCOCC3)cnc2c1)C(=O)OC(C)(C)C]

Intermediate 243 was prepared according to an analogous procedure as described for the synthesis of intermediate 163, using intermediate 239 and 3,5-difluorobenzylamine as starting materials (460 mg, 82%).

Preparation of Intermediate 245:

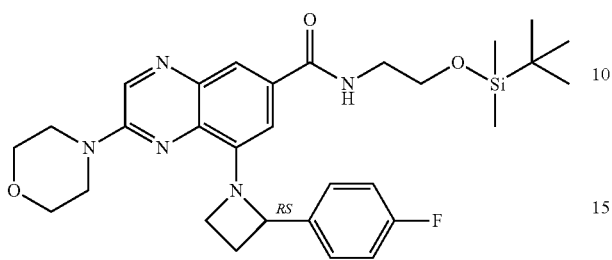

Intermediate 245 was prepared according to an analogous procedure as described for the synthesis of intermediate 163, using intermediate 162 and 2-(4-Fluorophenyl)azetidine as starting materials (700 mg, 61%).

Example A40

Preparation of Intermediate 174:

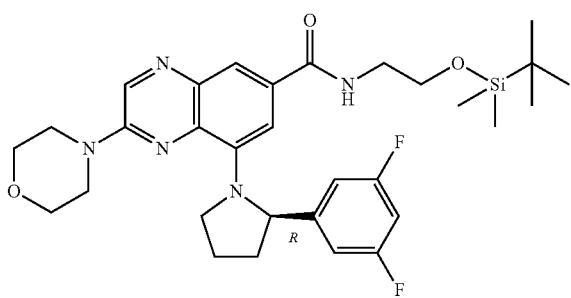

Intermediate 174 was prepared according to an analogous procedure as described for the synthesis of compound 1, using intermediate 162 and 2-(2R)-2-(3,5-difluorophenyl)pyrrolidine as starting materials, (200 mg; 33%) of intermediate 174.

Preparation of Intermediate 175:

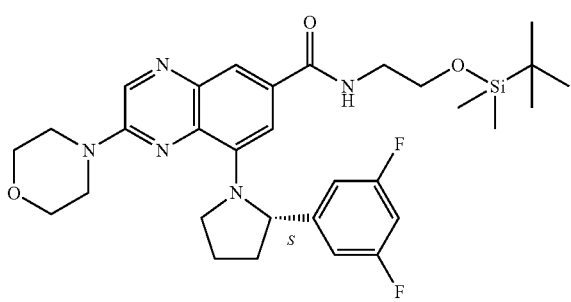

Intermediate 175 was prepared according to an analogous procedure as described for the synthesis of compound 1, using intermediate 162 and 2-(2S)-2-(3,5-difluorophenyl)pyrrolidine as starting materials, (260 mg; 43%) of intermediate 175.

Example A41

Preparation of Intermediate 176:

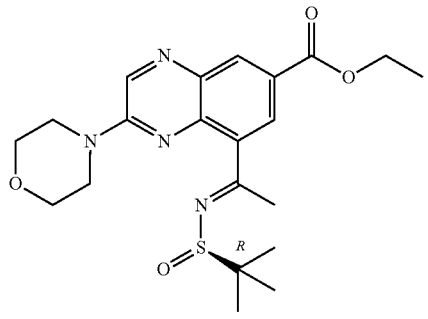

(E/Z configuration unknown)

Titanium(IV) ethoxide (2.66 mL, 12.68 mmol) was added dropwise to a solution of intermediate 10a (1 g, 3.17 mmol) and (R)-(+)-2-methyl-2-propanesulfmimide (0.672 g, 5.55 mmol) in THF (25 mL) at room temperature under $N_2$. The solution was refluxed for 24 h. The mixture was poured into brine and DCM was added. The precipitate was filtered through a short pad of Celite® which was washed with DCM. The organic layer was separated, dried over $MgSO_4$, filtered and evaporated until dryness. The residue (1.5 g) was purified by chromatography over silica gel (40 g of SiOH 15-40 µm; gradient: from 100% DCM to 95% DCM, 5% MeOH). The pure fractions were collected and the solvent was evaporated to give 600 mg (44%) of intermediate 176.

Alternative Preparation of Intermediate 176:

Titanium (IV) ethoxide (26.59 mL, 126.85 mmol) was added dropwise to a solution of intermediate 10a (10 g, 31.71 mmol) and (R)-(+)-2-methyl-2-propanesulfinamide 99% (7.68 g, 63.43 mmol) in cyclopentyl methyl ether (100 mL) at room temperature under $N_2$. The solution was refluxed for 3 h. The mixture was poured into brine and DCM was added. The precipitate was filtered through a short pad of Celite® and washed with DCM. The organic layer was separated, dried over $MgSO_4$, filtered and evaporated until dryness. The residue was crystallized from DIPE. The precipitate was filtered off and dried under vacuum to yield 13.03 g (y=95%, de=96.9) of intermediate 176.

Preparation of Intermediate 177a and Intermediate 177:

Intermediate 177a

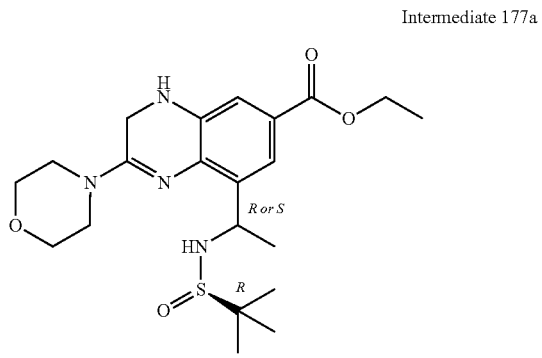

Intermediate 177

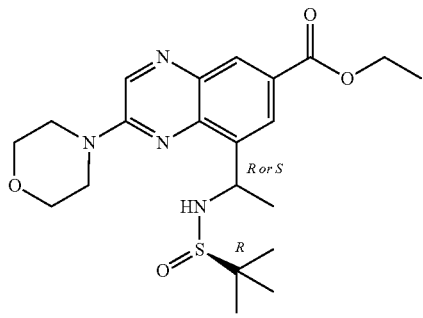

Sodium cyanoborohydride (1.1 g, 17.6 mmol) and acetic acid (2.01 mL, 35.14 mmol) were added to a solution of intermediate 176 (3.8 g, 8.78 mmol) in MeOH (50 mL) and DCM (50 mL) at −15° C. The solution was stirred at −15° C. for 5 h. The mixture was poured into water, basified with a 10% aqueous solution of K₂CO₃ and the resulting aqueous mixture was extracted with DCM. The combined organic layers were washed with brine (2×), dried over MgSO₄, filtered and evaporated. The residue (5.2 g) was purified by silica gel chromatography (Irregular SiOH 15-40 μm, 80 g; gradient from 100% DCM to 95% DCM, 5% MeOH). The pure fractions were collected and the solvent was evaporated until dryness to give 2.26 g of a mixture of intermediates 177 and 177a (40/60 by LCMS).

Preparation of Intermediate 177:

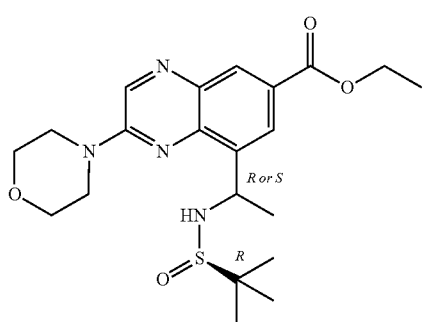

Manganese dioxide (0.876 g, 10.08 mmol) was added portionwise to a solution of intermediate 177a (1.1 g, 2.52 mmol) in DCM (40 mL) at room temperature. The mixture was stirred at rt for 3 h. The mixture was filtered through a pad of Celite®, washed with DCM and the solvent was evaporated to dryness to give 1.34 g (100%) of intermediate 177 (de: 90%).

Preparation of intermediate 178:

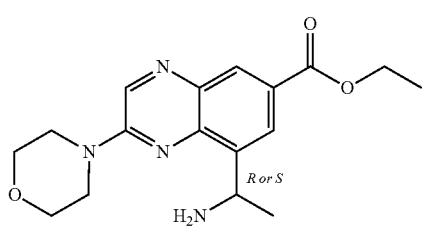 [SMILES: CCOC(=O)c1cc(C(C)N)c2nc(N3CCOCC3)cnc2c1]

To a solution of intermediate 177 (1.34 g, 3.08 mmol) in ACN (20 mL) was added hydrochloric acid in 1,4-Dioxane 4M (0.77 mL, 3.08 mmol). The mixture was stirred at rt for 1 h. The mixture was basified with a saturated aqueous solution of NaHCO₃. The aqueous layer was extracted with DCM (3×). The combined organic layers were dried over MgSO₄, filtered off and evaporated. The residue (1.5 g) was purified by silica gel chromatography (Irregular SiOH 15-40 μm 40 g; gradient from 100% DCM to 90% DCM, 10% MeOH). The pure fractions were collected and the solvent was evaporated until dryness to give 840 mg (82%) of intermediate 178 (ee: 89.6%).

Example A42

Preparation of Intermediate 179 (Identical to Intermediate 162):

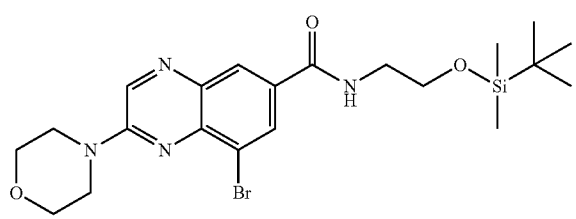 [SMILES: CC(C)(C)[Si](C)(C)OCCNC(=O)c1cc(Br)c2nc(N3CCOCC3)cnc2c1]

At 10° C., HBTU (10.093 g, 26.615 mmol) was added portion wise to a mixture of intermediate 4 (9 g, 26.615 mmol), MN-Di isopropyl ethyl amine (11.621 mL, 66.536 mmol) and 2-(t-butyldimethylsilyl)oxyethanamine (7 g, 39.922 mmol) in DMF (165 mL). The reaction mixture was stirred for 18 h. H₂O and EtOAc were added. The reaction mixture was extracted and the organic layer was separated, dried over MgSO₄, filtered and concentrated to give 22 g of a intermediate residue which was taken up with DCM. The precipitate was filtered. The mother layer was concentrated and purified by silica gel chromatography (330 g of SiO₂, 20-45 μm, gradient from 100% DCM to 95% DCM 5% MeOH 0.1% NH₄OH). The pure fractions were collected and evaporated until dryness to afford 9.6 g (73%) of intermediate 179.

Preparation of Intermediate 180:

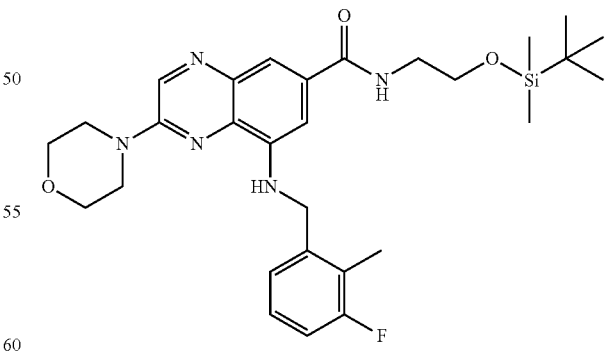

In a sealed tube, a mixture of intermediate 179 (1 g, 2.02 mmol), 3-fluoro-2-methylbenzylamine (0.262 mL, 2.0 mmol) and Cs₂CO₃ (1.315 g, 4.036 mmol) in tert-amyl alcohol (10 mL) was degassed with N₂. 2-Dicyclohexyphosphino-2′,6′-diisopropoxy-1,1′-biphenyl (47.09 mg, 0.101 mmol) and BrettPhos Precatalyst First Gen (80.6 mg, 0.101 mmol) were added. The reaction mixture was purged with N₂ and heated at 100° C. for 18 h. H₂O and EtOAc were added. The reaction mixture was extracted. The organic layer was separated, dried over MgSO₄, filtered and concentrate. The residue (1.35 g) was purified by silica gel chromatography (40 g of SiO₂, 20-45 µm, gradient from 100% DCM to 90% DCM 10% MeOH 0.1% NH₄OH). The pure fractions were collected and evaporated until dryness to afford 845 mg (76%) of intermediate 180 which was directly used in the next steps without any further purification.

Example A43

Preparation of Intermediate 181:

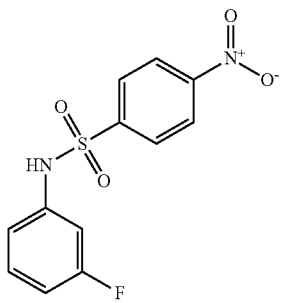 [SMILES: O=[N+]([O-])c1ccc(S(=O)(=O)Nc2cccc(F)c2)cc1]

3-fluoroaniline was treated with 4-nitrophenyl sulfonyl chloride in dichloromethane using pyridine as the base. The procedure was executed on 100 and 300 g scale of fluoroaniline in 90% average yield.

Preparation of Intermediate 182:

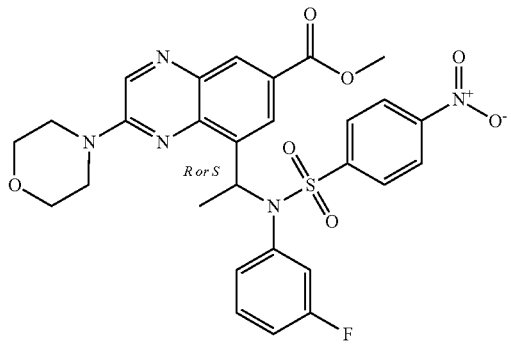 [SMILES: COC(=O)c1cc(C(C)N(c2cccc(F)c2)S(=O)(=O)c2ccc([N+](=O)[O-])cc2)c2nc(N3CCOCC3)cnc2c1]

Intermediate 15b (1.0 eq.) and intermediate 181 (1.5) were dissolved in THF (10 volumes). Then, at 0° C., tributylphosphine (n-Bu₃P) (3-4 equivalents) and di-isopropyl azodicarboxylate (DIAD) (3-4 equivalents) were added. The reaction is exothermic and keeping the temperature at 0° C. during the additions proved to be a critical parameter to avoid a significant decrease in e.e. (racemic material was obtained when the temperature was allowed to raise to 35° C. during the DIAD addition). After complete addition of the reagents, the temperature was increased to 30° C. and, after complete conversion (typically 16 hours), water was added. The solvent was switched to DCM for washing and extraction. DCM was then evaporated. The residue was slurried in 10 volumes of methanol and the precipitate was filtered. The procedure was respectively executed on 50 g scale of intermediate 15b with 3.0 equivalents of both n-Bu₃P and DIAD to give intermediate 182 with a 76% yield (e.e.: 75.1 and on 200 g scale of intermediate 15b with 4.0 equivalents of both n-Bu₃P and DIAD to give intermediate 182 with a 56% yield (e.e.: 82.5%).

Example A44

Preparation of Intermediate 184:

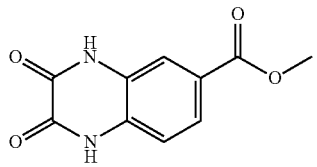 [SMILES: COC(=O)c1ccc2[nH]c(=O)c(=O)[nH]c2c1]

Condensation of methyl 3,4-diaminobenzoate with diethyl oxalate (8.0 equivalents) in toluene (10 volumes) was carried out at reflux for 88 hours. After complete conversion, the mixture was concentrated to a residue which was washed with MTBE. After drying intermediate 184 was obtained in 90% yield.

Preparation of Intermediate 185:

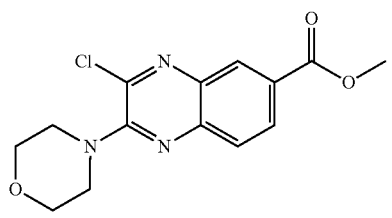 [SMILES: COC(=O)c1ccc2nc(N3CCOCC3)c(Cl)nc2c1]

Intermediate 184 was dissolved in 1,2-dichloroethane (10 volumes). Then, dimethylformamide was added (1.0 equivalent) followed by thionyl chloride (4.0 equivalents). The mixture was heated to 80° C. for 3 hours, cooled to 15° C. and water (5 volumes) was slowly added. After phase separation, the organic layer was washed twice with water (10 volumes) and the solvent was exchanged to 2-Me-THF (15 volumes). Triethylamine was added (3.0 equivalents) followed by morpholine (1.0 equivalents) and the reaction was stirred at room temperature. After complete conversion, water (10 volumes) was added and the layers were separated. Then, the aqueous phase was washed with 2-MeTHF (5 volumes). The combined organic layers were washed with water (5 volumes), concentrated to a residue to obtain a solid which was slurried in MTBE (5 volumes). The precipitate was filtered and dried to give intermediate 185 in 70% yield.

Preparation of Intermediate 186:

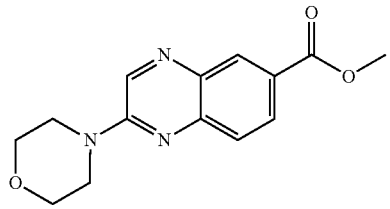 [SMILES: COC(=O)c1ccc2nc(N3CCOCC3)cnc2c1]

Intermediate 185 was dissolved in dichloromethane (10 volumes) and 1,8-diazabicyclo[5.4.0]undec-7-ene (2.0 equivalents) was added. Pd/C (10%, 50% wet, 7% mol) was added and the mixture was hydrogenated (50 psi) for 24 hours. When the conversion was complete, the mixture was filtered through a pad of Celite® and, to the filtrate, MnO₂ (0.1 equivalents) was added. The mixture was warmed to 30-40° C. then filtered again on Celite® and the filtrate was concentrated to 1-2 volumes. The solvent was exchanged to methyl tertiobutylether (5-7 volumes) and the mixture was cooled to 5-10° C. and stirred at the same temperature for 2 hours. The solid was filtered and dried to obtain intermediate 186 in 86% yield (99.4% purity).

Example A45

Preparation of Intermediate 190:

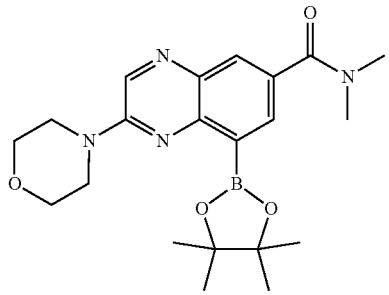 [SMILES: CN(C)C(=O)c1cc(B2OC(C)(C)C(C)(C)O2)c2nc(N3CCOCC3)cnc2c1]

A suspension of intermediate 5 (1.03 g, 2.72 mmol), Bis(Pinacolato)diboron (1.38 g, 5.44 mmol) and potassium acetate (1.07 g, 10.9 mmol) in 1,4-dioxane (10.5 mL) was degassed with nitrogen. Dichloro(diphenylphosphinoferrocene)palladium (99.5 mg, 0.136 mmol) was added and the mixture was heated to 100° C. overnight. The resulting solution was cooled down to room temperature, concentrated under reduced pressure, taken up into brine (50 mL) and extracted with EtOAc (3×100 mL). The combined organic layers were dried over MgSO₄, filtered and concentrated under reduced pressure. The residue was purified by silica gel chromatography (irregular SiOH, 15-40 µm, 50 g, mobile phase gradient: from DCM 100% to DCM 90%, MeOH 10%) to give a mixture of intermediate 190 and intermediate 191 (905 mg, ratio 55/45) as an orange foam.

Preparation of Intermediate 191:

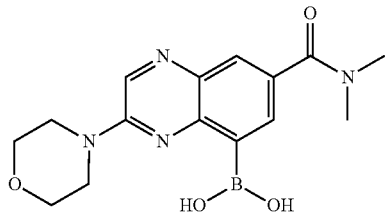 [SMILES: CN(C)C(=O)c1cc(B(O)O)c2nc(N3CCOCC3)cnc2c1]

Sodium Periodate (703 mg, 3.29 mmol) was added to a solution of a mixture of intermediate 190 and intermediate 191 (903 mg, ratio 55/45) in THF (5.52 mL) and water (17.5 mL) and the mixture was stirred at room temperature for 1 h. (43.8 mL, 43.8 mmol) was added and the reaction mixture was stirred at room temperature for 1 h. The resulting solution was quenched with water (50 mL) and extracted with a mixture of DCM/MeOH (8/2, 3×100 mL). The combined organic layers were dried over MgSO₄, filtered and concentrated under reduced pressure. The residue was purified by silica gel chromatography (irregular SiOH, 15-40 µm, 50 g, mobile phase gradient: from DCM 100% to DCM 90%, MeOH 10%) to give (780 mg, 100%) of intermediate 191 as a light orange powder.

Example A46

Preparation of Intermediate 192:

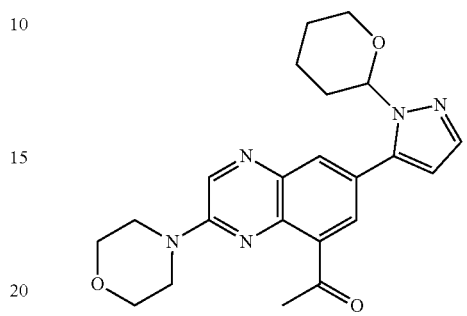

In a Schlenk tube, a solution of intermediate 55a (1 g; 2.97 mmol), 1-(tetrahydro-2H-pyran-2-yl)-1H-pyrazole-5-boronic acid pinacol ester (1.08 g; 3.87 mmol) and potassium carbonate (0.82 g; 5.95 mmol) in 1,4-dioxane (15 mL) and water (3 mL) was degassed under nitrogen. Pd.Cl₂ (dppf) .DCM (244 mg; 0.3 mmol) was added and the reaction mixture was heated at 95° C. for 24 hours. The mixture was cooled to rt, The mixture was poured into a mixture of water and EtOAc, then filtered through a pad of Celite®. The aqueous layer was extracted with EtOAc, The organic layer was washed with brine and dried over MgSO₄, filtered and evaporated to dryness, The resulting residue was taken-up with a mixture of Pentane and Et₂O. The precipitate was filtered to afford 0.42 g (35%) of intermediate 192. The filtrate was evaporated to dryness to afford additional 0.7 g (58%) of intermediate 192.

Preparation of Intermediate 193:

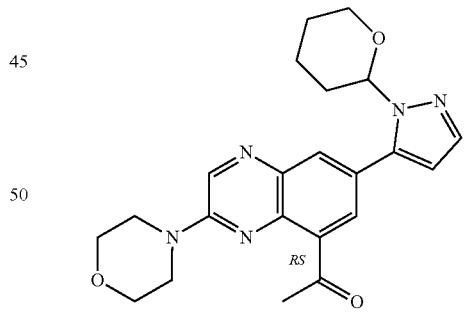

To a solution of intermediate 192 (0.42 g; 1.03 mmol) in MeOH (15 mL) and DCM (5 mL) was added sodium borohydride (43 mg; 1.13 mmol) and the mixture was stirred at 10° C. for 2 h. Then, DCM and water were added. The layers were separated. The aqueous layer was extracted with DCM (2×) and the combined organic layers were dried over MgSO₄, filtered off and evaporated in vacuo. The crude (0.45 g) was purified by silica gel chromatography (Stationary phase: irregular SiOH 15-40 µm 300 g, Mobile phase: 45% Heptane, 50% AcOEt, 5% MeOH, 0.1% NH₄OH) yielding 200 mg (47%) of intermediate 193.

Preparation of Intermediate 194:

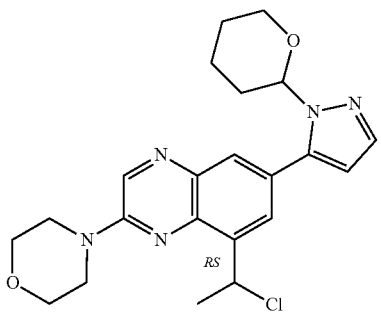 [SMILES: CC(Cl)c1cc(-c2ccnn2C2CCCCO2)cc2ncc(N3CCOCC3)nc12]

Intermediate 194 was prepared according to an analogous procedure as described for the synthesis of intermediate 52, using intermediate 193 (as starting material (directly used without purification for the next step).

Example A47

Preparation of Intermediate 197:

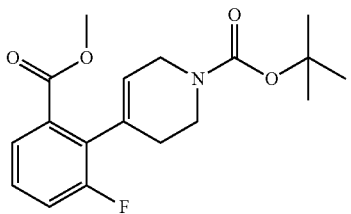 [SMILES: COC(=O)c1cccc(F)c1C1=CCN(C(=O)OC(C)(C)C)CC1]

The reaction was performed twice on 12.17 g of methyl-2-bromo-3-fluorobenzoate and the different reaction mixtures were mixed for the work-up and the purification.

Under $N_2$, to a mixture of methyl-2-bromo-3-fluorobenzoate (24.34 g, 104.45 mmol), tert-butyl-4-(4,4,5,5-tetramethyl-1,2,3,-dioxaborolan-2-yl)-5-6-dihydropyridine-1(2H)-carboxylate (48.44 g, 156.67 mmol) and $K_3PO_4$ (66.51 g, 313.34 mmol) in a mixture of 1,4-dioxane (250 mL) and distilled water (75 mL) was added [1,1'-Bis(diphenylphosphino)ferrocene]dichloropalladium (II), complex with dichloromethane (4.27 g, 5.22 mmol). The reaction mixture was heated to 100° C. overnight, poured out into water and filtered through a Celite® layer. The organic layer was extracted with DCM, separated, dried, filtered and concentrated to dryness. The residue (55.6 g) was purified by column chromatography on silica gel (Irregular SiOH, 15-40 µm, 220 g, mobile phase: 100% DCM). The fractions containing the product were collected and the solvent was evaporated until dryness. The resulting residue (37.9 g) was crystallized from pentane and the precipitate was filtered off and dried under vacuum to give 17.6 g (50%) of intermediate 197.

Preparation of Intermediate 198:

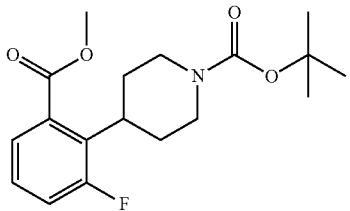 [SMILES: COC(=O)c1cccc(F)c1C1CCN(C(=O)OC(C)(C)C)CC1]

A mixture of intermediate 197 (16.50 g, 49.20 mmol) and Pearlman's catalyst (1.40 g, 9.84 mmol) in MeOH (170 mL) was hydrogenated in a Parr reactor (2 atmospheres) for 12 h at room temperature. After removal of $H_2$, the catalyst was filtered over a pad of Celite®, washed with DCM and the filtrate was concentrated to give 16.4 g (99%) of intermediate 198.

Preparation of Intermediate 199:

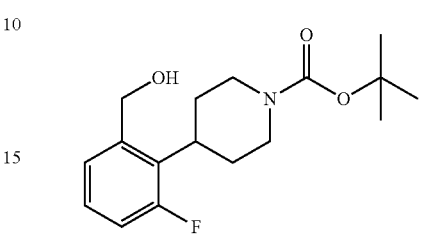

Lithium aluminium hydride (1.85 g, 48.61 mmol) was added portionwise to a mixture of intermediate 198 (16.40 g, 48.61 mmol) in THF (200 mL) at 5° C. under $N_2$. The mixture was stirred at 5° C. for 3 h. Then, EtOAc followed by water were added dropwise to the mixture at −5° C. The suspension was filtered through a pad of Celite®. The organic layer was separated, dried over $MgSO_4$, filtered and the solvent was evaporated to give 15.18 g (quantitative) of intermediate 199.

Preparation of Intermediate 200:

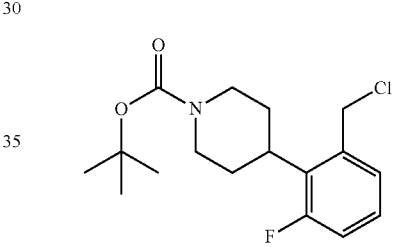

To a solution of intermediate 199 (9.23 g; 29.8) mmol) in DCM (100 mL) cooled to 0° C., was slowly added trimethylamine (6.22 mL; 44.7 mmol) followed by methasulfonylchoride (3.46 mL; 44.7 mmol). The mixture was stirred at room temperature overnight. Water was added and the product was extracted with DCM. The organic layer was dried over $MgSO_4$, filtered and concentrated till dryness. The residue was purified by silica gel chromatography (Irregular SiOH 15-40 µm 40 g, mobile phase: gradient from 80% Heptane, 20% AcOEt to 60% Heptane, 40% AcOEt). The pure fractions were collected and the solvent was evaporated until dryness to give (9.1 g, 93%) of intermediate 200.

Preparation of Intermediate 201:

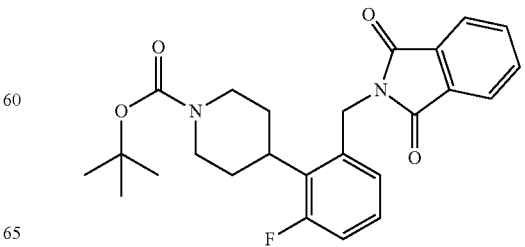

A mixture of intermediate 200 (3.15 g; 9.61 mmol), potassium phtalimide (1.87, 10.09 mmol) in DMF (24 mL) was stirred at room temperature for 3 days. The insoluble was filtered off, washed with diethylether and dried to afford (4.3 g, 100%) of intermediate 201.

Preparation of Intermediate 202:

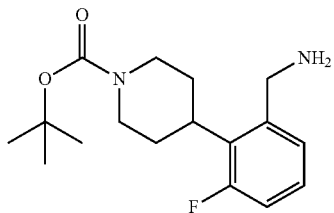 [SMILES: CC(C)(C)OC(=O)N1CCC(c2c(F)cccc2CN)CC1]

A mixture of intermediate 201 (4.3 g, 4.81 mmol), hydrazine monohydrate (2.2 mL, 35.87 mmol) in EtOH (142 mL) was heated to 80° C. for 3 h 30 hours. The reaction mixture was cooled to room temperature and evaporated to dryness. DCM was added and the residue was stirred for 10 min. The insoluble was filtered and washed with DCM. The filtrate was purified by silica gel chromatography (12 g of SiOH 35-40 μm, gradient from 100% DCM to 80% DCM 20% CH3OH 0.1% NH$_4$OH). The fractions were collected and evaporated until dryness to give (1.75 g, 58%) of intermediate 202.

Example A48

Preparation of Intermediate 205:

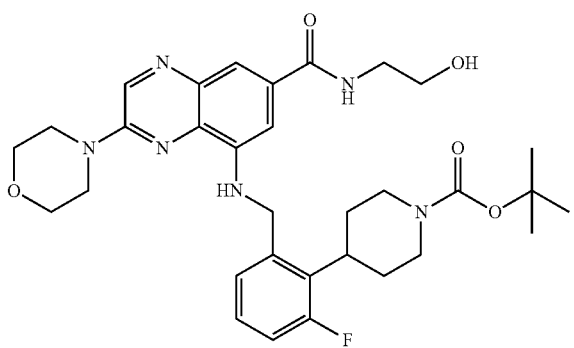 [SMILES: CC(C)(C)OC(=O)N1CCC(c2c(F)cccc2CNc2cc(C(=O)NCCO)cc3ncc(N4CCOCC4)nc23)CC1]

TBAF (1M in THF, 0.624 mL, 0.624 mmol) was added dropwise to a solution of intermediate 204 (0.41 g, 0.567 mmol) in THF (15 mL) at room temperature. The mixture was stirred for 3 h at room temperature. The solution was poured into ice water, extracted with EtOAc and washed with brine. The organic layer was dried over MgSO$_4$, filtered and evaporated to dryness to give 0.56 g of intermediate 205 which was directly used in the next step.

Example A49

Preparation of Intermediate 210:

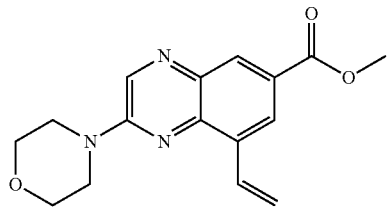 [SMILES: C=Cc1cc(C(=O)OC)cc2ncc(N3CCOCC3)nc12]

In a Schlenk reactor, a solution of intermediate 3a (5.00 g; 14.2 mmol), vinylboronic acid pinacolester (3.28 g; 21.3 mmol) and potassium phosphate (4.52 g; 21.3 mmol) in dioxane (120 mL) and water (30 mL) was purged with N$_2$. Then, PdCl$_2$(dppf).DCM (581 mg; 710 μmol) was added. The reaction mixture was purged again with N$_2$ and heated at 90° C. for 4 h. After cooling down to rt, the reaction mixture was diluted with EtOAc and washed successively with water and a saturated aqueous solution of NaCl. The organic layer was separated, dried over MgSO$_4$, filtered off and evaporated in vacuo. The residue (7.31 g) was purified by silica gel chromatography (Irregular SiOH 15-40 μm, 330 g, mobile phase: gradient from heptane 80%, EtOAc 20% to heptane 50%, EtOAc 50%) to give a pale yellow sticky solid which was triturated in Et$_2$O, the precipitate was filtered on a glass frit to give 2.32 g (55%) of intermediate 210 as a pale yellow solid.

Preparation of Intermediate 211:

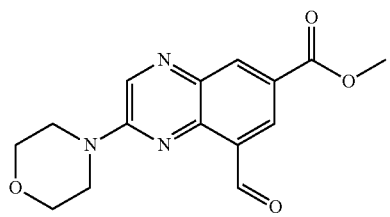 [SMILES: COC(=O)c1cc(C=O)c2nc(N3CCOCC3)cnc2c1]

A solution of intermediate 210 (2.32 g; 7.75 mmol), osmium tetroxide 2.5% in butanol (5.01 mL; 0.388 mmol), sodium periodate (5.80 g; 27.1 mmol) in THF (115 mL) and water (45 mL) was stirred at rt for 18 h. The reaction mixture was poured into ice water and EtOAc was added. The organic layer was separated, dried over MgSO$_4$, filtered off and evaporated in vacuo. The resulting residue was triturated in MeOH and the solid was filtered on a glass frit and dried in vacuo to give 1.86 g (80%) of intermediate 211 as a yellow-brown solid.

Preparation of Intermediate 212:

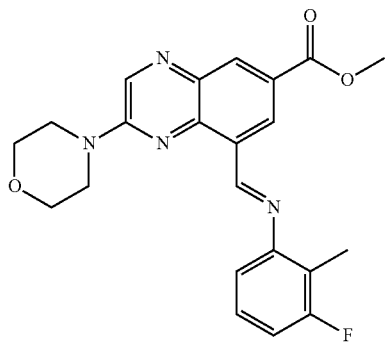 [SMILES: COC(=O)c1cc(/C=N/c2cccc(F)c2C)c2nc(N3CCOCC3)cnc2c1]

In a sealed tube, 3-fluoro-2-methylaniline (530 µL; 4.64 mmol) and molecular sieves 4 Å (4.60 g) were added to a solution of intermediate 211 (700 mg; 2.32 mmol) in dry DCM (22 mL). The reaction mixture was stirred at rt over the weekend. Additional molecular sieves 4 Å (1.20 g) was added and the mixture was stirred at rt for 20 h. Additional 3-fluoro-2-methylaniline (132 µL; 1.16 mmol) and molecular sieves 4 Å (500 mg) were added and the mixture was again stirred at rt for 20 h. The mixture was filtered on a glass frit and the filtrate was evaporated in vacuo to give 1.41 g of intermediate 212 as a yellow solid directly used in the next step without any further purification.

Preparation of Intermediate 214:

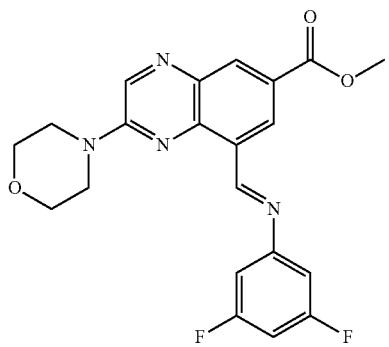 [SMILES: COC(=O)c1cc(/C=N/c2cc(F)cc(F)c2)c2nc(N3CCOCC3)cnc2c1]

Intermediate 214 was prepared according to an analogous procedure as described for the synthesis of intermediate 212 using intermediate 211 and 3,5-difluoroaniline as starting materials (516 mg, used without purification in the next step).

Example A50

Preparation of Intermediate 239:

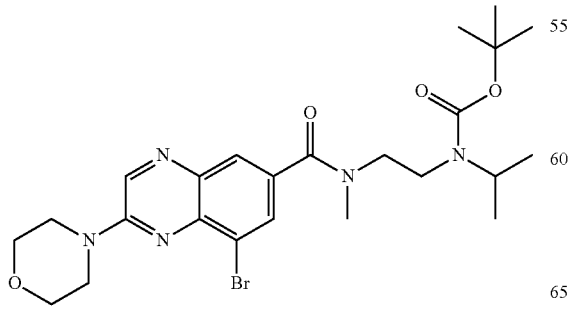

NaH (60% dispersion in mineral oil) (948.5 mg, 23.72 mmol) was added portionwise to a solution of intermediate 238 (5.6 g, 10.7 mmol) in DMF (60 mL) under nitrogen cooled to 0-5° C. (ice bath cooling). The mixture was stirred at 0-5° C. for 15 mn then iodomethane (1.41 mL, 22.59 mmol) was added. The reaction mixture was stirred at room temperature for 16 h. The reaction mixture was poured into water and the organic layer was extracted with EtOAc. The crude residue (4.5 g) was purified by silica gel chromatography to afford 4 g (66%) of intermediate 239.

Preparation of Intermediate 241

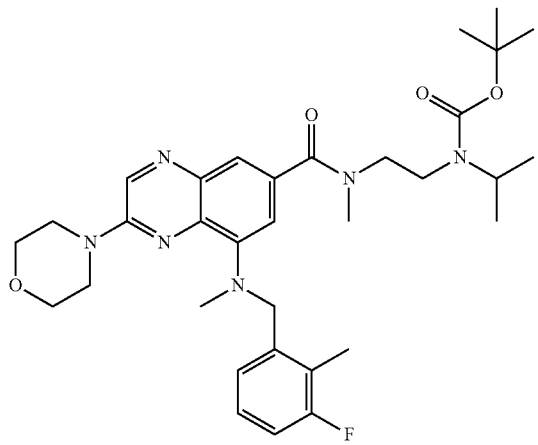 [SMILES: Cc1c(F)cccc1CN(C)c1cc(C(=O)N(C)CCN(C(=O)OC(C)(C)C)C(C)C)cc2ncc(N3CCOCC3)nc12]

Intermediate 241 was prepared according to an analogous procedure as described for the synthesis of intermediate 239 using intermediate 240 as starting material (19 mg, 4%).

Preparation of Intermediate 244

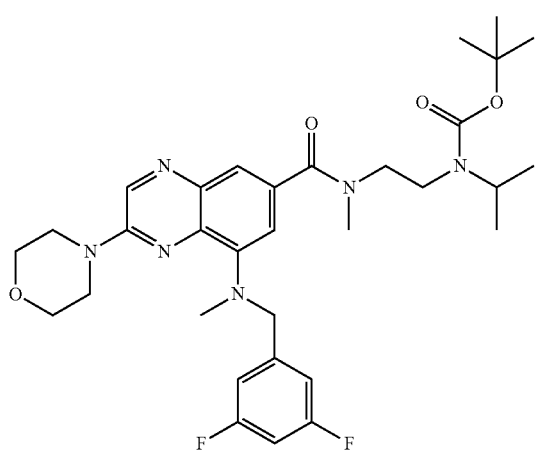 [SMILES: CC(C)N(CCN(C)C(=O)c1cc(N(C)Cc2cc(F)cc(F)c2)c2nc(N3CCOCC3)cnc2c1)C(=O)OC(C)(C)C]

Intermediate 244 was prepared according to an analogous procedure as described for the synthesis of intermediate 239 using intermediate 243 as starting material (42 mg, 9%).

B. Preparation of the Final Compounds

Example B1

Preparation of Compound 1, Compound 2 and Compound 26

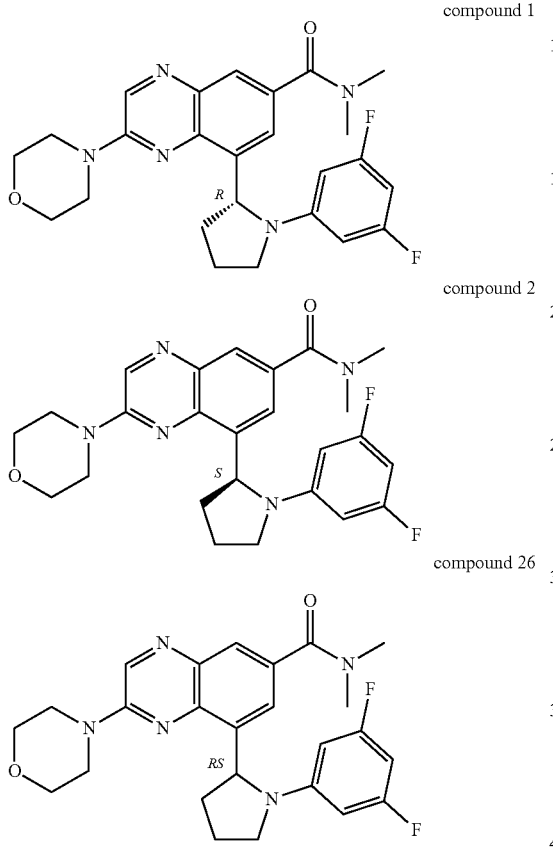

In a sealed tube, a mixture of intermediate 9 (1.1 g; 3.10 mmol), 1-bromo-3,5-difluorobenzene (0.53 mL; 4.64 mmol) and $Cs_2CO_3$ (4.03 g; 12.38 mmol) in 1,4-dioxane (10 mL) was degazed under $N_2$. Xantphos (179 mg; 0.31 mmol) and $Pd(OAc)_2$ (69 mg; 0.31 mmol) were added. The reaction mixture was heated at 100° C. for 5 h. The reaction mixture was poured into ice-water. EtOAc was added and the mixture was filtered through a pad of Celite®. The filtrate was separated and the organic layer was washed with brine, dried over $MgSO_4$, filtered and evaporated. The residue (1.54 g) was purified by chromatography over silica gel (irregular bare silica 150 g; mobile phase: 0.2% $NH_4OH$, 98% DCM, 2% MeOH). The pure fractions were collected and the solvent was evaporated to give 400 mg (28%) of compound 26. Compound 26 was purified by chiral SFC (CHIRALPAK AD-H; 5 µm 250×20 mm; mobile phase: 60% $CO_2$, 40% EtOH). The pure fractions were collected and the solvent was evaporated to give 2 fractions:

Fraction 1: 178 mg which was dissolved in ACN. Then, $Et_2O$ and heptane were added. A precipitate was filtered and dried to give 105 mg (7%) of compound 1. M.P.: 100° C. (K).

Fraction 2: 170 mg which was dissolved in ACN. Then, ECO and heptane were added. A precipitate was filtered and dried to give 93 mg (12%) of compound 2. M.P.: 100° C. (K).

Preparation of Compound 3 and Compound 4

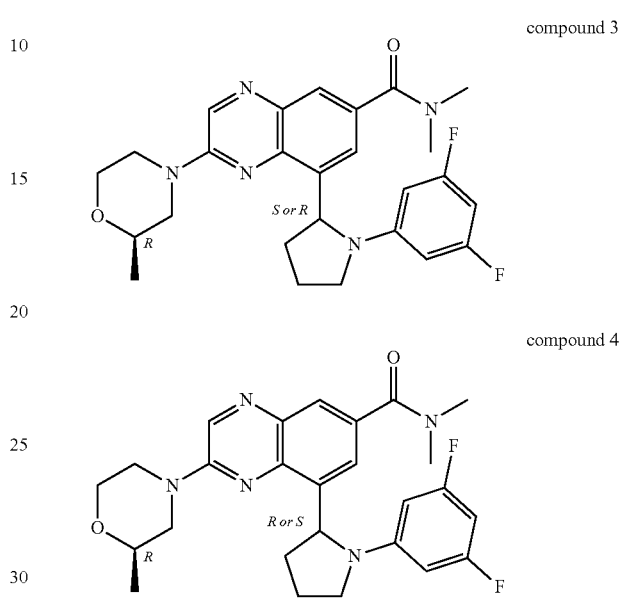

In a sealed vessel, 1-bromo-3,5-difluorobenzene (0.137 mL; 1.20 mmol) and $Cs_2CO_3$ (779 mg; 2.39 mmol) were added to a solution of intermediate 37 (300 mg; 0.80 mmol) in 1,4-dioxane (8 mL). The mixture was carefully degassed under vacuum and back-filled with $N_2$ (3×). Then, $Pd(OAc)_2$ (18 mg; 0.08 mmol) and xantphos (92 mg; 0.16 mmol) were added and the mixture was again carefully degassed under vacuum and back-filled with $N_2$ (3×). The reaction mixture was stirred at 100° C. overnight. The mixture was filtered through a pad of Celite®. The cake was washed with DCM/MeOH (9/1) and the filtrate was evaporated under vacuum. The residue was taken-up with DCM and washed with an aqueous solution of $NaHCO_3$. The layers were separated and the aqueous layer was extracted with DCM (2×). The combined organics layers were dried over $MgSO_4$, filtered and evaporated under vacuum. The residue (512 mg, green foam) was purified by chromatography over silica gel (Spherical bare silica; 5 µm 150×30.0 mm; gradient: from 98% DCM, 2% MeOH (+10% $NH_4OH$) to 90% DCM, 10% MeOH (+10% $NH_4OH$)). The pure fractions were collected and the solvent was evaporated. The residue (148 mg, green oil) was purified by achiral SFC (CHIRALPAK AD-H; 5 µm 250×20 mm; mobile phase: 70% $CO_2$, 30% EtOH (0.3% $iPrNH_2$)). The pure fractions were collected and the solvent was evaporated to give 2 fractions which were freeze-dried with water-ACN to give respectively 48 mg (13%, pale yellow fluffy solid) of compound 4 and 53 mg (14%, pale yellow fluffy solid) of compound 3.

Preparation Compound 7, Compound 8 and Compound 9

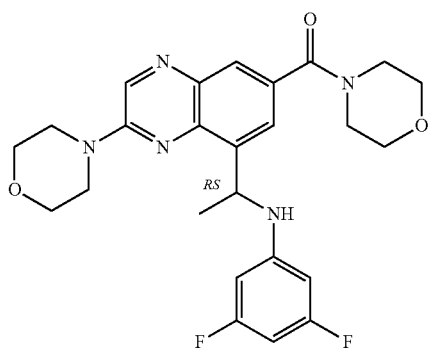
compound 7

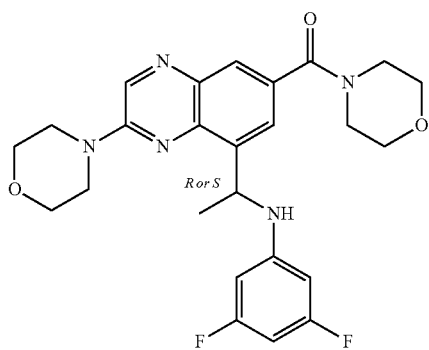
compound 8

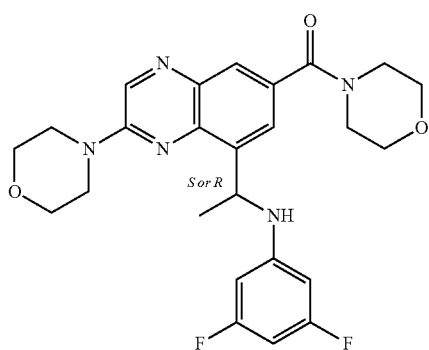
compound 9

In a sealed tube, a mixture of intermediate 44 (130 mg; 0.35 mmol), 1-bromo-3,5-difluorobenzene (48 µL; 0.42 mmol) and $Cs_2CO_3$ (228 mg; 0.70 mmol) in 2-methyl-2-butanol (1.70 mL) was purged with $N_2$. BrettPhos Precatalyst First Gen (14 mg; 17.5 µmol) was added. The reaction mixture was purged with $N_2$ and heated at 110° C. for 18 h. After cooling down to rt, additional 1-bromo-3,5-difluorobenzene (48 µL; 0.42 mmol) and $Cs_2CO_3$ (228 mg; 0.70 mmol) were added. The mixture was purged with $N_2$ and BrettPhos Precatalyst First Gen (14 mg; 17.5 µmol) was added. The mixture was purged with $N_2$ and heated at 110° C. for 18 h. After cooling down to rt, the crude was combined with another batch coming from a reaction performed on 20 mg of intermediate 44. EtOAc and water were added. The organic layer was separated. The aqueous layer was neutralized with solid $NH_4Cl$ and extracted with EtOAc (2×). The combined organic layers were dried over $MgSO_4$, filtered and evaporated under vacuum. The residue (277 mg, brown oil) was purified by chromatography over silica gel (Irregular SiOH 15-40 µm; 10 g; gradient: from 100% DCM to 90% DCM, 10% acetone). The pure fractions were collected and the solvent was evaporated to give a yellow oil which was triturated in $Et_2O$. The precipitate was filtered and dried under vacuum to give 122 mg (62%, yellow foam) of compound 7. M.P.: 206° C. (DSC).

86 mg of compound 7 was purified by chiral SFC (CHIRALCEL OJ-H; 5 µm 250×20 mm; mobile phase: 75% $CO_2$, 25% MeOH). The pure fractions were collected and the solvent was evaporated affording two fractions which were freeze-dried with water-ACN to give respectively 39 mg (20%, pale yellow fluffy solid) of compound 8 and 41 mg (21%, pale yellow fluffy solid) of compound 9.

Alternative Pathway:

In a sealed tube, a mixture of intermediate 45 (1.5 g; 20.91 mmol) and 3,5-difluoroaniline (1.9 g; 14.53 mmol) in DMF (250 mL) was stirred at 50° C. for 48 h. The solution was poured into ice-water. EtOAc was added and the mixture was filtered through a pad of Celite®. The product was extracted with EtOAc. The organic layer was dried over $MgSO_4$, filtered and evaporated to dryness. The residue (200 mg) was purified by chromatography over silica gel (irregular 15-40 µm; 40 g; mobile phase: 0.1% $NH_4OH$, 98% DCM, 2% MeOH). The pure fractions were collected and the solvent was evaporated to give 460 mg of compound 7.

260 mg of compound 7 were purified by chiral SFC (CHIRALCEL OJ-H 5 µm 250×20 mm; mobile phase: 75% $CO_2$, 25% MeOH (0.3% $iPrNH_2$)). The pure fractions were collected and the solvent was evaporated to give 111 mg of compound 8 (pure at 88% by $^1H$ NMR) and 102 mg of compound 9. 111 mg of compound 8 was purified by achiral SFC (CYANO 6 µm 150×21.2 mm; mobile phase: 85% $CO_2$, 15% MeOH (0.3% $iPrNH_2$)). The pure fractions were collected and the solvent was evaporated. The residue (98 mg) was crystallized with pentane and $Et_2O$. The precipitate was filtered and dried to give 49 mg of compound 8. M.P.: 100° C. (gum, K).

Preparation Compound 11, Compound 12 and Compound 13

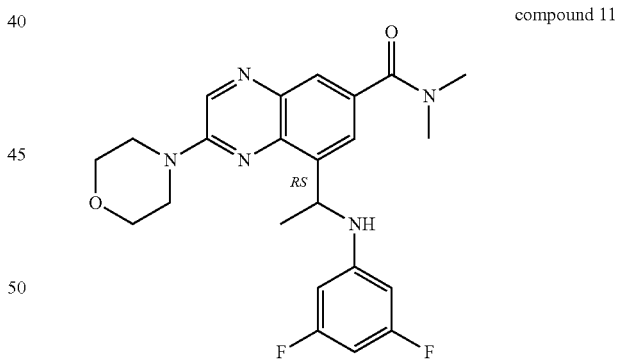
compound 11

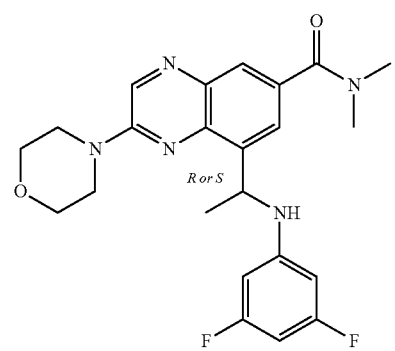
compound 12

-continued compound 13

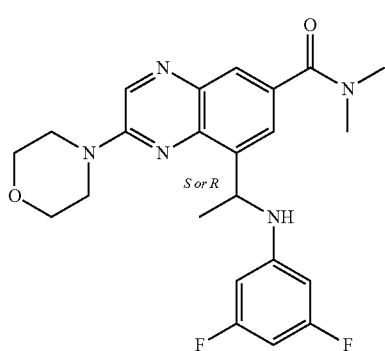

In a sealed tube, a mixture of intermediate 19 (283 mg; 0.86 mmol), 1-bromo-3,5-difluorobenzene (147 µL; 1.29 mmol) and $Cs_2CO_3$ (560 mg; 1.72 mmol) in 2-methyl-2-butanol (4.20 mL) was purged with $N_2$. BrettPhos Precatalyst First Gen (34 mg; 43 µmol) and BrettPhos (9 mg; 17 µmol) were added. The reaction mixture was purged with $N_2$ and heated at 110° C. for 18 h. After cooling down to rt, 1-bromo-3,5-difluorobenzene (147 µL; 1.29 mmol) and $Cs_2CO_3$ (560 mg; 1.72 mmol) were added. The mixture was purged with $N_2$ and BrettPhos Precatalyst First Gen (34 mg; 43 µmol) and BrettPhos (9 mg; 17 µmol) were added. The reaction mixture was purged with $N_2$ and heated at 110° C. for 18 h. After cooling down to rt, the crude was diluted with EtOAc and filtered through a pad of Celite®. The filtrate was evaporated under vacuum to dryness. The residue (700 mg, brown oil) was purified by chromatography over silica gel (Irregular SiOH 15-40 µm; 30 g; gradient: from 100% DCM to 95% DCM, 5% (iPrOH/$NH_4OH$ 90/10)). The pure fractions were collected and the solvent was evaporated to give yellow oil which was triturated with diethylether and dried in vacuum to give 323 mg (85%, pale yellow solid) of compound 11 (M.P.: 228° C. (DSC)). Compound 11 was purified by chiral SFC (CHIRALCEL OJ-H 5 µm 250×20 mm; mobile phase: 80% $CO_2$, 20% MeOH). The pure fractions were collected and the solvent was evaporated to give two fractions which were triturated with $Et_2O$, evaporated and dried under vacuum to give 116 mg (28%, off-white solid) of compound 12 (M.P.: 218° C. (DSC)) and 117 mg (28%, off-white solid) of compound 13 (M.P.: 217° C. (DSC)).

Preparation Compound 23 Compound 24 and Compound 25 compound 23

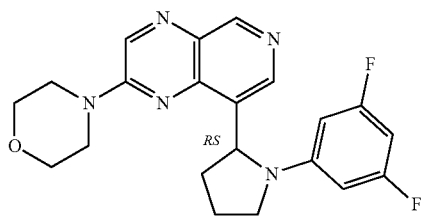

compound 24

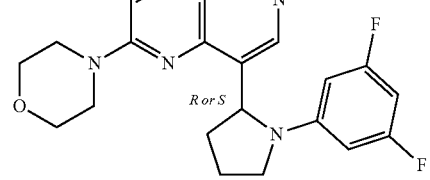

compound 25

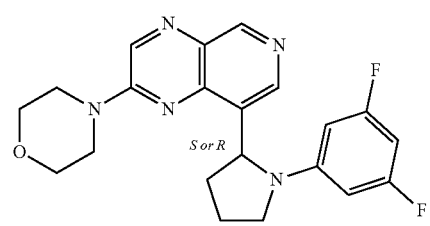

In a sealed tube, a mixture of intermediate 64 (360 mg; 1.26 mmol), 1-bromo-3,5-difluorobenzene (216 µL; 1.89 mmol) and sodium tert-butoxide (242 mg; 2.52 mmol) in 1,4-dioxane (13 mL) was degazed under $N_2$. Then, 2-(di-tert-butylphosphino)biphenyl (38 mg; 0.13 mmol) and $Pd_2(dba)_3$ (58 mg; 0.06 mmol) were added and the reaction mixture was heated at 100° C. for 18 h. The mixture was poured into water and filtered through a pad of Celite®. The organic layer was extracted with DCM, separated, dried over $MgSO_4$, filtered and evaporated to dryness. The residue (400 mg) was purified by chromatography over silica gel (SiOH 15 µm; gradient: from 100% DCM to 95% DCM, 5% MeOH, 0.1% $NH_4OH$). The pure fractions were collected and the solvent was evaporated. The residue (300 mg) was taken up with DIPE/CAN (drops). A solid was filtered and dried to give 160 mg (32%) of compound 23. Compound 23 was purified by chiral SFC (CHIRALCEL OD-H 5 µm 250×20 mm; mobile phase: 70% $CO_2$, 30% iPrOH (0.3% $iPrNH_2$)). The pure fractions were collected and the solvent was evaporated to give 64 mg (13%) of compound 24 (M.P.: 100° C. (gum, K)) and 70 mg (14%) of compound 25 (M.P.: 98° C. (gum, K)).

Preparation of Compound 27:

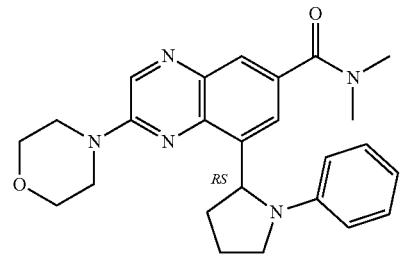 [SMILES: CN(C)C(=O)c1cc(C2CCCN2c2ccccc2)c2nc(N3CCOCC3)cnc2c1]

Compound 27 was prepared according to an analogous procedure as described for the synthesis of compound 1, using intermediate 9 and bromobenzene as starting materials (30 mg, 16%). M.P.: 80° C. (gum, K).

Preparation Compound 7, Compound 8 and Compound 9

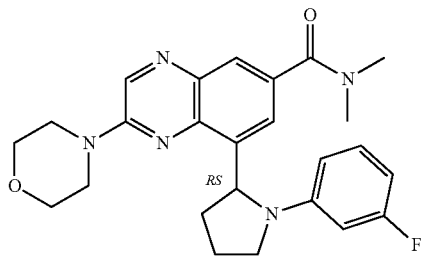 [SMILES: CN(C)C(=O)c1cc(C2CCCN2c2cccc(F)c2)c2nc(N3CCOCC3)cnc2c1]

Preparation of Compound 28:

Compound 28 was prepared according to an analogous procedure as described for the synthesis of compound 1, using intermediate 9 and 1-bromo-3-fluorobenzene as starting materials (46 mg, 24%). M.P.: 80° C. (gum, K).

Preparation Compound 29 and Compound 30 compopund 29

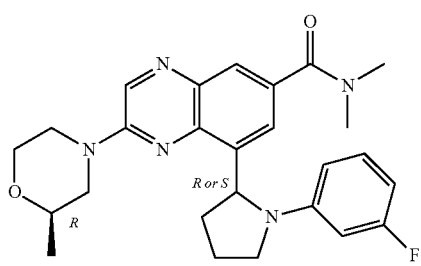

compopund 30

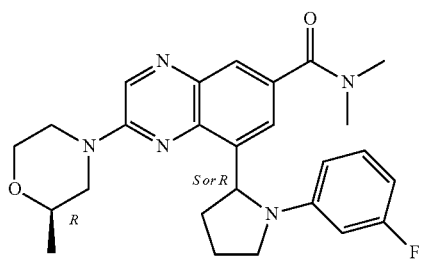

Compound 29 and compound 30 were prepared according to an analogous procedure as described for the synthesis of compound 3, using intermediate 37 and 1-bromo-3-fluorobenzene as starting material. The racemic compound was purified by achiral SFC (CHIRALPAK AD-H 5 μm 250×20 mm; mobile phase: 60% CO$_2$, 40% MeOH (0.3% iPrNH$_2$)). The pure fractions were collected and the solvent was evaporated to give two fractions which were freeze-dried with water-ACN to give respectively 39 mg (11%, pale green fluffy solid) of compound 29 and 33 mg (9%, pale green fluffy solid) of compound 30.

Preparation of Compound 31:

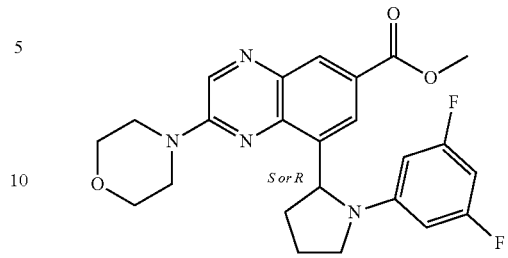

Compound 31 was prepared according to an analogous procedure as described for the synthesis of compound 1, using intermediate 25 and 1-bromo-3,5-difluorobenzene as starting materials (300 mg, 13%). M.P.: 213° C. (DSC).

Preparation of Compound 32:

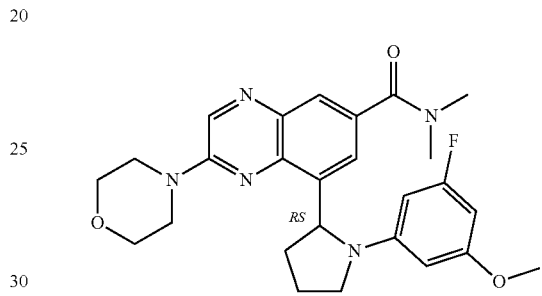

Compound 32 was prepared according to an analogous procedure as described for the synthesis of compound 1, using intermediate 9 and 3-bromo-5-fluoroanisole as starting materials (85 mg, 25%). M.P.: 80° C. (gum, K).

Preparation of Compound 35:

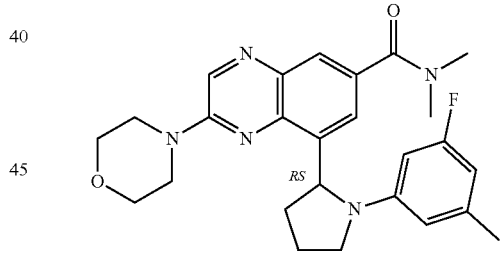

Compound 35 was prepared according to an analogous procedure as described for the synthesis of compound 1, using intermediate 9 and 3-bromo-5-fluorotoluene as starting materials (83 mg, 25%). M.P.: 80° C. (gum, K).

Preparation of Compound 36:

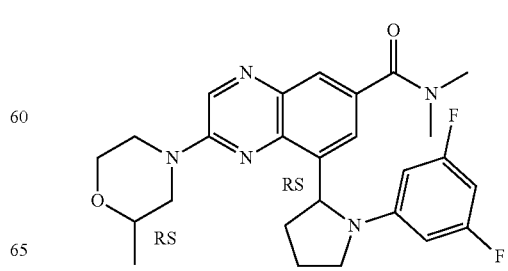

Compound 36 was prepared according to an analogous procedure as described for the synthesis of compound 1, using intermediate 71 and 1-bromo-3,5-difluorobenzene as starting materials (90 mg, 34%). Compound 36 was obtained as a mixture of 3 diastereoisomers.

Preparation of Compound 41:

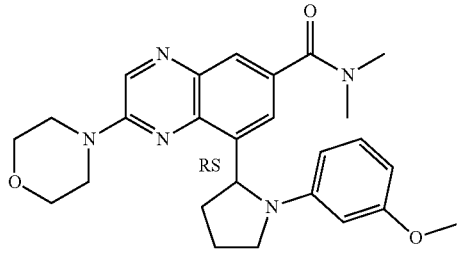 [SMILES: COc1cccc(N2CCCC2c2cc(C(=O)N(C)C)cc3ncc(N4CCOCC4)nc23)c1]

Compound 41 was prepared according to an analogous procedure as described for the synthesis of compound 1, using intermediate 9 and 3-bromoanisole as starting materials (freeze-dried, 16 mg, 3%). M.P.: 80° C. (gum, K).

Preparation of Compound 42:

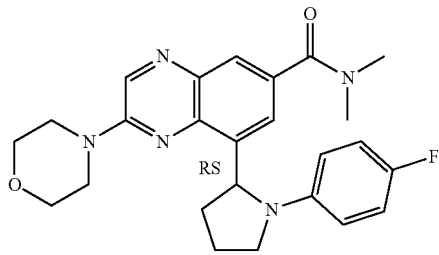 [SMILES: CN(C)C(=O)c1cc(C2CCCN2c2ccc(F)cc2)c2nc(N3CCOCC3)cnc2c1]

Compound 42 was prepared according to an analogous procedure as described for the synthesis of compound 23, using intermediate 9 and 4-bromofluorobenzene as starting materials (freeze-dried, 69 mg, 27%). M.P.: 80° C. (gum, K).

Preparation of Compound 44:

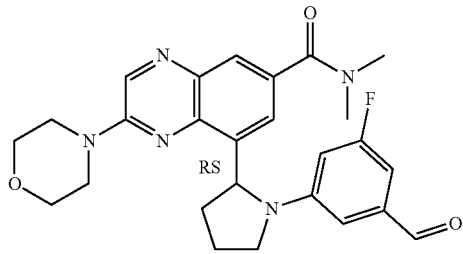 [SMILES: CN(C)C(=O)c1cc(C2CCCN2c2cc(F)cc(C=O)c2)c2nc(N3CCOCC3)cnc2c1]

Compound 44 was prepared according to an analogous procedure as described for the synthesis of compound 23, using intermediate 9 and 3-bromo-5-fluorobenzaldehyde as starting materials (95 mg, 24%). M.P.: 80° C. (gum, K).

Preparation Compound 52:

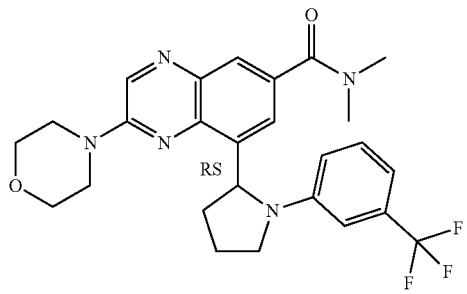 [SMILES: CN(C)C(=O)c1cc(C2CCCN2c2cccc(C(F)(F)F)c2)c2nc(N3CCOCC3)cnc2c1]

In a sealed tube, a mixture of intermediate 9 (100 mg; 0.28 mmol), 3-bromobenzotrifluoride (95 mg; 0.42 mmol) and $Cs_2CO_3$ (183 mg; 0.56 mmol) in 1,4-dioxane (3 mL) was degazed under $N_2$. Then, 2-(di-tert-butylphosphino)biphenyl (17 mg; 0.06 mmol) and $Pd_2(dba)_3$ (26 mg; 0.03 mmol) were added and the reaction mixture was heated at 100° C. for 24 h. The mixture was poured into water and filtered through a pad of Celite®. The organic layer was extracted with DCM, separated, dried over $MgSO_4$, filtered and evaporated to dryness. The residue (180 mg) was purified by chromatography over silica gel (Spherical bare silica 5 µm; 150×30.0 mm; gradient: from 98% DCM, 2% MeOH (+10% $NH_4OH$) to 92% DCM, 8% MeOH (+10% $NH_4OH$)). The pure fractions were collected and the solvent was evaporated. The residue (33 mg) was freeze-dried with water/ACN 80/20 to give 32 mg (23%) of compound 52. M.P.: 80° C. (gum, K).

Preparation compound 54:

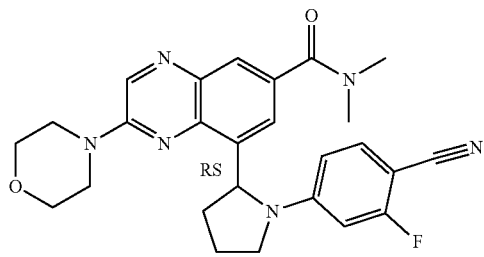 [SMILES: CN(C)C(=O)c1cc(C2CCCN2c2ccc(C#N)c(F)c2)c2nc(N3CCOCC3)cnc2c1]

Compound 54 was prepared according to an analogous procedure as described for the synthesis of compound 52, using intermediate 9 and 4-bromo-2-fluorobenzonitrile as starting materials (freeze-dried: 37 mg, 28%). M.P.: 80° C. (gum, K).

Preparation Compound 55:

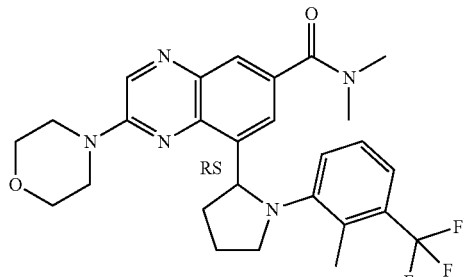

Compound 55 was prepared according to an analogous procedure as described for the synthesis of compound 52, using intermediate 9 and 2-bromo-2-methyl-3-(trifluoromethyl)benzene as starting materials (freeze-dried: 16 mg, 11%). M.P.: 80° C. (gum, K).

Preparation Compound 57:

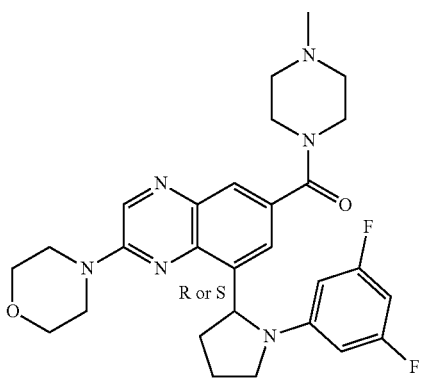 [SMILES: CN1CCN(C(=O)c2cc(C3CCCN3c3cc(F)cc(F)c3)c3nc(N4CCOCC4)cnc3c2)CC1]

Compound 57 was prepared according to an analogous procedure as described for the synthesis of compound 52, using intermediate 81 and 1-bromo-3,5-difluorobenzene as starting materials (freeze-dried: 31 mg, 24%, white powder). M.P.: 80° C. (gum, K).

Preparation Compound 58:

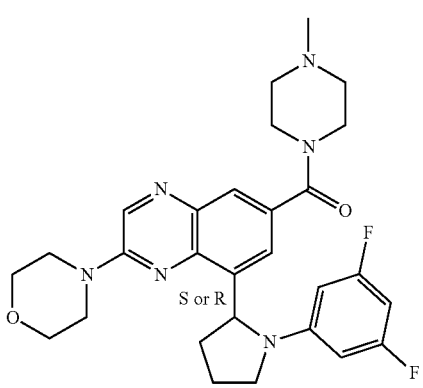 [SMILES: CN1CCN(C(=O)c2cc(C3CCCN3c3cc(F)cc(F)c3)c3nc(N4CCOCC4)cnc3c2)CC1]

Compound 58 was prepared according to an analogous procedure as described for the synthesis of compound 52, using intermediate 82 and 1-bromo-3,5-difluorobenzene as starting materials (freeze-dried: 36 mg, 28%, white powder). M.P.: 80° C. (gum, K).

Preparation Compound 85:

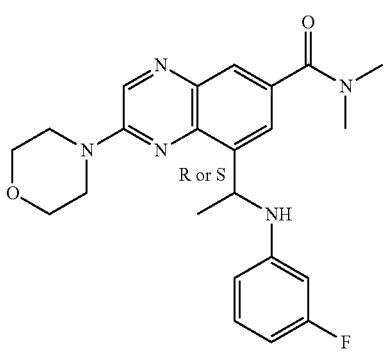 [SMILES: CC(Nc1cccc(F)c1)c1cc(C(=O)N(C)C)cc2ncc(N3CCOCC3)nc12]

Compound 85 was prepared according to an analogous procedure as described for the synthesis of compound 11, using intermediate 14 and 1-bromo-3-fluorobenzene as starting materials (freeze-dried: 36 mg, 29%, pale yellow fluffy solid).

Preparation of Compound 106 and Compound 107

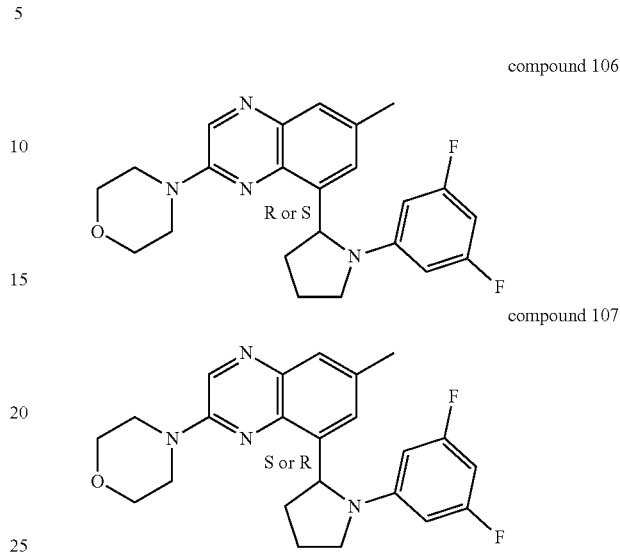

Compound 106 and compound 107 were prepared according to an analogous procedure as described for the synthesis of compound 52, using intermediate 114 and 1-bromo-3,5-difluorobenzene as starting materials. The residue (0.6 g) was purified by chromatography over silica gel (irregular 15-40 μm; 40 g; mobile phase: 50% heptane, 50% EtOAc). The pure fractions were collected and the solvent was evaporated. The residue (160 mg) was purified by chiral SFC (CHIRALCEL OD-H 5 μm; 250×20 mm; mobile phase: 80% $CO_2$, 20% EtOH (0.3% $iPrNH_2$)). The pure fractions were collected and the solvent was evaporated to give 57 mg (10%) of compound 106 (M.P.: 80° C., gum, K) and 60 mg (10%) of compound 107 (M.P.: 80-90° C., gum, K).

Preparation Compound 249:

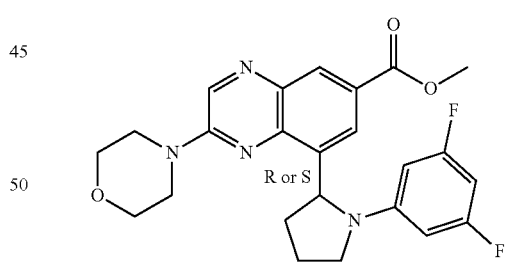

The experiment was performed 4 times on the same quantity (580 mg; 1.46 mmol) of intermediate 24.

In a sealed tube, a mixture of intermediate 24 (580 mg; 1.46 mmol), 1-bromo-3,5-difluorobenzene (0.29 mL; 2.54 mmol) and $Cs_2CO_3$ (1.1 g; 3.39 mmol) in 1,4-dioxane (20 mL) was degazed under $N_2$. 2-(di-tert-butylphosphino)biphenyl (101 mg; 0.34 mmol) and $Pd_2(dba)_3$ (155 mg; 0.17 mmol) were added. The reaction mixture was heated at 100° C. for 48 h. The reaction mixture was poured into ice-water and EtOAc was added, filtered through a pad of Celite®. The filtrate was separated and the organic layer was dried over $MgSO_4$, filtered and evaporated. The residue (4 g) was purified by chromatography over silica gel (irregular 15-40

μm 120 g; mobile phase: 65% heptane, 35% EtOAc). The pure fractions were collected and the solvent was evaporated to give 950 mg (31%) of compound 249. M.P.: 211° C. (DSC).

Preparation of Compound 252:

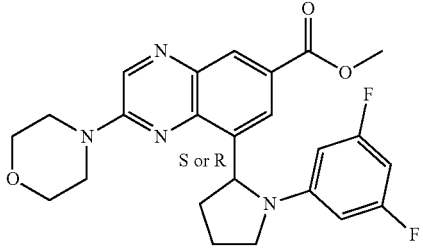 [SMILES: COC(=O)c1cc(C2CCCN2c2cc(F)cc(F)c2)c2nc(N3CCOCC3)cnc2c1]

In a sealed tube, a mixture of intermediate 25 (1.73 g; 5.05 mmol), 1-bromo-3,5-difluorobenzene (750 μL; 6.57 mmol) and $Cs_2CO_3$ (2.47 g; 7.58 mmol) in 1,4-dioxane (16 mL) was degazed under $N_2$. Xantphos (292 mg; 0.51 mmol) and $Pd_2(dba)_3$ (231 mg; 0.25 mmol) were added. Then, the reaction mixture was heated at 100° C. overnight. The mixture was poured into $H_2O$, filtered through a pad of Celite® and extracted with EtOAc. The organic layer was dried over $MgSO_4$, filtered and evaporated until dryness. The residue (1.5 g) was purified by chromatography over silica gel (irregular 15-40 μm; 80 g; mobile phase: 65% heptane, 35% EtOAc). The pure fractions were collected and the solvent was evaporated to give 1.04 g (60%) of intermediate 25 and an intermediate residue was taken-up with $Et_2O$ The precipitate was filtered and dried under vacuum to give 300 mg (13%) of compound 252.

Preparation of Compound 254:

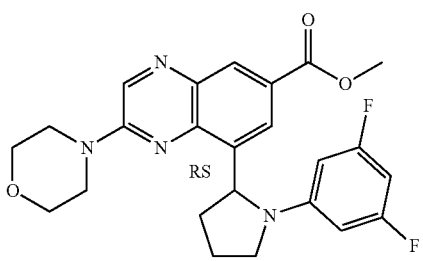 [SMILES: COC(=O)c1cc(C2CCCN2c2cc(F)cc(F)c2)c2nc(N3CCOCC3)cnc2c1]

The experiment was performed 12 times on the same quantity (475 mg; 1.39 mmol) of intermediate 23:

Compound 254 was prepared according to an analogous procedure as described for the synthesis of compound 249, using intermediate 23 and 1-bromo-3,5-difluorobenzene as starting materials (1.7 g, 22%).

Preparation of Compound 255:

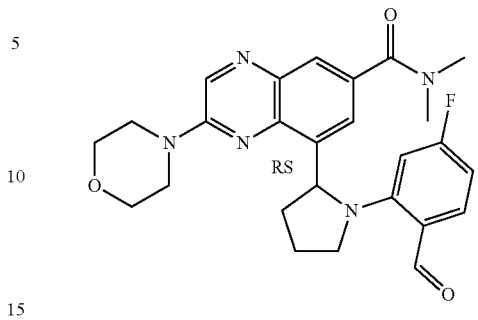

Compound 255 was prepared according to an analogous procedure as described for the synthesis of compound 249, using intermediate 9 and 2-bromo-4-fluorobenzaldehyde as starting materials (120 mg, 22%).

Preparation of Compound 274:

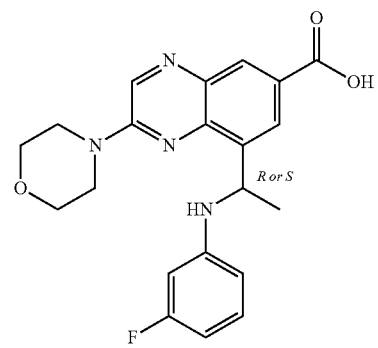 [SMILES: CC(Nc1cccc(F)c1)c1cc(C(=O)O)cc2ncc(N3CCOCC3)nc12]

In a sealed tube, a mixture of intermediate 178 (0.2 g; 0.605 mmol), 1-bromo-3-fluorobenzene (0.079 mL; 0.726 mmol) and $Cs_2CO_3$ (0.394 g; 1.21 mmol) in tert-amyl alcohol (3 mL) was degased with $N_2$. BrettPhos Precatalyst First Gen (24 mg, 0.0303 mmol) and Brettphos (6.5 mg; 0.012 mmol) were added. The reaction mixture was purged with $N_2$ and heated at 110° C. for 42 h. After cooling down to rt, the crude was poured into water, diluted with EtOAc and filtered on a pad of Celite®. The aqueous layer was acidified and extracted with DCM, the combinated layers were dried over $MgSO_4$, filtered and evaporated to give 94 mg (39%) of the compound 274 (ee: 90%).

Alternative Preparation of Compound 274:

Compound 262a was hydrolyzed in THF (10 volumes) using NaOH (1.0 M in water, 4 eq.) at 50° C. for 16 hours. The product was isolated by distillation of THF, dilution with water and pH adjustment to 6-7 with 2M HCl. The procedure was executed on 18 and 100 g scale of compound 262a and gave compound 274 in quantitative yield (e.e.: 97.9%).

Preparation of Compound 350:

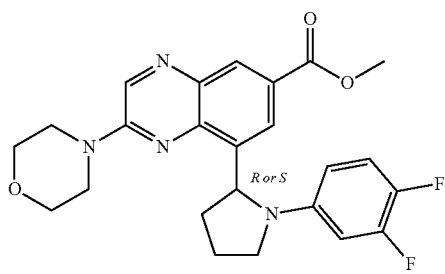 [SMILES: COC(=O)c1cc(C2CCCN2c2ccc(F)c(F)c2)c2nc(N3CCOCC3)cnc2c1]

Compound 350 was prepared according to an analogous procedure as described for the synthesis of compound 52, using intermediate 24 and 4-bromo-1,2-difluorobenzene as starting materials (250 mg, 19%).

Example B2

Preparation of Compound 84:

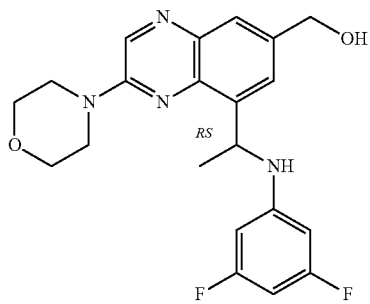 [SMILES: CC(Nc1cc(F)cc(F)c1)c1cc(CO)cc2ncc(N3CCOCC3)nc12]

A solution of thioglycolic acid (24 µL; 0.34 mmol) and 1,8-diazabicyclo(5.4.0)undec-7-ene (102 µL; 0.68 mmol) in ACN (2 mL) was added to a solution of intermediate 100 (100 mg; 0.17 mmol) in ACN (3 mL). The solution was stirred at rt for 15 min then DCM and 10% aqueous solution of $Na_2CO_3$ were added. The organic layer was separated and the aqueous layer was extracted with DCM (2×). The combined organic layers were dried over $MgSO_4$, filtered and evaporated in vacuum. The residue (60 mg) was purified by chromatography over silica gel (irregular bare silica 40 g; mobile phase: 0.4% $NH_4OH$, 96% DCM, 4% MeOH). The pure fractions were collected and the solvent was evaporated. The residue (36 mg) was purified by reverse phase (X-Bridge-C18; 5 µm 30*150 mm; gradient: from 75% $NH_4HCO_3$ 0.5%, 25% ACN to 35% $NH_4HCO_3$ 0.5%, 65% ACN). The pure fractions were collected and the solvent was evaporated to give 30 mg (44%) of compound 84. M.P.: 80° C. (gum, K).

Preparation of Compound 100:

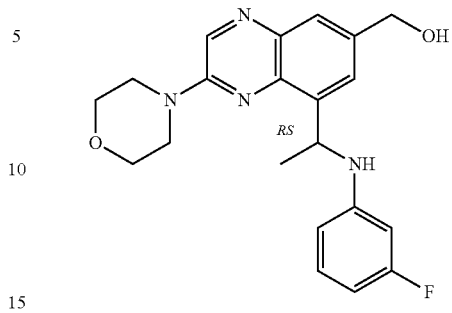

Compound 100 was prepared according to an analogous procedure as described for the synthesis of compound 84, using intermediate 108 as starting material (75 mg, 82%, pale yellow solid.

Preparation of Compound 136

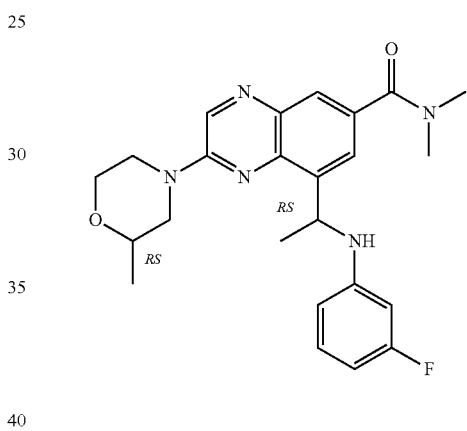

Compound 136 was prepared according to an analogous procedure as described for the synthesis of compound 84, using intermediate 128 as starting material (39 mg, 44%, off-white solid. M.P.: 184° C. (DSC).

Example B3

Preparation Compound 15 and Compound 16 compound 185

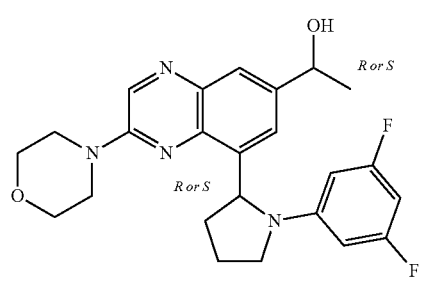

211
-continued compound 16

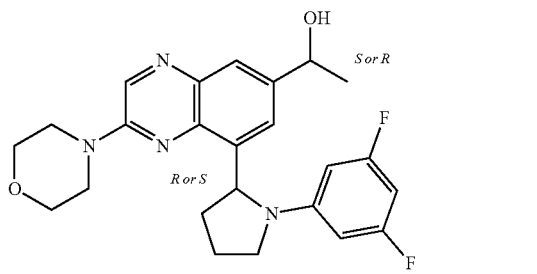

At 10° C., methylmagnesium bromide (0.27 mL; 0.82 mmol) was added to a solution of compound 250 (0.29 g; 0.68 mmol) in THF (8 mL) under $N_2$. The solution was stirred at 10° C. for 45 min. The solution was poured into a saturated $NH_4Cl$ solution and the product was extracted with EtOAc. The organic layer was dried over $MgSO_4$, filtered and evaporated to dryness. The residue (285 mg) was purified by chromatography over silica gel (irregular 15-40 μm; 12 g; mobile phase: 96% DCM, 4% MeOH, 0.1% $NH_4OH$). The pure fractions were collected and the solvent was evaporated to give 158 mg of fraction 1 and 56 mg of fraction 2. Fraction 1 was purified by reverse phase (X-Bridge-C18 5 μm 30*150 mm; gradient: from 65% $NH_4HCO_3$ 0.5%, 35% ACN to 25% $NH_4HCO_3$ 0.5%, 75% ACN). The pure fractions were collected and the solvent was evaporated. The residue (103 mg) was combined with 56 mg of fraction 2 to give 159 mg which were purified by achiral SFC (CHIRALPAK IC 5 μm 250×20 mm; mobile phase: 70% $CO_2$, 30% iPrOH (0.3% $iPrNH_2$)). The pure fractions were collected and the solvent was evaporated to give two fractions which were freeze-dried with water-ACN (80/20) to give 70 mg (23%, yellow powder) of compound 15 (M.P.: 80° C. (gums, K)) and 56 mg (15%, yellow powder) of compound 16 (M.P.: 80° C. (gums, K)).

Example B4

Preparation Compound 17:

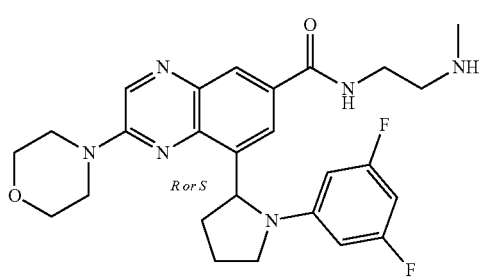 [SMILES: CNCCNC(=O)c1cc(C2CCCN2c2cc(F)cc(F)c2)c2nc(N3CCOCC3)cnc2c1]

At 0° C., HCl (4M in 1,4-dioxane) (0.31 mL; 1.26 mmol) was added to a solution of intermediate 49 (150 mg; 0.25 mmol) in ACN (6 mL). The reaction mixture was stirred at 0° C. for 1 h and at rt for 3 h. The solution was poured into ice-water and extracted with EtOAc. The organic layer was dried over $MgSO_4$, filtered and the solvent was evaporated. The residue (160 mg) was purified by chromatography over silica gel (irregular bare silica 40 g; mobile phase: 0.1% $NH_4OH$, 90% DCM, 10% MeOH). The pure fractions were collected and the solvent was evaporated until dryness to give 45 mg (36%) of compound 17. M.P.: 170° C. (K).

212
Preparation Compound 18:

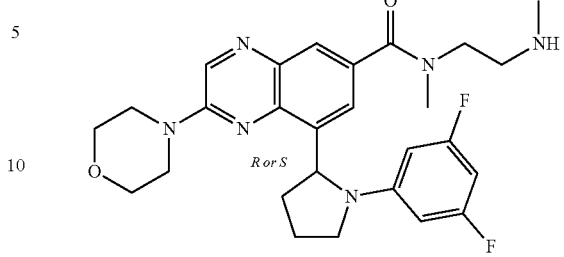

At 0° C., HCl (4M in 1,4-dioxane) (0.92 mL; 3.68 mmol) was added to a solution of intermediate 50 (450 mg; 0.74 mmol) in DCM (5 mL). The reaction mixture was stirred at 0° C. for 1 h and at rt for 3 h. The solution was poured into ice-water and extracted with EtOAc. The organic layer was dried over $MgSO_4$, filtered and the solvent was evaporated. The residue (265 mg) was purified by chromatography over silica gel (irregular 15-40 μm; 24 g; mobile phase: 60% heptane, 5% MeOH, 35% EtOAc). The pure fractions were collected and the solvent was evaporated to give 132 mg (35%, yellow foam) of 18. M.P.: 80° C. (gum, K).

Preparation of Compound 72:

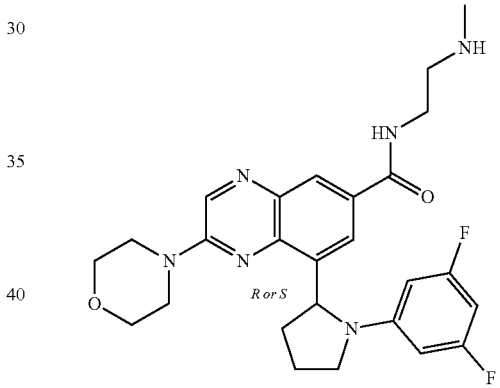

Compound 72 was prepared according to an analogous procedure as described for the synthesis of compound 17, using intermediate 85 as starting material (freeze-dried: 72 mg, 45%, yellow powder). M.P.: 80° C. (gum, K).

Preparation Compound 93:

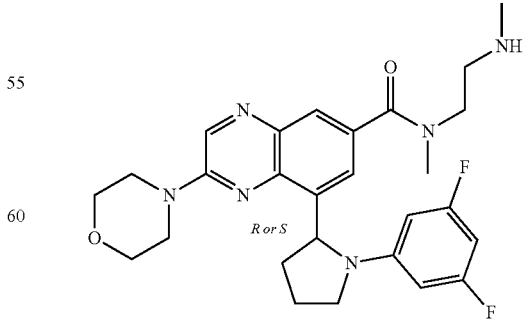

Compound 93 was prepared according to an analogous procedure as described for the synthesis of compound 18, using intermediate 103 as starting materials (32 mg, 14%, yellow foam). M.P.: 80° C. (gum, K).

Preparation Compound 122:

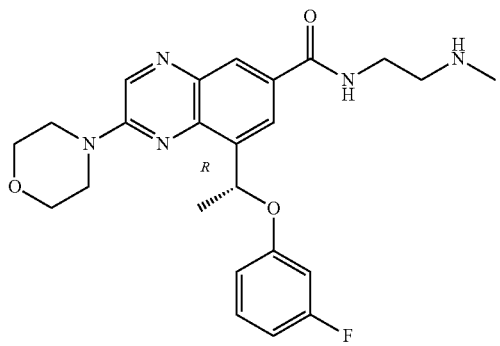

HCl (3M in cyclopentyl methyl ether) (0.3 mL; 0.9 mmol) was added to a solution of intermediate 118a (163 mg; 0.29 mmol) in 1,4-dioxane (3 mL). The reaction mixture was stirred at 50° C. for 2 h30. Then, more HCl (3M in cyclopentyl methyl ether) (0.3 mL; 0.9 mmol) was added and the reaction mixture was heated at 50° C. for 3 h. Water was added and the mixture was slowly basified with NaHCO₃ (solid). The layers were separated and the aqueous layer was extracted with DCM (2×) and DCM/MeOH (9/1) (2×). The combined organic layers were dried over MgSO₄, filtered and the solvent was evaporated. The residue (136 mg, orange oil) was purified by chromatography over silica gel (irregular SiOH; 15-40 μm; 4 g; gradient: from 97% DCM, 3% (MeOH/NH₄OH: 95/5) to 85% DCM, 15% (MeOH/NH₄OH: 95/5)). The pure fractions were collected and the solvent was evaporated. The residue (72 mg, pale yellow oil) was purified by reverse phase (X-Bridge-C18 5 μm 30*150 mm; gradient: from 75% (aq. NH₄HCO₃ 0.5%), 25% ACN to 35% (aq. NH₄HCO₃ 0.5%), 65% ACN). The pure fractions were collected and the solvent was evaporated to give 37 mg (28%, yellow foam) of compound 122.

Preparation Compound 123:

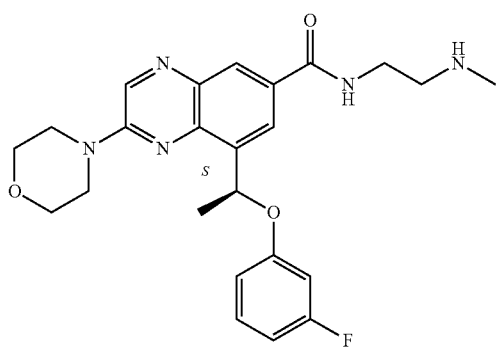

Compound 123 was prepared according to an analogous procedure as described for the synthesis of compound 122, using intermediate 118b as starting material (30 mg, 21%, pale yellow foam). M.P.: 80° C. (gum, K).

Preparation Compound 130:

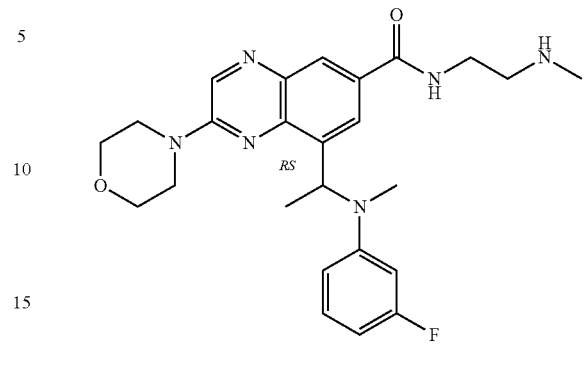

Compound 130 was prepared according to an analogous procedure as described for the synthesis of compound 17, using intermediate 122 as starting material (75 mg, 28%). M.P.: 159° C. (DSC).

Preparation Compound 132:

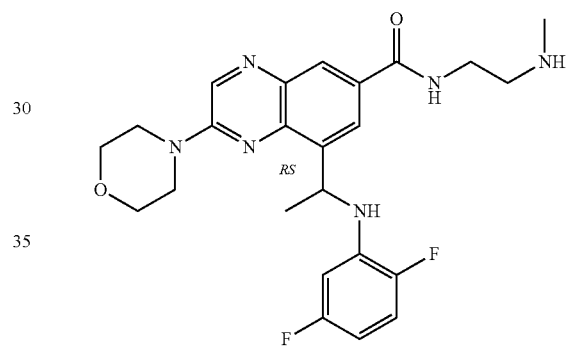

Compound 132 was prepared according to an analogous procedure as described for the synthesis of compound 17, using intermediate 125 as starting material (120 mg, 36%). M.P.: 80° C. (gum, K).

Preparation Compound 137:

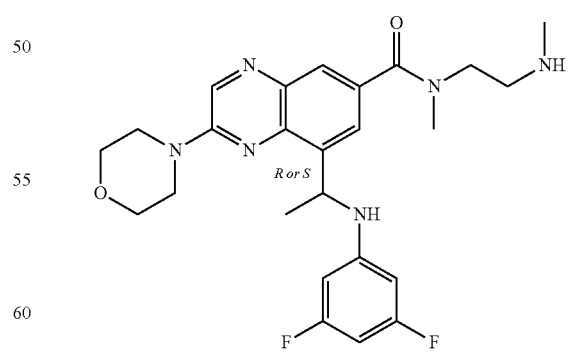

Compound 137 was prepared according to an analogous procedure as described for the synthesis of compound 17, using intermediate 129 as starting material (27 mg, 36%). M.P.: 80° C. (gum, K).

Preparation Compound 138:

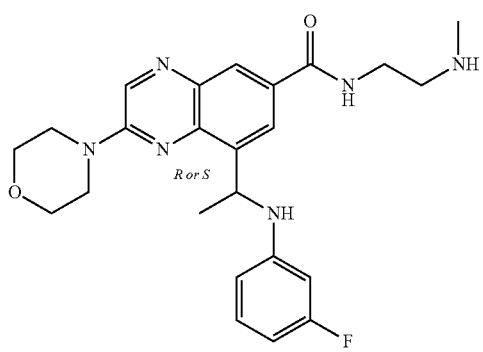 [SMILES: CNCCNC(=O)c1cc(C(C)Nc2cccc(F)c2)c2nc(N3CCOCC3)cnc2c1]

Compound 138 was prepared according to an analogous procedure as described for the synthesis of compound 122, using intermediate 132b as starting material (41 mg, 56%, yellow foam).

Preparation Compound 139:

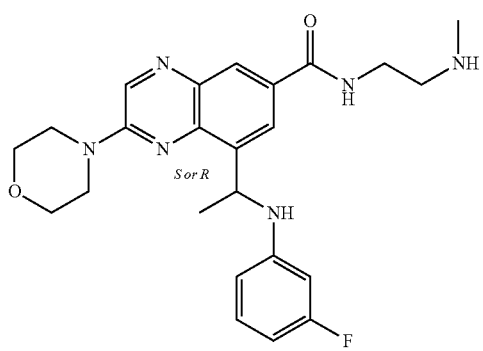 [SMILES: CNCCNC(=O)c1cc(C(C)Nc2cccc(F)c2)c2nc(N3CCOCC3)cnc2c1]

Compound 139 was prepared according to an analogous procedure as described for the synthesis of compound 122, using intermediate 132c as starting material (37 mg, 50%, yellow foam).

Preparation Compound 147:

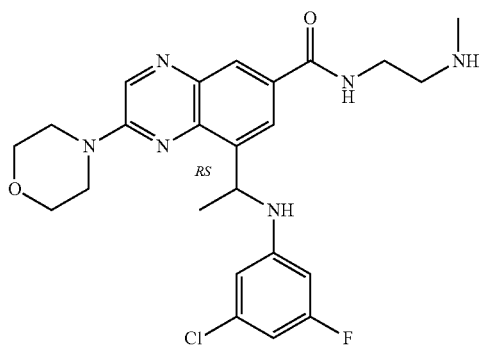 [SMILES: CNCCNC(=O)c1cc(C(C)Nc2cc(F)cc(Cl)c2)c2nc(N3CCOCC3)cnc2c1]

Compound 147 was prepared according to an analogous procedure as described for the synthesis of compound 17, using intermediate 135 as starting material (40 mg, 20%). M.P.: 80° C. (gum, K).

Preparation Compound 152:

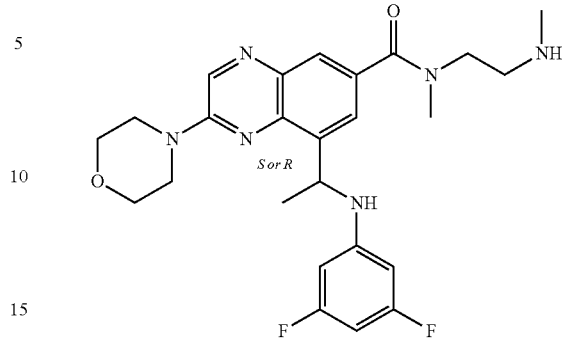

Compound 152 was prepared according to an analogous procedure as described for the synthesis of compound 17, using intermediate 136 as starting material (40 mg, 24%). M.P.: 80° C. (gum, K).

Preparation Compound 165:

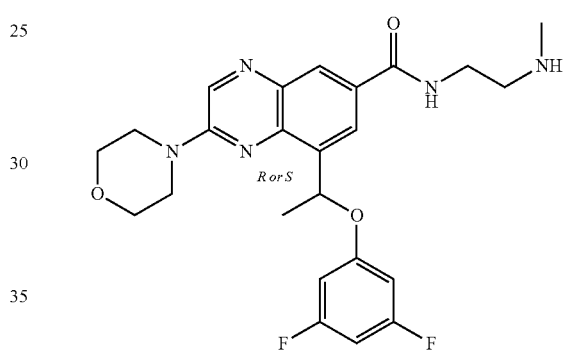

HCl (4M in 1,4-dioxane) (0.75 mL; 3.01 mmol) was added to a solution of intermediate 144 (297 mg; 0.52 mmol) in 1,4-dioxane (5 mL). The reaction mixture was stirred at 50° C. for 2 h30. Water was added and the mixture was slowly basified with 10% aqueous solution of $K_2CO_3$. The aqueous layer was extracted with EtOAc. The combined organic layers were dried over $MgSO_4$, filtered and the solvent was evaporated. The residue (210 mg) was purified by chromatography over silica gel (40 g; mobile phase: from 90% DCM, 10% MeOH, 0.5% $NH_4OH$ to 85% DCM, 14% MeOH, 1% $NH_4OH$). The pure fractions were collected and the solvent was evaporated to give 130 mg (53%) of compound 165. M.P.: 80° C. (gum, K).

Preparation Compound 166:

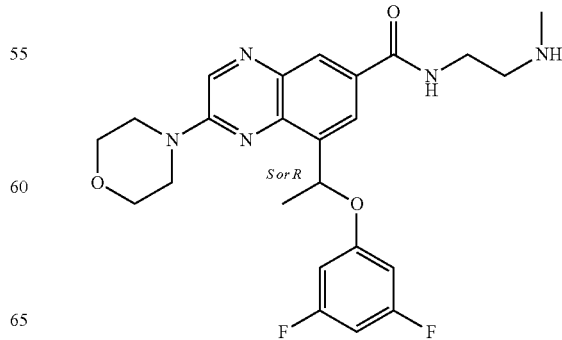

Compound 166 was prepared according to an analogous procedure as described for the synthesis of compound 165, using intermediate 145 as starting material (120 mg, 43%). M.P.: 80° C. (gum, K).

Preparation Compound 174:

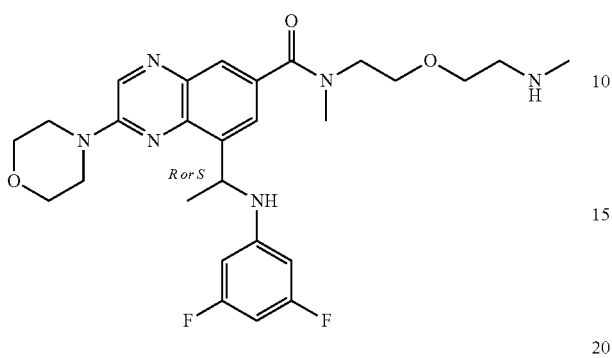

Compound 174 was prepared according to an analogous procedure as described for the synthesis of compound 165, using intermediate 148b as starting material (42 mg, 49%). M.P.: 80° C. (gum, K).

Preparation Compound 175:

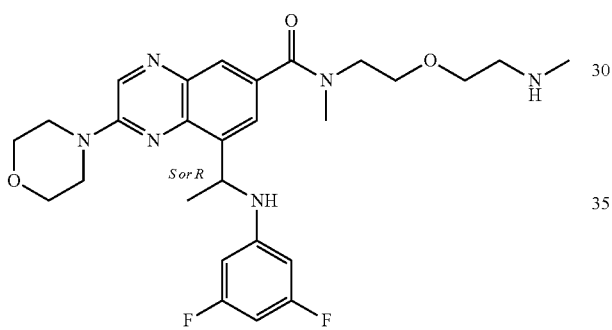

Compound 175 was prepared according to an analogous procedure as described for the synthesis of compound 165, using intermediate 148c as starting material (38 mg, 45%). M.P.: 80° C. (gum, K).

Preparation Compound 176:

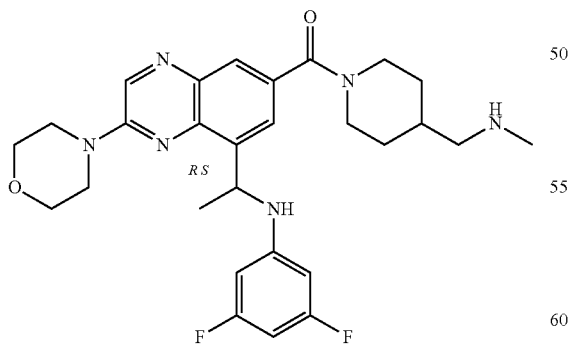

Compound 176 was prepared according to an analogous procedure as described for the synthesis of compound 165, using intermediate 149 as starting material (98 mg, 32%). The reaction mixture was stirred at 0° C. for 1 and at rt for 3 h.

Preparation Compound 224:

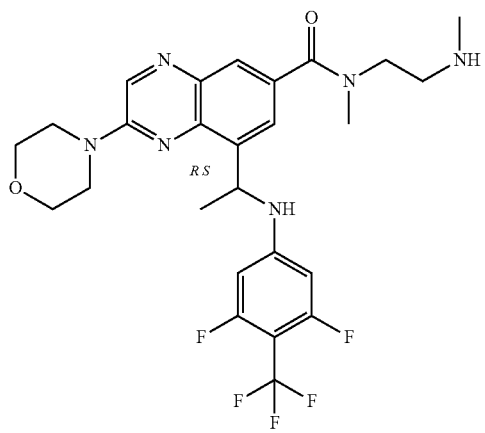 [SMILES: CNCCN(C)C(=O)c1cc(C(C)Nc2cc(F)c(C(F)(F)F)c(F)c2)c2nc(N3CCOCC3)cnc2c1]

Compound 224 was prepared according to an analogous procedure as described for the synthesis of compound 17, using intermediate 160 as starting material (crystallized from diethylether; 275 mg, 65%). M.P.: 163° C. (DSC).

Preparation of Compound 282, Compound 282a and Compound 282b compound 282

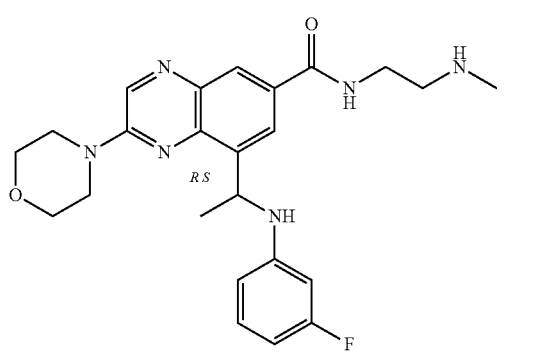

compound 282a

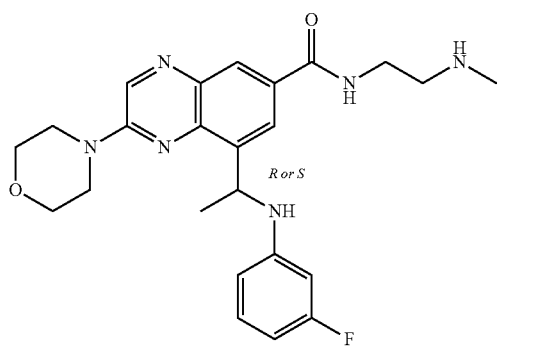

compound 282b

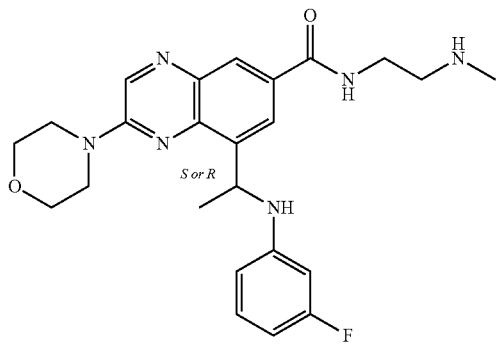

Compound 282 was prepared according to an analogous procedure as described for the synthesis of compound 17 using intermediate 187 as starting material. Crystallization from MeOH and Et$_2$O gave 520 mg of compound 282 (54%), MP: 100° C., gum, K). Compound 282 (440 mg) was purified by chiral SFC (CHIRALPAK AD-H 5 μm 250×20 mm; mobile phase: 50% CO$_2$, 50% EtOH (0.3% iPrNH$_2$)). The pure fractions were collected and the solvent was evaporated to give 189 mg of one compound which was crystallized from Et$_2$O giving 120 mg (12%) of compound 282a (MP: 100° C., gum, K) and 195 mg of another compound which was crystallized from Et$_2$O giving 116 mg (12%) of compound 182b (MP: 100° C., gum, K).

Preparation of Compound 296, Compound 296a and Compound 296b compound 296b

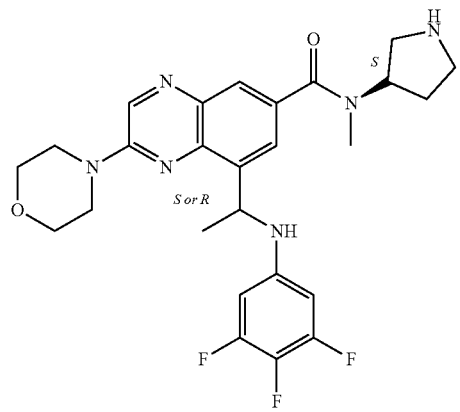

Compound 296 was prepared according to an analogous procedure as described for the synthesis of compound 17 using intermediate 188 as starting material (725 mg, 87%). Compound 296 (700 mg) was purified by chiral SFC (CHIRALCEL OJ-H 5 μm 250×20 mm; mobile phase: 88.2% CO$_2$, 11.8% MeOH (0.3% iPrNH$_2$)). The pure fractions were collected and the solvent was evaporated to give 219 mg of one compound which was crystallized from pentane giving 180 mg (21%) of compound 296a and 214 mg of other compound which was crystallized from pentane giving 161 mg (19%) of compound 296b.

Preparation of Compound 297, Compound 297a and Compound 297b compound 296

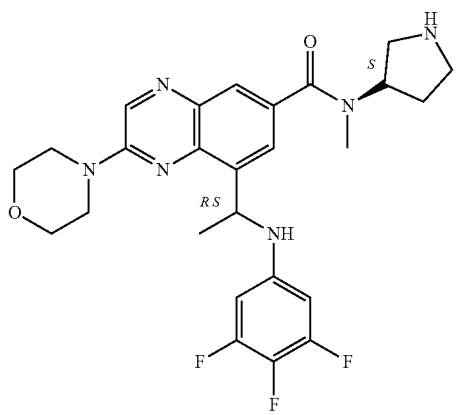

compound 297

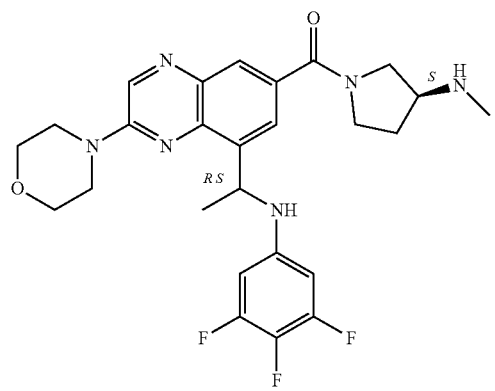

compound 296a

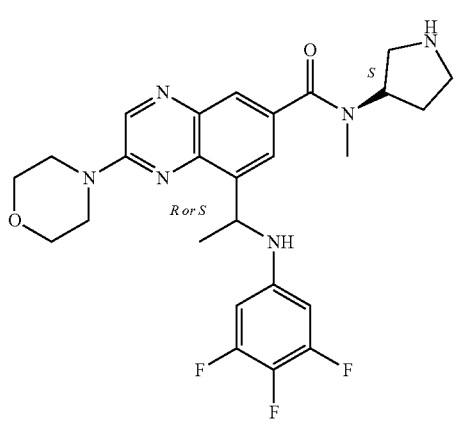

compound 297a compound 297b

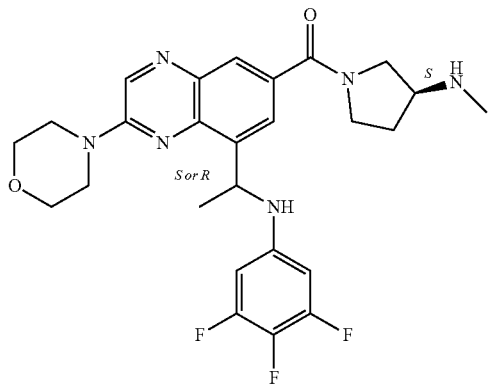

Compound 297 was prepared according to an analogous procedure as described for the synthesis of compound 17 using intermediate 189 as starting material (465 mg, 73%). Compound 297 was purified by chiral SFC (CHIRALPAK AD-H 5 µm 250×20 mm; mobile phase: 70% $CO_2$, 30% iPrOH (0.3% iPrNH$_2$)). The pure fractions were collected and the solvent was evaporated to give 179 mg of one compound which was crystallized from DIPE giving 136 mg (21%) of compound 297a and 136 mg of other compound which was crystallized from DIPE giving 103 mg (16%) of compound 297b.

Preparation of Compound 315a

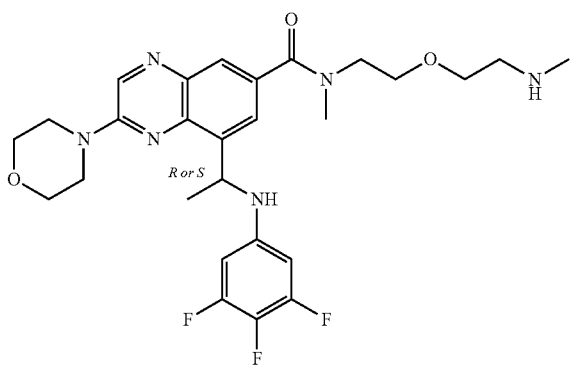 [SMILES: CNCCOCCN(C)C(=O)c1cc(C(C)Nc2cc(F)c(F)c(F)c2)c2nc(N3CCOCC3)cnc2c1]

Compound 315a was prepared according to an analogous procedure as described for the synthesis of compound 17 using intermediate 195a as starting material (84 mg, 44%, MP: 86° C., gum, K).

Preparation of Compound 315b

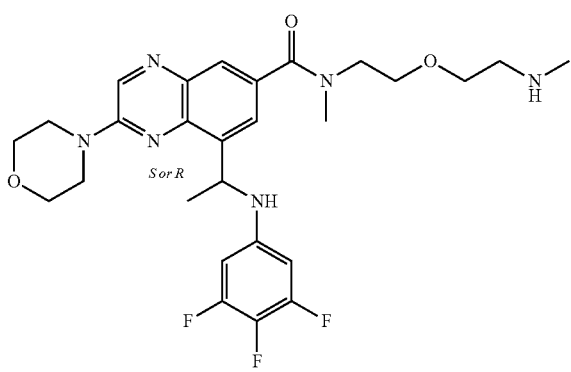 [SMILES: CNCCOCCN(C)C(=O)c1cc(C(C)Nc2cc(F)c(F)c(F)c2)c2nc(N3CCOCC3)cnc2c1]

Compound 315b was prepared according to an analogous procedure as described for the synthesis of compound 17, using intermediate 195b as starting material (96 mg, 38%, M.P.: 90° C. (gum, K).

Preparation of Compound 317

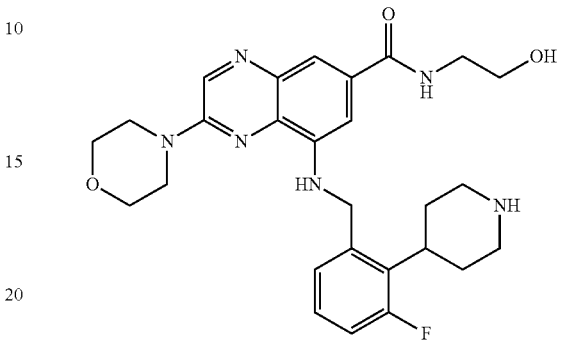

Trifluoroacetic acid (1.028 mL, 13.8 mmol) was added dropwise to a solution of intermediate 205 (0.56 g, 0.92 mmol) in DCM (15 mL) at 0° C. The solution was allowed to warm to room temperature and was stirred at room temperature overnight. The mixture was poured into water, basified with an aqueous solution of $K_2CO_3$ 10% and the compound was extracted with DCM. The organic layer was separated, dried over $MgSO_4$, filtered and concentrated. The residue (0.39 g) was purified via silica gel chromatography (Stationary phase: irregular bare silica 40 g, Mobile phase: 90% DCM, 10% MeOH (+10% $NH_4OH$)). The pure fractions were collected and the solvent was evaporated until dryness and the resulting residue was crystallized from DIPE. The precipitate was filtered off and dried in vacuo to give 107 mg (23%) of compound 317. M.P: 167° C. (DSC).

Preparation of Compound 318

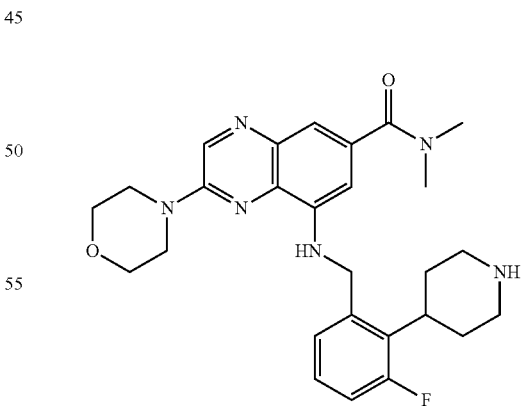

Compound 318 was prepared according to an analogous procedure as described for the synthesis of compound 317 using intermediate 203 as starting material (75 mg, 30%).

Preparation of Compound 322a:

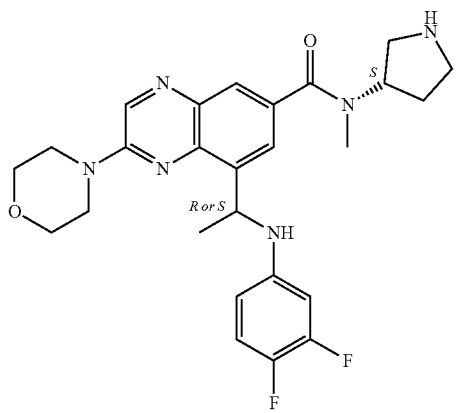

Compound 322a was prepared according to an analogous procedure as described for the synthesis of compound 17 using intermediate 206a as starting material (152 mg, 39%, MP: 122° C., K).

Preparation of Compound 322b:

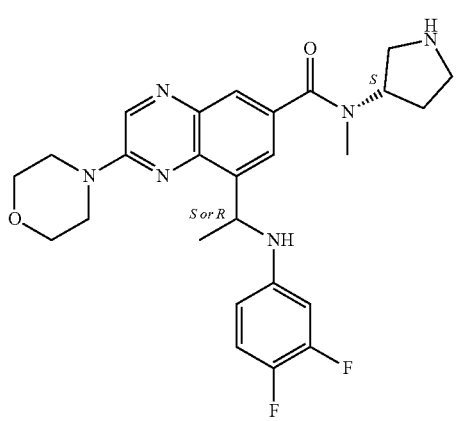

Compound 322b was prepared according to an analogous procedure as described for the synthesis of compound 17 using intermediate 206b as starting material (228 mg, 55%, MP: 80° C., K).

Preparation of Compound 323a:

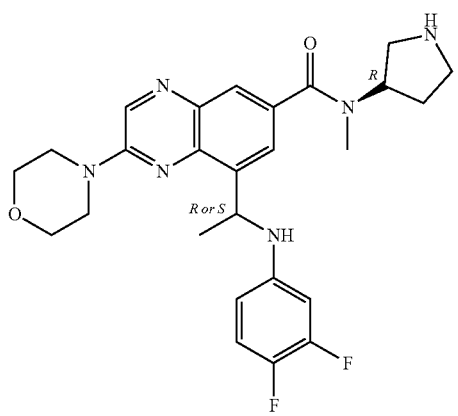

Compound 323a was prepared according to an analogous procedure as described for the synthesis of compound 17 using intermediate 207a as starting material (246 mg, 62%, MP: 126° C., K).

Preparation of Compound 323b:

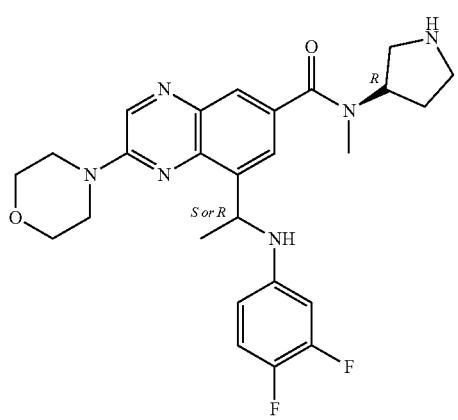

Compound 323b was prepared according to an analogous procedure as described for the synthesis of compound 17 using intermediate 207b as starting material (267 mg, 64%, MP: 130° C., K).

Preparation of Compound 324a:

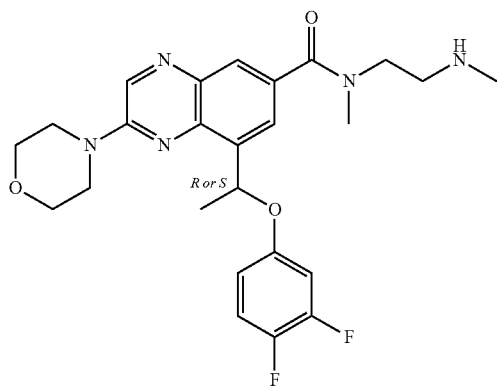 [SMILES: CNCCN(C)C(=O)c1cc(C(C)Oc2ccc(F)c(F)c2)c2nc(N3CCOCC3)cnc2c1]

Compound 324a was prepared according to an analogous procedure as described for the synthesis of compound 17 using intermediate 208a as starting material (158 mg, 37%, MP: 60° C., K).

Preparation of Compound 324b:

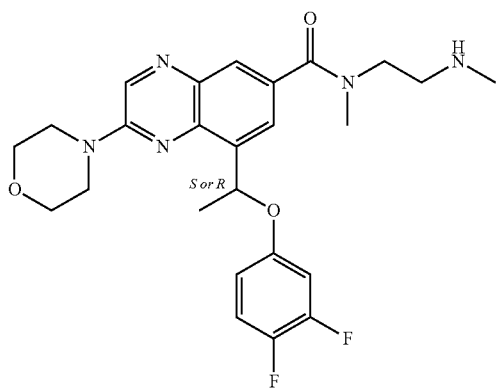 [SMILES: CNCCN(C)C(=O)c1cc(C(C)Oc2ccc(F)c(F)c2)c2nc(N3CCOCC3)cnc2c1]

Compound 324b was prepared according to an analogous procedure as described for the synthesis of compound 17 using intermediate 208b as starting material (100 mg, 23%, MP: 60° C., K).

Preparation of Compound 325a:

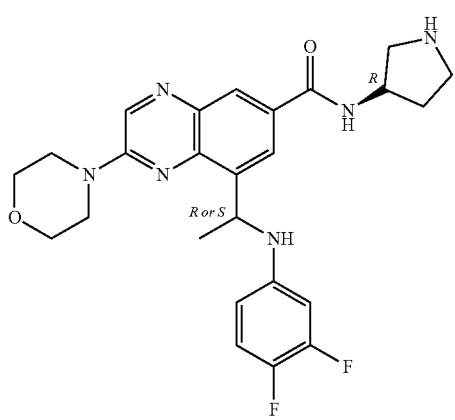

Compound 325a was prepared according to an analogous procedure as described for the synthesis of compound 17 using intermediate 209a as starting material (123 mg, 37%, MP: 144° C., K).

Preparation of Compound 325b:

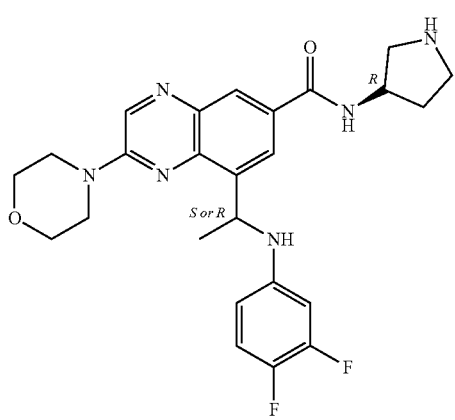

Compound 325b was prepared according to an analogous procedure as described for the synthesis of compound 17 using intermediate 209b as starting material (162 mg, 47%, MP: 138° C., K).

Preparation of Compound 329a:

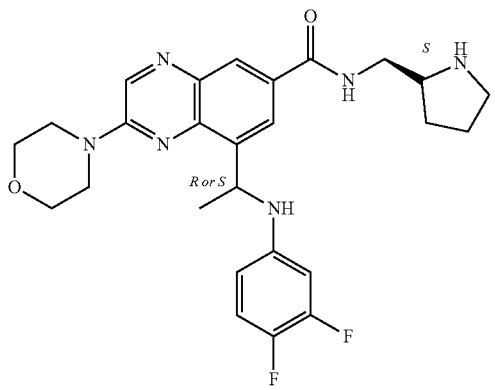

Compound 329a was prepared according to an analogous procedure as described for the synthesis of compound 17 using intermediate 213a as starting material (175 mg, 50%, MP: 121° C., K).

Preparation of Compound 329b:

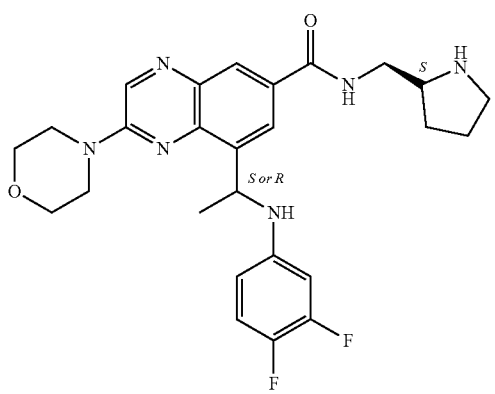

Compound 329b was prepared according to an analogous procedure as described for the synthesis of compound 17 using intermediate 213b as starting material (139 mg, 38%, MP: 124° C., K).

Preparation of Compound 335a:

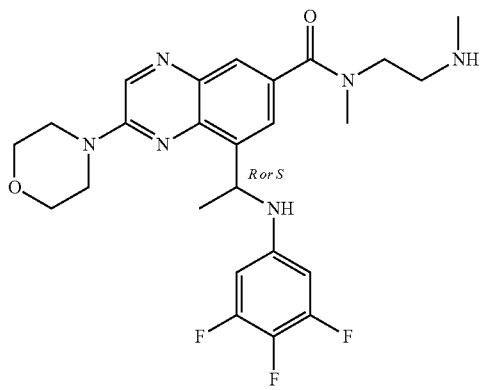 [SMILES: CNCCN(C)C(=O)c1cc(C(C)Nc2cc(F)c(F)c(F)c2)c2nc(N3CCOCC3)cnc2c1]

Compound 335a was prepared according to an analogous procedure as described for the synthesis of compound 17, using intermediate 215a as starting material (75 mg, 45%).

Preparation of Compound 335b:

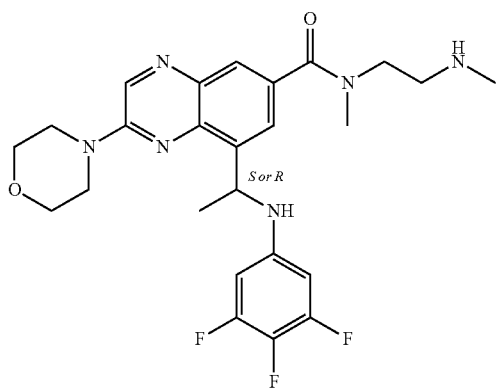 [SMILES: CNCCN(C)C(=O)c1cc(C(C)Nc2cc(F)c(F)c(F)c2)c2nc(N3CCOCC3)cnc2c1]

Compound 335b was prepared according to an analogous procedure as described for the synthesis of compound 17, using intermediate 315b (69 mg, 35%). M.P.: 80° C. (gum, K).

Preparation of Compound 340:

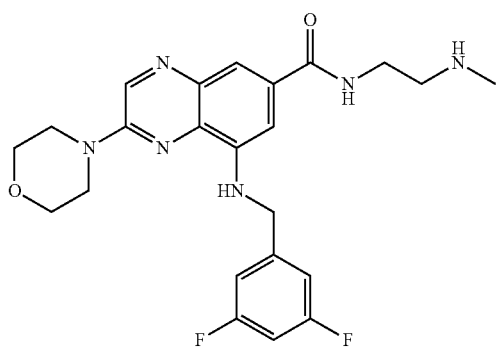 [SMILES: CNCCNC(=O)c1cc(NCc2cc(F)cc(F)c2)c2nc(N3CCOCC3)cnc2c1]

Compound 340 was prepared according to an analogous procedure as described for the synthesis of compound 165, using intermediate 218 as starting material (133 mg, 52%). M.P.: 180° C., DSC).

Preparation of Compound 344a:

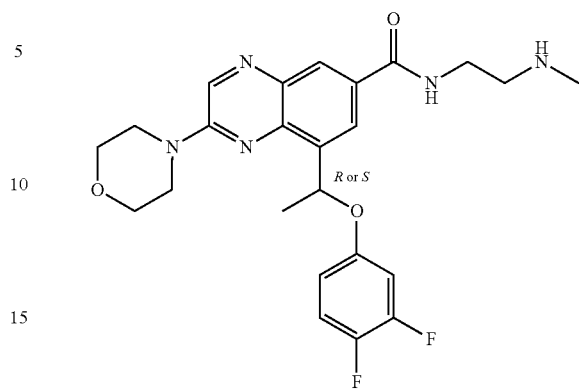

Compound 344a was prepared according to an analogous procedure as described for the synthesis of compound 17, using intermediate 220a as starting material (234 mg, 39%). M.P.: 75° C., gum K).

Preparation of Compound 344b:

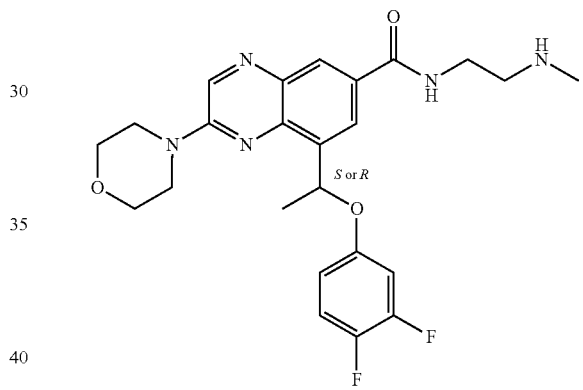

Compound 344b were prepared according to an analogous procedure as described for the synthesis of compound 17, using intermediate 220b as starting material (258 mg, 44%). M.P.: 75° C., gum K.

Preparation of Compound 345, Compound 345a and Compound 345b compound 345

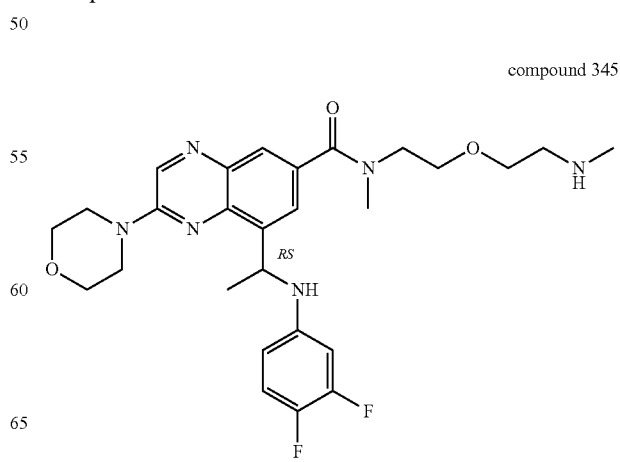

Preparation of Compound 352:

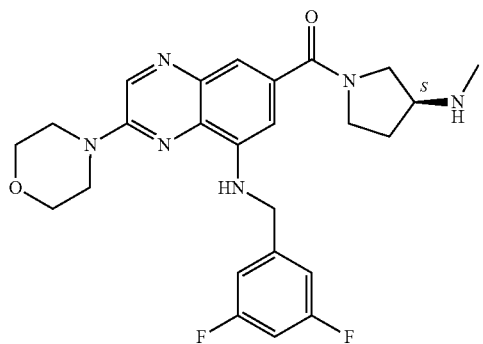

compound 345a

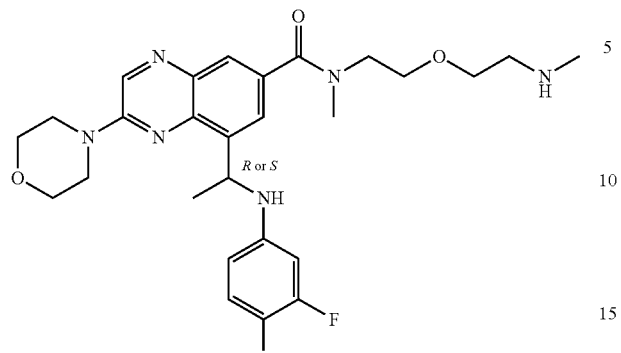

compound 345b

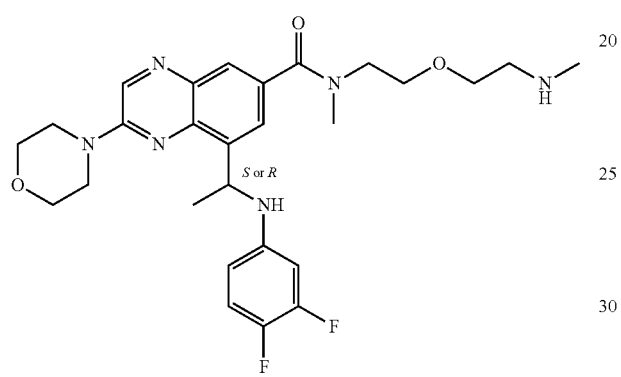

Compound 352 was prepared according to an analogous procedure as described for the synthesis of compound 17 using intermediate 223 as starting material (103 mg g; 32%).

Preparation of Compound 355:

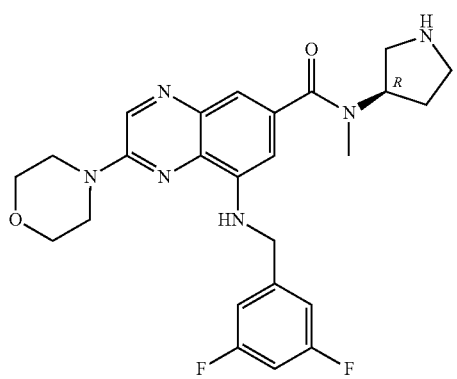

Compound 345 was prepared according to an analogous procedure as described for the synthesis of compound 17, using intermediate 221 as starting material (590 mg; 82%). The separation of the enantiomers from 590 mg compound 345 was performed via chiral SFC (Stationary phase: CHIRALPAK AD-H 5 μm 250×20 mm, Mobile phase: 70% $CO_2$, 30% EtOH). The pure fractions were collected and the solvent was evaporated affording 2 fractions which were respectively crystallized from pentane to give 153 mg (21%) compound 345a (M.P.: 80° C. (K)) and 127 mg (21%) of compound 345b (M.P.: 80° C. (K)).

Preparation of Compound 351:

Compound 355 was prepared according to an analogous procedure as described for the synthesis of compound 17 using intermediate 224 as starting material (179 mg, 28%). M.P.: gum (K)).

Preparation of Compound 356a:

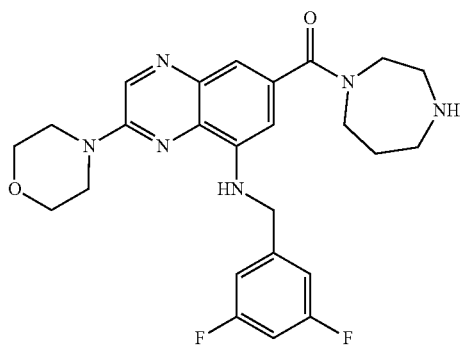

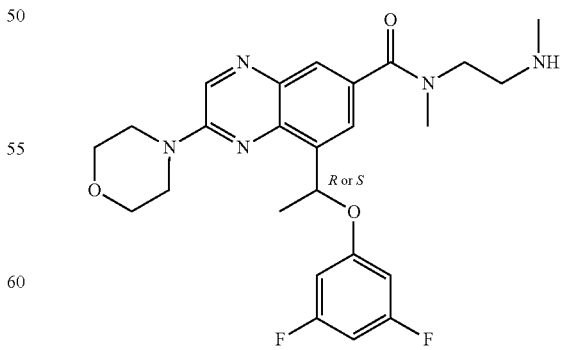

Compound 351 was prepared according to an analogous procedure as described for the synthesis of compound 17 using intermediate 222 as starting material (209 mg g; 29%).

Compound 356a was prepared according to an analogous procedure as described for the synthesis of compound 17 using intermediate 225a as starting material (24 mg, 67%).

Preparation of Compound 356b:

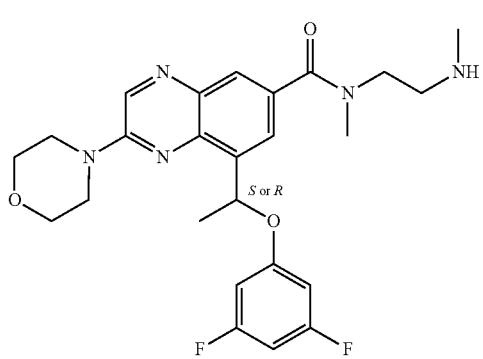 [SMILES: CNCCN(C)C(=O)c1cc(C(C)Oc2cc(F)cc(F)c2)c2nc(N3CCOCC3)cnc2c1]

Compound 356b was prepared according to an analogous procedure as described for the synthesis of compound 17, using intermediate 225b as starting material (26 mg, 70%).

Preparation of compound 359:

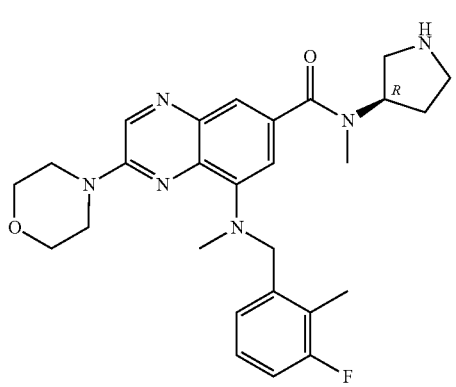

Compound 359 was prepared according to an analogous procedure as described for the synthesis of compound 17, using intermediate 226 as starting material (85 mg, 33%).

Preparation of Compound 362:

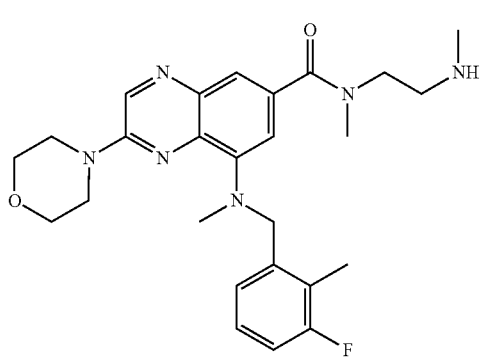 [SMILES: CNCCN(C)C(=O)c1cc(N(C)Cc2cccc(F)c2C)c2nc(N3CCOCC3)cnc2c1]

Compound 362 was prepared according to an analogous procedure as described for the synthesis of compound 17, using intermediate 227 as starting material (138 mg, 48%).

Preparation of Compound 365:

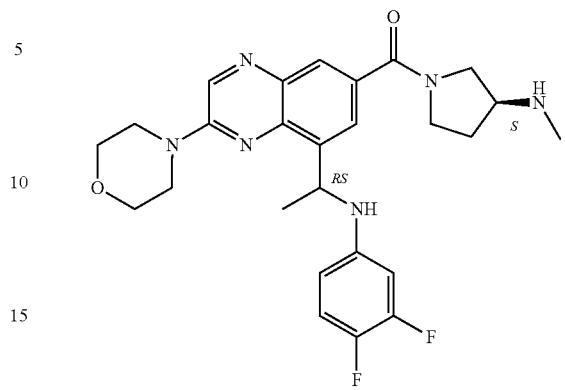

Compound 365 was prepared according to an analogous procedure as described for the synthesis of compound 17, using intermediate 228 as starting material (110 mg; 66%, M.P: 80° C. gum (K)).

Preparation of Compound 365 a:

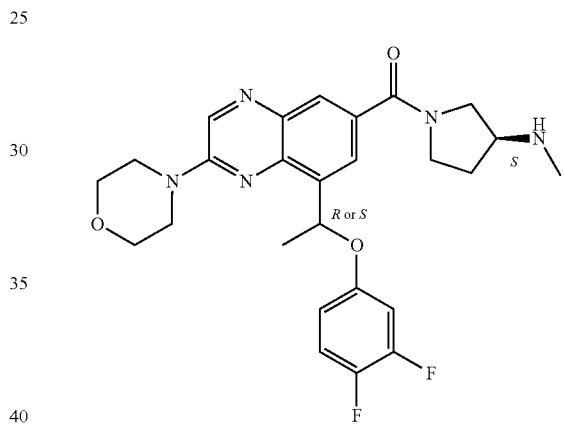

Compound 365a was prepared according to an analogous procedure as described for the synthesis of compound 17, using intermediate 228a as starting material (155 mg; 95%, M.P: 80° C. gum (K)).

Preparation of Compound 365b:

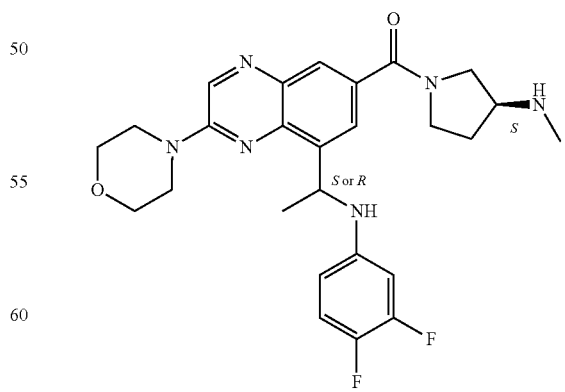

Compound 365b was prepared according to an analogous procedure as described for the synthesis of compound 17, using intermediate 228b as starting material (106 mg; 67%, M.P: 80° C. gum (K)).

Preparation of Compound 368:

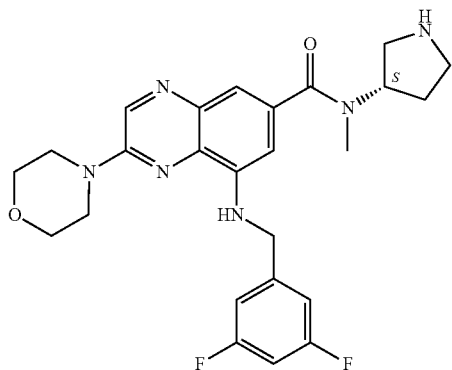

Compound 368 was prepared according to an analogous procedure as described for the synthesis of compound 17, using intermediate 229 as starting materials. (249 mg, 29%).

Preparation of Compound 370a:

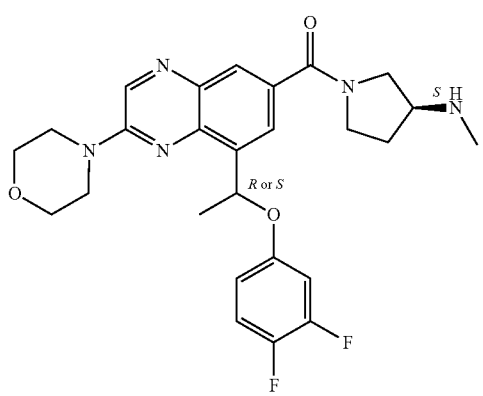

Compound 370a was prepared according to an analogous procedure as described for the synthesis of compound 17 using intermediate 230a as starting material (55 mg, 14%, M.P.: 128° C. (DSC).

Preparation of Compound 370b:

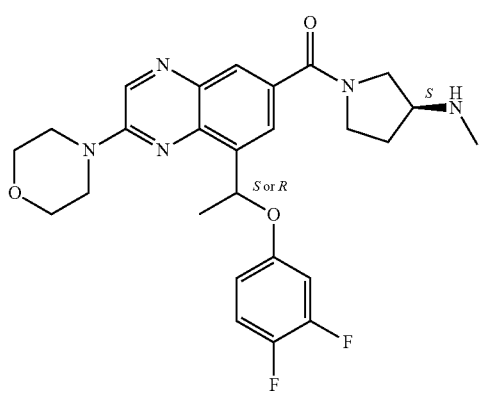

Compound 370b was prepared according to an analogous procedure as described for the synthesis of compound 17 using intermediate 270b as starting material (75 mg, 18%, M.P.: 80° C. (gum, K).

Preparation of Compound 371a:

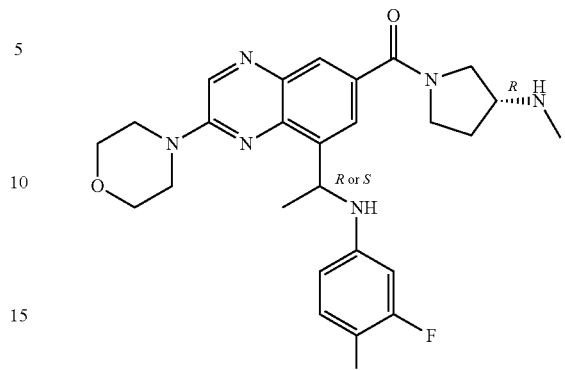

Compound 371a was prepared according to an analogous procedure as described for the synthesis of compound 17 using intermediate 231a as starting material (174 mg, 43%, M.P.: 114° C., (K)).

Preparation of Compound 371b:

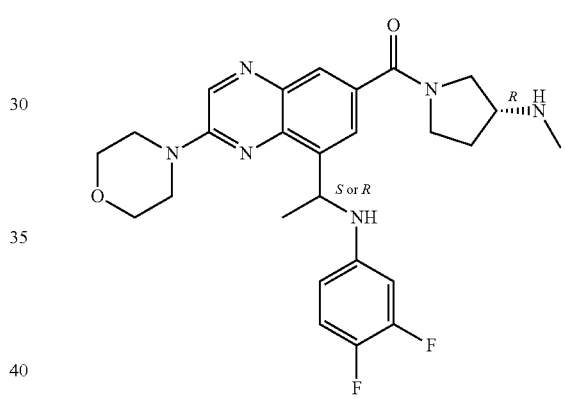

Compound 371b was prepared according to an analogous procedure as described for the synthesis of compound 17 using intermediate 271b as starting material (114 mg, 31%, M.P.: 107° C., (K)).

Preparation of Intermediate 372:

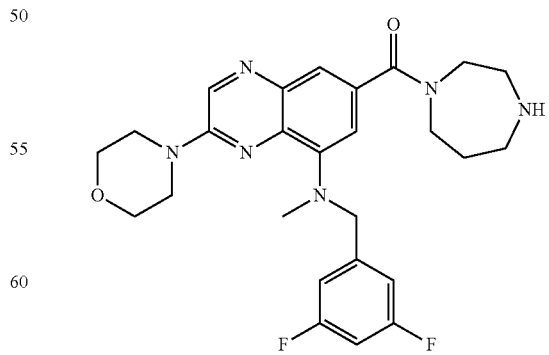

Compound 372 was prepared according to an analogous procedure as described for the synthesis of compound 17, using intermediate 232 as starting material (130 mg; 68%).

Preparation of Compound 374a:

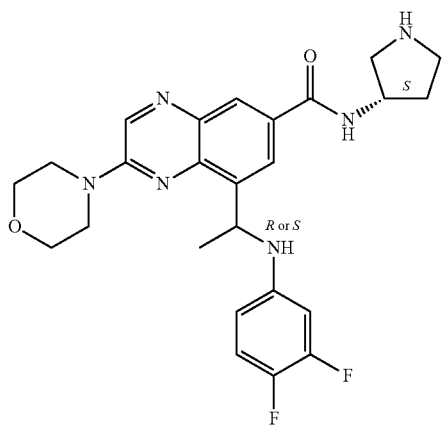

Compound 374a was prepared according to an analogous procedure as described for the synthesis of compound 17 using intermediate 233a as starting material (180 mg, 61%, M.P.: 132° C. (K)).

Preparation of Compound 374b:

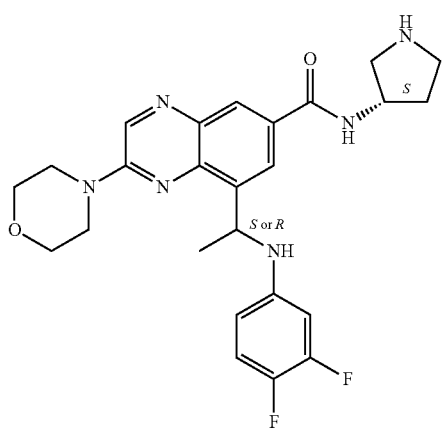

Compound 374b was prepared according to an analogous procedure as described for the synthesis of compound 17 using intermediate 233b as starting material (132 mg, 52%, M.P.: 130° C. (K)).

Preparation of Compound 376:

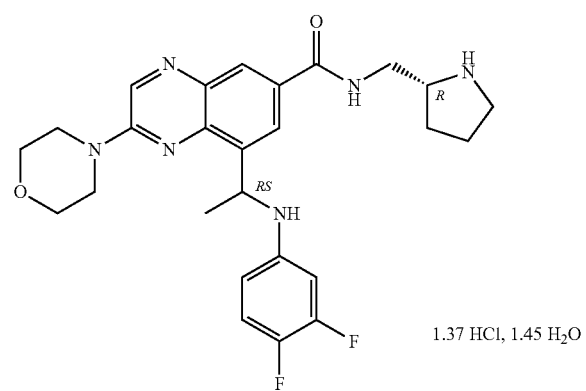

1.37 HCl, 1.45 $H_2O$

Compound 376 was prepared according to an analogous procedure as described for the synthesis of compound 17 using intermediate 234 as starting material. (26 mg, 4%, M.P.: gum at 130° C., (K))

Preparation of Compound 379a

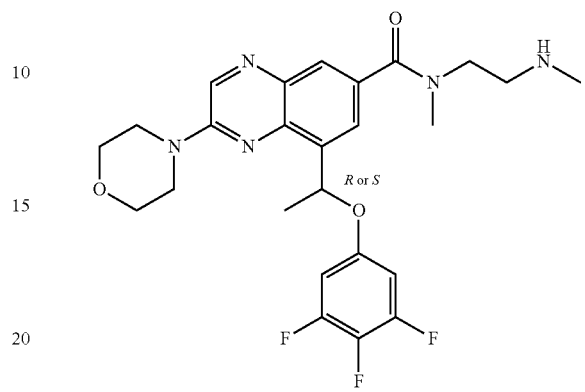

Compound 379a according to an analogous procedure as described for the synthesis of compound 17 using intermediate 235a as starting material (41 mg, 31%).

Preparation Compound 379b:

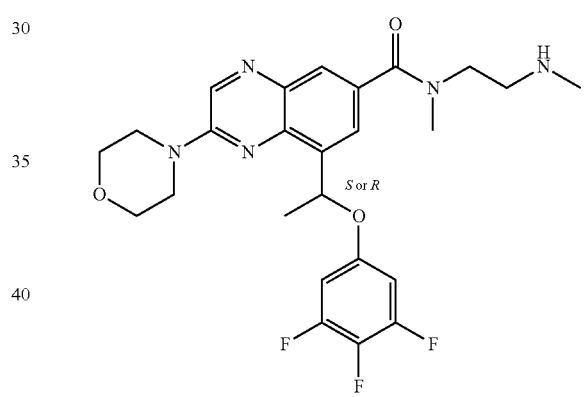

Compound 379b was prepared according to an analogous procedure as described for the synthesis of compound 17 using intermediate 235b as starting material (33 mg, 26%).

Preparation of Compound 380a:

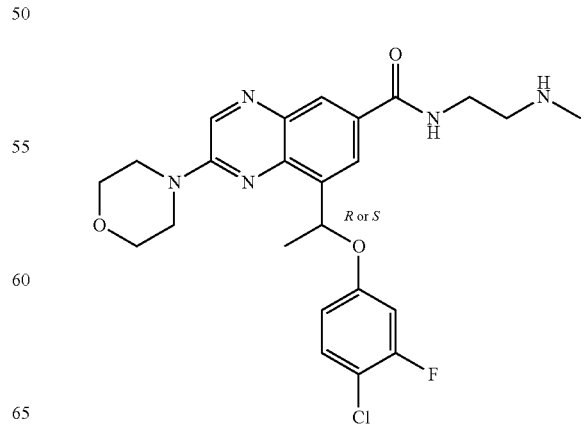

To a solution of intermediate 236a (105 mg; 0.179 mmol) in MeTHF (1.80 mL) was added HCl (357 μL; 1.07 mmol, 3M in cyclopentylmethyl ether). The solution was stirred at rt over the weekend then slowly basified with a saturated aqueous solution of NaHCO₃ and DCM was added. The organic layer was separated and the aqueous layer was extracted with DCM (2×). The combined organic layers were dried over MgSO₄, filtered off and evaporated. The crude (69 mg) was purified by silica gel chromatography (Irregular SiOH, 15-40 μm, 4 g, Grace, liquid loading (DCM), mobile phase gradient: from DCM 100% to DCM 90%, MeOH/aq. NH₃ (95:5) 10%) to give 40 mg of a pale yellow oil which was solubilized in ACN (1 mL), extended with water (9 mL) and freeze-dried to give 38 mg (44%) of compound 380a as a yellow fluffy solid.

Preparation of Compound 380b:

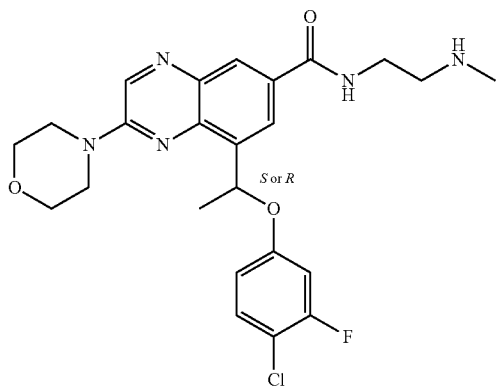

Compound 380b was prepared according to an analogous procedure as described for the synthesis of compound 380a using intermediate 236b as starting material. (26 mg, 27%).

Preparation of Compound 385:

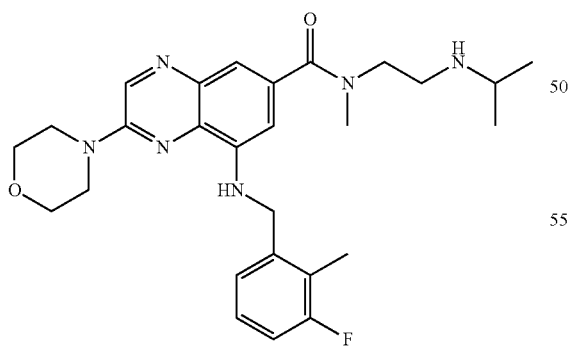

Compound 385 was prepared according to an analogous procedure as described for the synthesis of compound 17 using intermediate 240 as starting material (148 mg, 78%).

Preparation of Compound 386:

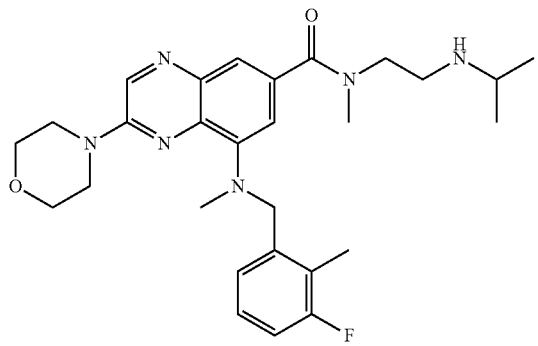 [SMILES: Cc1c(F)cccc1CN(C)c1cc(C(=O)N(C)CCNC(C)C)cc2ncc(N3CCOCC3)nc12]

Compound 386 was prepared according to an analogous procedure as described for the synthesis of compound 17 using intermediate 241 as starting material (11 mg, 62%)

Preparation of Intermediate 387:

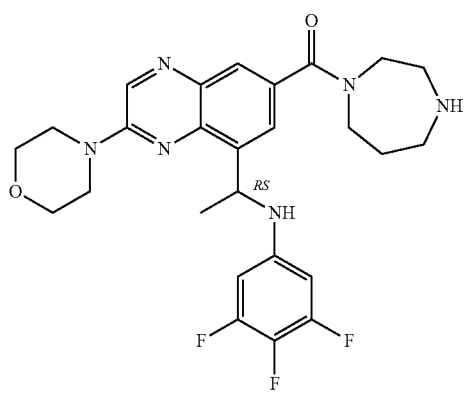 [SMILES: CC(Nc1cc(F)c(F)c(F)c1)c1cc(C(=O)N2CCCNCC2)cc2ncc(N3CCOCC3)nc12]

Compound 387 was prepared according to an analogous procedure as described for the synthesis of compound 17, using intermediate 242 as starting material (300 mg; 77%).

Preparation of Compound 389:

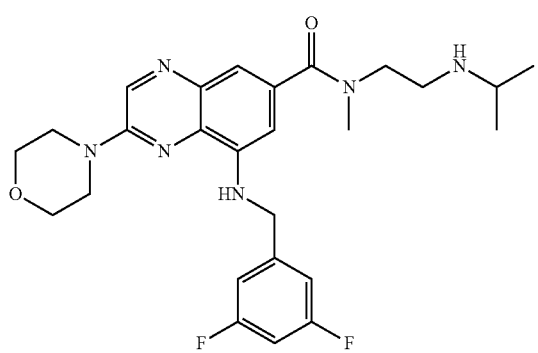 [SMILES: CC(C)NCCN(C)C(=O)c1cc(NCc2cc(F)cc(F)c2)c2nc(N3CCOCC3)cnc2c1]

Compound 389 was prepared according to an analogous procedure as described for the synthesis of compound 17, using intermediate 243 as starting material (90 mg, 71%).

Preparation of Compound 390:

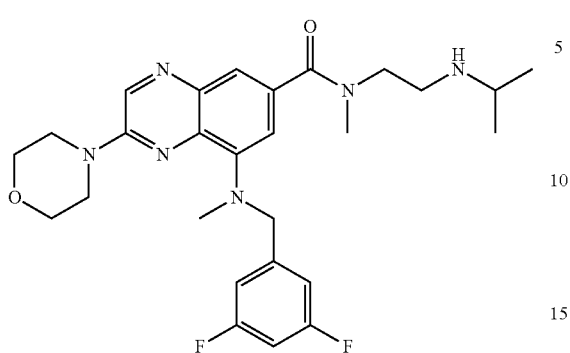

Compound 390 was prepared according to an analogous procedure as described for the synthesis of compound 17 using intermediate 244 as starting material (21 mg, 60%).

Preparation of Compound 122a:

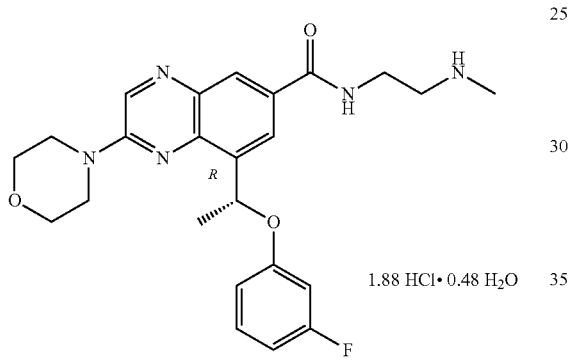

1.88 HCl • 0.48 H$_2$O

Compound 122a was prepared according to an analogous procedure as described for the synthesis of compound 17 using intermediate 118a as starting material (3.85 g, 34%, MP: 116° C. (DSC)).

Preparation of Compound 123 a:

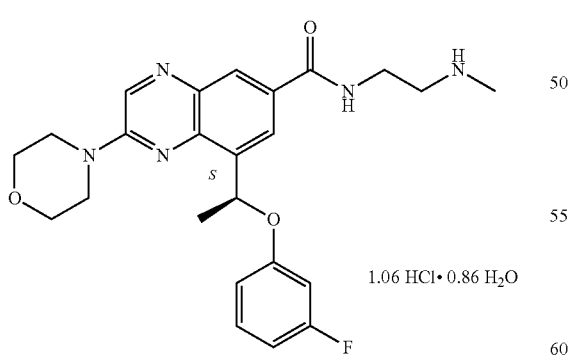

1.06 HCl • 0.86 H$_2$O

Compound 123a was prepared according to an analogous procedure as described for the synthesis of compound 17 using intermediate 118b as starting material (73 mg, 9%, MP: 130° C. (DSC)).

Preparation of Compound 404a:

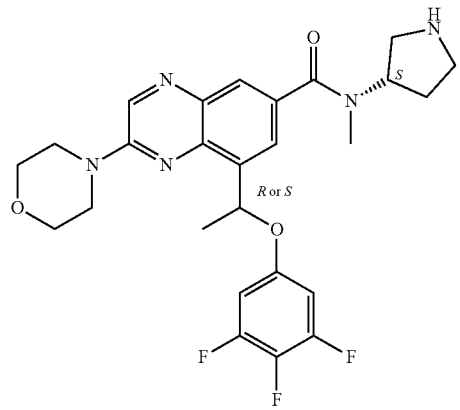

Compound 404a was prepared according to an analogous procedure as described for the synthesis of compound 317 using intermediate 346a as starting material (99 mg, 66%).

Preparation of Compound 404b:

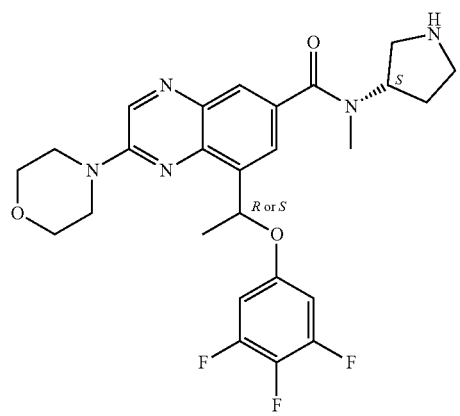

Compound 404b was prepared according to an analogous procedure as described for the synthesis of compound 317 using intermediate 346b as starting material (122 mg, 65%).

Preparation of Compound 405 a:

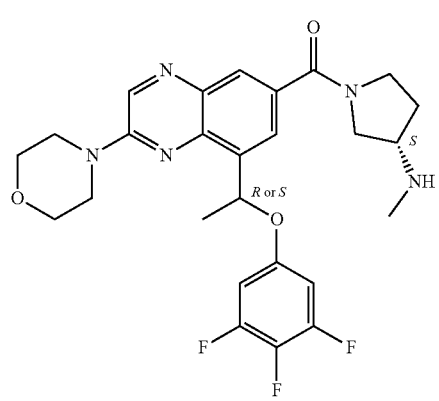

was prepared according to an analogous procedure as described for the synthesis of compound 317 using intermediate 347a as starting material (110 mg, 70%).

Preparation of Compound 405b:

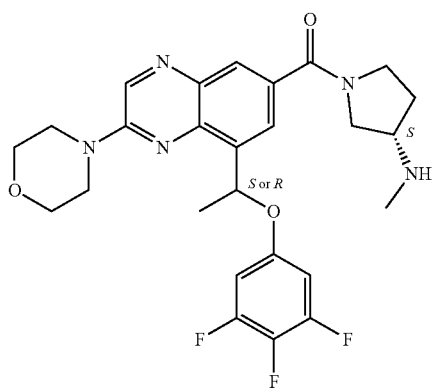

Compound 405b was prepared according to an analogous procedure as described for the synthesis of compound 317 using intermediate 347b as starting material (126 mg, 72%).

Preparation of Compound 406a:

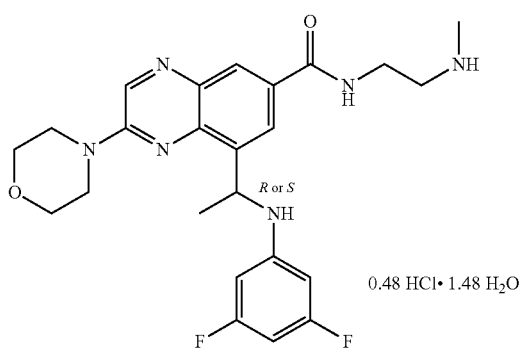 [SMILES: CNCCNC(=O)c1cc(C(C)Nc2cc(F)cc(F)c2)c2nc(N3CCOCC3)cnc2c1]

Compound 406a was prepared according to an analogous procedure as described for the synthesis of compound 17 using intermediate 348a as starting material (115 mg, 23%, gums at 80° C. (K)).

Preparation of Compound 406b:

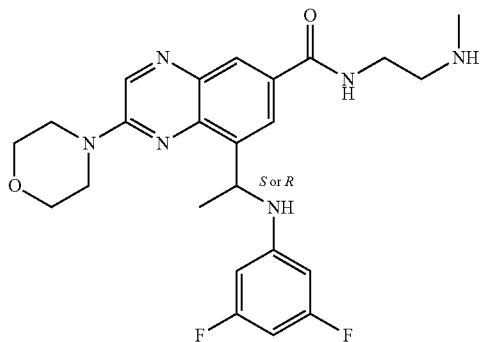 [SMILES: CNCCNC(=O)c1cc(C(C)Nc2cc(F)cc(F)c2)c2nc(N3CCOCC3)cnc2c1]

Compound 406b was prepared according to an analogous procedure as described for the synthesis of compound 17 using intermediate 348b as starting material (213 mg, 47%, gums at 80° C. (K)).

Example B5

Preparation compound 79:

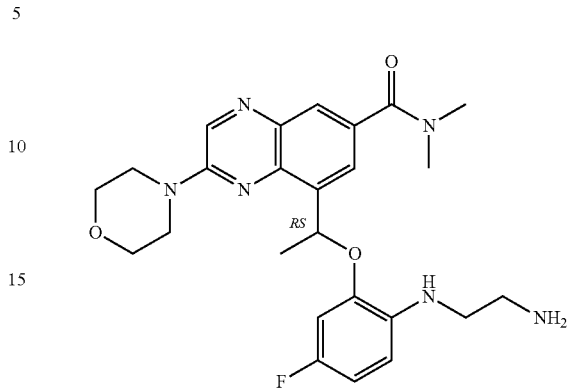

TFA (1.0 mL; 13.07 mmol) was added to a solution of intermediate 86 (180 mg; 0.31 mmol) in DCM (2 mL). The reaction mixture was stirred at rt for 4 h. The mixture was slowly quenched with a saturated solution of $NaHCO_3$. The mixture was then diluted with DCM and water. The layers were separated and the aqueous layer was basified with $K_2CO_3$ (pH 11). The aqueous layer was extracted with DCM. The combined organic layers were dried over $Na_2SO_4$, filtered and evaporated under vacuum. The residue (170 mg, greenish oil) was purifed by chromatography over silica gel (irregular SiOH; 15-40 μm; 4 g; gradient: from 99% DCM, 1% (MeOH/$NH_4OH$: 95/5) to 88% DCM, 12% (MeOH/$NH_4OH$: 95:5)). The pure fractions were collected and the solvent was evaporated. The resulting residue was freeze-dried with water/ACN to give 104 mg (70%, pale yellow fluffy solid) of compound 79.

Preparation of Compound 82:

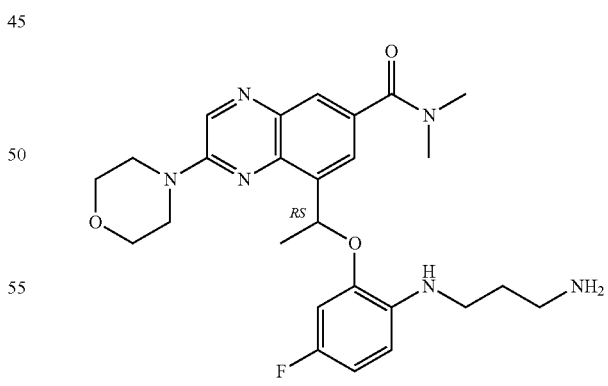

Compound 82 was prepared according to an analogous procedure as described for the synthesis of compound 79, using intermediate 97 as starting materials (freeze-dried: 125 mg, 42%).

Example B6

Preparation of compound 81:

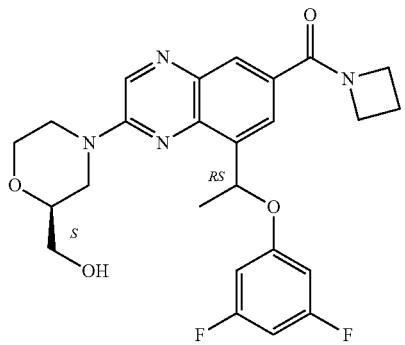

HCl (1M in H₂O) (404 µL; 404 µmol) was added to a solution of intermediate 94 (46 mg; 80.9 µmol) in acetone (1 mL). The reaction mixture was stirred at rt overnight. The mixture was quenched with a saturated aqueous solution of NaHCO₃. The mixture was evaporated in vacuum and the residue was taken up in DCM and water. The layers were separated and the organic layer was dried over MgSO₄, filtered and evaporated under vacuum. The residue (73 mg, yellow oil) was purified by reverse phase (X-Bridge-C18; 5 µm 30*150 mm; gradient: from 50% (aq. NH₄HCO₃ 0.5%), 50% MeOH to 100% MeOH). The pure fractions were collected and the solvent was evaporated. The residue was freeze-dried and the product (20.5 mg) was purified by achiral SFC (2 ETHYLPYRIDINE; 6 µm 150×21.2 mm; mobile phase: 85% CO₂, 15% MeOH). The pure fractions were collected and the solvent was evaporated. The residue was freeze-dried with water/ACN (8/2) to give 14 mg (36%) of compound 81.

Example B7

Preparation Compound 19:

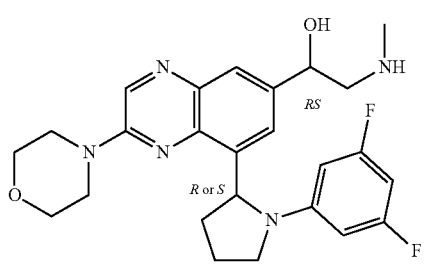 [SMILES: CNCC(O)c1cc(C2CCCN2c2cc(F)cc(F)c2)c2nc(N3CCOCC3)cnc2c1]

In a sealed glass, intermediate 51 (200 mg; 0.46 mmol) and methylamine (2M in THF) (2.28 mL; 4.56 mmol) in THF (4 mL) were stirred at 100° C. overnight. The resulting solution was poured into water and extracted with EtOAc. The organic layer was dried over MgSO₄, filtered and evaporated until dryness. The residue (245 mg) was purified by chromatography over silica gel (irregular 15-40 µm; 24 g; mobile phase: 90% DCM, 10% MeOH, 0.1% MEOH). The pure fractions were collected and the solvent was evaporated. The residue (79 mg) was purified by chromatography over silica gel (irregular 15-40 µm; 24 g; mobile phase: 90% DCM, 10% MeOH, 0.1% NH₄OH). The pure fractions were collected and the solvent was evaporated to give 41 mg (19%) of compound 19. M.P.: 80° C. (gum, K).

Preparation Compound 94 and Compound 95

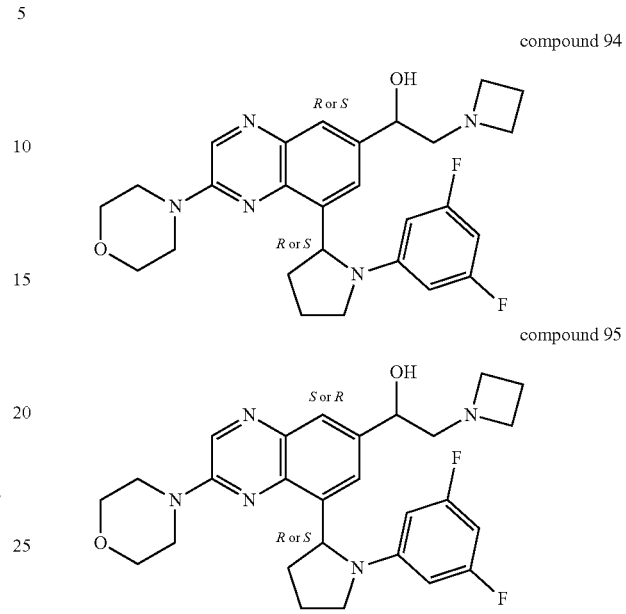

Compound 94 and compound 95 were prepared according to an analogous procedure as described for the synthesis of compound 19, using intermediate 51 and azetidine as starting materials. The residue (145 mg) was purified by chromatography over silica gel (irregular bare silica 12 g; gradient: from 95% DCM, 5% MeOH, 0.1% NH₄OH to 90% DCM, 10% MeOH, 0.1% NH₄OH). The pure fractions were collected and evaporated until dryness. The residue (89 mg) was purified by chiral SFC (CHIRALPAK IC 5 µm 250×20 mm; mobile phase: 55% CO₂, 45% EtOH (0.3% iPrNH₂)). The pure fractions were collected and the solvent was evaporated to give 25 mg of (16%) of compound 94 (M.P.: 80° C., gum, K) and 23 mg (15%) of compound 95 (M.P.: 80° C., gum, K).

Example B8

Preparation Compound 20:

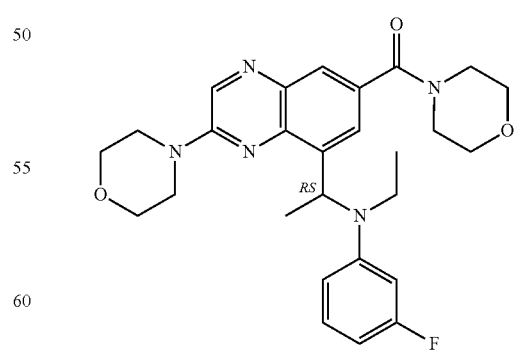

A solution of intermediate 52 (300 mg; 0.77 mmol) and N-ethyl-3-fluoroaniline (705 mg; 5.07 mmol) in DMF (3 mL) was heated at 60° C. for 2 days in a sealed glassware. The solution was cooled. Then, the mixture was poured into cooled water, basified with K₂CO₃ and the product was extracted with EtOAc. The organic layer was washed with H₂O, dried over MgSO₄, filtered and evaporated to dryness. The residue (450 mg) was purified by chromatography over silica gel (80 g; mobile phase: 50% heptane, 7% MeOH, 43% EtOAc, 0.5% NH₄OH). The pure fractions were collected and the solvent was evaporated. The residue (168 mg) of was purified by chromatography over silica gel (irregular bare silica 40 g; mobile phase: 42% heptane, 8% MeOH (+10% NH₄OH), 50% EtOAc). The pure fractions were collected and the solvent was evaporated to give 100 mg (26%) of compound 20. M.P.: 80° C. (gum, K).

Preparation Compound 80:

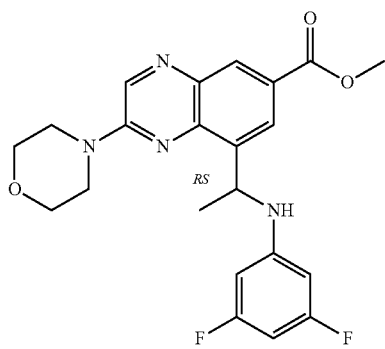 [SMILES: COC(=O)c1cc(C(C)Nc2cc(F)cc(F)c2)c2nc(N3CCOCC3)cnc2c1]

Compound 80 was prepared according to an analogous procedure as described for the synthesis of compound 20, using intermediate 87 and 3,5-difluoroaniline as starting materials (24 mg, 15%). M.P.: 244° C. (DSC).

Preparation Compound 97:

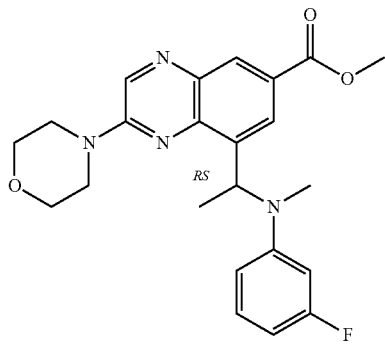 [SMILES: COC(=O)c1cc(C(C)N(C)c2cccc(F)c2)c2nc(N3CCOCC3)cnc2c1]

Compound 97 was prepared according to an analogous procedure as described for the synthesis of compound 20, using intermediate 105 and 3-fluoro-N-methylaniline as starting materials (405 mg, 22%). M.P.: 146° C. (DSC).

Preparation Compound 99:

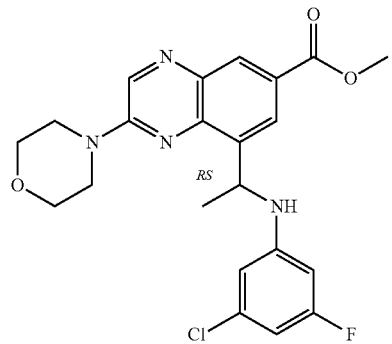 [SMILES: COC(=O)c1cc(C(C)Nc2cc(F)cc(Cl)c2)c2nc(N3CCOCC3)cnc2c1]

Compound 99 was prepared according to an analogous procedure as described for the synthesis of compound 20, using intermediate 87 and 3-chloro-5-fluoroaniline as starting materials (400 mg, 22%). M.P.: 189° C. (DSC).

Preparation Compound 104:

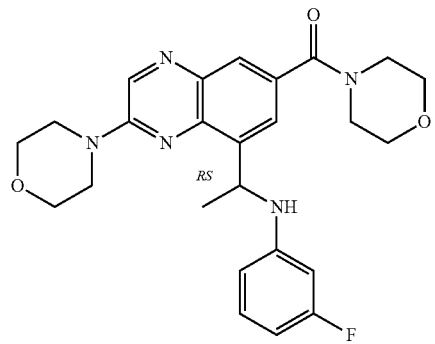 [SMILES: CC(Nc1cccc(F)c1)c1cc(C(=O)N2CCOCC2)cc2ncc(N3CCOCC3)nc12]

Compound 104 was prepared according to an analogous procedure as described for the synthesis of compound 20, using intermediate 45 and 3-fluoroaniline as starting materials (20 mg, 11%). M.P.: 80° C. (gum, K).

Preparation Compound 119:

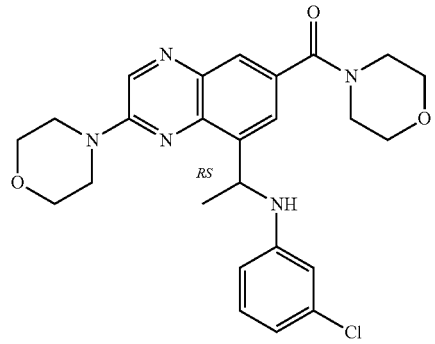 [SMILES: CC(Nc1cccc(Cl)c1)c1cc(C(=O)N2CCOCC2)cc2ncc(N3CCOCC3)nc12]

Compound 119 was prepared according to an analogous procedure as described for the synthesis of compound 20, using intermediate 52 and 3-chloroaniline as starting materials (23 mg, 19%). M.P.: 80° C. (K).

Preparation Compound 120:

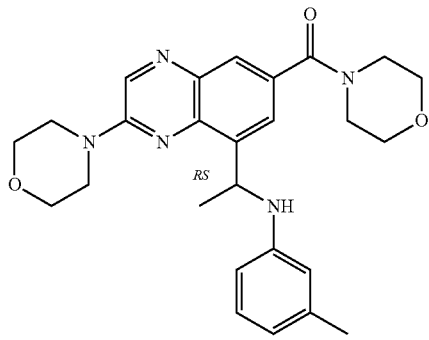 [SMILES: Cc1cccc(NC(C)c2cc(C(=O)N3CCOCC3)cc3ncc(N4CCOCC4)nc23)c1]

Compound 120 was prepared according to an analogous procedure as described for the synthesis of compound 20, using intermediate 52 and m-toluidine as starting materials (28 mg, 25%). M.P.: 80° C. (K).

Preparation Compound 121:

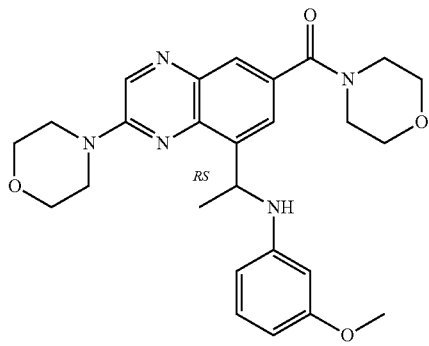 [SMILES: COc1cccc(NC(C)c2cc(C(=O)N3CCOCC3)cc3ncc(N4CCOCC4)nc23)c1]

Compound 121 was prepared according to an analogous procedure as described for the synthesis of compound 20, using intermediate 52 and m-anisidine as starting materials (24 mg, 20%). M.P.: 80° C. (K).

Preparation Compound 124:

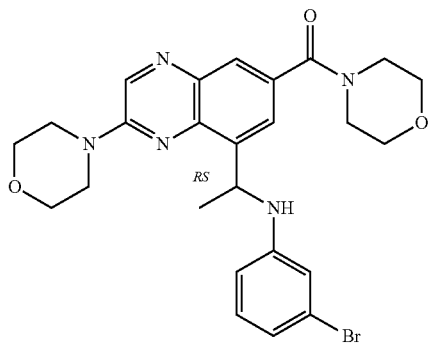 [SMILES: CC(Nc1cccc(Br)c1)c1cc(C(=O)N2CCOCC2)cc2ncc(N3CCOCC3)nc12]

Compound 124 was prepared according to an analogous procedure as described for the synthesis of compound 20, using intermediate 52 and 3-bromoaniline as starting materials (50 mg, 31%). M.P.: 80° C. (gum, K).

Preparation Compound 125:

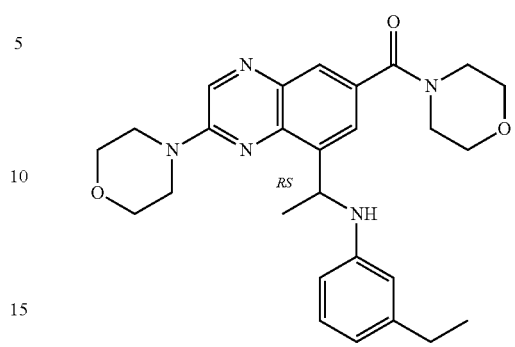

Compound 125 was prepared according to an analogous procedure as described for the synthesis of compound 20, using intermediate 52 and 3-ethylaniline as starting materials (50 mg, 34%). M.P.: 80° C. (gum, K).

Preparation Compound 126:

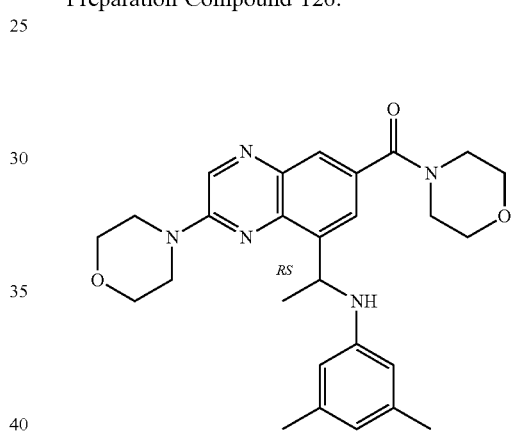

Compound 126 was prepared according to an analogous procedure as described for the synthesis of compound 20, using intermediate 52 and 3,5-dimethylaniline as starting materials (50 mg, 34%). M.P.: 80° C. (gum, K).

Preparation Compound 127 and Compound 128 compound 127

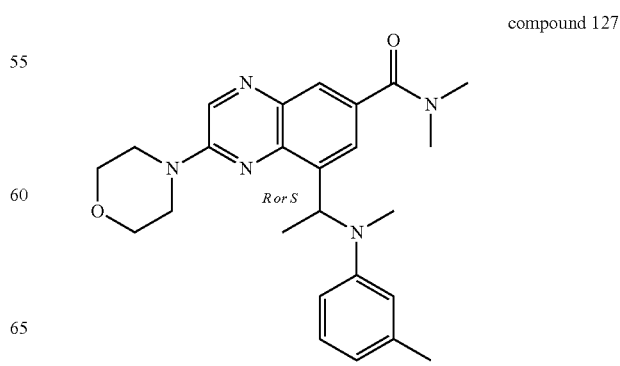

compound 128

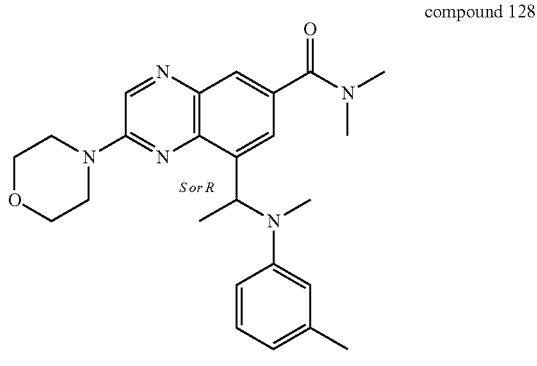

Compound 127 and compound 128 were prepared according to an analogous procedure as described for the synthesis of compound 20, using intermediate 119 and N-methyl-m-toluidine as starting materials. 80 mg (26%) of compound 127; M.P.: 80° C. (gum, K) and 85 mg (27%) of compound 128; M.P.: 80° C. (gum, K) were obtained after chiral SFC (Stationary phase: Chiralpak IA 5 µm 250*20 mm, Mobile phase: 70% $CO_2$, 30% iPOH (0.3% $iPrNH_2$)) purification.

Preparation Compound 129:

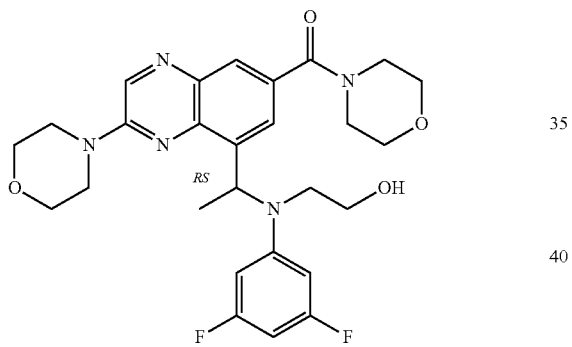

The solution of intermediate 52 (0.2 g; 0.51 mmol) and intermediate 121 (0.74 g; 2.6 mmol) in DMF (5 mL) was heated at 60° C. for 24 h in a sealed glassware. The solution was cooled down to rt and poured into cooled water. The mixture was basified with $K_2CO_3$ and the product was extracted with EtOAc. The organic layer was washed with $H_2O$, dried over $MgSO_4$, filtered and evaporated to dryness. The residue (677 mg) was taken-up with THF (20 mL) and tetrabutylammonium fluoride (3 mL; 10.2 mmol) was added. The reaction mixture was stirred at rt overnight. The solution was poured into cooled water and the product was extracted with EtOAc. The organic layer was dried over $MgSO_4$, filtered and evaporated to dryness. The residue (590 mg) was purified by chromatography over silica gel (irregular bare silica 40 g; mobile phase: 43% heptane, 7% MeOH (+10% $NH_4OH$), 50% EtOAc). The pure fractions were collected and the solvent was evaporated to give 39 mg (14%) of compound 129. M.P.: 80° C. (K).

Preparation Compound 131:

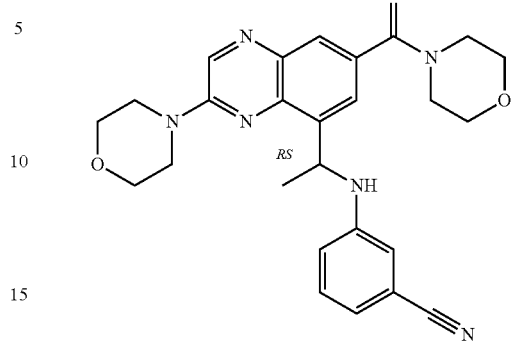

Compound 131 was prepared according to an analogous procedure as described for the synthesis of compound 20, using intermediate 52 and 3-aminobenzonitrile as starting materials (49 mg, 34%). M.P.: 80° C. (K).

Preparation Compound 133:

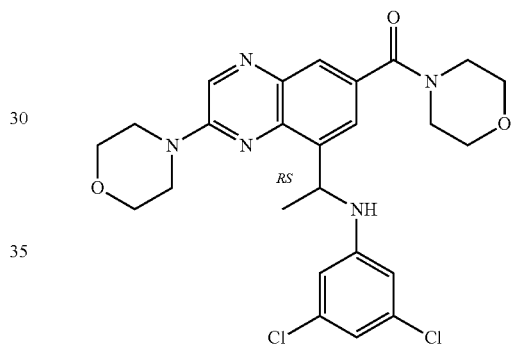

Compound 133 was prepared according to an analogous procedure as described for the synthesis of compound 20, using intermediate 52 and 3,5-dichloroaniline as starting materials (25 mg, 16%). M.P.: 80° C. (gum, K).

Preparation Compound 134:

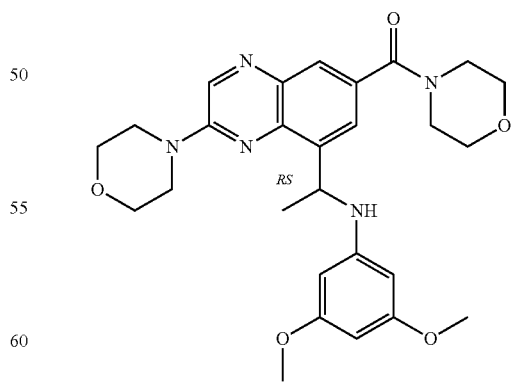

Compound 134 was prepared according to an analogous procedure as described for the synthesis of compound 20, using intermediate 52 and 3,5-dimethoxyaniline as starting materials (26 mg, 17%). M.P.: 80° C. (gum, K).

Preparation Compound 135:

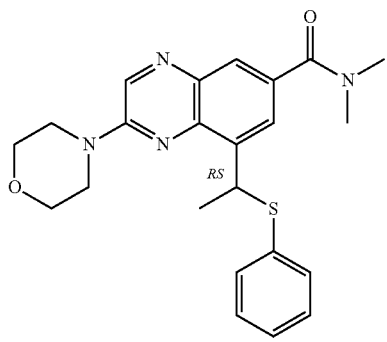 [SMILES: CC(Sc1ccccc1)c1cc(C(=O)N(C)C)cc2ncc(N3CCOCC3)nc12]

Compound 135 was prepared according to an analogous procedure as described for the synthesis of compound 20, using intermediate 119 and sodium thiophenolate as starting materials (148 mg, 58%, pale yellow solid). M.P.: 144° C. (DSC).

Preparation Compound 140 and Compound 141

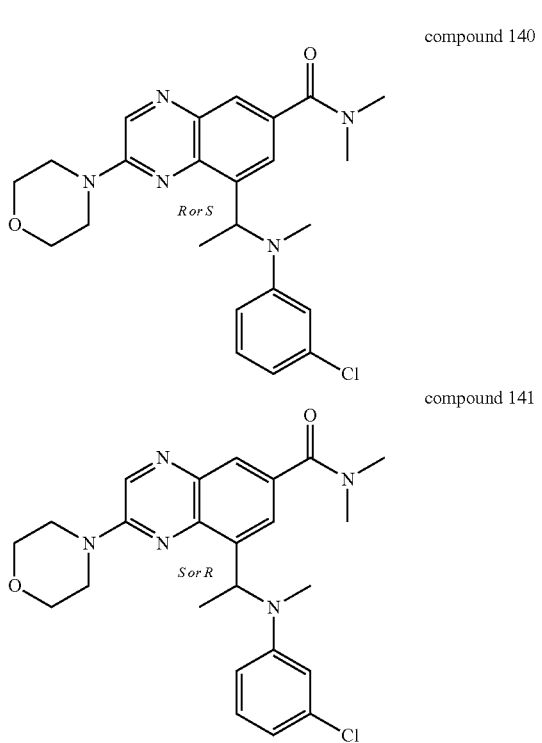

Compound 140 and compound 141 were prepared according to an analogous procedure as described for the synthesis of compound 20, using intermediate 119 and 3-chloro-N-methylaniline as starting materials. 69 mg (21%) of compound 140; M.P.: 80° C. (gum, K) and 69 mg (21%) of compound 141; M.P.: 80° C. (gum, K) were obtained after chiral SFC (Stationary phase: CHIRALCEL OJ-H 5 μm 250×20 mm, Mobile phase: 75% $CO_2$, 25% MeOH (0.3% i$PrNH_2$)) purification.

Preparation Compound 146:

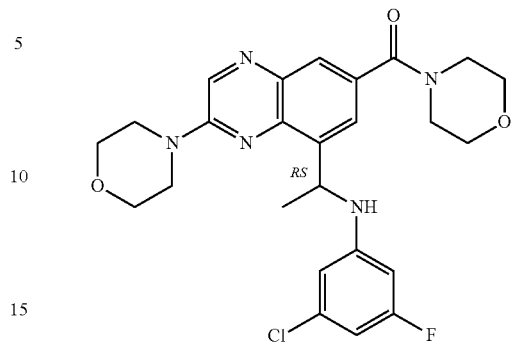

Compound 146 was prepared according to an analogous procedure as described for the synthesis of compound 20, using intermediate 52 and 3-chloro-5-fluoroaniline as starting materials (29 mg, 19%). M.P.: 80° C. (gum, K).

Preparation Compound 150:

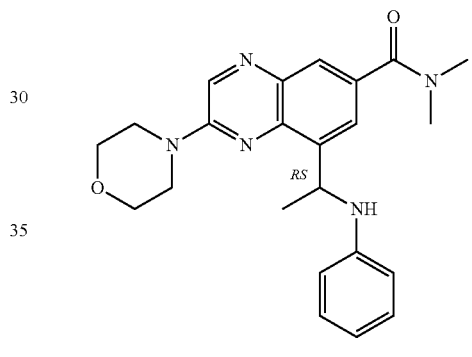

Compound 150 was prepared according to an analogous procedure as described for the synthesis of compound 20, using intermediate 119 and aniline as starting materials (75 mg, 26%). M.P.: 110° C. (K).

Preparation Compound 153:

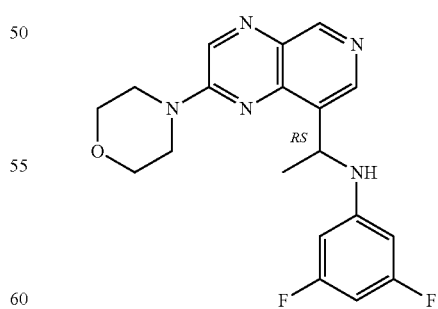

Compound 153 was prepared according to an analogous procedure as described for the synthesis of compound 20, using intermediate 139 and 3,5-difluoroaniline as starting materials (90 mg, 23%, pale yellow foam). M.P.: 90° C. (gum, K).

Preparation Compound 155:

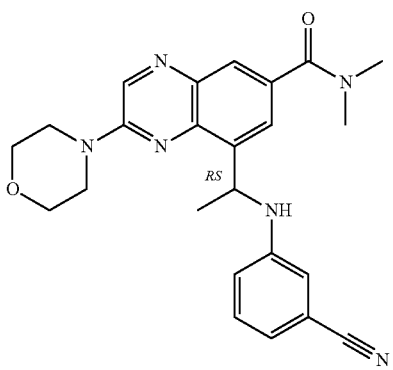 [SMILES: CC(Nc1cccc(C#N)c1)c1cc(C(=O)N(C)C)cc2ncc(N3CCOCC3)nc12]

Compound 155 was prepared according to an analogous procedure as described for the synthesis of compound 20, using intermediate 119 and 3-aminobenzonitrile as starting materials (57 mg, 18%). M.P.: 186° C. (DSC).

Preparation Compound 158 and Compound 159

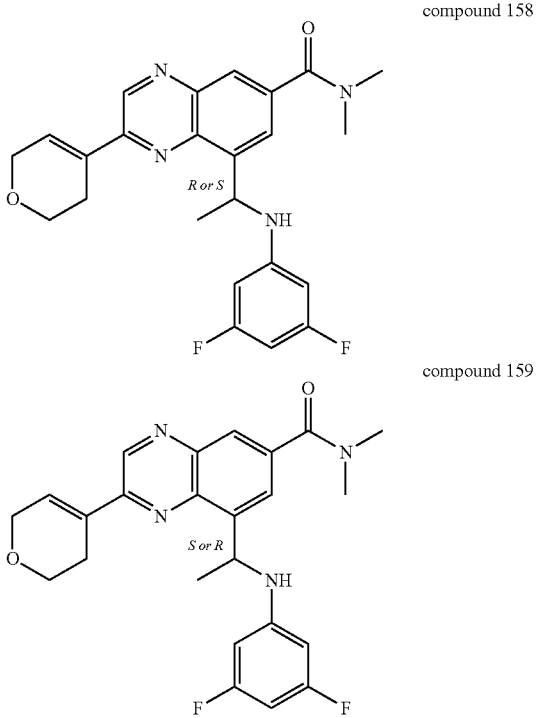 [SMILES: CC(Nc1cc(F)cc(F)c1)c1cc(C(=O)N(C)C)cc2ncc(C3=CCOCC3)nc12 ; CC(Nc1cc(F)cc(F)c1)c1cc(C(=O)N(C)C)cc2ncc(C3=CCOCC3)nc12]

3-Difluoroaniline (1.36 g; 10.55 mmol) was added to a solution of intermediate 20 ((730 mg; 2.11 mmol) in DMF (19 mL) under N$_2$. The solution was stirred at 60° C. for 7 days in a sealed tube. The solution was cooled, poured out into cooled water, basified with K$_2$CO$_3$. EtOAc was added. The product was extracted with EtOAc and the organic layer was concentrated. Et$_2$O was added and a precipitate was filtered off. The precipitate was purified via silica gel chromatography (SiO$_2$: 80 g, Mobile phase: 45% heptane 5% MeOH 50% EtOAc 0.5% NH$_4$OH). The pure fractions were collected and evaporated until dryness to give 450 mg of an impure fraction of the racemic compound. This residue was purified via silica gel chromatography (SiO$_2$: 80 g, Mobile phase: 67% heptane 3% MeOH 30% EtOAc 0.5% NH$_4$OH). The pure fractions were collected and evaporated until dryness to give of 322 mg (35%) of the racemic compound. Separation of the enantiomers was performed via chiral SFC (Stationary phase: CHIRALCEL OJ-H 5 µm 250×20 mm, Mobile phase: 85% CO$_2$, 15% MeOH (0.3% iPrNH$_2$)). The pure fractions were collected and evaporated until dryness to give 134 mg (14%) of compound 158 and 120 mg (13%) of compound 159.

Preparation Compound 167:

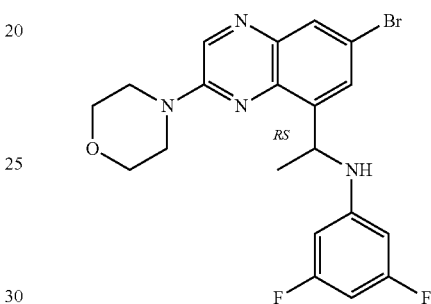

Compound 167 was prepared according to an analogous procedure as described for the synthesis of compound 20, using intermediate 145 and 3,5-difluoroaniline as starting materials (15 mg, 6%). M.P.: 80° C. (gum, K). The reaction mixture was stirred at 50° C. for 36 h.

Preparation of Compound 260:

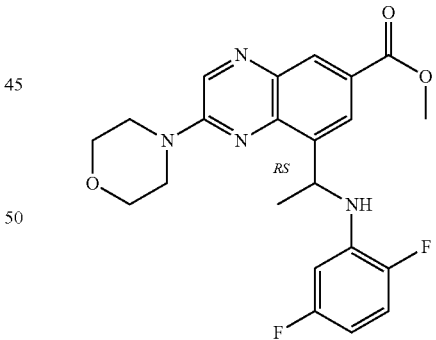

A mixture of intermediate 87 (1 g; 2.17 mmol), 2,5-difluoroaniline (1.1 mL; 10.84 mmol) in DMF (10 mL) was stirred at 50° C. for 48 h in a sealed tube. The solution was poured into cooled water. EtOAc was added and the mixture was filtered through a pad of Celite®. The product was extracted with EtOAc. The organic layer was dried over MgSO$_4$, filtered and evaporated to dryness. The residue (1.2 g) was crystallized from Et$_2$O and dried to give 0.32 g (34%, yellow solid) of compound 260.

Preparation of Compound 264:

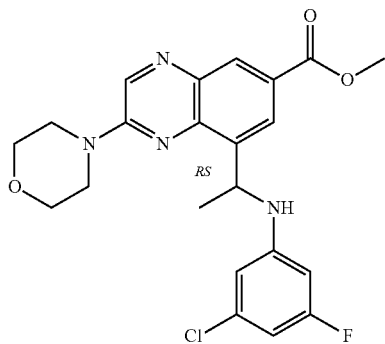

Compound 264 was prepared according to an analogous procedure as described for the synthesis of compound 262 (alternative pathway), using intermediate 87 and 3-chloro-5-fluoroaniline as starting materials (400 mg, 42%). The reaction mixture was stirred at 50° C. for 48 h. M.P.: 189° C. (DSC).

Preparation of Compound 266:

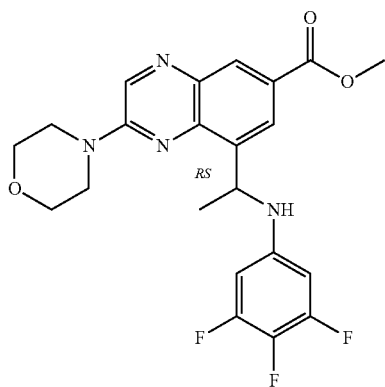 [SMILES: COC(=O)c1cc(C(C)Nc2cc(F)c(F)c(F)c2)c2nc(N3CCOCC3)cnc2c1]

Compound 266 was prepared according to an analogous procedure as described for the synthesis of compound 260, using intermediate 105 and 3,4,5-trifluoroaniline as starting materials (2.72 g, 64%, M.P.: 220° C. (K)). The reaction mixture was stirred at 60° C. for 4 days.

Preparation of Compound 269:

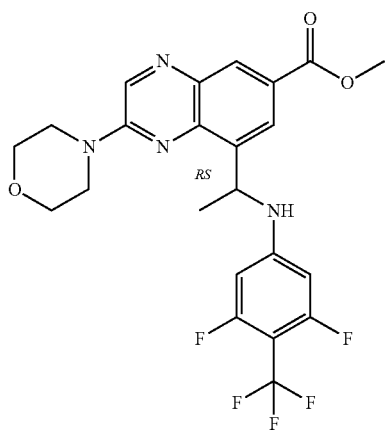 [SMILES: COC(=O)c1cc(C(C)Nc2cc(F)c(C(F)(F)F)c(F)c2)c2nc(N3CCOCC3)cnc2c1]

Compound 269 was prepared according to an analogous procedure as described for the synthesis of compound 262, using intermediate 105 and 3,5-difluoro-4-(trifluoromethyl) aniline as starting materials (crystallized from Et$_2$O; 865 mg; 34%).

Preparation of Compound 293:

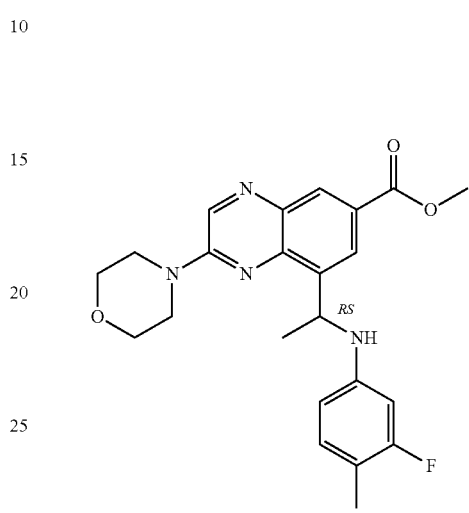

Compound 293 was prepared according to an analogous procedure as described for the synthesis of compound 20, using intermediate 105 and 4-methyl-3-fluoroaniline as starting material (4.12 g, 65%). M.P.: 186° C., K).

Preparation of Compound 304:

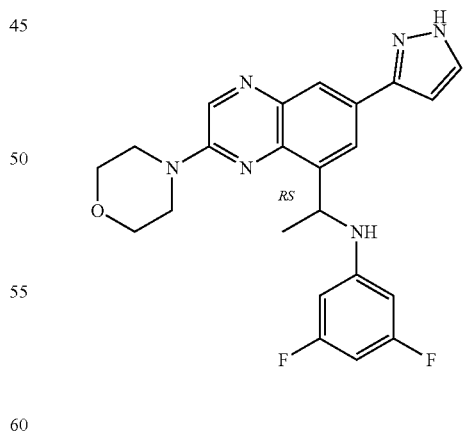

Compound 304 was prepared according to an analogous procedure as described for the synthesis of compound 20 using intermediate 194 find 3,5-difluoroaniline as starting materials (10 mg, 5%).

Example B9

Preparation Compound 156 and Compound 157 compound 156

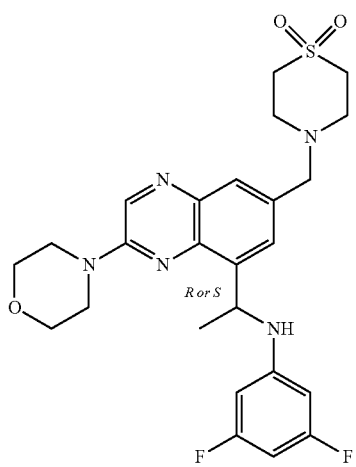

compound 157

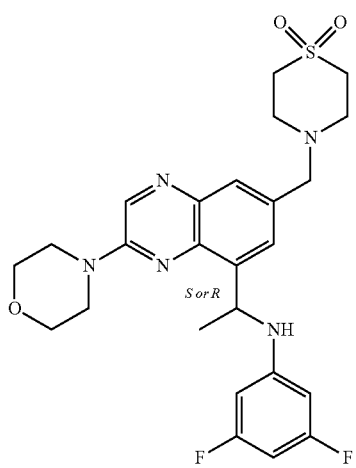

Thiomorpholine 1,1-dioxide (86 mg; 0.63 mmol) and K2CO$_3$ (117 mg; 0.85 mmol) were added to a mixture of intermediate 140 (177 mg; 0.42 mmol) in ACN (4 mL). The reaction mixture was stirred at 80° C. overnight. The mixture was cooling down to rt, combined with another batch coming from a reaction performed on 63 mg of intermediate 140 and poured into water. The organic layer was extracted with EtOAc, washed with brine, dried over MgSO$_4$, filtered and evaporated until dryness. The residue (420 mg) was purified by chromatography over silica gel (40 g; mobile phase: from 100% DCM to 98% DCM, 2% MeOH). The pure fractions were collected and the solvent was evaporated until dryness. The residue (racemic, 220 mg) was purified by chiral SFC (CHIRALPAK IC 5 μm; 250×20 mm; mobile phase: 60% CO$_2$, 40% EtOH). The pure fractions were collected and the solvent was evaporated to give 101 mg (34%) of compound 156 and 98 mg (33%) of compound 157.

Preparation Compound 160:

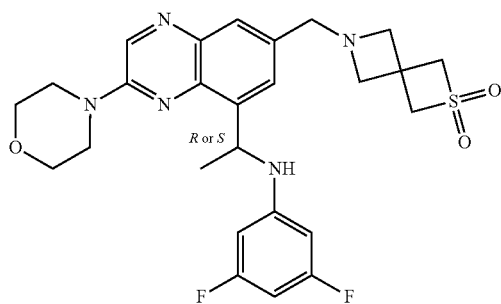 [SMILES: CC(Nc1cc(F)cc(F)c1)c1cc(CN2CC3(C2)CS(=O)(=O)C3)cc2ncc(N3CCOCC3)nc12]

Compound 160 was prepared according to an analogous procedure as described for the synthesis of compound 156, using intermediate 142 and 2-thia-6-aza-spiro[3.3]heptane 2,2-dioxide as starting materials (98 mg, 28%). M.P.: 229° C. (DSC).

Preparation Compound 161:

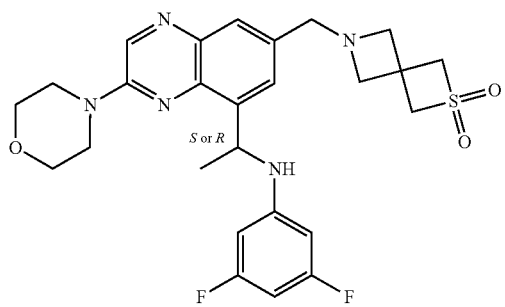

Compound 161 was prepared according to an analogous procedure as described for the synthesis of compound 156, using intermediate 143 and 2-thia-6-aza-spiro[3.3]heptane 2,2-dioxide as starting materials (109 mg, 31%). M.P.: 228° C. (DSC).

Preparation Compound 162:

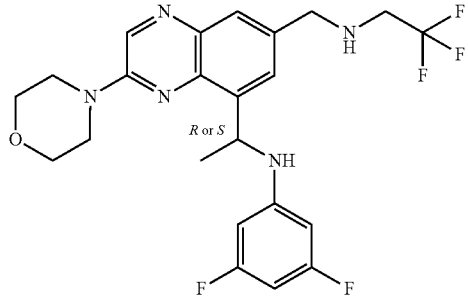 [SMILES: CC(Nc1cc(F)cc(F)c1)c1cc(CNCC(F)(F)F)cc2ncc(N3CCOCC3)nc12]

Compound 162 was prepared according to an analogous procedure as described for the synthesis of compound 156, using intermediate 142 and 2,2,2-trifluoroethylamine as starting materials (60 mg, 25%). M.P.: 80° C. (gum, K).

Preparation Compound 163:

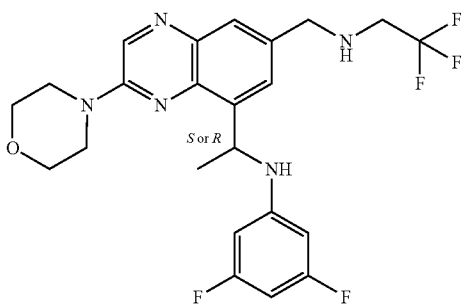 [SMILES: CC(Nc1cc(F)cc(F)c1)c1cc(CNCC(F)(F)F)cc2ncc(N3CCOCC3)nc12]

2.07 HCl 1.40 H$_2$O Compound 163 was prepared according to an analogous procedure as described for the synthesis of compound 156, using intermediate 143 and 2,2,2-trifluoroethylamine as starting materials. After the purification, the residue (140 mg) was dissolved in ACN, converted into hydrochloric acid salt ([HCl/iPrOH 5M]; 3 eq./V=0.17 mL]). The salt was filtered to give 150 mg (51%) of compound 163 (2.07 HCl 1.40 H$_2$O). M.P.: 239° C. (DSC).

Preparation Compound 164:

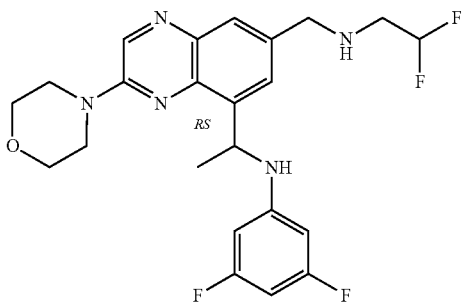 [SMILES: CC(Nc1cc(F)cc(F)c1)c1cc(CNCC(F)F)cc2ncc(N3CCOCC3)nc12]

Compound 164 was prepared according to an analogous procedure as described for the synthesis of compound 156, using intermediate 140 and 2,2-difluoroethylamine as starting materials (76 mg, 23%). M.P.: 116° C. (DSC).

Preparation Compound 168:

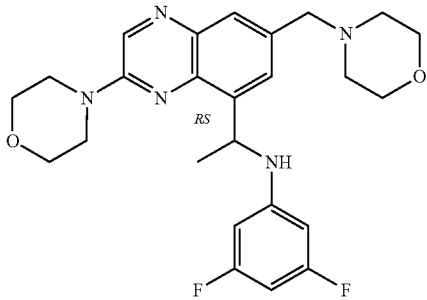 [SMILES: CC(Nc1cc(F)cc(F)c1)c1cc(CN2CCOCC2)cc2ncc(N3CCOCC3)nc12]

Compound 168 was prepared according to an analogous procedure as described for the synthesis of compound 156, using intermediate 140 and morpholine as starting materials (121 mg, 31%). M.P.: 165° C. (DSC).

Preparation Compound 173:

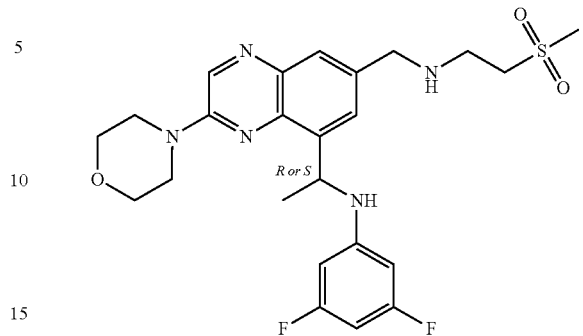

Compound 173 was prepared according to an analogous procedure as described for the synthesis of compound 156, using intermediate 142 and 2-(methylsulfonyl)-ethanamine hydrochloride as starting materials (65 mg, 21%). M.P.: 80° C. (gum, K).

Preparation Compound 192:

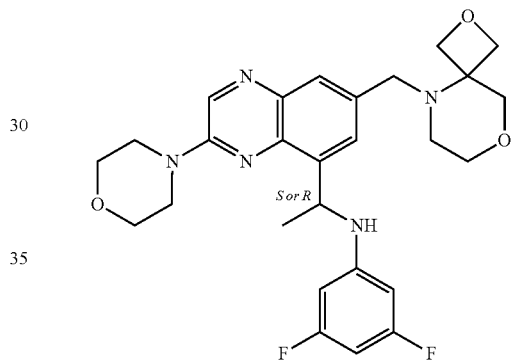

Compound 192 was prepared according to an analogous procedure as described for the synthesis of compound 156, using intermediate 143 and 2,8-Dioxa-5-azaspiro[3.5]nonane oxalate salt as starting materials (34 mg, 11%). M.P.: 229° C. (DSC).

Preparation Compound 193:

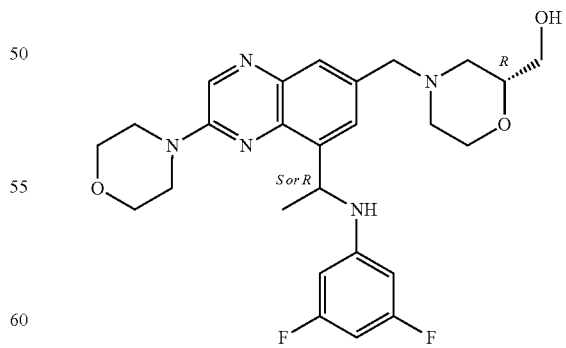

Compound 193 was prepared according to an analogous procedure as described for the synthesis of compound 156, using intermediate 143 and (R)-(2-Hydroxymethyl)morpholine HCl as starting materials (105 mg, 35%). M.P.: 80° C. (gum, K).

Preparation Compound 194:

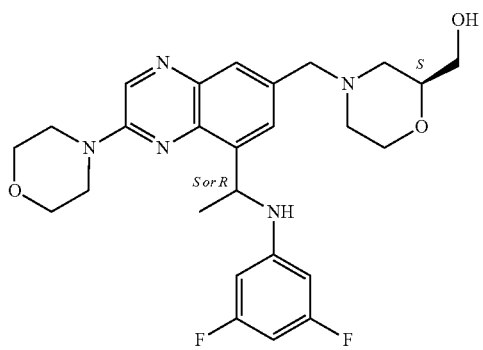

Compound 194 was prepared according to an analogous procedure as described for the synthesis of compound 156, using intermediate 143 and (S)-(2-Hydroxymethyl)morpholine HCl as starting materials (152 mg, 51%). M.P.: 80° C. (gum, K).

Preparation Compound 195:

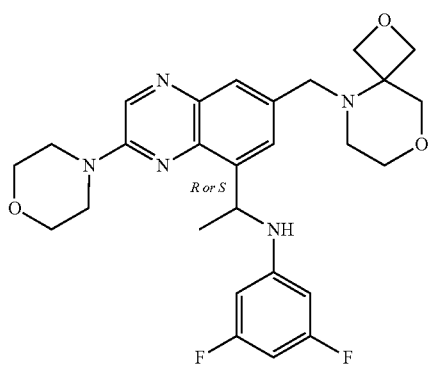 [SMILES: CC(Nc1cc(F)cc(F)c1)c1cc(CN2CCOCC23COC3)cc2ncc(N3CCOCC3)nc12]

Compound 195 was prepared according to an analogous procedure as described for the synthesis of compound 156, using intermediate 142 and 2,8-Dioxa-5-azaspiro[3.5]nonane oxalate salt as starting materials (110 mg, 43%). M.P.: 228° C. (DSC).

Preparation Compound 196:

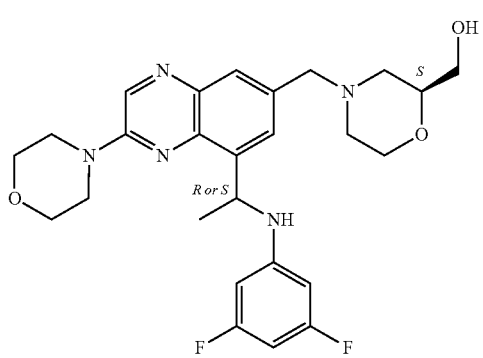

Compound 196 was prepared according to an analogous procedure as described for the synthesis of compound 156, using intermediate 142 and (S)-(2-Hydroxymethyl)morpholine HCl as starting materials (freeze-dried: 158 mg, 63%). M.P.: 80° C. (gum, K).

Preparation Compound 197:

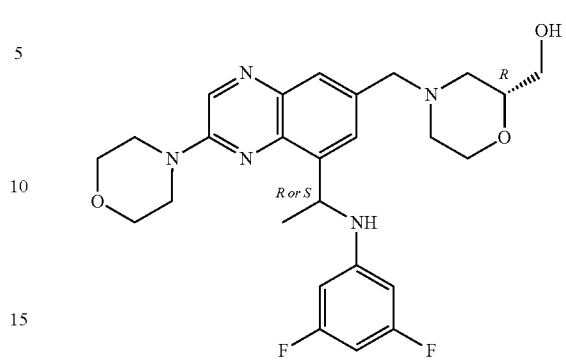

Compound 197 was prepared according to an analogous procedure as described for the synthesis of compound 156, using intermediate 142 and (R)-(2-Hydroxymethyl)morpholine HCl as starting materials (freeze-dried: 170 mg, 68%). M.P.: 80° C. (gum, K).

Preparation Compound 205:

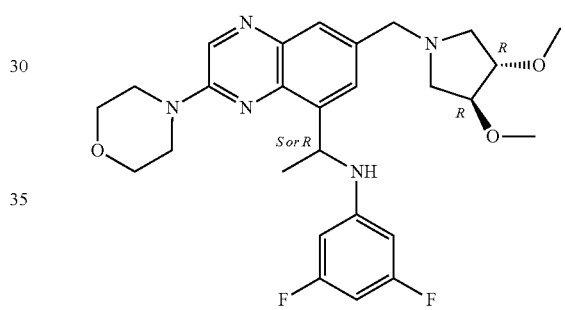

Compound 205 was prepared according to an analogous procedure as described for the synthesis of compound 156, using intermediate 143 and (3R,4R)-3,4-Dimethoxypyrrolidine hydrochloride as starting materials (85 mg, 35%). M.P.: 80° C. (gum, K).

Preparation Compound 206:

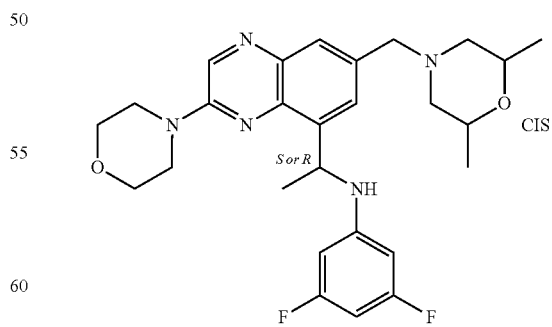

Compound 206 was prepared according to an analogous procedure as described for the synthesis of compound 156, using intermediate 143 and cis-2,6-dimethylmorpholine as starting materials (97 mg, 41%). M.P.: 80° C. (gum, K).

Preparation Compound 207:

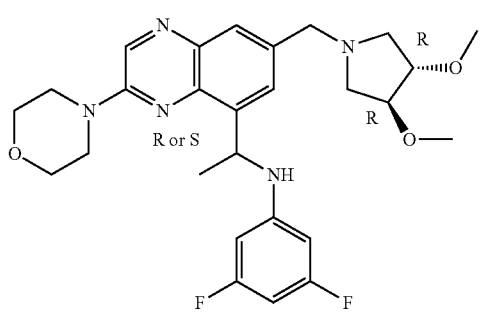

Compound 207 was prepared according to an analogous procedure as described for the synthesis of compound 156, using intermediate 142 and (3R,4R)-3,4-Dimethoxypyrrolidine hydrochloride as starting materials (freeze-dried: 94 mg, 35%). M.P.: 80° C. (gum, K).

Preparation Compound 208:

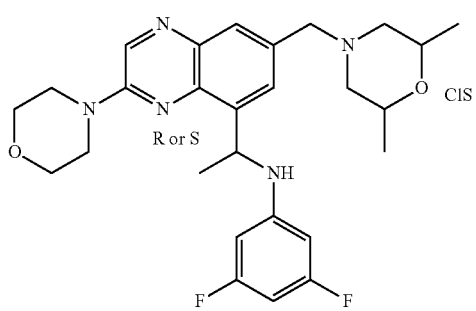

Compound 208 was prepared according to an analogous procedure as described for the synthesis of compound 156, using intermediate 142 and cis-2,6-dimethylmorpholine as starting materials (133 mg, 52%). M.P.: 80° C. (K).

Preparation Compound 210:

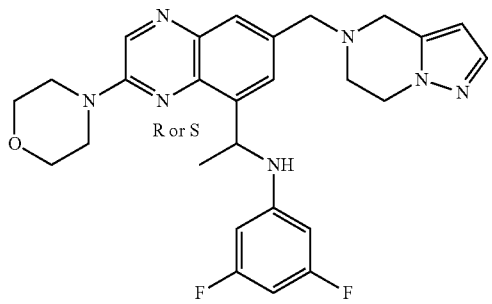 [SMILES: CC(Nc1cc(F)cc(F)c1)c1cc(CN2CCn3nccc3C2)cc2ncc(N3CCOCC3)nc12]

Compound 210 was prepared according to an analogous procedure as described for the synthesis of compound 156, using intermediate 142 and 4,5,6,7-tetrahydro-pyrazolo[1,5-a]pyrazine hydrochloride as starting materials (91 mg, 45%). M.P.: 80° C. (K).

Preparation Compound 222:

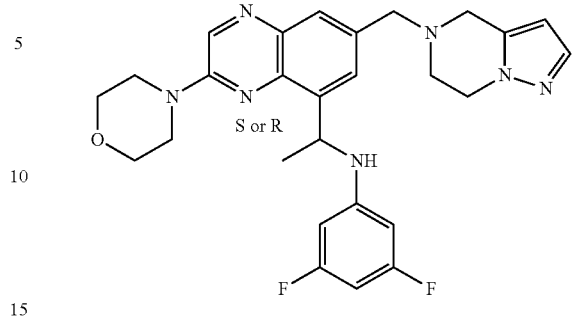

Compound 222 was prepared according to an analogous procedure as described for the synthesis of compound 156, using intermediate 143 and 4,5,6,7-tetrahydro-pyrazolo[1,5-a]pyrazine hydrochloride as starting materials (17 mg, 7%). M.P.: 163° C. (DSC).

Example B10

Preparation Compound 21 and Compound 22

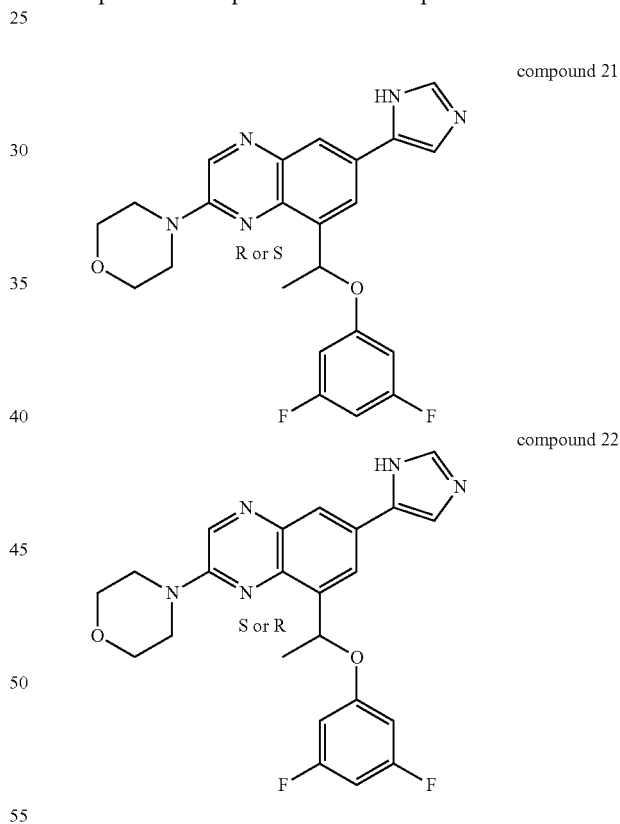

A solution of intermediate 58 (76 mg; 0.15 mmol) and p-toluenesulfonic acid monohydrate (6 mg; 29 μmol) in MeOH (6.38 mL) was heated at 50° C. for 3 days. The resulting solution was evaporated under reduced pressure. The residue was dissolved in EtOAc (10 mL) and washed with a saturated aqueous solution of NaHCO$_3$ (5 mL). The aqueous layer was extracted with EtOAc (2×10 mL). The combined organic layers were dried over MgSO$_4$, filtered and evaporated under reduced pressure. The residue was combined with another batch from 127 mg of intermediate 58 and purified by chromatography over silica gel (irregular SiOH; 15-40 μm; 24 g; gradient: from 100% EtOAc to 85% EtOAc, 15% MeOH (+5% NH$_4$OH)). The pure fractions were collected and the solvent was evaporated. The residue (105 mg, brown powder) was combined with another batch coming from a reaction performed on 165 mg of intermediate 58 and purified by reverse phase (X-Bridge-C18 5 µm 30*150 mm; gradient: from 65% aq. $NH_4HCO_3$ 0.5%, 35% ACN to 25% aq. $NH_4HCO_3$ 0.5%, 75% ACN). The pure fractions were collected and the solvent was evaporated. The residue (158 mg) was purified by chiral SFC (Lux cellulose 4; 5 µm 250*21.2 mm; mobile phase: 75% $CO_2$, 25% MeOH (0.3% iPrNH$_2$)). The pure fractions were collected and the solvent was evaporated to give 59 mg (19%, yellow powder) of compound 21 (M.P.: 184° C. (DSC)) and 54 mg (17%, yellow powder) of compound 22 (M.P.: 183° C. (DSC)).

Example B11

Preparation of Compound 177:

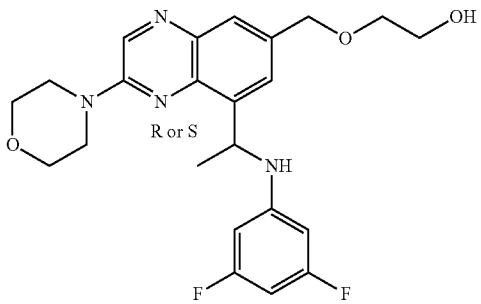 [SMILES: CC(Nc1cc(F)cc(F)c1)c1cc(COCCO)cc2ncc(N3CCOCC3)nc12]

TFA (0.8 mL; 10.27 mmol) was added at 10° C. to a solution of intermediate 150 (0.18 g; 0.34 mmol) in MeOH (20 mL). The reaction mixture was stirred at rt for 24 h. The solution was cooled and the mixture was poured into cooled water, basified with K2CO$_3$ and the product was extracted with EtOAc. The organic layer was dried over MgSO$_4$, filtered and evaporated to dryness. The residue (130 mg) was purified by chromatography over silica gel (irregular bare silica 10 g; mobile phase: 97% DCM, 3% MeOH, 0.1% NH$_4$OH). The pure fractions were collected and the solvent was evaporated. The residue (73 mg) was freeze-dried with ACN/water 20/80 to give 69 mg (45%, yellow powder) of compound 177. M.P.: 80° C. (gum, K)).

Preparation of Compound 178:

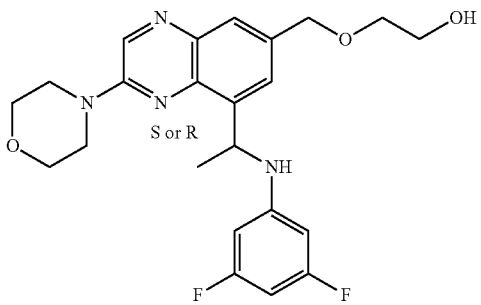 [SMILES: CC(Nc1cc(F)cc(F)c1)c1cc(COCCO)cc2ncc(N3CCOCC3)nc12]

Compound 178 was prepared according to an analogous procedure as described for the synthesis of compound 177, using intermediate 151 as starting materials (freeze-dried: 122 mg, 61%, yellow powder of compound 178; M.P.: 80° C. (gum, K).

Example B12

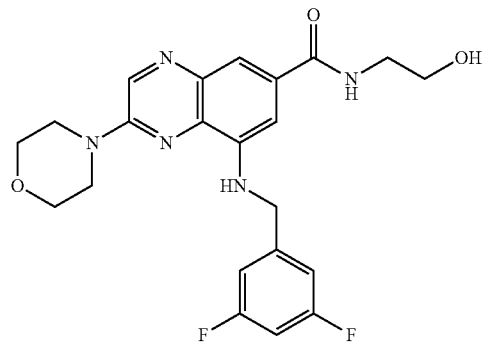 [SMILES: O=C(NCCO)c1cc(NCc2cc(F)cc(F)c2)c2nc(N3CCOCC3)cnc2c1]

Preparation of Compound 229:

TBAF (0.69 mL; 0.69 mmol) was added to a mixture of intermediate 163 (350 mg; 0.63 mmol) in THF (9 mL) and the reaction mixture was stirred at rt for 2 h. The mixture was concentrated and the residue was purified by chromatography over silica gel (SiOH 15 µm; 25 g mobile phase: 100% DCM to 90% DCM, 10% MeOH, 1% NH$_4$OH). The pure fractions were collected and the solvent was evaporated. The residue was crystallized with diisopropylether/ACN (drops) under sonicated. The precipitate was filtered and dried to give 195 mg (63%) of compound 229.

Preparation of Compound 230:

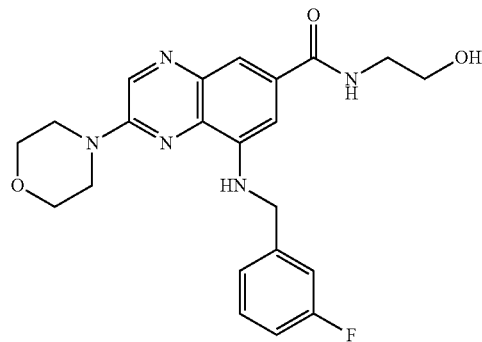 [SMILES: O=C(NCCO)c1cc(NCc2cccc(F)c2)c2nc(N3CCOCC3)cnc2c1]

Compound 230 was prepared according to an analogous procedure as described for the synthesis of compound 229, using intermediate 165 as starting material (186 mg, 79%, M.P.: 218° C. (DSC)).

Preparation of Compound 231:

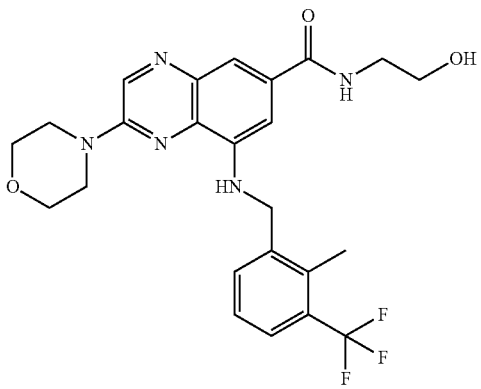 [SMILES: Cc1c(CNc2cc(C(=O)NCCO)cc3ncc(N4CCOCC4)nc23)cccc1C(F)(F)F]

Compound 231 was prepared according to an analogous procedure as described for the synthesis of compound 229, using intermediate 164 as starting material (102 mg, 42%)

Preparation of Compound 232:

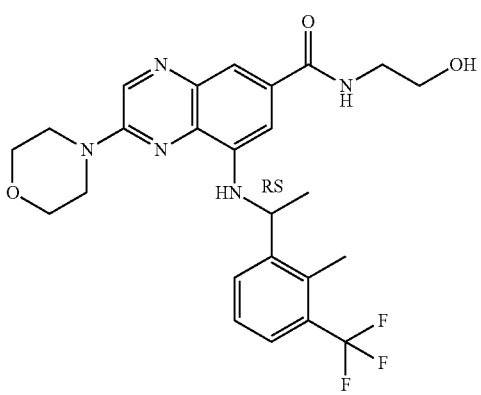 [SMILES: Cc1c(C(C)Nc2cc(C(=O)NCCO)cc3ncc(N4CCOCC4)nc23)cccc1C(F)(F)F]

Compound 232 was prepared according to an analogous procedure as described for the synthesis of compound 229, using intermediate 166 as starting material (197 mg, 82%, M.P.: 181° C. (DSC)).

Preparation of Compound 244:

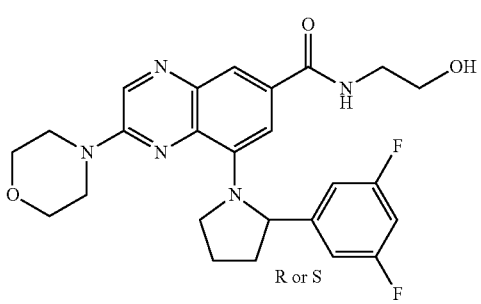 [SMILES: O=C(NCCO)c1cc(N2CCCC2c2cc(F)cc(F)c2)c2nc(N3CCOCC3)cnc2c1]

TBAF (0.37 mL, 1 M, 0.37 mmol) was added to a mixture of intermediate 174 (200 mg, 0.34 mmol) in THF (4.9 mL) and the reaction mixture was stirred at rt for 2 hours. The mixture was concentrated and the residue (420 mg) was purified by chromatography over silica gel (SiOH 15 μm, 25 g mobile phase: gradient from 98% DCM 2% MeOH 0.2% NH$_4$OH to 90% DCM 10% MeOH 0.1% NH$_4$OH). The pure fractions were collected. The solvent was evaporated and crystallized from DIPE/ACN to give 78 mg (48%) of compound 244

Preparation of Compound 245:

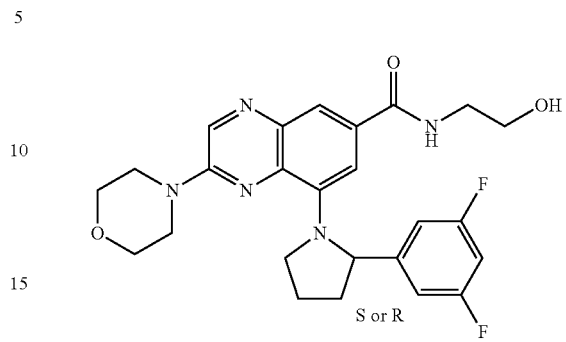

Compound 245 was prepared according to an analogous procedure as described for the synthesis of compound 244, using intermediate 175 as starting material, (87 mg; 41%) of compound 245.

Preparation of Compound 276:

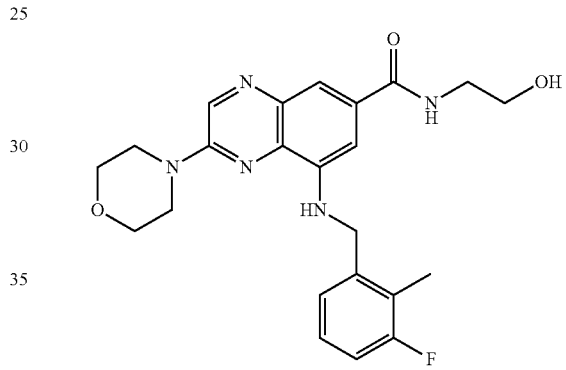

Tetrabutylammoniumfluoride (0.6 mL, 1 M in THF, 0.6 mmol) was added to a mixture of intermediate 180 (300 mg, 0.542 mmol) in THF (8 mL) and the reaction mixture was stirred at rt for 2 hours. The mixture was concentrated and the residue was purified by silica gel chromatography (SiO$_2$ 15 μm, 25 g, mobile phase: 98% DCM 2% MeOH 0.2% NH$_4$OH to 90% DCM 10% MeOH 1.1% NH$_4$OH). The pure fractions were concentrated and the resulting residue was crystallized from DIPE/ACN (drop) under sonication. The precipitate was filtered to give 155 mg (65%) of compound 276 (M.P.: 194° C. (DSC)).

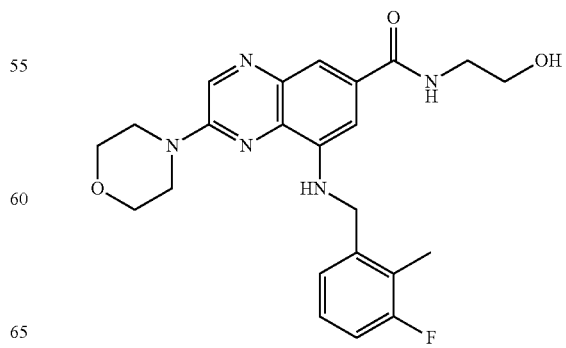

Preparation of Compound 336:

Compound 336 was prepared according to an analogous procedure as described for the synthesis of compound 229, using intermediate 216 as starting material (155 mg, 65%). M.P.: 195° C. (DSC).

Preparation of Compound 343:

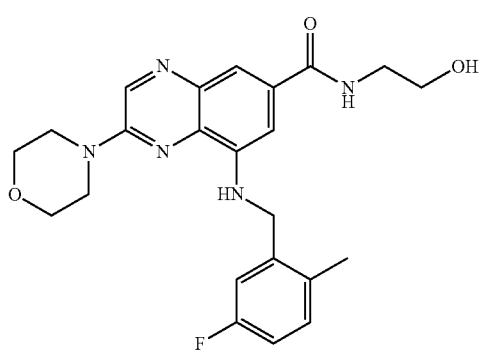 [SMILES: Cc1ccc(F)cc1CNc1cc(C(=O)NCCO)cc2ncc(N3CCOCC3)nc12]

Compound 343 was prepared according to an analogous procedure as described for the synthesis of compound 229, using intermediate 219 as starting material (955 mg, 57%).

Preparation of Compound 391, Compound 391a and Compound 391b

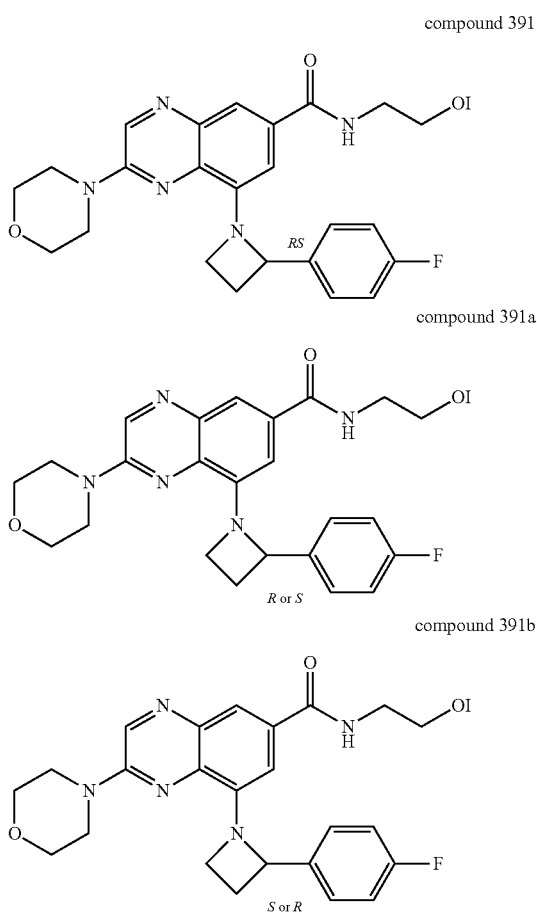

Compound 391 was prepared according to an analogous procedure as described for the synthesis of compound 229 using intermediate 245 as starting material (390 mg; 70%). The separation of the enantiomers was performed by chiral SFC (CHIRALPAK DIACEL OJ 250×20 mm; mobile phase: CO$_2$, EtOH-iPrOH (50-50)+0.4% iPrNH$_2$). The pure fractions were collected and the solvent was evaporated to give, after freeze-drying, 26 mg (5%) of compound 391a and 29 mg (5%) of compound 391b.

Example B13

Preparation of Compound 56:

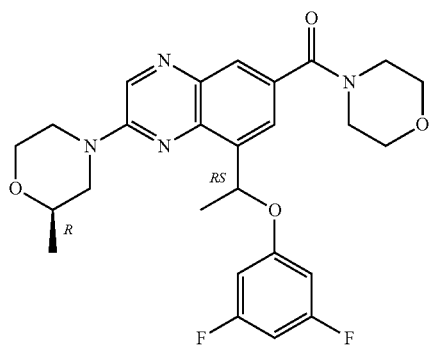

In a microwave vial, 3,5-difluorophenol (31 mg; 0.24 mmol) and PPh$_3$ (62 mg; 0.24 mmol) were added to a solution of intermediate 76 (61 mg; 0.16 mmol) in THF (1.6 mL). Then, di-tert-butyl azodicarboxylate (55 mg; 0.24 mmol) was added and the mixture was stirred at rt for 18 h. Then, more 3,5-difluorophenol (31 mg; 0.24 mmol), PPh$_3$ (62 mg; 0.24 mmol) and di-tert-butyl azodicarboxylate (55 mg; 0.24 mmol) were added successively and the mixture was stirred at 40° C. for 18 h. The mixture was combined with another batch coming from a reaction performed on 20 mg of intermediate 76. The mixture was evaporated under vacuum and taken-up in DCM. The organic layer was washed with a saturated solution of NaHCO$_3$, dried over MgSO$_4$, filtered and evaporated in vacuum. The residue (400 mg, yellow oil) was purified by chromatography over silica gel (irregular SiOH; 15-40 μm; 10 g; gradient: from 100% DCM to 96.5% DCM, 3.5% MeOH). The pure fractions were collected and the solvent was evaporated. The residue (160 mg, yellow solid) was purified by achiral SFC (CYANO 6 μm 150×21.2 mm; mobile phase: 92% CO$_2$, 8% MeOH). The pure fractions were collected and the solvent was evaporated. The residue was freeze-dried with water-ACN (80/20) to give 32 mg (31%, white fluffy solid) of 56. M.P.: 55° C. (DSC).

Preparation of Compound 68:

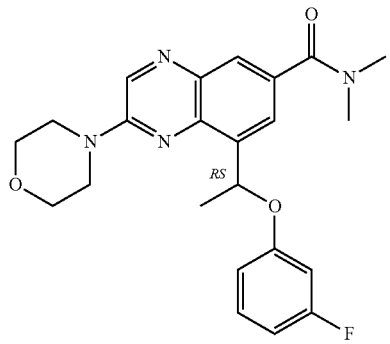 [SMILES: CC(Oc1cccc(F)c1)c1cc(C(=O)N(C)C)cc2ncc(N3CCOCC3)nc12]

Compound 68 was prepared according to an analogous procedure as described for the synthesis of compound 56, using intermediate 17 and 3-fluorophenol as starting materials (freeze-dried: 58 mg, 23%, yellow fluffy solid). M.P.: 49° C. (DSC).

Preparation Compound 73 and Compound 74

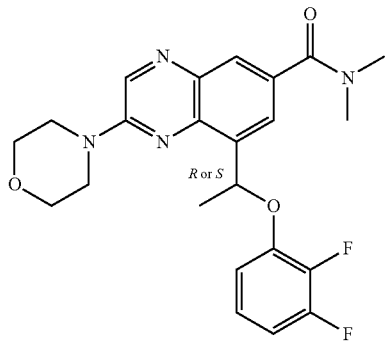

compound 73

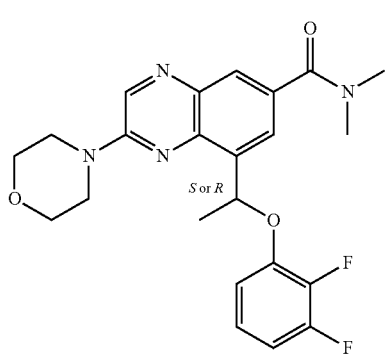

compound 74

Compound 73 and compound 74 were prepared according to an analogous procedure as described for the synthesis of compound 56, using intermediate 17 and 2,3-difluorophenol as starting materials. 63 mg (24%, yellow fluffy solid) of compound 73 and 64 mg (24%, pale fluffy solid) of compound 74 were obtained after chiral SFC (Stationary phase: CHIRALPAK AD-H 5 μm 250×20 mm, Mobile phase: 70% CO$_2$, 30% EtOH) purification.

Preparation of Compound 78:

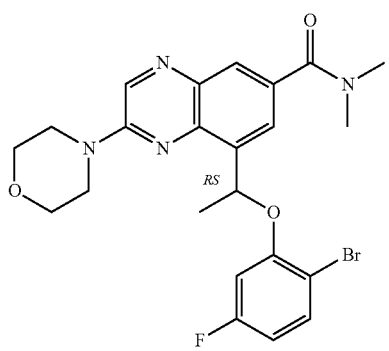 [SMILES: CC(Oc1cc(F)ccc1Br)c1cc(C(=O)N(C)C)cc2ncc(N3CCOCC3)nc12]

Compound 78 was prepared according to an analogous procedure as described for the synthesis of compound 56, using intermediate 17 and 2-bromo-5-fluorophenol as starting materials (freeze-dried: 24 mg, 3%, yellow fluffy solid). M.P.: 235° C. (DSC).

Preparation of Compound 151:

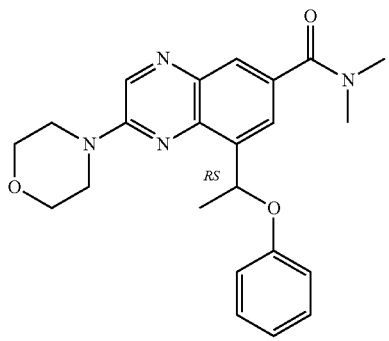 [SMILES: CC(Oc1ccccc1)c1cc(C(=O)N(C)C)cc2ncc(N3CCOCC3)nc12]

In a sealed glassware, phenol (41 mg; 0.43 mmol) and cyanomethylenetributylphosphorane (0.15 mL; 0.58 mmol) were added to a solution of intermediate 17 (100 mg; 0.29 mmol) in toluene (3 mL). The reaction mixture was stirred at 60° C. overnight. The mixture was evaporated under vacuum to dryness. The residue (350 mg, brown oil) was purified by chromatography over silica gel (40 g; mobile phase: 40% heptane, 10% MeOH, 50% EtOAc, 0.5% NH$_4$OH). The pure fractions were collected and the solvent was evaporated until dryness. The residue (120 mg) was purified by chromatography over silica gel (40 g; mobile phase: 45% heptane, 5% MeOH, 50% EtOAc, 0.5% NH$_4$OH). The pure fractions were collected and the solvent was evaporated to give 17 mg (14%) of compound 151. M.P.: 80° C. (gum, K).

Preparation of Compound 209:

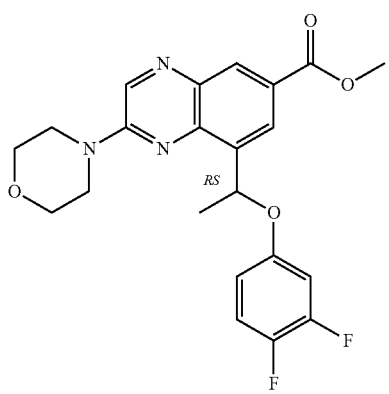 [SMILES: COC(=O)c1cc(C(C)Oc2ccc(F)c(F)c2)c2nc(N3CCOCC3)cnc2c1]

Compound 209 was prepared according to an analogous procedure as described for the synthesis of compound 151, using intermediate 15 and 3,4-difluorophenol as starting materials (crystallized from diethylether: 1.4 g, 52%). M.P.: 183° C. (DSC).

Preparation of Compound 247:

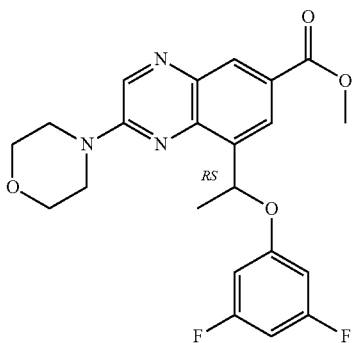 [SMILES: COC(=O)c1cc(C(C)Oc2cc(F)cc(F)c2)c2nc(N3CCOCC3)cnc2c1]

3,5-difluorophenol (480 mg; 3.69 mmol), di-tert-butyl azodicarboxylate (849 mg; 3.69 mmol) and PPh₃ (967 mg; 3.69 mmol) were added to a solution of intermediate 15 (1 g; 2.46 mmol) in THF (24 mL). The reaction mixture was stirred at rt overnight. Then, additional 3,5-difluorophenol (480 mg; 3.69 mmol), di-tert-butyl azodicarboxylate (849 mg; 3.69 mmol) and PPh₃ (967 mg; 3.69 mmol) were added and the mixture was stirred at 60° C. for 4 h. The mixture was filtered through a pad of Celite® and the filtrate was evaporated under vacuum. The residue was triturated in Et₂O, filtered and the filtrate was evaporated under vacuum. The resulting residue (2.5 g, orange oil) was purified chromatography over silica gel (regular SiOH 30 µm; 80 g; mobile phase: from 100% DCM to 70% DCM, 30% EtOAc). The pure fractions were collected and the solvent was evaporated to give 1.36 g (84%, yellow oil) of compound 247.

Preparation of Compound 256:

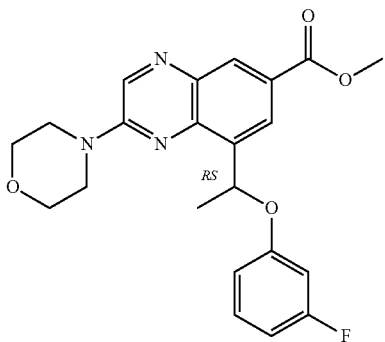 [SMILES: COC(=O)c1cc(C(C)Oc2cccc(F)c2)c2nc(N3CCOCC3)cnc2c1]

Compound 256 was prepared according to an analogous procedure as described for the synthesis of compound 247, using intermediate 15 and 3-fluorophenol as starting materials (1.44 g, 46%, yellow oil).

Alternative Pathway:

Compound 256 was prepared according to an analogous procedure as described for the synthesis of compound 277, using intermediate 15 and 3-fluorophenol as starting materials (1.57 g, 62%, yellow powder).

Preparation of Compound 277:

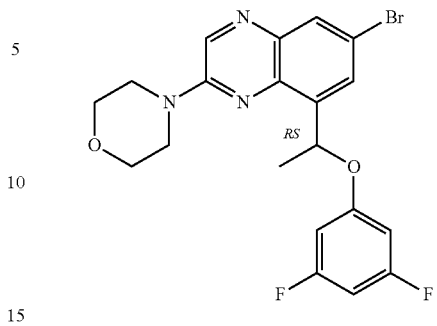

3,5-difluorophenol (228 mg; 1.76 mmol) and cyanomethylenetributylphosphorane (614 µL; 2.34 mmol) were successively added to a solution of intermediate 56 (396 mg; 1.17 mmol) in toluene (11.9 mL). The reaction mixture was heated at 60° C. overnight. The resulting solution was concentrated under reduced pressure. The residue was purified by chromatography over silica gel (irregular SiOH; 15-40 µm; 24 g; gradient: from 90% heptane, 9% EtOAc, 1% MeOH to 60% heptane, 36% EtOAc, 4% MeOH). The pure fractions were collected and the solvent was evaporated 330 mg (63%, pale orange powder) of compound 277.

Preparation of Compound 310:

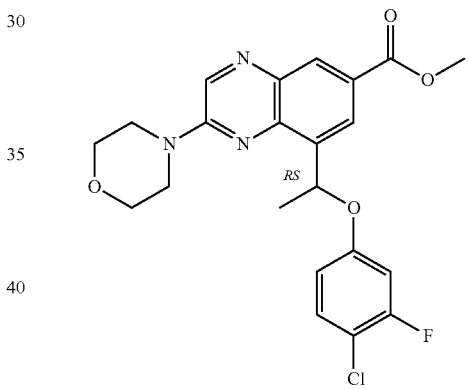

Compound 310 was prepared according to an analogous procedure as described for the synthesis of compound 151 using intermediate 15 and 4-chloro-3-fluorophenol as starting materials (1.75 g, 100%).

Preparation of Compound 377,

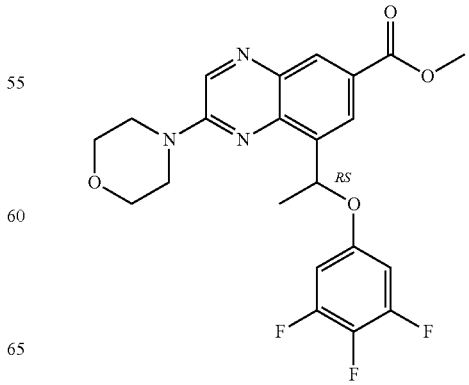

Compound 377 was prepared according to an analogous procedure as described for the synthesis of compound 151, using intermediate 15 and 3,4,5-Trifluorophenol as starting material (2.13 g, 62%).

Preparation of Compound 403, Compound 403a and Compound 403b

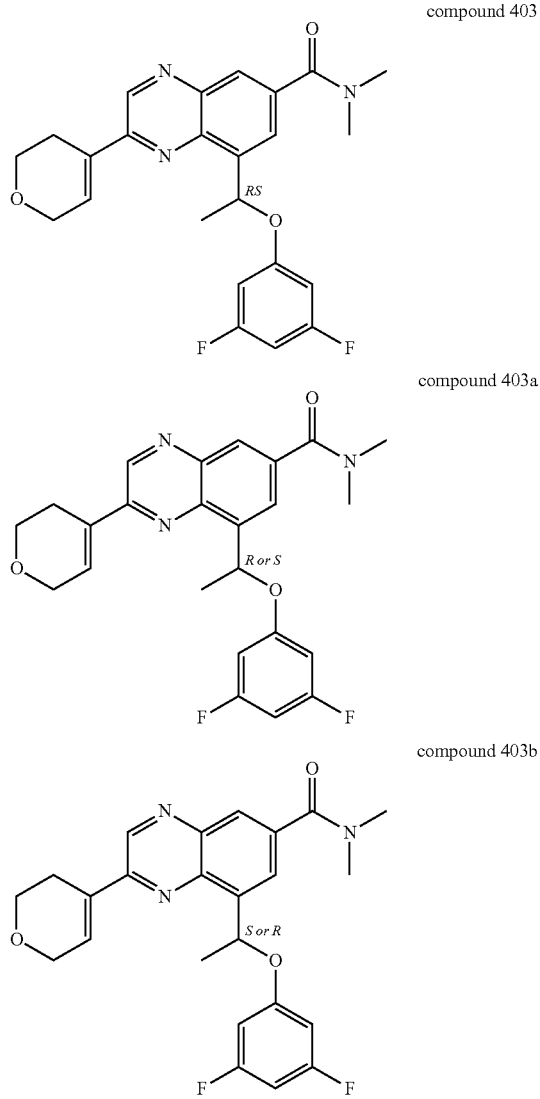

Compound 403 was prepared according to an analogous procedure as described for the synthesis of compound 247, using intermediate 17 and 3,5-difluorophenol as starting materials (233 mg, 99%).

The separation of the enantiomers was performed by chiral SFC (Stationary phase: CHIRALPAK AD-H 5 μm 250×20 mm, Mobile phase: 75% $CO_2$, 25% iPrOH). The pure fractions were mixed and the solvent was evaporated to afford respectively, after freeze-drying, 32 mg (15%) of compound 403a (MP: 53° C., DSC) and 31 mg (14%) of compound 403b (MP: 54° C., DSC).

Example B14

Preparation of Compound 96:

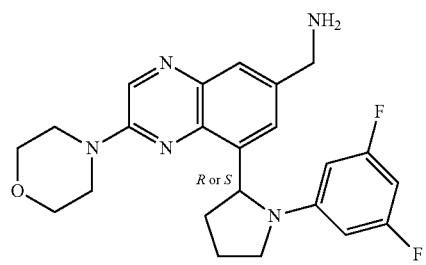 [SMILES: NCc1cc(C2CCCN2c2cc(F)cc(F)c2)c2nc(N3CCOCC3)cnc2c1]

Hydrazine hydrate (132 mg; 1.35 mmol) was added to a solution of intermediate 104 (750 mg; 1.35 mmol) in MeOH (20 mL). The solution was heated at reflux (70° C.) for 20 h. The solution was poured into cooled water and the organic layer was extracted with DCM, dried over $MgSO_4$, filtered and evaporated until dryness. The residue (425 mg) was purified by chromatography over silica gel (irregular 15-40 μm; 24 g; mobile phase: 90% DCM, 10% MeOH, 0.1% $NH_4OH$). The pure fractions were collected and evaporated. The residue (97 mg) was purified by chromatography over silica gel (irregular 15-40 μm; 24 g; mobile phase: 90% DCM, 10% MeOH, 0.1% $NH_4OH$). The pure fractions were collected and evaporated until dryness to give 45 mg (8%) of compound 96. M.P.: 80° C. (gum, K).

Example B15

Preparation of Compound 233:

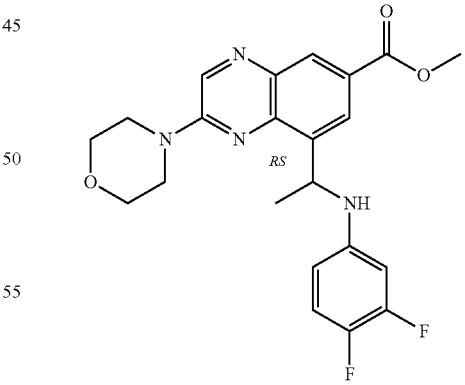

Compound 233 was prepared according to an analogous procedure as described for the synthesis of compound 262, using intermediate 105 and 3,4-difluoroaniline as starting material (7 g; 52%) M.P.: 210° C. (K)).

Preparation of Compound 235:

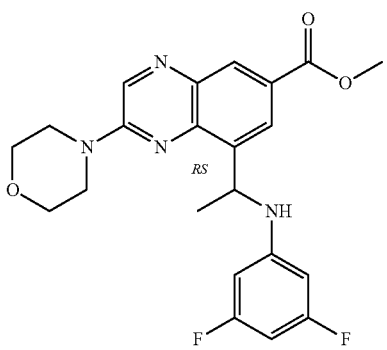 [SMILES: COC(=O)c1cc(C(C)Nc2cc(F)cc(F)c2)c2nc(N3CCOCC3)cnc2c1]

3,5-difluoroaniline (16.4 g; 0.13 mmol) was added to a solution of intermediate 105 (8.5 g; 0.025 mol) in DMF (200 mL) under $N_2$. The solution was stirred at 60° C. for 48 hours in a sealed tube. The solution was cooled, poured out into cooled water, basified with $K_2CO_3$ and EtOAc was added. The mixture was extracted with EtOAc and the organic layer was concentrated. The residue was taken up $Et_2O$ and a precipitate was filtered and dried given 7.2 g (66%) of compound 235.

Example B16

Preparation Compound 250:

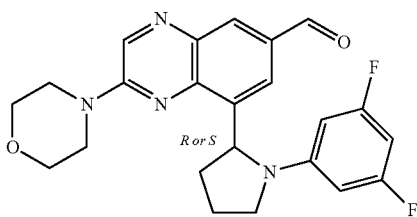 [SMILES: O=Cc1cc(C2CCCN2c2cc(F)cc(F)c2)c2nc(N3CCOCC3)cnc2c1]

$MnO_2$ (2.08 g; 24 mmol) was added portionwise to a solution of compound 10 (1.7 g; 3.99 mmol) in DCM (77 mL). The reaction mixture was stirred at rt overnight. The mixture was filtered through a pad of Celite® and the filtrate was evaporated to give 1.65 g (97%) of compound 250. M.P: 120° C. (K).

Preparation of Compound 271:

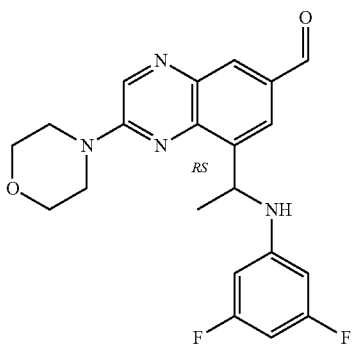 [SMILES: CC(Nc1cc(F)cc(F)c1)c1cc(C=O)cc2ncc(N3CCOCC3)nc12]

Manganese oxide (782 mg; 8.99 mmol) was added portionwise to a solution of compound 84 (600 mg; 1.5 mmol) in DCM (30 mL). The mixture was stirred at rt overnight. The mixture was filtered through a pad of Celite® and evaporated until dryness. Then, the residue was taken-up with diisopropylether to give 500 mg (83%) of compound 271. In case this compound was used in a conversion to another compound, it was used as such without further purification.

Example B17

Preparation of Compound 262:

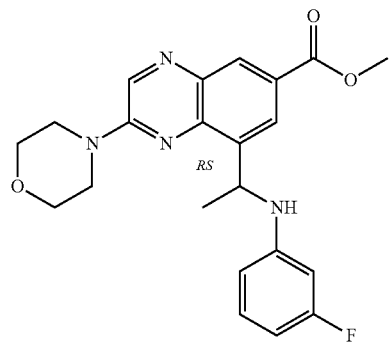 [SMILES: COC(=O)c1cc(C(C)Nc2cccc(F)c2)c2nc(N3CCOCC3)cnc2c1]

Thioglycolic acid (234 μL; 3.36 mmol) was added to a solution of intermediate 107 ((1 g; 1.68 mmol) and 1,8-diazabicyclo(5.4.0)undec-7-ene (1 mL; 6.72 mmol) in ACN (16 mL). The solution was stirred at rt for 1 h. Then DCM and 10% aqueous solution of $Na_2CO_3$ were added. The organic layer was separated and the aqueous layer was extracted with DCM (2×). The combined organic layers were dried over $MgSO_4$, filtered and evaporated under vacuum. The residue was purified by chromatography over silica gel (Irregular SiOH 15-40 μm; 30 g; gradient: from 100% DCM to 95% DCM, 5% MeOH/$NH_4OH$ (95/5)). The pure fractions were collected and the solvent was evaporated to give 2 fractions of compound 262 respectively 242 mg (35%, yellow solid) and 382 mg (55%, pale brown solid). Global yield: 90%

Alternative Pathway:

3-fluoroaniline (1.75 mL; 18.17 mmol) was added to a solution of intermediate 105 (1.05 g; 3.13 mmol) in DMF (12 mL) under $N_2$. The solution was stirred at 60° C. for 48 h in a sealed tube. The solution was cooling down to rt, then poured into cooled water and basified with $K_2CO_3$. EtOAc was added. The organic layer was extracted, washed with $H_2O$, dried over $MgSO_4$ and evaporated to dryness. The residue (3.4 g) was taken-up with DCM, MeOH and $Et_2O$. A precipitate was filtered, washed with a mixture of MeOH and $Et_2O$ and dried to give 0.66 g (51%) of compound 262. M.P.: 222° C. (DSC).

Preparation of Compound 262a and Compound 262b

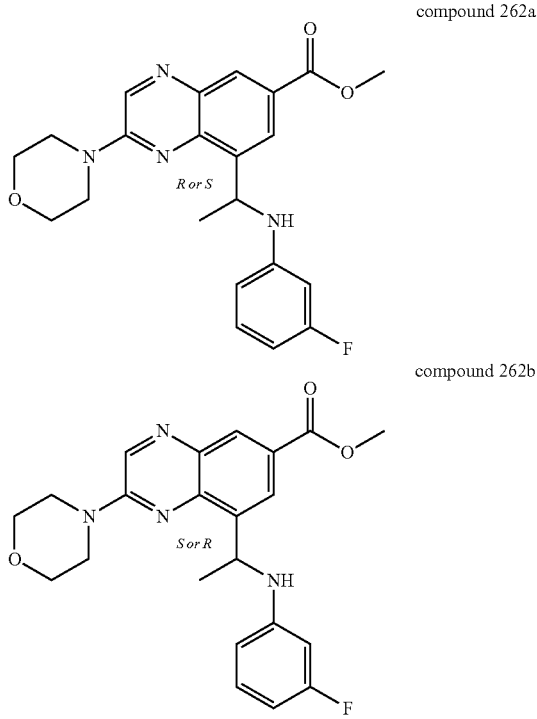

compound 262a compound 262b

Compound 262a and 262b were obtained after separation of compound 262 by SFC (Stationary phase: Chiralpak AD-H 5 µm 250*30 mm, Mobile phase: 70% $CO_2$, 25% iPrOH (0.3% $iPrNH_2$)). After concentration of the solvent, each fraction was crystallized from $Et_2O$ yielding, after filtration, 747 mg (37%) of compound 262a (M.P: 199.7° C. (DSC)) and 775 mg (39%) of compound 262b, (M.P: 199.5° C. (DSC)).

Alternative Preparation of Compound 262a:

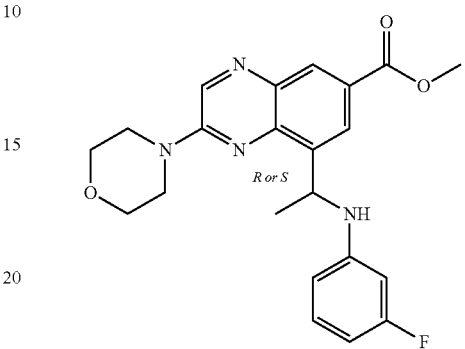

Intermediate 182 was dissolved in acetonitrile (10 volumes) and 1,8-diazabicyclo[5.4.0]undec-7-ene (4.0 eq.) and 2-mercaptoacetic acid (2.0 eq.) were added. The reaction mixture was stirred for 16 hours at room temperature. After concentration to about 2 volumes, water (7 volumes) was added. Compound 262a was isolated and dried in 92% yield (e.e.: 83.3%).

To improve the e.e., the solid obtained as described above was slurried twice in EtOAc according to the scheme below:

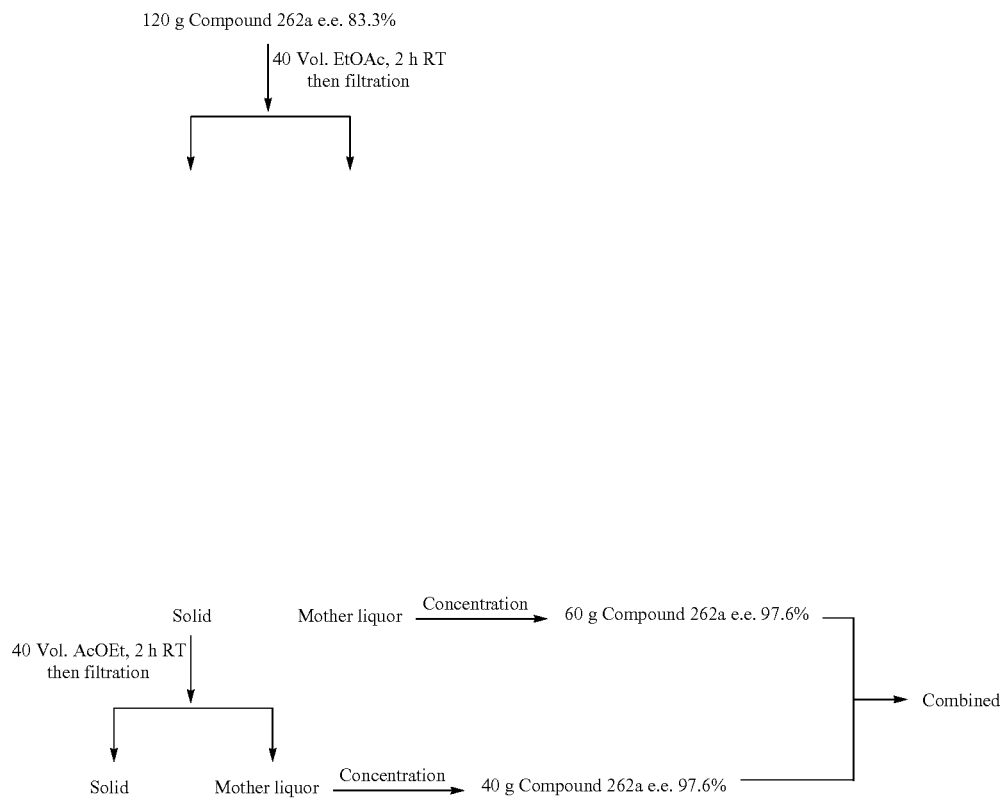

Example B18

Preparation of Compound 278:

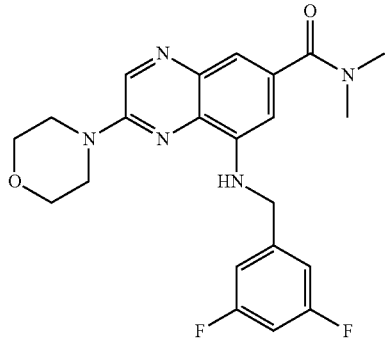 [SMILES: CN(C)C(=O)c1cc(NCc2cc(F)cc(F)c2)c2nc(N3CCOCC3)cnc2c1]

A mixture of intermediate 5 (200 mg; 0.55 mmol), 3,5-difluorobenzylamine (117.5 mg; 0.82 mmol) and cesium carbonate (535.2 mg; 1.64 mmol) in toluene (3 mL) was purged with nitrogen. Then, BrettPhos Precatalyst First Gen (4.4 mg; 0.0055 mmol) was added. The tube was sealed and the reaction was heated at 100° C. for 72 hours. Then, the reaction was cooled down to rt, poured onto water and filtered through a pad of Celite®. The aqueous layer was extracted with EtOAc. The organic layer was dried over $MgSO_4$, filtered and concentrated.

The residue (420 mg) was purified by silica gel chromatography (irregular SiOH, 30 g, mobile phase: 97% DCM 3% MeOH 0.1% $NH_4OH$). The fractions containing the product were mixed and concentrated to afford 225 mg of an intermediate fraction which was taken up with $Et_2O$. The resulting precipitate was filtered, washed with $Et_2O$ twice then dried to afford 80 mg (34%) of compound 278. M.P. 158° C. (K).

Preparation of Compound 288

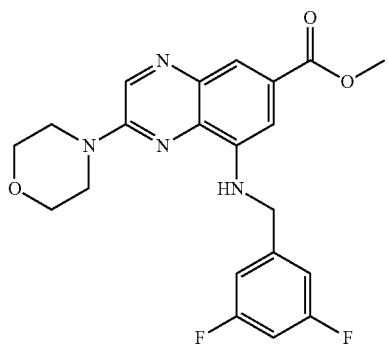 [SMILES: COC(=O)c1cc(NCc2cc(F)cc(F)c2)c2nc(N3CCOCC3)cnc2c1]

Compound 288 was prepared according to an analogous procedure as described for the synthesis of intermediate 163, using intermediate 3a as starting material and 3,5-difluorobenzylamine. (7.67 g; 66%)

Preparation of Compound 305

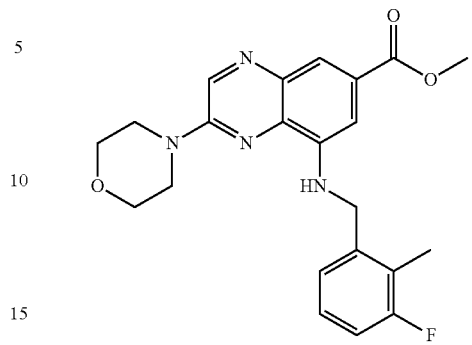

In a schlenk round flask, a mixture of intermediate 3a (10 g, 28.394 mmol), 3-Fluoro-2-methylbenzylamine 4.428 mL, 34.073 mmol) and cesium carbonate (18.503 g, 56.788 mmol) in tert-amyl alcohol (130 mL) was degazed with $N_2$. 2-Dicyclohexylphosphino-2',6'-diisopropoxybiphenyl (0.662 g, 1.42 mmol) and BrettPhos Precatalyst First Gen (1.134 g, 1.42 mmol) were added, The reaction mixture was purged with $N_2$ and heated at 100° C. for 18 h. The reaction mixture was poured into water and EtOAc. The organic layer was separated, washed with brine, dried over $MgSO_4$ and evaporated till dryness. The residue was taken up with DIPE. Then, the solid was filtered to give (7.8 g, 67%) of compound 305.

Preparation of Compound 383

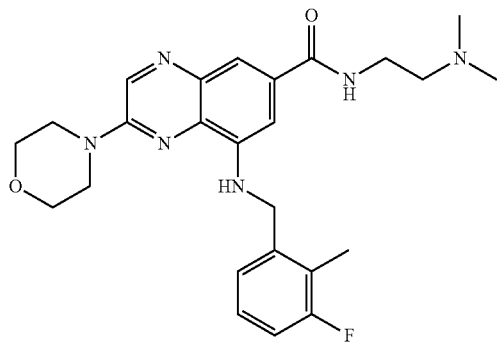 [SMILES: Cc1c(F)cccc1CNc1cc(C(=O)NCCN(C)C)cc2ncc(N3CCOCC3)nc12]

Compound 383 was prepared according to an analogous procedure as described for the synthesis of compound 305 using intermediate 237 and 3-fluoro-2-methylbenzylamine as starting materials (204 mg, 43%, M.P: 172° C. (DSC)).

Preparation of Compound 395, Compound 395a and Compound 395b compound 395

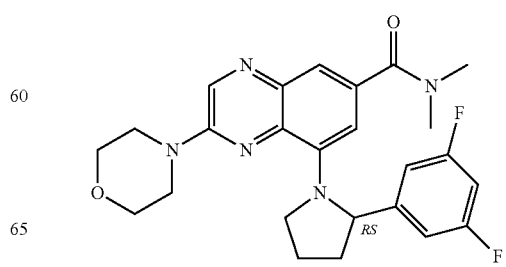

-continued compound 395a
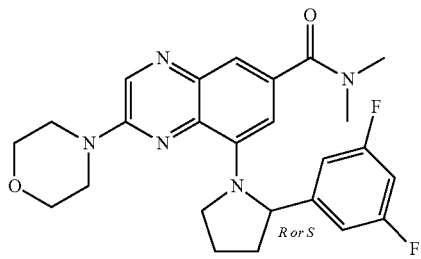

compound 395b
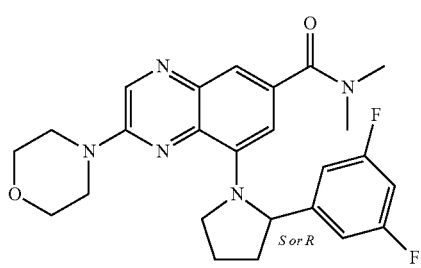

Compound 395 was prepared according to an analogous procedure as described for the synthesis of compound 1 using intermediate 5 and 2-(3,5-difluorophenyl)pyrrolidine as starting materials (133 mg, 42%, M.P: 80° C., gum (K)).

The separation of the enantiomers was performed by chiral SFC (Stationary phase: CHIRALPAK AD-H 5 μm 250×20 mm, Mobile phase: 75% CO$_2$, 25% iPrOH (0.3% iPrNH$_2$)). The pure fractions were mixed and the solvent was evaporated to afford, after freeze-drying, respectively 47 mg (15%) of compound 395a (MP: 90° C., gum, K) and 45 mg (14%) of compound 395b (MP: 102° C., K).

Preparation of Compound 396 (Mixture of 4 Unseparable Diastereoisomers)

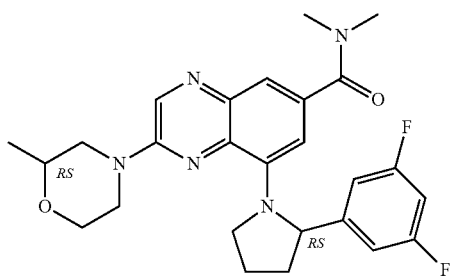 [SMILES: CC1CN(c2cnc3cc(C(=O)N(C)C)cc(N4CCCC4c4cc(F)cc(F)c4)c3n2)CCO1]

Compound 396 was prepared according to an analogous procedure as described for the synthesis of compound 1 using intermediate 5 and 2-(3,5-difluorophenyl)pyrrolidine as starting materials (89 mg, 50%).

Preparation of Compound 397, Compound 397a and Compound 397b compound 397
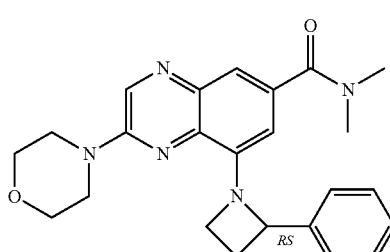

compound 397a
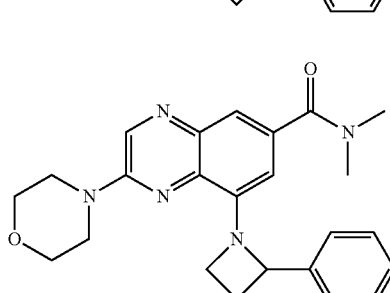

compound 397b
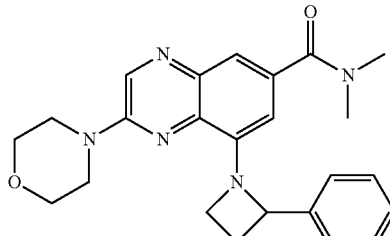

Compound 397 was prepared according to an analogous procedure as described for the synthesis of compound 1 using intermediate 5 and 2-(4-fluorophenyl)azetidine as starting materials (450 mg, 75%).

The separation of the enantiomers was performed by chiral SFC (Stationary phase: CHIRALCEL OJ-H 5 μm 250×20 mm, Mobile phase: 73% CO$_2$, 27% iPrOH). The pure fractions were mixed and the solvent was evaporated to afford, respectively, 60 mg of compound 397a (MP: 80° C., gum, K) and 92 mg of compound 397b (MP: 80° C., gum, K).

Preparation of Compound 398

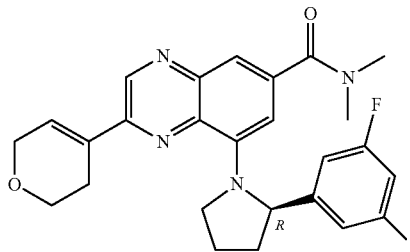

Compound 398 was prepared according to an analogous procedure as described for the synthesis of compound 1 using intermediate 28a and (2R)-2-(3,5-difluorophenyl)pyrrolidine as starting materials (32 mg, 28%).

Preparation of Compound 399

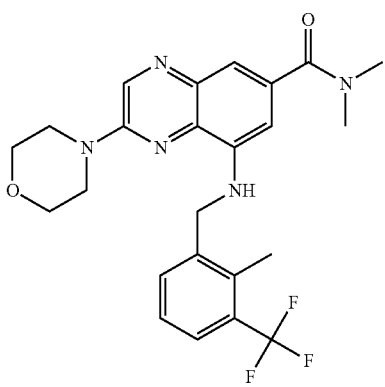 [SMILES: Cc1c(CNc2cc(C(=O)N(C)C)cc3ncc(N4CCOCC4)nc23)cccc1C(F)(F)F]

Compound 399 was prepared according to an analogous procedure as described for the synthesis of compound 278 using intermediate 5 and 2-Methyl-3-(trifluoromethyl)benzylamine as starting materials (55 mg, 21%, MP: 202° C. (K)).

Preparation of Compound 400

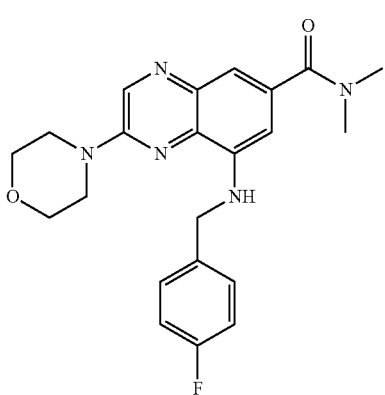 [SMILES: CN(C)C(=O)c1cc(NCc2ccc(F)cc2)c2nc(N3CCOCC3)cnc2c1]

Compound 400 was prepared according to an analogous procedure as described for the synthesis of compound 278 using intermediate 5 and 4-fluorobenzylamine as starting materials (92 mg, 41%, MP: 80° C., gum (K)).

Preparation of Compound 401

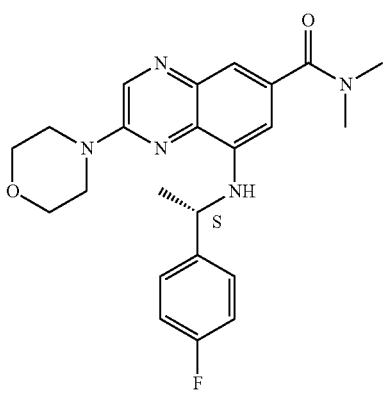

Compound 401 was prepared according to an analogous procedure as described for the synthesis of compound 278 using intermediate 5 and (S)-4-Fluoro-α-methylbenzylamine as starting materials (6 mg, 3%, MP: 80° C., gum (K)).

Preparation of Compound 402

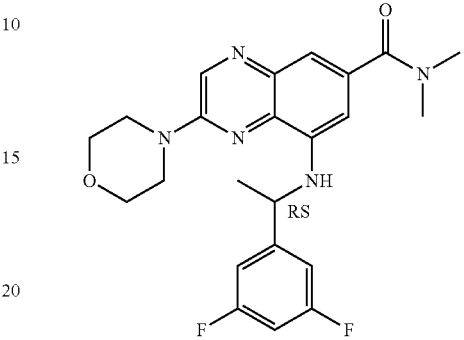

Compound 402 was prepared according to an analogous procedure as described for the synthesis of compound 278 using intermediate 5 and (RS)-1-(3,5-Difluorophenyl)ethylamine as starting materials (25 mg, 5%, MP: 80° C., gum (K)).

Example B19

Preparation of Compound 301

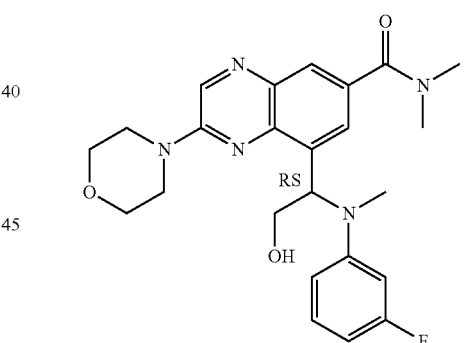

In a sealed tube, 3-fluoro-1-methylaniline (60.4 µL, 0.536 mmol) was added to a solution of intermediate 191 (177 mg, 0.536 mmol) and glycolaldehyde dimer (32.2 mg, 0.268 mmol) in hexafluoroisopropanol (1.07 mL). The mixture was stirred at room temperature for 14 days. The resulting solution was concentrated under reduced pressure. The crude product was purified by reverse phase (Stationary phase: X-Bridge-C18 5 µm 30*150 mm, Mobile phase: Gradient from 85% aq. NH$_4$HCO$_3$ 0.2%, 15% ACN to 45% aq. NH$_4$HCO$_3$ 0.2%, 55% ACN) to give compound 301 (18.6 mg, 8%, MP: 315° C., DSC) as a yellow powder

Example B20

Preparation of Compound 326

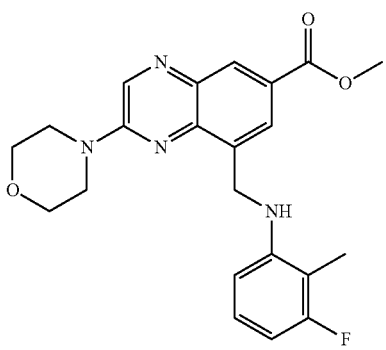 [SMILES: COC(=O)c1cc(CNc2cccc(F)c2C)c2nc(N3CCOCC3)cnc2c1]

To a solution of intermediate 212 (949 mg, 2.32 mmol) in DCM (23 mL) was added sodium triacetoxybororohydride (1.48 g, 6.97 mmol). The mixture was stirred at rt overnight then DCM and water were added. The organic layer was separated, dried over MgSO$_4$, filtered off and evaporated in vacuo to give 1.52 g of compound 326 as a yellow solid directly used in the next step without any further purification.

Preparation of Compound 330:

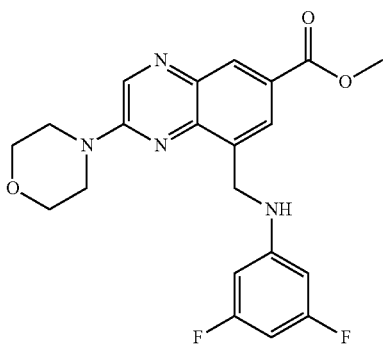 [SMILES: COC(=O)c1cc(CNc2cc(F)cc(F)c2)c2nc(N3CCOCC3)cnc2c1]

Compound 330 was prepared according to an analogous procedure as described for the synthesis of compound 326 using intermediate 214 as starting material (504 mg, used without purification in the next step).

Example B21

Preparation of Compound 339, Compound 339a and Compound 339b compound 397

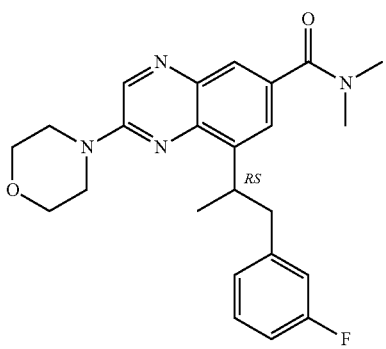

compound 339a

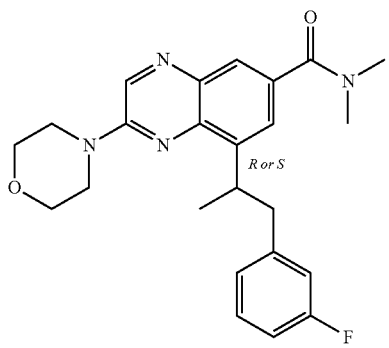

compound 339b

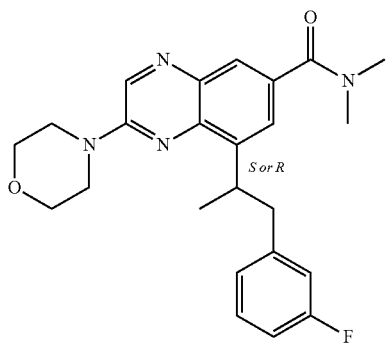

A solution of 3-fluorophenylacetone (110 mg, 0.723 mmol) and N-tosylhydrazine (135 mg, 0.723 mmol) in 1,4-dioxane (2.89 mL) was stirred at 80° C. for 1.5 h. K2CO$_3$ (150 mg, 1.08 mmol) and intermediate 191 (386 mg, 1.08 mmol) were successively added and the reaction mixture was heated to 110° C. for 3 days. The resulting solution was cooled down to room temperature and concentrated under reduced pressure. The residue was taken up in a saturated aqueous NaHCO$_3$ solution (10 mL) and extracted with DCM (3×20 mL). The combined organic layers were washed with a saturated aqueous NaHCO$_3$ solution (2×20 mL) and brine (20 mL), dried over MgSO$_4$, filtered and concentrated under reduced pressure.

The residue was purified by silica gel chromatography (irregular SiOH, 15-40 μm, 24 g, mobile phase gradient: from DCM 100% to DCM 80%, MeOH 20%) to give of an impure fraction of compound 339 as an orange foam This residue was purified by reverse phase (Stationary phase: X-Bridge-C18 5 μm 30*150 mm, Mobile phase: Gradient from 65% aq. NH$_4$HCO$_3$ 0.2%, 35% ACN to 25% aq. NH$_4$HCO$_3$ 0.2%, 75% ACN) to give 105 mg (34%) of compound 339 as a yellow powder. M: 117° C. (DSC).

Compound 339 was purified by chiral SFC (Stationary phase: CHIRALPAK AD-H 5 μm 250×20 mm, Mobile phase: 70% CO$_2$, 30% iPrOH) to give 2 fractions which were triturated in a mixture of pentane/Et$_2$O (5:1, 6 mL). The precipitates were filtered on glass frit to give 16.1 mg (5%) of compound 339a_as a light yellow powder (M.P: 131° C. (DSC) and 16.7 mg, (5%) of compound 339b as a light yellow powder (M.P: 128° C. (DSC).

C. Conversion to Final Compounds

Conversion C1

Preparation of Compound 5, Compound 6 and Compound 53

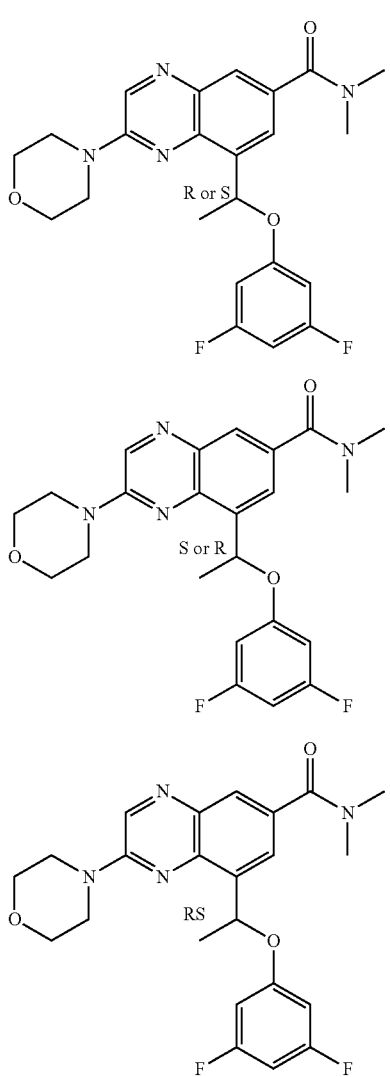

compound 5 compound 6 compound 53

DIPEA (0.42 mL; 2.41 mmol) and HBTU (365 mg; 0.963 mmol) were added to a solution of compound 248 (400 mg; 0.96 mmol) in dry DMF (9.5 mL). The reaction mixture was stirred at rt for 30 min. Then, dimethylamine (2M in THF) (0.72 mL; 1.44 mmol) was added and the reaction mixture was stirred at rt overnight. The mixture was evaporated in vacuum and the residue was taken-up with EtOAc. The organic layer was washed with a saturated aqueous solution of NaHCO$_3$, brine (2×), dried over MgSO$_4$, filtered and evaporated under vacuum. The residue (520 mg, beige foam) was purified by chromatography over silica gel (irregular SiOH 15-40 μm; 25 g; mobile phase: from 100% DCM to 40% DCM, 60% EtOAc). The pure fractions were collected and the solvent was evaporated to give 393 mg (92%) of compound 53. The residue (393 mg) was purified by chiral SFC (CHIRALPAK AD-H; 5 μm 250×20 mm; mobile phase: 75% CO$_2$, 25% EtOH). The pure fractions were collected and the solvent was evaporated to give two fractions which were freeze-dried with water-ACN to give 186 mg (44%, pale yellow fluffy solid) of compound 5 and 182 mg (43%, pale yellow fluffy solid) of compound 6.

Preparation of Compound 33: A

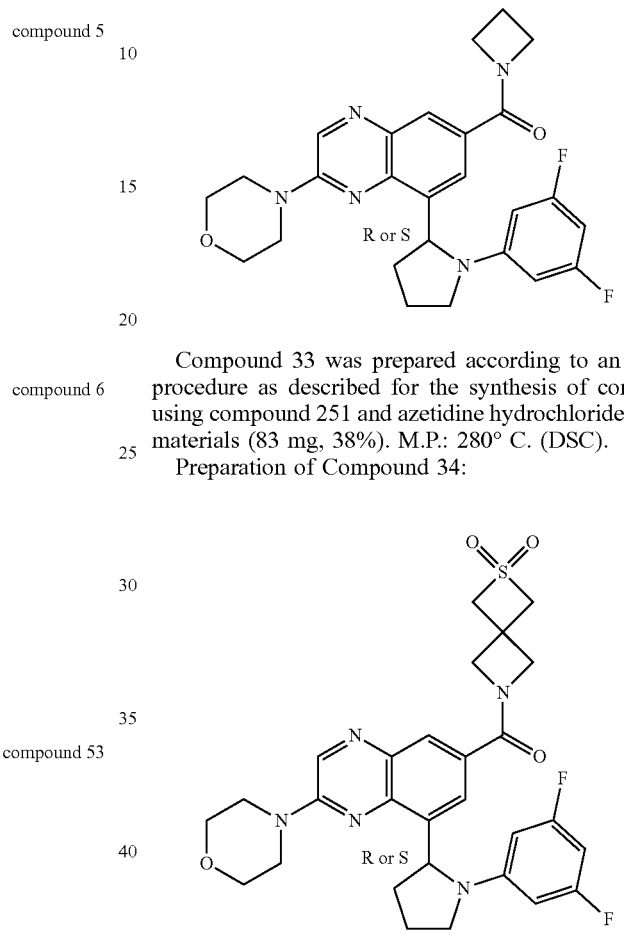

Compound 33 was prepared according to an analogous procedure as described for the synthesis of compound 5, using compound 251 and azetidine hydrochloride as starting materials (83 mg, 38%). M.P.: 280° C. (DSC).

Preparation of Compound 34:

Compound 34 was prepared according to an analogous procedure as described for the synthesis of compound 5, using compound 251 and 2-thia-6-azaspiro[3.3]heptane,2,2-dioxide,2,2,2-trifluoroacetate as starting materials (68 mg, 48%). M.P.: 160° C. (K).

Preparation of Compound 37:

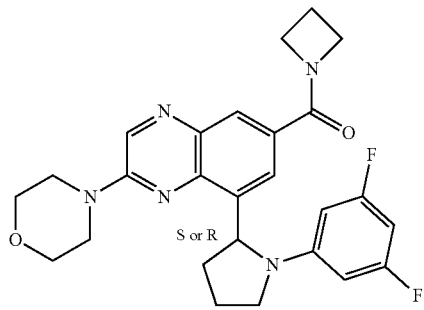 [SMILES: O=C(c1cc(C2CCCN2c2cc(F)cc(F)c2)c2nc(N3CCOCC3)cnc2c1)N1CCC1]

Compound 37 was prepared according to an analogous procedure as described for the synthesis of compound 5, using compound 253 and azetidine hydrochloride as starting materials (61 mg, 43%). M.P.: 276° C. (DSC).

Preparation of Compound 38:

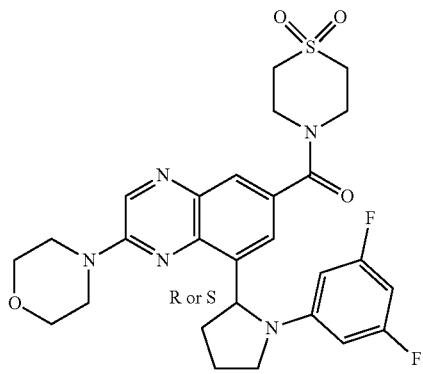 [SMILES: O=C(c1cc(C2CCCN2c2cc(F)cc(F)c2)c2nc(N3CCOCC3)cnc2c1)N1CCS(=O)(=O)CC1]

Compound 38 was prepared according to an analogous procedure as described for the synthesis of compound 5, using compound 251 and thiomorpholine 1,1-dioxide as starting materials (67 mg, 48%). M.P.: 146° C. (K).

Preparation of Compound 39:

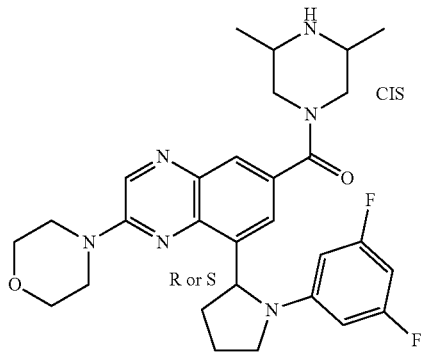

Under N2, at rt, 2,6-Dimethylpiperazine (44 mg; 0.38 mmol) was added to a solution of compound 251 (110 mg; 0.25 mmol), HBTU (142 mg; 0.38 mmol), and DIPEA (0.13 mL; 0.75 mmol) in DMF (3 mL). The solution was stirred at rt for 64 hours. The solution was poured into cooled water. The product was extracted with DCM and the organic layer was dried over MgSO$_4$, filtered and evaporated to dryness. The residue (180 mg) was purified by silica gel chromatography (Spherical bare silica 5 μm 150×30.0 mm, Mobile phase: Gradient from 98% DCM, 2% MeOH (+10% NH$_4$OH) to 88% DCM, 12% MeOH (+10% NH$_4$OH)). The fractions were collected and evaporated until dryness and freeze-dried with CH$_3$CN/water to afford 81 mg (60%) of compound 39. M.P.: 80° C. (gummed, K)).

Preparation of Compound 40:

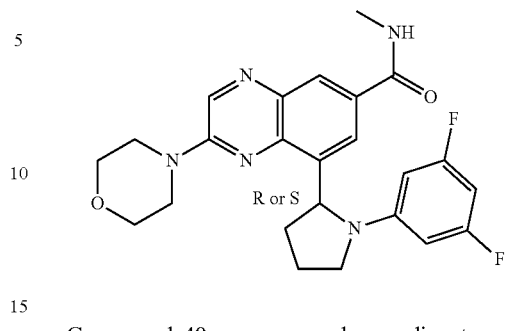

Compound 40 was prepared according to an analogous procedure as described for the synthesis of compound 5, using compound 251 and methylamine (2M in THF) as starting materials (freeze-dried: 51 mg, 35%, yellow powder). M.P.: 80° C. (gum, K).

Preparation of Compound 43:

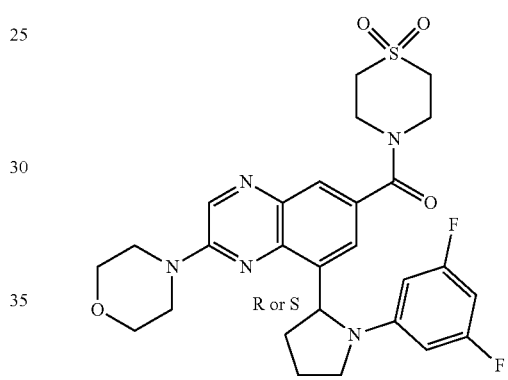

Compound 43 was prepared according to an analogous procedure as described for the synthesis of compound 5, using compound 253 and thiomorpholine 1,1-dioxide as starting materials (freeze-dried: 46 mg, 45%). M.P.: 80° C. (gum, K).

Preparation of Compound 46:

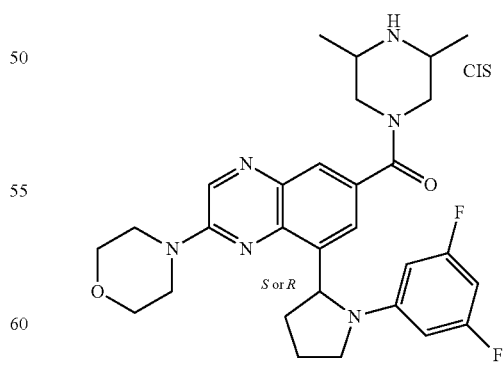

Compound 46 was prepared according to an analogous procedure as described for the synthesis of compound 5, using compound 253 and 2,6-dimethylpiperazine as starting materials (freeze-dried: 30 mg, 31%). M.P.: 80° C. (gum, K).

Preparation of Compound 47:

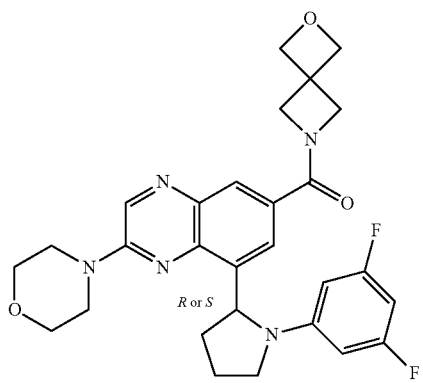 [SMILES: O=C(c1cc(C2CCCN2c2cc(F)cc(F)c2)c2nc(N3CCOCC3)cnc2c1)N1CC2(COC2)C1]

Compound 47 was prepared according to an analogous procedure as described for the synthesis of compound 5, using compound 251 and 2-oaxa-6 aza-spiro(3,3)heptane as starting materials (freeze-dried: 32 mg, 25%). M.P.: 80° C. (gum, K).

Preparation of Compound 50:

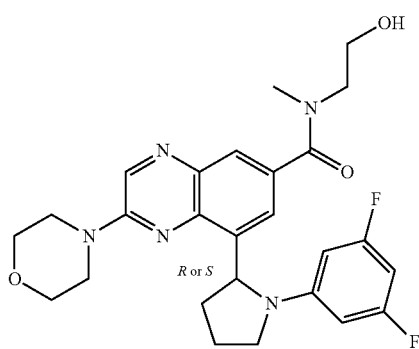 [SMILES: CN(CCO)C(=O)c1cc(C2CCCN2c2cc(F)cc(F)c2)c2nc(N3CCOCC3)cnc2c1]

Compound 50 was prepared according to an analogous procedure as described for the synthesis of compound 5, using compound 251 and 2-(methylamino)ethanol as starting materials (freeze-dried: 35 mg, 28%). M.P.: 80° C. (gum, K).

Preparation of Compound 51:

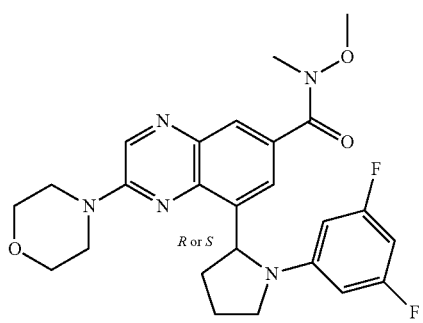 [SMILES: CON(C)C(=O)c1cc(C2CCCN2c2cc(F)cc(F)c2)c2nc(N3CCOCC3)cnc2c1]

Compound 51 was prepared according to an analogous procedure as described for the synthesis of compound 5, using compound 251 and N,O-dimethylhydroxylamine hydrochloride as starting materials (freeze-dried: 14 mg, 32%, yellow powder). M.P.: 80° C. (gum, K).

Preparation of Compound 59, compound 60 and compound 61

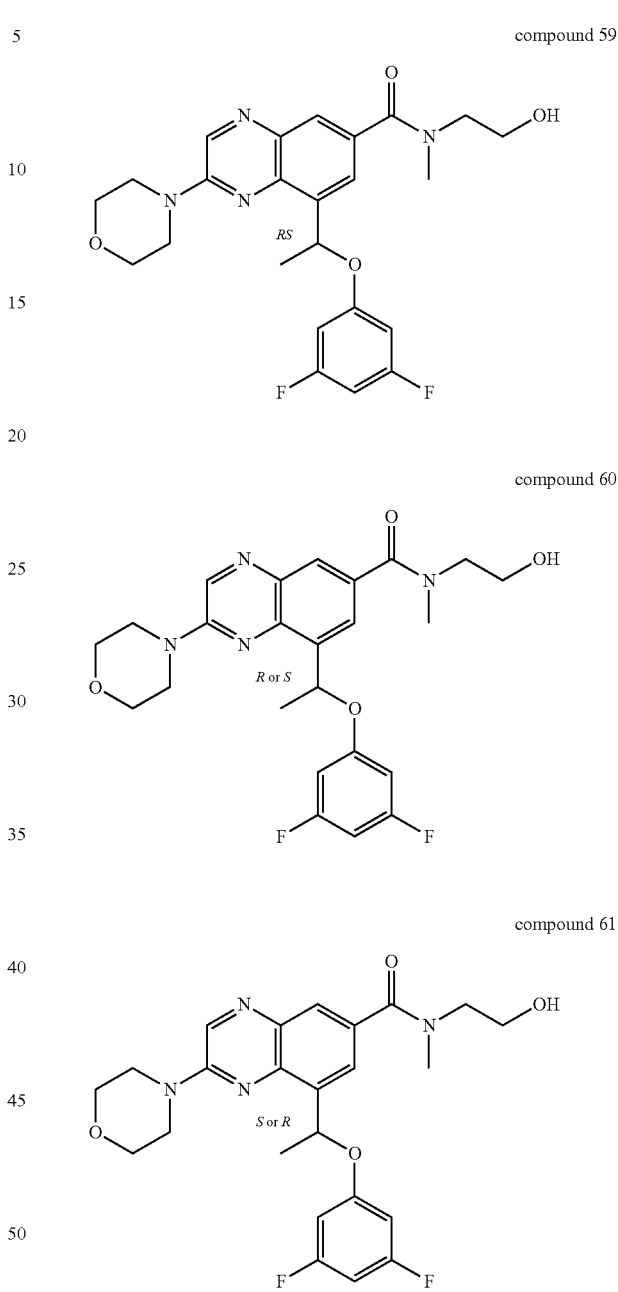

Compound 59, compound 60 and compound 61 were prepared according to an analogous procedure as described for the synthesis of compound 5, using compound 248 and 2-(methylamino)ethanol as starting material (388 mg, 85%, pale yellow solid of compound 59. Separation of the enantiomers by chiral SFC (Stationary phase: CHIRALPAK AD-IT 5 μm 250×20 mm, Mobile phase: 80% $CO_2$, 20% iPrOH (0.3% $iPrNH_2$)) of 355 mg of racemic compound 59 gave respectively 145 mg (32%, yellow fluffy solid) of compound 60 and 125 mg (27%, pale fluffy solid) of compound 61.

Preparation of Compound 63:

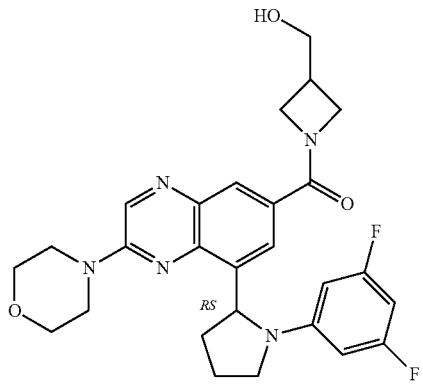 [SMILES: O=C(c1cc(C2CCCN2c2cc(F)cc(F)c2)c2nc(N3CCOCC3)cnc2c1)N1CC(CO)C1]

Compound 63 was prepared according to an analogous procedure as described for the synthesis of compound 5, using compound 62 and (azetidin-3-yl)methanol as starting materials (freeze-dried: 29 mg, 25%). M.P.: 100° C. (gum, K).

Preparation of Compound 64:

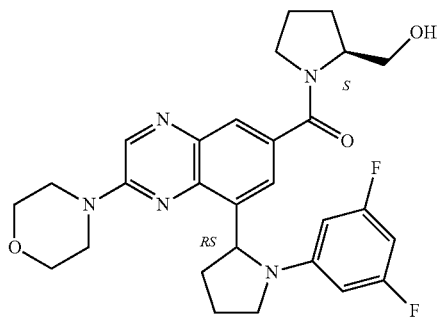

Compound 64 was prepared according to an analogous procedure as described for the synthesis of compound 5, using compound 62 and (S)-(+)-2-pyrrolidinemethanol as starting materials (freeze-dried: 51 mg, 43%). M.P.: 80° C. (gum, K).

Preparation of Compound 65:

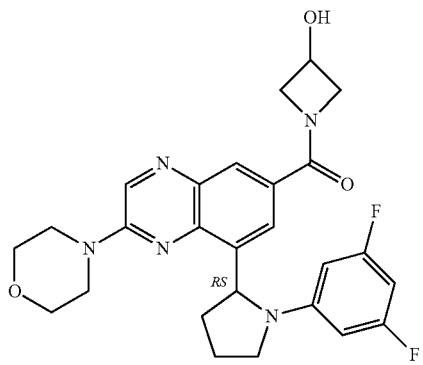 [SMILES: O=C(c1cc(C2CCCN2c2cc(F)cc(F)c2)c2nc(N3CCOCC3)cnc2c1)N1CC(O)C1]

Compound 65 was prepared according to an analogous procedure as described for the synthesis of compound 5, using compound 62 and 3-hydroxyazetidine hydrochloride as starting materials (freeze-dried: 51 mg, 45%). M.P.: 80° C. (gum, K).

Preparation of Compound 66:

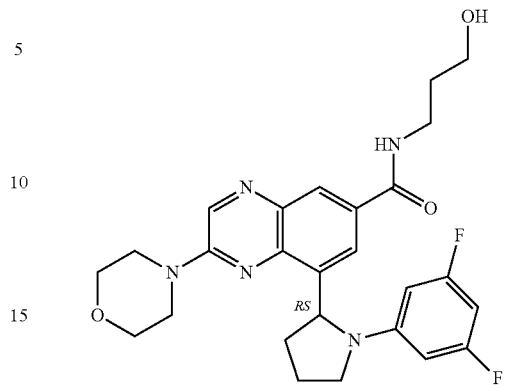

Compound 66 was prepared according to an analogous procedure as described for the synthesis of compound 5, using compound 62 and 3-amino-1-propanol as starting materials (freeze-dried: 46 mg, 41%). M.P.: 80° C. (gum, K).

Preparation of Compound 69:

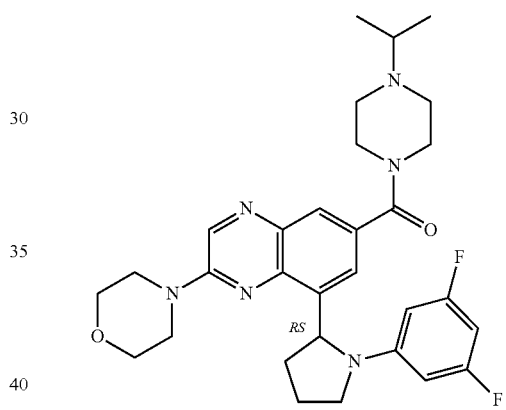

Compound 69 was prepared according to an analogous procedure as described for the synthesis of compound 5, using compound 62 and 1-isopropylpiperazine as starting materials (freeze-dried: 44 mg, 35%, white powder). M.P.: 80° C. (gum, K).

Preparation of Compound 70:

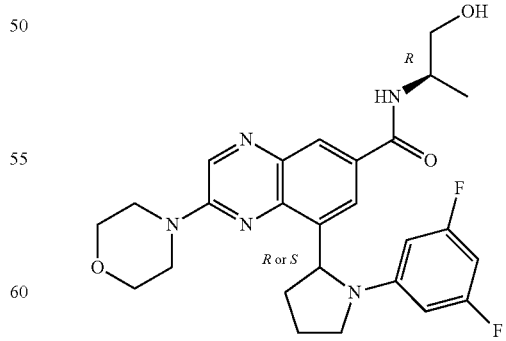

Compound 70 was prepared according to an analogous procedure as described for the synthesis of compound 5, using compound 251 and (2R)-aminopropan-1-ol as starting materials (freeze-dried: 77 mg, 57%, white powder). M.P.: 80° C. (gum, K).

Preparation of Compound 71:

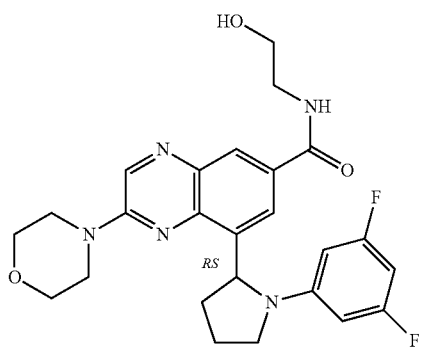 [SMILES: O=C(NCCO)c1cc(C2CCCN2c2cc(F)cc(F)c2)c2nc(N3CCOCC3)cnc2c1]

Compound 71 was prepared according to an analogous procedure as described for the synthesis of compound 5, using compound 62 and ethanolamine as starting materials (freeze-dried: 79 mg, 36%, yellow powder). M.P.: 80° C. (gum, K).

Preparation of Compound 75:

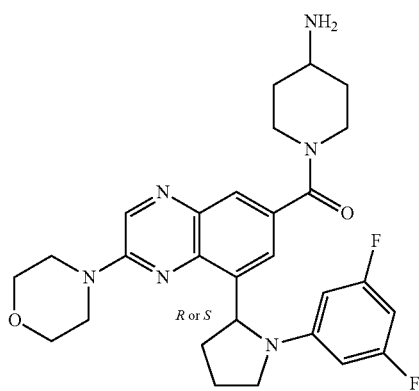 [SMILES: NC1CCN(C(=O)c2cc(C3CCCN3c3cc(F)cc(F)c3)c3nc(N4CCOCC4)cnc3c2)CC1]

Compound 75 was prepared according to an analogous procedure as described for the synthesis of compound 5, using compound 251 and 4-aminopiperidine as starting material (freeze-dried: 14 mg, 12%). M.P.: 80° C. (gum, K).

Preparation of Compound 86 and Compound 87 compound 86

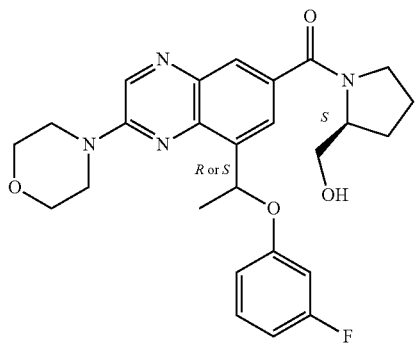

compound 87

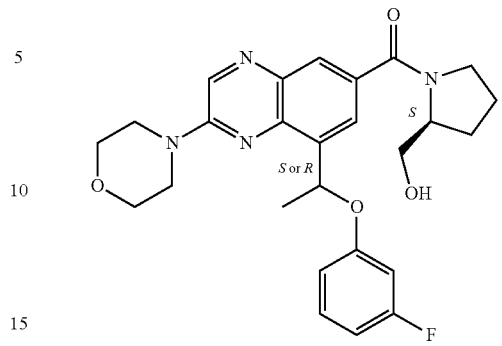

Compound 86 and compound 87 was prepared according to an analogous procedure as described for the synthesis of compound 5, using compound 257a and (S)-(+)-2-(pyrrolidinemethanol) as starting material. The residue (680 mg, orange oil) was purified by chromatography over silica gel (regular SiOH; 30 μm; 40 g; gradient: from 99.5% DCM, 0.5% MeOH to 95% DCM, 5% MeOH). The pure fractions were collected and the solvent was evaporated. The residue (340 mg, pale yellow foam) was purified by achiral SFC (CHIRALPAK AD-H; 5 μm; 250×20 mm; mobile phase: 65% $CO_2$, 35% EtOH). The pure fractions were collected and the solvent was evaporated to give two fractions which were solubilized in DCM, evaporated and dried under vacuum (50° C., 24 h) to give 115 mg (25%, pale yellow foam) of compound 86 (M.P.: 76° C., DSC) and 125 mg (28%, pale yellow foam) of compound 87 (M.P.: 74° C., DSC)

Preparation of Compound 90, Compound 91 and Compound 92 compound 90

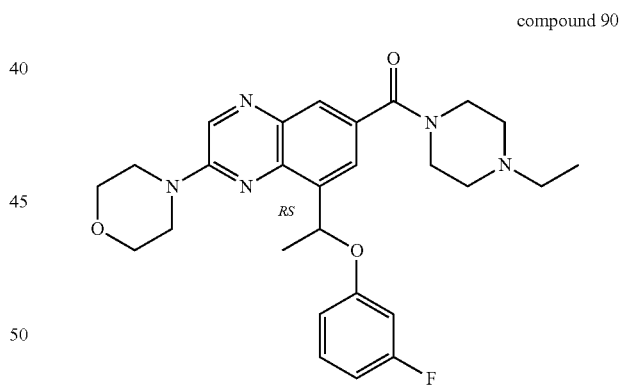

compound 91

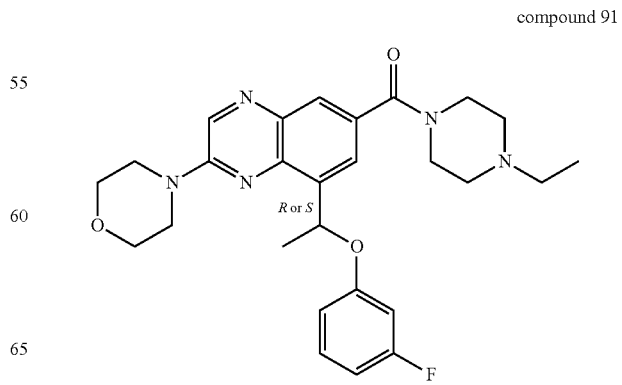

-continued compound 92

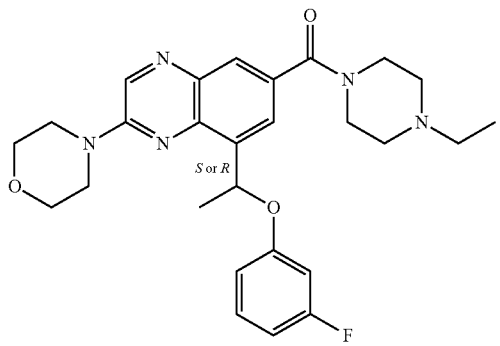

Preparation of Compound 113 and Compound 114 compound 113

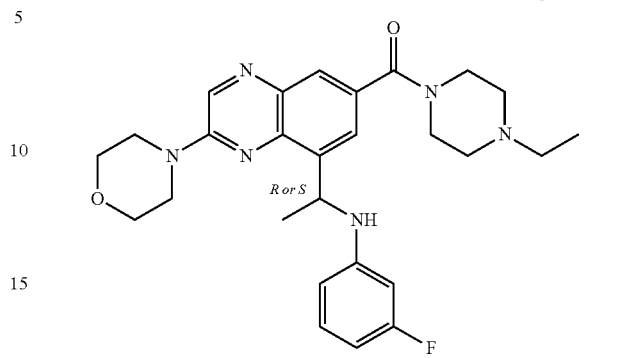

Compound 90, compound 91 and compound 92 was prepared according to an analogous procedure as described for the synthesis of compound 5, using compound 257a and 1-ethylpiperazine as starting material. The residue (420 mg, brown oil) was purified by chromatography over silica (irregular SiOH; 15-40 µm; 12 g; gradient: from 98% DCM, 2% MeOH to 94% DCM, 6% MeOH). The pure fractions were collected and the solvent was evaporated to give 2 fractions of compound 90 respectively:

Fraction A: 72 mg of compound 90. 30 mg of this fraction were solubilized in MeCN and washed with pentane. The MeCN layer was evaporated under vacuo and the solid was triturated in $Et_2O$ to give, after filtration, 21 mg of compound 90 (6%, off-white foam).

Fraction B: 270 mg of compound 90 which were combined with the residual 42 mg of fraction A. The resulting residue (312 mg) was purified by chiral SFC (CHIRALPAK AD-H 5 µm 250×20 mm; mobile phase: 70% $CO_2$, 30% EtOH (0.3% $iPrNH_2$)). The pure fractions were collected and the solvent was evaporated to give two fractions which were separately co-evaporated in DCM (2×) and dried under reduced pressure (16 h, 50° C.) to give respectively 92 mg (27%, pale yellow foam) of compound 91 and 101 mg (30%, pale yellow foam) of compound 92.

Preparation of Compound 105:

compound 114

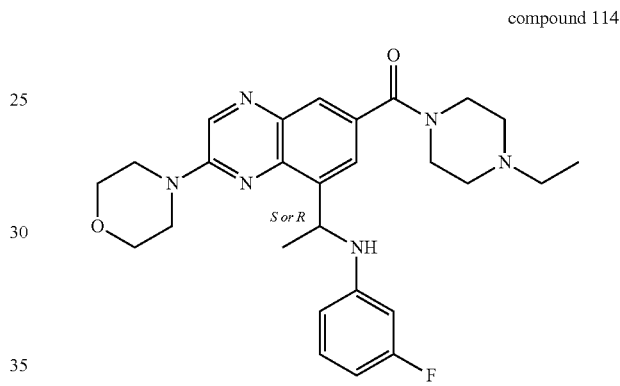

Compound 113 and compound 114 were prepared according to an analogous procedure as described for the synthesis of compound 5, using intermediate 117 and 1-ethylpiperazine as starting material (74 mg, 40%, pale yellow solid of compound 113; M.P.: 307° C. (DSC) and 74 mg, 40%, pale yellow solid of compound 114; M.P.: 303° C. (DSC) were obtained after chiral SFC (Stationary phase: Chiralpak AS-H 5 µm 250*20 mm, Mobile phase: 60% C02, 40% MeOH (0.3% $iPrNH_2$)) purification).

Preparation of Compound 115 and Compound 116 compound 115

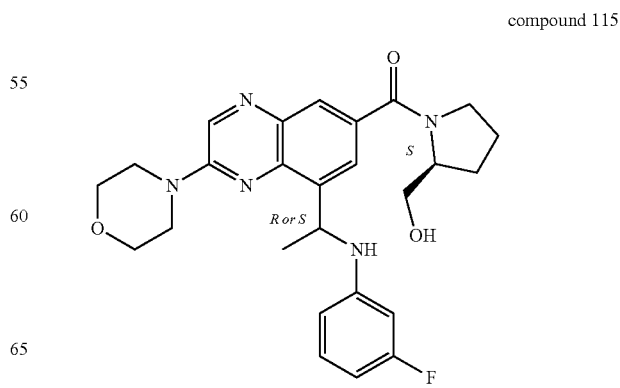

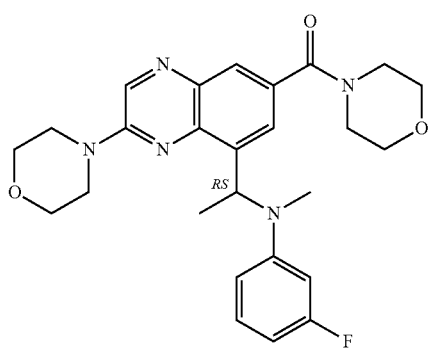 [SMILES: CC(c1cc(C(=O)N2CCOCC2)cc2ncc(N3CCOCC3)nc12)N(C)c1cccc(F)c1]

Compound 105 was prepared according to an analogous procedure as described for the synthesis of compound 5, using compound 98 and morpholine as starting materials (96 mg, 52%). M.P.: 161° C. (DSC).

compound 116

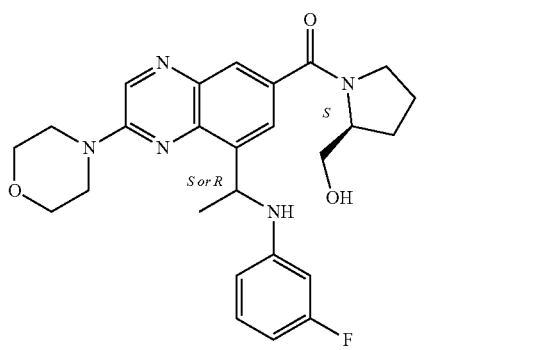

Compound 115 and compound 116 were prepared according to an analogous procedure as described for the synthesis of compound 5, using compound 263 and L-prolinol as starting materials (67 mg, 33%, pale yellow solid of compound 115; M.P.: 327° C. (DSC) and 77 mg, 37%, pale yellow solid of compound 116; M.P.: 332° C. (DSC) were obtained after chiral SFC (Stationary phase: CHIRALCEL OJ-H 5 μm 250×20 mm, Mobile phase: 80% CO$_2$, 20% EtOH (0.3% iPrNH$_2$)) purification).

Preparation of Compound 117 and Compound 118 compound 117

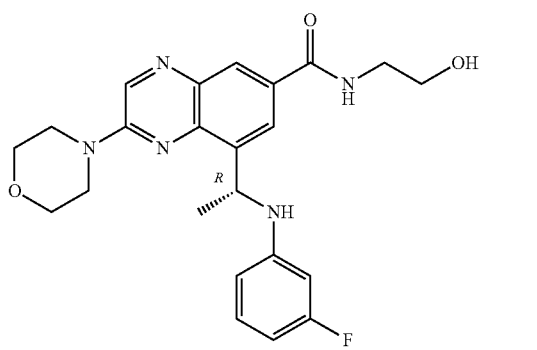

compound 118

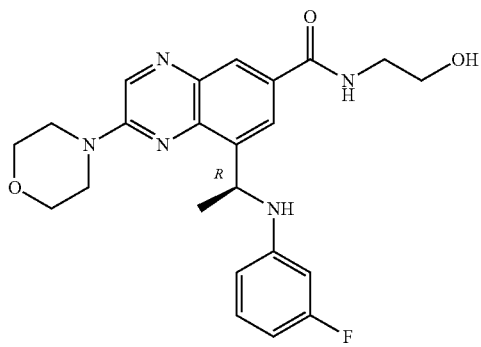

To a solution of compound 263 (120.0 mg; 303 μmol), HBTU (230 mg; 0.605 mmol), and DIPEA (313 μL; 1.82 mmol) in DMF (3 mL) was added 2-aminoethanol (36.3 μL; 0.605 mmol). The solution was stirred at room temperature for 1 h. Then, water and DCM were added. The organic layer was separated, dried over MgSO$_4$, filtered off, evaporated under vacuum and purified by silica gel chromatography (Irregular SiOH 15-40 μm, 24 g, liquid injection (DCM), mobile phase gradient: from DCM 100% to DCM 90%, iPrOH/aq NH$_3$ (95:5) 10%) to give 144 mg (yellow foam) of racemic compound. The separation of the enantiomers was performed by chiral SFC (CHIRALCEL OJ-H 5 μm 250×20 mm; Mobile phase: 70% CO$_2$, 30% EtOH (0.3% iPrNH$_2$)) The pure fractions were collected and the solvent was evaporated to give 63 mg (41%, pale yellow solid) of compound 117 and 67 mg (43%) of compound 118 (M.P.: 237° C., DSC).

Alternative Preparation of Compound 117:

To a solution of compound 274 (94 mg, 0.237 mmol), HBTU (0.179 g, 0.474 mmol), and DIPEA (0.245 mL, 1.423 mmol) in DMF (3 mL) was added 2-aminoethanol (0.028 mL, 0.474 mmol) under N$_2$. The solution was stirred at rt for 15 h. The solution was cooled and the mixture was poured into cooled water, the product was extracted with EtOAc. The organic layer was washed with H$_2$O, separated, dried over MgSO$_4$, filtered and evaporated to dryness. The residue 120 mg was purified by chromatography over silica gel (Irregular SiOH 15-40 μm 24 g: gradient from 98% DCM, 2% MeOH to 90% DCM, 10% MeOH, 0.1% NH$_4$OH). The pure fractions were collected and the solvent was evaporated until dryness to give 32 g (31%) of compound 117 (ee=91.8%)

Preparation of Compound 117:

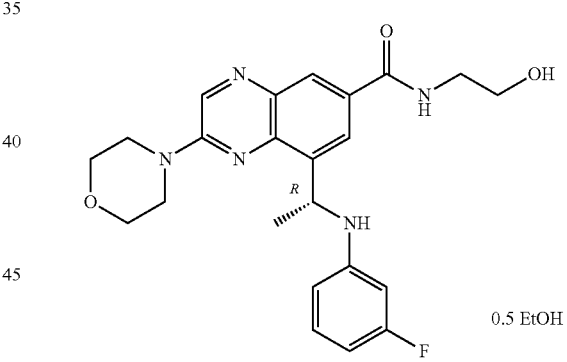

Compound 274 was coupled with ethanolamine (2.0 eq.) in DMF (3 volumes) using DIPEA (6.0 eq.) and HBTU (N,N,N',N'-tetramethyl-<9-(1H-benzotriazol-1-yl)uronium hexafluorophosphate) (2.0 eq) at room temperature. After complete reaction the mixture was diluted with EtOAc, washed with 5% NaHCO$_3$ and concentrated to a residue. The solid was then slurried in THF (10 volumes) to improve the purity and the e.e. The procedure was executed respectively on 20 and 95 g scale of compound 274 and gave compound 117 in an average yield of 77% (e.e: 99.4%). The batches were then combined and for removing the THF, the resulting solid was dissolved in ethanol. The solvent was evaporated to a residue twice, and the residing solid was then dried at 50° C. under reduced pressure overnight to obtain 90 g of compound 174a as a hemi-ethanolate solvate (e.e: 99.4%).

Preparation of Compound 142:

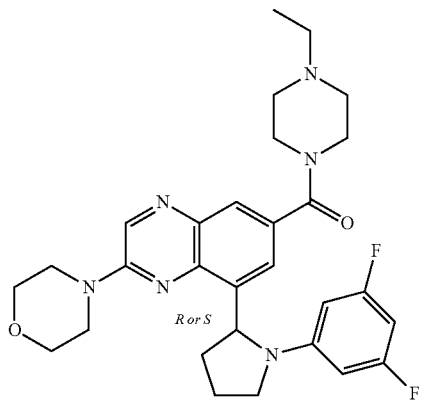 [SMILES: CCN1CCN(C(=O)c2cc(C3CCCN3c3cc(F)cc(F)c3)c3nc(N4CCOCC4)cnc3c2)CC1]

Compound 142 was prepared according to an analogous procedure as described for the synthesis of compound 5, using compound 251 and 1-ethylpiperazine as starting materials (107 mg, 80%). M.P.: 80° C. (gum, K).

Preparation of Compound 143:

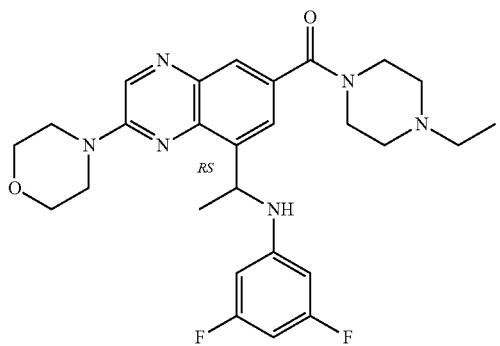 [SMILES: CCN1CCN(C(=O)c2cc(C(C)Nc3cc(F)cc(F)c3)c3nc(N4CCOCC4)cnc3c2)CC1]

Compound 143 was prepared according to an analogous procedure as described for the synthesis of compound 5, using compound 83a and 1-ethylpiperazine as starting materials (136 mg, 74%). M.P.: 80° C. (gum, K).

Preparation of Compound 144:

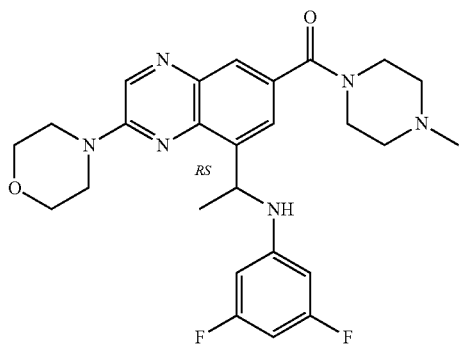 [SMILES: CC(Nc1cc(F)cc(F)c1)c1cc(C(=O)N2CCN(C)CC2)cc2ncc(N3CCOCC3)nc12]

Compound 144 was prepared according to an analogous procedure as described for the synthesis of compound 5, using compound 83a and 1-methylpiperazine as starting materials (156 mg, 87%). M.P.: 80° C. (gum, K).

Preparation of Compound 145:

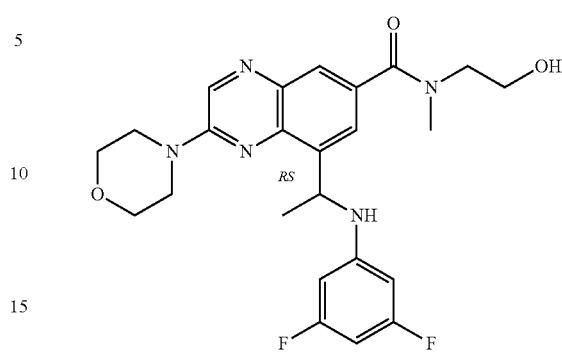

Compound 145 was prepared according to an analogous procedure as described for the synthesis of compound 5, using compound 83a and 2-(methylamino)ethanol as starting materials (134 mg, 79%). M.P.: 80° C. (gum, K).

Preparation of Compound 148:

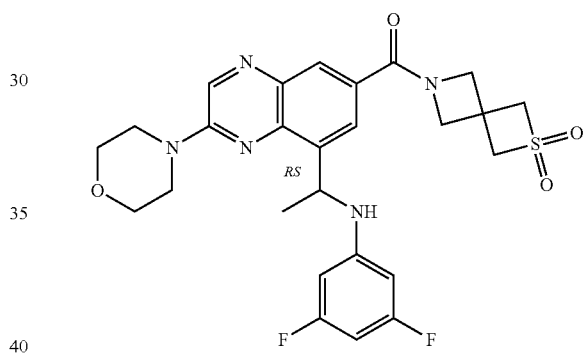

Compound 148 was prepared according to an analogous procedure as described for the synthesis of compound 5, using compound 83a and 2-thia-6-aza-spiro[3.3]heptane 2,2 dioxide as starting materials (124 mg, 47%).

Preparation of Compound 149:

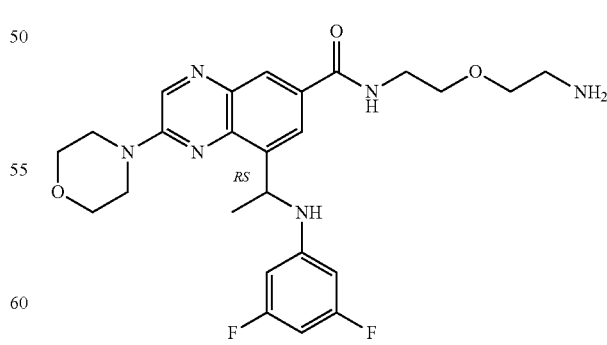

Compound 149 was prepared according to an analogous procedure as described for the synthesis of compound 5, using compound 83a and 2,2'-oxybis(ethylamine) as starting materials (48 mg, 26%). M.P.: 80° C. (gum, K).

Preparation of Compound 169:

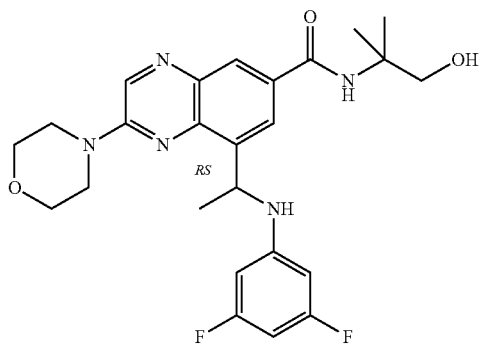 [SMILES: CC(Nc1cc(F)cc(F)c1)c1cc(C(=O)NC(C)(C)CO)cc2ncc(N3CCOCC3)nc12]

Compound 169 was prepared according to an analogous procedure as described for the synthesis of compound 5, using compound 83 a and 2-amino-2-methyl-1-propanol as starting materials (89 mg, 25%). M.P.: 217° C. (DSC).

Preparation of Compound 171 and Compound 172 compound 171

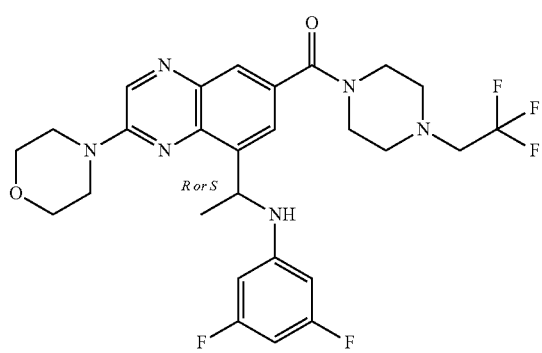

compound 172

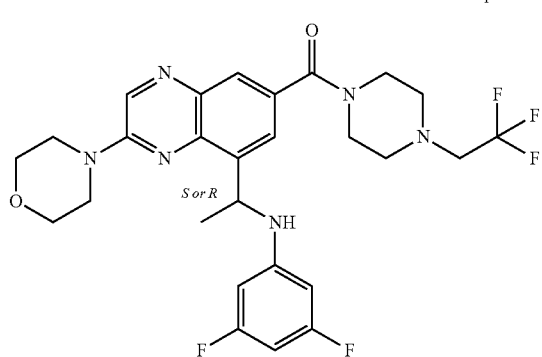

Compound 171 and compound 172 were prepared according to an analogous procedure as described for the synthesis of compound 5, using compound 83a and 1-(2,2,2-trifluoroethyl)piperazine as starting materials (104 mg, 38%, compound 171 (M.P.: 125° C. (gum, K)) and 100 mg, 37%, compound 172 (M.P.: 130° C. (gum, K)) were obtained after chiral SFC (Stationary phase: CHIRALCEL OJ-H 5 μm 250×20 mm, Mobile phase: 85% $CO_2$, 15% MeOH (0.3% $iPrNH_2$)) purification).

Preparation of Compound 180, Compound 181 and Compound 182 compound 180

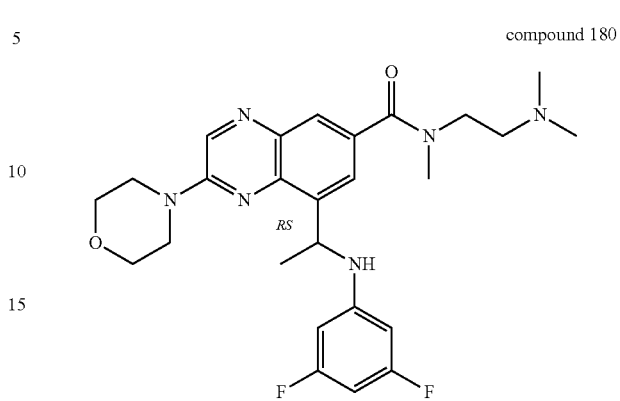

compound 181

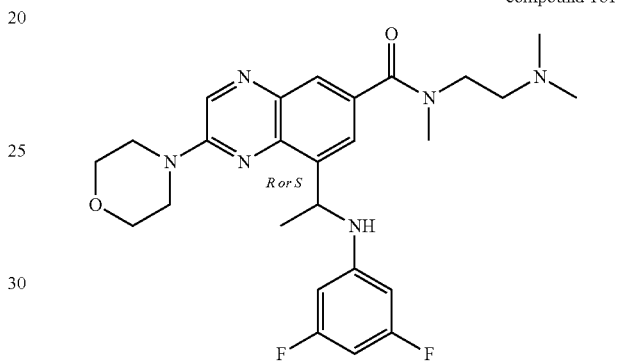

compound 182

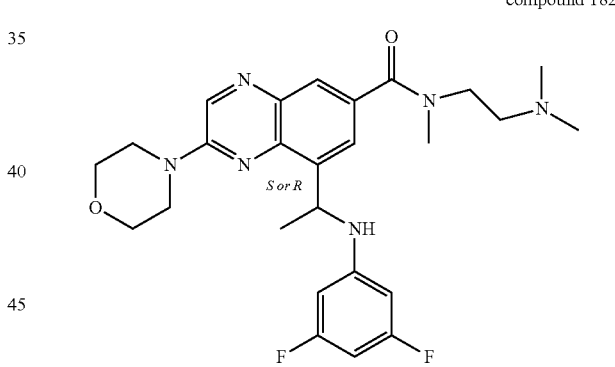

N,N,N'-trimethylethylenediamine (185 μL; 1.45 mmol) was added to a solution of compound 83a (300 mg; 0.72 mmol), HBTU (549 mg; 1.45 mmol) and DIPEA (0.75 mL; 4.34 mmol) in Me-THF (10 mL). The reaction mixture was stirred at rt for 16 h. The mixture was poured into water, extracted with EtOAc and washed with brine (2×). The organic layer was dried over $MgSO_4$, filtered and the solvent was evaporated. The residue (520 mg) was purified by column chromatography over silica gel (40 g; mobile phase: from 100% DCM to 97% DCM, 3% MeOH, 0.3% $NH_4OH$). The pure fractions were collected and the solvent was evaporated to give 295 mg (82%) of compound 180. M.P.: 148° C. (K). Compound 180 was purified by chiral SFC (AS-H 5 μm 250*20 mm; mobile phase: 80% $CO_2$, 20% EtOH). The pure fractions were collected and the solvent was evaporated to give two fractions which were crystallized in diethylether, filtered and dried under vacuum to give 38 mg (11%) of compound 181 (M.P.: 134° C., DSC) and 60 mg (16%) of compound 182 (M.P.: 134° C., DSC).

307

Preparation of Compound 183, Compound 184 and Compound 185

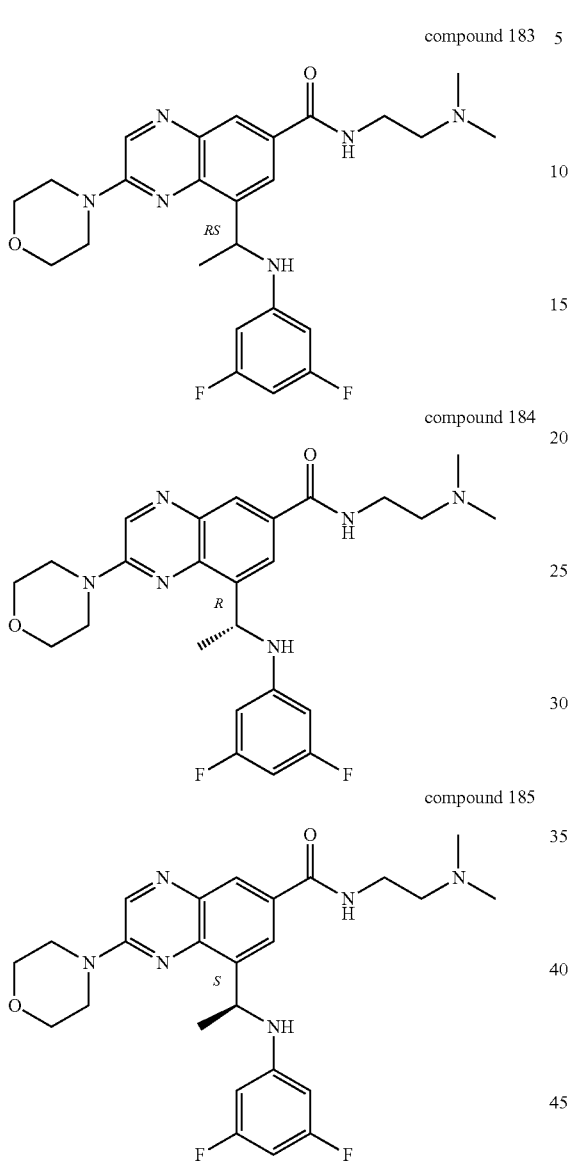

compound 183 compound 184 compound 185

To a solution of compound 83a (300 mg; 0.72 mol), HBTU (550 mg; 1.45 mmol) and DIPEA (0.75 mL; 4.34 mmol) in DMF (6 mL) was added N,N-dimethylethylenediamine (0.16 mL; 1.45 mmol) and the mixture was stirred at rt for 16 h. The mixture was poured into water and extracted with EtOAc. The organic layer was washed with brines (×2), dried over MgSO$_4$, filtrated and evaporated until dryness. The residue was purified via silica gel chromatography (Stationary phase: 40 g, Mobile phase from: 100% DCM to 97% DCM 3% MeOH 0.3% NH$_4$OH. The pure fractions were collected and evaporated until dryness to give 290 mg (83%) of compound 183. Separation of the enantiomers was performed via chiral SFC (Stationary phase: CHIRALCEL OJ-H 5 μm 250×20 mm, Mobile phase: 85% CO$_2$, 15% MeOH (0.3% iPrNH$_2$)). The pure fractions were collected and evaporated until dryness. Each fractions were crystallized form Et$_2$O to give 70 mg (20%) of compound 184 (M.P.: 157° C. (DSC)), and 58 mg (20%) of compound 185 (M.P.: 152° C. (DSC)).

308

Preparation of Compound 188 and Compound 189

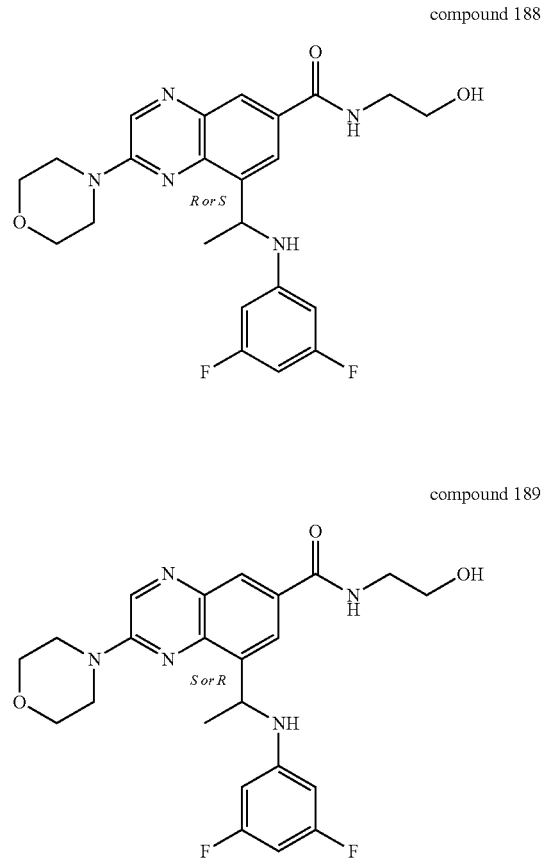 [SMILES: CC(Nc1cc(F)cc(F)c1)c1cc(C(=O)NCCO)cc2ncc(N3CCOCC3)nc12 ; CC(Nc1cc(F)cc(F)c1)c1cc(C(=O)NCCO)cc2ncc(N3CCOCC3)nc12]

compound 188 compound 189

Compound 188 and compound 189 were prepared according to an analogous procedure as described for the synthesis of compound 5, using compound 83a and 2-aminoethanol as starting materials (82 mg, 25%, compound 188 (M.P.: 80° C. (gum, K)) and 94 mg, 87%, compound 189 (M.P.: 80° C. (gum, K)) were obtained after chiral SFC (Stationary phase: CHIRALCEL OJ-H 5 μm 250×20 mm, Mobile phase: 75% CO$_2$, 25% EtOH (0.3% iPrNH$_2$)) purification).

Preparation of Compound 198, Compound 199 and Compound 200

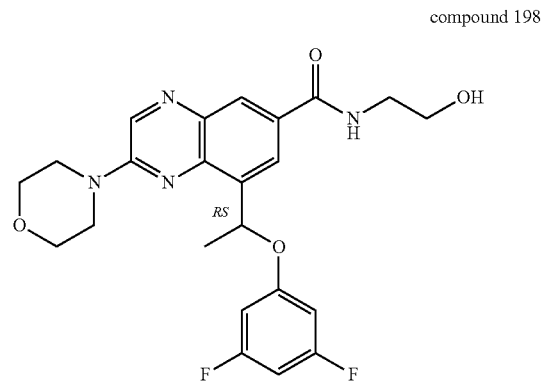

compound 198 compound 199

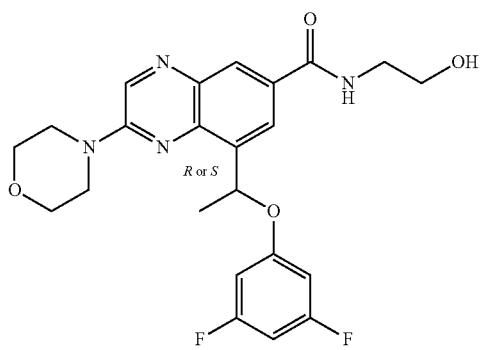

compound 200

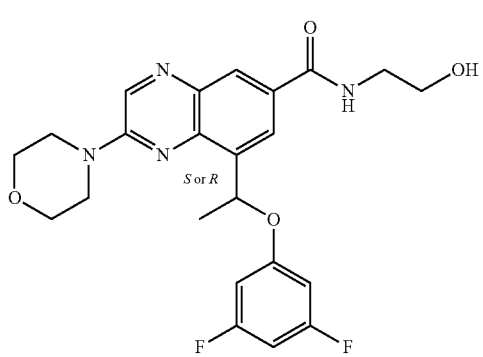

Compounds 198, 199 and 200 were prepared according to an analogous procedure as described for the synthesis of compound 5, using compound 39 and 2-aminoethanol as starting materials. 130 mg (24%) of compound 198 were obtained after crystallization in a mixture of Et₂O/DCM. M.P.: 171° C. (DSC). Compound 198 was purified by chiral SFC (CHIRALCEL OJ-H 5 μm 250×20 mm; mobile phase: 90% CO₂, 10% MeOH). The pure fractions were collected and the solvent was evaporated. Each residue was crystallized from DCM/diethylether. Each precipitate was filtered and dried under vacuum to give 68 mg (12%) of compound 199 (M.P.: 140° C., K) and 57 mg (10%) of compound 200 (M.P.: 115° C., gum, K).

Preparation of Compound 201 and Compound 202 compound 201

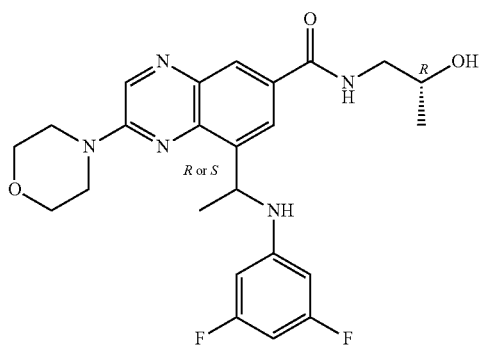

compound 202

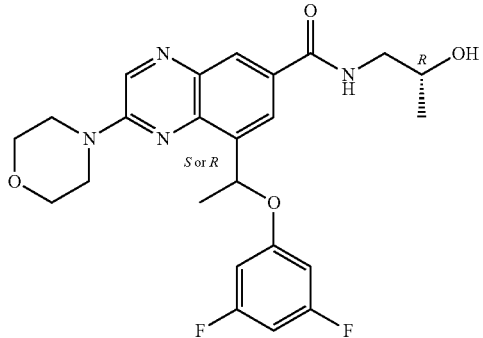

Compound 201 and compound 202 were prepared according to an analogous procedure as described for the synthesis of compound 5, using compound 83a and (2R)-(−)-1-aminopropan-2-ol as starting materials. 253 mg (22%) of compound 201 (M.P.: 70° C., DSC) and 276 mg (24%) of compound 202 were obtained after chiral SFC (Stationary phase: CHIRALCEL OJ-H 5 μm 250×20 mm, Mobile phase: 83% CO₂, 17% MeOH (0.3% iPrNH₂)) purification.

Preparation of Compound 203 and Compound 204 compound 203

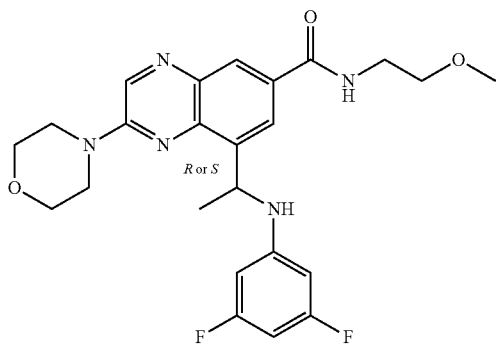

compound 204

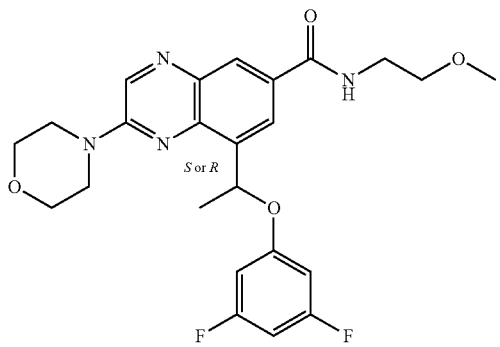

Compound 203 and compound 204 were prepared according to an analogous procedure as described for the synthesis of compound 5, using compound 83a and 2-methoxyethylamine as starting material (after purification to separate the enantiomers from 280 mg of racemic compound and crystallization from diethylether; 28 mg (8%) of compound 203 (M.P.: 118° C., DSC) and 76 mg (22%) of compound 204 (M.P.: 80° C., gum, K).

311

Preparation of Compound 211 and Compound 212 compound 211

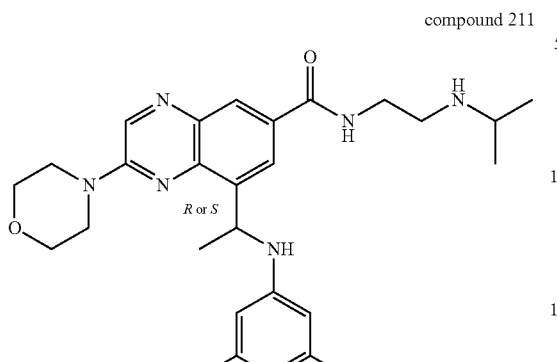

compound 212

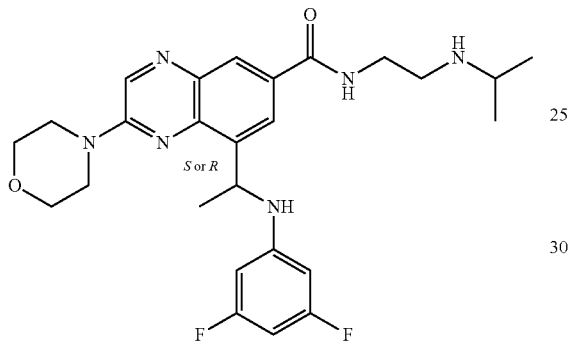

A solution of compound 83a (1 g; 2.41 mmol), HBTU (1.37 g; 3.62 mmol) and DIPEA (1.25 mL; 7.24 mmol) in DMF (25 mL) was stirred at rt for 15 min. Then, N-isopropylethylenediamine (0.46 mL; 3.62 mmol) was added and the solution was stirred at rt for 15 h. The product was poured in ice water and extracted with EtOAc. The organic layer was washed with brine (×2), dried over $MgSO_4$, filtered and evaporated until dryness. The residue was purified by silica gel chromatography (Stationary phase: irregular SiOH 15-40 μm 300 g MERCK, Mobile phase: 0.1% $NH_4OH$, 95% DCM, 0.5% MeOH). The fractions containing the product were mixed and concentrated to afford 720 mg of the racemate.

This racemate was purified by chiral SFC (Stationary phase: CHIRALCEL OJ-H 5 μm 250×20 mm, Mobile phase: 90% $CO_2$, 10% MeOH (0.3% $iPrNH_2$)). The fractions containing the products were mixed and concentrated to afford 320 mg of fraction A and 315 mg of fraction B.

Fraction A was crystallized from a mixture of $DCM/Et_2O$. The precipitate was filtered off and dried under vacuum to give 280 mg (23%) of compound 211 (M.P.: 206° C. (DSC)).

Fraction B was crystallized from a mixture of $DCM/Et_2O$. The precipitate was filtered off and dried under vacuum to give 250 mg (21%) of compound 212 (M.P.: 204° C. (DSC)).

312

Preparation of Compound 213 and Compound 214 compound 213

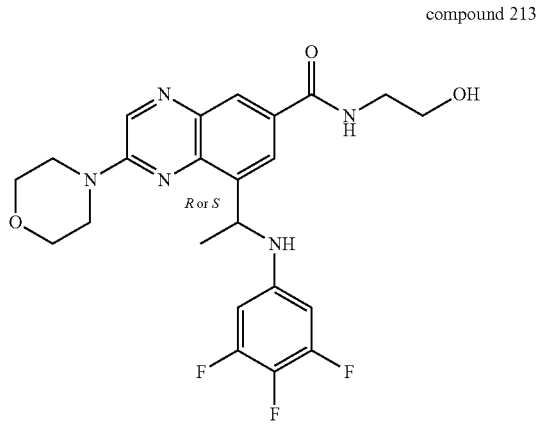

compound 214

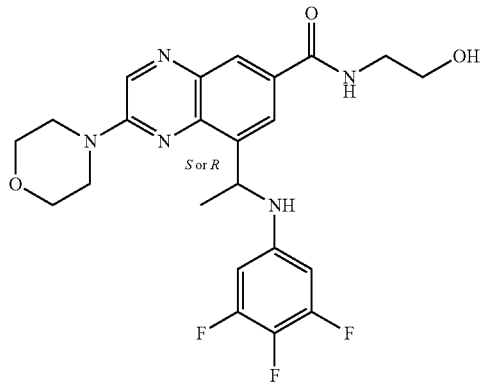

Compound 213 and compound 214 were prepared according to an analogous procedure as described for the synthesis of compound 5, using compound 170 and 2-aminoethanol as starting materials. 117 mg (27%) of compound 213 (M.P.: 80° C., gum, K) and 136 mg (31%) of compound 214 (M.P.: 80° C., gum, K) were obtained after chiral SFC (Stationary phase: CHIRALCEL OJ-H 5 μm 250×20 mm, Mobile phase: 80% $CO_2$, 20% MeOH (0.3% $iPrNH_2$)) purification.

Preparation of Compound 217:

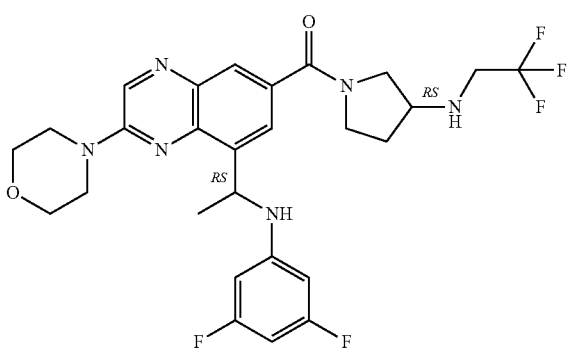 [SMILES: CC(Nc1cc(F)cc(F)c1)c1cc(C(=O)N2CCC(NCC(F)(F)F)C2)cc2ncc(N3CCOCC3)nc12]

Compound 217 (undefined mixture of 4 diastereoisomers) was prepared according to an analogous procedure as described for the synthesis of compound 5, using compound 83a and 3-(trifluoroacetamido)pyrrolidine as starting materials (crystallized from diisopropylether; 120 mg, 29%).

Preparation of Compound 218, Compound 219 and Compound 220

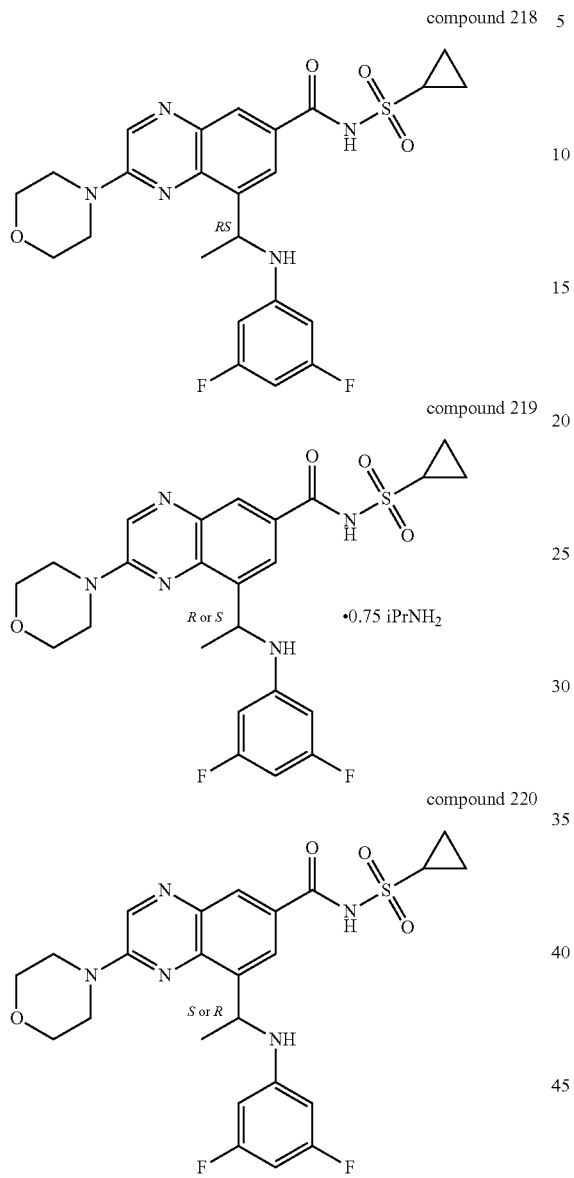

1,1'-Carbonyldiimidazole (324 mg; 2.0 mmol) was added to a solution of compound 83a (690 mg; 1.67 mmol) in Me-THF (14 mL) and the mixture was heated at reflux for 2 h. The mixture was cooled down to rt and cyclopropanesulphonamide (202 mg; 1.67 mmol) and 1,8-diazabicyclo[5.4.0]undec-7-ene (370 µL; 2.50 mmol) were added. The mixture was stirred at rt overnight. The mixture was poured into water. The organic layer was extracted with DCM, separated, dried over MgSO$_4$, filtered and evaporated. The residue was purified by chromatography over silica gel (Irregular SiOH 15-40 µm; 40 g; gradient: from 100% DCM to 90% DCM, 10% MeOH, 0.1% MEOH). The pure fractions were collected and the solvent was evaporated until dryness to give 970 mg of compound 218. A part (106 mg) was crystallized from DIPE. The precipitate was filtered off and dried under vacuum to give 59 mg of compound 218.

The rest of the compound 218 was purified by chiral SFC (CHIRALCEL OJ-H 5 µm; 250×20 mm; mobile phase: 60% CO$_2$, 40% MeOH (0.3% iPrNH$_2$)). The pure fractions were collected and the solvent was evaporated to give two fractions which were crystallized from diisopropylether. Each precipitate was filtered off and dried under vacuum to give 312 mg (33%) of compound 219 and 248 mg (29%) of compound 220.

Preparation of Compound 223:

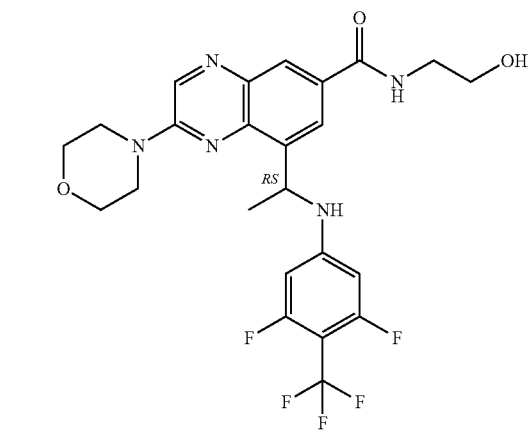 [SMILES: CC(Nc1cc(F)c(C(F)(F)F)c(F)c1)c1cc(C(=O)NCCO)cc2ncc(N3CCOCC3)nc12]

Compound 223 was prepared according to an analogous procedure as described for the synthesis of compound 5, using compound 159 and 2-aminoethanol as starting materials (crystallized from DCM; 195 mg, 60%). M.P.: 200° C. (DSC).

Preparation of Compound 226, Compound 227 and Compound 228

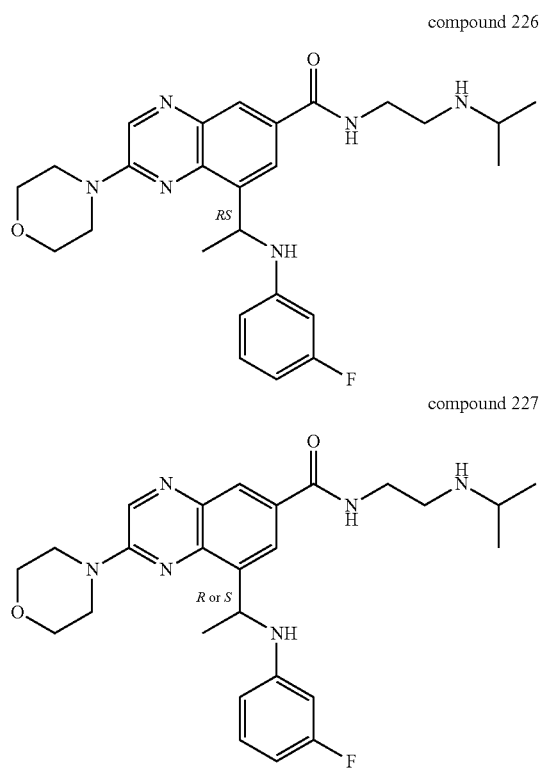

compound 228

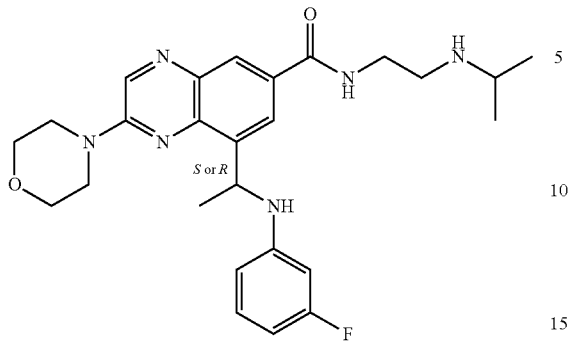

compound 237b

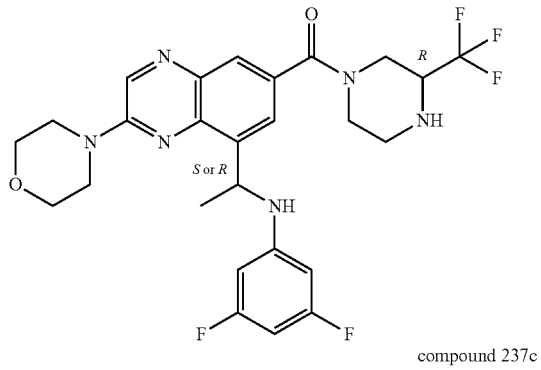

compound 237c

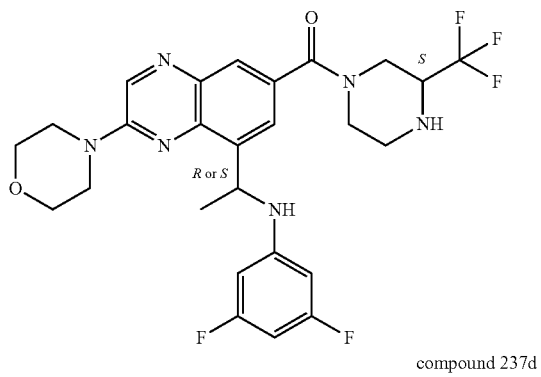

compound 237d

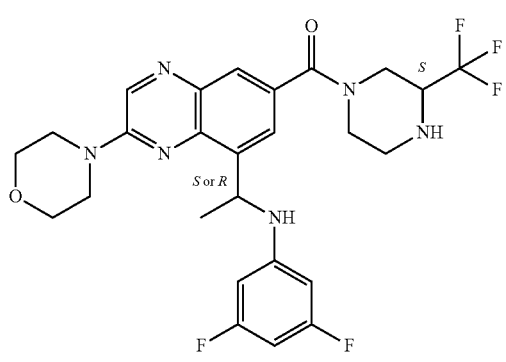

Compounds 226, 227 and 228 were prepared according to an analogous procedure as described for the synthesis of compound 5, using compound 263 and N-isopropylethylenediamine as starting materials. After crystallization from diethylether 192 mg (49%) of compound were obtained. M.P.: 158° C. (DSC). Compound 226 was purified by chiral SFC (CHIRALPAK AD-H 5 μm; 250×20 mm; mobile phase: 60% $CO_2$, 40% EtOH). The pure fractions were collected and the solvent was evaporated. Each residue was freeze-dried with ACN/water (20/80) to give 74 mg (19%, yellow powder) of compound 227 (M.P.: 80° C., gum, K) and 76 mg (20%, yellow powder) of compound 228 (M.P.: 80° C., gum, K).

Preparation of Compound 237, Compound 237a, Compound 237b, Compound 237c and Compound 237d compound 237

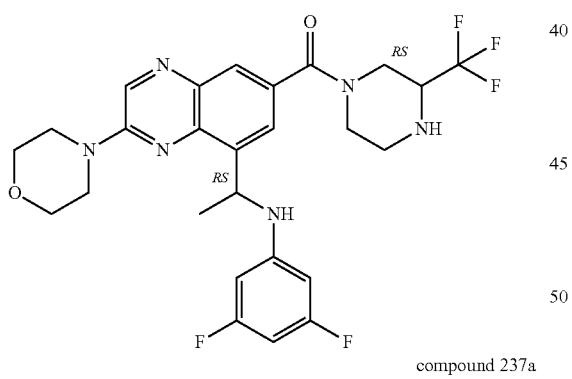

compound 237a

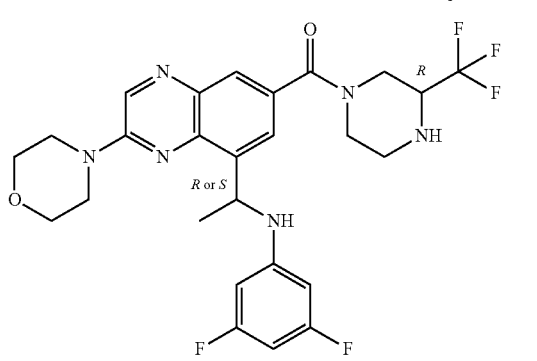

Compound 237 was prepared according to an analogous procedure as described for the synthesis of compound 5, using compound 236 and 2-Trifluoromethylpiperazine (R/S: 80/20) as starting materials. The residue (700 mg) was purified by chromatography over silica gel (irregular 15-40 μm; mobile phase: 97% DCM, 3% MeOH (+10% $NH_4OH$)). The pure fractions were collected and the solvent was evaporated. The residue (500 mg) was crystallized from Heptane and $Et_2O$. The precipitate was filtered and dried to give (0.45 g, 67% of compound 237 (M.P: 105° C. (Kofler). Compound 237 was further purified by chiral SFC (CHIRALCEL OJ-H; 5 μm 250×20 mm; mobile phase: 80% $CO_2$, 20% MeOH (0.3% $iPrNH_2$)). The pure fractions were collected and the solvent was evaporated to give 2 fractions of diastereoisomers. The first fraction of diastereoisomers was purified by chiral SFC (CHIRALPAK AD-H, 5 μ*250*20 mm; mobile phase 85% $CO_2$, 15% EtOH (0.3% $iPrNH_2$)). The pure fractions were collected and the solvent was evaporated to give 2 fractions. The first one (122 mg) was crystallized from $Et_2O$ to give after filtration 94 mg of compound 237b (M.P: 120° C. (Kofler)) and the second one (38 mg) was freeze-dried with water-ACN to give 33 mg (5%) of compound 237d (M.P.: 80° C. (Kofler). The second fraction was purified by chiral SFC (CHIRALPAK AD-H, 5 μ*250*20 mm; mobile phase 82% CO₂, 18% EtOH (0.3% iPrNH₂)). The pure fractions were collected and the solvent was evaporated to give 2 fractions. The first one (120 mg) was crystallized from Et₂O to give after filtration 66 mg (10%) of compound 237a (M.P.:120° C. (Kofler) and the second one (43 mg) was freeze-dried with water-ACN to give 40 mg (6%) of compound 237c (M.P.:80° C. (Kofler)).

Preparation of Compound 238:

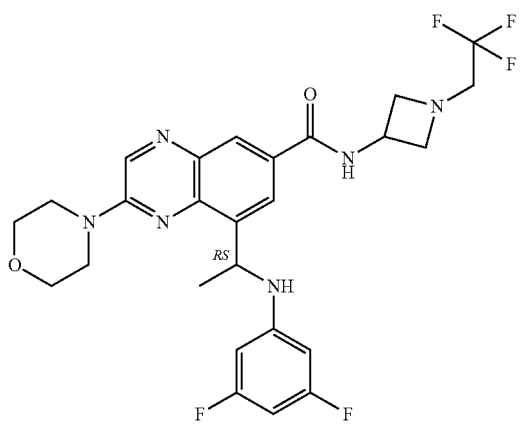 [SMILES: CC(Nc1cc(F)cc(F)c1)c1cc(C(=O)NC2CN(CC(F)(F)F)C2)cc2ncc(N3CCOCC3)nc12]

Compound 238 (was prepared according to an analogous procedure as described for the synthesis of compound 5, using compound 236 and 1-(2,2,2-trifluroethyl)-3-azetidi-amine as starting materials (Heptane/Et₂O, 350 mg, 45%). M.P: 110° C. (gum, K).

Preparation of Compound 243, Compound 243a and Compound 243b compound 243

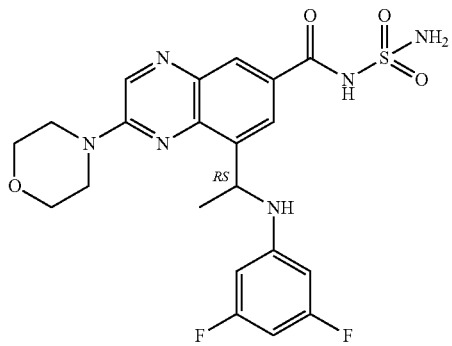

-continued compound 243a

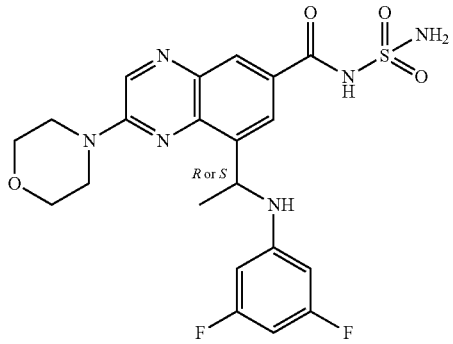

compound 243b

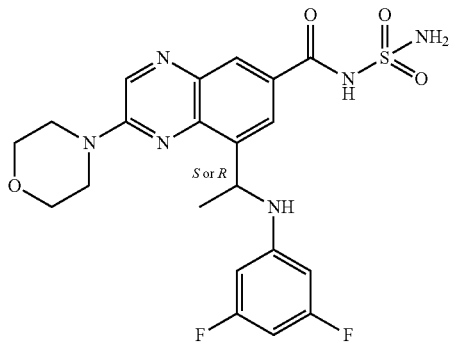

Compound 243 (was prepared according to an analogous procedure as described for the synthesis of compound 5, using compound 236 and sulfamide as starting materials. The residue (480 mg) was purified by chromatography over silica gel (irregular 15-40 μm; 40 g, mobile phase: 100% DCM). The pure fractions were collected; The solvent was evaporated and a part of product was crystallized from DIPE. The precipitate was filtered and dried to give (41 mg) of compound 243. The residue was purified by chiral SFC (CHIRALPAK AD-H, 5 μ*250*20 mm; mobile phase 60% CO₂, 40% MeOH). The pure fractions were collected and the solvent was evaporated to give 2 fractions which were taken up DCM and evaporated to give 98 mg (20%) of compound 243a (M.P.:160° C. (Kofler)) and 96 mg (20%) of compound 243b (M.P: 200° C. (Kofler))

Preparation of Compound 246, Compound 246a and Compound 246b compound 246

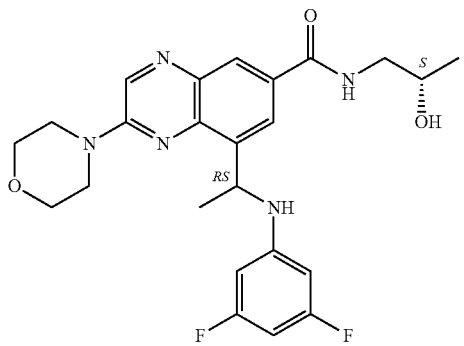

compound 246a

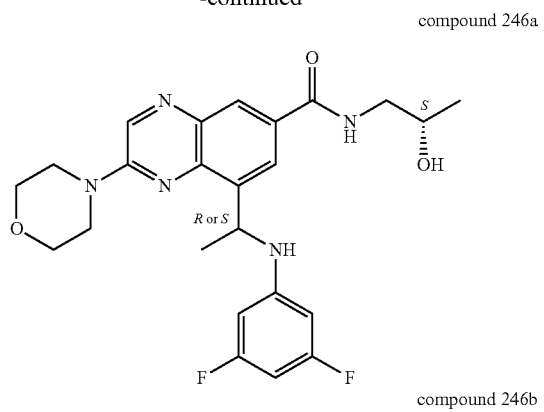

compound 246b

Compound 246 was prepared according to an analogous procedure as described for the synthesis of compound 5, using compound 236 and (2S)-1-amino-2-propanol as starting materials. The residue (580 mg) was purified by chromatography over silica gel (irregular 15-40 µm; 40 g, mobile phase: gradient from 100% DCM to 97% DCM 3% MeOH 0.3% NH₄OH). The pure fractions were collected and the solvent was evaporated to give 345 mg of compound 246. This compound was purified by chiral SFC (CHIRALCEL OJ-H, 5 µ*250*20 mm; mobile phase 75% CO₂, 25% MeOH (0.3% iPrNH₂)). The pure fractions were collected and the solvent was evaporated to give 2 fractions which were crystallized from Et₂O and dried to give 123 mg (36%) of compound 246a and 118 mg (34%) of compound 246b (M.P: 75° C. (DSC)).

Preparation of Compound 272, Compound 272a and Compound 272b compound 272a

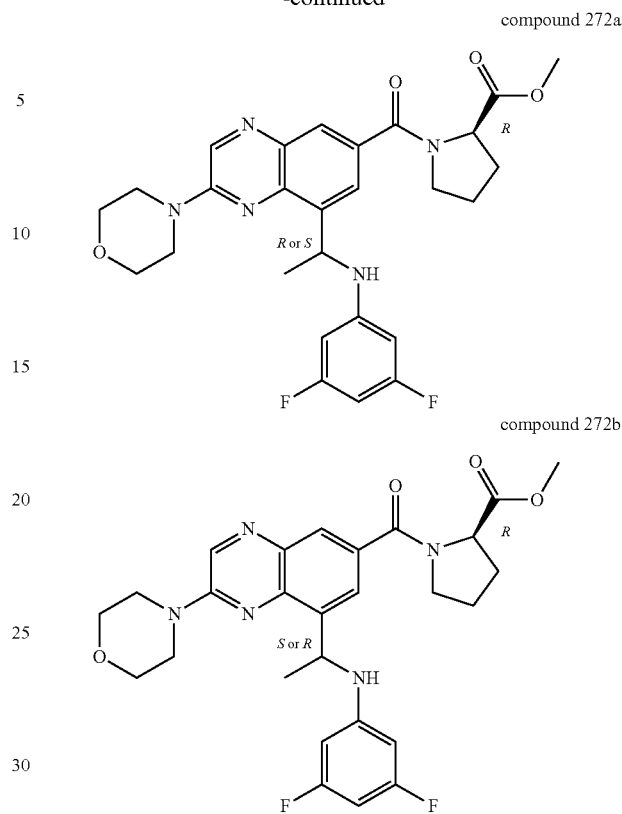

compound 272b

Compound 272 was prepared according to an analogous procedure as described for the synthesis of compound 5, using compound 236 and D-proline methylester hydrochloride as starting materials The residue was purified by chromatography over silica gel (irregular bare silica 40 g; mobile phase: gradient from 100% DCM to 0.1% MEOH, 90% DCM, 10% MeOH). The pure fractions were collected and the solvent was evaporated to give 250 mg (78%) of compound 272. Compound 272 was purified by chiral SFC (CHIRALCEL OJ-H; 5 µm 250×20 mm; mobile phase: 75% CO₂, 25% MeOH). The pure fractions were collected and the solvent was evaporated to give respectively 87 mg (27%) of compound 272a and 86 mg (27%) of compound 272b.

Preparation of Compound 273, Compound 273a and Compound 273b compound 272  compound 273

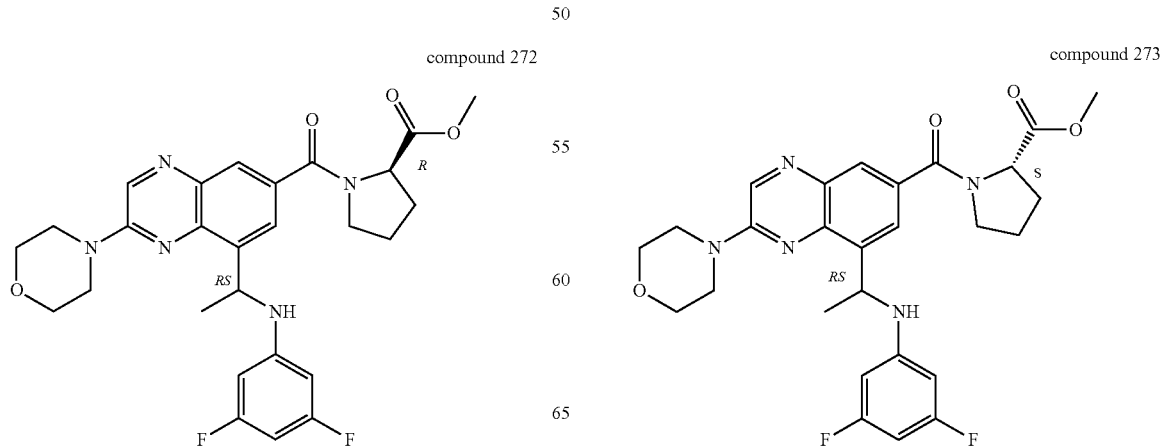

-continued compound 273a compound 2723b

Compound 273 was prepared according to an analogous procedure as described for the synthesis of compound 5, using compound 236 and L-proline methylester hydrochloride as starting material The residue was purified by chromatography over silica gel (irregular bare silica 40 g; mobile phase: gradient from 100% DCM to 0.1% NH₄OH, 90% DCM, 10% MeOH). The pure fractions were collected and the solvent was evaporated to give 320 mg of compound 273. Compound 273 was purified by chiral SFC (CHIRALCEL OJ-H; 5 µm 250×20 mm; mobile phase: 80% CO₂, 20% MeOH). The pure fractions were collected and the solvent was evaporated to give respectively 105 mg (33%) of compound 273a and 96 mg (32%) of compound 273b.

Preparation of Compound 279, Compound 279a and Compound 279b compound 279

-continued compound 279a compound 279b

Compound 279 was prepared according to an analogous procedure as described for the synthesis of compound 5 using compound 234 and 2-aminoethanol as starting materials (570 mg, 65%). M.P=77° C. DSC.

Compound 179 was purified by chiral SFC (Stationary phase: CHIRALPAK AD-H 5 µm 250×20 mm, Mobile phase: 55% C02, 45% EtOH (0.3% iPrNH2)) to give 150 mg of each enantiomers which were freeze-dried with a mixture of ACN and water (1/3) giving 90 mg (10%) of compound 279a (M.P.: 80° C., gum, K) and 100 mg (11%) of compound 279b (M.P.: 80° C., gum, K).

Preparation of Compound 280, Compound 280a and Compound 280b compound 280

-continued compound 280a

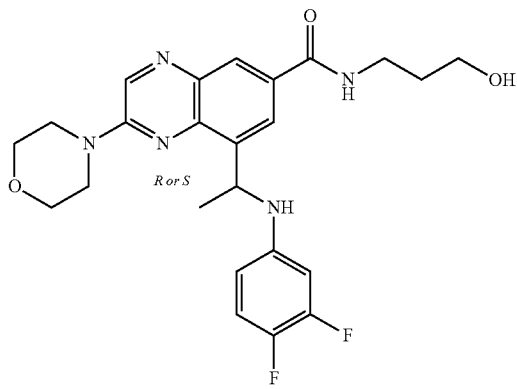

compound 280b

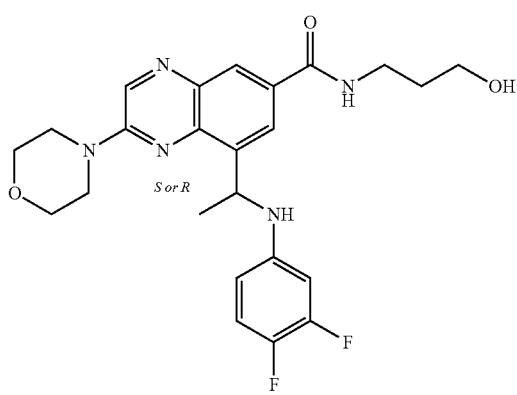

Compound 280 was prepared according to an analogous procedure as described for the synthesis of compound 5 using compound 234 and 3-Amino-1-propanol as starting materials (330 mg, 72%, M.P: 164° C., DSC).

Compound 280 was purified by chiral SFC (CHIRAL-PAK AD-H 5 μm 250×20 mm; mobile phase: 60% CO₂, 40% MeOH). The pure fractions were collected and the solvent was evaporated to give 140 mg of one compound which were freeze-dried with a mixture of ACN and water (1/3) giving 105 mg (10%) of compound 280a: (MP: 80° C., gum, K) and 135 mg of another compound which were freeze-dried with a mixture of ACN and water (1/3) giving 120 mg (26%) of compound 280b (MP: 80° C., gum, K).

Preparation of Compound 281, Compound 281a and Compound 281b compound 281

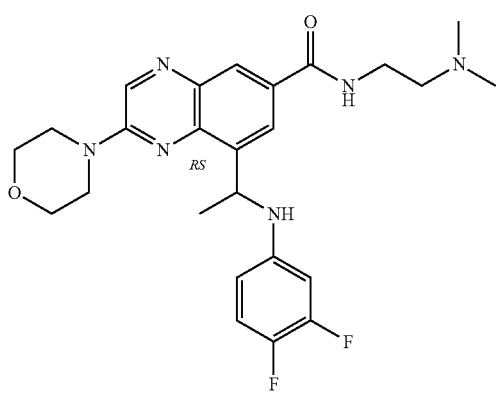

compound 281a

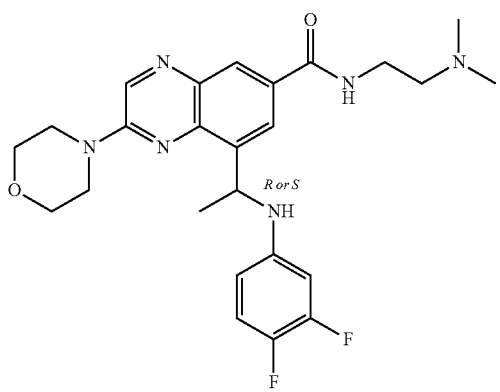

compound 281b

Compound 281 was prepared according to an analogous procedure as described for the synthesis of compound 5, using compound 234 and N,N-dimethylethylenediamine as starting materials (570 mg, 100%, M.P=80° C., K)

Compound 281 was purified by chiral SFC (CHIRAL-PAK AD-H 5 μm 250×20 mm; mobile phase: 60% CO₂, 40% MeOH). The pure fractions were collected and the solvent was evaporated to give 253 mg of one compound which was crystallized from pentane giving 136 mg (23%) of compound 281a (MP: 102° C., K) and 234 mg of another compound which was crystallized from pentane giving 164 mg (28%) of compound 281b (MP: 80° C., gum, K).

Preparation of Compound 283a and Compound 283b

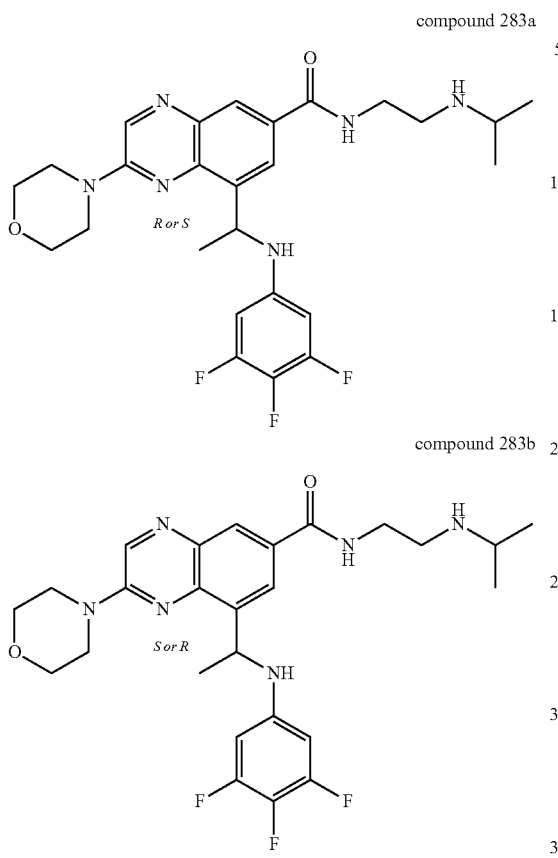

compound 283a compound 283b

Compound 283a and compound 283b were prepared according to an analogous procedure as described for the synthesis of compound 5, using compound 170 and N-isopropylethylenediamine as starting materials giving 290 mg (97%) of a racemic intermediate compound which was purified by chiral SFC (CHIRALPAK AD-H 5 μm 250×20 mm; mobile phase: 60% CO$_2$, 40% EtOH (0.3% iPrNH$_2$)). The pure fractions were collected and the solvent was evaporated to give 102 mg of one compound which was crystallized from Et$_2$O giving 63 mg (21%) of compound 283a: (MP: 173° C., DSC) and 105 mg of other compound which was crystallized from Et$_2$O giving 60 mg (20%) of compound 283b: (MP: 170° C., DSC).

Preparation of Compound 284a and Compound 284b

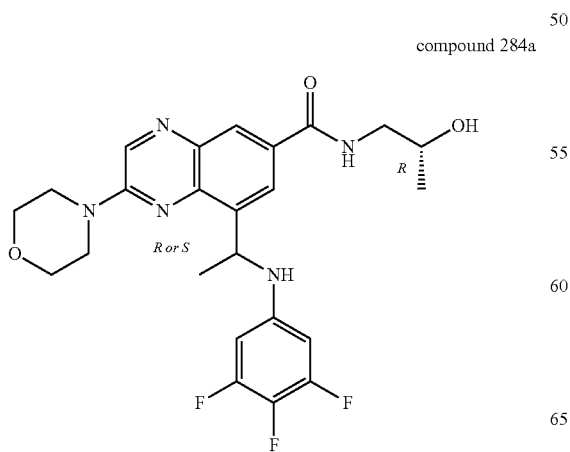

compound 284a

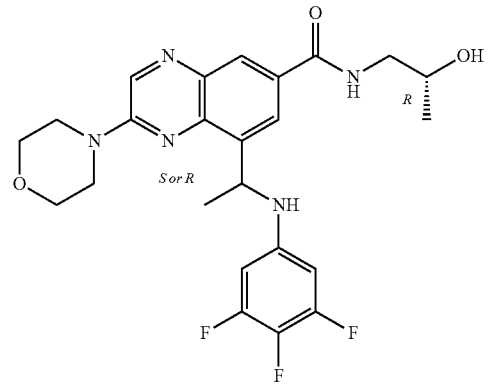

compound 284b

Compound 284a and compound 284b were prepared according to an analogous procedure as described for the synthesis of compound 5 using compound 170 and (2R)-(−)-1-aminopropan-2-ol as starting materials giving 745 mg (84%) of aracemic compound, which was purified by chiral SFC (CHIRALCEL OJ-H 5 μm 250×20 mm; mobile phase: 83% CO$_2$, 17% EtOH (0.3% iPrNH$_2$)). The pure fractions were collected and the solvent was evaporated to give 323 mg of one compound which was crystallized from pentane giving 190 mg (21%) of compound 284a (MP: 113° C., K) and 368 mg of another compound which was crystallized from pentane giving 240 mg (27%) of compound 284b (MP: 112° C., K).

Preparation of Compound 286, Compound 286a and Compound 286b

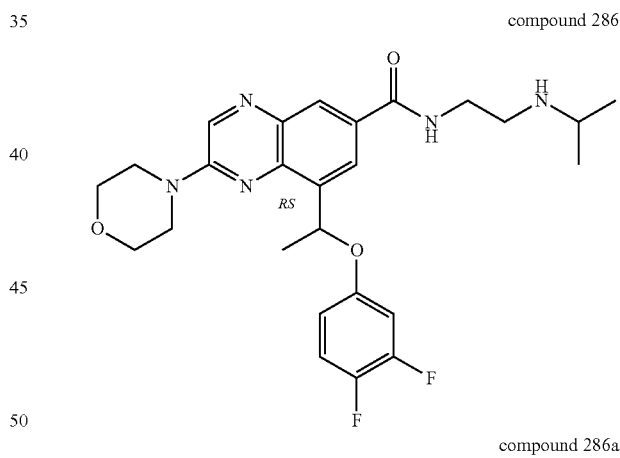

compound 286

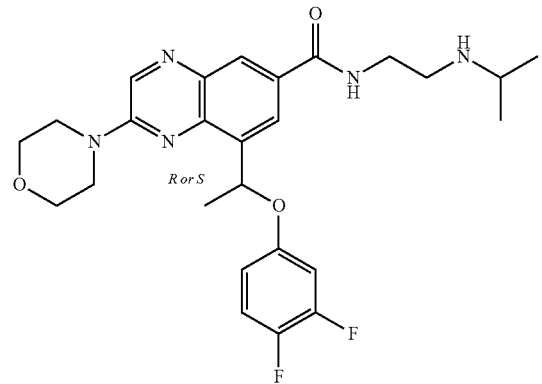

compound 286a compound 286b

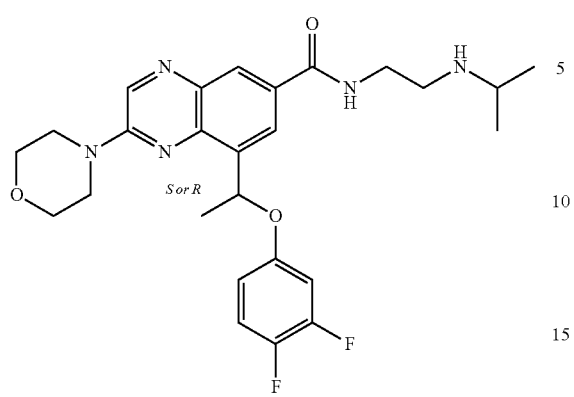

compound 287b

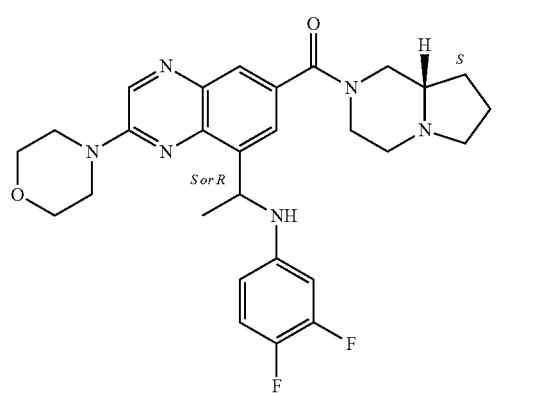

Compound 286 was prepared according to an analogous procedure as described for the synthesis of compound 5 using compound 285 and N-isopropylethylenediamine, as starting materials (645 mg, 67%, MP: 85° C., gum, K).

Compound 286 (598 mg) was purified by chiral SFC (CHIRALPAK AD-H 5 μm 250×30 mm; mobile phase: 65% $CO_2$, 35% EtOH (0.3% iPrNH$_2$)). The pure fractions were collected and the solvent was evaporated to give 262 mg of one compound which was crystallized from Et$_2$O giving 187 mg (19%) of compound 286a (MP: 85° C., gum, K) and 231 mg of other compound which was crystallized from Et$_2$O giving 220 mg (23%) of compound 286b (MP: 85° C., gum, K).

Preparation of Compound 287, Compound 287a and Compound 287b

Compound 287 was prepared according to an analogous procedure as described for the synthesis of compound 5 using compound 234 and (6S)-1,4-diazabicyclo[4,3,0]nonane as starting materials (1.03 g, 82%, M.P=80° C., gum, K).

Compound 287 (980 mg) was purified by chiral SFC (CHIRALPAK AD-H 5 μm 250×20 mm; mobile phase: 70% $CO_2$, 30% MeOH (0.3% iPrNH$_2$)). The pure fractions were collected and the solvent was evaporated to give 274 mg (22%) of one compound which was crystallized from DIPE giving 255 mg (20%) of compound 287a (MP: 90° C., K) and 185 mg of other compound which was crystallized from Et$_2$O giving 130 mg (10%) of compound 287b (MP: 95° C., gum, K).

Preparation of Compound 292, Compound 292a and Compound 292b

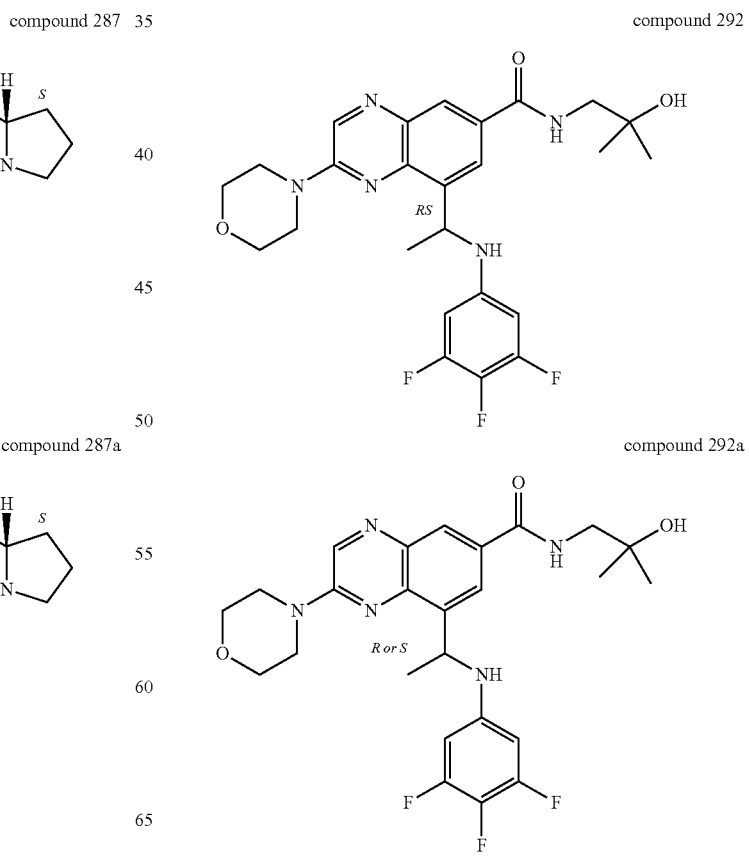

compound 292b

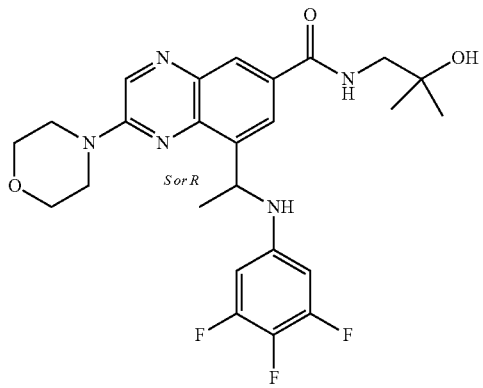

compound 295b

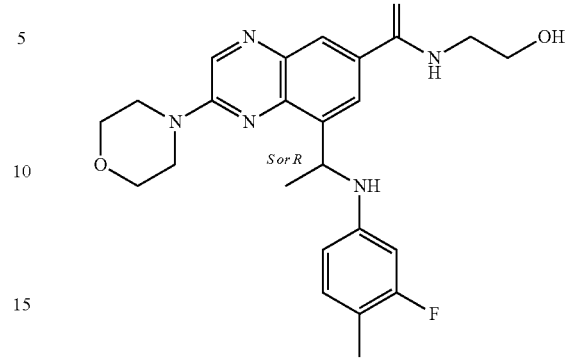

Compound 292 was prepared according to an analogous procedure as described for the synthesis of compound 5 using compound 170 and 1-amino-2-methylpropan-2-ol as starting materials (650 mg, 93%, MP: 80° C., gum, K).

Compound 292 (650 mg) was purified by chiral SFC (CHIRALCEL OJ-H 5 μm 250×20 mm; mobile phase: 80% CO$_2$, 20% MeOH (0.3% iPrNH$_2$)). The pure fractions were collected and the solvent was evaporated to give 310 mg of one compound which was crystallized from pentane and Et$_2$O giving 186 mg (27%) of compound 292a (MP: 110° C., gum, K) and 305 mg of other compound which was crystallized from pentane and Et$_2$O giving 190 mg (27%) of compound 292b (MP: 110° C., gum, K).

Preparation of Compound 295, Compound 295a and Compound 295b:

Compound 295 was prepared according to an analogous procedure as described for the synthesis of compound 5 using compound 294 and ethanol amine as starting materials (700 mg, 79%, MP: 80° C., gum, (K)).

Compound 295 was purified by chiral SFC (CHIRALPAK IC-H 5 μm 250×30 mm; mobile phase: 60% CO$_2$, 40% iPrOH (0.3% iPrNH$_2$)). The pure fractions were collected and the solvent was evaporated to give 276 mg of one compound which was crystallized from pentane giving 244 mg (28%) of compound 295a (MP: 120° C., gum, K) and 291 mg of other compound which was crystallized from pentane giving 225 mg (25%) of compound 295b (MP: 120° C., gum, K).

Preparation of Compound 298a and Compound 298b compound 298a

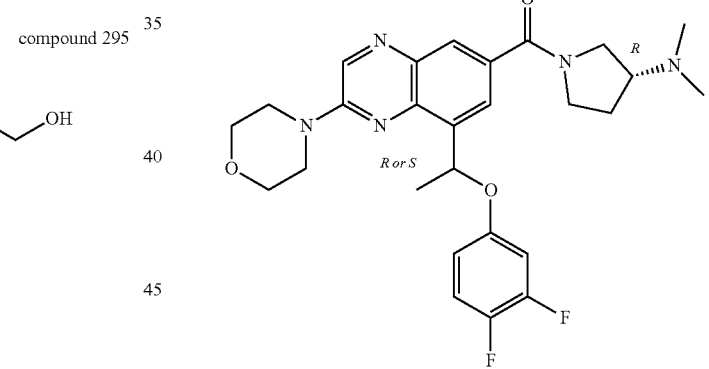

compound 295

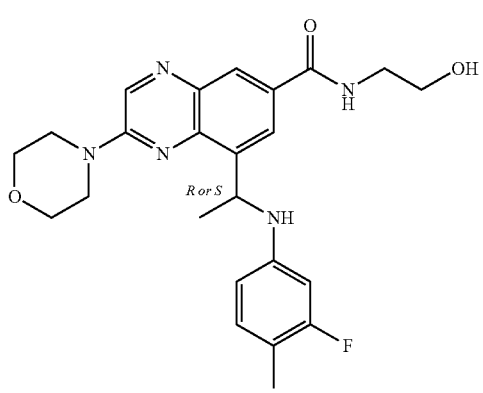

compound 295a

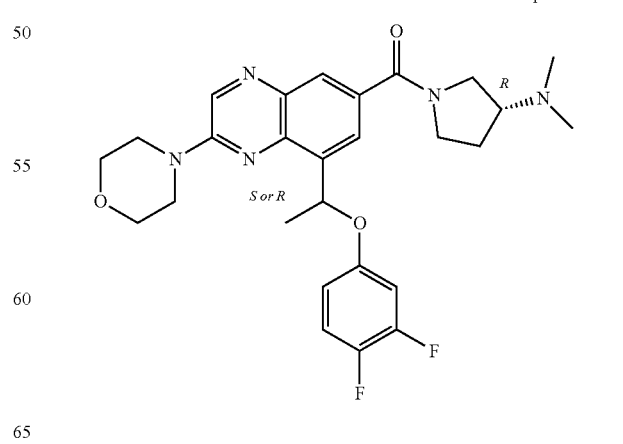

compound 298b

Compound 298a and compound 298b were prepared according to an analogous procedure as described for the synthesis of compound 5 using compound 285 and (R)-(+)-3-(Dimethylamino)pyrrolidine as starting materials. The separation of the enantiomers from 360 mg of racemic compound was performed by chiral SFC (CHIRALPAK AD-IT 5 μm 250×30 mm; mobile phase: 60% CO$_2$, 40% EtOH (0.3% iPrNH$_2$)). The pure fractions were collected and the solvent was evaporated to give one compound which was crystallized from pentane and Et$_2$O giving 74 mg (20%) of compound 298a (MP: 100° C., gum, K) and the other compound which was crystallized from pentane and Et$_2$O giving 45 mg (12%) of compound 298b (MP: 100° C., gum, K).

Preparation of Compound 299a and Compound 299b

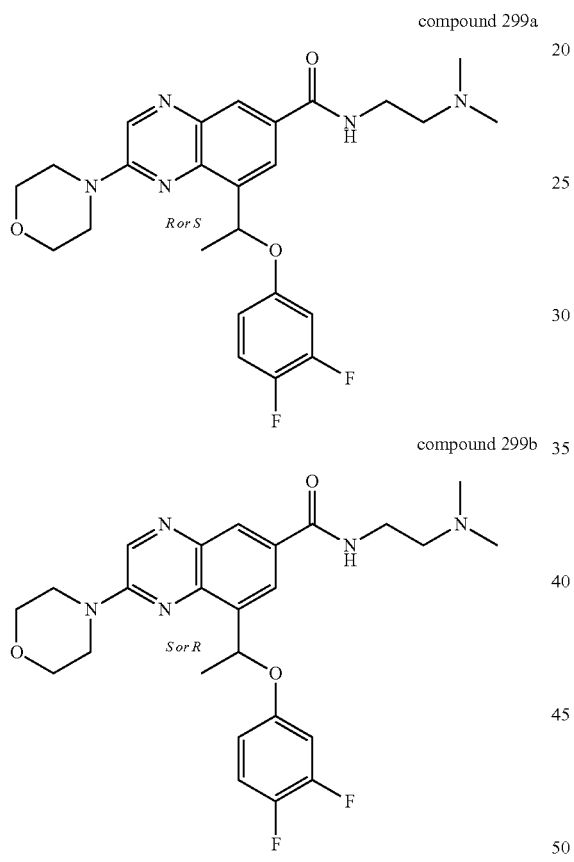

Compound 299a and compound 299b were prepared according to an analogous procedure as described for the synthesis of compound 5 using compound 285 and N,N-dimethylethylenediamine as starting materials. The separation of the enantiomers from 440 mg of racemic compound was performed by chiral SFC (CHIRALPAK AD-H 5 μm 250×20 mm; mobile phase: 78% CO$_2$, 22% EtOH (0.3% iPrNH$_2$)). The pure fractions were collected and the solvent was evaporated to give one compound which was crystallized from DCM and Et$_2$O giving 98 mg (17%) of compound 299a (MP: 100° C., gum, K) and the other compound which was crystallized from DCM and Et$_2$O giving 86 mg (15%) of compound 299b (MP: 100° C., gum, K).

Preparation of Compound 300, Compound 300a and Compound 300b

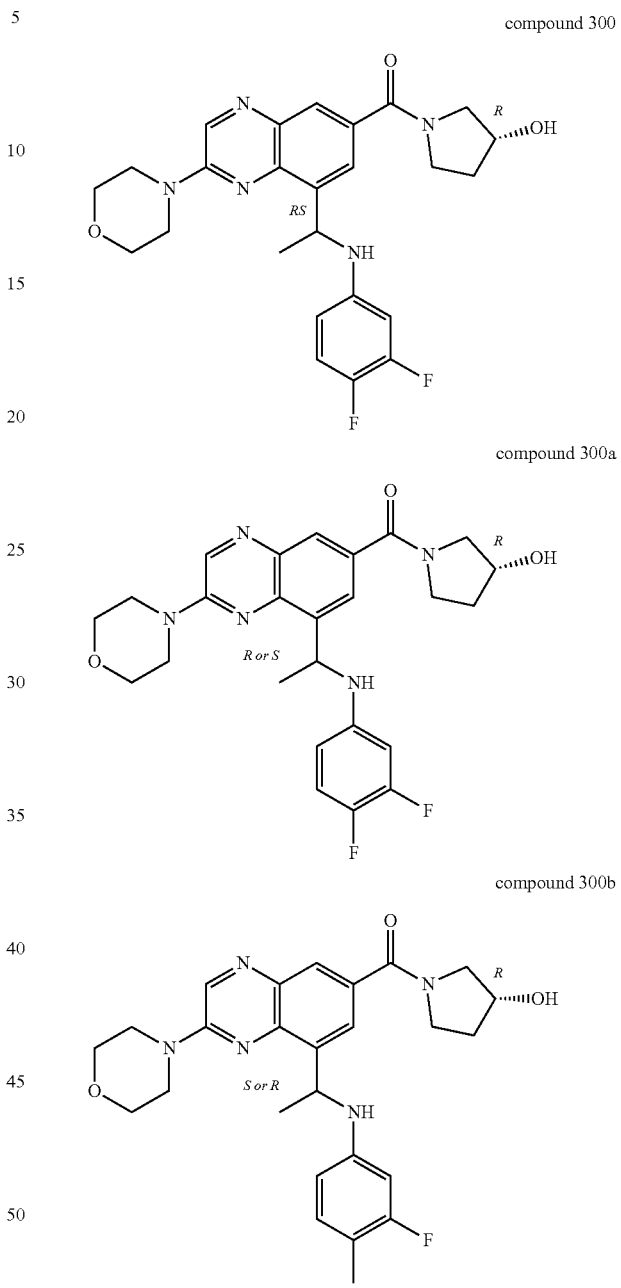

Compound 300 was prepared according to an analogous procedure as described for the synthesis of compound 5 using compound 234 and (R)-(−)-3-pyrrolidinol as starting materials. (723 mg, 88%).

Compound 300 was purified by chiral SFC (CHIRALPAK DIACEL AD 250×30 mm; mobile phase: CO$_2$, iPrOH (0.4% iPrNH$_2$)). The pure fractions were collected and the solvent was evaporated to give one compound which was crystallized from Et$_2$O giving 152 mg (19%) of compound 300a (MP: 140° C., K) and another compound which was crystallized from Et$_2$O giving 130 mg (16%) of compound 300b (MP: 135° C., K).

Preparation of Compound 302, Compound 302a and Compound 302b

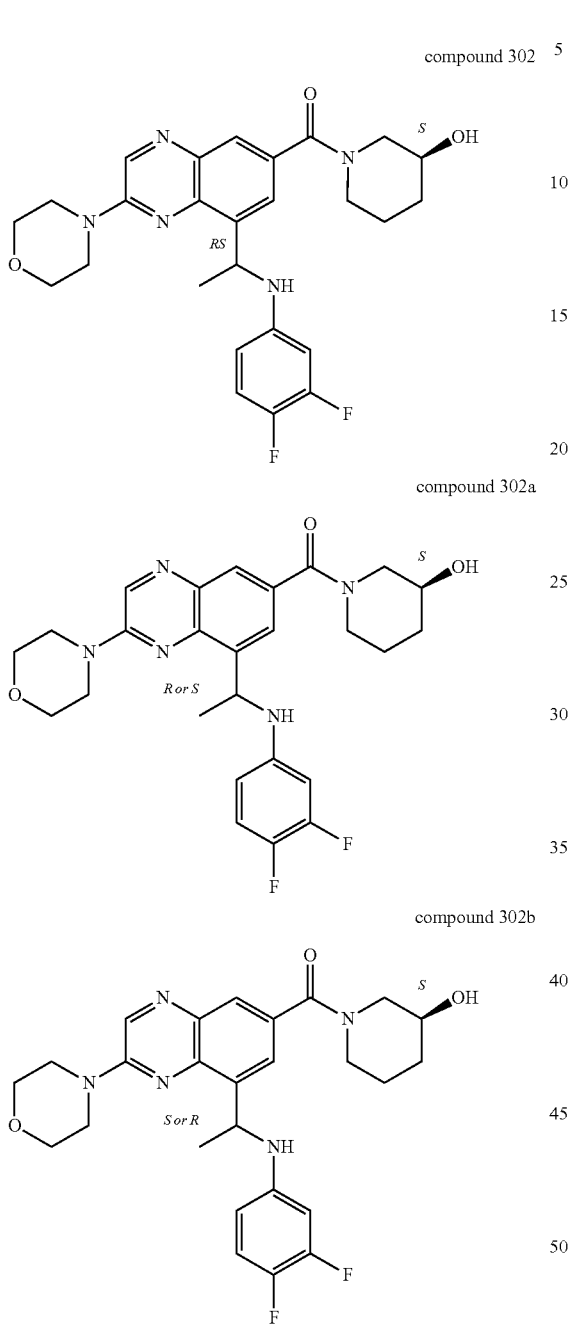

compound 302 compound 302a compound 302b

Compound 302 was prepared according to an analogous procedure as described for the synthesis of compound 5 using compound 234 and (S)-3-hydroxypiperidine hydrochloride as starting materials. (637 mg, 100%, MP:80° C., K). Compound 302 was purified by chiral SFC (CHIRALPAK AS-H 5 μm 250×20 mm; mobile phase: 65% CO₂, 35% EtOH (0.3% iPrNH₂)). The pure fractions were collected and the solvent was evaporated to give 376 mg of one compound which was crystallized from pentane giving 90 mg (15%) of compound 302a (MP: 135° C., K) and 245 mg of another compound which was crystallized from pentane giving 245 mg (41%) of compound 302b (MP: 135° C., K).

Preparation of Compound 308:

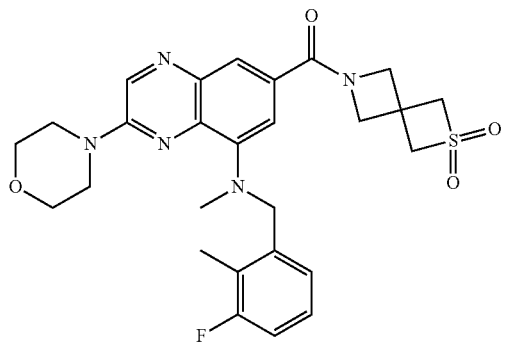 [SMILES: Cc1c(F)cccc1CN(C)c1cc(C(=O)N2CC3(C2)CS(=O)(=O)C3)cc2ncc(N3CCOCC3)nc12]

Compound 308 was prepared according to an analogous procedure as described for the synthesis of compound 5 using compound 307 find 2-Thia-6-azaspiro[3.3]heptane, 2,2-dioxide as starting materials (156 mg, 59%, MP: 195° C., DSC).

Preparation of Compound 309, Compound 309a and Compound 309b

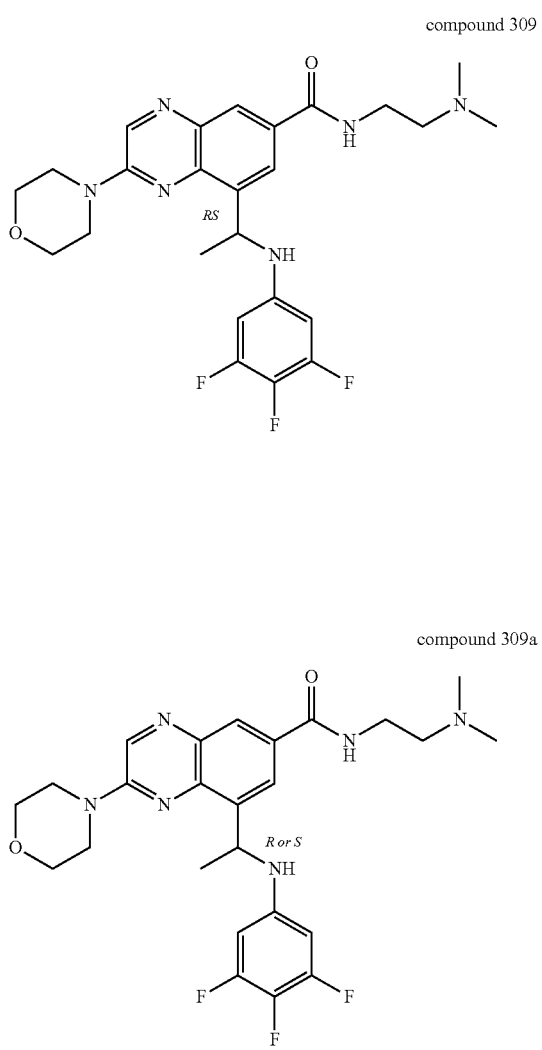

compound 309 compound 309a

-continued compound 309b

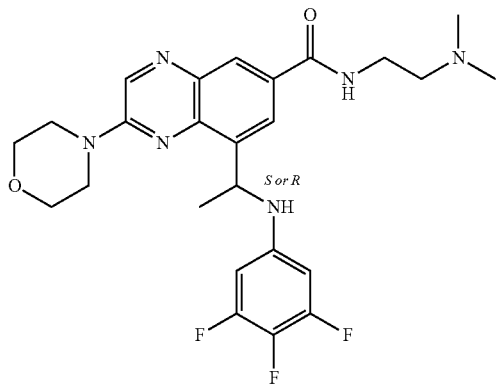

Compound 309 was prepared according to an analogous procedure as described for the synthesis of compound 5 using compound 170 and N,N-dimethylethylenediamine as starting materials (610 mg, 100%). Compound 309 was purified by chiral SFC (CHIRALPAK AD-H 5 µm 250×30 mm; mobile phase: 70% CO$_2$, 30% EtOH (0.3% iPrNH$_2$)). The pure fractions were collected and the solvent was evaporated to give 208 mg of one compound which was crystallized from Et2O giving 192 mg (33%) of compound 309a and 192 mg of another compound which was crystallized from pentane giving 192 mg (33%) of compound 309b.

Preparation of Compound 312, Compound 312a and Compound 312b compound 312

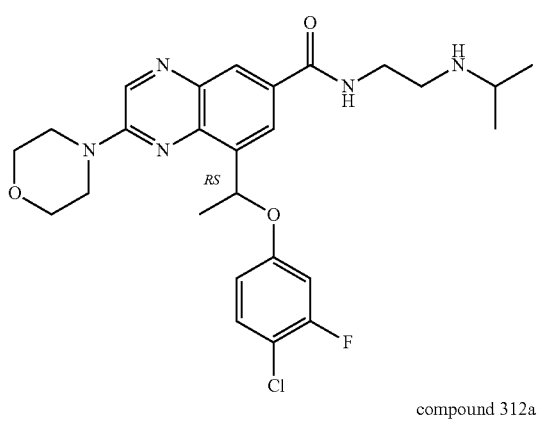

compound 312a

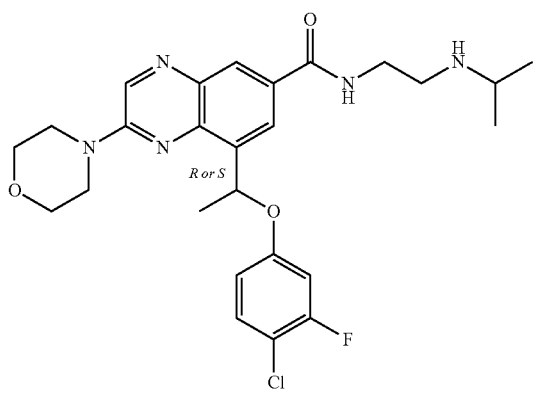

-continued compound 312b

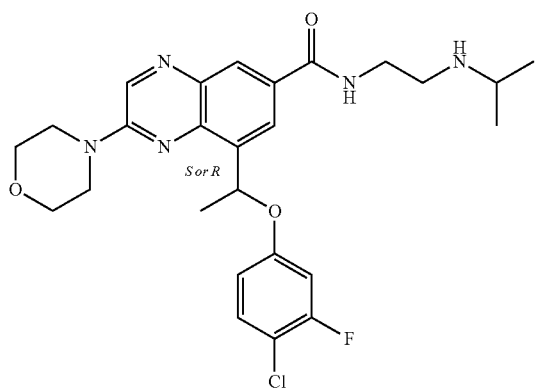

To a solution of compound 311 (150 mg; 0.347 mmol), N-diisopropylethylenediamine (52.6 µL; 0.417 mmol) and DIPEA (120 µL; 0.695 mmol) in DMF (3 mL) was added COMU (223 mg; 0.521 mmol). The solution was stirred at rt for 18 h then combined with another reaction performed on 50 mg of compound 311. Water and EtOAc were added. The organic layer was separated and the aqueous layer was extracted with EtOAc (3×). The combined organic layers were washed with a saturated aqueous solution of NaCl (3×), dried over MgSO$_4$, filtered off and evaporated in vacuo.

The crude (438 mg) was purified by silica gel chromatography (Stationary phase: irregular bare silica 40 g, Mobile phase: 0.5% aq. NEE, 94% DCM, 6% MeOH) to give 149 mg of compound 312 as a yellow oil.

Compound 312 was purified by chiral SFC (Stationary phase: CHIRALPAK AD-H 5 µm 250×20 mm, Mobile phase: 65% CO$_2$, 35% iPOH (0.3% iPrNH$_2$)) to give 55 mg of impure compound 312a as a yellow oil and 58 mg of impure compound 312b as a yellow oil. Impure compound 312a was purified by silica gel chromatography (Irregular SiOH 15-40 µm, 4 g Grace, mobile phase gradient: from DCM 100% to DCM 95%, MeOH/aq NEE (95:5) 5%) to give 49 mg of a yellow oil which were solubilized in ACN (1 mL), extended with water (9 mL) and freeze-dried to give 46 mg of compound 312a as a pale yellow fluffy solid.

Impure compound 312b was purified by silica gel chromatography (Irregular SiOH 15-40 µm, 4 g Grace, mobile phase gradient: from DCM 100% to DCM 95%, MeOH/aq NH3 (95:5) 5%) to give 47 mg of a yellow oil which were solubilized in ACN (1 mL), extended with water (9 mL) and freeze-dried to give 45 mg of compound 312b as a pale yellow fluffy solid.

337

Preparation of Compound 313, Compound 313a and Compound 313b

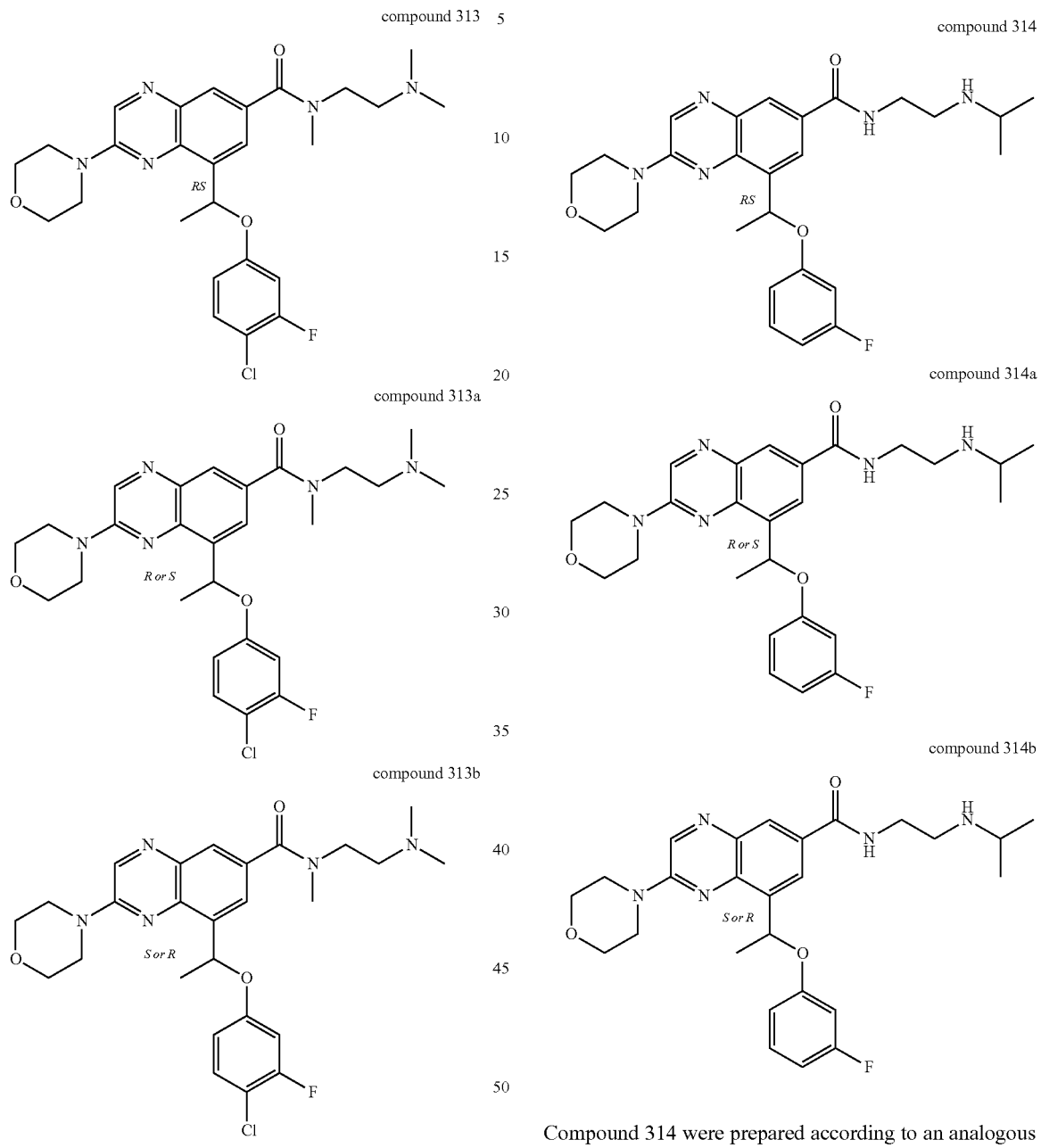

compound 313 compound 313a compound 313b

Compound 313 was prepared according to an analogous procedure as described for the synthesis of compound 312 using compound 311 and N,N,N'-trimethylethylenediamine as starting materials (197 mg). Compound 313 was purified by chiral SFC (CHIRALPAK AD-H 5 μm 250×20 mm; mobile phase: 80% $CO_2$, 20% EtOH (0.3% $iPrNH_2$)). The pure fractions were collected and each enantiomer was again purified by silica gel chromatography. The fractions containing the products were mixed and the solvent was evaporated to give one compound (44 mg) which was freeze-dried from pentane and $H_2O$ giving 42 mg (23%) of compound 313a and the other compound (43 mg) which was freeze-dried from pentane and $H_2O$ giving 42 mg (23%) of compound 313b.

338

Preparation of Compound 314 Compound 314a and Compound 314b compound 314 compound 314a compound 314b

Compound 314 were prepared according to an analogous procedure as described for the synthesis of compound 5 using compound 257a and N-isopropylethylenediamine as starting materials giving 250 mg (57%) of compound 314, which was purified by chiral SFC (CHIRALPAK DIACEL AD 250×20 mm; mobile phase: $CO_2$, EtOH-iPrOH 50/50 (0.4% $iPrNH_2$)). The pure fractions were collected and the solvent was evaporated to give 113 mg of one compound which was freeze-dried with pentane and $H_2O$ giving 86 mg (20%) of compound 314a (MP: 80° C., gum, K) and 99 mg of other compound which was freeze-dried with pentane and $H_2O$ giving 79 mg (18%) of compound 414b (MP: 80° C., gum, K).

Preparation of Compound 319, Compound 319a and Compound 319b

Preparation of Compound 320, Compound 320a and Compound 320b

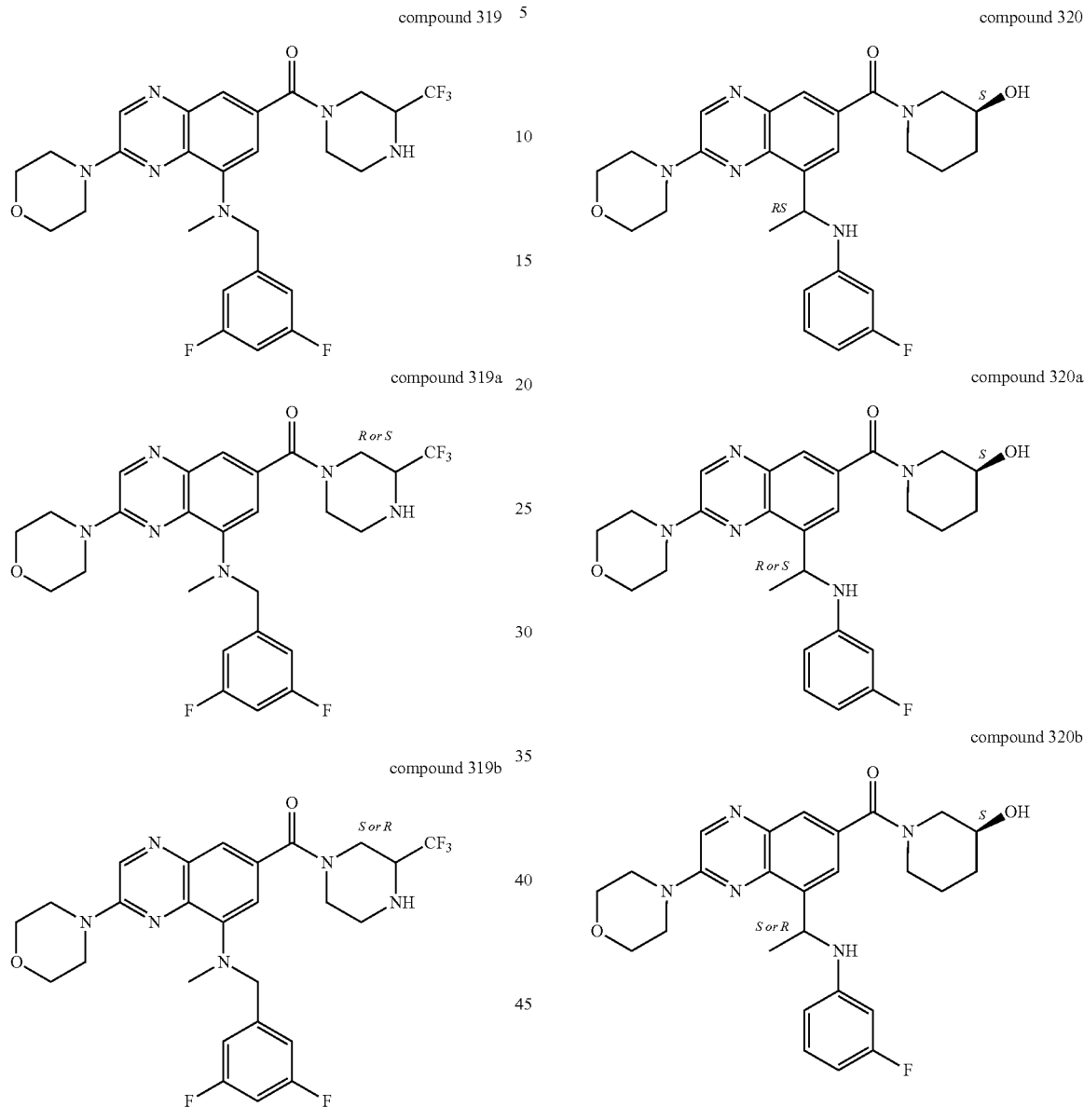

Compound 319 was prepared and compound 78IPIL were prepared according to an analogous procedure as described for the synthesis of compound 5 using compound 291 and (±)-2-(Trifluoromethyl)piperazine as starting materials (517 mg; 97%).

Compound 319 was separated by chiral SFC (CHIRALPAK AS-H 5 μm 250×20 mm; mobile phase: 80% CO$_2$, 20% EtOH (0.3% iPrNH$_2$)). The pure fractions were collected and the solvent was evaporated to give one compound (186 mg) which was freeze-dried with pentane and H$_2$O giving 182 mg (34%) of compound 319a and second compound (184 mg) which was freeze-dried with pentane and H$_2$O giving 166 mg (31%) of compound 319b.

Compound 320 was prepared according to an analogous procedure as described for the synthesis of compound 5 using compound 263 and (S)-3-hydroxypiperidine hydrochloride as starting materials (800 mg; 94%).

The separation of the enantiomers from 800 mg of compound 320 was performed by chiral SFC (CHIRALCEL OJ-H 5 μm 250×20 mm; mobile phase: 82% CO$_2$, 18% EtOH (0.3% iPrNH$_2$)). The pure fractions were collected and the solvent was evaporated to give one compound (354 mg) which was crystallized from DCM and pentane giving 248 mg (29%) of compound 320a (MP: 110° C., K) and a second compound (407 mg) which was crystallized from DCM and pentane giving 300 mg (35%) of compound 320b (MP: 136° C., K).

Preparation of Compound 321, Compound 321a and Compound 321b:

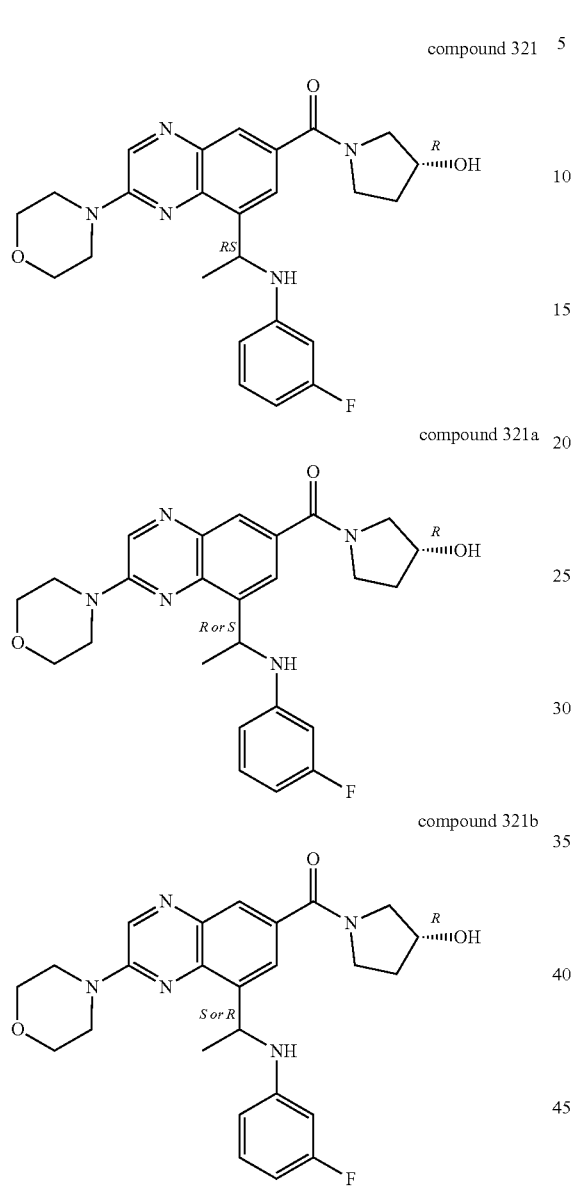

compound 321 compound 321a compound 321b

Compound 321 was prepared according to an analogous procedure as described for the synthesis of compound 5 using compound 263 and (R)-(+)-3-hydroxypyrrolidine as starting materials (700; 85%).

The separation of the enantiomers from 700 mg of compound 321 was made by chiral SFC (CHIRALPAK AD-H 5 μm 250×30 mm; mobile phase: 70% CO$_2$, 30% iPrOH (0.3% iPrNH$_2$)). The pure fractions were collected and the solvent was evaporated to give one compound (337 mg) which was crystallized from DCM and pentane giving 262 mg (32%) of compound 321a (MP: 118° C., K) and a second compound (367 mg) which was crystallized from DCM and pentane giving 265 mg (32%) of compound 321b (MP: 128° C., K).

Preparation of Compound 328:

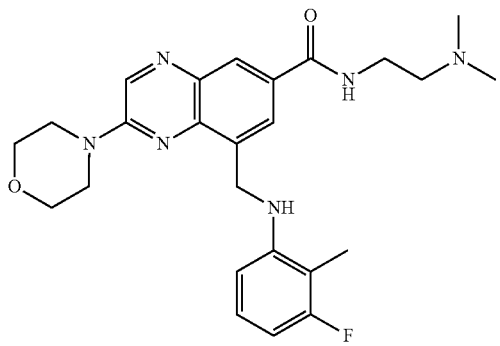 [SMILES: Cc1c(F)cccc1NCc1cc(C(=O)NCCN(C)C)cc2ncc(N3CCOCC3)nc12]

To a solution of compound 327 (200 mg; 0.505 mmol), N,N-dimethylethylenediamine (83 μL; 0.76 mmol) and diisopropylethyl amine (174 μL; 1.01 mmol) in DMF (5 mL) was added COMU (324 mg; 0.757 mmol). The solution was stirred at room temperature for 1 h. Then, water and EtOAc were added. The organic layer was separated and the aqueous layer was extracted with EtOAc (3×). The combined organic layers were washed with a saturated aqueous solution of NaCl (3×), dried over MgSO, filtered off and evaporated in vacuo. The residue (brown oil) was purified by silica gel chromatography (Irregular SiOH 15-40 μm, 24 g, mobile phase gradient: from DCM 100% to DCM 90%, MeOH/aq NH$_3$ (95:5) 10%) to give 252 mg of a yellow oil. This fraction was further purified by silica gel chromatography (Irregular SiOH 15-40 μm, 10 g, liquid loading (DCM), mobile phase gradient: from heptane 70%, EtOAc/(MeOH/aq. NH$_3$ (95:5)) (80:20) 30%) to heptane 30%, EtOAc/(MeOH/aq. NH$_3$ (95:5)) (80:20) 70%) to give 206 mg of a yellow film which was again further purified by silica gel chromatography (Irregular SiOH, 15-40 μm, 10 g, dry loading, mobile phase: heptane 80%, EtOAc/(MeOH/aq. NH$_3$ (95:5)) (80:20) 20%) to give 138 mg of a yellow film. This fraction was triturated in Et$_2$O. The solvent was evaporated in vacuo and the precipitate dried under high vacuum (50° C., 18 h) to give 136 mg (58%) of compound 328 as a yellow solid (MP: 98° C., DSC).

Preparation of Compound 332

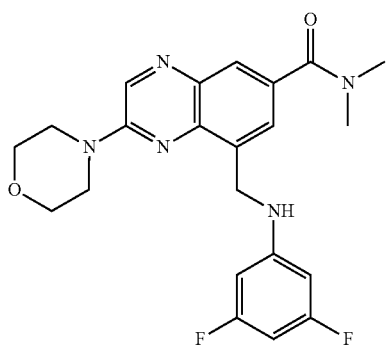 [SMILES: CN(C)C(=O)c1cc(CNc2cc(F)cc(F)c2)c2nc(N3CCOCC3)cnc2c1]

Compound 332 was prepared according to an analogous procedure as described for the synthesis of compound 312 using compound 331 and dimethylamine (solution 2M in THF) as starting materials (96 mg, 50%, MP: 169° C., DSC).

Preparation of Compound 333

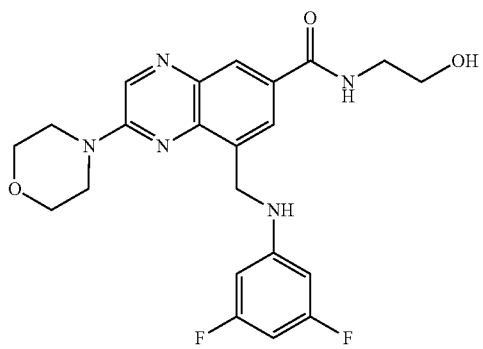 [SMILES: O=C(NCCO)c1cc(CNc2cc(F)cc(F)c2)c2nc(N3CCOCC3)cnc2c1]

Compound 333 was prepared according to an analogous procedure as described for the synthesis of compound 312 using compound 331 and ethanolamine as starting materials (80 mg, 68%, MP: 265° C., DSC).

Preparation of Compound 334, Compound 334a and Compound 334b compound 334

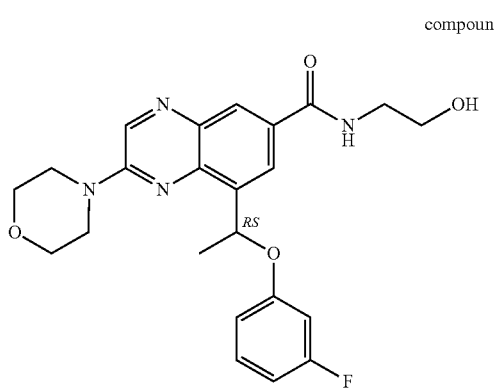

compound 334a

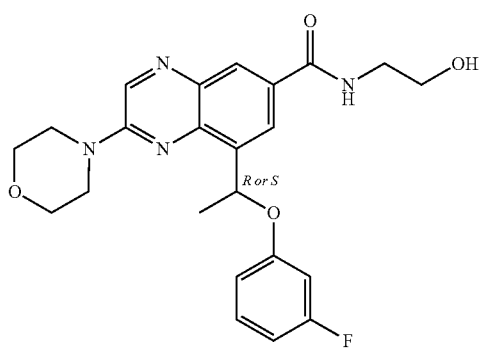

compound 334b

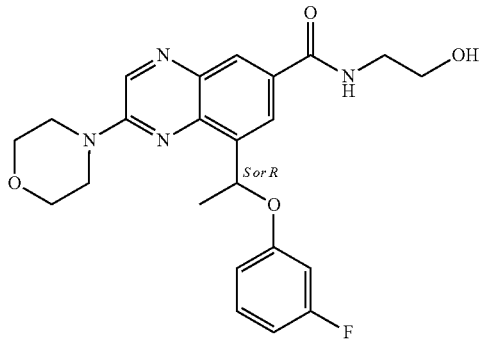

Compound 334 prepared according to an analogous procedure as described for the synthesis of compound 5 using compound 257a and 2-aminoethanol as starting material. The residue (280 mg) was purified by chromatography over silica (irregular SiOH; 15-40 µm; 30 g; gradient: from 95% DCM, 5% MeOH to 93% DCM, 7% MeOH). The pure fractions were collected and the solvent was evaporated to give 150 mg (54%) of compound 334.

The separation of the enantiomers from 150 mg of compound 334 was performed by chiral SFC (CHIRALCEL OD-H 5 µm 250×20 mm; mobile phase: 70% $CO_2$, 30% uiPrOH). The pure fractions were collected and the solvent was evaporated to give two fractions which were crystallized from $Et_2O$ to give respectively 70 mg (16%) of compound 334a (M.P.: 136° C., DSC) and 71 mg (11%) of compound 334b (M.P.: 134° C., DSC).

Preparation of Compound 338, Compound 338a and Compound 338b compound 338

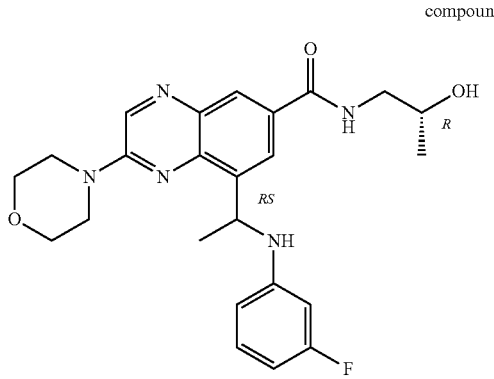

compound 338a

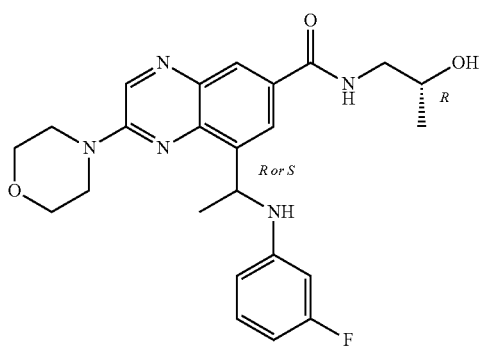

-continued

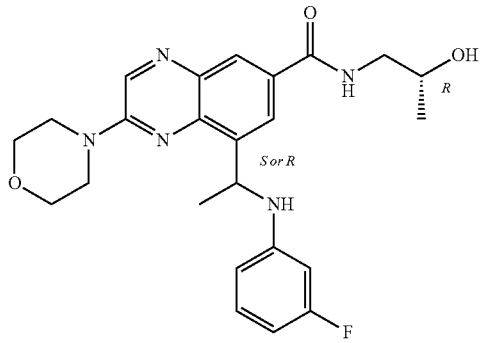

compound 338b

Compound 338 was prepared according to an analogous procedure as described for the synthesis of compound 5, using compound 263 and (2R)-(−)-1-Aminopropan-2-ol as starting material (Crystallization from DIPE; 360 mg, 72%). The separation of the enantiomers from 309 mg of compound 338 was performed by chiral SFC (CHIRALPAK AD-H 5 μm; 250×20 mm; mobile phase: 75% CO$_2$, 25% EtOH). The pure fractions were collected and the solvent was evaporated, and each fraction was crystallized from DIPE to afford 112 mg (22%), of compound 338a (M.P.: 90° C. (DSC)) and 108 mg (21%) of compound 338b (M.P.: 91° C. (DSC))

Preparation of Compound 342:

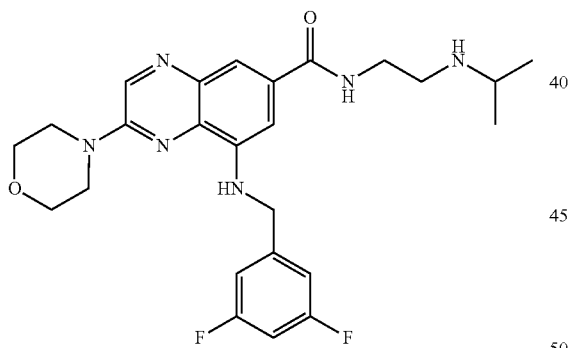

A solution of compound 289 (100 mg, 0.25 mmol), HATU (142.45 mg, 0.375 mmol) and Et$_3$N 0.104 mL, 0.749 mmol) in Me-THF (5 mL) was stirred at rt for 15 min. Then, N-isopropylethylenediamine (47.26 μL, 0.375 mmol) was added and the solution was stirred at rt for 5 h. The reaction mixture was poured in ice water and extracted with EtOAc. The organic layer was washed with brine (×2), dried over MgSO$_4$, filtered and evaporated until dryness. The resulting residue was purified via silica gel chromatography (Stationary phase: irregular SiOH 15-40 μm, 40 g, Mobile phase: 95% DCM, 5% MeOH, 0.5% NH4OH) to afford 75 mg (62%) of compound 342.

Preparation of Compound 346, Compound 346a, and Compound 346b

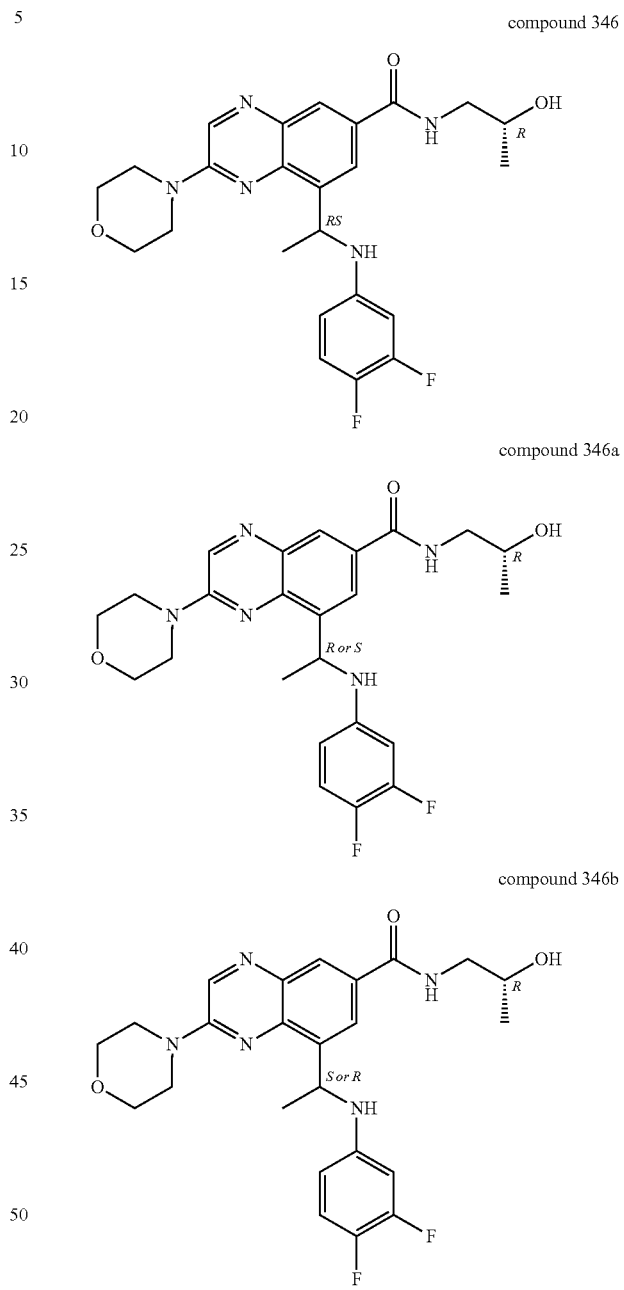

Compound 346 was prepared according to an analogous procedure as described for the synthesis of compound 5, using compound 234 and (2R)-(−)-1-aminopropan-2-ol as starting material (460 mg; 81%).

The separation of the enantiomers from 460 mg of compound 346 was performed via chiral SFC (Stationary phase: CHIRALPAK IC 5 μm 250×20 mm, Mobile phase: 83% CO$_2$, 17% EtOH (0.3% iPrNH$_2$)). The pure fractions were collected and evaporated until dryness and crystallized from pentane to give 115 mg (20%) of compound 346a (M.P.: 107° C. (K)) and 107 mg (19%) of compound 26 (M.P.: 106° C. (K)).

347
Preparation of Compound 347, Compound 347a and Compound 347b

348
Preparation of Compound 348, Compound 348a and Compound 348b

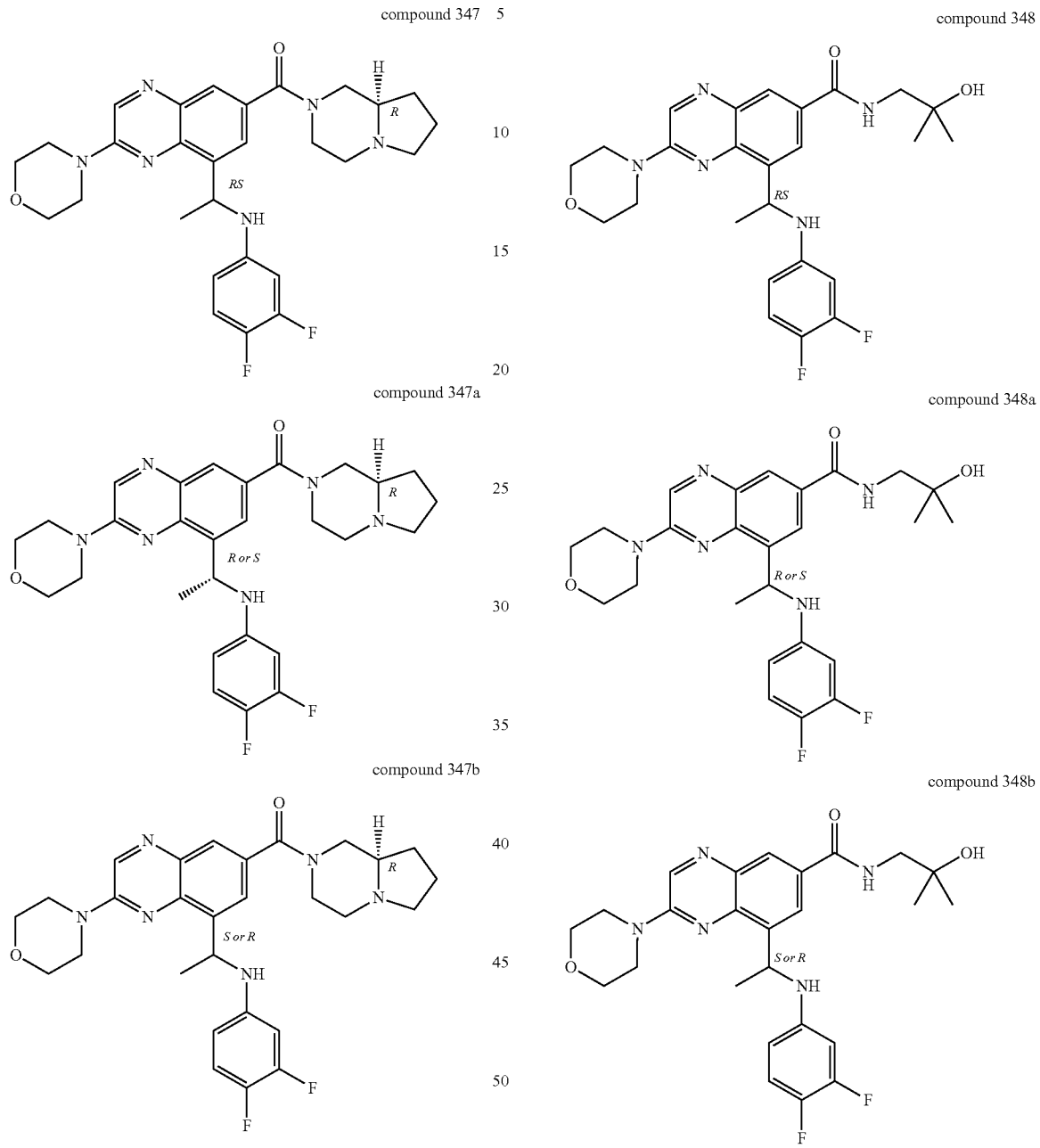

compound 347 compound 347a compound 347b compound 348 compound 348a compound 348b

Compound 347 was prepared according to an analogous procedure as described for the synthesis of compound 5, using compound 234 and (R)-1,4-diazabicyclo[4.3.0]nonane as starting material. (1 g; 79%; M.P.: 170° C. (DSC)).

The separation of the enantiomers from 950 mg of compound 347 was performed via chiral SFC (Stationary phase: Chiralpak AS-H 5 µm 250*20 mm, Mobile phase: 50% $CO_2$, 50% MeOH (0.3% iPrNH$_2$)). The pure fractions were collected and evaporated until dryness and crystallized from a mixture of pentane/DCM (19/1) to give 400 mg (32%) of compound 347a (M.P.: 125° C. (K)) and 317 mg (30%) of compound 347b (M.P.: 125° C. (K)).

Compound 348 was prepared according to an analogous procedure as described for the synthesis of compound 5, using compound 234 and 1-amino-2-methyl-2-propanol as starting materials (540 mg; 92%).

The separation of the enantiomers from 540 mg of compound 348 was performed via SFC (Stationary phase: CHIRALCEL OJ-H 5 µm 250×20 mm, Mobile phase: 86% $CO_2$, 14% EtOH (0.3% iPrNH$_2$)). The pure fractions were collected and evaporated until dryness and crystallized from pentane to give 157 mg (27) of compound 348a (M.P.: 102° C. (K)) and 173 mg (30%) of compound 348b (M.P.: 102° C. (K)).

349

Preparation of Compound 349, Compound 349a and Compound 349b

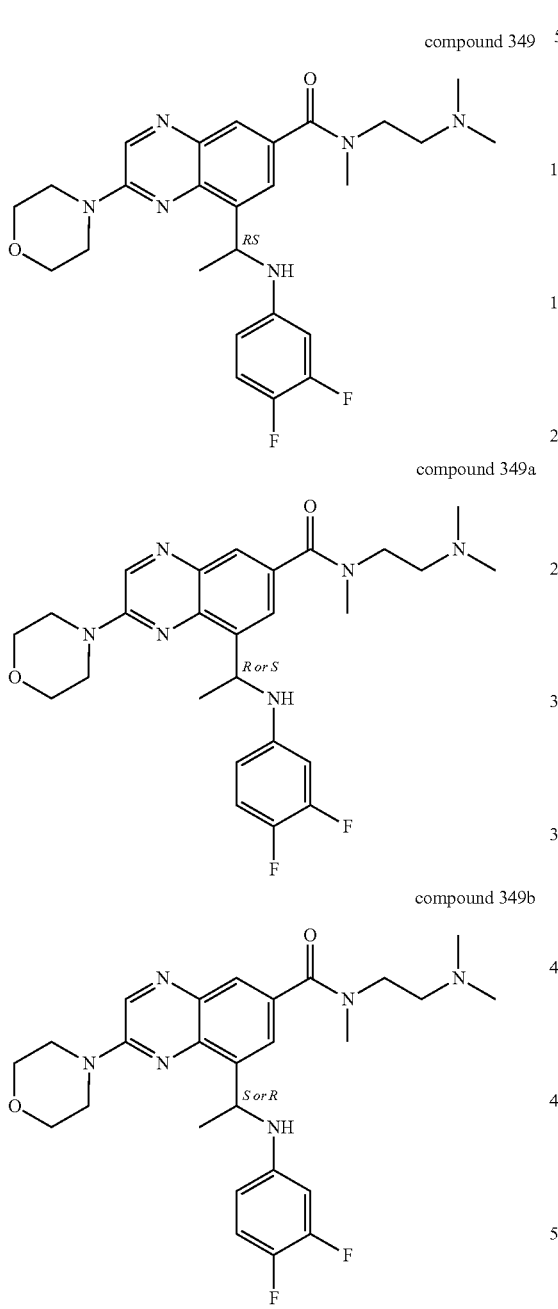

Compound 349 was prepared according to an analogous procedure as described for the synthesis of compound 5, using compound 234 and N,N,N'-Trimethylenediamine as starting materials (480 mg; 80%).

The separation of the enantiomers from 480 mg of compound 349 was performed via chiral SFC (Stationary phase: CHIRALPAK AD-H 5 μm 250×20 mm, Mobile phase: 83% CO$_2$, 17% EtOH (0.3% iPrNH2)). The pure fractions were collected and evaporated until dryness and crystallized from pentane to give 131 mg (22%) of compound 349a (M.P.: 82° C. (K)) and 131 mg (22%) of compound 349b (M.P.: 82° C. (K)).

350

Preparation of Compound 353:

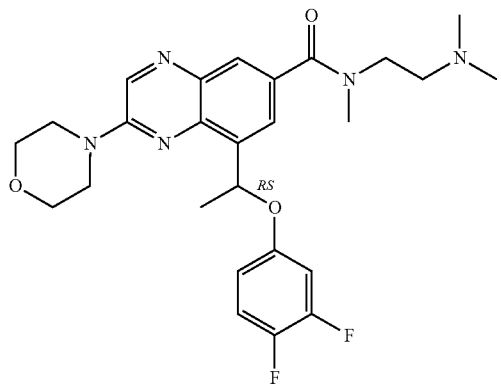 [SMILES: CC(Oc1ccc(F)c(F)c1)c1cc(C(=O)N(C)CCN(C)C)cc2ncc(N3CCOCC3)nc12]

Compound 353 was prepared according to an analogous procedure as described for the synthesis of compound 5 using compound 285 and N,N,N'-tri methyl ethylene diamine as starting material (350 mg, 58%, 80° C., (K)).

Preparation of Compound 354:

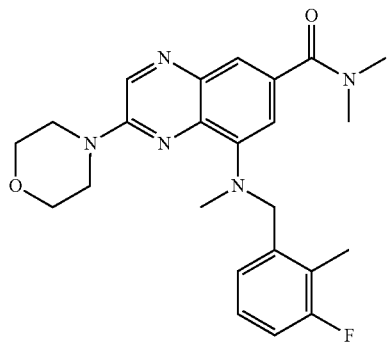 [SMILES: Cc1c(F)cccc1CN(C)c1cc(C(=O)N(C)C)cc2ncc(N3CCOCC3)nc12]

Compound 354 was prepared according to an analogous procedure as described for the synthesis of compound 5 using compound 307 as starting material (72 mg, 41%), Preparation of Compound 357, Compound 357a and Compound 357b

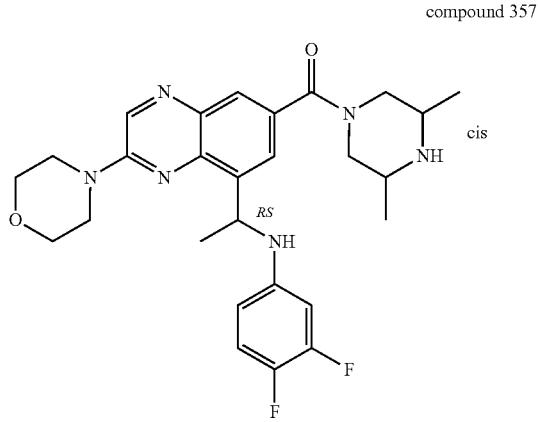

351

-continued compound 357a

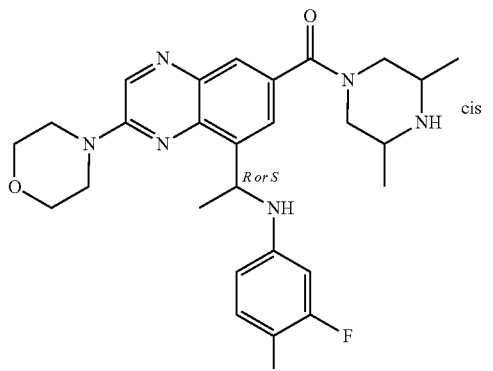

compound 357b

Compound 357 prepared according to an analogous procedure as described for the synthesis of compound 5, using compound 234 and cis 2,6-dimethylpiperazine as starting materials (570 mg; 92%).

The separation of the enantiomers from 570 mg of compound 357 was performed via SFC (Chiralpak AS-H 5 µm 250*20 mm, Mobile phase: 45% $CO_2$, 55% EtOH (0.3% iPrNH$_2$)) The pure fractions were collected and the solvent was evaporated. Each fraction was crystallized from pentane to give, after filtration, 191 mg (31%) of compound 43 (M.P.: 116° C. (K)) and 170 mg (38%) of compound 44 b (M.P.: 120° C. (K))

Preparation of Compound 358:

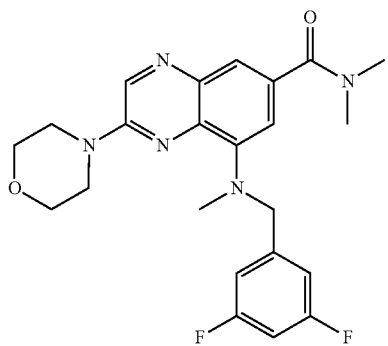 [SMILES: CN(C)C(=O)c1cc(N(C)Cc2cc(F)cc(F)c2)c2nc(N3CCOCC3)cnc2c1]

Compound 358 was prepared according to an analogous procedure as described for the preparation of compound 5, using compound 291 and dimethylamine as starting materials (126 mg of 60%).

352

Preparation of Compound 363 Compound 363a and Compound 363b

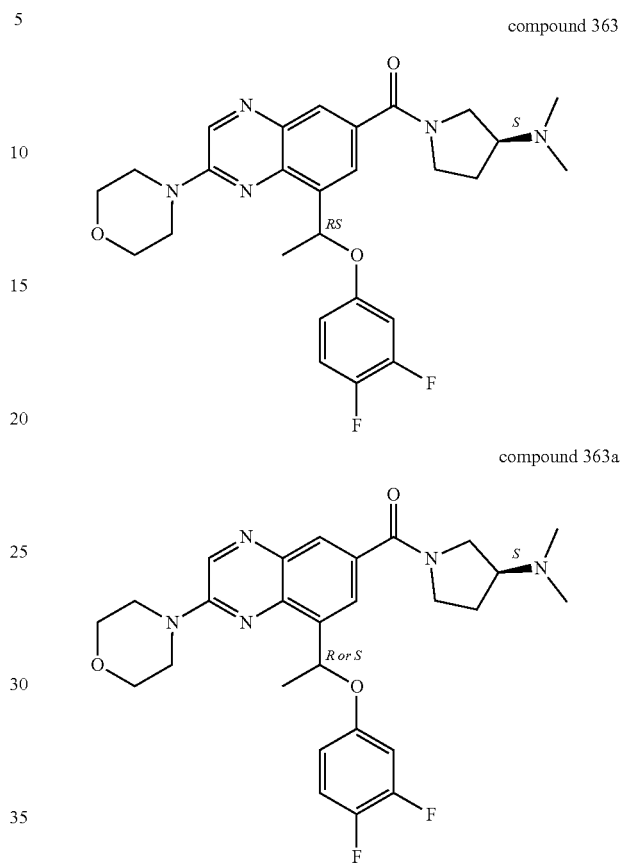

Compound 363 was prepared according to an analogous procedure as described for the synthesis of compound 5 starting from compound 285 and (S)-(+)-3-(dimethylamino) pyrolidine The separation of the enantiomers was performed by SFC (Stationary phase: Chiralpak Diacel AD 20×250 mm, Mobile phase: $CO_2$, iPrOH+0.4 iPrNH$_2$). The pure fractions were mixed and concentrated to afford 20 mg (5%) of compound 363a (M.P.: 80° C., gum K) and 70 mg (19%) of compound 363b (M.P.: 80° C., gum K)

353

Preparation of Compound 364, Compound 364a and Compound 364b

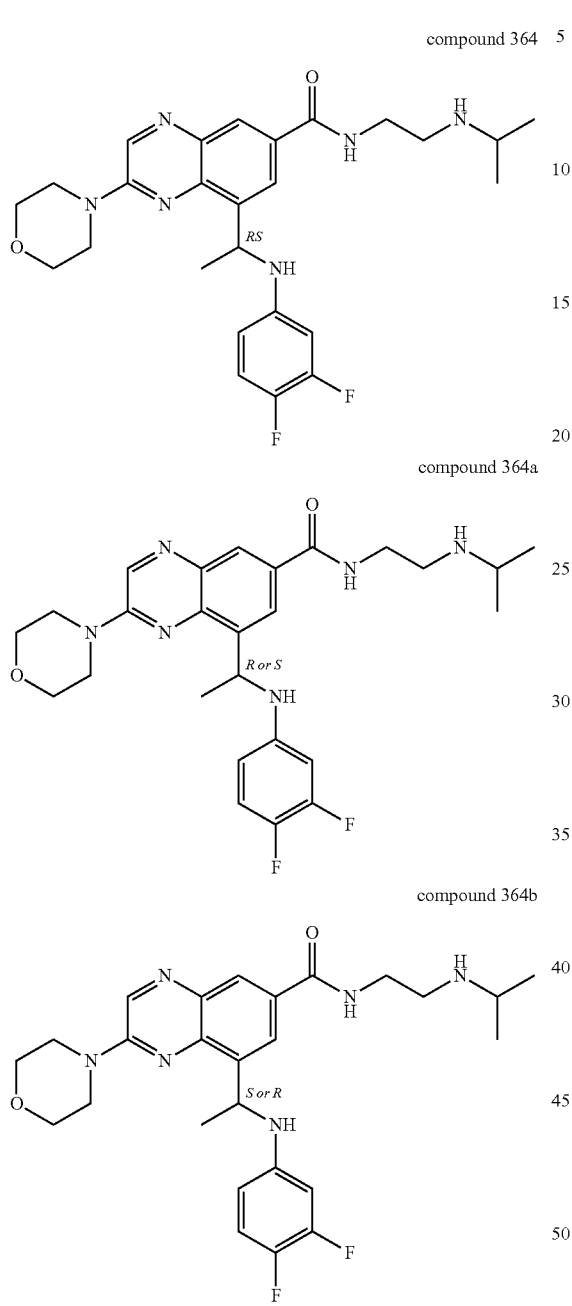

Compound 364 was prepared according to an analogous procedure as described for the synthesis of compound 5, using compound 234 and N-isopropylehtylenediamine as starting materials (280 mg, 58%, M.P.: 80° C. gum (K)).

The separation of the enantiomers was performed by chiral SFC (CHIRALPAK AD-H 5 μm; 250×20 mm; mobile phase: 60% $CO_2$, 40% EtOH (0.3% iPrNH2)). The pure fractions were collected and the solvent was evaporated. Each fraction was crystallized from a mixture of DCM/Et2O and gave, after filtration, 90 mg (18%) of compound 364a (M.P.: 80° C., gum (K)) and 89 mg (18%) of compound 364b (M.P.: 80° C., gum (K)).

354

Preparation of Compound 366:

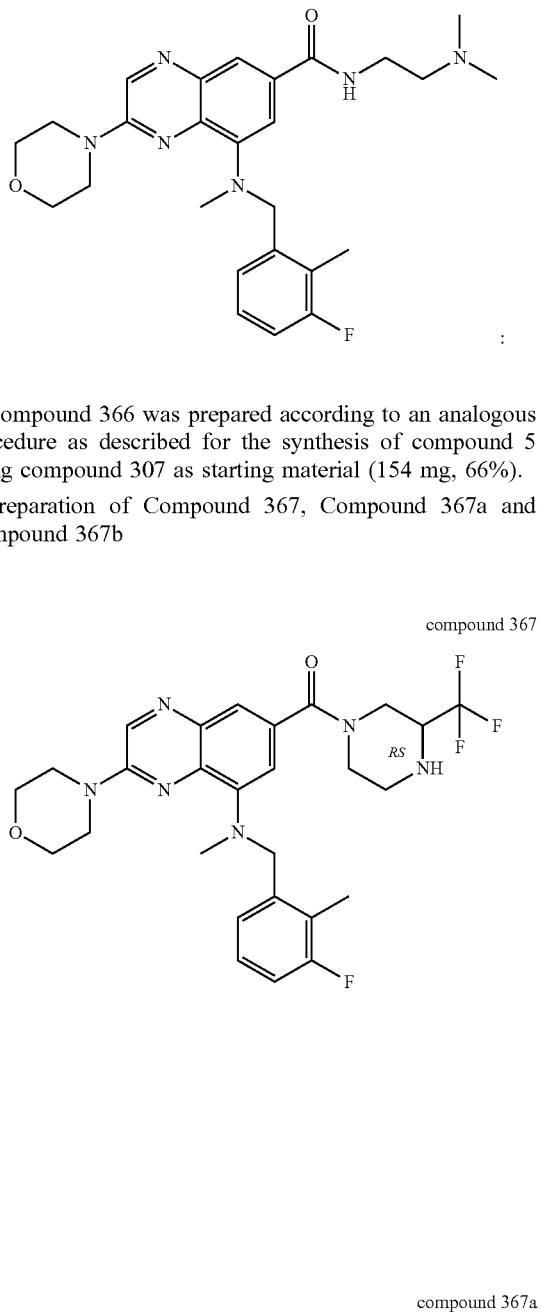

Compound 366 was prepared according to an analogous procedure as described for the synthesis of compound 5 using compound 307 as starting material (154 mg, 66%).

Preparation of Compound 367, Compound 367a and Compound 367b

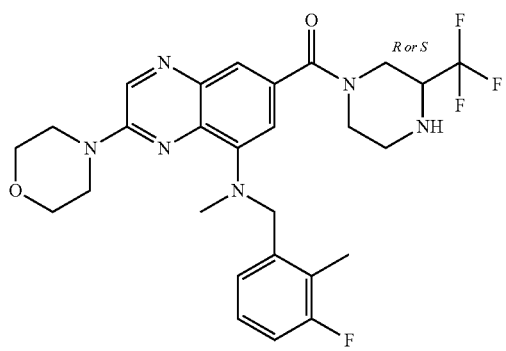

compound 367b

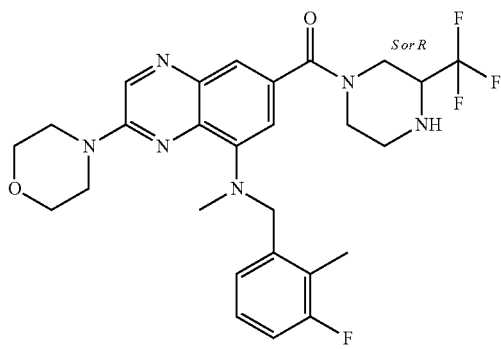 [SMILES: Cc1c(F)cccc1CN(C)c1cc(C(=O)NCCN(C)C)cc2ncc(N3CCOCC3)nc12]

Compound 367 was prepared according to an analogous procedure as described for the synthesis of compound 5 using compound 307 and (+/−)-2-(Trifluoromethyl)piperazine as starting material (453 mg, 85%).

The separation of the enantiomers from 453 mg of compound 367 was performed chiral SFC (CHIRALPAK AD-H 5 μm; 250×30 mm; mobile phase: 70% $CO_2$, 30% EtOH (0.3% $iPrNH_2$)). The pure fractions were collected and each fraction was crystallized from a mixture of Pentane/Et2O to give, after filtration, 119 mg (22%) of compound 367a and 127 mg (24%) of compound 367b.

Preparation of Compound 369, Compound 369a and Compound 369b compound 369 compound 369a

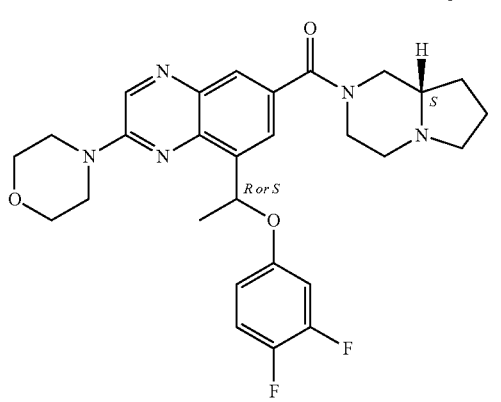

compound 369b

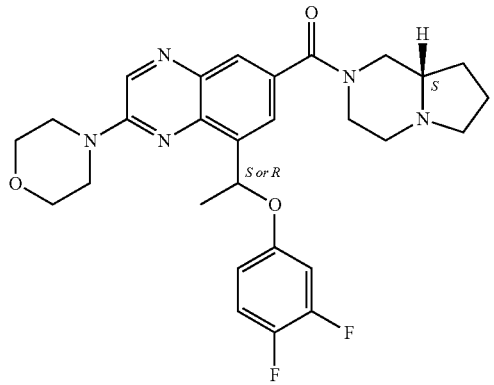

Compound 369 was prepared according to an analogous procedure as described for the synthesis of compound 5, using compound 285 and (6S)-1,4-diazabicyclo[4.3.0]nonane as starting materials (800 mg; 96%).

The separation of the enantiomers was performed by chiral SFC (Stationary phase: Chiralpak Diacel AD 20×250 mm, Mobile phase: $CO_2$, EtOH+0.4 $iPrNH_2$). The pure fractions were mixed and concentrated to afford fraction A (470 mg) and fraction B (450 mg). Fraction A was taken up with a mixture of Et2O/pentane. The precipitate was filtered to afford 180 mg (22%) of compound 369a (22%). Fraction B was taken up with a mixture of DCM/pentane. The precipitate was filtered to afford 140 mg (17%) of compound 369b (M.P.: 147° C., (DSC K)).

Preparation of Compound 375:

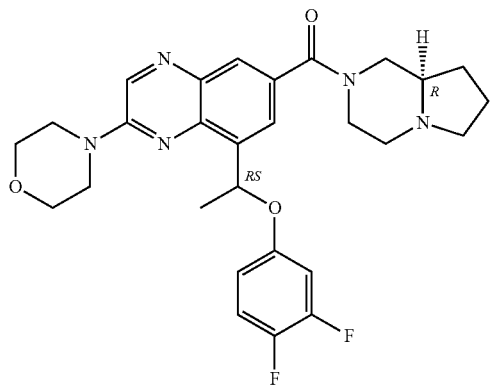

Compound 375 was prepared according to an analogous procedure as described for the synthesis of compound 5, using compound 285 and (R)-1,4-Diazabicyclo[4.3.0]nonane as starting materials (250 mg, 20%, M.P: 80° Gum (K)).

Preparation of Compound 381:

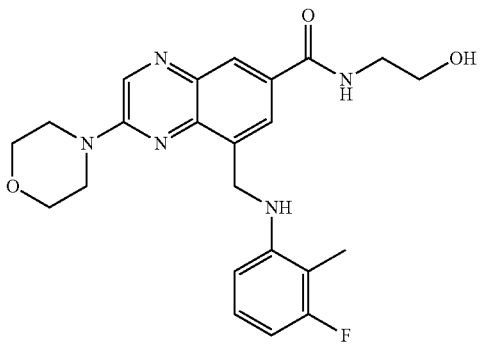 [SMILES: Cc1c(F)cccc1NCc1cc(C(=O)NCCO)cc2ncc(N3CCOCC3)nc12]

Compound 381 was prepared according to an analogous procedure as described for the synthesis of compound 312 using compound 327 and 2-aminoethanol as starting materials. (162 mg, 73%).

Preparation of Compound 382:

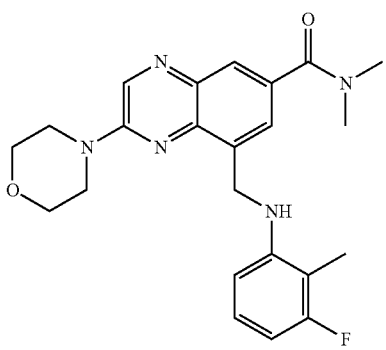 [SMILES: Cc1c(F)cccc1NCc1cc(C(=O)N(C)C)cc2ncc(N3CCOCC3)nc12]

Compound 382 was prepared according to an analogous procedure as described for the synthesis of compound 312 broux using compound 327 and dimethyl amine (2M solution in THF) as starting materials (136 mg, 64%, M.P: 150° C. (DSC)).

Preparation of Compound 384:

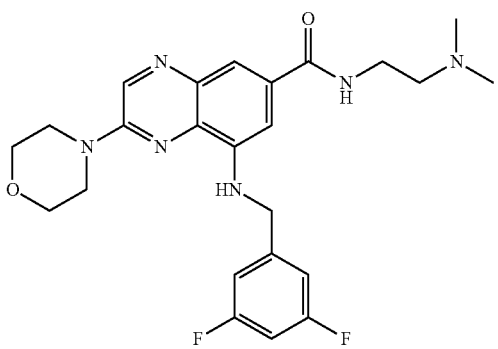 [SMILES: CN(C)CCNC(=O)c1cc(NCc2cc(F)cc(F)c2)c2nc(N3CCOCC3)cnc2c1]

Compound 384 was prepared according to an analogous procedure as described for the synthesis of compound 5, using compound 289 and N,N-dimethylethylenediamine as starting materials (66 mg, 19%).

Preparation of Compound 392, Compound 392a and Compound 392b

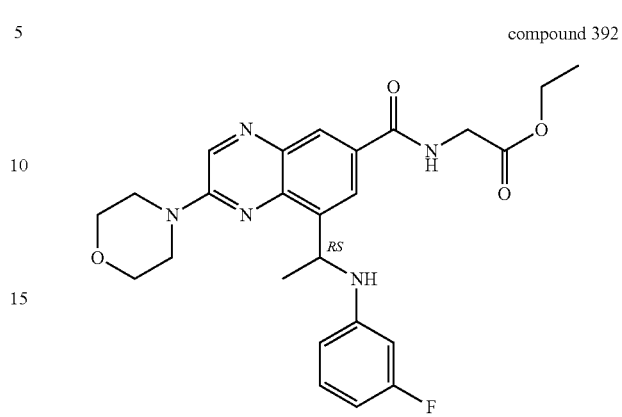

compound 392

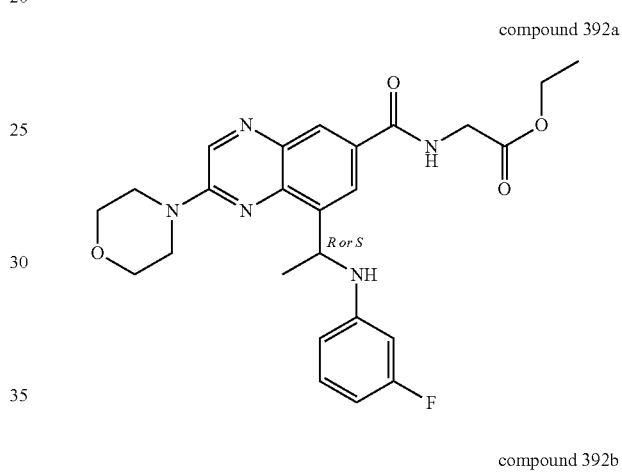

compound 392a

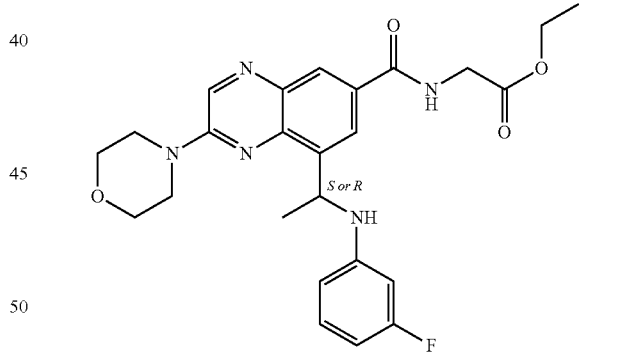

compound 392b

Compound 392 was prepared according to an analogous procedure as described for the synthesis of compound 5, using compound 263 and glycine ethyl ester hydrochloride as starting materials (727 mg, 66%).

The separation of the enantiomers was performed by chiral SFC (Stationary phase: Chiralpak AD-H 5 μm 250*30 mm, Mobile phase: 60% $CO_2$, 40% EtOH (0.3% iPrNH$_2$)). The fractions containing the products were concentrated to afford, after freeze-drying in a mixture of ACN/water (20/80), 220 mg (20%) of compound 392a (MP: 80° C., gum, Kofler) and 215 mg (20%) of compound 392b.

Preparation of Compound 394:

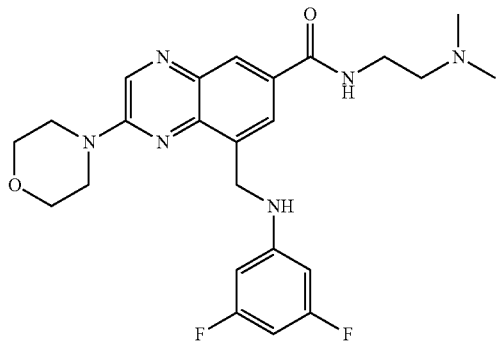 [SMILES: CN(C)CCNC(=O)c1cc(CNc2cc(F)cc(F)c2)c2nc(N3CCOCC3)cnc2c1]

Compound 394 was prepared according to an analogous procedure as described for the synthesis of compound 312, using compound 331 and N,N-dimethylethylenediamine as starting materials (86 mg, MP: 161° C. (DSC)).

Preparation of Compound 407, Compound 407a, Compound 407b compound 407

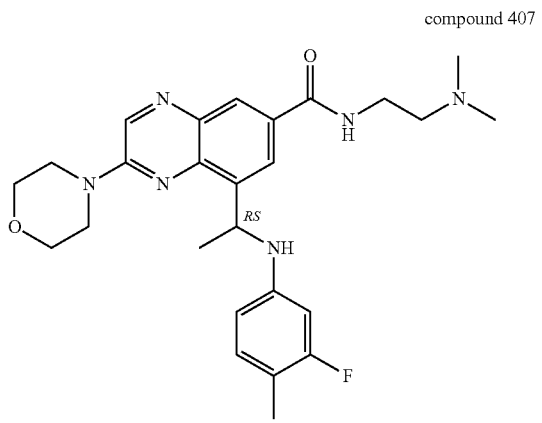

compound 407a compound 407b

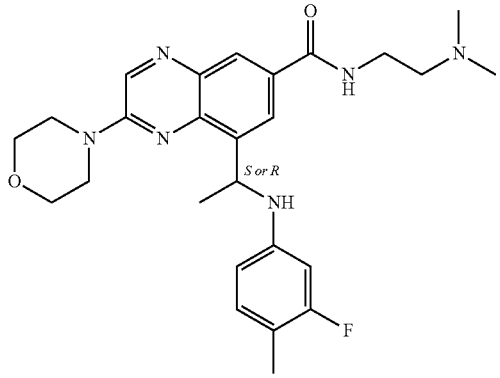

Compound 407 was prepared according to an analogous procedure as described for the synthesis of compound 5, using compound 294 and N,N-dimethylethylenediamine as starting materials (588 mg, 85%).

The separation of the enantiomers was performed by chiral SFC (Stationary phase: CHIRALPAK AD-H 5 μm 250×20 mm, Mobile phase: 60% $CO_2$, 40% EtOH (0.3% $iPrNH_2$)). The fractions containing the products were concentrated to afford, after freeze-drying in a mixture of ACN/water (20/80), 232 mg (34%) of compound 407a (MP: 115° C., Kofler) and 170 mg (25%) of compound 407b (MP: 105° C., Kofler).

Preparation of Compound 408, Compound 408a and Compound 408b compound 408

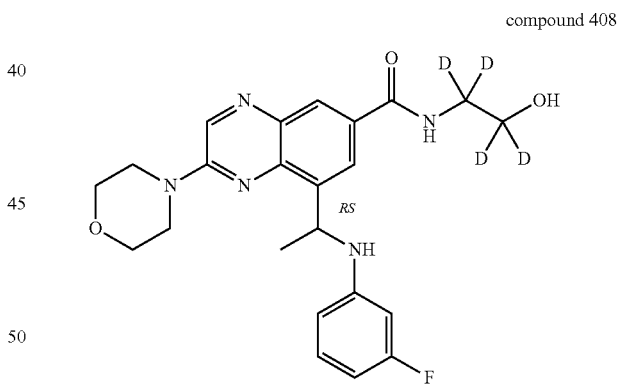

compound 408a

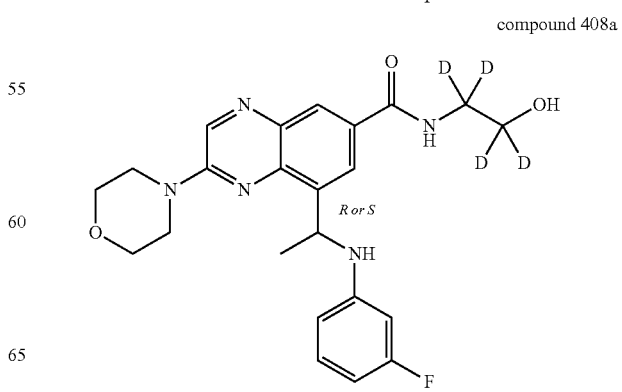

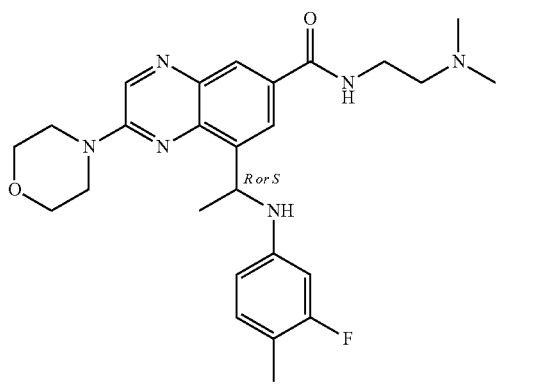

compound 408b

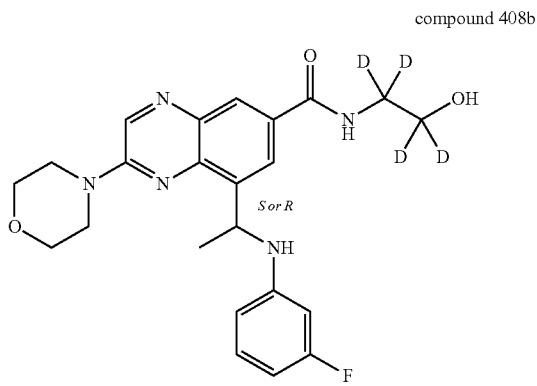

Compound 408 was prepared according to an analogous procedure as described for the synthesis of compound 5, using compound 263 and ethanol-1,1,2,2-d4-amine as starting materials (400 mg, 71%).

The separation of the enantiomers was performed by chiral SFC (Stationary phase: CHIRALPAK IC 5 µm 250× 30 mm, Mobile phase: 55% $CO_2$, 45% iPOH (0.3% iPrNH$_2$)). The fractions containing the products were concentrated to afford, after crystallization from EtOH, 161 mg (28%) of compound 408a (MP: 127° C., DSC) and 131 mg (22%) of compound 408b (MP: 123° C., DSC).

Coversion C2

Preparation Compound 10:

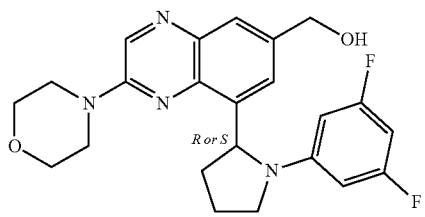 [SMILES: OCc1cc(C2CCCN2c2cc(F)cc(F)c2)c2nc(N3CCOCC3)cnc2c1]

Diisobutylaluminium hydride (solution 20% in toluene) (15.8 mL; 3.79 mmol) was added dropwise to a solution of compound 249 (860 mg; 1.89 mmol) in THF (50 mL) at −70° C. under N$_2$. The mixture was stirred at −70° C. for 1 h30. The solution was poured into ice-water. EtOAc was added and the mixture was filtered through a pad of Celite®. The product was extracted with EtOAc. Then, the organic layer was dried over MgSO$_4$, filtered and evaporated to dryness. The residue (820 mg) was purified by chromatography over silica gel (irregular bare silica 40 g; mobile phase: 97% DCM, 3% MeOH, 0.1% NH$_4$OH). The pure fractions were collected and the solvent was evaporated to give 594 mg which was recrystallized with diethylether. The precipitate was filtered and dried to give 425 mg (52%) of compound 10. M.P.: 189° C. (DSC).

Preparation Compound 88 and Compound 89

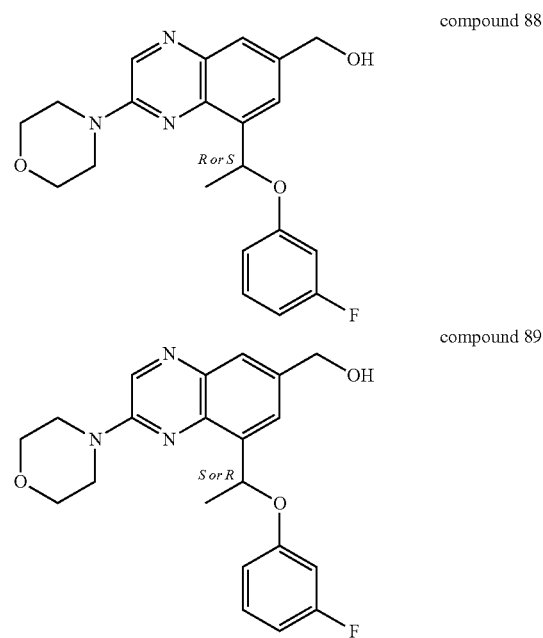

Compound 88 and compound 89 were prepared according to an analogous procedure as described for the synthesis of compound 10, using compound 257a as starting materials. After purification by chromatography over silica gel (irregular SiOH; 15-40 µm; 30 g; gradient: from 65% heptane, 31.5% EtOAc, 3.5% MeOH to 30% heptane, 63% EtOAc, 7% MeOH), the resulting residue (409 mg, pale yellow foam) was purified by chiral SFC (CHIRALPAK AD-H 5 µm 250×20 mm; mobile phase: 75% $CO_2$, 25% MeOH). The pure fractions were collected and the solvent was evaporated to give two fractions which were separately co-evaporated in DCM (×2) and dried under reduced pressure (16 h, 50° C.) to give respectively 144 mg (28%, pale yellow foam) of compound 88 and 160 mg (30%, pale yellow foam) of compound 89.

Preparation Compound 111

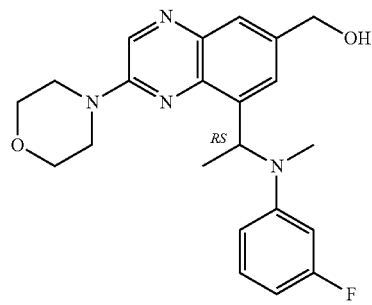 [SMILES: CC(c1cc(CO)cc2ncc(N3CCOCC3)nc12)N(C)c1cccc(F)c1]

Diisobutylaluminium hydride (solution 20% in toluene) (1.96 mL; 0.47 mmol) was added dropwise to a solution of compound 97 (100 mg; 0.24 mmol) in THF (7 mL) at −70° C. under N$_2$. The mixture was stirred at −70° C. for 2 h. The solution was poured into ice-water. EtOAc was added and the mixture was filtered through a pad of Celite®. The product was extracted with EtOAc. Then the organic layer was dried over MgSO$_4$, filtered and evaporated to dryness.

The residue (100 mg) was purified by chromatography over silica gel (irregular bare silica 10 g; mobile phase: 97% DCM, 3% MeOH, 0.1% NH₄OH). The pure fractions were collected and the solvent was evaporated. The residue (59 mg; impure compound 111) was taken-up with DCM. Oxygen was bubbled in the solution for 30 min and the solution was stirred at rt overnight. Then, the solution was evaporated to dryness. The residue (54 mg) was purified by reverse phase (X-Bridge-C18 5 μm; 30*150 mm; gradient: from 65% NH₄HCO₃ 0.5%, 35% ACN to 25% NH₄HCO₃ 0.5%, 75% ACN). The pure fractions were collected and the solvent was evaporated to give 30 mg (32%) of compound 111. M.P.: 80° C. (K).

Preparation Compound 84, Compound 154a and Compound 154b

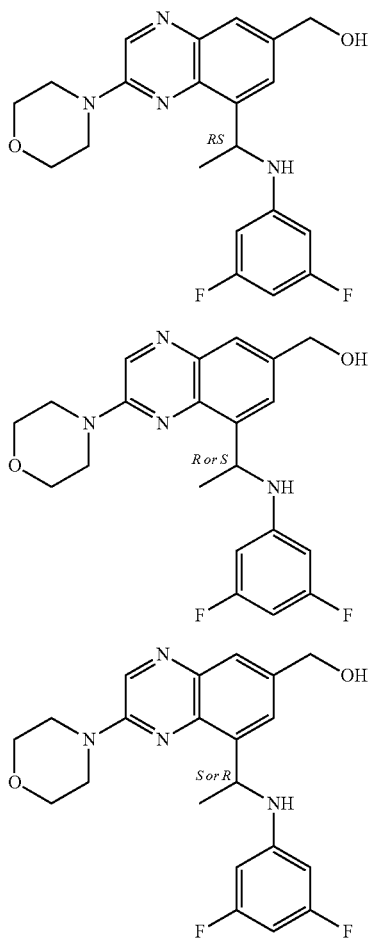

compound 84 compound 154a compound 154b

Compound 84, compound 154a and compound 154b were prepared according to an analogous procedure as described for the synthesis of compound 111, using compound 80 as starting material. Compound 84 (2.6 g) was purified by chiral SFC (CHIRALCEL OJ-H; 5 μm 250×20 mm; mobile phase: 65% CO₂, 35% EtOH (0.3% iPrNH₂)). The pure fractions were collected and the solvent was evaporated to give two fractions, which were separately taken-up in diethylether and heptane, filtered and dry under vacuum to give respectively 220 mg (5%) of compound 154a and 210 mg (5%) of compound 154b. M.P.: 90° C. (K).

Preparation of Compound 303:

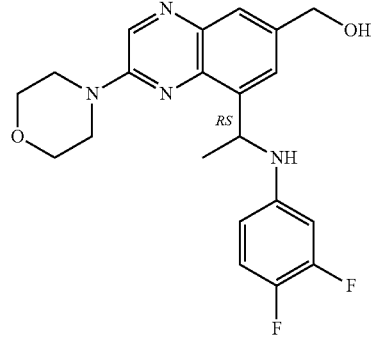 [SMILES: CC(Nc1ccc(F)c(F)c1)c1cc(CO)cc2ncc(N3CCOCC3)nc12]

Compound 303 was prepared according to an analogous procedure as described for the synthesis of compound 10 using compound 233 (as starting material. (100 mg, 33%, MP:138° C., DSC).

Conversion C3

Preparation of Compound 45:

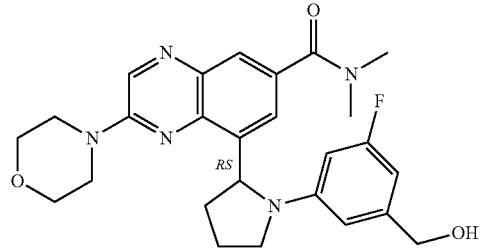 [SMILES: CN(C)C(=O)c1cc(C2CCCN2c2cc(F)cc(CO)c2)c2nc(N3CCOCC3)cnc2c1]

NaBH₄ (7 mg; 0.19 mmol) was added to a solution of compound 44 (90 mg; 0.19 mmol) in MeOH (2 mL) at 5° C. The reaction mixture was stirred at 5° C. for 4 h. The mixture was poured into H₂O, filtered through a pad of Celite® and extracted with EtOAc. The organic layer was dried over MgSO₄, filtered and evaporated until dryness. The residue (110 mg) was purified by chromatography over silica gel (irregular 15-40 μm; 30 g; mobile phase: 97% DCM, 3% MeOH, 0.1% NH₄OH). The pure fractions were collected and evaporated until dryness. The residue (65 mg) was freeze-dried with water/ACN 80/20 to give 62 mg (69%, yellow solid) of compound 45. M.P.: 80° C. (gum, K).

Conversion C4

Preparation compound 14:

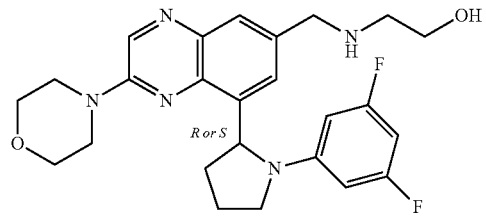 [SMILES: OCCNCc1cc(C2CCCN2c2cc(F)cc(F)c2)c2nc(N3CCOCC3)cnc2c1]

2-aminoethanol (0.21 mL; 3.53 mmol) was added to a solution of compound 250 (150 mg; 0.35 mmol) in MeOH (7 mL) and the reaction mixture was stirred at rt for 4 h.

Then sodium borohydride (20 mg; 0.53 mmol) was added portionwise at 0° C. and the reaction mixture was stirred at rt for 1 h30. Water was added and the product extracted with EtOAc. The organic layer was washed with brine (2×), dried over MgSO₄, filtered and evaporated to dryness. The residue (200 mg) was purified by chromatography over silica gel (irregular 15-40 μm; mobile phase: 90% DCM, 10% MeOH, 0.1% NH₄OH). The pure fractions were collected and the solvent was evaporated to give 145 mg (88%) of compound 14. M.P.: 140° C. (K).

Preparation Compound 76:

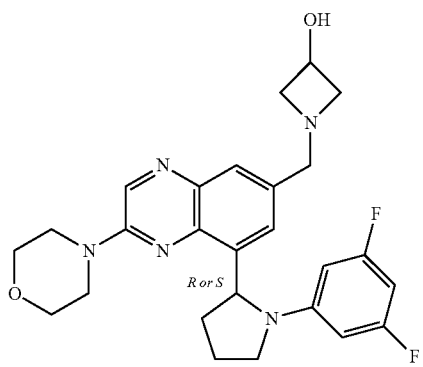 [SMILES: OC1CN(Cc2cc(C3CCCN3c3cc(F)cc(F)c3)c3nc(N4CCOCC4)cnc3c2)C1]

Compound 250 (100 mg; 0.24 mmol) was added to a solution of 3-hydroxyazetidine hydrochloride (258 mg; 2.36 mmol) and sodium acetate (193 mg; 2.36 mmol) in MeOH (3 mL). The reaction mixture was stirred at rt for 4 h. Then, sodium borohydride (18 mg; 0.47 mmol) was added portionwise at 0° C. and the reaction mixture was stirred at rt for 1 h30. Water was added and the product extracted with EtOAc. The organic layer was washed with brine (2×), dried over MgSO₄, filtered and evaporated to dryness. The residue (210 mg) was purified by chromatography over silica gel (irregular 15-40 μm; 24 g; mobile phase: 90% DCM, 10% MeOH, 0.1% NH₄OH). The pure fractions were collected and the solvent was evaporated to give 115 mg (100%) of compound 76. M.P.: 90° C. (DSC).

Preparation Compound 77:

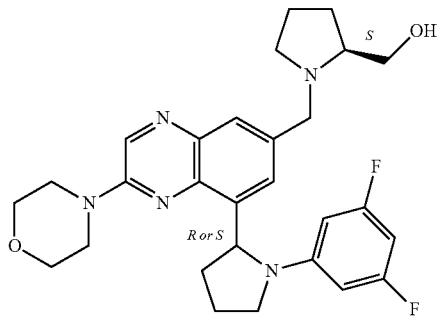

Compound 77 was prepared according to an analogous procedure as described for the synthesis of compound 76, using compound 250 and L-prolinol as starting materials (freeze-dried: 48 mg, 80%). M.P.: 80° C. (gum, K).

Preparation Compound 101:

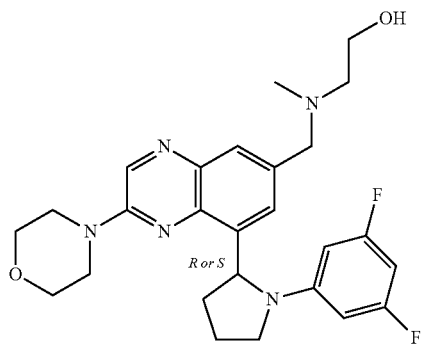 [SMILES: CN(CCO)Cc1cc(C2CCCN2c2cc(F)cc(F)c2)c2nc(N3CCOCC3)cnc2c1]

Compound 101 was prepared according to an analogous procedure as described for the synthesis of compound 76, using compound 250 and 2-(methylamino)ethanol as starting materials (72 mg, 63%). M.P.: 80° C. (gum, K).

Preparation Compound 102:

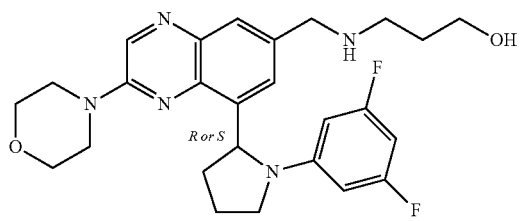 [SMILES: OCCCNCc1cc(C2CCCN2c2cc(F)cc(F)c2)c2nc(N3CCOCC3)cnc2c1]

Compound 102 was prepared according to an analogous procedure as described for the synthesis of compound 14, using compound 250 and 3-amino-1-propanol as starting materials (55 mg, 48%). M.P.: 80° C. (gum, K).

Preparation Compound 103:

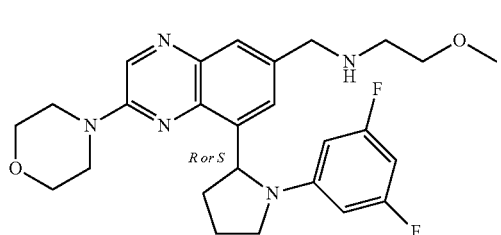 [SMILES: COCCNCc1cc(C2CCCN2c2cc(F)cc(F)c2)c2nc(N3CCOCC3)cnc2c1]

Compound 103 was prepared according to an analogous procedure as described for the synthesis of compound 14, using compound 250 and 2-methoxyethylamine as starting materials (83 mg, 73%). M.P.: 80° C. (gum, K).

Preparation Compound 112:

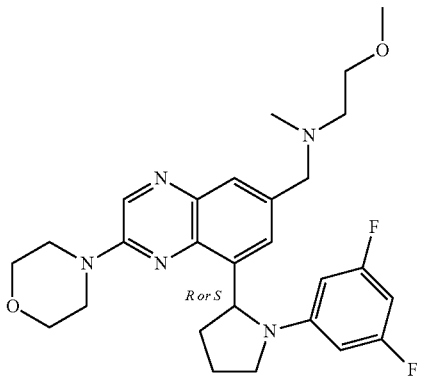 [SMILES: COCCN(C)Cc1cc(C2CCCN2c2cc(F)cc(F)c2)c2nc(N3CCOCC3)cnc2c1]

Compound 112 was prepared according to an analogous procedure as described for the synthesis of compound 76, using compound 250 and N-(2-(methoxyethyl)methylamine as starting materials (76 mg, 22%). M.P.: 80° C. (gum, K).

Coversion C5

Preparation Compound 48:

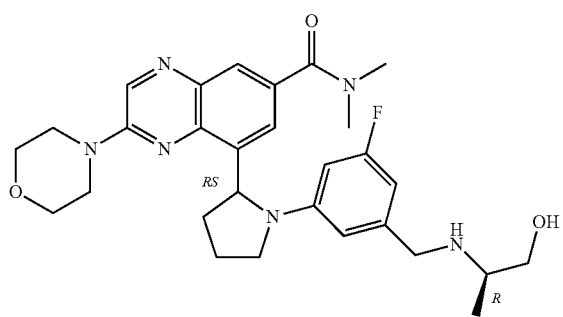

Compound 48 was prepared according to an analogous procedure as described for the synthesis of compound 14, using compound 44 and D-alaninol as starting materials (freeze-dried: 27 mg, 48%). M.P.: 80° C. (gum, K).

Preparation Compound 49:

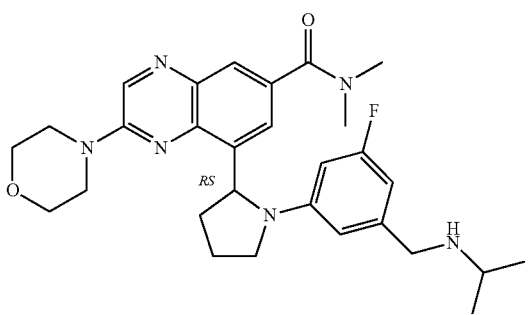 [SMILES: CC(C)NCc1cc(F)cc(N2CCCC2c2cc(C(=O)N(C)C)cc3ncc(N4CCOCC4)nc23)c1]

Compound 49 was prepared according to an analogous procedure as described for the synthesis of compound 14, using compound 44 and isopropylamine as starting materials (freeze-dried: 14 mg, 21%). M.P.: 80° C. (gum, K).

Preparation Compound 67:

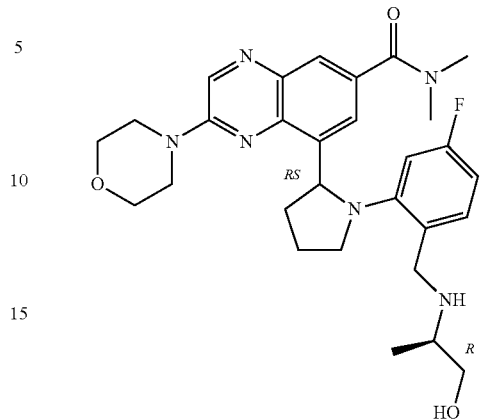

Compound 67 was prepared according to an analogous procedure as described for the synthesis of compound 14, using compound 44 and D-alaninol as starting material (freeze-dried: 25 mg, 20%). M.P.: 80° C. (gum, K).

Coversion C6

Preparation of Compound 251:

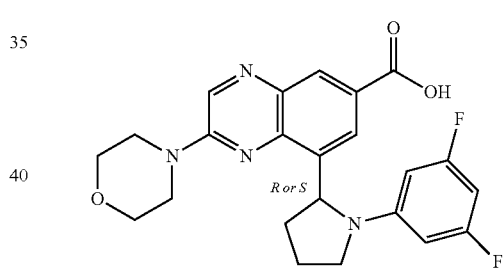

A solution of lithium hydroxide monohydrate (370 mg; 8.8 mmol) in water (3 mL) was added to a mixture of compound 249 (400 mg; 0.88 mmol) in THF (12 mL) at rt. The reaction mixture was heated at 50° C. for 15 h. The mixture was cooled down to rt. Ice-water was added and the solution was slowly acidified with a 3N aqueous solution of HCl. A precipitate was filtered, washed with $Et_2O$ and dried to give 226 mg of fraction 1. The filtrate was extracted with EtOAc. The organic layer was dried over $MgSO_4$, filtered and evaporated. The residue (88 mg) was combined with fraction 1 (226 mg) and the resulting residue (314 mg) was purified by reverse phase (X-Bridge-C18 5 μm; 30*150 mm; gradient: from 75% $NH_4HCO_3$ 0.5%, 25% ACN to 35% $NH_4HCO_3$ 0.5%, 65% ACN). The pure fractions were collected and the solvent was evaporated to give 196 mg (51%) of compound 251. M.P.: 299° C. (DSC).

Preparation of Compound 62:

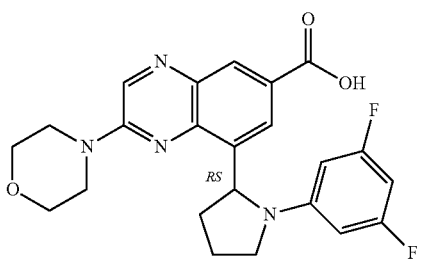 [SMILES: O=C(O)c1cc(C2CCCN2c2cc(F)cc(F)c2)c2nc(N3CCOCC3)cnc2c1]

Compound 62 was prepared according to an analogous procedure as described for the synthesis of compound 251, using compound 254 as starting material (1.05 g, 86%; after recrystallization from 150 mg: 58 mg, 5% of compound 62. M.P.: >260° C. (K).

Preparation of Compound 83a, Compound 83b and Compound 83c compound 83a

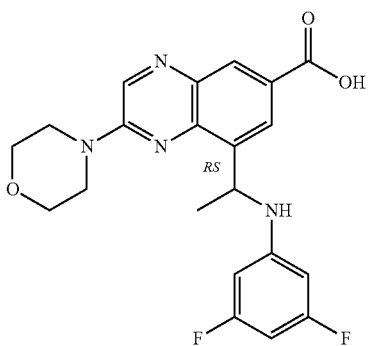

compound 83b

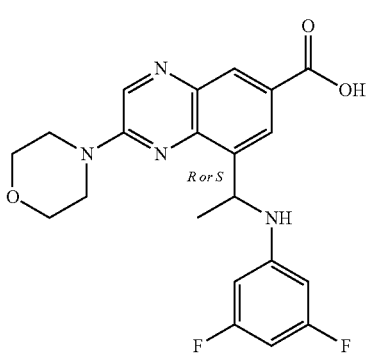

compound 83c

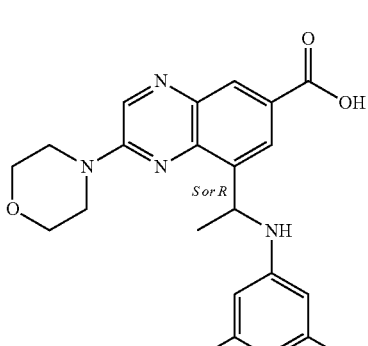

Compound 83a, compound 83b and compound 83c were prepared according to an analogous procedure as described for the synthesis of compound 251, using compound 80 as starting material. A first reaction gave 56 mg (41%) of compound 83a. M.P.: 240° C. (DSC). A second reaction gave 1.3 g of compound 83a was further purified by chiral SFC (Chiralpak IA 5 µm; 250*20 mm; mobile phase: 60% $CO_2$, 40% iPrOH (0.3% $iPrNH_2$)). The pure fractions were collected and the solvent was evaporated to give two fractions which were separately taken-up with $H_2O$, acidified with 3N aqueous solution of HCl. The precipitate were filtered, washed with $H_2O$ and diethylether and dried to give respectively 287 mg (26%) of compound 83b (M.P.: 180° C., DSC) and 278 mg (25%) of compound 83c (M.P.: 157° C., DSC).

Preparation of Compound 98:

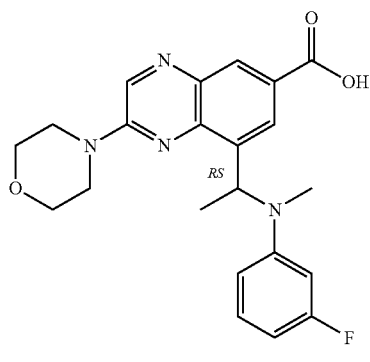 [SMILES: CC(c1cc(C(=O)O)cc2ncc(N3CCOCC3)nc12)N(C)c1cccc(F)c1]

Compound 98 was prepared according to an analogous procedure as described for the synthesis of compound 251, using compound 97 as starting material (after recrystallization: 177 mg, 77%. M.P.: 240° C. (DSC).

Preparation of Compound 170:

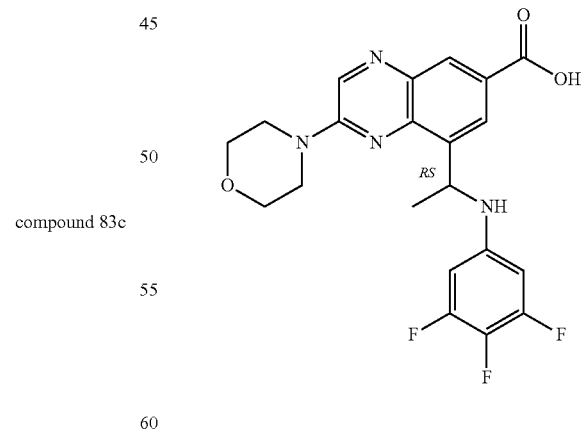

Compound 170 was prepared according to an analogous procedure as described for the synthesis of compound 251, using compound 266 as starting material (1.15 g, 88%. M.P.: 285° C. (DSC).

Preparation of Compound 234:

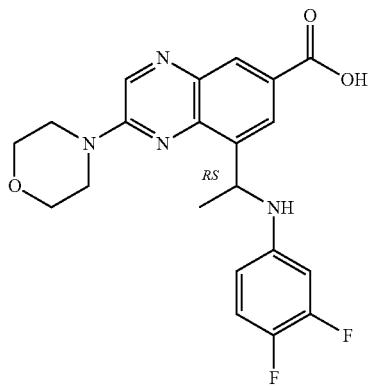 [SMILES: CC(Nc1ccc(F)c(F)c1)c1cc(C(=O)O)cc2ncc(N3CCOCC3)nc12]

Compound 234 was prepared according to an analogous procedure as described for the synthesis of compound 251, using compound 233 as starting material. (8.57 g, 95%).

Preparation of Compound 236:

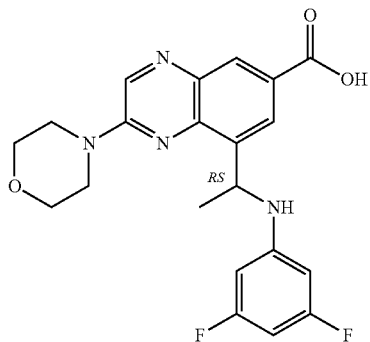

Compound 236 was prepared according to an analogous procedure as described for the synthesis of compound 251, using compound 235 as starting material. (11 g; 96%) of compound 236. M.P: 240° C. (DSC)

Preparation of compound 239:

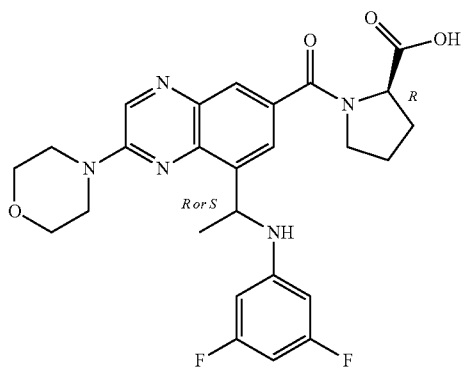

Compound 239 was prepared according to an analogous procedure as described for the synthesis of compound 251, using compound 272a as starting material. The reaction was stirred at rt overnight. (44 mg; 52%) of compound 239.

Preparation of Compound 240:

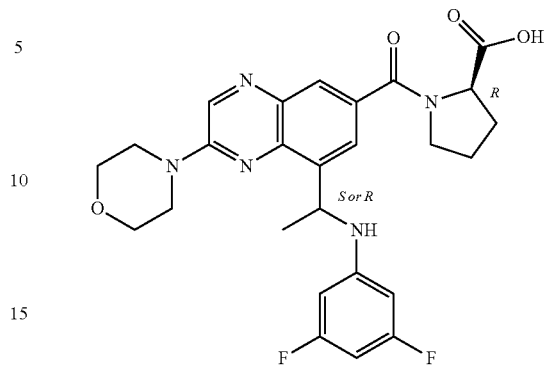

1.73 $H_2O$ 0.68 HCl Compound 240 was prepared according to an analogous procedure as described for the synthesis of compound 251, using compound 272b as starting material. The reaction was stirred at rt overnight. (42 mg; 50%) of compound 240 (1.73 $H_2O$ 0.68 HCl).

Preparation of Compound 241:

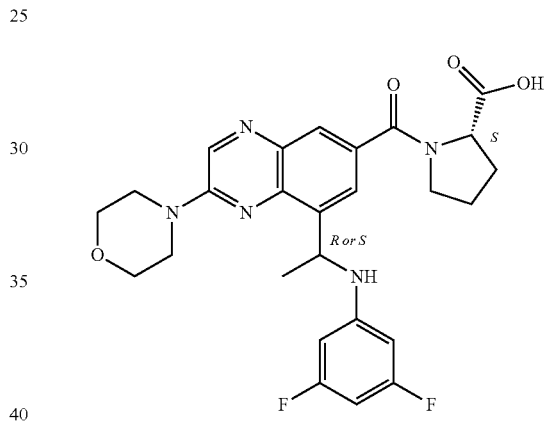

Compound 241 was prepared according to an analogous procedure as described for the synthesis of compound 251, using compound 273a as starting material. The reaction was stirred at rt overnight. (76 mg; 73%) of compound 241.

Preparation of Compound 242:

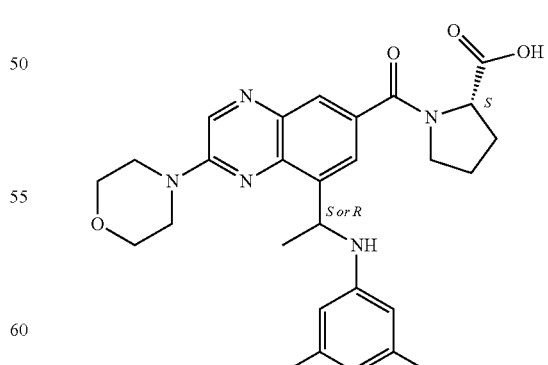

Compound 242 was prepared according to an analogous procedure as described for the synthesis of compound 251, using compound 273b as starting material. The reaction was stirred at rt overnight. (76 mg; 73%) of compound 242.

Preparation compound 248:

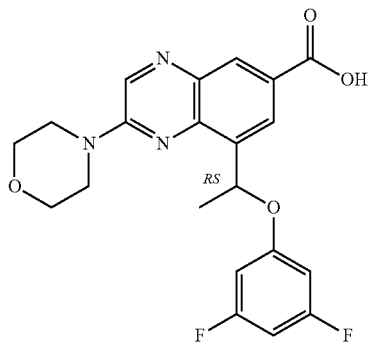 [SMILES: CC(Oc1cc(F)cc(F)c1)c1cc(C(=O)O)cc2ncc(N3CCOCC3)nc12]

To a solution of compound 248 (1.36 g, 2.05 mmol) in THF (10 mL) and MeOH (10 mL) was added an aqueous solution of NaOH (6.16 mL, 1 M, 6.16 mmol). The mixture was stirred at rt over the weekend. The mixture was evaporated and the resulting residue was slowly acidified with an aqueous solution of HCl (1N). The precipitate was filtered to give 797 mg (93%; yellow oil) of compound 248.

Preparation of Compound 253:

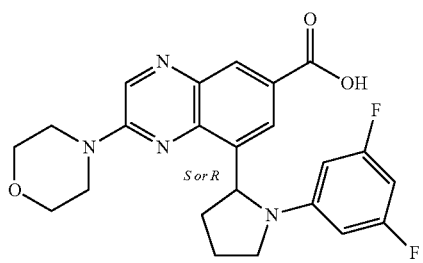 [SMILES: O=C(O)c1cc(C2CCCN2c2cc(F)cc(F)c2)c2nc(N3CCOCC3)cnc2c1]

Compound 253 was prepared according to an analogous procedure as described for the synthesis of compound 251, using compound 252 as starting material (200 mg, 88%). The product was used without purification in the next step.

Preparation of Compound 257a, Compound 257b and Compound 257c compound 257a

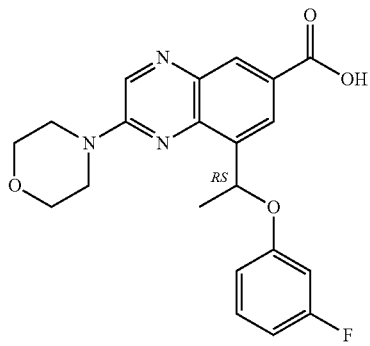

compound 257b

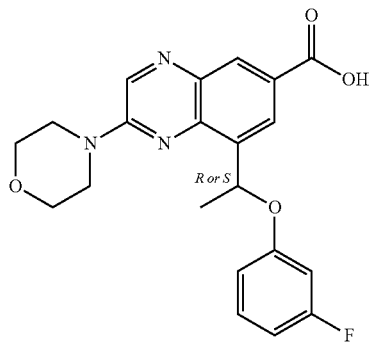

compound 257c

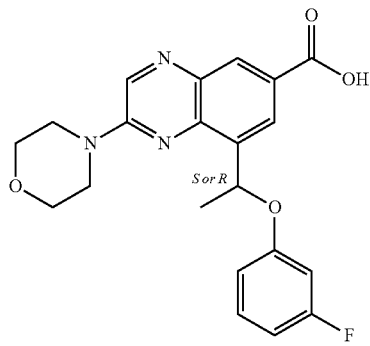

Compound 257a was prepared according to an analogous procedure as described for the synthesis of compound 248, using compound 256 as starting material. The reaction mixture was heated at 50° C. for 1 h. The mixture was cooled down to rt and evaporated in vacuum. The residue was slowly acidified with 1N aqueous solution of HCl, filtered and dried under vacuum. Compound 257a (994 mg, 98%, yellow solid) was purified by chiral SFC (Chiralpak AD-H 5 μm 250*30 mm; mobile phase: 80% $CO_2$, 20% iPrOH (0.3% $iPrNH_2$)). The pure fractions were collected and the solvent was evaporated to give 196 mg (yellow oil) of fraction 1 and 145 mg (yellow oil) of fraction 2. Fraction 1 was purified by chromatography over silica gel (irregular SiOH; 15-40 μm; 10 g; gradient: from 96% DCM, 4% MeOH/$NH_4OH$ (95/5) to 82% DCM, 18% MeOH/$NH_4OH$ (95/5)). The pure fractions were collected and the solvent was evaporated. The residue (109 mg, pale yellow oil) was purified by reverse phase (X-Bridge-C18 5 μm 30*150 mm; gradient: from 85% (aq. $NH_4HCO_3$ 0.5%), 15% ACN to 45% (aq. $NH_4HCO_3$ 0.5%), 55% ACN). The pure fractions were collected and the solvent was evaporated. The residue was co-evaporated in DCM/pentane (1/4) and dried under vacuum (50° C., 16 h) to give 66 mg (7%, pale yellow solid) of compound 257b. Fraction 2 was purified by chromatography over silica gel (irregular SiOH; 15-40 μm; 10 g; gradient: from 96% DCM, 4% MeOH/$NH_4OH$ (95/5) to 80% DCM, 20% MeOH/$NH_4OH$ (95/5)). The pure fractions were collected and the solvent was evaporated. The residue was triturated in DCM/pentane (1/4), filtered and dried under vacuum (50° C., 16 h) to give 119 mg (12%, pale yellow solid) of compound 257c.

Preparation of Compound 261:

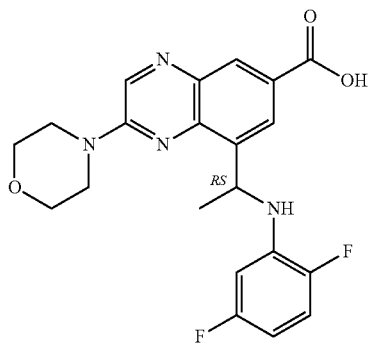 [SMILES: CC(Nc1cc(F)ccc1F)c1cc(C(=O)O)cc2ncc(N3CCOCC3)nc12]

Compound 261 was prepared according to an analogous procedure as described for the synthesis of compound 251, using compound 260 as starting material (280 mg, 90%, yellow solid).

Preparation of Compound 263:

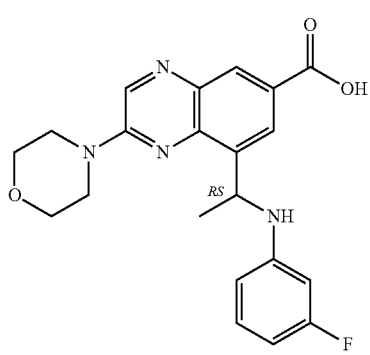 [SMILES: CC(Nc1cccc(F)c1)c1cc(C(=O)O)cc2ncc(N3CCOCC3)nc12]

Compound 263 was prepared according to an analogous procedure as described for the synthesis of compound 248, using compound 262 as starting material (577 mg, 96%, yellow solid).

Alternative Pathway:

Compound 263 was prepared according to an analogous procedure as described for the synthesis of compound 251, using compound 262 as starting material (217 mg, quant.). The reaction mixture was stirred at 50° C. for 15 h. The product was used without purification for the next step.

Preparation of Compound 265:

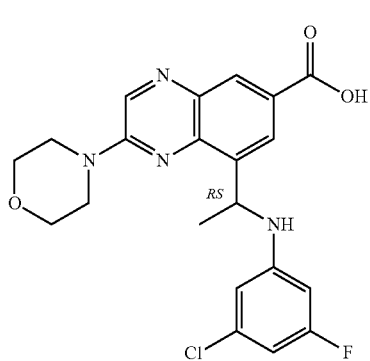 [SMILES: CC(Nc1cc(F)cc(Cl)c1)c1cc(C(=O)O)cc2ncc(N3CCOCC3)nc12]

Compound 265 was prepared according to an analogous procedure as described for the synthesis of compound 251, using compound 264 as starting material (170 mg, 47%, yellow solid). The product was used without purification in the next step.

Preparation of Compound 270:

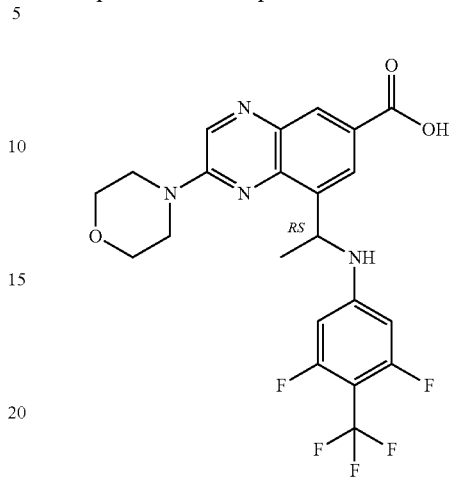

Compound 270 was prepared according to an analogous procedure as described for the synthesis of compound 251 using compound 269 as starting material (890 mg; 100%). The product was used without purification for the next step.

Preparation of Compound 285:

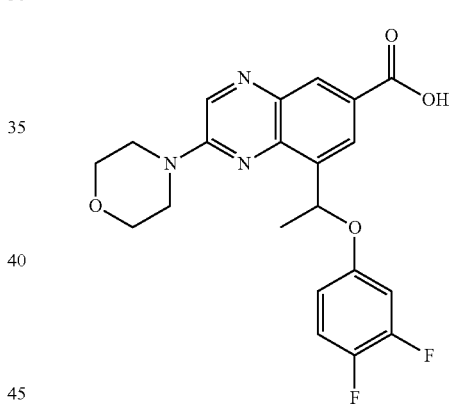

Compound 285 was prepared according to an analogous procedure as described for the synthesis of compound 251 using compound 209 as starting material (3.5 g, 90%).

Preparation of Compound 289:

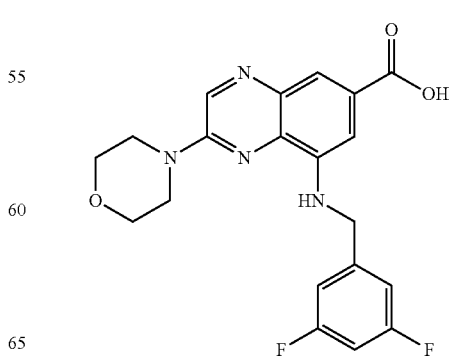

Compound 289 was prepared according to an analogous procedure as described for the synthesis of compound 251, using compound 288 as starting material (3.98 g, 84%).

Preparation of Compound 291:

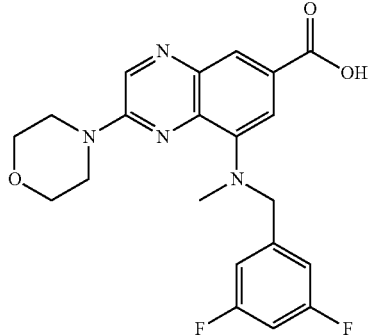 [SMILES: CN(Cc1cc(F)cc(F)c1)c1cc(C(=O)O)cc2ncc(N3CCOCC3)nc12]

compound 291 was prepared according to an analogous procedure as described for the synthesis of compound 251, using compound 290 as starting material (300 mg, 48%).

Preparation of Compound 294:

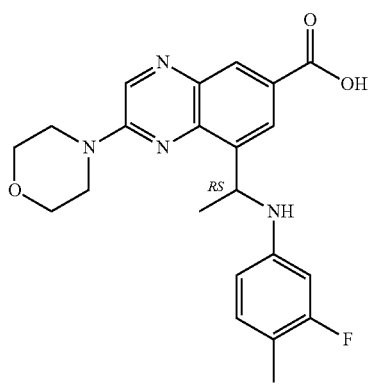 [SMILES: Cc1ccc(NC(C)c2cc(C(=O)O)cc3ncc(N4CCOCC4)nc23)cc1F]

Compound 294 was prepared according to an analogous procedure as described for the synthesis of compound 25 Fusing compound 293 as starting material (3.8 g, 95%).

Preparation of Compound 307:

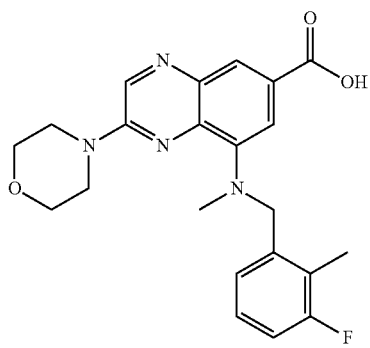 [SMILES: Cc1c(F)cccc1CN(C)c1cc(C(=O)O)cc2ncc(N3CCOCC3)nc12]

Compound 307 was prepared according to an analogous procedure as described for the synthesis of compound 83a using compound 306 as starting material (2.8 g; 113%).

Preparation of Compound 311:

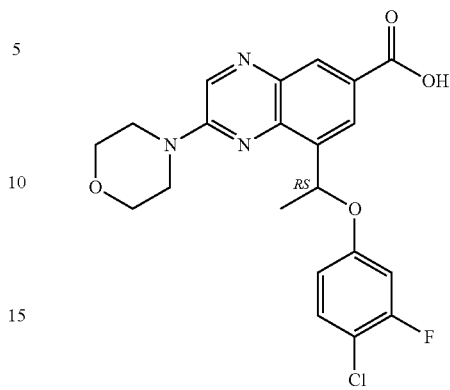

Compound 311 was prepared according to an analogous procedure as described for the synthesis of compound 248 using compound 310 as starting material (1 g, 59%).

Preparation of Compound 327:

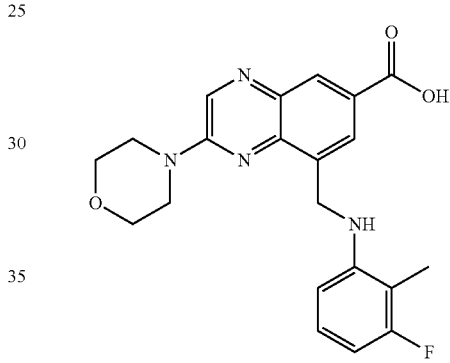

To a suspension of compound 326 (1.52 g; 3.70 mmol) in MeTHF (15 mL) and MeOH (15 mL) was added a 1M aqueous solution of sodium hydroxide (22.2 mL; 22.2 mmol). The mixture was heated at 40° C. for 1 h then at 50° C. for 1 h. After cooling down to rt, the crude was concentrated in vacuo. The residue was slowly acidified with a 1N aqueous solution of HCl (until pH #4) and the precipitate formed was filtered on a glass frit. The solid was taken up in EtOH and evaporated in vacuo to give 900 mg (61%) of compound 327 as a yellow solid.

Preparation of Compound 331:

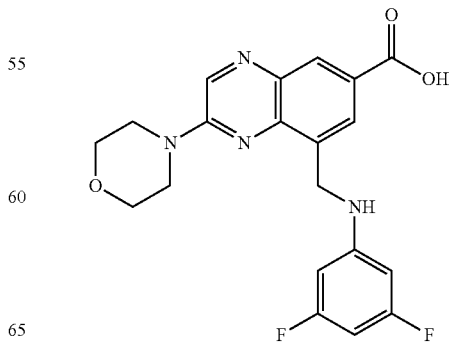

Compound 331 was prepared according to an analogous procedure as described for the synthesis of compound 327 using compound 330 as starting material (298 mg, 61%).

Preparation of Compound 378:

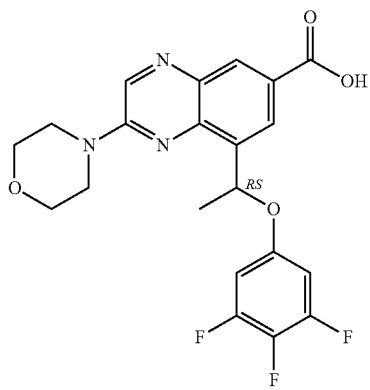 [SMILES: CC(Oc1cc(F)c(F)c(F)c1)c1cc(C(=O)O)cc2ncc(N3CCOCC3)nc12]

Compound 378 (was prepared according to an analogous procedure as described for the synthesis of compound 248, using compound 377 as starting material (1.67 g, 99%).

Preparation of Compound 393 a:

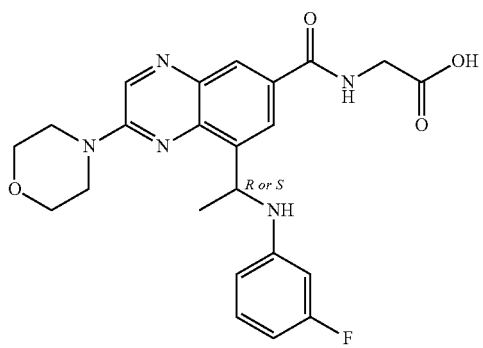 [SMILES: CC(Nc1cccc(F)c1)c1cc(C(=O)NCC(=O)O)cc2ncc(N3CCOCC3)nc12]

Compound 393a was prepared according to an analogous procedure as described for the synthesis of compound 251, using compound 393a as starting material (108 mg, 57%, MP: 115° C., gum, Kofler).

Preparation of Compound 393b:

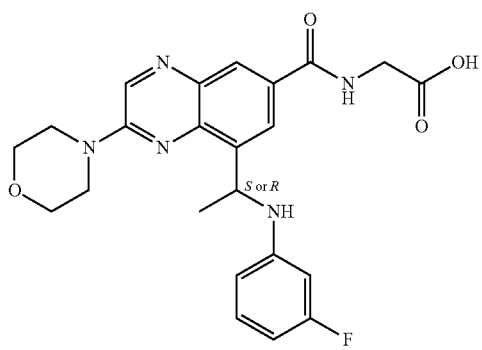 [SMILES: CC(Nc1cccc(F)c1)c1cc(C(=O)NCC(=O)O)cc2ncc(N3CCOCC3)nc12]

Compound 393b was prepared according to an analogous procedure as described for the synthesis of compound 251, using compound 393b as starting material (110 mg, 51%, MP: 196° C., DSC).

Conversion C7

Preparation of Compound 186 and Compound 187 compound 186

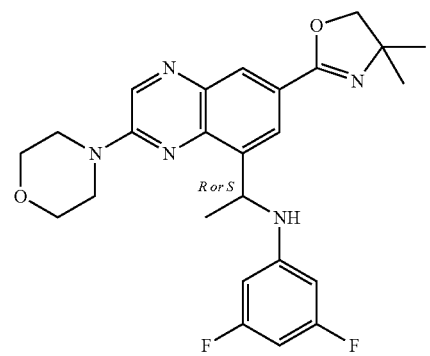

Intermediate 187

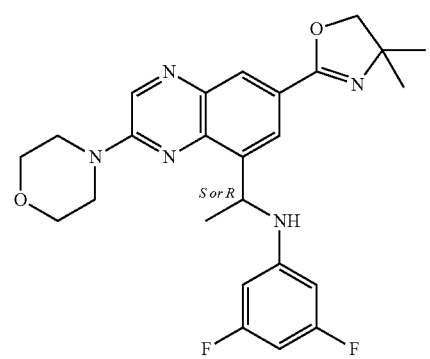

At 0° C., thionyl chloride (0.5 mL; 7.21 mmol) was added to a solution of compound 169 (350 mg; 0.72 mmol) in DCM (7 mL). The reaction mixture was stirred at rt overnight. The mixture was poured into ice and 10% aqueous solution of $K_2CO_3$, then extracted with EtOAc. The organic layer was washed with brine, dried over $MgSO_4$, filtered and evaporated until dryness. The residue (320 mg) was combined with another batch coming from a reaction performed on 206 mg of compound 169. The two residues were purified together by column chromatography over silica gel (40 g, mobile phase; from 100% DCM to 97% DCM, 3% MeOH, 0.3% $NH_4OH$). The pure fractions were collected and evaporated. The residue (333 mg) was purified by chiral SFC (CHIRALCEL OJ-H 5 µm 250×20 mm; mobile phase: 80% $CO_2$, 20% EtOH (0.3% $iPrNH_2$)). The pure fractions were collected and evaporated to give 136 mg (25%) of compound 186 (M.P.: 80° C. (gum, K)) and 139 mg (26%) of compound 187 (M.P.: 80° C. (gum, K)).

Conversion C8

Preparation of Compound 225:

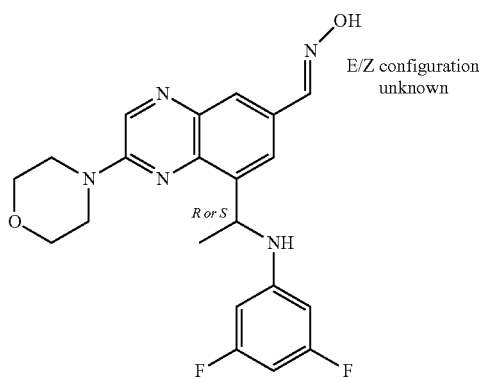 [SMILES: CC(Nc1cc(F)cc(F)c1)c1cc(/C=N/O)cc2ncc(N3CCOCC3)nc12]

A mixture of compound 271 (200 mg; 0.50 mmol), hydroxylamine hydrochloride (105 mg; 1.51 mmol) in EtOH (10 mL) and water (3 mL) was heated at 100° C. for 5 h. The mixture was poured into water and extracted with DCM. The organic layer was dried over MgSO$_4$, filtered and evaporated to dryness. The residue (200 mg) was purified by chromatography over silica gel (irregular SiOH 15-40 µm; 300 g; mobile phase: 96% DCM, 4% MeOH, 0.1% NH$_4$OH). The pure fractions were collected and the solvent was evaporated. The residue (110 mg) was crystallized from diethylether. The yellow precipitate was filtered off and dried to give 75 mg (36%) of compound 225. M.P.: 80° C. (gum, K).

Conversion C9

Preparation of Compound 290:

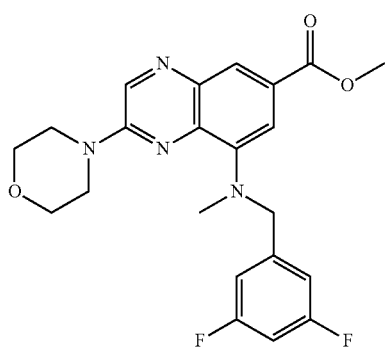 [SMILES: COC(=O)c1cc(N(C)Cc2cc(F)cc(F)c2)c2nc(N3CCOCC3)cnc2c1]

NaH (60% dispersion in mineral oil) (202.7 mg, 5.07 mmol) was added portion wise to a solution of compound 289 (1 g, 2.41 mmol) in DMF (10 mL) under nitrogen at 0-5° C. (ice bath cooling). The mixture was stirred at 0-5° C. for 15 mn then, iodomethane (300 µL, 4.83 mmol) was added. The reaction mixture was stirred at room temperature for 16 h, poured onto iced water and extracted with EtOAc, the organic layer was washed with water, dried over MgSO$_4$ and evaporated to dryness, The residue was purified by silica gel chromatography to give 650 mg (63%) of compound 290.

Preparation of Compound 306:

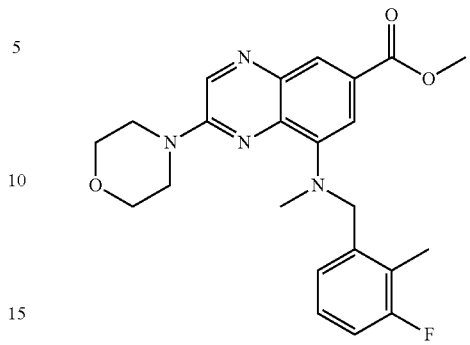

NaH (60% dispersion in miral oil; 1.023 g, 25.582 mmol) was added portionwise to a solution of compound 305 (5 g, 12.18 mmol) in DMF (50 mL) under nitrogen at 0-5° C. (ice bath cooling). The mixture was stirred at 0-5° C. for 15 mn then, iodomethane (1.52 mL, 24.36 mmol) was added. The reaction mixture was stirred at room temperature for 16 h. The reaction mixture was poured into cooled water. The product was extracted with AcOEt and the organic layer was evaporated to dryness. The residue (6.6 g) was purified by silica gel chromatography (120 g of SiOH 20-45 µm, gradient from 40/60 to 10/90 Heptane/EtOAc). The fractions were collected and evaporated until dryness to afford 1.9 g (37%) of compound 306.

Conversion C10

Preparation of Compound 341:

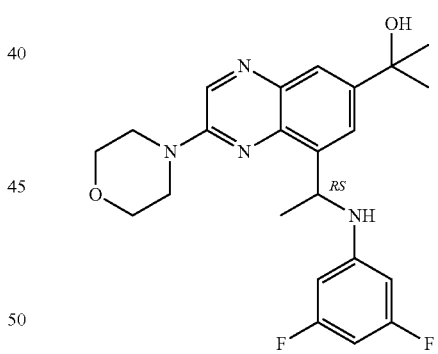

Under N$_2$ at 10° C., methylmagnesium bromide 3M in Et$_2$O (467 µL; 1.4 mmol) was added to a solution of compound 80 (300 mg, 0.7 mmol) in THF (12 mL). The solution was stirred at 10° C. for 2 hours. The solution was cooled and the mixture was poured into cooled water and a 10% NH$_4$Cl solution. The product was extracted with EtOAc. The organic layer was separated, dried over MgSO$_4$, filtered and evaporated to dryness. The residue (300 mg) was purified via silica gel chromatography (Stationary phase: irregular bare silica 40 g, Mobile phase: 98% DCM, 2% MeOH, 0.1% NH$_4$OH). The pure fractions were collected and the solvent was evaporated. The residue was freeze-dried with acetonitrile/water (20/80) to give 40 mg (13%) of compound 341 as yellow powder. M.P.: 80° C., gum, K.

Conversion C11

Preparation of Compound 360 and Compound 361

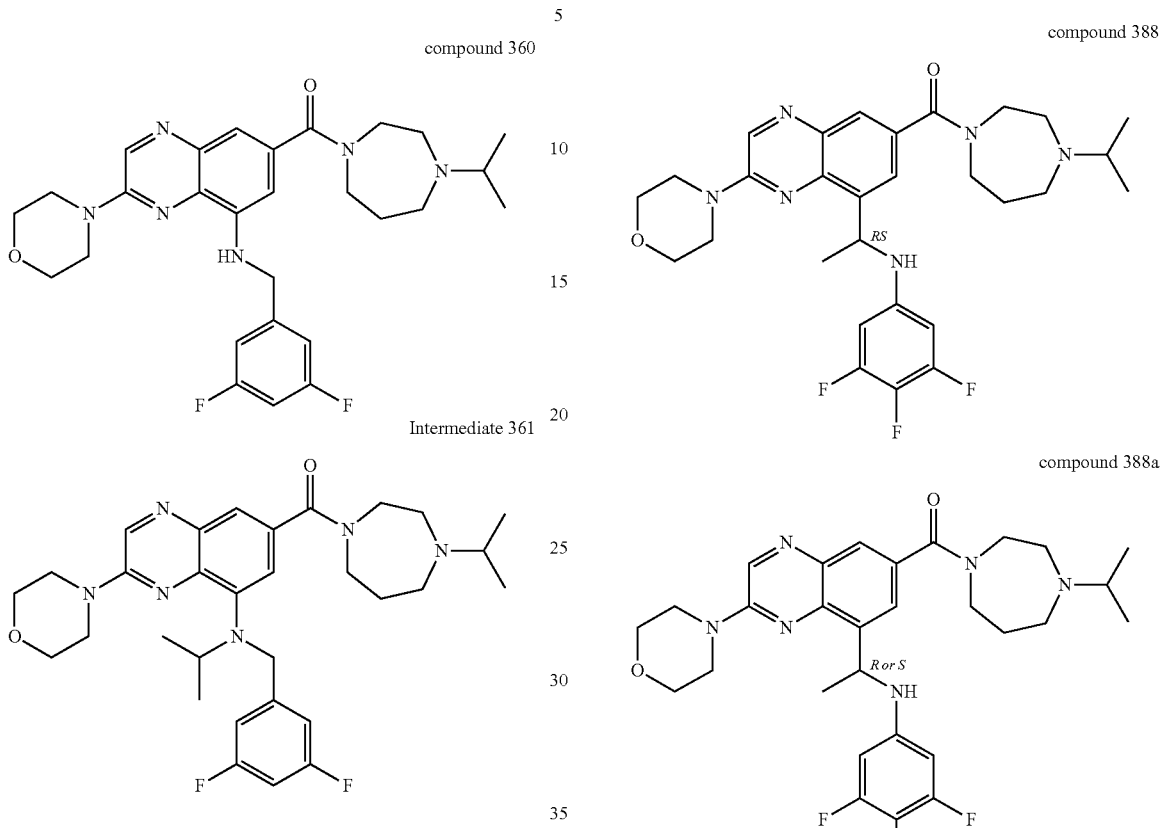

Compound 351 (210 mg, 0.435 mmol), 2-iodopropane (47.87 µL, 1.7 g/mL, 0.479 mmol) and $Cs_2CO_3$ (425.393 mg, 1.306 mmol) in ACN (10 mL) were stirred at 80° C. for 18 h. Then, the mixture was poured into water and extracted with EtOAc. The organic layer was dried over $MgSO_4$, filtered off and evaporated in vacuo. The residue (325 mg) was purified by silica gel chromatography (12 g of SiOH 15 µm, gradient from 98/2/0.2 to 90/10/1). The fractions were collected and evaporated until dryness to give 90 mg (39%) of compound 360 and 30 mg (12%) of compound 361.

Preparation of Compound 373:

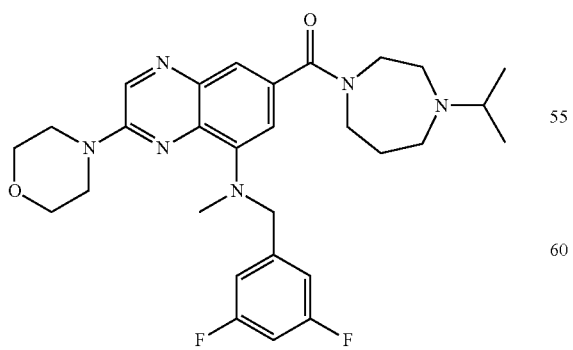

Compound 373 was prepared according to an analogous procedure as described for the synthesis of compound 360 using compound 372 as starting material (105 mg; 92%).

Preparation of compound 388, compound 388a and 388b

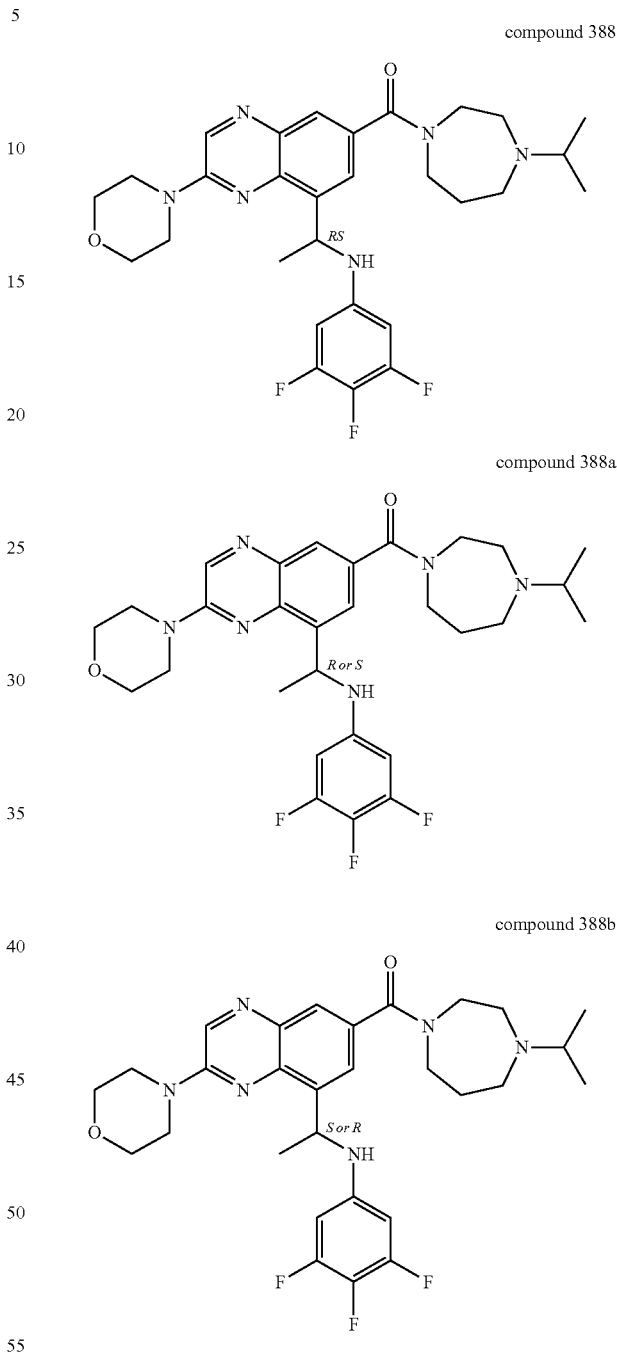

Compound 388 was prepared according to an analogous procedure as described for the synthesis of compound 360 using compound 387 as starting material (90 mg; 28%). The separation of the enantiomers from 90 mg of compound 388 was performed by chiral SFC (CHIRALPAK AD-H 5 µm 250×20 mm; mobile phase: 70% $CO_2$, 30% iPrOH (0.3% $iPrNH_2$). The pure fractions were collected and the solvent was evaporated to give, after freeze-drying, 46 mg (14%) of compound 388a and 47 mg (14%) of compound 388b.

Coversion C12

Preparation of Compound 117a

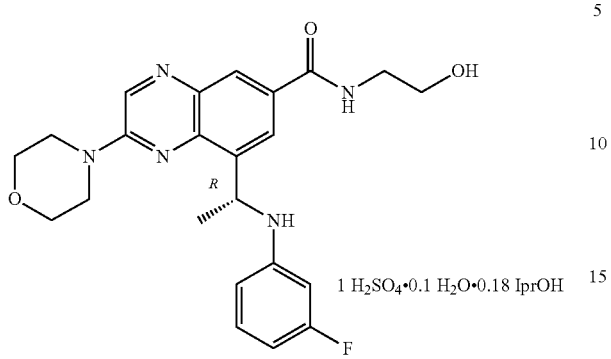

1 H₂SO₄•0.1 H₂O•0.18 IprOH

Compound 117 (1 g; 2.17 mmol) was dissolved in isopropanol (32 mL) at room temperature. Then, a solution of sulfuric acid (58 μL; 1.082 mmol) was added dropwise. A precipitate appeared slowly and the mixture was stirred for 2 hours at room temperature. The precipitate was filtered and dried at 60° C. under vacuum to give 693 mg (58%) of compound 117a (MP: 179° C., DSC).

Preparation of Compound 118a

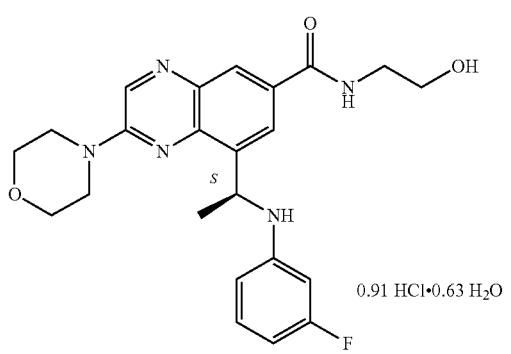

0.91 HCl•0.63 H₂O

Compound 118 (0.5 g; 1.14 mmol) was dissolved in MeTHF (20 mL) at room temperature. Then, a solution of HCl, 4M in dioxane (284 μL; 1.14 mmol) was added dropwise. A precipitate appeared slowly and the mixture was stirred for overnight at room temperature. The precipitate was filtered and dried at 60° C. under vacuum to give 411 mg (75%) of compound 118a.

Preparation of Compound 184a

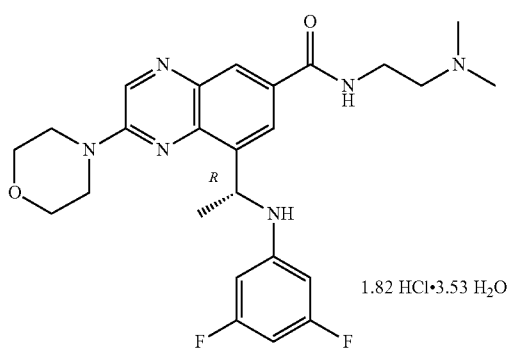

1.82 HCl•3.53 H₂O

At 0° C., a solution of HCl, 4M in dioxane (516 μL; 2.06 mmol) was added to a solution of compound 184 (0.5 g; 1.03 mmol) dissolved in MeOH (10 mL). The solution was allowed to reach slowly room temperature and stirred for several days. Et₂O was added; the red precipitate was filtered and dried to give 554 mg (87%) of compound 184a (gum at 80° C., K).

Preparation of Compound 184b

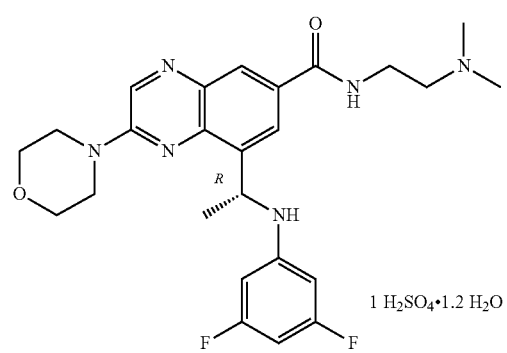

1 H₂SO₄•1.2 H₂O

At 0° C., sulfuric acid (33 μL; 0.619 mmol) was added to a solution of compound 184 (0.3 g; 0.619 mmol) dissolved in EtOH (3 mL). The solution was allowed to reach slowly room temperature and stirred overnight. Et₂O was added; the precipitate was filtered and dried to give 360 mg (97%) of compound 184b (MP: 270° C.; DSC).

Preparation of Compound 184c

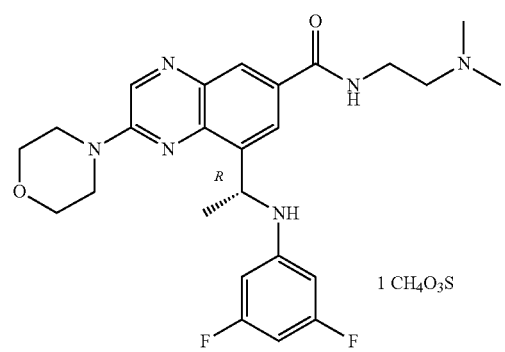

1 CH₄O₃S

At 0° C., methane sulfonic acid (40 μL; 0.619 mmol) was added to a solution of compound 184 (0.3 g; 0.619 mmol) dissolved in EtOH (3 mL). The solution was allowed to reach slowly room temperature and stirred overnight. Et₂O was added; the yellow precipitate was filtered and dried to give 320 mg (89%) of compound 184c (MP: 74° C., DSC).

Analytical Part

LCMS (Liquid Chromatography/Mass Spectrometry)

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software. Compounds are described by their experimental retention times (Rt) and ions. If not specified differently in the table of data, the reported molecular ion corresponds to the [M+H]$^+$ (protonated molecule) and/or [M−H]$^−$ (deprotonated molecule). In case the compound was not directly ionizable the type of adduct is specified (i.e. [M+NH$_4$]$^+$, [M+HCOO]$^−$, etc. . . . ). For molecules with multiple isotopic patterns (e.g. Br, Cl), the reported value is the one obtained for the lowest isotope mass. All results were obtained with experimental uncertainties that are commonly associated with the method used. Hereinafter, "SQD" means Single Quadrupole Detector, "RT" room temperature, "BEH" bridged ethylsiloxane/silica hybrid, "DAD" Diode Array Detector.

TABLE

LCMS Method codes (Flow expressed in mL/min; column temperature (T) in ° C.; Run time in minutes).

| Method code | Instrument | Column | Mobile phase | gradient | Flow Column T | Run time |
|---|---|---|---|---|---|---|
| Method 1 | Waters: Acquity UPLC ® - DAD and Quattro Micro ™ | Waters: BEH C18 (1.7 μm, 2.1 × 100 mm) | A: 95% CH$_3$COONH$_4$ 7 mM/5% CH$_3$CN, B: CH$_3$CN | 84.2% A for 0.49 min, to 10.5% A in 2.18 min, held for 1.94 min, back to 84.2% A in 0.73 min, held for 0.73 min. | 0.343 40 | 6.2 |
| Method 2 | Waters: Acquity UPLC ® H-Class - DAD and SQD 2 | Waters: BEH C18 (1.7 μm, 2.1 × 100 mm) | A: 95% CH$_3$COONH$_4$ 7 mM/5% CH$_3$CN, B: CH$_3$CN | From 84.2% A to 10.5% A in 2.18 min, held for 1.94 min, back to 84.2% A in 0.73 min, held for 0.73 min. | 0.343 40 | 6.1 |
| Method 3 | Waters: Alliance ® - DAD and ZQ ™ | Waters Atlantis ® C18 (5 μm, 3.9 × 100 mm) | A: CH$_3$COONH$_4$ 7 mM, B: CH$_3$CN, C: 0.2% HCOOH | 50% A/0% B for 1.5 min, to 10% A/80% B in 3.5 min, held for 4 min, back to 50% A/0% B in 1.5 min, held for 1.5 min. | 0.8 30 | 12 |

DSC

For a number of compounds, melting points (MP) were determined with a DSC1 (Mettler-Toledo). Melting points were measured with a temperature gradient of 10° C./minute. Maximum temperature was 350° C. Values are peak values."

For a number of compounds, melting points were obtained with a Kofler hot bench, consisting of a heated plate with linear temperature gradient, a sliding pointer and a temperature scale in degrees Celsius.

NMR The NMR experiments were carried out using a Bruker Avance 500 III using internal deuterium lock and equipped with reverse triple-resonance ($^1$H, $^{13}$C, $^{15}$N TXI) probe head or using a Bruker Avance DRX 400 spectrometer at ambient temperature, using internal deuterium lock and equipped with reverse double-resonance ($^1$H, $^{13}$C, SEI) probe head with z gradients and operating at 400 MHz for the proton and 100 MHz for carbon. Chemical shifts (δ) are reported in parts per million (ppm).

OR

Optical Rotation (OR) is measured with a polarimeter 341 Perkin Elmer. The polarized light is passed through a sample with a path length of 1 decimeter and a sample concentration of 0.2 to 0.4 gram per 100 milliliters. 2 to 4 mg of the product in vial are weight, then dissolved with 1 to 1.2 ml of spectroscopy solvent (e.g. Dimethylformamide). The cell is filled with the solution and put into the polarimeter at a temperature of 20° C. The OR is read with 0.004° precision.

Calculation of the concentration: weight in gram×100/volume in ml $[\alpha]_d^{20}$: (read rotation×100)/(1.000 dm×concentration).

$d$ is sodium D line (589 nanometer).

TABLE

Co. No. means compound number; Retention time (R$_t$) in min; MP means melting point (° C.); dec means decomposition; n.d. means not determined.

| Co. No. | MP (° C.) | Kofler (K) or DSC | Rt | [M + H]$^+$ or [M + Na]$^+$ or fragments | Method HPLC |
|---|---|---|---|---|---|
| 1 | 100 | K | 3.10 | 468 | 1 |
| 2 | 80 (gum) | K | 3.11 | 468 | 1 |

TABLE-continued

Co. No. means compound number; Retention time (R$_t$) in min; MP means melting point (° C.); dec means decomposition; n.d. means not determined.

| Co. No. | MP (° C.) | Kofler (K) or DSC | Rt | [M + H]$^+$ or [M + Na]$^+$ or fragments | Method HPLC |
|---|---|---|---|---|---|
| 3 | n.d. | — | 3.27 | 482 | 1 |
| 4 | n.d. | — | 3.26 | 482 | 1 |
| 5 | n.d. | — | 2.98 | 443 | 1 |
| 6 | n.d. | — | 2.98 | 443 | 1 |
| 7 | 206 | DSC | 2.80 | 484 | 1 |
| 8 | 100 (gum) | K | 2.80 | 484 | 1 |
| 9 | n.d. | — | 2.80 | 484 | 1 |
| 10 | 189 | DSC | 3.06 | 427 | 1 |
| 11 | 228 | DSC | 2.82 | 442 | 1 |
| 12 | 218 | DSC | 2.82 | 442 | 1 |
| 13 | 217 | DSC | 2.82 | 442 | 1 |
| 14 | 140 | K | 2.69 | 470 | 1 |
| 15 | 80 (gum) | K | 3.18 | 441 | 1 |
| 16 | 80 (gum) | K | 3.18 | 441 | 1 |
| 17 | 170 | K | 2.64 | 497 | 1 |
| 18 | 80 (gum) | K | 2.69 | 511 | 1 |
| 19 | 80 (gum) | K | 2.64 | 470 | 1 |
| 20 | 80 (gum) | K | 3.04 | 494 | 1 |
| 21 | 184 | DSC | 2.78 | 438 | 1 |
| 22 | 183 | DSC | 2.78 | 438 | 1 |
| 23 | n.d. | — | 3.05 | 398 | 1 |

TABLE-continued

Co. No. means compound number; Retention time ($R_t$) in min; MP means melting point (° C.); dec means decomposition; n.d. means not determined.

| Co. No. | MP (° C.) | Kofler (K) or DSC | Rt | [M + H]+ or [M + Na]+ or fragments | Method HPLC |
|---|---|---|---|---|---|
| 24 | 100 (gum) | K | 3.05 | 398 | 1 |
| 25 | 98 (gum) | K | 3.05 | 398 | 1 |
| 26 | 80 (gum) | K | 3.10 | 468 | 1 |
| 27 | 80 (gum) | K | 3.06 | 432 | 1 |
| 28 | 80 (gum) | K | 3.06 | 450 | 1 |
| 29 | n.d. | — | 3.22 | 464 | 1 |
| 30 | n.d. | — | 3.23 | 464 | 1 |
| 31 | 213 | DSC | 3.49 | 455 | 1 |
| 32 | 80 (gum) | K | 3.03 | 480 | 1 |
| 33 | 280 | DSC | 3.12 | 480 | 1 |
| 34 | 160 | K | 2.92 | 570 | 1 |
| 35 | 80 (gum) | K | 3.23 | 464 | 1 |
| 36 | n.d. | — | 3.28 | 482 | 1 |
| 37 | 276 | DSC | 3.12 | 480 | 1 |
| 38 | 146 | K | 2.95 | 558 | 1 |
| 39 | 80 (gum) | K | 2.84 | 537 | 1 |
| 40 | 80 (gum) | K | 2.96 | 454 | 1 |
| 41 | 80 (gum) | K | 2.98 | 462 | 1 |
| 42 | 80 (gum) | K | 3.07 | 450 | 1 |
| 43 | 80 (gum) | K | 2.93 | 558 | 1 |
| 44 | 80 (gum) | K | 2.85 | 478 | 1 |
| 45 | 80 (gum) | K | 2.57 | 480 | 1 |
| 46 | 80 (gum) | K | 2.83 | 537 | 1 |
| 47 | 80 (gum) | K | 2.92 | 522 | 1 |
| 48 | 80 (gum) | K | 2.33 | 537 | 1 |
| 49 | 80 (gum) | K | 2.40 | 521 | 1 |
| 50 | 80 (gum) | K | 2.84 | 498 | 1 |
| 51 | 80 (gum) | K | 3.22 | 484 | 1 |
| 52 | 80 (gum) | K | 3.29 | 500 | 1 |
| 53 | n.d. | — | 2.99 | 443 | 1 |
| 54 | 80 (gum) | K | 2.81 | 475 | 1 |
| 55 | 80 (gum) | K | 3.45 | 514 | 1 |
| 56 | 55 | DSC | 3.10 | 499 | 1 |
| 57 | 80 (gum) | K | 2.97 | 523 | 1 |
| 58 | 80 (gum) | K | 2.97 | 523 | 1 |
| 59 | n.d. | — | 2.69 | 473 | 1 |
| 60 | n.d. | — | 2.69 | 473 | 1 |
| 61 | n.d. | — | 2.69 | 473 | 1 |
| 62 | >260 | K | 2.30 | 441 | 1 |
| 63 | 100 (gum) | K | 2.77 | 510 | 1 |
| 64 | 80 (gum) | K | 3.02 | 524 | 1 |
| 65 | 80 (gum) | K | 2.76 | 496 | 1 |
| 66 | 80 (gum) | K | 2.81 | 498 | 1 |
| 67 | 80 (gum) | K | 2.27 | 537 | 1 |
| 68 | 49 | DSC | 2.89 | 425 | 1 |
| 69 | 80 (gum) | K | 3.28 | 551 | 1 |
| 70 | 80 (gum) | K | 2.88 | 498 | 1 |
| 71 | 80 (gum) | K | 2.77 | 484 | 1 |
| 72 | 80 (gum) | K | 2.60 | 497 | 1 |
| 73 | n.d. | — | 2.89 | 483 | 1 |
| 74 | n.d. | — | 2.89 | 483 | 1 |
| 75 | 80 (gum) | K | 2.50 | 523 | 1 |
| 76 | 90 | DSC | 2.81 | 482 | 1 |
| 77 | 80 (gum) | K | 3.09 | 510 | 1 |
| 78 | 235 | DSC | 3.08 | 503 | 1 |
| 79 | n.d. | — | 2.14 | 483 | 1 |
| 80 | 244 | DSC | 3.18 | 429 | 1 |
| 81 | n.d. | — | 2.62 | 485 | 1 |
| 82 | n.d. | — | 5.81 | 511 | 3 |
| 83a | 240 | DSC | 2.12 | 415 | 1 |
| 83b | 180 | DSC | 2.10 | Fragment m/z 286 (weak 414.9) | 1 |
| 83c | 157 | DSC | 2.10 | Fragment m/z 286 (weak 415.0) | 1 |
| 84 | 80 (gum) | K | 2.76 | 401 | 1 |
| 85 | n.d. | — | 2.74 | 424 | 1 |
| 86 | 76 | DSC | 2.79 | 481 | 1 |
| 87 | 74 | DSC | 2.77 | 481 | 1 |
| 88 | n.d. | — | 2.83 | 384 | 1 |
| 89 | n.d. | — | 2.83 | 384 | 1 |
| 90 | n.d. | — | 2.88 | 494 | 1 |
| 91 | n.d. | — | 2.88 | 494 | 1 |
| 92 | n.d. | — | 2.88 | 494 | 1 |
| 93 | 80 (gum) | K | 2.92 | 497 | 1 |
| 94 | 80 (gum) | K | 2.71 | 496 | 1 |
| 95 | 80 (gum) | K | 2.73 | 496 | 1 |
| 96 | 80 (gum) | K | 2.71 | 426 | 1 |
| 97 | 146 | DSC | 3.46 | 425 | 1 |
| 98 | 240 | DSC | 2.15 | 411 | 1 |
| 99 | 189 | DSC | 3.33 | 445 | 1 |
| 100 | n.d. | — | 2.66 | 383 | 1 |
| 101 | 80 (gum) | K | 2.99 | 484 | 1 |
| 102 | 80 (gum) | K | 2.68 | 484 | 1 |
| 103 | 80 (gum) | K | 3.04 | 484 | 1 |
| 104 | 80 (gum) | K | 2.70 | 466 | 1 |
| 105 | 161 | DSC | 2.92 | 480 | 1 |
| 106 | 80 (gum) | K | 3.74 | 411 | 1 |
| 107 | 80-90 (gum) | K | 3.74 | 411 | 1 |
| 111 | 80 | K | 2.91 | 397 | 1 |
| 112 | 80 (gum) | K | 3.46 | 498 | 1 |
| 113 | 307 | DSC | 2.70 | 493 | 1 |
| 114 | 303 | DSC | 2.70 | 493 | 1 |
| 115 | 327 | DSC | 2.65 | 480 | 1 |
| 116 | 332 | DSC | 2.64 | 480 | 1 |
| 117 | n.d. | — | 2.44 | 440 | 1 |
| 117a | 179 | DSC | 2.46 | 440 | 1 |
| 118 | 237 | DSC | 2.44 | 440 | 1 |
| 118a | n.d. | — | 2.45 | 440 | 1 |
| 119 | 80 | K | 2.84 | 482 | 1 |
| 120 | 80 | K | 2.76 | 462 | 1 |
| 121 | 80 | K | 2.59 | 478 | 1 |
| 122 | n.d. | — | 2.40 | 454 | 1 |
| 122a | 116 | DSC | 2.31 | 454 | 1 |
| 123 | n.d. | — | 2.40 | 454 | 1 |
| 123a | 130 | DSC | 2.34 | 454 | 1 |
| 124 | 80 (gum) | K | 2.88 | 526 | 1 |
| 125 | 80 (gum) | K | 2.91 | 476 | 1 |
| 126 | 80 (gum) | K | 2.89 | 476 | 1 |
| 127 | 80 (gum) | K | 3.09 | 434 | 1 |
| 128 | 80 (gum) | K | 3.09 | 434 | 1 |
| 129 | 80 | K | 2.63 | 528 | 1 |
| 130 | 159 | DSC | 2.50 | 467 | 1 |
| 131 | 80 | K | 2.55 | 473 | 1 |
| 132 | 80 (gum) | K | 2.39 | 471 | 1 |
| 133 | 80 (gum) | K | 3.06 | 516 | 2 |
| 134 | 80 (gum) | K | 2.28 | 508 | 2 |
| 135 | 144 | DSC | 2.90 | 423 | 1 |
| 136 | 184 | DSC | 2.67 | 438 | 2 |
| 137 | 80 (gum) | K | 2.20 | 485 | 2 |
| 138 | n.d. | — | 2.11 | 453 | 2 |
| 139 | n.d. | — | 2.11 | 453 | 2 |
| 140 | 80 (gum) | K | 2.86 | 454 | 2 |
| 141 | 80 (gum) | K | 2.86 | 454 | 2 |
| 142 | 80 (gum) | K | 2.84 | 537 | 2 |
| 143 | 80 (gum) | K | 2.53 | 511 | 2 |
| 144 | 80 (gum) | K | 2.40 | 497 | 2 |
| 145 | 80 (gum) | K | 2.30 | 472 | 2 |
| 146 | 80 (gum) | K | 2.92 | Fragment m/z 355 (weak 500) | 1 |
| 147 | 80 (gum) | K | 2.56 | 487 | 1 |
| 148 | n.d. | — | 2.68 | 544 | 1 |
| 149 | 80 (gum) | K | 2.40 | 501 | 1 |
| 150 | 110 | K | 2.67 | 406 | 1 |
| 151 | 80 (gum) | K | 2.84 | 407 | 1 |
| 152 | 80 (gum) | K | 2.47 | 485 | 1 |
| 153 | 90 (gum) | K | 2.73 | 372 | 1 |
| 154a | n.d. | — | 2.76 | 401 | 1 |
| 154b | 90 | K | 2.76 | 401 | 1 |
| 155 | 186 | DSC | 2.58 | 431 | 1 |

TABLE-continued

Co. No. means compound number; Retention time ($R_t$) in min; MP means melting point (° C.); dec means decomposition; n.d. means not determined.

| Co. No. | MP (° C.) | Kofler (K) or DSC | Rt | [M + H]⁺ or [M + Na]⁺ or fragments | Method HPLC |
|---|---|---|---|---|---|
| 156 | n.d. | — | 2.88 | Fragment m/z 383 (weak 518) | 1 |
| 157 | n.d. | — | 2.88 | Fragment m/z 383 (weak 518) | 1 |
| 158 | n.d. | — | 2.96 | 439 | 1 |
| 159 | n.d. | — | 2.96 | 439 | 1 |
| 160 | 229 | DSC | 2.79 | Fragment m/z 383 (weak 530) | 1 |
| 161 | 228 | DSC | 2.79 | 530 | 1 |
| 162 | 80 (gum) | K | 3.22 | Fragments m/z 353 and 383 | 1 |
| 163 | 239 | DSC | 3.21 | Fragments m/z 353 and 383 | 1 |
| 164 | 116 | DSC | 3.05 | Fragments m/z 335 and 383 | 1 |
| 165 | 80 (gum) | K | 2.50 | 472 | 1 |
| 166 | 80 (gum) | K | 2.51 | 472 | 1 |
| 167 | 80 (gum) | K | 3.45 | 449 | 1 |
| 168 | 165 | DSC | 3.00 | 470 | 1 |
| 169 | 217 | DSC | 2.79 | 486 | 1 |
| 170 | 285 | DSC | 2.15 | Fragment m/z 286 (weak 433) | 1 |
| 171 | 125 gum | K | 3.12 | 565 + fragment m/z 436 | 1 |
| 172 | 130 gum | K | 3.12 | 565 | 1 |
| 173 | 80 gum | K | 2.71 | 506 + fragment m/z 383 | 1 |
| 174 | 80 gum | K | 2.49 | 529 | 1 |
| 175 | 80 gum | K | 2.48 | 529 | 1 |
| 176 | n.d. | — | 2.41 | 525 + fragment m/z 313 | 1 |
| 177 | 80 gum | K | 2.77 | 467 [M + Na]⁺ + fragment m/z 316 | 1 |
| 178 | 80 gum | K | 2.77 | 467 [M + Na]⁺ + fragment m/z 316 | 1 |
| 180 | 148 | K | 2.58 | 499 | 1 |
| 181 | 134 | DSC | 2.51 | 499 | 1 |
| 182 | 134 | DSC | 2.50 | 499 | 1 |
| 183 | 145 | K | 2.46 | 485 | 1 |
| 184 | 157 | DSC | 2.42 | 485 | 1 |
| 184a | 80° C. (gum) | K | 2.54 | 485 | 1 |
| 184b | 270 | DSC | 2.57 | 485 | 1 |
| 184c | 74 | DSC | 2.57 | 485 | 1 |
| 185 | 152 | DSC | 2.40 | 485 | 1 |
| 186 | 80 (gum) | K | 3.18 | 468 | 1 |
| 187 | 80 (gum) | K | 3.18 | 468 | 1 |
| 188 | 80 (gum) | K | 2.52 | 458 + fragment m/z 329 | 1 |
| 189 | 80 (gum) | K | 2.52 | 458 + fragment m/z 329 | 1 |
| 192 | 229 | DSC | 3.00 | 512 + fragment m/z 383 | 1 |
| 193 | 80 (gum) | K | 2.70 | 500 + 522 [M + Na]⁺ + fragment m/z 371 + 383 | 1 |
| 194 | 80 (gum) | K | 2.69 | 500 + 522 [M+Na]⁺ + fragments m/z 371 + 383 | 1 |
| 195 | 228 | DSC | 2.99 | 411 + fragment m/z 383 | 1 |
| 196 | 80 (gum) | K | 2.69 | 500 + fragment m/z 383 | 1 |
| 197 | 80 (gum) | K | 2.68 | 500 + fragment m/z 383 | 1 |
| 198 | 171 | DSC | 2.61 | 459 | 1 |
| 199 | 140 | K | 2.50 | 459 | 1 |
| 200 | 115 gum | K | 2.50 | 459 | 1 |
| 201 | | | 2.61 | 472 | 1 |
| 202 | 70 | DSC | 2.61 | 472 | 1 |
| 203 | 118 | DSC | 2.75 | 472 | 1 |
| 204 | 80 (gum) | K | 2.75 | 472 | 1 |
| 205 | 80 (gum) | K | 3.08 | 514 | 1 |
| 206 | 80 (gum) | K | 3.27 | 498 | 1 |
| 207 | 80 (gum) | K | 3.09 | 514 | 1 |
| 208 | 80 | K | 3.28 | 498 | 1 |
| 209 | 183 | DSC | 3.36 | 430 | 1 |
| 210 | 80 | K | 2.98 | 506 | 1 |
| 211 | 206 | DSC | 2.53 | 499 | 1 |
| 212 | 204 | DSC | 2.52 | 499 | 1 |
| 213 | 80 (gum) | K | 2.58 | 476 | 1 |
| 214 | 80 (gum) | K | 2.58 | 476 | 1 |
| 217 | n.d. | — | 2.94 | 565 | 1 |
| 218 | n.d. | — | 2.23 | 518 | 1 |
| 219 | n.d. | — | 2.20 | 389 | 1 |
| 220 | n.d. | — | 2.20 | 389 | 1 |
| 222 | 163 | DSC | 2.98 | 506 | 1 |
| 223 | 200 | DSC | 2.76 | 526 | 1 |
| 224 | 163 | DSC | 2.66 | 553 | 1 |
| 225 | 80 (gum) | K | 2.85 | 414 + fragment m/z 285 | 1 |
| 226 | 158 | DSC | 2.39 | 481 | 1 |
| 227 | 80 (gum) | K | 2.37 | 481 | 1 |
| 228 | 80 (gum) | K | 2.35 | 481 | 1 |
| 229 | n.d. | — | 2.36 | 444 | 1 |
| 230 | 218 | DSC | 2.27 | 426 | 1 |
| 231 | n.d. | — | 2.61 | 490 | 1 |
| 232 | 181 | DSC | 2.46 | 458 | 1 |
| 233 | 192 | Kofler | n.d. | n.d. | — |
| 236 | 240 | DSC | 2.12 | 415 | 1 |
| 237 | 80 | K | 2.83 | 551 | 1 |
| 237a | 120 | DSC | 2.85 | 551 | 1 |
| 237b | 120 | DSC | 2.84 | 551 | 1 |
| 237c | 80 | K | 2.85 | 551 | 1 |
| 237d | 80 | K | 2.86 | 551 | 1 |
| 238 | 110 | K | 2.94 | 551 | 1 |
| 239 | n.d. | — | 2.11 | 512 | 1 |
| 240 | n.d. | — | 2.10 | 512 | 1 |
| 241 | n.d. | — | 2.10 | 512 | 1 |
| 242 | n.d. | — | 2.12 | 512 | 1 |
| 243 | n.d. | — | 2.13 | 493 | 1 |
| 243a | 160 | K | 2.10 | 493 | 1 |
| 243b | 200 | K | 2.10 | 493 | 1 |
| 244 | n.d. | — | 2.51 | 484 | 1 |
| 245 | n.d. | — | 2.50 | 484 | 1 |
| 246a | n.d. | — | 2.56 | 472 | 1 |
| 246b | 75 | DSC | 2.54 | 472 | Method 1 |
| 249 | 211 | DSC | n.d. | n.d. | — |
| 250 | 120 | K | n.d. | n.d. | — |
| 251 | 299 | DSC | n.d. | n.d. | — |
| 262 | 222 | DSC | n.d. | n.d. | — |
| 262a | 199.7 | DSC | 3.10 | 411 | 1 |

TABLE-continued

Co. No. means compound number; Retention time ($R_t$) in min; MP means melting point (° C.); dec means decomposition; n.d. means not determined.

| Co. No. | MP (° C.) | Kofler (K) or DSC | Rt | [M + H]⁺ or [M + Na]⁺ or fragments | Method HPLC |
|---|---|---|---|---|---|
| 262b | 199.5 | DSC | 3.10 | 411 | 1 |
| 264 | 189 | DSC | n.d. | n.d. | — |
| 266 | 220 | K | n.d. | n.d. | — |
| 276 | 194 | DSC | 2.39 | 440 | 1 |
| 278 | 158 | K | 2.65 | 428 | 1 |
| 279 | 77 | DSC | 2.41 | 457 | 1 |
| 279a | 80 (gum) | K | 2.48 | 457 | 1 |
| 279b | 80 (gum) | K | 2.48 | 457 | 1 |
| 280 | 164 | DSC | 2.44 | 471 | 1 |
| 280a | 80 (gum) | K | 2.51 | 471 | 1 |
| 280b | 80 (gum) | K | 2.51 | 471 | 1 |
| 281 | 80 (gum) | K | 2.37 | 484 | 1 |
| 281a | 102 | K | 2.45 | 484 | 1 |
| 281b | 80 (gum) | K | 2.44 | 484 | 1 |
| 282 | 100 (gum) | K | 2.14 | 452 | 1 |
| 282a | 100 (gum) | K | 2.33 | 452 | 1 |
| 282b | 100 (gum) | K | 2.34 | 452 | 1 |
| 283a | 173 | DSC | 2.51 | 516 | 1 |
| 283b | 170 | DSC | 2.52 | 516 | 1 |
| 284a | 113 | K | 2.66 | 489 | 1 |
| 284b | 112 | K | 2.66 | 489 | 1 |
| 286 | 85 (gum) | K | 2.61 | 499 | 1 |
| 286a | 85 (gum) | K | 2.59 | 499 | 1 |
| 286b | 85 (gum) | K | 2.59 | 499 | 1 |
| 287 | 80 (gum) | K | 2.78 | 522 | 1 |
| 287a | 90 (gum) | K | 2.78 | 522 | 1 |
| 287b | 95 | K | 2.78 | 522 | 1 |
| 292 | 80 (gum) | K | 2.74 | 503 | 1 |
| 292a | 110 (gum) | K | 2.74 | 503 | 1 |
| 292b | 110 (gum) | K | 2.74 | 503 | 1 |
| 293 | 186 | K | 3.18 | 425 | 1 |
| 294 | n.d. | — | n.d. | n.d. | — |
| 295 | 80 (gum) | K | 2.55 | 453 | 1 |
| 295a | 120 (gum) | K | 2.56 | 453 | 1 |
| 295b | 120 (gum) | K | 2.56 | 453 | 1 |
| 296 | n.d. | — | 2.51 | 514 | 1 |
| 296a | n.d. | — | 2.50 | 514 | 1 |
| 296b | n.d. | — | 2.52 | 514 | 1 |
| 297 | n.d. | — | 2.50 | 514 | 1 |
| 297a | n.d. | — | 2.52 | 514 | 1 |
| 297b | n.d. | — | 2.52 | 514 | 1 |
| 298a | 100 (gum) | K | 2.74 | 511 | 1 |
| 298b | 100 (gum) | K | 2.75 | 511 | 1 |
| 299a | 100 (gum) | K | 2.55 | 485 | 1 |
| 299b | 100 (gum) | K | 2.55 | 485 | 1 |
| 300 | n.d. | n.d. | 2.48 | 483 | 1 |
| 300a | 140 | K | 2.49 | 483 | 1 |
| 300b | 135 | K | 2.49 | 483 | 1 |
| 301 | 315 | DSC | 2.44 | 453 | 1 |
| 302 | 80 (GUM) | K | 2.61 | 497 | 1 |
| 302a | 135 | K | 2.62 | 497 | 1 |
| 302b | 135 | K | 2.62 | 497 | 1 |
| 303 | 138 | DSC | 2.70 | 400 | 1 |
| 304 | n.d. | — | 2.87 | 436 | 1 |
| 308 | 195 | DSC | 2.78 | 539 | 1 |
| 309 | n.d. | — | n.d. | n.d. | — |
| 309a | n.d. | — | 2.58 | 502 | 1 |
| 309b | n.d. | — | 2.59 | 502 | 1 |
| 312a | n.d. | — | 2.75 | 515 | 1 |
| 312b | n.d. | — | 2.75 | 515 | 1 |
| 313a | n.d. | — | 2.86 | 515 | 1 |
| 313b | n.d. | — | 2.87 | 515 | 1 |
| 314a | 80 (gum) | K | 2.55 | 481 | 1 |
| 314b | 80 (gum) | K | 2.54 | 481 | 1 |
| 315a | 86 (gum) | K | 2.30 | 546 | 2 |
| 315b | 90 | K | 2.29 | 547 | 1 |
| 317 | 167 | DSC | 1.92 | 509 | 1 |
| 318 | n.d. | — | 2.11 | 492 | 1 |
| 319a | n.d. | — | 2.90 | 550 | 1 |
| 319b | n.d. | — | 2.90 | 550 | 1 |
| 320a | 110 | K | 2.57 | 479 | 1 |
| 320b | 136 | K | 2.58 | 479 | 1 |
| 321a | 118 | K | 2.44 | 465 | 1 |
| 321b | 128 | K | 2.44 | 465 | 1 |
| 322a | 122 | K | 2.40 | 496 | 1 |
| 322b | 80 | K | 2.39 | 496 | 1 |
| 323a | 126 | K | 2.39 | 496 | 1 |
| 323b | 130 | K | 2.41 | 496 | 1 |
| 324a | 60 | K | 2.45 | 485 | 1 |
| 324b | 60 | K | 2.45 | 485 | 1 |
| 325a | 144 | K | 2.39 | 482 | 1 |
| 325b | 138 | K | 2.38 | 482 | 1 |
| 328 | 98 | DSC | 2.48 | 466 | 1 |
| 329a | 121 | K | 2.46 | 496 | 1 |
| 329b | 124 | K | 2.46 | 496 | 1 |
| 332 | 169 | DSC | 2.75 | 427 | 1 |
| 333 | 265 | DSC | 2.46 | 443 | 1 |
| 334a | 136 | DSC | 2.50 | 441 | 1 |
| 334b | 134 | DSC | 2.58 | 441 | 1 |
| 335a | n.d. | — | 2.55 | 503 | 1 |
| 335b | 80 (gum) | K | 2.52 | 503 | 1 |
| 336 | 194 | DSC | 2.40 | 440 | 1 |
| 338 | n.d. | — | 2.43 | 454 | 1 |
| 338a | 89.8 | DSC | 2.49 | 454 | 1 |
| 338b | 90.8 | DSC | 2.49 | 454 | 1 |
| 339 | 117 | DSC | 2.89 | 423 | 1 |
| 339a | 131 | DSC | 2.97 | 423 | 1 |
| 339b | 129 | DSC | 2.96 | 423 | 1 |
| 340 | 180 | DSC | 2.19 | 457 | 1 |
| 341 | 80 | K | 2.89 | 429 | 1 |
| 342 | n.d. | — | 2.31 | 485 | 1 |
| 343 | n.d. | — | 2.32 | 440 | 1 |
| 344a | 75 | K | 2.36 | 472 | 1 |
| 344b | 75 | K | 2.37 | 472 | 1 |
| 345a | 80 | K | 2.38 | 529 | 1 |
| 345b | 80 | K | 2.38 | 529 | 1 |
| 346a | 107 | K | 2.54 | 472 | 1 |
| 346b | 106 | K | 2.54 | 472 | 1 |
| 347 | 170 | DSC | 2.78 | 523 | 1 |
| 347a | 125 | K | 2.80 | 523 | 1 |
| 347b | 125 | K | 2.80 | 523 | 1 |
| 348a | 102 | K | 2.62 | 486 | 1 |
| 348b | 102 | K | 2.62 | 486 | 1 |
| 349a | 82 | K | 2.55 | 499 | 1 |
| 349b | 82 | K | 2.55 | 499 | 1 |
| 351 | n.d. | — | 2.22 | 483 | 1 |
| 352 | n.d. | — | 2.25 | 483 | 1 |
| 353 | 80 (gum) | K | 2.69 | 500 | 1 |
| 354 | n.d. | — | 2.97 | 438 | 1 |
| 355 | 80 (gum) | K | 2.26 | 483 | 1 |
| 357a | 116 | K | 2.55 | 511 | 1 |
| 357b | 120 | K | 2.55 | 511 | 1 |
| 358 | 80 (gum) | K | 2.86 | 442 | 1 |
| 359 | n.d. | — | 2.51 | 493 | 1 |
| 360 | n.d. | — | 2.58 | 525 | 1 |
| 362 | n.d. | — | 2.51 | 481 | 1 |
| 363a | 80 (gum) | K | 2.76 | 512 | 1 |
| 363b | 80 (gum) | K | 2.75 | 512 | 1 |
| 364 | 80 (gum) | K | 2.50 | 499 | 1 |
| 364a | 80 (gum) | K | 2.47 | 499 | 1 |
| 364b | 80 (gum) | K | 2.48 | 499 | 1 |
| 365 | 80 (gum) | K | 2.39 | 497 | 1 |
| 365a | 80 (gum) | K | 2.41 | 497 | 1 |
| 365b | 80 (gum) | K | 2.40 | 497 | 1 |
| 366 | 154 | DSC | 2.51 | 489 | 1 |
| 367a | n.d. | — | 3.01 | 547 | 1 |
| 367b | n.d. | — | 3.01 | 547 | 1 |
| 368 | n.d. | — | 2.26 | 483 | 1 |
| 369a | n.d. | — | 2.99 | 524 | 1 |
| 369b | 147 | DSC | 2.99 | 524 | 1 |
| 370a | 128 | DSC | 2.48 | 498 | 1 |
| 370b | 80 (gum) | K | 2.50 | 498 | 1 |
| 371a | 114 | K | 2.40 | 497 | 1 |
| 371b | 107 | K | 2.40 | 497 | 1 |

TABLE-continued

Co. No. means compound number; Retention time ($R_t$) in min; MP means melting point (° C.); dec means decomposition; n.d. means not determined.

| Co. No. | MP (° C.) | Kofler (K) or DSC | Rt | [M + H]⁺ or [M + Na]⁺ or fragments | Method HPLC |
|---|---|---|---|---|---|
| 373 | n.d. | — | 2.79 | 539 | 1 |
| 374a | 132 | K | 2.36 | 483 | 1 |
| 374b | 130 | K | 2.38 | 483 | 1 |
| 375 | 80 | K | 2.99 | 524 | 1 |
| 376 | 130 gum | K | 2.48 | 497 | 1 |
| 379a | n.d. | — | 2.60 | 504 | 1 |
| 379b | n.d. | — | 2.59 | 504 | 1 |
| 380a | n.d. | — | 2.59 | 488 | 1 |
| 380b | n.d. | — | 2.60 | 488 | 1 |
| 381 | n.d. | — | 2.48 | 440 | 1 |
| 382 | 150 | DSC | 2.80 | 424 | 1 |
| 383 | 172 | DSC | 2.44 | 467 | 1 |
| 384 | n.d. | — | 2.36 | 471 | 1 |
| 385 | n.d. | — | 2.50 | 495 | 1 |
| 386 | n.d. | — | 2.65 | 509 | 1 |
| 388a | n.d. | — | 2.88 | 557 | 1 |
| 388b | n.d. | — | 2.88 | 557 | 1 |
| 389 | n.d. | — | 2.36 | 499 | 1 |
| 390 | n.d. | — | 2.53 | 513 | 1 |
| 391 | n.d. | — | 2.42 | 452 | 1 |
| 391a | n.d. | — | 2.32 | 452 | 1 |
| 391b | n.d. | — | 2.32 | 452 | 1 |
| 392a | 80 (gum) | K | 2.79 | 482 | 1 |
| 392b | n.d. | — | 2.79 | 482 | 1 |
| 393a | 115 (gum) | K | 1.99 | 454 | 1 |
| 393b | 196 | DSC | 1.99 | 454 | 1 |
| 394 | 161 | DSC | 2.41 | 471 | 1 |
| 395 | 80 (gum) | K | 2.97 | 468 | 1 |
| 395a | 90 (gum) | K | 2.97 | 468 | 1 |
| 395b | 102 | K | 2.97 | 468 | 1 |
| 396 | n.d. | — | 3.14 | 482 | 1 |
| 397 | 70 (gum) | K | 2.82 | 436 | 1 |
| 397a | 80 (gum) | K | 2.83 | 436 | 1 |
| 397b | 80 (gum) | K | 2.83 | 436 | 1 |
| 398 | n.d. | — | 3.10 | 465 | 1 |
| 399 | 202 | K | 2.96 | 474 | 1 |
| 400 | 80 (gum) | K | 2.60 | 410 | 1 |
| 401 | 80 (gum) | K | 2.78 | 424 | 1 |
| 402 | 80 (gum) | K | 2.83 | 442 | 1 |
| 403a | 53 | DSC | 3.13 | 440 | 1 |
| 403b | 54 | DSC | 3.13 | 440 | 1 |
| 404a | n.d. | — | 2.60 | 516 | 1 |
| 404b | n.d. | — | 2.58 | 516 | 1 |
| 405a | n.d. | — | 2.59 | 516 | 1 |
| 405b | n.d. | — | 2.58 | 516 | 1 |
| 406a | 80 (gum) | K | 2.47 | 471 | 1 |
| 406b | 80 (gum) | K | 2.47 | 471 | 1 |
| 407a | 115 | K | 2.58 | 481 | 1 |
| 407b | 105 | K | 2.59 | 481 | 1 |
| 408a | 127 | DSC | 2.47 | 444 | 1 |
| 408b | 123 | DSC | 2.47 | 444 | 1 |

OR data: Solvent: DMF; temperature: 20° C.; wavelength: 589 nm ('Co. No.' means Compound Number; 'OR' means optical rotation; 'Conc.' means concentration in g/100 mL)

| Co. No. | OR (°) | Conc. |
|---|---|---|
| 1 | −292.75 | 0.392 |
| 2 | +316.79 | 0.401 |
| 5 | −412.51 | 0.331 |
| 6 | +421.30 | 0.342 |
| 8 | −382.23 | 0.266 |
| 9 | +375.10 | 0.253 |
| 10 | −402.40 | 0.258 |
| 12 | −414.74 | 0.285 |
| 13 | +416.86 | 0.261 |
| 21 | −320.83 | 0.264 |
| 22 | +317.85 | 0.297 |
| 24 | −498.40 | 0.281 |
| 25 | +527.65 | 0.327 |
| 31 | +352.63 | 0.244 |
| 33 | −295.09 | 0.265 |
| 34 | −239.57 | 0.278 |
| 37 | +274.14 | 0.263 |
| 38 | −238.83 | 0.291 |
| 40 | −301.03 | 0.290 |
| 43 | +228.28 | 0.290 |
| 47 | −243.13 | 0.276 |
| 51 | −294.42 | 0.236 |
| 57 | −213.58 | 0.202 |
| 58 | +231.82 | 0.220 |
| 60 | +341.54 | 0.321 |
| 61 | +421.30 | 0.342 |
| 73 | −348.84 | 0.301 |
| 74 | +343.7 | 0.270 |
| 83b | −513.10 | 0.229 |
| 83c | −496.67 | 0.330 |
| 85 | −363.50 | 0.194 |
| 88 | −459.09 | 0.264 |
| 89 | +464.44 | 0.270 |
| 91 | −348.27 | 0.245 |
| 92 | +357.52 | 0.262 |
| 103 | −309.92 | 0.259 |
| 106 | −432.69 | 0.260 |
| 107 | +391.95 | 0.236 |
| 113 | +308.69 | 0.224 |
| 114 | −337.35 | 0.191 |
| 117 | −429.65 | 0.185 |
| 117a | −342.13 | 0.254 |
| 118 | +404.14 | 0.198 |
| 118a | +359.47 | 0.338 |
| 122 | −3145.76 | 0.197 |
| 122a | −314.81 | 0.216 |
| 123 | +367.55 | 0.218 |
| 123a | +317.06 | 0.293 |
| 127 | −105.60 | 0.250 |
| 128 | +107.53 | 0.242 |
| 137 | −365.95 | 0.173 |
| 138 | −373.79 | 0.237 |
| 139 | +395.19 | 0.270 |
| 140 | +73.81 | 0.279 |
| 141 | +76.81 | 0.292 |
| 152 | +335.71 | 0.280 |
| 154a | −466.21 | 0.191 |
| 154b | +480.87 | 0.274 |
| 156 | −317.47 | 0.256 |
| 157 | +307.31 | 0.260 |
| 158 | −249.76 | 0.208 |
| 159 | +259.50 | 0.203 |
| 160 | −335.79 | 0.190 |
| 161 | +318.44 | 0.242 |
| 162 | −340.81 | 0.241 |
| 163 | +292.77 | 0.188 |
| 165 | −370.38 | 0.260 |
| 166 | +366.30 | 0.270 |
| 171 | −313.87 | 0.252 |
| 172 | +311.51 | 0.304 |
| 174 | +378.33 | 0.240 |
| 175 | −335.27 | 0.258 |
| 177 | −401.08 | 0.185 |
| 178 | +427.32 | 0.194 |
| 181 | +295.85 | 0.265 |
| 182 | −324.34 | 0.189 |
| 184 | −376.8 | 0.250 |
| 185 | +301.82 | 0.275 |
| 186 | −400.67 | 0.300 |
| 187 | +402.33 | 0.314 |
| 188 | −394.49 | 0.254 |
| 189 | +420.35 | 0.226 |
| 192 | +285.27 | 0.258 |
| 195 | −339.85 | 0.266 |
| 199 | −350.00 | 0.260 |
| 200 | +343.06 | 0.288 |
| 203 | −401.47 | 0.327 |

-continued

| Co. No. | OR (°) | Conc. |
|---|---|---|
| 210 | −334.15 | 0.244 |
| 211 | −380.48 | 0.251 |
| 212 | +360.74 | 0.298 |
| 213 | −393.33 | 0.315 |
| 214 | +398.92 | 0.277 |
| 219 | −341.38 | 0.290 |
| 220 | +346.21 | 0.290 |
| 222 | +265.31 | 0.245 |
| 227 | −372.39 | 0.268 |
| 228 | +372.09 | 0.258 |
| 237a | −335.17 | 0.290 |
| 237b | +319.70 | 0.264 |
| 243a | −341.33 | 0.354 |
| 243b | +375.76 | 0.445 |
| 244 | +88.00 | 0.200 |
| 245 | −67.62 | 0.245 |
| 249 | −343.79 | 0.239 |
| 250 | −374.62 | 0.231 |
| 251 | −327.17 | 0.254 |
| 252 | +352.63 | 0.244 |
| 257b | +413.08 | 0.193 |
| 257c | −367.10 | 0.207 |
| 262a | −494.03 | 0.268 |
| 262b | +483.66 | 0.257 |
| 279a | −387.27 | 0.267 |
| 279b | +401.56 | 0.256 |
| 280a | −358.62 | 0.290 |
| 280b | 352.99 | 0.251 |
| 281a | −353.28 | 0.259 |
| 281b | +334.32 | 0.303 |
| 282a | −373.79 | 0.237 |
| 282b | +395.19 | 0.27 |
| 283a | −347.53 | 0.324 |
| 283b | +307.65 | 0.327 |
| 286a | +308.51 | 0.282 |
| 286b | −285.98 | 0.271 |
| 292a | −342.13 | 0.224 |
| 292b | +354.32 | 0.238 |
| 295a | −409.09 | 0.253 |
| 295b | +409.72 | 0.288 |
| 296a | −299.27 | 0.275 |
| 296b | +264.91 | 0.285 |
| 297a | +292.92 | 0.24 |
| 297b | −303.53 | 0.238 |
| 298a | −255.68 | 0.273 |
| 298b | +391.81 | 0.293 |
| 299a | −336.73 | 0.245 |
| 299b | +316.61 | 0.289 |
| 309a | −344.58 | 0.249 |
| 309b | +347.21 | 0.269 |
| 312a | +400.77 | 0.26 |
| 312b | −362.14 | 0.28 |
| 313a | −316 | 0.25 |
| 313b | +407.69 | 0.26 |
| 314a | +346.67 | 0.255 |
| 314b | −342.01 | 0.269 |
| 315a | +285.04 | 0.274 |
| 315b | −304.43 | 0.271 |
| 319a | +6.84 | 0.263 |
| 319b | −8.3 | 0.277 |
| 324a | −303.6 | 0.25 |
| 324b | +346.84 | 0.269 |
| 325a | +334.04 | 0.285 |
| 325b | −376 | 0.25 |
| 329a | −315.38 | 0.26 |
| 329b | +321.85 | 0.27 |
| 334a | −379.05 | 0.269 |
| 334b | +344.92 | 0.305 |
| 335a | −307.47 | 0.255 |
| 335b | +302.73 | 0.33 |
| 339a | −84.62 | 0.272 |
| 339b | +87.02 | 0.222 |
| 344a | −341.31 | 0.259 |
| 344b | +325.98 | 0.254 |
| 345a | −309.67 | 0.300 |
| 345b | +313.61 | 0.294 |
| 348a | −301.71 | 0.297 |

-continued

| Co. No. | OR (°) | Conc. |
|---|---|---|
| 348b | +358.89 | 0.253 |
| 349a | −330.45 | 0.312 |
| 349b | +322.3 | 0.287 |
| 352 | +18.94 | 0.396 |
| 355 | +25.61 | 0.285 |
| 357a | +350.18 | 0.285 |
| 357b | −342.9 | 0.331 |
| 359 | −16.73 | 0.269 |
| 363a | −376.21 | 0.269 |
| 363b | +260.7 | 0.57 |
| 367a | +5.62 | 0.267 |
| 367b | −9.6 | 0.267 |
| 368 | −40.22 | 0.271 |
| 369a | −333.22 | 0.304 |
| 369b | +146.67 | 0.266 |
| 370a | −333.42 | 0.304 |
| 370b | +340.23 | 0.266 |
| 374a | −294.40 | 0.25 |
| 374b | +376.33 | 0.3 |
| 379a | −353.65 | 0.274 |
| 379b | +316.25 | 0.277 |
| 380a | +381.39 | 0.274 |
| 380b | −401.88 | 0.266 |
| 388a | +279.3 | 0.256 |
| 388b | −273.06 | 0.271 |
| 391a | −287.94 | 0.257 |
| 391b | −301.54 | 0.260 |
| 392a | −384.21 | 0.248 |
| 393a | −381.05 | 0.281 |
| 393b | +315.51 | 0.245 |
| 395a | −142.92 | 0.365 |
| 395b | +171.98 | 0.335 |
| 397a | +33.21 | 0.268 |
| 397b | −35.66 | 0.258 |
| 398 | −120.03 | 0.319 |
| 403a | −246.42 | 0.723 |
| 403b | +236.25 | 0.245 |
| 404a | +302.98 | 0.235 |
| 404b | −327.05 | 0.233 |
| 405a | +341.45 | 0.226 |
| 405b | −329.15 | 0.223 |
| 406a | −390.85 | 0.308 |
| 406b | +394.78 | 0.287 |
| 407a | −356 | 0.25 |
| 407b | +347.54 | 0.242 |
| 408a | −400.66 | 0.302 |
| 408b | +390.38 | 0.312 |

SFC-MS Methods:

General Procedure for SFC-MS Methods

The SFC measurement was performed using an Analytical Supercritical fluid chromatography (SFC) system composed by a binary pump for delivering carbon dioxide ($CO_2$) and modifier, an autosampler, a column oven, a diode array detector equipped with a high-pressure flow cell standing up to 400 bars. If configured with a Mass Spectrometer (MS) the flow from the column was brought to the (MS). It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

TABLE

Analytical SFC-MS Methods (Flow expressed in mL/min; column temperature (T) in ° C.; Run time in minutes, Backpressure (BPR) in bars).

| Method number | column | mobile phase | gradient | Flow Col T | Run time BPR |
|---|---|---|---|---|---|
| 1 | Daicel Chiralpak ® AD-H column (5 μm, 150 × 4.6 mm) | A: $CO_2$ B: EtOH(+0.3% iPrNH$_2$) | 25% B hold 7 min, | 3 35 | 7 100 |
| 2 | Daicel Chiralpak ® AD-H column (5 μm, 150 × 4.6 mm) | A: $CO_2$ B: EtOH(+0.3% iPrNH$_2$) | 30% B hold 7 min, | 3 35 | 7 100 |
| 3 | Daicel Chiralpak ® AD-H column (5 μm, 150 × 4.6 mm) | A: $CO_2$ B: EtOH(+0.3% iPrNH$_2$) | 40% B hold 7 min, | 3 35 | 7 100 |
| 4 | Daicel Chiralpakl ® AS-3 column (3 μm, 100 × 4.6 mm) | A: CO2 B: EtOH(+0.3% iPrNH2) | 20% B hold 3 min, | 3.5 35 | 3 103 |
| 5 | Daicel Chiralpakl ® AS-3 column (3 μm, 100 × 4.6 mm) | A: CO2 B: MeOH(+0.3% iPrNH2) | 25% B hold 3 min, | 3.5 35 | 3 103 |
| 6 | Daicel Chiralcel ® OJ-H column (5 μm, 150 × 4.6 mm) | A: $CO_2$ B: EtOH(+0.3% iPrNH$_2$) | 15% B hold 7 min, | 3 35 | 7 100 |
| 7 | Daicel Chiralcel ® OJ-H column (5 μm, 150 × 4.6 mm) | A: $CO_2$ B: EtOH(+0.3% iPrNH$_2$) | 25% B hold 7 min, | 3 35 | 7 100 |
| 8 | Daicel Chiralcel ® OJ-H column (5 μm, 150 × 4.6 mm) | A: $CO_2$ B: MeOH(+0.3% iPrNH$_2$) | 20% B hold 7 min, | 3 35 | 7 100 |
| 9 | Daicel Chiralcel ® OJ-H column (5 μm, 150 × 4.6 mm) | A: $CO_2$ B: MeOH(+0.3% iPrNH$_2$) | 25% B hold 7 min, | 3 35 | 7 100 |
| 10 | Daicel Chiralpakl ® AD-3 column (3 μm, 100 × 4.6 mm) | A: $CO_2$ B: EtOH(+0.3% iPrNH$_2$) | 25% B hold 3 min, | 3.5 35 | 3 103 |
| 11 | Daicel Chiralpakl ® AD-3 column (3 μm, 100 × 4.6 mm) | A: $CO_2$ B: EtOH(+0.3% iPrNH$_2$) | 40% B hold 3 min, | 3.5 35 | 3 103 |

TABLE

Analytical SFC-MS data - $R_t$ means retention time (in minutes), method refers to the method used for (SFC)MS analysis of enantiomerically pure compounds.

| Co. No. | Rt | Chiral purity UV Area % | Method number |
|---|---|---|---|
| 237c | 1.43 | 100 | 9 |
| 237d | 1.78 | 99.69 | 9 |
| 364a | 0.79 | 100 | 11 |
| 364b | 2.00 | 100 | 11 |
| 365a | 5.31 | 100 | 2 |
| 365b | 6.44 | 100 | 2 |
| 392b | 3.96 | 100 | 3 |
| 207* | 2.42 | 55 | 6 |
| 208 | 1.65 | 100 | 8 |
| 371a | 2.14 | 100 | 1 |
| 371b | 2.6 | 99.48 | 1 |
| 322a | 1.41 | 99.46 | 5 |
| 322b | 1.81 | 99.33 | 5 |
| 323a | 1.32 | 97.97 | 5 |
| 323b | 1.77 | 99.09 | 5 |
| 201 | 1.87 | 100 | 8 |
| 202 | 2.84 | 100 | 8 |
| 205 | 3.71 | 45 | 6 |
| 284a | 1.56 | 100 | 7 |
| 284b | 1.96 | 99.46 | 7 |
| 338a | 2.16 | 100 | 7 |
| 338b | 2.7 | 99.44 | 7 |
| 287a | 1.61 | 100 | 10 |
| 287b | 1.96 | 95.36 | 10 |
| 201 | 2.08 | 100 | 8 |
| 202 | 3.07 | 100 | 8 |
| 347a | 5.02 | 100 | 1 |
| 347b | 4.48 | 100 | 1 |
| 302a | 1.43 | 100 | 4 |
| 302b | 1.89 | 100 | 4 |
| 300a | 3.24 | 100 | 2 |
| 300b | 4.73 | 100 | 2 |

*Co. No. 207 is a mixture of 2 diastereoisomers $^1$H NMR (500 MHz, DMSO-d$_6$) 5 ppm 9.44 (s, 1H) 7.94 (d, J=1.9 Hz, 1H) 7.75 (d, 0.7=1.6 Hz, 1H) 7.32 (br s, 1H) 7.06 (d, J=7.9 Hz, 1H) 6.12-6.24 (m, 1H) 6.06-6.12 (m, 2H) 5.66 (quin, J=6.9 Hz, 1H) 4.40 (q, J=2.5 Hz, 2H) 3.93 (t, J=5.5 Hz, 2H) 3.01 (s, 3H) 2.74-2.88 (m, 5H) 1.56 (d, J=6.9 Hz, 3H)

Compound 14 $^1$H NMR data:
Compound 117: $^1$H NMR (500 MHz, DMSO-d$_6$) 5 ppm 8.93 (s, 1H) 8.55 (t, J=5.5 Hz, 1H) 8.27 (d, J=2.2 Hz, 1H) 8.11 (d, J=2.2 Hz, 1H) 6.88-6.98 (m, 1H) 6.70 (d, J=7.3 Hz, 1H) 6.24-6.32 (m, 1H) 6.14-6.23 (m, 2H) 5.44 (quin, J=6.8 Hz, 1H) 4.72 (t, 0.7=5.7 Hz, 1H) 3.73-3.88 (m, 8H) 3.51 (q, J=6.0 Hz, 2H) 3.28-3.33 (m, 2H) 1.49 (d, J=6.6 Hz, 3H)

Compound 184: $^1$H NMR (500 MHz, DMSO-d$_6$) 5 ppm 8.93 (s, 1H) 8.49 (t, J=5.5 Hz, 1H) 8.25 (d, J=1.9 Hz, 1H) 8.08 (d, J=1.9 Hz, 1H) 7.02 (d, J=7.3 Hz, 1H) 5.98-6.18 (m, 3H) 5.44 (q, J=6.8 Hz, 1H) 3.73-3.90 (m, 8H) 3.36 (q, J=6.6 Hz, 2H) 2.40 (t, 0.7=6.8 Hz, 2H) 2.17 (s, 6H) 1.49 (d, J=6.9 Hz, 3H)

Compound 276: $^1$H NMR (500 MHz, DMSO-d$_6$) δ ppm 8.85 (s, 1H) 8.38 (br t, J=5.4 Hz, 1H) 7.61 (d, J=1.3 Hz, 1H) 7.09-7.18 (m, 1H) 6.96-7.08 (m, 2H) 6.90 (d, J=0.9 Hz, 1H) 6.76 (br t, J=6.1 Hz, 1H) 4.70 (t, J=5.7 Hz, 1H) 4.55 (br d, J=6.3 Hz, 2H) 3.73-3.88 (m, 8H) 3.48 (q, J=6.0 Hz, 2H) 3.29 (q, J=6.2 Hz, 2H) 2.29 (s, 3H)

Compound 158: $^1$H NMR (500 MHz, DMSO-d$_6$) δ ppm 8.86 (s, 1H) 7.69 (s, 1H) 7.23 (d, J=1.3 Hz, 1H) 6.25 (br t, J=9.5 Hz, 1H) 5.97 (br d, J=10.4 Hz, 2H) 5.61 (br d, 0.7=7.6 Hz, 1H) 4.46 (br s, 1H) 3.70-3.86 (m, 11H) 3.36-3.46 (m, 3H) 2.44-2.50 (m, 1H) 1.81-2.09 (m, 3H)

Compound 12: $^1$H NMR (500 MHz, DMSO-d$_6$) δ ppm 8.91 (s, 1H) 7.74 (d, J=1.9 Hz, 1H) 7.59 (d, J=1.9 Hz, 1H) 6.99 (d, J=7.6 Hz, 1H) 6.14 (tt, J=9.5, 2.2 Hz, 1H) 6.04-6.09 (m, 2H) 5.44 (quin, J=6.9 Hz, 1H) 3.75-3.89 (m, 8H) 2.74-3.09 (m, 6H) 1.50 (d, J=6.6 Hz, 3H)

Compound 39: $^1$H NMR (400 MHz, DMSO-d$_6$) δ ppm 8.92 (s, 1H) 7.72 (s, 1H) 7.06 (br s, 1H) 6.26 (br t, J=9.6 Hz, 1H) 5.97 (br d, J=10.1 Hz, 2H) 5.58 (d, J=8.1 Hz, 1H) 4.27 (br s, 1H) 3.64-3.98 (m, 9H) 3.40 (br q, J=7.6 Hz, 1H) 3.15 (br s, 1H) 2.60 (br s, 2H) 2.10-2.44 (m, 4H) 1.77-2.07 (m, 3H) 0.39-1.10 (m, 6H).

Compound 211: $^1$H NMR (500 MHz, DMSO-d$_6$) δ ppm 8.94 (s, 1H) 8.55 (t, J=5.1 Hz, 1H) 8.27 (d, J=1.9 Hz, 1H) 8.08 (d, J=1.9 Hz, 1H) 7.07 (d, J=7.3 Hz, 1H) 6.12 (tt, 0.7=9.5, 2.0 Hz, 1H) 6.06 (br d, J=11.0 Hz, 2H) 5.44 (quin, J=6.8 Hz, 1H) 3.72-3.92 (m, 8H) 3.28-3.32 (m, 2H, partially obscured by solvent peak) 2.61-2.78 (m, 3H) 1.61 (br s, 1H) 1.49 (d, J=6.6 Hz, 3H) 0.96 (d, J=6.0 Hz, 6H)

Compound 328: $^1$H NMR (500 MHz, DMSO-d$_6$) δ ppm 8.93 (s, 1H) 8.50 (br t, J=5.5 Hz, 1H) 8.25 (s, 1H) 8.01 (s, 1H) 6.85 (q, J=7.9 Hz, 1H) 6.32 (t, J=9.0 Hz, 1H) 6.18 (d, 0.7=8.2 Hz, 1H) 5.99 (br t, J=6.0 Hz, 1H) 4.80 (br d, J=5.7 Hz, 2H) 3.71-3.94 (m, 8H) 3.34-3.37 (m, 2H, partially obscured by solvent peak) 2.39 (br t, J=6.9 Hz, 2H) 2.16 (s, 6H) 2.09 (s, 3H)

Pharmacology Update

Enzyme Binding Assays (KINOMEscan®)

Kinase enzyme binding affinities of compounds disclosed herein were determined using the KINOMEscan technology performed by DiscoveRx Corporation, San Diego, Calif., USA (www.kinomescan.com). Table A reports the obtained Kd values (nM), with the Kd being the inhibitor binding constant:

| Co. No. | Kd PIK3Cα_h (nM) | Kd PIK3Cβ_h (nM) | Kd PIK3Cδ_h (nM) | Kd PIK3Cγ_h (nM) | Kd MTOR_h (nM) |
|---|---|---|---|---|---|
| 1 | 34 | 0.3 | 15 | 313 | 28184 |
| 2 | 12276 | 1086 | 16407 | >30200 | >30200 |
| 3 | 47 | 1 | 20 | 229 | 17783 |
| 4 | 23442 | 1698 | 22909 | >30200 | >30200 |
| 5 | 1587 | 2 | 225 | 7977 | 25119 |
| 6 | 26003 | 1894 | 16923 | >30200 | >30200 |
| 7 | 513 | 2 | 245 | 10000 | >30200 |
| 8 | 396 | 1 | 109 | 3864 | 20893 |
| 9 | 27542 | 417 | 18197 | >30200 | >30200 |
| 10 | 142 | 0.5 | 74 | 336 | >30200 |
| 11 | 631 | 1 | 275 | 2512 | >30200 |
| 12 | 276 | 0.4 | 75 | 1137 | 26331 |
| 13 | 23855 | 182 | 5888 | >30200 | >30200 |
| 14 | 174 | 0.2 | 36 | 229 | >10000 |
| 15 | 234 | 1 | 43 | 372 | >30200 |
| 16 | 93 | 1 | 16 | 126 | 16982 |
| 17 | 25 | 0.1 | 3 | 107 | 12303 |
| 18 | 5 | 0.1 | 1 | 37 | 21878 |
| 19 | 363 | 0.2 | 29 | 309 | 18197 |
| 20 | 3631 | 17 | 1549 | 22387 | 21878 |
| 21 | 4786 | 63 | 2239 | 15849 | 19953 |
| 22 | 15136 | 5623 | 18621 | >30200 | 21878 |
| 23 | 324 | 1 | 331 | 724 | 15136 |
| 24 | 302 | 1 | 245 | 372 | 18621 |
| 25 | 12303 | 37 | 4677 | 12883 | >30200 |
| 26 | 174 | 2 | 117 | 1318 | >30200 |
| 27 | 269 | 1 | 58 | 1622 | >30200 |
| 28 | 107 | 1 | 29 | 832 | >30200 |
| 29 | 10233 | 1660 | 21878 | >30200 | 23442 |
| 30 | 39 | 1 | 18 | 407 | 21878 |
| 31 | >32000 | >32000 | >32000 | >32000 | >32000 |
| 32 | 120 | 1 | 85 | 646 | >30200 |
| 33 | 58 | 1 | 47 | 389 | >30200 |
| 34 | 50 | 0.4 | 30 | 933 | >30200 |
| 35 | 162 | 2 | 151 | 1905 | >30200 |
| 36 | 224 | 2 | 107 | 1585 | 15849 |
| 37 | 6166 | 20 | 2884 | >30200 | >30200 |
| 38 | 3 | 0.4 | 6 | 933 | >30200 |
| 39 | 14 | 0.2 | 7 | 214 | >30200 |
| 40 | 56 | 1 | 35 | 309 | 17378 |
| 41 | 389 | 1 | 141 | 1380 | >30200 |
| 42 | 331 | 1 | 56 | 1479 | >30200 |
| 43 | 4677 | 316 | 7244 | 1096 | >30200 |
| 44 | 234 | 1 | 174 | 631 | 23442 |
| 45 | 170 | 3 | 126 | 2089 | 31623 |
| 46 | 9333 | 85 | 9550 | >30200 | >30200 |
| 47 | 41 | 0.2 | 32 | 759 | 14791 |
| 48 | 2455 | 28 | 724 | 14791 | >30200 |
| 49 | 2188 | 16 | 933 | 7586 | >30200 |

-continued

| Co. No. | Kd PIK3Cα_h (nM) | Kd PIK3Cβ_h (nM) | Kd PIK3Cδ_h (nM) | Kd PIK3Cγ_h (nM) | Kd MTOR_h (nM) |
|---|---|---|---|---|---|
| 50 | 11 | 0.2 | 8 | 87 | 8913 |
| 51 | 55 | 1 | 39 | 339 | >30200 |
| 52 | 6166 | 38 | 4898 | 13804 | >30200 |
| 53 | 2951 | 3 | 692 | 21380 | >30200 |
| 54 | 16218 | 115 | 7079 | >30200 | 26915 |
| 55 | >30200 | 3981 | >30200 | >30200 | >30200 |
| 56 | 6607 | 13 | 2630 | >30200 | >30200 |
| 57 | 49 | 0.4 | 31 | 525 | 25119 |
| 58 | 1995 | 9 | 912 | 18621 | >30200 |
| 59 | 1202 | 3 | 331 | 10715 | >30200 |
| 60 | 22909 | 490 | 15488 | >30200 | >30200 |
| 61 | 676 | 2 | 209 | 5248 | >30200 |
| 62 | 25 | 1 | 51 | 234 | 2042 |
| 63 | 79 | 0.5 | 27 | 891 | 8128 |
| 64 | 224 | 1 | 58 | 1288 | 15136 |
| 65 | 38 | 1 | 17 | 200 | 10715 |
| 66 | 65 | 2 | 79 | 676 | 16982 |
| 67 | 2455 | 18 | 617 | 20893 | >30200 |
| 68 | 3162 | 3 | 589 | 15136 | 22387 |
| 69 | 891 | 3 | 195 | 3090 | >30200 |
| 70 | 339 | 2 | 148 | 1096 | 19055 |
| 71 | 251 | 1 | 138 | 794 | 22387 |
| 72 | 56 | 0.2 | 17 | 204 | 20417 |
| 73 | 2042 | 9 | 282 | 19498 | >30200 |
| 74 | 8511 | 603 | 5623 | >30200 | 23442 |
| 75 | 30 | 0.1 | 2 | 4 | >30200 |
| 76 | 50 | 0.1 | 19 | 251 | >30200 |
| 77 | 363 | 0.3 | 100 | 646 | >30200 |
| 78 | 3715 | 15 | 1175 | 13490 | >30200 |
| 79 | 2291 | 2 | 204 | 19953 | >30200 |
| 80 | >30200 | 50 | 7586 | 24547 | >30200 |
| 81 | 19055 | 30 | 2630 | 29512 | >30200 |
| 82 | 12303 | 15 | 166 | >30200 | >30200 |
| 84 | 692 | 1 | 96 | 1288 | 8511 |
| 85 | 257 | 0.3 | 41 | 1660 | 562 |
| 86 | 3467 | 15 | 537 | 21380 | >30200 |
| 87 | 22909 | 1380 | 9550 | >30200 | >30200 |
| 88 | 2138 | 5 | 603 | 4677 | 14125 |
| 89 | 7244 | 832 | 11749 | 9550 | 13490 |
| 90 | 9120 | 17 | 741 | 22909 | >30200 |
| 91 | 4467 | 10 | 1230 | 21380 | >30200 |
| 92 | 16218 | 1023 | 16596 | >30200 | >30200 |
| 93 | 219 | 0.3 | 33 | 191 | 21878 |
| 94 | 79 | 0.1 | 29 | 178 | 21380 |
| 95 | 295 | 0.5 | 178 | 1096 | >30200 |
| 96 | 363 | 0.4 | 83 | 302 | 17378 |
| 97 | 19055 | 214 | >30200 | >30200 | >30200 |
| 98 | 479 | 47 | 955 | 437 | 2239 |
| 99 | 9772 | 52 | 4677 | 11482 | >30200 |
| 100 | 1288 | 1 | 295 | 1738 | 14125 |
| 101 | 263 | 0.4 | 40 | 398 | >30200 |
| 102 | 245 | 0.2 | 31 | 398 | >30200 |
| 103 | 1134 | 3 | 1001 | 2995 | 24547 |
| 104 | 1349 | 3 | 263 | 17783 | >30200 |
| 105 | 3890 | 8 | 871 | 28184 | >30200 |
| 106 | 3162 | 6 | 1000 | 3311 | >30200 |
| 107 | >30200 | 363 | 23442 | >30200 | >30200 |
| 111 | 6026 | 16 | 1820 | 1479 | 10000 |
| 112 | 955 | 1 | 204 | 2399 | >30200 |
| 113 | >30200 | 1023 | >30200 | >10000 | >30200 |
| 114 | 1622 | 1 | 186 | 6918 | >30200 |
| 115 | 1660 | 2 | 324 | 10000 | >30200 |
| 116 | >30200 | 2884 | 30200 | >30200 | >30200 |
| 117 | 1105 | 3 | 324 | 3412 | 17128 |
| 118 | 14232 | 204 | 10192 | 2851 | >30200 |
| 119 | 2239 | 2 | 490 | 11749 | >30200 |
| 120 | 6761 | 14 | 2188 | >30200 | >30200 |
| 121 | 5370 | 10 | 1585 | >30200 | >30200 |
| 122 | 2884 | 0.3 | 151 | 5623 | 25704 |
| 123 | 9333 | 91 | 2239 | 12589 | 16596 |
| 124 | 1072 | 4 | 575 | 7762 | 8128 |
| 125 | 6457 | 68 | 5888 | >30200 | >30200 |
| 126 | 6918 | 13 | 1288 | >30200 | >30200 |
| 127 | 6457 | 32 | 2291 | 21878 | 25704 |
| 128 | 4898 | 1122 | 15136 | 12303 | 21380 |

-continued

| Co. No. | Kd PIK3Cα_h (nM) | Kd PIK3Cβ_h (nM) | Kd PIK3Cδ_h (nM) | Kd PIK3Cγ_h (nM) | Kd MTOR_h (nM) |
|---|---|---|---|---|---|
| 129 | 1778 | 3 | 1072 | 8913 | 9772 |
| 130 | 363 | 0.5 | 135 | 240 | 6166 |
| 131 | 3162 | 11 | 2512 | 19953 | >30200 |
| 132 | 832 | 0.5 | 115 | 2188 | 11482 |
| 133 | 5754 | 3 | 263 | 26303 | >30200 |
| 134 | >30200 | 87 | 6310 | >30200 | >30200 |
| 135 | 10000 | 195 | 3802 | 17378 | 11220 |
| 136 | 2344 | 3 | 355 | 5129 | 15136 |
| 137 | 138 | 0.1 | 9 | 501 | >30200 |
| 138 | 398 | 0.1 | 56 | 2150 | 30903 |
| 139 | 3765 | 41 | 4423 | 3433 | 18621 |
| 140 | 14791 | 5129 | 15849 | 25119 | >30200 |
| 141 | 6607 | 6 | 776 | 8128 | >30200 |
| 142 | 209 | 0.5 | 59 | 741 | >30200 |
| 143 | 2818 | 2 | 389 | 9550 | >30200 |
| 144 | 1738 | 2 | 437 | 5623 | >30200 |
| 145 | 537 | 1 | 102 | 1862 | 23442 |
| 146 | 1905 | 2 | 933 | 8128 | >30200 |
| 147 | 776 | 0.4 | 129 | 1148 | >30200 |
| 148 | 1072 | 1 | 316 | 8128 | >30200 |
| 149 | 2951 | 2 | 398 | 2344 | >30200 |
| 150 | 2884 | 3 | 501 | 3715 | >30200 |
| 151 | 3631 | 8 | 813 | 8710 | >30200 |
| 152 | 3981 | 10 | 1820 | 8710 | >30200 |
| 153 | 5370 | 8 | 1175 | 2692 | 16218 |
| 155 | 2138 | 6 | 759 | 6607 | >30200 |
| 156 | 398 | 2 | 363 | >30200 | >30200 |
| 157 | 13183 | 102 | 19953 | >30200 | >30200 |
| 158 | 339 | 0.4 | 120 | 2291 | >30200 |
| 159 | >30200 | 110 | 23442 | >30200 | >30200 |
| 160 | 813 | 2 | 575 | 9772 | 19498 |
| 161 | >30200 | 776 | >30200 | >30200 | >30200 |
| 162 | 3981 | 9 | 1230 | 24547 | >30200 |
| 163 | >30200 | 832 | 16218 | >30200 | >30200 |
| 164 | 2399 | 4 | 1096 | 13804 | >30200 |
| 165 | 1778 | 0.3 | 182 | 5495 | 14125 |
| 166 | 16596 | 19 | 4074 | 14791 | 21878 |
| 167 | 17378 | 26 | 7762 | 12883 | >30200 |
| 168 | 3631 | 17 | 1862 | >30200 | >30200 |
| 169 | 4074 | 8 | 1122 | 5370 | 18621 |
| 170 | 617 | 5 | 288 | 2239 | 4365 |
| 171 | 2188 | 3 | 575 | >30200 | >30200 |
| 172 | >30200 | 1259 | >30200 | >30200 | >30200 |
| 173 | 832 | 1 | 372 | 3548 | 24547 |
| 174 | >30200 | 1202 | 26303 | >30200 | >30200 |
| 175 | 1698 | 0.4 | 112 | 2570 | >30200 |
| 176 | 1995 | 1 | 102 | 3467 | >30200 |
| 177 | 1380 | 2 | 170 | 6918 | 23988 |
| 178 | >30200 | 1096 | 16596 | >30200 | >30200 |
| 180 | 891 | 0.1 | 49 | 2188 | >30200 |
| 181 | 5012 | 117 | 20417 | 17783 | >30200 |
| 182 | 126 | 0.3 | 32 | 912 | >30200 |
| 183 | 2512 | 0.1 | 102 | 1738 | >30200 |
| 184 | 599 | 0.2 | 57 | 994 | 18905 |
| 185 | 5754 | 29 | 5370 | 4266 | >30200 |
| 186 | 6310 | 10 | 1778 | 27542 | >30200 |
| 187 | >30200 | 1047 | >30200 | >30200 | >30200 |
| 188 | 851 | 1 | 182 | 2291 | 16218 |
| 189 | >30200 | 2512 | 28184 | 4467 | >30200 |
| 192 | >30200 | 9120 | >30200 | >30200 | >30200 |
| 193 | >30200 | 158 | 17783 | >30200 | >30200 |
| 194 | >30200 | 1820 | >30200 | >30200 | >30200 |
| 195 | 1950 | 2 | 479 | 12883 | >30200 |
| 196 | 2818 | 5 | 813 | 15849 | >30200 |
| 197 | 692 | 3 | 302 | 13804 | >30200 |
| 198 | 11220 | 22 | 3162 | 15488 | >30200 |
| 199 | 4898 | 68 | 5495 | 11749 | 28840 |
| 200 | >30200 | 2399 | >30200 | >30200 | >30200 |
| 201 | 1455 | 2 | 710 | 4451 | 16549 |
| 202 | >30200 | 3948 | >30200 | 3325 | 6026 |
| 203 | 1660 | 5 | 912 | 6607 | 21380 |
| 204 | >30200 | 1072 | >30200 | 14454 | >30200 |
| 205 | >30200 | 204 | 17378 | >30200 | >30200 |
| 206 | >30200 | 7079 | >30200 | >30200 | >30200 |
| 207 | 5248 | 6 | 891 | 16218 | 7943 |

-continued

| Co. No. | Kd PIK3Cα_h (nM) | Kd PIK3Cβ_h (nM) | Kd PIK3Cδ_h (nM) | Kd PIK3Cγ_h (nM) | Kd MTOR_h (nM) |
|---|---|---|---|---|---|
| 208 | 3467 | 8 | 1413 | >30200 | >30200 |
| 209 | >30200 | 316 | 11482 | 16982 | >30200 |
| 210 | 3162 | 12 | 1023 | >30200 | >30200 |
| 211 | 3369 | 1 | 190 | 3599 | 20198 |
| 212 | 7093 | 12 | 3291 | 5073 | 13804 |
| 213 | 2089 | 2 | 269 | 3236 | 7762 |
| 214 | >30200 | 1230 | >30200 | 4571 | >30200 |
| 217 | 2138 | 4 | 1288 | 23988 | >30200 |
| 218 | 537 | 5 | 1175 | 3090 | 3311 |
| 219 | 93 | 1 | 275 | 955 | 3311 |
| 220 | 25704 | 2754 | >30200 | 25704 | 6457 |
| 222 | >30200 | 759 | >30200 | >30200 | >30200 |
| 223 | >30200 | 4786 | >30200 | 13804 | >30200 |
| 224 | 27542 | 186 | 4467 | >30200 | >30200 |
| 225 | 4677 | 6 | 537 | 2512 | >30200 |
| 226 | 2570 | 1 | 275 | 5623 | 28840 |
| 227 | 1778 | 1 | 339 | 3802 | >30200 |
| 228 | 6166 | 603 | 15488 | 4074 | >30200 |
| 229 | 3890 | 7 | 1738 | 20417 | 12589 |
| 230 | 7079 | 12 | 759 | 18197 | 12023 |
| 231 | 16982 | 52 | >3311 | >30200 | >10000 |
| 232 | 16218 | 98 | 2818 | >30200 | 13183 |
| 234 | n.d. | n.d. | n.d. | n.d. | n.d. |
| 235 | >32000 | 50 | 7586 | 24547 | >32000 |
| 236 | 112 | 2 | 158 | 813 | 1318 |
| 237 | 288 | 1 | 138 | 9333 | >30200 |
| 238 | 5013 | 8 | 2211 | 12306 | >30200 |
| 239 | 603 | 2 | 316 | 1288 | 10471 |
| 240 | 9333 | 2239 | 17378 | 18197 | >30200 |
| 241 | 427 | 8 | 589 | 5370 | 22387 |
| 242 | 15849 | 4786 | 17783 | >30200 | >30200 |
| 243 | 66 | 1 | 71 | 145 | 1905 |
| 244 | 8318 | 741 | 4169 | 12589 | 19953 |
| 245 | 8710 | 72 | 1047 | 13183 | 21878 |
| 249 | 794 | 4 | 955 | 2399 | >30200 |
| 250 | 339 | 1 | 219 | 955 | 14454 |
| 251 | 8 | 0.3 | 23 | 65 | 676 |
| 252 | >30200 | >30200 | >30200 | >30200 | >30200 |
| 262 | n.d. | n.d. | n.d. | n.d. | n.d. |
| 264 | 9772 | 52 | 4677 | 11482 | >30200 |
| 272 | 4898 | 5 | 1995 | >30200 | >30200 |
| 273 | 6310 | 8 | 2754 | >10000 | >30200 |
| 276 | 1950 | 4 | 871 | 9120 | 10965 |
| 278 | 2089 | 8 | 1738 | 15849 | 19498 |
| 279 | 5370 | 5 | 372 | 6457 | 19055 |
| 280 | 5129 | 6 | 427 | 11220 | >30200 |
| 281 | 3162 | 0.3 | 91 | 3548 | >30200 |
| 282 | 832 | 0.2 | 68 | 1820 | 23442 |
| 286 | 7413 | 18 | 2042 | 16982 | >30200 |
| 287 | 2692 | 13 | 977 | 26303 | >30200 |
| 291 | 550 | 407 | 2818 | 513 | 10233 |
| 292 | 6607 | 16 | 1698 | 27542 | >30200 |
| 293 | >30200 | >30200 | >30200 | >30200 | >30200 |
| 295 | 7244 | 309 | 7762 | 6310 | 30903 |
| 296 | 2951 | 1 | 166 | 6457 | >30200 |
| 297 | 1862 | 0.3 | 110 | 1950 | >30200 |
| 300 | 2692 | 4 | 513 | 16982 | >30200 |
| 301 | 5370 | 43 | 3236 | 1514 | 15136 |
| 302 | 1950 | 5 | 380 | 15488 | >30200 |
| 303 | 3548 | 9 | 457 | 3890 | 18621 |
| 304 | 7244 | 62 | 6761 | 19953 | >30200 |
| 308 | >30200 | 324 | 7244 | >30200 | >30200 |
| 309 | n.d. | n.d. | n.d. | n.d. | n.d. |
| 316 | 12883 | 21 | 1380 | >30200 | >30200 |
| 317 | 6166 | 13 | 708 | 20893 | >30200 |
| 318 | 3467 | 6 | 288 | >30200 | >30200 |
| 328 | 1905 | 0.2 | 324 | 6607 | 17783 |
| 332 | 2951 | 15 | 4266 | 21380 | >30200 |
| 333 | 5248 | 37 | 7413 | 17378 | >30200 |
| 336 | 1950 | 4 | 871 | 9120 | 10965 |
| 337 | 3981 | 35 | 3802 | 7943 | >30200 |
| 338 | 2344 | 12 | 2951 | 4365 | >30200 |
| 339 | 5888 | 427 | 2455 | 9333 | 16218 |
| 340 | 1514 | 2 | 372 | 5012 | 12023 |
| 341 | 3388 | 17 | 1479 | 8128 | 21380 |

-continued

| Co. No. | Kd PIK3Cα_h (nM) | Kd PIK3Cβ_h (nM) | Kd PIK3Cδ_h (nM) | Kd PIK3Cγ_h (nM) | Kd MTOR_h (nM) |
|---|---|---|---|---|---|
| 342 | 3802 | 9 | 1000 | 26915 | 16596 |
| 343 | 2188 | 22 | 3311 | 10000 | >10000 |
| 347 | 3715 | 4 | 407 | 28840 | >30200 |
| 350 | n.d. | n.d. | n.d. | n.d. | n.d. |
| 351 | 2512 | 21 | 1698 | 2138 | >30200 |
| 352 | 2291 | 2 | 1000 | 9772 | >30200 |
| 353 | 5012 | 4 | 692 | >30200 | >30200 |
| 354 | 8128 | 63 | 2399 | 28184 | >30200 |
| 355 | 4786 | 13 | 2884 | 20893 | 13183 |
| 358 | 10000 | 148 | 2239 | 17783 | >30200 |
| 359 | 11327 | 43 | 796 | 28840 | 6463 |
| 360 | 6761 | 42 | 11749 | 26915 | >30200 |
| 361 | 2951 | 2 | 490 | 9772 | 19055 |
| 362 | 2951 | 2 | 490 | 9772 | 19055 |
| 364 | 7413 | 5 | 813 | 13804 | >30200 |
| 365 | 2089 | 1 | 117 | 2884 | >30200 |
| 366 | 1047 | 4 | 123 | 1318 | 4266 |
| 368 | 5370 | 7 | 1413 | >30200 | >30200 |
| 373 | >30200 | 158 | 5248 | >30200 | >30200 |
| 375 | 18621 | 117 | 2188 | >30200 | >30200 |
| 376 | 4266 | 1 | 295 | 5129 | >30200 |
| 381 | 3548 | 26 | 3802 | 8318 | >30200 |
| 382 | >30200 | 17 | 5012 | >30200 | >30200 |
| 383 | 1230 | 1 | 234 | 7943 | 7079 |
| 384 | 2692 | 1 | 575 | 15849 | 19953 |
| 385 | 933 | 1 | 347 | 6166 | 16596 |
| 386 | 3236 | 15 | 692 | 14791 | 24547 |
| 389 | 3162 | 5 | 2188 | >30200 | >30200 |
| 390 | 16596 | 78 | 3236 | 22387 | >30200 |
| 391 | 5495 | 251 | 3388 | 12023 | 24547 |
| 394 | 3236 | 0.2 | 776 | 12589 | 23442 |
| 395 | 3467 | 33 | 2239 | 14125 | 18197 |
| 396 | 7762 | 120 | 2042 | 20893 | >30200 |
| 397 | 2692 | 36 | 661 | 22909 | >30200 |
| 398 | 10715 | 257 | 5754 | >30200 | >30200 |
| 399 | 2818 | 45 | 5248 | 9333 | >30200 |
| 400 | 2344 | 24 | 1585 | 18621 | 26303 |
| 401 | 1862 | 550 | 12303 | >30200 | 11482 |
| 402 | 4467 | 44 | 4074 | >30200 | >30200 |
| 117a | n.d. | n.d. | n.d. | n.d. | n.d. |
| 118a | n.d. | n.d. | n.d. | n.d. | n.d. |
| 122a | 3702 | 3 | 660 | 7969 | 14125 |
| 123a | 10233 | 107 | 5129 | 11482 | 16982 |
| 154a | 437 | 1 | 98 | 741 | 8511 |
| 154b | 20893 | 490 | 14791 | 7762 | 25119 |
| 184a | 806 | 0.1 | 74 | 1483 | 21880 |
| 184b | 589 | 0.1 | 66 | 1096 | 19953 |
| 184c | 829 | 0.1 | 54 | 1268 | 23988 |
| 237a | 105 | 1 | 204 | 5012 | >30200 |
| 237b | 8710 | 74 | 7762 | >30200 | >30200 |
| 237c | 372 | 4 | 234 | 5495 | >30200 |
| 237d | 12589 | 240 | 19498 | >30200 | >30200 |
| 243a | 39 | 0.5 | 69 | 100 | 1479 |
| 243b | 1660 | 14 | 3388 | 1950 | 1349 |
| 246a | 813 | 4 | 3890 | 6761 | 26915 |
| 246b | >30200 | 16596 | >30200 | 6166 | >30200 |
| 257b | 851 | 22 | 468 | 3090 | 2818 |
| 257c | 1698 | 603 | 3020 | 3162 | 1660 |
| 262a | >30200 | 1778 | 24547 | >30200 | >30200 |
| 262b | >30200 | 11482 | >30200 | >30200 | >30200 |
| 279a | 2188 | 7 | 513 | 5623 | 21380 |
| 279b | 26303 | 1905 | 30200 | 6457 | >30200 |
| 280a | 1698 | 12 | 562 | 12023 | 20893 |
| 280b | 22387 | 813 | 21380 | 24547 | >30200 |
| 281a | 1514 | 0.3 | 72 | 4074 | 23442 |
| 281b | 6166 | 151 | 3467 | 7413 | >30200 |
| 283a | 12023 | 7 | 1549 | 19055 | >30200 |
| 283b | >30200 | 1380 | 18197 | 29512 | >30200 |
| 284a | 2076 | 10 | 939 | 8137 | 19055 |
| 284b | >30200 | 2145 | >30200 | 5070 | >30200 |
| 286a | 10233 | 182 | 5754 | >30200 | 25704 |
| 286b | 6026 | 2 | 355 | 16218 | >30200 |
| 287a | 1738 | 3 | 234 | 20893 | >30200 |
| 287b | 9333 | 27 | 2951 | >30200 | >30200 |
| 292a | 2818 | 17 | 603 | 21878 | 32359 |

-continued

| Co. No. | Kd PIK3Cα_h (nM) | Kd PIK3Cβ_h (nM) | Kd PIK3Cδ_h (nM) | Kd PIK3Cγ_h (nM) | Kd MTOR_h (nM) |
|---|---|---|---|---|---|
| 292b | >30200 | 14791 | >30200 | >30200 | >30200 |
| 295a | 6457 | 288 | 6761 | >30200 | 14454 |
| 295b | >30200 | 19498 | >30200 | 4571 | >30200 |
| 296a | 1380 | 1 | 170 | 3236 | >30200 |
| 296b | >30200 | 14 | 9333 | >30200 | >30200 |
| 297a | 16982 | 26 | 6310 | 15136 | >30200 |
| 297b | 1023 | 0.5 | 112 | 1479 | >30200 |
| 298a | 4786 | 4 | 724 | 24547 | >30200 |
| 298b | 23988 | 186 | 10233 | >30200 | >30200 |
| 299a | 6310 | 1 | 269 | 10965 | >30200 |
| 299b | 13183 | 60 | 5248 | 19498 | >30200 |
| 300a | 1479 | 2 | 191 | 5495 | >30200 |
| 300b | 23988 | 537 | 23442 | >30200 | >30200 |
| 302a | >30200 | 1318 | >30200 | >30200 | >30200 |
| 302b | 1096 | 3 | 186 | 11749 | >30200 |
| 309a | 1096 | 0.1 | 59 | 1738 | 19953 |
| 309b | 4898 | 18 | 2344 | 5623 | >30200 |
| 312a | 15488 | 1148 | 10000 | >30200 | >10000 |
| 312b | 5129 | 26 | 1862 | 28184 | 19953 |
| 313a | 5012 | 3 | 851 | 26303 | >30200 |
| 313b | 14454 | 302 | 5495 | >30200 | >30200 |
| 314a | 17378 | 417 | 6026 | 30200 | 19055 |
| 314b | 8913 | 2 | 1000 | 16596 | >30200 |
| 315a | >30200 | 2239 | >30200 | >30200 | >30200 |
| 315b | 2754 | 1 | 162 | 5495 | >30200 |
| 319a | 9120 | 200 | 2818 | >30200 | >30200 |
| 319b | 4365 | 59 | 1023 | >30200 | >30200 |
| 320a | 513 | 2 | 182 | 4467 | >30200 |
| 320b | 11482 | 69 | 5129 | >30200 | >30200 |
| 321a | 832 | 1 | 174 | 4677 | >30200 |
| 321b | 18621 | 166 | 7413 | >30200 | >30200 |
| 322a | 29512 | 513 | 23988 | >30200 | >30200 |
| 322b | 2188 | 0.3 | 68 | 6166 | >30200 |
| 323a | >30200 | 1000 | 28840 | >30200 | >30200 |
| 323b | 3802 | 1 | 182 | 3090 | >30200 |
| 324a | 1738 | 0.5 | 83 | 7244 | >30200 |
| 324b | 4898 | 229 | 3090 | 22387 | >30200 |
| 325a | 10715 | 1318 | 11482 | 14125 | >30200 |
| 325b | 3020 | 4 | 525 | 12023 | 9120 |
| 329a | 339 | 0.1 | 26 | 2754 | 22909 |
| 329b | 6026 | 42 | 1778 | 6310 | 22909 |
| 334a | 5370 | 19 | 1072 | 12883 | 26915 |
| 334b | 21380 | 457 | 7586 | 10965 | 17378 |
| 335a | 466 | 0.2 | 33 | 1218 | 18621 |
| 335b | 8315 | 11 | 3421 | 13490 | >30200 |
| 338a | 1514 | 11 | 1072 | 7244 | 25704 |
| 338b | 22909 | 851 | >30200 | 2344 | 19953 |
| 339a | 4571 | 112 | 2089 | 10715 | >30200 |
| 339b | 759 | 316 | 1950 | 2188 | 6457 |
| 344a | 2138 | 2 | 288 | 8318 | >30200 |
| 344b | 8128 | 166 | 3802 | 14125 | >30200 |
| 345a | 4365 | 2 | 282 | 14791 | >30200 |
| 345b | >30200 | 724 | 22909 | >30200 | >30200 |
| 346a | 2512 | 3 | 955 | 9550 | 30903 |
| 346b | 23442 | 741 | 20893 | 2754 | >30200 |
| 347a | >30200 | 2692 | >30200 | >30200 | >30200 |
| 347b | 3890 | 2 | 355 | 25704 | >30200 |
| 348a | 3020 | 10 | 912 | 29512 | >30200 |
| 348b | >30200 | 1318 | 25704 | >30200 | >30200 |
| 349a | 813 | 0.2 | 36 | 4266 | >30200 |
| 349b | 4677 | 14 | 2754 | 25704 | >30200 |
| 356a | n.d. | n.d. | n.d. | n.d. | n.d. |
| 356b | n.d. | n.d. | n.d. | n.d. | n.d. |
| 357a | 22909 | 3311 | 16218 | >30200 | >30200 |
| 357b | 933 | 1 | 158 | 8128 | >30200 |
| 363a | 10965 | 10 | 417 | 26915 | >30200 |
| 363b | 31623 | 1288 | 16982 | >30200 | 27542 |
| 364a | 2455 | 1 | 204 | 6918 | >30200 |
| 364b | 7079 | 372 | 7762 | 8128 | >30200 |
| 365a | 5248 | 1 | 204 | 10233 | >30200 |
| 365b | 15488 | 251 | 4169 | 22909 | >30200 |
| 367a | 4074 | 63 | 1148 | 23442 | 29512 |
| 367b | 2455 | 35 | 427 | >30200 | 28184 |
| 369a | 7244 | 20 | 525 | >30200 | 25119 |
| 369b | >30200 | 3311 | 28840 | >30200 | >30200 |

-continued

| Co. No. | Kd PIK3Cα_h (nM) | Kd PIK3Cβ_h (nM) | Kd PIK3Cδ_h (nM) | Kd PIK3Cγ_h (nM) | Kd MTOR_h (nM) |
| --- | --- | --- | --- | --- | --- |
| 370a | 1230 | 0.3 | 107 | 2630 | >30200 |
| 370b | >30200 | 550 | 15488 | >30200 | >30200 |
| 371a | 1514 | 0.3 | 83 | 1047 | >30200 |
| 371b | 12589 | 20 | 5012 | 10965 | >30200 |
| 374a | 2455 | 0.3 | 141 | 5888 | >30200 |
| 374b | 13490 | 98 | 5754 | 21878 | >30200 |
| 379a | 9772 | 2 | 813 | >30200 | >30200 |
| 379b | >30200 | 1259 | >30200 | >30200 | >30200 |
| 380a | 9120 | 1047 | 7244 | 10000 | 19055 |
| 380b | 3802 | 5 | 1202 | 8913 | 18621 |
| 388a | >30200 | 933 | >30200 | >30200 | >30200 |
| 388b | 2188 | 3 | 200 | 2399 | >30200 |
| 391a | >30200 | 10715 | >30200 | >30200 | 16982 |
| 391b | >30200 | 19498 | >30200 | >30200 | >30200 |
| 392a | 3981 | 21 | 2818 | 14125 | 20417 |
| 392b | n.d. | n.d. | n.d. | n.d. | n.d. |
| 393a | 437 | 11 | 1230 | 1380 | 6761 |
| 393b | 10965 | 2291 | 25704 | 6607 | 15849 |
| 395a | 3467 | 33 | 1259 | 17783 | >30200 |
| 395b | 3981 | 631 | 3548 | 32359 | 18621 |
| 397a | 3631 | 1413 | 10715 | 25119 | 15488 |
| 397b | 1862 | 25 | 871 | 12303 | >30200 |
| 403a | 1479 | 3 | 331 | 8913 | >30200 |
| 403b | >30200 | 3162 | 17378 | >30200 | >30200 |
| 404a | >30200 | 1514 | >30200 | >30200 | >30200 |
| 404b | 5248 | 1 | 1072 | 16596 | >30200 |
| 405a | >30200 | 501 | 7413 | >30200 | >30200 |
| 405b | 5012 | 1 | 219 | 4677 | 20893 |
| 406a | 372 | 0.1 | 39 | 1047 | 22909 |
| 406b | 7413 | 141 | 3467 | 3802 | >30200 |
| 407a | 2042 | 7 | 724 | 7943 | 10471 |
| 407b | 4365 | 339 | 2951 | 3802 | >30200 |
| 408a | 1445 | 3 | 331 | 4266 | 26303 |
| 408b | 23442 | 324 | 17378 | 8128 | >30200 |
| 83a | 112 | 2 | 158 | 813 | 1318 |
| 83b | 170 | 1 | 129 | 562 | 1288 |
| 83c | 3090 | 158 | 4898 | 2692 | 3090 |

Cellular Assays:

Cellular activity of PI3Kβ inhibitors was determined by quantifying the phosphorylation of Akt in PC-3 cells. Akt phosphorylated at Ser473 and Thr308 were measured using an enzyme-linked immunosorbent assay (ELISA; Meso Scale Discovery (MSD), Gaithersburg, Md.) and specific primary antibodies from MSD.

On day 1, PC3 cells (ATCC #CRL-14351) were seeded into PerkinElmer MW96 plates at 25.000 cells per well, in 75 µl complete culture medium (DMEM high glucose, AQmedia™, D0819, Sigma-Aldrich) containing 10% heat inactivated PCS and incubated at 37° C., 5% CO2 during 24 hours. On day 2, compound or DMSO (0.3%) was added and cells were further incubated for 60 min at 37° C. 5% CO2 in a total volume of 100 µl of medium.

The phosphoprotein assay was executed according to vendor instructions in the Phospho-Akt (Ser473) Assay Whole Cell Lysate Kit (MSD #K15100D-3) and the Phospho-Akt (Thr308) Assay Whole Cell Lysate Kit (MSD #K151DYD-3) using the lysis, blocking and wash buffer provided.

Briefly, at the end of the cell treatment period, media were removed by aspiration and adherent cells were lysed in 50 µl ice-cold lysis buffer. MSD plates are supplied pre-coated with capture antibodies for Phospho-Akt (Ser473 and Thr308). After blocking, lysates from tissue culture plates were added and plates were washed. Then, a solution containing the detection antibody (anti-total Akt conjugated with an electrochemiluminescent compound-MSD Sulfo-tag label) was added. The signals were detected using an MSB SECTOR Imager 6000 and are proportional to the phospho-Akt titres.

Data were processed. The percentage of inhibition was plotted against the log concentration of test compounds, and the sigmoidal log concentration-effect curve of best fit was calculated by nonlinear regression analysis. From these concentration-response curves, the $IC_{50}$ values were calculated. Five concentrations were used for curve fitting.

Table B reports the obtained $IC_{50}$ values (nM):

| Co. No. | $IC_{50}$ pAkt_S473 (nM) | $IC_{50}$ pAkt_Thr308 (nM) |
| --- | --- | --- |
| 1 | 2 | 3 |
| 2 | >513 | >513 |
| 3 | 3 | ~3 |
| 4 | >513 | >513 |
| 5 | 100 | 99 |
| 6 | >513 | >513 |
| 7 | 42 | 21 |
| 8 | 25 | 20 |
| 9 | >513 | >513 |
| 10 | 4 | 3 |
| 11 | 81 | 42 |
| 12 | 18 | 9 |
| 13 | >513 | >513 |
| 14 | 31 | 11 |
| 15 | 4 | 2 |
| 16 | ~5 | 2 |
| 17 | ~3 | 1 |

Table B reports the obtained IC$_{50}$ values (nM):

| Co. No. | IC$_{50}$ pAkt_S473 (nM) | IC$_{50}$ pAkt_Thr308 (nM) |
|---|---|---|
| 18 | 1 | 0.3 |
| 19 | 15 | 10 |
| 20 | 363 | 372 |
| 21 | 513 | ~501 |
| 22 | >513 | >513 |
| 23 | ~68 | 42 |
| 24 | 36 | 30 |
| 25 | >513 | >513 |
| 26 | 4 | ~1.35 |
| 27 | 22 | 14 |
| 28 | 5 | 6 |
| 29 | >513 | >513 |
| 30 | 5 | ~4 |
| 31 | >513 | >513 |
| 32 | 12 | 17 |
| 33 | 3 | 4 |
| 34 | <0.8 | 3 |
| 35 | ~39 | ~26.92 |
| 36 | 10 | 5 |
| 37 | 200 | 126 |
| 38 | ~0.8 | 1 |
| 39 | 7 | 5 |
| 40 | 7 | 4 |
| 41 | 31 | 22 |
| 42 | 16 | 11 |
| 43 | >513 | 331 |
| 44 | 74 | 66 |
| 45 | 166 | 72 |
| 46 | >513 | >513 |
| 47 | 3 | 4 |
| 48 | >513 | ~457 |
| 49 | >513 | 468 |
| 50 | 1 | 1 |
| 51 | 3 | 3 |
| 52 | >513 | 240 |
| 53 | 214 | 148 |
| 54 | >513 | >513 |
| 55 | >513 | >513 |
| 56 | >513 | 148 |
| 57 | ~5 | 4 |
| 58 | >513 | 295 |
| 59 | 263 | 110 |
| 60 | >513 | >513 |
| 61 | 182 | 123 |
| 62 | 52 | 32 |
| 63 | 9 | 4 |
| 64 | 13 | 6 |
| 65 | 6 | 2 |
| 66 | 13 | 6 |
| 67 | 195 | 166 |
| 68 | 257 | 148 |
| 69 | 117 | ~32 |
| 70 | ~45 | 23 |
| 71 | ~15 | 13 |
| 72 | 2 | 1 |
| 73 | >513 | 331 |
| 74 | >513 | >513 |
| 75 | 2 | 1 |
| 76 | 7 | 7 |
| 77 | ~76 | ~51 |
| 78 | ~219 | ~295 |
| 79 | 158 | 123 |
| 80 | ~214 | ~79 |
| 81 | ~490 | 219 |
| 82 | >513 | >513 |
| 84 | 56 | 32 |
| 85 | 48 | 78 |
| 86 | 513 | 263 |
| 87 | >513 | >513 |
| 88 | 178 | 89 |
| 89 | >513 | >513 |
| 90 | >513 | >513 |
| 91 | >513 | 234 |
| 92 | >513 | >513 |
| 93 | 41 | 28 |
| 94 | 8 | 12 |
| 95 | 34 | 18 |
| 96 | 25 | 20 |
| 97 | >513 | >513 |
| 98 | >513 | >513 |
| 99 | >513 | 355 |
| 100 | 145 | 68 |
| 101 | 21 | 14 |
| 102 | 22 | 23 |
| 103 | 65 | 28 |
| 104 | 110 | 55 |
| 105 | 302 | 138 |
| 106 | 105 | 62 |
| 107 | >513 | >513 |
| 111 | 389 | 162 |
| 112 | 174 | ~62 |
| 113 | >513 | >513 |
| 114 | 50 | 18 |
| 115 | 66 | 31 |
| 116 | >513 | >513 |
| 117 | 49 | 44 |
| 118 | >513 | >513 |
| 119 | 105 | 81 |
| 120 | 479 | 269 |
| 121 | 347 | ~331 |
| 122 | 40 | 26 |
| 123 | >513 | >513 |
| 124 | 151 | 93 |
| 125 | >513 | >513 |
| 126 | 427 | 275 |
| 127 | ~457 | 331 |
| 128 | >513 | >513 |
| 129 | 112 | 105 |
| 130 | 89 | 65 |
| 131 | 501 | 363 |
| 132 | 52 | 37 |
| 133 | 59 | 32 |
| 134 | >513 | >513 |
| 135 | >513 | >513 |
| 136 | 178 | 65 |
| 137 | 1 | 1 |
| 138 | 3 | 2 |
| 139 | 132 | 249 |
| 140 | 479 | >513 |
| 141 | 182 | 102 |
| 142 | 10 | 7 |
| 143 | 102 | 30 |
| 144 | 59 | 28 |
| 145 | ~32 | 9 |
| 146 | 83 | 38 |
| 147 | 10 | 6 |
| 148 | 68 | 30 |
| 149 | 251 | 138 |
| 150 | 138 | 91 |
| 151 | 490 | 66 |
| 152 | 62 | 87 |
| 153 | 316 | 316 |
| 155 | 437 | 339 |
| 156 | 42 | 51 |
| 157 | >513 | 417 |
| 158 | 23 | 20 |
| 159 | >513 | >513 |
| 160 | 58 | 23 |
| 161 | >513 | >513 |
| 162 | 209 | 91 |
| 163 | >513 | >513 |
| 164 | 145 | 71 |
| 165 | 45 | 11 |
| 166 | >513 | >513 |
| 167 | >513 | ~427 |
| 168 | 214 | 112 |
| 169 | 200 | 102 |
| 170 | >513 | >513 |

Table B reports the obtained IC$_{50}$ values (nM):

| Co. No. | IC$_{50}$ pAkt_S473 (nM) | IC$_{50}$ pAkt_Thr308 (nM) |
|---|---|---|
| 171 | 155 | 102 |
| 172 | >513 | >513 |
| 173 | 78 | 52 |
| 174 | >513 | >513 |
| 175 | 9 | 11 |
| 176 | 16 | 15 |
| 177 | 60 | 42 |
| 178 | >513 | >513 |
| 180 | 3 | 1 |
| 181 | ~447 | ~398 |
| 182 | 1 | 0 |
| 183 | 6 | 3 |
| 184 | 2 | 2 |
| 185 | ~331 | 148 |
| 186 | 339 | 182 |
| 187 | >513 | >513 |
| 188 | 22 | 15 |
| 189 | >513 | >513 |
| 192 | >513 | >513 |
| 193 | >513 | >513 |
| 194 | >513 | >513 |
| 195 | ~102 | 47 |
| 196 | 182 | 91 |
| 197 | 65 | 43 |
| 198 | >513 | 200 |
| 199 | >513 | 309 |
| 200 | n.d. | n.d. |
| 201 | 42 | 26 |
| 202 | >513 | >513 |
| 203 | 98 | 44 |
| 204 | >513 | >513 |
| 205 | >513 | >513 |
| 206 | >513 | >513 |
| 207 | 372 | 105 |
| 208 | 186 | 83 |
| 209 | >513 | >513 |
| 210 | 245 | 151 |
| 211 | 36 | 22 |
| 212 | 398 | 328 |
| 213 | 33 | 25 |
| 214 | >513 | >513 |
| 217 | 79 | 49 |
| 218 | >513 | >513 |
| 219 | >513 | >513 |
| 220 | >513 | >513 |
| 222 | >513 | >513 |
| 223 | >513 | >513 |
| 224 | 468 | >513 |
| 225 | 102 | 87 |
| 226 | 20 | 13 |
| 227 | 27 | 20 |
| 228 | >513 | 347 |
| 229 | 186 | 96 |
| 230 | 145 | 141 |
| 231 | ~457 | 398 |
| 232 | >513 | >513 |
| 234 | n.d. | n.d. |
| 235 | 214 | 79 |
| 236 | >513 | >513 |
| 237 | 20 | 11 |
| 238 | 219 | 157 |
| 239 | >513 | >513 |
| 240 | >513 | >513 |
| 241 | >513 | >513 |
| 242 | >513 | >513 |
| 243 | >513 | >513 |
| 244 | >513 | >513 |
| 245 | >513 | >513 |
| 249 | 71 | 52 |
| 250 | 5 | 6 |
| 251 | 52 | 23 |
| 252 | >513 | >513 |
| 262 | n.d. | n.d. |
| 264 | >513 | 355 |
| 272 | 151 | ~85 |
| 273 | 447 | ~257 |
| 276 | 85 | 46 |
| 278 | 295 | 178 |
| 279 | 145 | 115 |
| 280 | ~275 | 158 |
| 281 | 15 | 15 |
| 282 | 7 | 6 |
| 286 | 398 | 245 |
| 287 | 151 | 48 |
| 291 | n.d. | n.d. |
| 292 | 437 | 234 |
| 293 | n.d. | n.d. |
| 295 | >513 | >513 |
| 296 | 42 | 14 |
| 297 |  | 20 |
| 300 | 71 | 85 |
| 301 | >513 | 427 |
| 302 | 76 | 76 |
| 303 | 87 | 79 |
| 304 | >513 | 295 |
| 308 | >513 | >513 |
| 309 | n.d. | n.d. |
| 316 | >513 | >513 |
| 317 | >513 | >513 |
| 318 | >513 | ~295 |
| 328 | 9 | 9 |
| 332 | ~316 | 112 |
| 333 | >513 | 148 |
| 336 | 85 | 46 |
| 337 | 204 | 71 |
| 338 | 275 | 98 |
| 339 | >513 | >513 |
| 340 | 76 | 50 |
| 341 | 46 | 26 |
| 342 | n.d. | n.d. |
| 343 | 389 | 178 |
| 347 | 219 | 63 |
| 350 | n.d. | n.d. |
| 351 | n.d. | n.d. |
| 352 | 14 | 21 |
| 353 | 52 | 18 |
| 354 | >513 | >513 |
| 355 | >513 | 437 |
| 358 | >513 | >513 |
| 359 | >513 | >513 |
| 360 | >513 | >513 |
| 361 | 229 | 263 |
| 362 | 229 | 263 |
| 364 | 49 | 43 |
| 365 | 20 | 13 |
| 366 | 102 | 91 |
| 368 | 120 | ~23 |
| 373 | >513 | >513 |
| 375 | n.d. | n.d. |
| 376 | 105 | 85 |
| 381 | 209 | 117 |
| 382 | 513 | 91 |
| 383 | 23 | 6 |
| 384 | 20 | 7 |
| 385 | 32 | 20 |
| 386 | >513 | >513 |
| 389 | 39 | 28 |
| 390 | n.d. | n.d. |
| 391 | >513 | >513 |
| 394 | ~26.3 | 18 |
| 395 | >513 | >513 |
| 396 | >513 | >513 |
| 397 | >513 | >513 |
| 398 | >513 | >513 |
| 399 | >513 | >513 |
| 400 | 457 | ~371.54 |
| 401 | >513 | >513 |
| 402 | >513 | >513 |

Table B reports the obtained IC$_{50}$ values (nM):

| Co. No. | IC$_{50}$ pAkt_S473 (nM) | IC$_{50}$ pAkt_Thr308 (nM) |
|---|---|---|
| 117a | n.d. | n.d. |
| 118a | n.d. | n.d. |
| 122a | 12 | 9 |
| 123a | >513 | 380 |
| 154a | 30 | 23 |
| 154b | >513 | >513 |
| 184a | 3 | 2 |
| 184b | 3 | 2 |
| 184c | 4 | 2 |
| 237a | 6 | 4 |
| 237b | >513 | >513 |
| 237c | 26 | 11 |
| 237d | >513 | >513 |
| 243a | >513 | >513 |
| 243b | >513 | >513 |
| 246a | 44 | 24 |
| 246b | n.d. | n.d. |
| 257b | >513 | >513 |
| 257c | >513 | >513 |
| 262a | n.d. | n.d. |
| 262b | n.d. | n.d. |
| 279a | 58 | 41 |
| 279b | 59 | >513 |
| 280a | 87 | 45 |
| 280b | >513 | >513 |
| 281a | 5 | 3 |
| 281b | >513 | >513 |
| 283a | 81 | 52 |
| 283b | n.d. | n.d. |
| 284a | 90 | 61 |
| 284b | >513 | >513 |
| 286a | >513 | >513 |
| 286b | n.d. | 204 |
| 287a | 31 | 34 |
| 287b | >513 | 417 |
| 292a | 155 | 98 |
| 292b | >513 | >513 |
| 295a | >513 | >513 |
| 295b | >513 | >513 |
| 296a | 23 | 16 |
| 296b | 468 | 339 |
| 297a | 200 | 204 |
| 297b | 7 | 3 |
| 298a | 135 | 47 |
| 298b | 501 | >513 |
| 299a | ~45 | 56 |
| 299b | >513 | >513 |
| 300a | 29 | 19 |
| 300b | n.d. | n.d. |
| 302a | >513 | >513 |
| 302b | 54 | 39 |
| 309a | 9 | 8 |
| 309b | 363 | 282 |
| 312a | >513 | >513 |
| 312b | >513 | >513 |
| 313a | 257 | 166 |
| 313b | >513 | >513 |
| 314a | ~407 | >513 |
| 314b | 191 | n.d. |
| 315a | 195 | >20.42 |
| 315b | ~110 | ~85 |
| 319a | >513 | >513 |
| 319b | >513 | >513 |
| 320a | 20 | 17 |
| 320b | n.d. | n.d. |
| 321a | 18 | 8 |
| 321b | n.d. | n.d. |
| 322a | >513 | >513 |
| 322b | 42 | 26 |
| 323a | n.d. | n.d. |
| 323b | 209 | 100 |
| 324a | 13 | 10 |
| 324b | n.d. | n.d. |
| 325a | n.d. | n.d. |
| 325b | >513 | 263 |
| 329a | 14 | 6 |
| 329b | >513 | >513 |
| 334a | 339 | 219 |
| 334b | >513 | >513 |
| 335a | 5 | 2 |
| 335b | 188 | 207 |
| 338a | 115 | 68 |
| 338b | >513 | >513 |
| 339a | >513 | 407 |
| 339b | >513 | >513 |
| 344a | >102 | 56 |
| 344b | >513 | ~513 |
| 345a | 79 | 28 |
| 345b | >513 | >513 |
| 346a | 178 | 68 |
| 346b | >513 | >513 |
| 347a | >513 | >513 |
| 347b | 85 | 60 |
| 348a | 288 | 138 |
| 348b | >513 | >513 |
| 349a | 4 | 2 |
| 349b | 479 | 302 |
| 356a | n.d. | n.d. |
| 356b | n.d. | n.d. |
| 357a | >513 | >513 |
| 357b | 30 | 14 |
| 363a | ~126 | 74 |
| 363b | n.d. | n.d. |
| 364a | 35 | 26 |
| 364b | >513 | >513 |
| 365a | 52 | 35 |
| 365b | n.d. | n.d. |
| 367a | >513 | >513 |
| 367b | >513 | >513 |
| 369a | ~363 | 251 |
| 369b | >513 | >513 |
| 370a | 107 | 40 |
| 370b | >513 | >513 |
| 371a | 10 | 2 |
| 371b | >513 | 251 |
| 374a | 32 | 17 |
| 374b | >513 | >513 |
| 379a | ~29 | 22 |
| 379b | n.d. | n.d. |
| 380a | n.d. | n.d. |
| 380b | >513 | >513 |
| 388a | n.d. | n.d. |
| 388b | 38 | 19 |
| 391a | n.d. | n.d. |
| 391b | n.d. | n.d. |
| 392a | n.d. | n.d. |
| 392b | n.d. | n.d. |
| 393a | >513 | >513 |
| 393b | >513 | >513 |
| 395a | >513 | >513 |
| 395b | >513 | >513 |
| 397a | >513 | >513 |
| 397b | ~513 | >513 |
| 403a | ~275 | ~132 |
| 403b | >513 | >513 |
| 404a | >513 | >513 |
| 404b | 398 | 295 |
| 405a | >513 | >513 |
| 405b | 44 | 33 |
| 406a | 8 | 4 |
| 406b | >513 | >513 |
| 407a | n.d. | n.d. |
| 407b | n.d. | n.d. |
| 408a | n.d. | n.d. |
| 408b | n.d. | n.d. |
| 83a | >513 | >513 |

-continued

Table B reports the obtained $IC_{50}$ values (nM):

| Co. No. | $IC_{50}$ pAkt_S473 (nM) | $IC_{50}$ pAkt_Thr308 (nM) |
|---|---|---|
| 83b | >513 | >513 |
| 83c | >513 | >513 |

Prophetic Composition Examples

"Active ingredient" (a.i.) as used throughout these examples relates to a compound of Formula (I), including any tautomer or stereoisomeric form thereof, or a N-oxide, a pharmaceutically acceptable addition salt or a solvate thereof; in particular to any one of the exemplified compounds.

Typical examples of recipes for the formulation of the invention are as follows:

1, Tablets

| Active ingredient | 5 to 50 mg |
|---|---|
| Di-calcium phosphate | 20 mg |
| Lactose | 30 mg |
| Talcum | 10 mg |
| Magnesium stearate | 5 mg |
| Potato starch | ad 200 mg |

2. Suspension

An aqueous suspension is prepared for oral administration so that each milliliter contains 1 to 5 mg of active ingredient, 50 mg of sodium carboxymethyl cellulose, 1 mg of sodium benzoate, 500 mg of sorbitol and water ad 1 ml.

3. Injectable

A parenteral composition is prepared by stirring 1.5% (weight/volume) of active ingredient in 0.9% NaCl solution or in 10% by volume propylene glycol in water.

4. Ointment

| Active ingredient | 5 to 1000 mg |
|---|---|
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

The invention claimed is:

1. A method for inhibiting phosphoinositide-3-kinase activity in a human in need thereof, comprising administering to the human a therapeutically effective amount of a compound of the following formula:

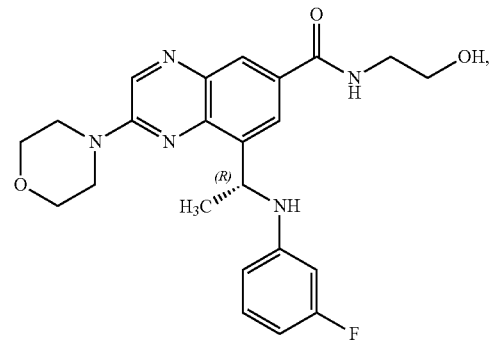

or a pharmaceutically acceptable addition salt thereof.

2. The method of claim 1, wherein the human suffers from a disease or condition selected from the group consisting of allergy, asthma, an autoimmune disorder, a cancer, a cardiovascular disease, graft rejection, an inflammatory disease, a kidney disease, a lung injury, multiorgan failure, a neurodegenerative disease, pancreatitis, platelet aggregation, sperm motility, and transplantation rejection.

3. The method of claim 2, wherein the disease or condition is a cancer.

4. The method of claim 3, wherein the cancer is prostate cancer.

* * * * *